US012558146B2

(12) United States Patent
Schwarz et al.

(10) Patent No.: US 12,558,146 B2
(45) Date of Patent: Feb. 24, 2026

(54) METHODS AND DEVICES FOR AESTHETIC TREATMENT OF BIOLOGICAL STRUCTURES BY RADIOFREQUENCY AND MAGNETIC ENERGY

(71) Applicant: BTL Medical Solutions A.S., Prague (CZ)

(72) Inventors: Tomás Schwarz, Prague (CZ); Frantisek Lang, Volyně (CH)

(73) Assignee: BTL Medical Solutions A.S., Prague (CZ)

( * ) Notice: Subject to any disclaimer, the term of this patent is extended or adjusted under 35 U.S.C. 154(b) by 1078 days.

(21) Appl. No.: 17/500,612

(22) Filed: Oct. 13, 2021

(65) Prior Publication Data

US 2022/0096142 A1 Mar. 31, 2022

Related U.S. Application Data

(63) Continuation-in-part of application No. 17/067,208, filed on Oct. 9, 2020, now Pat. No. 12,156,689, which (Continued)

(51) Int. Cl.

*A61B 18/14* (2006.01)
*A61B 18/00* (2006.01)

(Continued)

(52) U.S. Cl.

CPC .......... *A61B 18/14* (2013.01); *A61B 18/1206* (2013.01); *A61B 18/18* (2013.01);

(Continued)

(58) Field of Classification Search

CPC ..... A61B 18/14; A61B 18/1206; A61B 18/18; A61B 2018/00315; A61B 2018/00571;

(Continued)

(56) References Cited

U.S. PATENT DOCUMENTS

| | | | |
|---|---|---|---|
| 1,050,280 | A | 1/1913 | Kruger |
| 1,068,831 | A | 7/1913 | Worthington |

(Continued)

FOREIGN PATENT DOCUMENTS

| | | | |
|---|---|---|---|
| AU | 747678 | B2 | 5/2002 |
| AU | 2011265424 | B2 | 7/2014 |

(Continued)

OTHER PUBLICATIONS

US 10,398,895 B2, 09/2019, Schwarz (withdrawn)

(Continued)

*Primary Examiner* — Carrie R Dorna
*Assistant Examiner* — Joshua Daryl D Lannu
(74) *Attorney, Agent, or Firm* — Sterne, Kessler, Goldstein & Fox P.L.L.C.

(57) ABSTRACT

A device for providing a magnetic treatment by evoking muscle contraction by a time-varying magnetic field and providing a RF treatment by heating biological structure. The device includes an applicator having an RF electrode and a magnetic field generating device. The device may also include a main unit, a human machine interface, and a control unit. The control unit adjusts a signal provided to the RF electrode and creates an RF circuit, and also adjusts the signal provided to the magnetic field generating device and creates a magnetic circuit electrically insulated from the RF circuit. The RF circuit may include a power source and a power amplifier, and the magnetic circuit may include an energy storage to supply the magnetic field generating device with electric current.

20 Claims, 90 Drawing Sheets

Related U.S. Application Data is a continuation-in-part of application No. 16/844,822, filed on Apr. 9, 2020, now Pat. No. 11,247,063.

(60) Provisional application No. 62/932,259, filed on Nov. 7, 2019, provisional application No. 62/832,738, filed on Apr. 11, 2019, provisional application No. 62/832,688, filed on Apr. 11, 2019.

(51) Int. Cl.

| | |
|---|---|
| ***A61B 18/12*** | (2006.01) |
| ***A61B 18/18*** | (2006.01) |
| ***A61B 90/00*** | (2016.01) |
| ***A61N 1/40*** | (2006.01) |
| ***A61N 2/00*** | (2006.01) |
| ***A61N 7/00*** | (2006.01) |

(52) U.S. Cl.

CPC ............... *A61B 2018/00315* (2013.01); *A61B 2018/00571* (2013.01); *A61B 2018/00702* (2013.01); *A61B 2018/00791* (2013.01); *A61B 2018/126* (2013.01)

(58) Field of Classification Search

CPC A61B 2018/00702; A61B 2018/00791; A61B 2018/126; A61B 2090/064; A61N 2007/0021; A61N 2007/0039; A61N 1/403; A61N 7/00; A61N 2/00

See application file for complete search history.

(56) References Cited

U.S. PATENT DOCUMENTS

| | | | |
|---|---|---|---|
| 1,973,387 | A | 9/1934 | Neymann et al. |
| 2,021,676 | A | 11/1935 | Wood et al. |
| 3,163,161 | A | 12/1964 | Jacques et al. |
| 3,566,877 | A | 3/1971 | Smith et al. |
| 3,658,051 | A | 4/1972 | MacLean et al. |
| 3,709,228 | A | 1/1973 | Barker |
| 3,841,306 | A | 10/1974 | Hallgren et al. |
| 3,915,151 | A | 10/1975 | Kraus |
| 3,946,349 | A | 3/1976 | Haldeman, III |
| 3,952,751 | A | 4/1976 | Yarger |
| 3,971,387 | A | 7/1976 | Mantell |
| 4,068,292 | A | 1/1978 | Berry et al. |
| 4,143,661 | A | 3/1979 | LaForge et al. |
| 4,197,851 | A | 4/1980 | Fellus |
| 4,237,898 | A | 12/1980 | Whalley |
| 4,261,364 | A | 4/1981 | Haddad et al. |
| 4,305,115 | A | 12/1981 | Armitage |
| 4,315,503 | A | 2/1982 | Ryaby et al. |
| 4,392,040 | A | 7/1983 | Rand et al. |
| 4,454,883 | A | 6/1984 | Fellus |
| 4,456,001 | A | 6/1984 | Pescatore |
| 4,550,714 | A | 11/1985 | Talish et al. |
| 4,556,056 | A | 12/1985 | Fischer et al. |
| 4,665,898 | A | 5/1987 | Costa et al. |
| 4,674,482 | A | 6/1987 | Waltonen et al. |
| 4,674,505 | A | 6/1987 | Pauli et al. |
| 4,723,536 | A | 2/1988 | Rauscher et al. |
| 4,736,752 | A | 4/1988 | Munck et al. |
| 4,850,959 | A | 7/1989 | Findl |
| 4,889,526 | A | 12/1989 | Rauscher et al. |
| 4,907,602 | A | 3/1990 | Sanders |
| 4,957,480 | A | 9/1990 | Morenings |
| 4,989,604 | A | 2/1991 | Fang |
| 4,993,413 | A | 2/1991 | Mcleod et al. |
| 5,061,234 | A | 10/1991 | Chaney |
| 5,067,940 | A | 11/1991 | Liboff et al. |
| 5,085,227 | A | 2/1992 | Ramon |
| 5,085,626 | A | 2/1992 | Frey |
| 5,143,063 | A | 9/1992 | Fellner |
| 5,156,587 | A | 10/1992 | Montone |
| 5,169,380 | A | 12/1992 | Brennan |
| 5,181,902 | A | 1/1993 | Erickson et al. |
| 5,199,951 | A | 4/1993 | Spears |
| 5,246,438 | A | 9/1993 | Langberg |
| 5,334,181 | A | 8/1994 | Rubinsky et al. |
| 5,339,217 | A | 8/1994 | Cohen et al. |
| 5,344,384 | A | 9/1994 | Ostrow et al. |
| 5,401,233 | A | 3/1995 | Erickson et al. |
| 5,415,617 | A | 5/1995 | Kraus |
| 5,419,344 | A | 5/1995 | Dewitt |
| 5,433,737 | A | 7/1995 | Aimone |
| 5,433,740 | A | 7/1995 | Yamaguchi |
| 5,562,706 | A | 10/1996 | Lauterbach et al. |
| 5,584,863 | A | 12/1996 | Rauch et al. |
| 5,620,463 | A | 4/1997 | Drolet |
| 5,660,836 | A | 8/1997 | Knowlton |
| 5,674,218 | A | 10/1997 | Rubinsky et al. |
| 5,690,692 | A | 11/1997 | Fleming |
| 5,691,873 | A | 11/1997 | Masaki |
| 5,718,662 | A | 2/1998 | Jalinous |
| 5,720,773 | A | 2/1998 | Lopez-Carlos et al. |
| 5,725,471 | A | 3/1998 | Davey et al. |
| 5,755,753 | A | 5/1998 | Knowlton |
| 5,766,124 | A | 6/1998 | Polson |
| 5,769,778 | A | 6/1998 | Abrams et al. |
| 5,782,743 | A | 7/1998 | Russell |
| 5,799,917 | A | 9/1998 | Li |
| 5,807,232 | A | 9/1998 | Espinoza et al. |
| 5,857,957 | A | 1/1999 | Lin |
| 5,904,712 | A | 5/1999 | Axelgaard |
| 5,908,444 | A | 6/1999 | Azure |
| 5,919,219 | A | 7/1999 | Knowlton |
| 5,968,527 | A | 10/1999 | Litovitz |
| 5,984,854 | A | 11/1999 | Ishikawa et al. |
| 6,017,337 | A | 1/2000 | Pira |
| 6,032,675 | A | 3/2000 | Rubinsky |
| 6,038,485 | A | 3/2000 | Axelgaard |
| 6,042,531 | A | 3/2000 | Holcomb |
| 6,047,215 | A | 4/2000 | McClure et al. |
| 6,050,994 | A | 4/2000 | Mashall |
| 6,063,108 | A | 5/2000 | Salansky et al. |
| 6,067,474 | A | 5/2000 | Schulman et al. |
| 6,086,525 | A | 7/2000 | Davey et al. |
| 6,094,599 | A | 7/2000 | Bingham et al. |
| 6,099,459 | A | 8/2000 | Jacobson |
| 6,099,523 | A | 8/2000 | Kim et al. |
| 6,117,066 | A | 9/2000 | Abrams et al. |
| 6,132,361 | A | 10/2000 | Epstein et al. |
| 6,132,392 | A | 10/2000 | Stone |
| 6,141,985 | A | 11/2000 | Cluzeau et al. |
| 6,155,966 | A | 12/2000 | Parker |
| 6,161,757 | A | 12/2000 | Morris |
| 6,179,769 | B1 | 1/2001 | Ishikawa et al. |
| 6,179,770 | B1 | 1/2001 | Mould |
| 6,179,771 | B1 | 1/2001 | Mueller |
| 6,200,259 | B1 | 3/2001 | March |
| 6,213,933 | B1 | 4/2001 | Lin |
| 6,223,750 | B1 | 5/2001 | Ishikawa et al. |
| 6,246,905 | B1 | 6/2001 | Mogul |
| 6,255,815 | B1 | 7/2001 | Davey |
| 6,261,301 | B1 | 7/2001 | Knesch et al. |
| 6,273,862 | B1 | 8/2001 | Privitera et al. |
| 6,273,884 | B1 | 8/2001 | Altshuler et al. |
| 6,280,376 | B1 | 8/2001 | Holcomb |
| 6,282,448 | B1 | 8/2001 | Katz et al. |
| D447,806 | S | 9/2001 | Davey et al. |
| 6,311,090 | B1 | 10/2001 | Knowlton |
| 6,324,430 | B1 | 11/2001 | Zarinetchi et al. |
| 6,324,432 | B1 | 11/2001 | Rigaux et al. |
| 6,334,069 | B1 | 12/2001 | George et al. |
| 6,334,074 | B1 | 12/2001 | Spertell |
| 6,350,276 | B1 | 2/2002 | Knowlton |
| 6,366,814 | B1 | 4/2002 | Boveja et al. |
| 6,402,678 | B1 | 6/2002 | Fischell et al. |
| 6,413,255 | B1 | 7/2002 | Stern |
| 6,418,345 | B1 | 7/2002 | Tepper et al. |
| 6,424,864 | B1 | 7/2002 | Matsuura |
| 6,425,852 | B1 | 7/2002 | Epstein et al. |
| 6,443,883 | B1 | 9/2002 | Ostrow et al. |
| 6,445,955 | B1 | 9/2002 | Michelson et al. |

(56) References Cited

U.S. PATENT DOCUMENTS 6,447,440 B1 9/2002 Markoll
6,453,202 B1 9/2002 Knowlton
6,461,375 B1 10/2002 Baudry et al.
6,491,620 B1 12/2002 Davey
6,500,110 B1 12/2002 Davey et al.
6,520,903 B1 2/2003 Yamashiro
6,527,694 B1 3/2003 Ishikawa et al.
6,527,695 B1 3/2003 Davey et al.
6,537,197 B1 3/2003 Ruohonen et al.
6,569,078 B2 5/2003 Ishikawa et al.
6,591,138 B1 7/2003 Fischell et al.
6,605,080 B1 8/2003 Altshuler et al.
6,635,053 B1 10/2003 Lalonde et al.
6,658,301 B2 12/2003 Loeb et al.
6,662,054 B2 12/2003 Kreindel et al.
6,663,556 B2 12/2003 Barker
6,663,659 B2 12/2003 McDaniel
6,701,185 B2 3/2004 Burnett et al.
6,702,808 B1 3/2004 Kreindel et al.
6,713,733 B2 3/2004 Kochman et al.
6,735,481 B1 5/2004 Bingham et al.
6,738,667 B2 5/2004 Deno et al.
6,749,624 B2 6/2004 Knowlton
6,827,681 B2 12/2004 Tanner et al.
6,849,040 B2 2/2005 Ruohonen et al.
6,860,852 B2 3/2005 Schonenberger et al.
6,871,099 B1 3/2005 Whitehurst et al.
6,879,859 B1 4/2005 Boveja
6,889,090 B2 5/2005 Kreindel
6,920,883 B2 7/2005 Bessette et al.
6,926,660 B2 8/2005 Miller
6,939,287 B1 9/2005 Ardizzone et al.
6,939,344 B2 9/2005 Kreindel
6,960,202 B2 11/2005 Cluzeau et al.
6,990,427 B2 1/2006 Kirsch et al.
7,008,370 B2 3/2006 Tanner et al.
7,024,239 B2 4/2006 George et al.
7,030,764 B2 4/2006 Smith et al.
7,041,100 B2 5/2006 Kreindel
7,083,580 B2 8/2006 Bernabei
7,104,947 B2 9/2006 Riehl
7,153,256 B2 12/2006 Riehl et al.
7,186,209 B2 3/2007 Jacobson et al.
7,211,082 B2 5/2007 Hall et al.
7,217,265 B2 5/2007 Hennings et al.
7,238,183 B2 7/2007 Kreindel
7,276,020 B2 10/2007 Becker et al.
7,276,058 B2 10/2007 Altshuler et al.
7,294,101 B2 11/2007 Fischell et al.
7,309,309 B2 12/2007 Wang et al.
7,318,821 B2 1/2008 Lalonde et al.
7,320,664 B2 1/2008 Riehl et al.
7,351,252 B2 4/2008 Altshuler et al.
7,367,341 B2 5/2008 Anderson et al.
7,367,936 B2 5/2008 Myers et al.
7,369,895 B2 5/2008 Hurtado
7,372,271 B2 5/2008 Roozen et al.
7,376,460 B2 5/2008 Bernabei
7,396,326 B2 7/2008 Ghiron et al.
7,407,478 B2 8/2008 Zangen et al.
7,494,458 B2 2/2009 Fischell et al.
7,496,401 B2 2/2009 Bernabei
7,520,848 B2 4/2009 Schneider et al.
7,520,849 B1 4/2009 Simon
7,520,875 B2 4/2009 Bernabei
7,524,276 B2 4/2009 Muntermann
7,532,926 B2 5/2009 Bernabei
7,560,058 B2 7/2009 Riehl et al.
7,571,003 B2 8/2009 Pozzato
7,591,776 B2 9/2009 Phillips et al.
7,601,115 B2 10/2009 Riehl
7,601,116 B2 10/2009 Fischell et al.
7,608,035 B2 10/2009 Farone
7,614,996 B2 11/2009 Riehl et al.
7,618,429 B2 11/2009 Mulholland
7,630,774 B2 12/2009 Karni et al.
7,643,883 B2 1/2010 Kreindel
7,651,459 B2 1/2010 Cameron et al.
7,697,998 B2 4/2010 Axelgaard
7,697,999 B2 4/2010 Axelgaard
7,699,768 B2 4/2010 Kishawi et al.
7,706,885 B2 4/2010 Farone
7,711,431 B2 5/2010 Tanner et al.
7,740,574 B2 6/2010 Pilla et al.
7,744,523 B2 6/2010 Epstein
7,753,836 B2 7/2010 Peterchev
7,783,348 B2 8/2010 Gill et al.
7,785,358 B2 8/2010 Lach
7,824,324 B2 11/2010 Riehl et al.
7,854,232 B2 12/2010 Aho et al.
7,854,754 B2 12/2010 Ting et al.
7,857,746 B2 12/2010 Riehl
7,857,775 B2 12/2010 Rosenberg et al.
7,901,373 B2 3/2011 Tavger
7,909,786 B2 3/2011 Bonnefin et al.
7,914,469 B2 3/2011 Torbati
7,925,066 B2 4/2011 Ruohonen et al.
7,945,321 B2 5/2011 Bernabei
7,946,973 B2 5/2011 Peterchev
7,953,500 B2 5/2011 Bingham et al.
7,963,903 B2 6/2011 Ghiron et al.
7,976,451 B2 7/2011 Zangen et al.
7,981,146 B2 7/2011 Korb et al.
7,998,053 B2 8/2011 Aho
8,029,432 B2 10/2011 Dennis
8,035,385 B2 10/2011 Tomiha et al.
8,052,591 B2 11/2011 Mishelevich et al.
RE43,007 E 12/2011 Lalonde et al.
8,088,058 B2 1/2012 Juliana et al.
8,105,254 B2 1/2012 Guantera et al.
8,118,722 B2 2/2012 Riehl et al.
8,128,549 B2 3/2012 Testani et al.
8,133,191 B2 3/2012 Rosenberg et al.
8,137,258 B1 3/2012 Dennis et al.
8,137,259 B1 3/2012 Dennis
8,170,643 B2 5/2012 Turner et al.
8,172,835 B2 5/2012 Leyh et al.
8,177,702 B2 5/2012 Riehl et al.
8,192,474 B2 6/2012 Levinson
8,204,446 B2 6/2012 Scheer et al.
8,246,529 B2 8/2012 Riehl et al.
8,251,986 B2 8/2012 Chornenky et al.
8,262,556 B2 9/2012 Fischell et al.
8,265,763 B2 9/2012 Fahey
8,265,910 B2 9/2012 Mishelevich et al.
8,267,850 B2 9/2012 Schneider et al.
8,271,090 B1 9/2012 Hartman et al.
8,275,442 B2 9/2012 Allison
8,277,371 B2 10/2012 Zangen et al.
8,285,390 B2 10/2012 Levinson et al.
8,303,478 B2 11/2012 Lebosse et al.
8,335,566 B2 12/2012 Muller et al.
8,337,539 B2 12/2012 Ting et al.
8,366,756 B2 2/2013 Tucek et al.
8,376,825 B2 2/2013 Guinn et al.
8,376,925 B1 2/2013 Dennis et al.
8,388,510 B2 3/2013 Zangen et al.
8,428,735 B2 4/2013 Littlewood et al.
8,435,166 B2 5/2013 Burnett et al.
8,454,591 B2 6/2013 Leyh et al.
8,457,751 B2 6/2013 Pozzato
8,465,408 B2 6/2013 Phillips et al.
8,475,354 B2 7/2013 Phillips et al.
8,480,554 B2 7/2013 Phillips et al.
8,493,286 B1 7/2013 Agrama
8,506,468 B2 8/2013 Ghiron et al.
8,517,908 B2 8/2013 Riehl et al.
8,523,753 B2 9/2013 Schneider et al.
8,523,927 B2 9/2013 Levinson et al.
8,548,599 B2 10/2013 Zarsky et al.
8,565,888 B2 10/2013 Buhlmann et al.
8,579,953 B1 11/2013 Dunbar et al.
8,585,568 B2 11/2013 Phillips et al.
8,585,617 B2 11/2013 Mashiach et al.

(56) References Cited

U.S. PATENT DOCUMENTS 8,588,930 B2 11/2013 DiUbaldi et al.
8,593,245 B2 11/2013 Zeng et al.
8,603,073 B2 12/2013 Allison
8,608,634 B2 12/2013 Zangen et al.
8,641,710 B2 2/2014 Doty et al.
8,646,239 B2 2/2014 Rulon
8,657,731 B2 2/2014 Riehl et al.
8,657,732 B2 2/2014 Vasishta
8,666,492 B2 3/2014 Muller et al.
8,676,338 B2 3/2014 Levinson
8,684,901 B1 4/2014 Zabara
8,700,176 B2 4/2014 Azar et al.
8,702,774 B2 4/2014 Baker et al.
8,721,572 B1 5/2014 Linder et al.
8,723,628 B2 5/2014 Mishelevich et al.
8,725,270 B2 5/2014 Towe
8,731,657 B1 5/2014 Shambayati et al.
8,740,765 B1 6/2014 Fischell et al.
8,768,454 B2 7/2014 Sham et al.
8,771,163 B2 7/2014 Zangen et al.
8,771,326 B2 7/2014 Myeong et al.
8,777,831 B2 7/2014 Aho
8,788,040 B2 7/2014 Haessler
8,788,044 B2 7/2014 John
8,788,060 B2 7/2014 Nebrigic et al.
8,795,148 B2 8/2014 Schneider et al.
8,801,589 B2 8/2014 Peterchev et al.
8,825,166 B2 9/2014 John
8,834,547 B2 9/2014 Anderson et al.
8,840,608 B2 9/2014 Anderson et al.
8,845,508 B2 9/2014 Schneider et al.
8,864,641 B2 10/2014 Riehl et al.
8,868,177 B2 10/2014 Simon et al.
8,870,737 B2 10/2014 Phillips et al.
8,888,672 B2 11/2014 Phillips et al.
8,888,673 B2 11/2014 Phillips et al.
8,906,009 B2 12/2014 Nebrigic et al.
8,909,342 B2 12/2014 Lozano
8,915,948 B2 12/2014 Altshuler et al.
8,926,490 B2 1/2015 Phillips et al.
8,932,338 B2 1/2015 Lim et al.
8,956,273 B2 2/2015 Mishelevich et al.
8,956,274 B2 2/2015 Schneider et al.
8,961,386 B2 2/2015 Phillips et al.
8,979,727 B2 3/2015 Ron Edoute et al.
8,985,331 B2 3/2015 Guenter et al.
8,998,791 B2 4/2015 Ron Edoute et al.
9,002,477 B2 4/2015 Burnett
9,008,793 B1 4/2015 Cosman, Sr. et al.
9,015,057 B2 4/2015 Phillips et al.
9,020,590 B1 4/2015 Honeycutt et al.
9,028,469 B2 5/2015 Jones et al.
9,031,659 B2 5/2015 Campbell et al.
9,033,861 B2 5/2015 Fischell et al.
9,037,247 B2 5/2015 Simon et al.
9,044,595 B2 6/2015 Araya et al.
9,061,128 B2 6/2015 Hall et al.
9,067,052 B2 6/2015 Moses et al.
9,072,891 B1 7/2015 Rao
9,078,634 B2 7/2015 Gonzales et al.
9,089,719 B2 7/2015 Simon et al.
9,101,524 B2 8/2015 Aghion
9,132,031 B2 9/2015 Levinson et al.
9,144,513 B2 9/2015 Paulson
9,149,650 B2 10/2015 Shanks et al.
9,168,096 B2 10/2015 Kreindel
9,233,207 B2 1/2016 Polyakov et al.
9,233,257 B1 1/2016 Zabara
9,254,395 B1 2/2016 Shambayati
9,261,574 B2 2/2016 Boskamp et al.
9,265,690 B2 2/2016 Kriksunov et al.
9,295,840 B1 3/2016 Thacker et al.
9,308,120 B2 4/2016 Anderson et al.
9,314,368 B2 4/2016 Allison et al.
9,326,910 B2 5/2016 Eckhouse et al.
9,339,641 B2 5/2016 Rajguru et al.
9,358,068 B2 6/2016 Schomacker et al.
9,358,149 B2 6/2016 Anderson et al.
9,375,345 B2 6/2016 Levinson et al.
9,387,339 B2 7/2016 Sham et al.
9,398,975 B2 7/2016 Müller et al.
9,408,745 B2 8/2016 Levinson et al.
9,414,759 B2 8/2016 Lang et al.
9,433,797 B2 9/2016 Pilla et al.
9,439,805 B2 9/2016 Gonzales et al.
9,446,258 B1 9/2016 Schwarz
9,468,774 B2 10/2016 Žársk et al.
9,526,912 B1 12/2016 Fischell et al.
9,532,832 B2 1/2017 Ron Edoute et al.
9,545,523 B2 1/2017 Nanda
9,550,067 B1 1/2017 Fischell et al.
9,561,357 B2 2/2017 Hall et al.
9,561,384 B1 2/2017 Fischell et al.
9,586,048 B2 3/2017 Ternes et al.
9,586,057 B2 3/2017 Ladman et al.
9,596,920 B2 3/2017 Shalev et al.
9,597,225 B1 3/2017 Guerrieri
9,610,429 B2 4/2017 Harris et al.
9,610,459 B2 4/2017 Burnett et al.
9,615,854 B2 4/2017 Matsushita
9,616,217 B1 4/2017 Pensler et al.
9,636,516 B2 5/2017 Schwarz
9,636,519 B2 5/2017 Ladman et al.
9,649,220 B2 5/2017 Anderson et al.
9,655,770 B2 5/2017 Levinson et al.
9,675,800 B2 6/2017 Li et al.
9,675,815 B1 6/2017 Fischell et al.
9,694,194 B2 7/2017 Ron Edoute et al.
9,707,121 B2 7/2017 Hyde et al.
9,713,567 B2 7/2017 Guantera et al.
9,724,533 B1 8/2017 Fischell et al.
9,737,238 B2 8/2017 Wright et al.
9,737,434 B2 8/2017 Allison
9,757,584 B2 9/2017 Burnett
9,782,324 B2 10/2017 Crunick et al.
9,814,897 B2 11/2017 Ron Edoute et al.
9,844,460 B2 12/2017 Weber et al.
9,844,461 B2 12/2017 Levinson et al.
9,849,299 B2 12/2017 Sham et al.
9,849,302 B1 12/2017 Fischell et al.
9,855,166 B2 1/2018 Anderson et al.
9,861,421 B2 1/2018 O'Neil et al.
9,861,520 B2 1/2018 Baker et al.
9,867,996 B2 1/2018 Zarsky et al.
9,901,743 B2 2/2018 Ron Edoute et al.
9,919,161 B2 3/2018 Schwarz
9,937,358 B2 4/2018 Schwarz
9,962,553 B2 5/2018 Schwarz et al.
9,968,797 B2 5/2018 Sham et al.
9,974,519 B1 5/2018 Schwarz
9,974,684 B2 5/2018 Anderson et al.
9,980,765 B2 5/2018 Avram et al.
9,981,143 B2 5/2018 Ron Edoute et al.
9,999,780 B2 6/2018 Weyh et al.
10,029,112 B1 7/2018 Fischell et al.
10,037,867 B2 7/2018 Godyak
10,039,929 B1 8/2018 Schwarz et al.
10,039,930 B2 8/2018 Vallejo et al.
10,046,160 B1 8/2018 Kern
10,080,906 B2 9/2018 Schwarz
10,092,346 B2 10/2018 Levinson
10,111,770 B2 10/2018 Harris et al.
10,111,774 B2 10/2018 Gonzales et al.
10,124,187 B2 11/2018 Schwarz et al.
10,183,172 B2 1/2019 Ghiron et al.
10,195,010 B2 2/2019 Sanders
10,195,427 B2 2/2019 Kent et al.
10,195,453 B2 2/2019 Schwarz
10,195,454 B2 2/2019 Yamashiro
10,195,456 B2 2/2019 Cabrerizo et al.
10,201,380 B2 2/2019 DeBenedictis et al.
10,232,172 B1 3/2019 O et al.
10,245,439 B1 4/2019 Schwarz et al.
10,271,900 B2 4/2019 Marchitto et al.

(56) References Cited

U.S. PATENT DOCUMENTS

| | | | |
|---|---|---|---|
| 10,279,185 | B2 | 5/2019 | Meadows et al. |
| 10,342,988 | B2 | 7/2019 | Midorikawa et al. |
| 10,363,419 | B2 | 7/2019 | Simon et al. |
| 10,413,745 | B2 | 9/2019 | Riehl |
| 10,463,869 | B2 | 11/2019 | Ron Edoute et al. |
| 10,471,269 | B1 | 11/2019 | Schwarz et al. |
| 10,471,271 | B1 | 11/2019 | John |
| 10,478,588 | B2 | 11/2019 | Walpole et al. |
| 10,478,633 | B2 | 11/2019 | Schwarz et al. |
| 10,478,634 | B2 | 11/2019 | Schwarz et al. |
| 10,493,293 | B2 | 12/2019 | Schwarz et al. |
| 10,518,098 | B2 | 12/2019 | Hong et al. |
| 10,525,277 | B1 | 1/2020 | Chau |
| 10,549,109 | B2 | 2/2020 | Schwarz |
| 10,549,110 | B1 | 2/2020 | Schwarz et al. |
| 10,556,121 | B2 | 2/2020 | Gurfein |
| 10,556,122 | B1 | 2/2020 | Schwarz et al. |
| 10,569,094 | B2 | 2/2020 | Schwarz |
| 10,569,095 | B1 | 2/2020 | Schwarz et al. |
| 10,583,287 | B2 | 3/2020 | Schwarz |
| 10,589,117 | B1 | 3/2020 | Fischell et al. |
| 10,596,366 | B2 | 3/2020 | Sama |
| 10,596,386 | B2 | 3/2020 | Schwarz et al. |
| 10,610,696 | B1 | 4/2020 | Peled |
| 10,632,321 | B2 | 4/2020 | Schwarz et al. |
| 10,639,490 | B2 | 5/2020 | Simon et al. |
| 10,661,093 | B2 | 5/2020 | Ron Edoute et al. |
| 10,675,819 | B2 | 6/2020 | Li et al. |
| 10,688,310 | B2 | 6/2020 | Schwarz et al. |
| 10,695,575 | B1 | 6/2020 | Schwarz et al. |
| 10,695,576 | B2 | 6/2020 | Schwarz et al. |
| 10,709,894 | B2 | 7/2020 | Schwarz et al. |
| 10,709,895 | B2 | 7/2020 | Schwarz et al. |
| 10,773,094 | B1 | 9/2020 | Rzasa et al. |
| 10,806,943 | B2 | 10/2020 | Sokolowski |
| 10,821,295 | B1 | 11/2020 | Schwarz et al. |
| 10,835,418 | B1 | 11/2020 | Darbandi et al. |
| 10,849,784 | B2 | 12/2020 | Jurna et al. |
| 10,898,710 | B1 | 1/2021 | Sanderford |
| 10,946,195 | B2 | 3/2021 | Strohl |
| 11,052,251 | B2 | 7/2021 | Muller et al. |
| 11,141,219 | B1 | 10/2021 | Schwarz |
| 11,185,690 | B2 | 11/2021 | Schwarz |
| 11,207,540 | B2 | 12/2021 | Zangen et al. |
| 11,247,039 | B2 | 2/2022 | Schwarz |
| 11,247,063 | B2 | 2/2022 | Schwarz et al. |
| 11,253,717 | B2 | 2/2022 | Schwarz et al. |
| 11,253,718 | B2 | 2/2022 | Prouza et al. |
| 11,266,850 | B2 | 3/2022 | Prouza et al. |
| 11,266,852 | B2 | 3/2022 | Schwarz et al. |
| 11,278,732 | B2 | 3/2022 | Casalino et al. |
| 11,420,061 | B2 | 8/2022 | Caparso et al. |
| 11,464,994 | B2 | 10/2022 | Schwarz et al. |
| 11,478,638 | B2 | 10/2022 | Toong et al. |
| 11,484,263 | B2 | 11/2022 | Leaper |
| 11,484,725 | B2 | 11/2022 | Schwarz et al. |
| 11,484,727 | B2 | 11/2022 | Schwarz |
| 11,529,514 | B2 | 12/2022 | Bolea et al. |
| 11,534,619 | B2 | 12/2022 | Schwarz et al. |
| 11,564,861 | B1 | 1/2023 | Gaines |
| 11,590,356 | B2 | 2/2023 | Schwarz et al. |
| 11,607,556 | B2 | 3/2023 | Schwarz |
| 11,672,999 | B1 | 6/2023 | John |
| 11,679,255 | B2 | 6/2023 | Schwarz et al. |
| 11,679,270 | B2 | 6/2023 | Schwarz et al. |
| 11,691,024 | B2 | 7/2023 | Schwarz et al. |
| 11,779,767 | B1 | 10/2023 | John |
| 11,794,029 | B2 | 10/2023 | Schwarz et al. |
| 11,806,528 | B2 | 11/2023 | Schwarz et al. |
| 11,819,689 | B1 | 11/2023 | Gaines et al. |
| 11,964,155 | B1 | 4/2024 | Soin et al. |
| 2001/0011152 | A1 | 8/2001 | Ishikawa et al. |
| 2001/0018547 | A1 | 8/2001 | Mechlenburg et al. |
| 2001/0031906 | A1 | 10/2001 | Ishikawa et al. |
| 2001/0031999 | A1 | 10/2001 | Carter et al. |
| 2002/0010414 | A1 | 1/2002 | Coston et al. |
| 2002/0049483 | A1 | 4/2002 | Knowlton |
| 2002/0058972 | A1 | 5/2002 | Minogue et al. |
| 2002/0082466 | A1 | 6/2002 | Han |
| 2002/0103411 | A1 | 8/2002 | Bailey et al. |
| 2002/0128686 | A1 | 9/2002 | Minogue et al. |
| 2002/0143365 | A1 | 10/2002 | Herbst |
| 2002/0143373 | A1 | 10/2002 | Courtnage et al. |
| 2002/0151887 | A1 | 10/2002 | Stern et al. |
| 2002/0160436 | A1 | 10/2002 | Markov et al. |
| 2002/0165590 | A1 | 11/2002 | Crowe et al. |
| 2002/0193709 | A1 | 12/2002 | Bolze et al. |
| 2003/0028072 | A1 | 2/2003 | Fischell et al. |
| 2003/0032900 | A1 | 2/2003 | Ella |
| 2003/0032950 | A1 | 2/2003 | Altshuler et al. |
| 2003/0050527 | A1 | 3/2003 | Fox et al. |
| 2003/0056281 | A1 | 3/2003 | Hasegawa |
| 2003/0074037 | A1 | 4/2003 | Moore et al. |
| 2003/0078646 | A1 | 4/2003 | Axelgaard |
| 2003/0093133 | A1 | 5/2003 | Crowe et al. |
| 2003/0097162 | A1 | 5/2003 | Kreindel |
| 2003/0130711 | A1 | 7/2003 | Pearson et al. |
| 2003/0134545 | A1 | 7/2003 | McAdams et al. |
| 2003/0139740 | A1 | 7/2003 | Kreindel |
| 2003/0139789 | A1 | 7/2003 | Tvinnereim et al. |
| 2003/0149451 | A1 | 8/2003 | Chomenky et al. |
| 2003/0153958 | A1 | 8/2003 | Yamazaki et al. |
| 2003/0158585 | A1 | 8/2003 | Burnett |
| 2003/0199866 | A1 | 10/2003 | Stern et al. |
| 2003/0216729 | A1 | 11/2003 | Marchitto et al. |
| 2003/0220635 | A1 | 11/2003 | Knowlton et al. |
| 2003/0220674 | A1 | 11/2003 | Anderson et al. |
| 2003/0236487 | A1 | 12/2003 | Knowlton |
| 2004/0015163 | A1 | 1/2004 | Buysse et al. |
| 2004/0034346 | A1 | 2/2004 | Stern et al. |
| 2004/0039279 | A1 | 2/2004 | Ruohonen |
| 2004/0044385 | A1 | 3/2004 | Fenn et al. |
| 2004/0073079 | A1 | 4/2004 | Altshuler et al. |
| 2004/0077977 | A1 | 4/2004 | Ella et al. |
| 2004/0093042 | A1 | 5/2004 | Altshuler et al. |
| 2004/0102768 | A1 | 5/2004 | Cluzeau et al. |
| 2004/0111087 | A1 | 6/2004 | Stern et al. |
| 2004/0152943 | A1 | 8/2004 | Zimmerman et al. |
| 2004/0162583 | A1 | 8/2004 | Bingham et al. |
| 2004/0171970 | A1 | 9/2004 | Schleuniger et al. |
| 2004/0193000 | A1 | 9/2004 | Riehl |
| 2004/0193003 | A1 | 9/2004 | Mechlenburg et al. |
| 2004/0206365 | A1 | 10/2004 | Knowlton |
| 2004/0210214 | A1 | 10/2004 | Knowlton |
| 2004/0210282 | A1 | 10/2004 | Flock et al. |
| 2004/0210287 | A1 | 10/2004 | Greene |
| 2004/0230226 | A1 | 11/2004 | Bingham et al. |
| 2004/0260210 | A1 | 12/2004 | Ella et al. |
| 2004/0267169 | A1 | 12/2004 | Sun et al. |
| 2005/0004632 | A1 | 1/2005 | Benedict |
| 2005/0038313 | A1 | 2/2005 | Ardizzone |
| 2005/0049543 | A1 | 3/2005 | Anderson et al. |
| 2005/0075701 | A1 | 4/2005 | Shafer |
| 2005/0075702 | A1 | 4/2005 | Shafer |
| 2005/0080466 | A1 | 4/2005 | Homer |
| 2005/0085865 | A1 | 4/2005 | Tehrani |
| 2005/0085866 | A1 | 4/2005 | Tehrani |
| 2005/0085874 | A1 | 4/2005 | Davis et al. |
| 2005/0090814 | A1 | 4/2005 | Lalonde et al. |
| 2005/0096711 | A1 | 5/2005 | Adib |
| 2005/0107656 | A1 | 5/2005 | Jang et al. |
| 2005/0134193 | A1 | 6/2005 | Myers et al. |
| 2005/0148808 | A1 | 7/2005 | Cameron et al. |
| 2005/0159737 | A1 | 7/2005 | Kreindel |
| 2005/0177203 | A1 | 8/2005 | Brighton et al. |
| 2005/0182457 | A1 | 8/2005 | Thrope et al. |
| 2005/0187599 | A1 | 8/2005 | Sharkey et al. |
| 2005/0203504 | A1 | 9/2005 | Wham et al. |
| 2005/0215987 | A1 | 9/2005 | Slatkine |
| 2005/0216062 | A1 | 9/2005 | Herbst |
| 2005/0228210 | A1 | 10/2005 | Muntermann |
| 2005/0251120 | A1 | 11/2005 | Anderson et al. |
| 2005/0251229 | A1 | 11/2005 | Pilla et al. |
| 2006/0004244 | A1 | 1/2006 | Phillips et al. |

(56) References Cited

U.S. PATENT DOCUMENTS

| | | | |
|---|---|---|---|
| 2006/0020236 | A1 | 1/2006 | Ben-Nun |
| 2006/0036194 | A1 | 2/2006 | Schultheiss et al. |
| 2006/0036300 | A1 | 2/2006 | Kreindel |
| 2006/0047281 | A1 | 3/2006 | Kreindel |
| 2006/0064082 | A1 | 3/2006 | Bonutti |
| 2006/0064140 | A1 | 3/2006 | Whitehurst et al. |
| 2006/0069420 | A1 | 3/2006 | Rademacher et al. |
| 2006/0094924 | A1 | 5/2006 | Riehl |
| 2006/0100550 | A1 | 5/2006 | Schultheiss et al. |
| 2006/0100552 | A1 | 5/2006 | Schultheiss et al. |
| 2006/0106375 | A1 | 5/2006 | Werneth et al. |
| 2006/0149337 | A1 | 7/2006 | John |
| 2006/0152301 | A1 | 7/2006 | Rohwedder |
| 2006/0161039 | A1 | 7/2006 | Juliana et al. |
| 2006/0170486 | A1 | 8/2006 | Tranchina et al. |
| 2006/0173518 | A1 | 8/2006 | Kreindel |
| 2006/0183252 | A1 | 8/2006 | Lee |
| 2006/0184214 | A1 | 8/2006 | McDaniel |
| 2006/0187607 | A1 | 8/2006 | Mo |
| 2006/0195168 | A1 | 8/2006 | Dunbar et al. |
| 2006/0199992 | A1 | 9/2006 | Eisenberg et al. |
| 2006/0206103 | A1 | 9/2006 | Altshuler et al. |
| 2006/0206163 | A1 | 9/2006 | Wahlstrand et al. |
| 2006/0206180 | A1 | 9/2006 | Alcidi |
| 2006/0229487 | A1 | 10/2006 | Goodwin et al. |
| 2006/0253176 | A1 | 11/2006 | Caruso et al. |
| 2006/0259102 | A1 | 11/2006 | Slatkine |
| 2006/0271028 | A1 | 11/2006 | Altshuler et al. |
| 2006/0271110 | A1 | 11/2006 | Vernon et al. |
| 2006/0287566 | A1 | 12/2006 | Zangen et al. |
| 2006/0293719 | A1 | 12/2006 | Naghavi |
| 2007/0010766 | A1 | 1/2007 | Gil et al. |
| 2007/0010861 | A1 | 1/2007 | Anderson et al. |
| 2007/0015951 | A1 | 1/2007 | Culhane |
| 2007/0016274 | A1 | 1/2007 | Boveja et al. |
| 2007/0027411 | A1 | 2/2007 | Ella et al. |
| 2007/0060862 | A1 | 3/2007 | Sun et al. |
| 2007/0078373 | A1 | 4/2007 | Sharma et al. |
| 2007/0083237 | A1 | 4/2007 | Teruel |
| 2007/0088413 | A1 | 4/2007 | Weber et al. |
| 2007/0088419 | A1 | 4/2007 | Fiorina et al. |
| 2007/0093806 | A1 | 4/2007 | Desai et al. |
| 2007/0100195 | A1 | 5/2007 | Goodwin et al. |
| 2007/0135811 | A1 | 6/2007 | Hooven |
| 2007/0142753 | A1 | 6/2007 | Warlick et al. |
| 2007/0142886 | A1 | 6/2007 | Fischell et al. |
| 2007/0173749 | A1 | 7/2007 | Williams et al. |
| 2007/0173805 | A1 | 7/2007 | Weinberg et al. |
| 2007/0173908 | A1 | 7/2007 | Begnaud |
| 2007/0173916 | A1 | 7/2007 | Axelgaard |
| 2007/0179534 | A1 | 8/2007 | Firlik et al. |
| 2007/0198071 | A1 | 8/2007 | Ting et al. |
| 2007/0208340 | A1 | 9/2007 | Ganz et al. |
| 2007/0232966 | A1 | 10/2007 | Applebaum et al. |
| 2007/0238944 | A1 | 10/2007 | Axelgaard |
| 2007/0239073 | A1 | 10/2007 | Schaden et al. |
| 2007/0239080 | A1 | 10/2007 | Schaden et al. |
| 2007/0244530 | A1 | 10/2007 | Ren |
| 2007/0255085 | A1 | 11/2007 | Kishawi et al. |
| 2007/0255355 | A1 | 11/2007 | Altshuler et al. |
| 2007/0255362 | A1 | 11/2007 | Levinson et al. |
| 2007/0260107 | A1 | 11/2007 | Mishelevich et al. |
| 2007/0270795 | A1 | 11/2007 | Francischelli et al. |
| 2007/0270924 | A1 | 11/2007 | McCann et al. |
| 2007/0270925 | A1 | 11/2007 | Levinson |
| 2007/0276451 | A1 | 11/2007 | Rigaux |
| 2007/0282156 | A1 | 12/2007 | Konings |
| 2007/0293911 | A1 | 12/2007 | Crowe et al. |
| 2007/0293918 | A1 | 12/2007 | Thompson et al. |
| 2007/0299482 | A1 | 12/2007 | Littlewood et al. |
| 2008/0009885 | A1 | 1/2008 | Del Giglio |
| 2008/0021506 | A1 | 1/2008 | Grocela |
| 2008/0046053 | A1 | 2/2008 | Wagner et al. |
| 2008/0058699 | A1 | 3/2008 | Hause et al. |
| 2008/0077201 | A1 | 3/2008 | Levinson et al. |
| 2008/0077202 | A1 | 3/2008 | Levinson |
| 2008/0077211 | A1 | 3/2008 | Levinson et al. |
| 2008/0082094 | A1 | 4/2008 | McPherson et al. |
| 2008/0082153 | A1 | 4/2008 | Gadsby et al. |
| 2008/0103407 | A1 | 5/2008 | Bolea et al. |
| 2008/0103559 | A1 | 5/2008 | Thacker et al. |
| 2008/0103565 | A1 | 5/2008 | Altshuler et al. |
| 2008/0109048 | A1 | 5/2008 | Moffitt |
| 2008/0114199 | A1 | 5/2008 | Riehl et al. |
| 2008/0114423 | A1 | 5/2008 | Grenon et al. |
| 2008/0132971 | A1 | 6/2008 | Pille et al. |
| 2008/0139871 | A1 | 6/2008 | Muntermann |
| 2008/0146865 | A1 | 6/2008 | Muntermann |
| 2008/0161636 | A1 | 7/2008 | Hurme et al. |
| 2008/0161883 | A1 | 7/2008 | Conor |
| 2008/0167585 | A1 | 7/2008 | Khen et al. |
| 2008/0177128 | A1 | 7/2008 | Riehl et al. |
| 2008/0183167 | A1 | 7/2008 | Britva et al. |
| 2008/0183251 | A1 | 7/2008 | Azar et al. |
| 2008/0183252 | A1 | 7/2008 | Khen |
| 2008/0188915 | A1 | 8/2008 | Mills et al. |
| 2008/0188947 | A1 | 8/2008 | Sanders |
| 2008/0195181 | A1 | 8/2008 | Cole |
| 2008/0200749 | A1 | 8/2008 | Zheng et al. |
| 2008/0200778 | A1 | 8/2008 | Taskinen et al. |
| 2008/0208287 | A1 | 8/2008 | Palermo et al. |
| 2008/0221504 | A1 | 9/2008 | Aghion |
| 2008/0228520 | A1 | 9/2008 | Day et al. |
| 2008/0234534 | A1 | 9/2008 | Mikas et al. |
| 2008/0234609 | A1 | 9/2008 | Kreindel et al. |
| 2008/0246573 | A1 | 10/2008 | Souder et al. |
| 2008/0249350 | A1 | 10/2008 | Marchitto et al. |
| 2008/0255572 | A1 | 10/2008 | Zeller et al. |
| 2008/0255637 | A1 | 10/2008 | Oishi |
| 2008/0262287 | A1 | 10/2008 | Dussau |
| 2008/0262574 | A1 | 10/2008 | Briefs et al. |
| 2008/0269593 | A1 | 10/2008 | Weinstock |
| 2008/0269851 | A1 | 10/2008 | Deem et al. |
| 2008/0275289 | A1 | 11/2008 | Olree et al. |
| 2008/0287839 | A1 | 11/2008 | Rosen et al. |
| 2008/0287948 | A1 | 11/2008 | Newton et al. |
| 2008/0288035 | A1 | 11/2008 | Gill et al. |
| 2008/0294211 | A1 | 11/2008 | Moffitt |
| 2008/0306325 | A1 | 12/2008 | Burnett et al. |
| 2008/0306326 | A1 | 12/2008 | Epstein |
| 2008/0312647 | A1 | 12/2008 | Knopp et al. |
| 2008/0312651 | A1 | 12/2008 | Pope et al. |
| 2009/0005631 | A1 | 1/2009 | Simenhaus et al. |
| 2009/0012508 | A1 | 1/2009 | Dougal |
| 2009/0018384 | A1 | 1/2009 | Boyden et al. |
| 2009/0018611 | A1 | 1/2009 | Campbell et al. |
| 2009/0018623 | A1 | 1/2009 | Levinson et al. |
| 2009/0018624 | A1 | 1/2009 | Levinson et al. |
| 2009/0018625 | A1 | 1/2009 | Levinson et al. |
| 2009/0018626 | A1 | 1/2009 | Levinson et al. |
| 2009/0018627 | A1 | 1/2009 | Levinson et al. |
| 2009/0018628 | A1 | 1/2009 | Burns et al. |
| 2009/0024192 | A1 | 1/2009 | Mulholland |
| 2009/0024193 | A1 | 1/2009 | Altshuler et al. |
| 2009/0030352 | A1 | 1/2009 | Schultheiss et al. |
| 2009/0036803 | A1 | 2/2009 | Warlick et al. |
| 2009/0036938 | A1 | 2/2009 | Shipley et al. |
| 2009/0036958 | A1 | 2/2009 | Mehta |
| 2009/0043185 | A1 | 2/2009 | McAdams et al. |
| 2009/0043188 | A1 | 2/2009 | Raischer |
| 2009/0043293 | A1 | 2/2009 | Pankratov et al. |
| 2009/0062885 | A1 | 3/2009 | Brighton et al. |
| 2009/0062897 | A1 | 3/2009 | Axelgaard |
| 2009/0082690 | A1 | 3/2009 | Phillips et al. |
| 2009/0083071 | A1 | 3/2009 | Phillips et al. |
| 2009/0093740 | A1 | 4/2009 | Helgeson et al. |
| 2009/0099405 | A1 | 4/2009 | Schneider et al. |
| 2009/0105706 | A1 | 4/2009 | Livneh |
| 2009/0108969 | A1 | 4/2009 | Sims et al. |
| 2009/0118722 | A1 | 5/2009 | Ebbers et al. |
| 2009/0118789 | A1 | 5/2009 | Buhlmann et al. |
| 2009/0118790 | A1 | 5/2009 | Van Herk |
| 2009/0149300 | A1 | 6/2009 | Chen |
| 2009/0149925 | A1 | 6/2009 | Macdonald et al. |

(56) References Cited

U.S. PATENT DOCUMENTS

2009/0149929 A1 6/2009 Levinson et al.
2009/0149930 A1 6/2009 Schenck
2009/0156958 A1 6/2009 Mehta et al.
2009/0163761 A1 6/2009 Culhane
2009/0198144 A1 8/2009 Phillips et al.
2009/0204015 A1 8/2009 Phillips et al.
2009/0209840 A1 8/2009 Axelgaard
2009/0210028 A1 8/2009 Rigaux et al.
2009/0216293 A1 8/2009 Sasaki et al.
2009/0221938 A1 9/2009 Rosenberg et al.
2009/0227830 A1 9/2009 Pillutla et al.
2009/0227831 A1 9/2009 Burnett et al.
2009/0234423 A1 9/2009 Vetanze
2009/0240096 A1 9/2009 Riehl et al.
2009/0248004 A1 10/2009 Altshuler et al.
2009/0254007 A1 10/2009 Schultheiss et al.
2009/0254144 A1 10/2009 Bhadra et al.
2009/0254154 A1 10/2009 De Taboada et al.
2009/0270945 A1 10/2009 Markoll et al.
2009/0270947 A1 10/2009 Stone et al.
2009/0281464 A1 11/2009 Cioanta et al.
2009/0284339 A1 11/2009 Choi et al.
2009/0306648 A1 12/2009 Podhajsky et al.
2009/0312679 A1 12/2009 Elliott et al.
2009/0319002 A1 12/2009 Simon
2009/0326528 A1 12/2009 Karni et al.
2009/0326571 A1 12/2009 Mulholland
2010/0004536 A1 1/2010 Rosenberg
2010/0004715 A1 1/2010 Fahey
2010/0016761 A1 1/2010 Rosenberg
2010/0016850 A1 1/2010 Ron Edoute et al.
2010/0023097 A1 1/2010 Peterson et al.
2010/0030298 A1 2/2010 Martens et al.
2010/0036191 A1 2/2010 Walter et al.
2010/0036368 A1 2/2010 England et al.
2010/0042180 A1 2/2010 Mueller et al.
2010/0049188 A1 2/2010 Nelson et al.
2010/0062633 A1 3/2010 Puttinger et al.
2010/0069704 A1 3/2010 Peterchev
2010/0081971 A1 4/2010 Allison
2010/0087699 A1 4/2010 Peterchev
2010/0087816 A1 4/2010 Roy
2010/0094379 A1 4/2010 Meadows et al.
2010/0106064 A1 4/2010 Kreindel et al.
2010/0114191 A1 5/2010 Newman
2010/0121131 A1 5/2010 Mathes
2010/0125314 A1 5/2010 Bradley et al.
2010/0130945 A1 5/2010 Laniado et al.
2010/0137760 A1 6/2010 Schulz et al.
2010/0145399 A1 6/2010 Johari et al.
2010/0152522 A1 6/2010 Roth et al.
2010/0152824 A1 6/2010 Allison
2010/0160712 A1 6/2010 Burnett et al.
2010/0168501 A1 7/2010 Burnett et al.
2010/0174225 A1 7/2010 Pesach et al.
2010/0179372 A1 7/2010 Glassman
2010/0179373 A1 7/2010 Pille et al.
2010/0185042 A1 7/2010 Schneider et al.
2010/0197993 A1 8/2010 Vasishta
2010/0198102 A1 8/2010 Moore
2010/0210894 A1 8/2010 Pascual-Leone et al.
2010/0217253 A1 8/2010 Mehta
2010/0217349 A1 8/2010 Fahey
2010/0222629 A1 9/2010 Burnett et al.
2010/0228075 A1 9/2010 Lu
2010/0228250 A1 9/2010 Brogna
2010/0228304 A1 9/2010 Kriksunov et al.
2010/0256438 A1 10/2010 Mishelevich et al.
2010/0256439 A1 10/2010 Schneider et al.
2010/0261992 A1 10/2010 Axelgaard
2010/0274327 A1 10/2010 Carroll et al.
2010/0274329 A1 10/2010 Bradley et al.
2010/0280582 A1 11/2010 Baker et al.
2010/0286470 A1 11/2010 Schneider et al.
2010/0286691 A1 11/2010 Kerr et al.
2010/0298623 A1 11/2010 Mishelevich et al.
2010/0298895 A1 11/2010 Ghaffari et al.
2010/0309689 A1 12/2010 Coulson
2010/0312166 A1 12/2010 Castel
2010/0315225 A1 12/2010 Teague
2010/0324611 A1 12/2010 Deming et al.
2010/0331602 A1 12/2010 Mishelevich et al.
2010/0331603 A1 12/2010 Szecsi
2010/0331604 A1 12/2010 Okamoto et al.
2011/0004261 A1 1/2011 Sham et al.
2011/0007745 A1 1/2011 Schultz et al.
2011/0009737 A1 1/2011 Manstein
2011/0009923 A1 1/2011 Lee
2011/0015464 A1 1/2011 Riehl et al.
2011/0015625 A1 1/2011 Adanny et al.
2011/0015687 A1 1/2011 Nebrigic et al.
2011/0021863 A1 1/2011 Burnett et al.
2011/0046432 A1 2/2011 Simon et al.
2011/0046523 A1 2/2011 Altshuler et al.
2011/0054564 A1 3/2011 Valencia
2011/0054566 A1 3/2011 Nathanson
2011/0060179 A1 3/2011 Aho et al.
2011/0065976 A1 3/2011 Chornenky et al.
2011/0066216 A1 3/2011 Ting et al.
2011/0077451 A1 3/2011 Marchitto et al.
2011/0081333 A1 4/2011 Shantha et al.
2011/0082383 A1 4/2011 Cory et al.
2011/0087312 A1 4/2011 Shanks et al.
2011/0105826 A1 5/2011 Mishelevich et al.
2011/0106220 A1 5/2011 DeGiorgio et al.
2011/0112520 A1 5/2011 Michael
2011/0118722 A1 5/2011 Lischinsky et al.
2011/0125203 A1 5/2011 Simon et al.
2011/0125213 A1 5/2011 Simon et al.
2011/0130617 A1 6/2011 Dennis et al.
2011/0130618 A1 6/2011 Ron et al.
2011/0130713 A1 6/2011 Dufay
2011/0130796 A1 6/2011 Louise
2011/0133872 A1 6/2011 Souder
2011/0137381 A1 6/2011 Lee et al.
2011/0152965 A1 6/2011 Mashiach et al.
2011/0152967 A1 6/2011 Simon et al.
2011/0160810 A1 6/2011 Griffith
2011/0172735 A1 7/2011 Johari
2011/0172752 A1 7/2011 Bingham et al.
2011/0172756 A1 7/2011 Doerr et al.
2011/0190569 A1 8/2011 Simon et al.
2011/0196438 A1 8/2011 Mnozil et al.
2011/0202058 A1 8/2011 Eder et al.
2011/0207988 A1 8/2011 Ruohonen
2011/0208182 A1 8/2011 Szasz et al.
2011/0218464 A1 9/2011 Iger
2011/0224761 A1 9/2011 Manstein
2011/0230701 A1 9/2011 Simon et al.
2011/0237921 A1 9/2011 Askin, III et al.
2011/0238050 A1 9/2011 Allison et al.
2011/0238051 A1 9/2011 Levinson et al.
2011/0245735 A1 10/2011 Eckhouse et al.
2011/0245900 A1 10/2011 Turner et al.
2011/0263925 A1 10/2011 Bratton
2011/0270360 A1 11/2011 Harris et al.
2011/0273251 A1 11/2011 Mishelevich et al.
2011/0275881 A1 11/2011 Aho
2011/0275927 A1 11/2011 Wagner et al.
2011/0275963 A1 11/2011 Wagner et al.
2011/0276107 A1 11/2011 Simon et al.
2011/0276108 A1 11/2011 Crowe et al.
2011/0295160 A1 12/2011 Hart
2011/0300079 A1 12/2011 Martens et al.
2011/0306905 A1 12/2011 Novak et al.
2011/0306943 A1 12/2011 Dunbar et al.
2011/0319700 A1 12/2011 Schneider
2012/0016177 A1 1/2012 Mishelevich et al.
2012/0016359 A1 1/2012 Podhajsky
2012/0022518 A1 1/2012 Levinson
2012/0029264 A1 2/2012 Roth et al.
2012/0029394 A1 2/2012 Babaev
2012/0029596 A1 2/2012 Barker
2012/0035608 A1 2/2012 Marchitto et al.

(56) References Cited

U.S. PATENT DOCUMENTS

| | | | |
|---|---|---|---|
| 2012/0041296 | A1 | 2/2012 | Garstka et al. |
| 2012/0046598 | A1 | 2/2012 | Kardos et al. |
| 2012/0046653 | A1 | 2/2012 | Welches et al. |
| 2012/0053396 | A1 | 3/2012 | Deegan et al. |
| 2012/0053449 | A1 | 3/2012 | Moses et al. |
| 2012/0053645 | A1 | 3/2012 | Ayanoor-Vitikkate et al. |
| 2012/0083709 | A1 | 4/2012 | Parker et al. |
| 2012/0083858 | A1 | 4/2012 | Yarnitsky |
| 2012/0101326 | A1 | 4/2012 | Simon et al. |
| 2012/0101366 | A1 | 4/2012 | Ruohonen et al. |
| 2012/0108883 | A1 | 5/2012 | Peterchev |
| 2012/0108884 | A1 | 5/2012 | Bechler et al. |
| 2012/0109241 | A1 | 5/2012 | Rauscher |
| 2012/0116271 | A1 | 5/2012 | Caruso et al. |
| 2012/0116477 | A1 | 5/2012 | Crowe et al. |
| 2012/0143281 | A1 | 6/2012 | Birkill et al. |
| 2012/0150079 | A1 | 6/2012 | Rosenberg |
| 2012/0150266 | A1 | 6/2012 | Shalev et al. |
| 2012/0157747 | A1 | 6/2012 | Rybski et al. |
| 2012/0157804 | A1 | 6/2012 | Rogers et al. |
| 2012/0158100 | A1 | 6/2012 | Schomacker |
| 2012/0172653 | A1 | 7/2012 | Chornenky et al. |
| 2012/0191018 | A1 | 7/2012 | Willeford |
| 2012/0191169 | A1 | 7/2012 | Rothstein et al. |
| 2012/0195100 | A1 | 8/2012 | Saitoh et al. |
| 2012/0197361 | A1 | 8/2012 | Gonzales et al. |
| 2012/0203054 | A1 | 8/2012 | Riehl et al. |
| 2012/0203146 | A1 | 8/2012 | Uebelacker et al. |
| 2012/0203320 | A1 | 8/2012 | Digiore et al. |
| 2012/0215210 | A1 | 8/2012 | Brown et al. |
| 2012/0226139 | A1 | 9/2012 | Peyman |
| 2012/0226272 | A1 | 9/2012 | Chernov et al. |
| 2012/0226330 | A1 | 9/2012 | Kolen et al. |
| 2012/0239120 | A1 | 9/2012 | Karni et al. |
| 2012/0239123 | A1 | 9/2012 | Weber et al. |
| 2012/0240940 | A1 | 9/2012 | Paraschac et al. |
| 2012/0245483 | A1 | 9/2012 | Lundqvist |
| 2012/0253098 | A1 | 10/2012 | George et al. |
| 2012/0259382 | A1 | 10/2012 | Trier et al. |
| 2012/0265111 | A1 | 10/2012 | Glenzer et al. |
| 2012/0265193 | A1 | 10/2012 | Lischinsky et al. |
| 2012/0271206 | A1 | 10/2012 | Shalev et al. |
| 2012/0271294 | A1 | 10/2012 | Barthe et al. |
| 2012/0277587 | A1 | 11/2012 | Adanny et al. |
| 2012/0302821 | A1 | 11/2012 | Burnett |
| 2012/0303076 | A1 | 11/2012 | Fahey |
| 2012/0310033 | A1 | 12/2012 | Muntermann |
| 2012/0310035 | A1 | 12/2012 | Schneider et al. |
| 2012/0310311 | A1 | 12/2012 | Elkah |
| 2012/0323232 | A1 | 12/2012 | Wolf et al. |
| 2012/0330090 | A1 | 12/2012 | Sham et al. |
| 2012/0330394 | A1 | 12/2012 | Dar et al. |
| 2013/0006039 | A1 | 1/2013 | Sadler |
| 2013/0006324 | A1 | 1/2013 | Bradley |
| 2013/0012755 | A1 | 1/2013 | Slayton |
| 2013/0023748 | A1 | 1/2013 | Afanasewicz et al. |
| 2013/0030239 | A1 | 1/2013 | Weyh et al. |
| 2013/0035680 | A1 | 2/2013 | Ben-Haim et al. |
| 2013/0035745 | A1 | 2/2013 | Ahmed et al. |
| 2013/0042876 | A1 | 2/2013 | Hermanson et al. |
| 2013/0053620 | A1 | 2/2013 | Susedik et al. |
| 2013/0066309 | A1 | 3/2013 | Levinson |
| 2013/0071805 | A1 | 3/2013 | Doll et al. |
| 2013/0072925 | A1 | 3/2013 | Ben-Haim et al. |
| 2013/0072930 | A1 | 3/2013 | Ben-Haim et al. |
| 2013/0073001 | A1 | 3/2013 | Campbell |
| 2013/0079684 | A1 | 3/2013 | Rosen et al. |
| 2013/0085317 | A1 | 4/2013 | Feinstein |
| 2013/0085551 | A1 | 4/2013 | Bachinski et al. |
| 2013/0096363 | A1 | 4/2013 | Schneider et al. |
| 2013/0103127 | A1 | 4/2013 | Mueller et al. |
| 2013/0116758 | A1 | 5/2013 | Levinson et al. |
| 2013/0116759 | A1 | 5/2013 | Levinson et al. |
| 2013/0123568 | A1 | 5/2013 | Hamilton et al. |
| 2013/0123629 | A1 | 5/2013 | Rosenberg et al. |
| 2013/0123764 | A1 | 5/2013 | Zarsky et al. |
| 2013/0123765 | A1 | 5/2013 | Zarsky et al. |
| 2013/0131764 | A1 | 5/2013 | Grove |
| 2013/0137918 | A1 | 5/2013 | Phillips et al. |
| 2013/0138193 | A1 | 5/2013 | Durand et al. |
| 2013/0144106 | A1 | 6/2013 | Phillips et al. |
| 2013/0144107 | A1 | 6/2013 | Phillips et al. |
| 2013/0144108 | A1 | 6/2013 | Phillips et al. |
| 2013/0144280 | A1 | 6/2013 | Eckhouse et al. |
| 2013/0150650 | A1 | 6/2013 | Phillips et al. |
| 2013/0150651 | A1 | 6/2013 | Phillips et al. |
| 2013/0150653 | A1 | 6/2013 | Borsody |
| 2013/0158440 | A1 | 6/2013 | Allison |
| 2013/0158634 | A1 | 6/2013 | Ron et al. |
| 2013/0158636 | A1 | 6/2013 | Ting et al. |
| 2013/0172959 | A1 | 7/2013 | Azoulay |
| 2013/0178693 | A1 | 7/2013 | Neuvonen et al. |
| 2013/0178764 | A1 | 7/2013 | Eckhouse et al. |
| 2013/0184693 | A1 | 7/2013 | Neev |
| 2013/0190744 | A1 | 7/2013 | Avram et al. |
| 2013/0190838 | A1 | 7/2013 | Caparso |
| 2013/0218242 | A1 | 8/2013 | Schomacker |
| 2013/0226275 | A1 | 8/2013 | Duncan |
| 2013/0238043 | A1 | 9/2013 | Beardall et al. |
| 2013/0238061 | A1 | 9/2013 | Ron et al. |
| 2013/0238062 | A1 | 9/2013 | Ron Edoute et al. |
| 2013/0238066 | A1 | 9/2013 | Boggs et al. |
| 2013/0245731 | A1 | 9/2013 | Allison |
| 2013/0253384 | A1 | 9/2013 | Anderson et al. |
| 2013/0253493 | A1 | 9/2013 | Anderson et al. |
| 2013/0253494 | A1 | 9/2013 | Anderson et al. |
| 2013/0253495 | A1 | 9/2013 | Anderson et al. |
| 2013/0253496 | A1 | 9/2013 | Anderson et al. |
| 2013/0261374 | A1 | 10/2013 | Elder |
| 2013/0261683 | A1 | 10/2013 | Soikum et al. |
| 2013/0267759 | A1 | 10/2013 | Jin |
| 2013/0267760 | A1 | 10/2013 | Jin |
| 2013/0267943 | A1 | 10/2013 | Hancock |
| 2013/0274841 | A1 | 10/2013 | Eckhous et al. |
| 2013/0282085 | A1 | 10/2013 | Lischinsky et al. |
| 2013/0282095 | A1 | 10/2013 | Mignolet et al. |
| 2013/0289433 | A1 | 10/2013 | Jin et al. |
| 2013/0303904 | A1 | 11/2013 | Barthe et al. |
| 2013/0304159 | A1 | 11/2013 | Simon et al. |
| 2013/0317281 | A1 | 11/2013 | Schneider et al. |
| 2013/0317282 | A1 | 11/2013 | Ron Edoute et al. |
| 2013/0317580 | A1 | 11/2013 | Simon et al. |
| 2013/0331637 | A1 | 12/2013 | Greff |
| 2013/0331913 | A1 | 12/2013 | Levi et al. |
| 2013/0338424 | A1 | 12/2013 | Pascual-Leone et al. |
| 2013/0338483 | A1 | 12/2013 | Neuvonen et al. |
| 2014/0005645 | A1 | 1/2014 | Ben-Haim et al. |
| 2014/0005758 | A1 | 1/2014 | Ben-Yehuda et al. |
| 2014/0005759 | A1 | 1/2014 | Fahey et al. |
| 2014/0005760 | A1 | 1/2014 | Levinson et al. |
| 2014/0012064 | A1 | 1/2014 | Riehl et al. |
| 2014/0018767 | A1 | 1/2014 | Harris et al. |
| 2014/0024882 | A1 | 1/2014 | Chornenky et al. |
| 2014/0025033 | A1 | 1/2014 | Mirkov et al. |
| 2014/0025142 | A1 | 1/2014 | Zarksy et al. |
| 2014/0046114 | A1 | 2/2014 | Nishikawa et al. |
| 2014/0046232 | A1 | 2/2014 | Sham et al. |
| 2014/0046339 | A1 | 2/2014 | Bonutti |
| 2014/0046423 | A1 | 2/2014 | Rajguru et al. |
| 2014/0049377 | A1 | 2/2014 | Krusor et al. |
| 2014/0051962 | A1 | 2/2014 | Krusor et al. |
| 2014/0052029 | A1 | 2/2014 | Khen et al. |
| 2014/0066786 | A1 | 3/2014 | Naghavi et al. |
| 2014/0067010 | A1 | 3/2014 | Sumners et al. |
| 2014/0067025 | A1 | 3/2014 | Levinson et al. |
| 2014/0074203 | A1 | 3/2014 | Na et al. |
| 2014/0081069 | A1 | 3/2014 | Tai |
| 2014/0081348 | A1 | 3/2014 | Fischell |
| 2014/0081353 | A1 | 3/2014 | Cook et al. |
| 2014/0081359 | A1 | 3/2014 | Sand |
| 2014/0088674 | A1 | 3/2014 | Bradley |
| 2014/0121446 | A1 | 5/2014 | Phillips et al. |
| 2014/0135565 | A9 | 5/2014 | Schneider |
| 2014/0141938 | A1 | 5/2014 | Dristle |

(56) References Cited

U.S. PATENT DOCUMENTS

2014/0142669 A1 5/2014 Cook et al.
2014/0148870 A1 5/2014 Burnett
2014/0163305 A1 6/2014 Watterson
2014/0179980 A1 6/2014 Phillips et al.
2014/0194790 A1 7/2014 Crunick et al.
2014/0194946 A1 7/2014 Thomas et al.
2014/0194958 A1 7/2014 Chabal et al.
2014/0200388 A1 7/2014 Schneider et al.
2014/0207217 A1 7/2014 Lischinsky et al.
2014/0213844 A1 7/2014 Pilla et al.
2014/0221725 A1 8/2014 Mishelevich et al.
2014/0221990 A1 8/2014 Kreindel
2014/0228620 A1 8/2014 Vasishta
2014/0235926 A1 8/2014 Zangen et al.
2014/0235927 A1 8/2014 Zangen et al.
2014/0235928 A1 8/2014 Zangen et al.
2014/0235929 A1 8/2014 Rohan
2014/0236139 A1 8/2014 Payman
2014/0236262 A1 8/2014 You et al.
2014/0243933 A1 8/2014 Ginggen
2014/0249352 A1 9/2014 Zangen et al.
2014/0249353 A1 9/2014 Pesola et al.
2014/0249355 A1 9/2014 Martinez
2014/0249601 A1 9/2014 Bachinski et al.
2014/0249609 A1 9/2014 Zarsky et al.
2014/0249613 A1 9/2014 Kaib
2014/0257071 A1 9/2014 Curran et al.
2014/0257145 A1 9/2014 Emery et al.
2014/0257443 A1 9/2014 Baker et al.
2014/0276248 A1 9/2014 Hall et al.
2014/0276252 A1 9/2014 Hyde et al.
2014/0276357 A1 9/2014 Sheftel et al.
2014/0276693 A1 9/2014 Altshuler et al.
2014/0277219 A1 9/2014 Nanda
2014/0277302 A1 9/2014 Weber et al.
2014/0296933 A1 10/2014 Haessler
2014/0296934 A1 10/2014 Gozani et al.
2014/0303425 A1 10/2014 Pilla et al.
2014/0303525 A1 10/2014 Sitharaman
2014/0303682 A1 10/2014 Siff
2014/0303696 A1 10/2014 Anderson et al.
2014/0303697 A1 10/2014 Anderson et al.
2014/0309628 A1 10/2014 Vaynberg et al.
2014/0316188 A1 10/2014 Peterchev et al.
2014/0316310 A1 10/2014 Ackermann et al.
2014/0316393 A1 10/2014 Levinson
2014/0316485 A1 10/2014 Ackermann et al.
2014/0324118 A1 10/2014 Simon et al.
2014/0324120 A1 10/2014 Bogie et al.
2014/0330067 A1 11/2014 Jordan
2014/0330336 A1 11/2014 Errico et al.
2014/0336545 A1 11/2014 Bonutti
2014/0336721 A1 11/2014 Simon et al.
2014/0336730 A1 11/2014 Simon et al.
2014/0336733 A1 11/2014 Nebrigic et al.
2014/0342428 A1 11/2014 Goodwin et al.
2014/0343351 A1 11/2014 Tojo et al.
2014/0350438 A1 11/2014 Papirov et al.
2014/0357935 A1 12/2014 Ilmoniemi et al.
2014/0364841 A1 12/2014 Kornstein
2014/0364920 A1 12/2014 Doan et al.
2014/0371515 A1 12/2014 John
2014/0371802 A1 12/2014 Mashiach et al.
2014/0371812 A1 12/2014 Ackermann et al.
2014/0378875 A1 12/2014 Ron Edoute et al.
2015/0005569 A1 1/2015 Missoli
2015/0005759 A1 1/2015 Welches et al.
2015/0005852 A1 1/2015 Hershey et al.
2015/0018667 A1 1/2015 Radman et al.
2015/0018692 A1 1/2015 Neuvonen et al.
2015/0018895 A1 1/2015 El Achhab et al.
2015/0018910 A1 1/2015 Chen
2015/0025299 A1 1/2015 Ron Edoute et al.
2015/0025545 A1 1/2015 Grenon et al.
2015/0038768 A1 2/2015 Saitoh et al.
2015/0073401 A1 3/2015 Kreindel
2015/0080769 A1 3/2015 Lotsch
2015/0087888 A1 3/2015 Hurme et al.
2015/0088105 A1 3/2015 Fatemi
2015/0088212 A1 3/2015 De Ridder
2015/0094788 A1 4/2015 Pierenkemper
2015/0100112 A1 4/2015 Chang et al.
2015/0112118 A1 4/2015 Mishelevich et al.
2015/0112412 A1 4/2015 Anderson et al.
2015/0119849 A1 4/2015 Aronhalt et al.
2015/0119949 A1 4/2015 Tscherch et al.
2015/0123661 A1 5/2015 Yui et al.
2015/0126914 A1 5/2015 Crunick et al.
2015/0127075 A1 5/2015 Ward et al.
2015/0133717 A1 5/2015 Ghiron et al.
2015/0133718 A1 5/2015 Schneider et al.
2015/0140633 A1 5/2015 Vladila
2015/0141877 A1 5/2015 Feldman
2015/0148858 A1 5/2015 Kaib
2015/0148877 A1 5/2015 Thakkar et al.
2015/0151137 A1 6/2015 Hynninen et al.
2015/0157873 A1 6/2015 Sokolowski
2015/0157874 A1 6/2015 Aho et al.
2015/0165186 A1 6/2015 Dar et al.
2015/0165226 A1 6/2015 Simon et al.
2015/0165232 A1 6/2015 Altshuler et al.
2015/0165238 A1 6/2015 Slayton et al.
2015/0174002 A1 6/2015 Burbank et al.
2015/0174399 A1 6/2015 Moore
2015/0190630 A1 7/2015 Kent et al.
2015/0190648 A1 7/2015 Fischell et al.
2015/0196772 A1 7/2015 Ghiron et al.
2015/0202428 A1 7/2015 Miller
2015/0202454 A1 7/2015 Burnett
2015/0209574 A1 7/2015 Farhat et al.
2015/0213724 A1 7/2015 Shoshani
2015/0216719 A1 8/2015 DeBenedictis et al.
2015/0216720 A1 8/2015 DeBenedictis et al.
2015/0216816 A1 8/2015 O'Neil et al.
2015/0217125 A1 8/2015 Chornenky et al.
2015/0217127 A1 8/2015 Fischell et al.
2015/0223975 A1 8/2015 Anderson et al.
2015/0224321 A1 8/2015 Staeuber et al.
2015/0227680 A1 8/2015 Mainkar et al.
2015/0238248 A1 8/2015 Thompson et al.
2015/0238771 A1 8/2015 Zarsk et al.
2015/0246238 A1 9/2015 Moses et al.
2015/0265830 A1 9/2015 Simon et al.
2015/0265836 A1 9/2015 Simon et al.
2015/0272776 A1 10/2015 Gonzales et al.
2015/0273220 A1 10/2015 Osypka et al.
2015/0283022 A1 10/2015 Lee et al.
2015/0283025 A1 10/2015 Ledany
2015/0283026 A1 10/2015 Rosenberg
2015/0283383 A1 10/2015 Ternes et al.
2015/0290028 A1 10/2015 Isserow et al.
2015/0297909 A1 10/2015 Peashock
2015/0306403 A1 10/2015 Langer et al.
2015/0306419 A1 10/2015 Domankevitz
2015/0314133 A1 11/2015 Yamashiro
2015/0328077 A1 11/2015 Levinson
2015/0328475 A1 11/2015 Kim et al.
2015/0335875 A1 11/2015 Goldwasser et al.
2015/0335877 A1 11/2015 Jeffery et al.
2015/0342661 A1 12/2015 Ron Edoute
2015/0342780 A1 12/2015 Levinson et al.
2015/0351690 A1 12/2015 Toth et al.
2015/0360045 A1 12/2015 Fischell et al.
2015/0367141 A1 12/2015 Goetz et al.
2015/0375005 A1 12/2015 Segal
2016/0001092 A1 1/2016 Solehmainen
2016/0008273 A1 1/2016 Sheftel et al.
2016/0008619 A1 1/2016 Pell et al.
2016/0015588 A1 1/2016 Tamiya et al.
2016/0015995 A1 1/2016 Leung et al.
2016/0016013 A1 1/2016 Capelli et al.
2016/0020070 A1 1/2016 Kim et al.
2016/0022349 A1 1/2016 Woloszko et al.
2016/0030763 A1 2/2016 Midorikawa et al.

(56) References Cited

U.S. PATENT DOCUMENTS

| | | | |
|---|---|---|---|
| 2016/0038183 | A1 | 2/2016 | Ignon et al. |
| 2016/0045728 | A1 | 2/2016 | Lockwood et al. |
| 2016/0045755 | A1 | 2/2016 | Chun et al. |
| 2016/0051401 | A1 | 2/2016 | Yee et al. |
| 2016/0051827 | A1 | 2/2016 | Ron et al. |
| 2016/0059027 | A1 | 3/2016 | Zangen et al. |
| 2016/0066977 | A1 | 3/2016 | Neal et al. |
| 2016/0066994 | A1 | 3/2016 | Shanks |
| 2016/0067474 | A1 | 3/2016 | Muessig et al. |
| 2016/0067516 | A1 | 3/2016 | Schneider et al. |
| 2016/0067517 | A1 | 3/2016 | Burnett |
| 2016/0067518 | A1 | 3/2016 | Mishelevich et al. |
| 2016/0082253 | A1 | 3/2016 | Moffitt et al. |
| 2016/0082290 | A1 | 3/2016 | Hart |
| 2016/0086458 | A1 | 3/2016 | Biggs |
| 2016/0089550 | A1 | 3/2016 | DeBenedictis et al. |
| 2016/0096025 | A1 | 4/2016 | Moffitt et al. |
| 2016/0096032 | A9 | 4/2016 | Schneider |
| 2016/0100977 | A1 | 4/2016 | Lee et al. |
| 2016/0106982 | A1 | 4/2016 | Cakmak et al. |
| 2016/0106994 | A1 | 4/2016 | Crosby |
| 2016/0106995 | A1 | 4/2016 | Järnefelt et al. |
| 2016/0114181 | A1 | 4/2016 | Vaynberg et al. |
| 2016/0121112 | A1 | 5/2016 | Azar |
| 2016/0121118 | A1 | 5/2016 | Franke et al. |
| 2016/0129273 | A1 | 5/2016 | Park |
| 2016/0129274 | A1 | 5/2016 | Park |
| 2016/0136415 | A1 | 5/2016 | Bunch |
| 2016/0136462 | A1 | 5/2016 | Lewis, Jr. et al. |
| 2016/0144175 | A1 | 5/2016 | Simon et al. |
| 2016/0150494 | A1 | 5/2016 | Tabet et al. |
| 2016/0151637 | A1 | 6/2016 | Abe et al. |
| 2016/0158528 | A1 | 6/2016 | Gonterman |
| 2016/0158548 | A1 | 6/2016 | Ackermann et al. |
| 2016/0158571 | A1 | 6/2016 | Goadsby |
| 2016/0158574 | A1 | 6/2016 | Eckhouse et al. |
| 2016/0175193 | A1 | 6/2016 | Jung |
| 2016/0175605 | A1 | 6/2016 | Borsody |
| 2016/0184585 | A1 | 6/2016 | Kealey et al. |
| 2016/0184601 | A1 | 6/2016 | Gleich et al. |
| 2016/0193006 | A1 | 7/2016 | Azoulay |
| 2016/0193466 | A1 | 7/2016 | Burnett |
| 2016/0206895 | A1 | 7/2016 | Zangen et al. |
| 2016/0206896 | A1 | 7/2016 | Zangen et al. |
| 2016/0213426 | A1 | 7/2016 | Ben-Haim et al. |
| 2016/0213924 | A1 | 7/2016 | Coleman et al. |
| 2016/0213943 | A1 | 7/2016 | Mauger et al. |
| 2016/0220834 | A1 | 8/2016 | Schwarz |
| 2016/0220837 | A1 | 8/2016 | Jin |
| 2016/0228178 | A1 | 8/2016 | Lei |
| 2016/0228698 | A1 | 8/2016 | Horton et al. |
| 2016/0236004 | A1 | 8/2016 | Fischell et al. |
| 2016/0243375 | A1 | 8/2016 | Simon et al. |
| 2016/0243376 | A1 | 8/2016 | Phillips |
| 2016/0250494 | A1 | 9/2016 | Sakaki et al. |
| 2016/0256685 | A1 | 9/2016 | Haessler |
| 2016/0256689 | A1 | 9/2016 | Vallejo et al. |
| 2016/0256702 | A1 | 9/2016 | Schwarz et al. |
| 2016/0256703 | A1 | 9/2016 | Schwarz et al. |
| 2016/0270951 | A1 | 9/2016 | Martins et al. |
| 2016/0271392 | A1 | 9/2016 | Vallejo et al. |
| 2016/0303393 | A1 | 10/2016 | Riehl et al. |
| 2016/0310315 | A1 | 10/2016 | Smith |
| 2016/0310756 | A1 | 10/2016 | Boll et al. |
| 2016/0317346 | A1 | 11/2016 | Kovach |
| 2016/0317803 | A1 | 11/2016 | Sama |
| 2016/0317827 | A1 | 11/2016 | Schwarz et al. |
| 2016/0324684 | A1 | 11/2016 | Levinson et al. |
| 2016/0338900 | A1 | 11/2016 | Khen et al. |
| 2016/0339239 | A1 | 11/2016 | Yoo et al. |
| 2016/0346561 | A1 | 12/2016 | Ron Edoute et al. |
| 2016/0354035 | A1 | 12/2016 | Reihl et al. |
| 2016/0354237 | A1 | 12/2016 | Gonzales et al. |
| 2016/0361560 | A1 | 12/2016 | Bean |
| 2016/0367795 | A1 | 12/2016 | Ackermann et al. |
| 2017/0001024 | A1 | 1/2017 | Prouza |
| 2017/0001025 | A1 | 1/2017 | Schwarz et al. |
| 2017/0001026 | A1 | 1/2017 | Schwarz et al. |
| 2017/0001027 | A1 | 1/2017 | Ladman et al. |
| 2017/0001028 | A1 | 1/2017 | Ladman et al. |
| 2017/0001029 | A1 | 1/2017 | Pribula et al. |
| 2017/0001030 | A1 | 1/2017 | Pribula et al. |
| 2017/0007309 | A1 | 1/2017 | DeBenedictis et al. |
| 2017/0021188 | A1 | 1/2017 | Lu |
| 2017/0027595 | A1 | 2/2017 | Bonutti |
| 2017/0027596 | A1 | 2/2017 | Bonutti |
| 2017/0028166 | A1 | 2/2017 | Walpole et al. |
| 2017/0028212 | A1 | 2/2017 | Roth et al. |
| 2017/0036019 | A1 | 2/2017 | Matsushita |
| 2017/0043177 | A1 | 2/2017 | Ron Edoute et al. |
| 2017/0049612 | A1 | 2/2017 | Hussain et al. |
| 2017/0050019 | A1 | 2/2017 | Ron Edoute et al. |
| 2017/0050038 | A1 | 2/2017 | Cosman |
| 2017/0056651 | A1 | 3/2017 | Li et al. |
| 2017/0071790 | A1 | 3/2017 | Grenon et al. |
| 2017/0072212 | A1 | 3/2017 | Ladman et al. |
| 2017/0087009 | A1 | 3/2017 | Badawi et al. |
| 2017/0087373 | A1 | 3/2017 | Schwarz |
| 2017/0095207 | A1 | 4/2017 | Thomas et al. |
| 2017/0100585 | A1 | 4/2017 | Hall et al. |
| 2017/0105869 | A1 | 4/2017 | Frangineas, Jr. |
| 2017/0106201 | A1 | 4/2017 | Schwarz et al. |
| 2017/0106203 | A1 | 4/2017 | Schneider et al. |
| 2017/0112568 | A1 | 4/2017 | Epstein |
| 2017/0113058 | A1 | 4/2017 | Schneider |
| 2017/0120066 | A1 | 5/2017 | Phillips et al. |
| 2017/0120067 | A1 | 5/2017 | Prouza |
| 2017/0136254 | A1 | 5/2017 | Simon et al. |
| 2017/0143958 | A1 | 5/2017 | Shalev et al. |
| 2017/0151436 | A1 | 6/2017 | Flaherty et al. |
| 2017/0151443 | A1 | 6/2017 | Mishelevich et al. |
| 2017/0156907 | A1 | 6/2017 | Harris et al. |
| 2017/0156973 | A1 | 6/2017 | Hart |
| 2017/0157397 | A1 | 6/2017 | Lockwood et al. |
| 2017/0157398 | A1 | 6/2017 | Wong et al. |
| 2017/0157430 | A1 | 6/2017 | Cheatham, III et al. |
| 2017/0165470 | A1 | 6/2017 | Jeffery |
| 2017/0165473 | A1 | 6/2017 | Bihler et al. |
| 2017/0165497 | A1 | 6/2017 | Lu |
| 2017/0171666 | A1 | 6/2017 | Biggs |
| 2017/0173347 | A1 | 6/2017 | Schwarz et al. |
| 2017/0182334 | A1 | 6/2017 | Altshuler et al. |
| 2017/0182335 | A1 | 6/2017 | Altshuler et al. |
| 2017/0189227 | A1 | 7/2017 | Brunson et al. |
| 2017/0189703 | A1 | 7/2017 | Lei |
| 2017/0189704 | A1 | 7/2017 | Palero et al. |
| 2017/0189707 | A1 | 7/2017 | Zabara |
| 2017/0196731 | A1 | 7/2017 | DeBenedictis et al. |
| 2017/0197077 | A1 | 7/2017 | Harpak et al. |
| 2017/0203117 | A1 | 7/2017 | Biginton et al. |
| 2017/0209708 | A1 | 7/2017 | Schwarz |
| 2017/0216593 | A1 | 8/2017 | Lee |
| 2017/0232267 | A1 | 8/2017 | Riehl et al. |
| 2017/0239079 | A1 | 8/2017 | Root et al. |
| 2017/0239467 | A1 | 8/2017 | Shalev et al. |
| 2017/0252574 | A1 | 9/2017 | Cabrerizo et al. |
| 2017/0259065 | A1 | 9/2017 | Baru et al. |
| 2017/0259077 | A1 | 9/2017 | Jin |
| 2017/0266443 | A1 | 9/2017 | Rajguru et al. |
| 2017/0266460 | A1 | 9/2017 | Upton et al. |
| 2017/0266461 | A1 | 9/2017 | Boll et al. |
| 2017/0280889 | A1 | 10/2017 | Koch |
| 2017/0281935 | A1 | 10/2017 | De Oliveira et al. |
| 2017/0290708 | A1 | 10/2017 | Rapp |
| 2017/0291036 | A1 | 10/2017 | Pell et al. |
| 2017/0296837 | A1 | 10/2017 | Jin |
| 2017/0296838 | A1 | 10/2017 | Asahina et al. |
| 2017/0304614 | A1 | 10/2017 | Yoo et al. |
| 2017/0304641 | A1 | 10/2017 | Eisenmann et al. |
| 2017/0304642 | A1 | 10/2017 | Ron Edoute et al. |
| 2017/0304645 | A1 | 10/2017 | Schomacker et al. |
| 2017/0312536 | A1 | 11/2017 | Phillips et al. |
| 2017/0319378 | A1 | 11/2017 | Anderson et al. |
| 2017/0325992 | A1 | 11/2017 | DeBenedictis et al. |

(56) References Cited

U.S. PATENT DOCUMENTS

2017/0325993 A1 11/2017 Jimenez et al.
2017/0326042 A1 11/2017 Zeng et al.
2017/0326346 A1 11/2017 Jimenez et al.
2017/0326357 A1 11/2017 Sacristan et al.
2017/0326377 A1 11/2017 Neuvonen et al.
2017/0333705 A1 11/2017 Schwarz
2017/0333725 A1 11/2017 Hotani
2017/0340385 A1 11/2017 Reinhard et al.
2017/0340884 A1 11/2017 Franke et al.
2017/0340894 A1 11/2017 Rohan
2017/0348143 A1 12/2017 Rosen et al.
2017/0348539 A1 12/2017 Schwarz et al.
2017/0354530 A1 12/2017 Shagdar et al.
2017/0354818 A1 12/2017 De Toni et al.
2017/0361095 A1 12/2017 Mueller et al.
2017/0368332 A1 12/2017 Ackermann et al.
2017/0372006 A1 12/2017 Mainkar et al.
2018/0000347 A1 1/2018 Perez et al.
2018/0000533 A1 1/2018 Boll et al.
2018/0001101 A1 1/2018 Hulings et al.
2018/0001106 A1 1/2018 Schwarz
2018/0001107 A1 1/2018 Schwarz et al.
2018/0021565 A1 1/2018 Dar et al.
2018/0028831 A1 2/2018 Ron Edoute et al.
2018/0036548 A1 2/2018 Nusse
2018/0043151 A1 2/2018 Ejiri et al.
2018/0043175 A1 2/2018 Karpf
2018/0056083 A1 3/2018 Jin
2018/0064575 A1 3/2018 Vaynberg et al.
2018/0064950 A1 3/2018 Segal
2018/0064952 A1 3/2018 Zangen et al.
2018/0071544 A1 3/2018 Ghiron et al.
2018/0071545 A1 3/2018 Saitoh et al.
2018/0085580 A1 3/2018 Perez et al.
2018/0099141 A1 4/2018 Chang
2018/0103991 A1 4/2018 Linhart et al.
2018/0104484 A1 4/2018 Ryaby et al.
2018/0104504 A1 4/2018 Jin
2018/0116905 A1 5/2018 Capelli et al.
2018/0116906 A1 5/2018 Hirashiki et al.
2018/0117322 A1 5/2018 Chang et al.
2018/0125416 A1 5/2018 Schwarz et al.
2018/0126184 A1 5/2018 Phillips et al.
2018/0133473 A1 5/2018 Yoo et al.
2018/0133478 A1 5/2018 Caparso et al.
2018/0133490 A1 5/2018 Taff et al.
2018/0133498 A1 5/2018 Chornenky et al.
2018/0140860 A1 5/2018 Ledany
2018/0153736 A1 6/2018 Mills et al.
2018/0153760 A1 6/2018 Rosen et al.
2018/0154137 A1 6/2018 Ackermann et al.
2018/0154165 A1 6/2018 Schneider
2018/0154188 A1 6/2018 Altshuler et al.
2018/0161197 A1 6/2018 Baker et al.
2018/0171327 A1 6/2018 Goodwin et al.
2018/0177996 A1 6/2018 Gozani et al.
2018/0178026 A1 6/2018 Riehl et al.
2018/0185081 A1 7/2018 O'Neil et al.
2018/0185189 A1 7/2018 Weber et al.
2018/0192942 A1 7/2018 Clark et al.
2018/0193640 A1 7/2018 Murphy et al.
2018/0200503 A1 7/2018 Ryaby et al.
2018/0214300 A1 8/2018 Anderson et al.
2018/0221660 A1 8/2018 Suri et al.
2018/0228646 A1 8/2018 Gonzales et al.
2018/0229048 A1* 8/2018 Sikora .................... A61N 2/002
2018/0229049 A1 8/2018 Phillips et al.
2018/0236254 A1* 8/2018 Schwarz ................ A61N 2/002
2018/0250056 A1 9/2018 Avram et al.
2018/0250521 A1 9/2018 Wolfel et al.
2018/0256887 A1 9/2018 Wingeier et al.
2018/0256906 A1 9/2018 Pivonka et al.
2018/0263677 A1 9/2018 Hilton et al.
2018/0264245 A1 9/2018 Edwards et al.
2018/0271767 A1 9/2018 Jimenez et al.
2018/0272118 A1 9/2018 Goldwasser et al.
2018/0280711 A1 10/2018 Sekino et al.
2018/0280714 A1 10/2018 Souder
2018/0289533 A1 10/2018 Johnson et al.
2018/0296831 A1 10/2018 Matsushita
2018/0304079 A1 10/2018 Kim et al.
2018/0310950 A1 11/2018 Yee et al.
2018/0318597 A1 11/2018 Simon et al.
2018/0325729 A1 11/2018 Rynerson
2018/0333576 A1 11/2018 Rigaux
2018/0339151 A1 11/2018 De Toni et al.
2018/0339168 A1 11/2018 Cobley et al.
2018/0345012 A1 12/2018 Schwarz et al.
2018/0345014 A1 12/2018 Gozani et al.
2018/0345032 A1 12/2018 Lu
2018/0345833 A1 12/2018 Gallagher et al.
2018/0353767 A1 12/2018 Biginton
2018/0361154 A1 12/2018 Levin
2018/0369062 A1 12/2018 Khen et al.
2018/0369601 A1 12/2018 Saitoh et al.
2019/0000524 A1 1/2019 Rosen et al.
2019/0000529 A1 1/2019 Kothare et al.
2019/0000663 A1 1/2019 Anderson et al.
2019/0001139 A1 1/2019 Mishra et al.
2019/0015661 A1 1/2019 Leonhardt et al.
2019/0022392 A1 1/2019 Franke et al.
2019/0029876 A1 1/2019 Anderson et al.
2019/0030356 A1 1/2019 Schwarz
2019/0046791 A1 2/2019 Ebbers et al.
2019/0046810 A1 2/2019 Carmeli et al.
2019/0053870 A1 2/2019 Azoulay
2019/0053871 A1 2/2019 Moosmann et al.
2019/0053940 A1 2/2019 Biser et al.
2019/0053941 A1 2/2019 Samson
2019/0053967 A1 2/2019 Moosmann et al.
2019/0054306 A1 2/2019 Steinke et al.
2019/0060659 A1 2/2019 Ginhoux et al.
2019/0070428 A1 3/2019 Phillips et al.
2019/0099599 A1 4/2019 Kreindel
2019/0111255 A1 4/2019 Errico et al.
2019/0111273 A1 4/2019 Ghiron et al.
2019/0117965 A1 4/2019 Iger et al.
2019/0125442 A1 5/2019 Hancock et al.
2019/0125477 A1 5/2019 Azoulay
2019/0126036 A1 5/2019 Franco-Obregon
2019/0126041 A1 5/2019 Kerselaers
2019/0133673 A1 5/2019 Boll et al.
2019/0134390 A1 5/2019 Shimada et al.
2019/0134414 A1 5/2019 Prouza et al.
2019/0143116 A1 5/2019 Mowery et al.
2019/0151604 A1 5/2019 Harper et al.
2019/0151655 A1 5/2019 Hall et al.
2019/0151657 A1 5/2019 Tyulmankov et al.
2019/0160286 A1 5/2019 Yang et al.
2019/0167978 A1 6/2019 Ackermann et al.
2019/0168012 A1 6/2019 Biginton
2019/0183562 A1 6/2019 Widgerow
2019/0184171 A1 6/2019 Mustakos et al.
2019/0192219 A1 6/2019 Kreindel
2019/0192853 A1 6/2019 Kim et al.
2019/0192872 A1 6/2019 Schwarz et al.
2019/0192873 A1 6/2019 Schwarz et al.
2019/0192874 A1 6/2019 Shukla
2019/0192875 A1 6/2019 Schwarz et al.
2019/0201280 A1 7/2019 Bak et al.
2019/0201705 A1 7/2019 Schwarz et al.
2019/0201706 A1 7/2019 Schwarz et al.
2019/0206545 A1 7/2019 Mainkar et al.
2019/0209836 A1 7/2019 Yakoub et al.
2019/0209856 A1 7/2019 Segal
2019/0217090 A1 7/2019 Ryaby et al.
2019/0217114 A1 7/2019 Luzi
2019/0224490 A1 7/2019 Goadsby et al.
2019/0240486 A1 8/2019 Simon et al.
2019/0247654 A1 8/2019 Alyagon et al.
2019/0255346 A1 8/2019 Ghiron
2019/0255347 A1 8/2019 Masotti et al.
2019/0269909 A1 9/2019 Gozani et al.
2019/0269931 A1 9/2019 Riehl et al.

(56) References Cited

U.S. PATENT DOCUMENTS

| | | | |
|---|---|---|---|
| 2019/0275320 | A1 | 9/2019 | Kim et al. |
| 2019/0282804 | A1 | 9/2019 | Ackermann et al. |
| 2019/0290533 | A1 | 9/2019 | Le et al. |
| 2019/0290537 | A1 | 9/2019 | Engles et al. |
| 2019/0290925 | A1 | 9/2019 | Gellman et al. |
| 2019/0290928 | A1 | 9/2019 | Biginton |
| 2019/0298998 | A1 | 10/2019 | Coleman et al. |
| 2019/0299016 | A1 | 10/2019 | Altman |
| 2019/0299018 | A1 | 10/2019 | Chornenky et al. |
| 2019/0314629 | A1 | 10/2019 | Kreindel |
| 2019/0314638 | A1 | 10/2019 | Kreindel |
| 2019/0328478 | A1 | 10/2019 | Schuele |
| 2019/0329065 | A1 | 10/2019 | Gandel |
| 2019/0336196 | A1 | 11/2019 | Wolf et al. |
| 2019/0336765 | A1 | 11/2019 | Charlesworth et al. |
| 2019/0336783 | A1 | 11/2019 | Sokolowski |
| 2019/0336787 | A1 | 11/2019 | Kweon et al. |
| 2019/0343714 | A1 | 11/2019 | Gordon |
| 2019/0344089 | A1 | 11/2019 | Jadwizak et al. |
| 2019/0344091 | A1 | 11/2019 | Fischer |
| 2019/0350646 | A1 | 11/2019 | Kreindel |
| 2019/0358465 | A1 | 11/2019 | Segal |
| 2019/0358466 | A1 | 11/2019 | Leung et al. |
| 2019/0365462 | A1 | 12/2019 | Casalino |
| 2019/0366076 | A1 | 12/2019 | Simon et al. |
| 2019/0374773 | A1 | 12/2019 | Simon et al. |
| 2019/0381314 | A1 | 12/2019 | Howard |
| 2019/0388697 | A1 | 12/2019 | Pell et al. |
| 2019/0388698 | A1 | 12/2019 | Schwarz et al. |
| 2020/0000428 | A1 | 1/2020 | Kim et al. |
| 2020/0001103 | A1 | 1/2020 | Schwarz et al. |
| 2020/0016422 | A1 | 1/2020 | Ron Edoute et al. |
| 2020/0016423 | A1 | 1/2020 | Ron Edoute et al. |
| 2020/0022866 | A1 | 1/2020 | Cohen et al. |
| 2020/0030622 | A1 | 1/2020 | Weyh et al. |
| 2020/0030655 | A1 | 1/2020 | Wu et al. |
| 2020/0037079 | A1 | 1/2020 | Biggs |
| 2020/0037080 | A1 | 1/2020 | Biggs |
| 2020/0038674 | A1 | 2/2020 | John |
| 2020/0038675 | A1 | 2/2020 | Neuvonen et al. |
| 2020/0054395 | A1 | 2/2020 | Marchitto et al. |
| 2020/0054519 | A1 | 2/2020 | Engles et al. |
| 2020/0054890 | A1 | 2/2020 | Schwarz et al. |
| 2020/0061385 | A1 | 2/2020 | Schwarz et al. |
| 2020/0061386 | A1 | 2/2020 | Schwarz et al. |
| 2020/0078212 | A1 | 3/2020 | See |
| 2020/0078599 | A1 | 3/2020 | Chen et al. |
| 2020/0086123 | A1 | 3/2020 | Kibler et al. |
| 2020/0086134 | A1 | 3/2020 | Johnson et al. |
| 2020/0086314 | A1 | 3/2020 | Wang et al. |
| 2020/0093297 | A1 | 3/2020 | Dennewald |
| 2020/0094066 | A1 | 3/2020 | Heath |
| 2020/0100837 | A1 | 4/2020 | Ben-Haim et al. |
| 2020/0100932 | A1 | 4/2020 | Hermanson et al. |
| 2020/0101291 | A1 | 4/2020 | Yakovlev et al. |
| 2020/0101308 | A1 | 4/2020 | Ilmoniemi et al. |
| 2020/0108266 | A1 | 4/2020 | Chou |
| 2020/0114160 | A1 | 4/2020 | Blendermann |
| 2020/0121924 | A1 | 4/2020 | Sama |
| 2020/0121984 | A1 | 4/2020 | Sama |
| 2020/0129759 | A1 | 4/2020 | Schwarz |
| 2020/0138540 | A1 | 5/2020 | Azoulay |
| 2020/0139148 | A1 | 5/2020 | Schwarz et al. |
| 2020/0146881 | A1 | 5/2020 | Linder et al. |
| 2020/0147392 | A1 | 5/2020 | Doan et al. |
| 2020/0155221 | A1 | 5/2020 | Marchitto et al. |
| 2020/0155841 | A1 | 5/2020 | Bhagat et al. |
| 2020/0155866 | A1 | 5/2020 | Lu |
| 2020/0163827 | A1 | 5/2020 | Hart |
| 2020/0171297 | A1 | 6/2020 | Kirson et al. |
| 2020/0179690 | A1 | 6/2020 | Schepis et al. |
| 2020/0197696 | A1 | 6/2020 | Nagel et al. |
| 2020/0197717 | A1 | 6/2020 | Ishikawa et al. |
| 2020/0206522 | A1 | 7/2020 | Riehl et al. |
| 2020/0206524 | A1 | 7/2020 | Katznelson et al. |
| 2020/0222069 | A1 | 7/2020 | Bonutti |
| 2020/0222708 | A1 | 7/2020 | Simon et al. |
| 2020/0230431 | A1 | 7/2020 | Saitoh et al. |
| 2020/0237424 | A1 | 7/2020 | Hunziker et al. |
| 2020/0237612 | A1 | 7/2020 | Liu et al. |
| 2020/0238076 | A1 | 7/2020 | Ackermann et al. |
| 2020/0238098 | A1 | 7/2020 | Chornenky et al. |
| 2020/0246617 | A1 | 8/2020 | Errico et al. |
| 2020/0251203 | A1 | 8/2020 | Mainkar et al. |
| 2020/0254256 | A1 | 8/2020 | Moffitt et al. |
| 2020/0268597 | A1 | 8/2020 | Gordon |
| 2020/0269062 | A1 | 8/2020 | Chou |
| 2020/0276435 | A1 | 9/2020 | Ryaby et al. |
| 2020/0281642 | A1 | 9/2020 | Kreindel |
| 2020/0281813 | A1 | 9/2020 | Chao |
| 2020/0289826 | A1 | 9/2020 | Leonhardt |
| 2020/0289837 | A1 | 9/2020 | Lowin et al. |
| 2020/0289838 | A1 | 9/2020 | Schwarz et al. |
| 2020/0297995 | A1 | 9/2020 | Toong et al. |
| 2020/0306554 | A1 | 10/2020 | Ron Edoute et al. |
| 2020/0316379 | A1 | 10/2020 | Yoo et al. |
| 2020/0316396 | A1 | 10/2020 | Jin |
| 2020/0323680 | A1 | 10/2020 | Hussain et al. |
| 2020/0324133 | A1 | 10/2020 | Schwarz et al. |
| 2020/0330782 | A1 | 10/2020 | Zabara |
| 2020/0352633 | A1 | 11/2020 | Treen et al. |
| 2020/0353244 | A1 | 11/2020 | Yamazaki |
| 2020/0353256 | A1 | 11/2020 | Vallejo et al. |
| 2020/0353273 | A1 | 11/2020 | Zucco |
| 2020/0353274 | A1 | 11/2020 | Ansari et al. |
| 2020/0360681 | A1 | 11/2020 | Lay |
| 2020/0376263 | A1 | 12/2020 | Zhu |
| 2020/0384281 | A1 | 12/2020 | Jin |
| 2020/0390997 | A1 | 12/2020 | Jovanov |
| 2020/0398055 | A1 | 12/2020 | Flaherty et al. |
| 2020/0398057 | A1 | 12/2020 | Esteller et al. |
| 2020/0398070 | A1 | 12/2020 | Phillips et al. |
| 2020/0406050 | A1 | 12/2020 | Casanova et al. |
| 2021/0001139 | A1 | 1/2021 | Shukla |
| 2021/0007668 | A1 | 1/2021 | Leaper |
| 2021/0008369 | A1 | 1/2021 | Crosson |
| 2021/0008382 | A1 | 1/2021 | Vaidya |
| 2021/0015552 | A1 | 1/2021 | Curran et al. |
| 2021/0022914 | A1 | 1/2021 | Badawi |
| 2021/0023364 | A1 | 1/2021 | Shalev et al. |
| 2021/0023365 | A1 | 1/2021 | Lo et al. |
| 2021/0023380 | A1 | 1/2021 | Zheng et al. |
| 2021/0031040 | A1 | 2/2021 | Franke et al. |
| 2021/0038891 | A1 | 2/2021 | Goldfarb |
| 2021/0038894 | A1 | 2/2021 | Mowery et al. |
| 2021/0038907 | A1 | 2/2021 | Riehl |
| 2021/0052216 | A1 | 2/2021 | Badawi et al. |
| 2021/0052893 | A1 | 2/2021 | Suri et al. |
| 2021/0052894 | A1 | 2/2021 | Sanderford |
| 2021/0052911 | A1 | 2/2021 | Fischer |
| 2021/0065590 | A1 | 3/2021 | Huang et al. |
| 2021/0093858 | A1 | 4/2021 | Thakkar et al. |
| 2021/0093880 | A1 | 4/2021 | Zhong et al. |
| 2021/0106429 | A1 | 4/2021 | Pacca |
| 2021/0106824 | A1 | 4/2021 | Caparso et al. |
| 2021/0106842 | A1 | 4/2021 | Zangen et al. |
| 2021/0138232 | A1 | 5/2021 | Paz et al. |
| 2021/0146119 | A1 | 5/2021 | Prouza et al. |
| 2021/0146150 | A1 | 5/2021 | Frangineas, Jr. et al. |
| 2021/0146151 | A1 | 5/2021 | Phillips et al. |
| 2021/0161590 | A1 | 6/2021 | Kreindel |
| 2021/0162211 | A1 | 6/2021 | Chase et al. |
| 2021/0169325 | A1 | 6/2021 | Thomas et al. |
| 2021/0169682 | A1 | 6/2021 | Alvarez et al. |
| 2021/0170188 | A1 | 6/2021 | Paulus |
| 2021/0170189 | A1 | 6/2021 | Souder |
| 2021/0178174 | A1 | 6/2021 | Lowin et al. |
| 2021/0187278 | A1 | 6/2021 | Lu |
| 2021/0196197 | A1 | 7/2021 | Leaper |
| 2021/0196957 | A1 | 7/2021 | Yakovlev et al. |
| 2021/0205131 | A1 | 7/2021 | Grenon et al. |
| 2021/0205631 | A1 | 7/2021 | Ghiron et al. |
| 2021/0212634 | A1 | 7/2021 | Leaper |
| 2021/0213283 | A1 | 7/2021 | Yoo et al. |

(56) References Cited

U.S. PATENT DOCUMENTS

2021/0219062 A1 7/2021 Biggs
2021/0228898 A1 7/2021 Ghiron
2021/0235901 A1 8/2021 Dennewald
2021/0236809 A1 8/2021 Ackermann et al.
2021/0260369 A1 8/2021 Steier
2021/0260398 A1 8/2021 Bilston et al.
2021/0268299 A1 9/2021 Casalino et al.
2021/0268300 A1 9/2021 Peled
2021/0275747 A1 9/2021 Sobel et al.
2021/0275825 A1 9/2021 Kreindel
2021/0283395 A1 9/2021 Kreindel
2021/0283411 A1 9/2021 Dietz
2021/0283412 A1 9/2021 Neuvonen et al.
2021/0290969 A1 9/2021 Shukla
2021/0298817 A1 9/2021 Schwarz et al.
2021/0299420 A1 9/2021 Sobel et al.
2021/0299446 A1 9/2021 Errico et al.
2021/0330102 A1 10/2021 Monico
2021/0330987 A1 10/2021 Sun et al.
2021/0361343 A1 11/2021 Gershonowitz
2021/0361938 A1 11/2021 Gershonowitz
2021/0361939 A1 11/2021 Müller-Bruhn
2021/0361964 A1 11/2021 Pargger et al.
2021/0361965 A1 11/2021 Yakobson
2021/0361967 A1 11/2021 Cohen et al.
2021/0369381 A1 12/2021 Azoulay
2021/0386992 A1 12/2021 Simon et al.
2022/0001168 A1 1/2022 Ko
2022/0001175 A1 1/2022 Ko
2022/0003112 A1 1/2022 Leach et al.
2022/0008244 A1 1/2022 Hart et al.
2022/0008741 A1 1/2022 Chornenky et al.
2022/0015942 A1 1/2022 Biser et al.
2022/0016413 A1 1/2022 John et al.
2022/0023654 A1 1/2022 Carmeli et al.
2022/0031408 A1 2/2022 Cai et al.
2022/0032052 A1 2/2022 Kent
2022/0032079 A1 2/2022 Riehl et al.
2022/0036584 A1 2/2022 Sun et al.
2022/0037071 A1 2/2022 Kim et al.
2022/0062622 A1 3/2022 Errico et al.
2022/0062634 A1 3/2022 Masko et al.
2022/0079502 A1 3/2022 Simon et al.
2022/0079811 A1 3/2022 Kleinman et al.
2022/0080217 A1 3/2022 Peterchev et al.
2022/0096146 A1 3/2022 Vaynberg et al.
2022/0111223 A1 4/2022 Taylor et al.
2022/0125546 A1 4/2022 Azoulay
2022/0126095 A1 4/2022 Rajguru et al.
2022/0126109 A1 4/2022 Katznelson et al.
2022/0152379 A1 5/2022 Frangineas, Jr. et al.
2022/0152394 A1 5/2022 Levin
2022/0152409 A1 5/2022 Frangineas, Jr. et al.
2022/0161042 A1 5/2022 Lu
2022/0161043 A1 5/2022 Phillips et al.
2022/0161044 A1 5/2022 Phillips et al.
2022/0168136 A1 6/2022 Badawi et al.
2022/0168584 A1 6/2022 Schwarz et al.
2022/0176101 A1 6/2022 Ryaby et al.
2022/0176114 A1 6/2022 Shalev
2022/0176142 A1 6/2022 Ghiron et al.
2022/0176144 A1 6/2022 Velasco et al.
2022/0184379 A1 6/2022 Lindenthaler et al.
2022/0184389 A1 6/2022 Shalev
2022/0184390 A1 6/2022 Johari et al.
2022/0184409 A1 6/2022 Schwarz et al.
2022/0192580 A1 6/2022 Toth et al.
2022/0193437 A1 6/2022 Leung et al.
2022/0203112 A1 6/2022 Iger et al.
2022/0211573 A1 7/2022 Capelli et al.
2022/0212006 A1 7/2022 Rondoni et al.
2022/0226645 A1 7/2022 Shalev
2022/0226646 A1 7/2022 Shalev
2022/0226647 A1 7/2022 Shalev
2022/0226648 A1 7/2022 Shalev
2022/0226649 A1 7/2022 Shalev
2022/0226662 A1 7/2022 Casalino et al.
2022/0233851 A1 7/2022 Shalev
2022/0241107 A1 8/2022 Kim
2022/0241604 A1 8/2022 Lee
2022/0249836 A1 8/2022 Schwarz et al.
2022/0266008 A1 8/2022 Saltis
2022/0273962 A1 9/2022 Prouza et al.
2022/0280785 A1 9/2022 Rynerson
2022/0280799 A1 9/2022 Altman
2022/0288409 A1 9/2022 Järnefelt
2022/0362570 A1 11/2022 Pemberton
2022/0370006 A1 11/2022 Zieger
2022/0370814 A1 11/2022 Epshtein et al.
2022/0370818 A1 11/2022 Taylor et al.
2022/0378359 A1 12/2022 Simon et al.
2022/0379114 A1 12/2022 Kent
2022/0395681 A1 12/2022 Martinot
2022/0401256 A1 12/2022 Durand
2023/0001181 A1 1/2023 Paz et al.
2023/0001224 A1 1/2023 Shukla
2023/0013787 A1 1/2023 Sitt
2023/0059748 A1 2/2023 Simon et al.
2023/0065587 A1 3/2023 Shnaiderman et al.
2023/0079691 A1 3/2023 Schwarz et al.
2023/0092226 A1 3/2023 Ko et al.
2023/0108122 A1 4/2023 Click et al.
2023/0123145 A1 4/2023 Ko
2023/0124830 A1 4/2023 Doan et al.
2023/0125236 A1 4/2023 Sandell et al.
2023/0128482 A1 4/2023 Gayes et al.
2023/0130856 A1 4/2023 Sandell et al.
2023/0148962 A1 5/2023 Leaper
2023/0165721 A1 6/2023 Kleinman et al.
2023/0191076 A1 6/2023 Lee et al.
2023/0191144 A1 6/2023 Ko
2023/0200904 A1 6/2023 Brockett et al.
2023/0201589 A1 6/2023 Schwarz
2023/0201621 A1 6/2023 Gries
2023/0211170 A1 7/2023 Gin
2023/0211171 A1 7/2023 Gries
2023/0211172 A1 7/2023 Oliveros
2023/0218915 A1 7/2023 Casalino et al.
2023/0226368 A1 7/2023 Schwarz et al.
2023/0240784 A1 8/2023 Azoulay
2023/0241384 A1 8/2023 Schwarz et al.
2023/0241405 A1 8/2023 Schwarz et al.
2023/0241407 A1 8/2023 Cassano et al.
2023/0248989 A1 8/2023 Gries
2023/0285767 A1 9/2023 Kim
2023/0293354 A1 9/2023 Rao et al.
2023/0293901 A1 9/2023 Yun
2023/0293903 A1 9/2023 Jarnefelt
2023/0310878 A1 10/2023 Yoon et al.
2023/0355967 A1 11/2023 Kishi et al.
2023/0355998 A1 11/2023 Müller-Bruhn et al.
2023/0364413 A1 11/2023 Romaniw et al.
2023/0364439 A1 11/2023 Müller-Bruhn et al.
2023/0368599 A1 11/2023 Ruggiero et al.
2023/0372724 A1 11/2023 Casalino et al.
2023/0381499 A1 11/2023 Simon et al.
2023/0381504 A1 11/2023 Yoo et al.
2023/0381507 A1 11/2023 Errico et al.
2023/0381530 A1 11/2023 Kim
2023/0398352 A1 12/2023 Errico et al.
2023/0405306 A1 12/2023 Simon et al.
2023/0405319 A1 12/2023 Simon et al.
2023/0414931 A1 12/2023 Shapiro et al.
2023/0414960 A1 12/2023 Ghiron et al.
2023/0414961 A1 12/2023 Gries
2024/0001110 A1 1/2024 Ko
2024/0001114 A1 1/2024 Shalev
2024/0009450 A1 1/2024 Ko
2024/0009476 A1 1/2024 Krinke et al.
2024/0017083 A1 1/2024 Soekadar et al.
2024/0024692 A1 1/2024 Khan
2024/0024693 A1 1/2024 Gonzales
2024/0042227 A1 2/2024 Lee et al.
2024/0042228 A1 2/2024 Ghiron et al.

(56) References Cited

U.S. PATENT DOCUMENTS

| | | | |
|---|---|---|---|
| 2024/0075309 | A1 | 3/2024 | Paulus |
| 2024/0100321 | A1 | 3/2024 | Wasserman et al. |
| 2024/0148300 | A1 | 5/2024 | Schepis et al. |
| 2024/0173559 | A1 | 5/2024 | Cohen et al. |
| 2024/0216707 | A1 | 7/2024 | Liang et al. |
| 2024/0316357 | A1 | 9/2024 | Kishi et al. |
| 2024/0316358 | A1 | 9/2024 | Kishi et al. |
| 2024/0342497 | A1 | 10/2024 | Phillips et al. |
| 2024/0342499 | A1 | 10/2024 | Kataja et al. |
| 2025/0025715 | A1 | 1/2025 | Florou et al. |
| 2025/0065144 | A1 | 2/2025 | Ansari et al. |
| 2025/0090855 | A1 | 3/2025 | Roth et al. |
| 2025/0108228 | A1 | 4/2025 | Song et al. |
| 2025/0127653 | A1 | 4/2025 | Sandstrom |

FOREIGN PATENT DOCUMENTS

| | | | |
|---|---|---|---|
| AU | 2012200610 | B2 | 7/2014 |
| AU | 2012244313 | B2 | 11/2014 |
| AU | 2014203094 | B2 | 7/2015 |
| AU | 2015227382 | A1 | 10/2015 |
| AU | 2013207657 | B2 | 11/2015 |
| BR | PI 0701434 | A2 | 11/2008 |
| BR | PI0812502 | A2 | 6/2015 |
| CA | 2484880 | A1 | 4/2006 |
| CA | 2845438 | C | 5/2014 |
| CA | 2915928 | A1 | 12/2014 |
| CA | 2604112 | C | 7/2016 |
| CA | 3019140 | A1 | 10/2017 |
| CA | 3019410 | A1 | 10/2017 |
| CA | 3023821 | A1 | 11/2017 |
| CH | 714113 | A2 | 3/2019 |
| CN | 86204070 | U | 9/1987 |
| CN | 87203746 | U | 12/1987 |
| CN | 87215926 | U | 7/1988 |
| CN | 1026953 | C | 12/1994 |
| CN | 1027958 | C | 3/1995 |
| CN | 2192348 | Y | 3/1995 |
| CN | 1206975 | C | 6/2005 |
| CN | 101234231 | A | 8/2008 |
| CN | 101327358 | A | 12/2008 |
| CN | 201906360 | U | 7/2011 |
| CN | 102319141 | A | 1/2012 |
| CN | 102711706 | A | 10/2012 |
| CN | 102847231 | A | 1/2013 |
| CN | 202637725 | U | 1/2013 |
| CN | 202822496 | U | 3/2013 |
| CN | 103079640 | A | 5/2013 |
| CN | 203123345 | U | 8/2013 |
| CN | 203169831 | U | 9/2013 |
| CN | 102319141 | B | 8/2014 |
| CN | 204767045 | U | 11/2015 |
| CN | 205698901 | U | 11/2016 |
| CN | 106540375 | A | 3/2017 |
| CN | 106606819 | A | 5/2017 |
| CN | 206613045 | U | 11/2017 |
| CN | 107569773 | A | 1/2018 |
| CN | 107613914 | A | 1/2018 |
| CN | 107802956 | A | 3/2018 |
| CN | 207462462 | U | 6/2018 |
| CN | 108355240 | A | 8/2018 |
| CN | 108853728 | A | 11/2018 |
| CN | 108882992 | A | 11/2018 |
| CN | 109310516 | A | 2/2019 |
| CN | 208511024 | U | 2/2019 |
| CN | 208710812 | U | 4/2019 |
| CN | 109745620 | A | 5/2019 |
| CN | 208809311 | U | 5/2019 |
| CN | 109865196 | A | 6/2019 |
| CN | 110180083 | A | 8/2019 |
| CN | 209221337 | U | 8/2019 |
| CN | 209221338 | U | 8/2019 |
| CN | 110339480 | A | 10/2019 |
| CN | 210770219 | U | 6/2020 |
| CN | 111408041 | A | 7/2020 |
| CN | 211097114 | U | 7/2020 |
| CN | 211357457 | U | 8/2020 |
| CN | 111728712 | A | 10/2020 |
| CN | 111840804 | A | 10/2020 |
| CN | 111939460 | A | 11/2020 |
| CN | 112023260 | A | 12/2020 |
| CN | 112023270 | A | 12/2020 |
| CN | 112221015 | A | 1/2021 |
| CN | 212416683 | U | 1/2021 |
| CN | 212516751 | U | 2/2021 |
| CN | 112472506 | A | 3/2021 |
| CN | 112494815 | A | 3/2021 |
| CN | 112582159 | A | 3/2021 |
| CN | 212700107 | U | 3/2021 |
| CN | 212730732 | U | 3/2021 |
| CN | 112891749 | A | 6/2021 |
| CN | 112915390 | A | 6/2021 |
| CN | 112932933 | A | 6/2021 |
| CN | 113041500 | A | 6/2021 |
| CN | 113041502 | A | 6/2021 |
| CN | 213432603 | U | 6/2021 |
| CN | 213554920 | U | 6/2021 |
| CN | 113082529 | A | 7/2021 |
| CN | 113274646 | A | 8/2021 |
| CN | 113317962 | A | 8/2021 |
| CN | 213911989 | U | 8/2021 |
| CN | 213994598 | U | 8/2021 |
| CN | 214099374 | U | 8/2021 |
| CN | 214105531 | U | 9/2021 |
| CN | 113499542 | A | 10/2021 |
| CN | 113647936 | A | 11/2021 |
| CN | 214971184 | U | 12/2021 |
| CN | 215025228 | U | 12/2021 |
| CN | 215081635 | U | 12/2021 |
| CN | 215084285 | U | 12/2021 |
| CN | 215309722 | U | 12/2021 |
| CN | 114209957 | A | 3/2022 |
| CN | 216091295 | U | 3/2022 |
| CN | 216091887 | U | 3/2022 |
| CN | 114344725 | A | 4/2022 |
| CN | 216169399 | U | 4/2022 |
| CN | 216365670 | U | 4/2022 |
| CN | 114504729 | A | 5/2022 |
| CN | 114588546 | A | 6/2022 |
| CN | 114712160 | A | 7/2022 |
| CN | 216986082 | U | 7/2022 |
| CN | 115083724 | A | 9/2022 |
| CN | 115212462 | A | 10/2022 |
| CN | 217526108 | U | 10/2022 |
| CN | 217548800 | U | 10/2022 |
| CN | 115282486 | A | 11/2022 |
| CN | 115364376 | A | 11/2022 |
| CN | 217908619 | U | 11/2022 |
| CN | 217908621 | U | 11/2022 |
| CN | 115454185 | A | 12/2022 |
| CN | 217960287 | U | 12/2022 |
| CN | 218129587 | U | 12/2022 |
| CN | 115591124 | A | 1/2023 |
| CN | 115639868 | A | 1/2023 |
| CN | 115645737 | A | 1/2023 |
| CN | 115645748 | A | 1/2023 |
| CN | 218220824 | U | 1/2023 |
| CN | 219049396 | U | 5/2023 |
| CN | 116271528 | A | 6/2023 |
| CN | 116328189 | A | 6/2023 |
| CN | 116350949 | A | 6/2023 |
| CN | 219110650 | U | 6/2023 |
| CN | 116650831 | A | 8/2023 |
| CN | 219462335 | U | 8/2023 |
| CN | 219614745 | U | 9/2023 |
| CN | 117180084 | A | 12/2023 |
| CN | 117205444 | A | 12/2023 |
| CN | 220778839 | U | 4/2024 |
| CN | 220778841 | U | 4/2024 |
| CN | 118267627 | A | 7/2024 |
| CN | 119607423 | A | 3/2025 |
| CZ | 33663 | U1 | 1/2020 |
| CZ | 2022299 | A3 | 1/2024 |
| DE | 718637 | C | 3/1942 |

(56) References Cited

FOREIGN PATENT DOCUMENTS

| | | | |
|---|---|---|---|
| DE | 1118902 | B | 12/1961 |
| DE | 2748780 | A1 | 5/1978 |
| DE | 3205048 | A1 | 8/1983 |
| DE | 3340974 | A1 | 5/1985 |
| DE | 3610474 | A1 | 10/1986 |
| DE | 3825165 | A1 | 1/1990 |
| DE | 3340974 | C2 | 7/1994 |
| DE | 69318706 | T2 | 1/1999 |
| DE | 10062050 | A1 | 4/2002 |
| DE | 102004006192 | A1 | 9/2005 |
| DE | 60033756 | T2 | 6/2007 |
| DE | 202006009799 | U1 | 10/2007 |
| DE | 102007044445 | A1 | 3/2009 |
| DE | 202010005501 | U1 | 8/2010 |
| DE | 102009023855 | A1 | 12/2010 |
| DE | 102009049145 | A1 | 4/2011 |
| DE | 102009050010 | A1 | 5/2011 |
| DE | 102010004307 | A1 | 7/2011 |
| DE | 102006024467 | B4 | 4/2012 |
| DE | 102011014291 | A1 | 9/2012 |
| DE | 102012220121 | B3 | 9/2013 |
| DE | 102014106797 | B3 | 1/2015 |
| DE | 102013211859 | B4 | 7/2015 |
| DE | 102014001185 | A1 | 7/2015 |
| DE | 202017107602 | U1 | 2/2018 |
| DE | 102016116399 | A1 | 3/2018 |
| DE | 202019100373 | U1 | 3/2019 |
| DE | 102017122942 | A1 | 4/2019 |
| DE | 102017123854 | A1 | 4/2019 |
| DE | 102017125678 | A1 | 5/2019 |
| DE | 202018106565 | U1 | 10/2019 |
| DE | 202020100975 | U1 | 3/2020 |
| DE | 202016008884 | U1 | 7/2020 |
| DE | 102010014157 | B4 | 2/2021 |
| DE | 102021111627 | A1 | 11/2022 |
| DK | 0633008 | T3 | 3/1999 |
| EA | 000494 | B1 | 8/1999 |
| EA | 002087 | B1 | 12/2001 |
| EA | 002179 | B1 | 2/2002 |
| EA | 003851 | B1 | 10/2003 |
| EA | 007347 | B1 | 8/2006 |
| EA | 007975 | B1 | 2/2007 |
| EP | 0048451 | A1 | 3/1982 |
| EP | 0039206 | B1 | 10/1984 |
| EP | 0209246 | A1 | 1/1987 |
| EP | 0459101 | A1 | 12/1991 |
| EP | 0459401 | A1 | 12/1991 |
| EP | 0633008 | A1 | 1/1995 |
| EP | 0788813 | A1 | 8/1997 |
| EP | 0633008 | B1 | 5/1998 |
| EP | 0692993 | B1 | 9/1999 |
| EP | 1022034 | A1 | 7/2000 |
| EP | 1916013 | A1 | 4/2008 |
| EP | 2069014 | A2 | 6/2009 |
| EP | 1883447 | B1 | 9/2009 |
| EP | 2139560 | A1 | 1/2010 |
| EP | 2124800 | B1 | 11/2010 |
| EP | 1917935 | B1 | 1/2011 |
| EP | 2308559 | A2 | 4/2011 |
| EP | 2139560 | B1 | 5/2012 |
| EP | 2461765 | A1 | 6/2012 |
| EP | 2564895 | A1 | 3/2013 |
| EP | 1863569 | B1 | 5/2013 |
| EP | 2069014 | B1 | 6/2013 |
| EP | 1850781 | B1 | 7/2013 |
| EP | 2614807 | A1 | 7/2013 |
| EP | 2676700 | A2 | 12/2013 |
| EP | 2694159 | A2 | 2/2014 |
| EP | 2749259 | A1 | 7/2014 |
| EP | 2814445 | A1 | 12/2014 |
| EP | 2856986 | A1 | 4/2015 |
| EP | 2878336 | A1 | 6/2015 |
| EP | 2564894 | B1 | 11/2015 |
| EP | 3009167 | A1 | 4/2016 |
| EP | 2501352 | B1 | 7/2016 |
| EP | 3209246 | A1 | 8/2017 |
| EP | 3342379 | A1 | 7/2018 |
| EP | 3389532 | A1 | 10/2018 |
| EP | 3415199 | A1 | 12/2018 |
| EP | 3434323 | A1 | 1/2019 |
| EP | 3476433 | A1 | 5/2019 |
| EP | 3479872 | A1 | 5/2019 |
| EP | 3656442 | A1 | 5/2020 |
| EP | 3666325 | A1 | 6/2020 |
| EP | 3721939 | A1 | 10/2020 |
| EP | 3744392 | A1 | 12/2020 |
| EP | 3772362 | A1 | 2/2021 |
| EP | 3797825 | A1 | 3/2021 |
| EP | 3988164 | A1 | 4/2022 |
| EP | 3988165 | A1 | 4/2022 |
| EP | 4046660 | A1 | 8/2022 |
| EP | 4406469 | A1 | 7/2024 |
| ES | 2118925 | T3 | 10/1998 |
| ES | 2300569 | T3 | 6/2008 |
| ES | 2305698 | T3 | 11/2008 |
| ES | 2359581 | T3 | 5/2011 |
| ES | 2533145 | A2 | 4/2015 |
| ES | 2533145 | B1 | 7/2016 |
| ES | 2533145 | R1 | 10/2018 |
| FR | 2987275 | A1 | 8/2013 |
| FR | 2970656 | B1 | 6/2014 |
| FR | 3039072 | A1 | 1/2017 |
| FR | 3041881 | A1 | 4/2017 |
| FR | 3061012 | A1 | 6/2018 |
| FR | 3071395 | A1 | 3/2019 |
| GB | 260116 | A | 10/1926 |
| GB | 304587 | A | 3/1930 |
| GB | 390500 | A | 4/1933 |
| GB | 871672 | A | 6/1961 |
| GB | 2176009 | A | 12/1986 |
| GB | 2188238 | A | 9/1987 |
| GB | 2176009 | B | 12/1989 |
| GB | 2261820 | A | 6/1993 |
| GB | 2286660 | A | 8/1995 |
| GB | 2298370 | A | 9/1996 |
| GB | 2395907 | B | 12/2004 |
| GB | 2459157 | A | 10/2009 |
| GB | 2504984 | A | 2/2014 |
| GB | 2521240 | A | 6/2015 |
| GB | 2521609 | A | 7/2015 |
| GB | 2549466 | A | 10/2017 |
| GB | 2552004 | A | 1/2018 |
| GB | 2552810 | A | 2/2018 |
| GB | 2554043 | A | 3/2018 |
| GB | 2555809 | A | 5/2018 |
| GB | 2567872 | A | 5/2019 |
| GB | 2568051 | A | 5/2019 |
| GB | 2587392 | A | 3/2021 |
| GB | 2591692 | A | 8/2021 |
| GB | 2602603 | A | 7/2022 |
| GB | 2634713 | A | 4/2025 |
| GR | 3027678 | T3 | 11/1998 |
| IT | 1217550 | B | 3/1990 |
| IT | RE20120010 | A1 | 8/2013 |
| IT | UB20159823 | A1 | 7/2017 |
| IT | 201800002490 | U1 | 11/2019 |
| IT | 201800005119 | A1 | 11/2019 |
| JP | S5541836 | U | 3/1980 |
| JP | H 07135376 | A | 5/1995 |
| JP | H 09276418 | A | 10/1997 |
| JP | H105270 | A | 1/1998 |
| JP | 2002513621 | A | 5/2002 |
| JP | 2002299026 | A | 10/2002 |
| JP | 2003085523 | A | 3/2003 |
| JP | 2003305131 | A | 10/2003 |
| JP | 2005245585 | A | 9/2005 |
| JP | 2006130055 | A | 5/2006 |
| JP | 4178762 | B2 | 11/2008 |
| JP | 4324673 | B2 | 9/2009 |
| JP | 2009297350 | A | 12/2009 |
| JP | 2010504792 | A | 2/2010 |
| JP | 2010063007 | A | 3/2010 |
| JP | 2010207268 | A | 9/2010 |
| JP | 2010533054 | A | 10/2010 |

(56) References Cited

FOREIGN PATENT DOCUMENTS

| | | | |
|---|---|---|---|
| JP | 2011194176 | A | 10/2011 |
| JP | 4837723 | B2 | 12/2011 |
| JP | 2013012285 | A | 1/2013 |
| JP | 2013063285 | A | 4/2013 |
| JP | 2013066597 | A | 4/2013 |
| JP | 2013116271 | A | 6/2013 |
| JP | 3192971 | U | 9/2014 |
| JP | 2015208504 | A | 11/2015 |
| JP | 2017023286 | A | 2/2017 |
| JP | 2017070427 | A | 4/2017 |
| JP | 2017518857 | A | 7/2017 |
| JP | 2018501927 | A | 1/2018 |
| JP | 2018018650 | A | 2/2018 |
| JP | 2018187510 | A | 11/2018 |
| JP | 2018534028 | A | 11/2018 |
| JP | 2022044180 | A | 3/2022 |
| JP | 2023174724 | A | 12/2023 |
| JP | 2024082438 | A | 6/2024 |
| KR | 20010095888 | A | 11/2001 |
| KR | 200261417 | Y1 | 3/2002 |
| KR | 20030004976 | A | 1/2003 |
| KR | 20030065126 | A | 8/2003 |
| KR | 100484618 | B1 | 4/2005 |
| KR | 100491988 | B1 | 5/2005 |
| KR | 200407524 | Y1 | 1/2006 |
| KR | 100556230 | B1 | 3/2006 |
| KR | 200410065 | Y1 | 3/2006 |
| KR | 100841596 | B1 | 6/2008 |
| KR | 20090063618 | A | 6/2009 |
| KR | 20090095143 | A | 9/2009 |
| KR | 100936914 | B1 | 1/2010 |
| KR | 1020100026107 | A | 3/2010 |
| KR | 101022244 | B1 | 3/2011 |
| KR | 101050069 | B1 | 7/2011 |
| KR | 20110123474 | A | 11/2011 |
| KR | 20110123831 | A | 11/2011 |
| KR | 20120037011 | A | 4/2012 |
| KR | 101233286 | B1 | 2/2013 |
| KR | 101233287 | B1 | 2/2013 |
| KR | 101275228 | B1 | 6/2013 |
| KR | 20130072244 | A | 7/2013 |
| KR | 101292289 | B1 | 8/2013 |
| KR | 20130106977 | A | 10/2013 |
| KR | 20130128391 | A | 11/2013 |
| KR | 101413022 | B1 | 7/2014 |
| KR | 101415141 | B1 | 7/2014 |
| KR | 101447532 | B1 | 10/2014 |
| KR | 101511444 | B1 | 4/2015 |
| KR | 20150049386 | A | 5/2015 |
| KR | 20150058102 | A | 5/2015 |
| KR | 20150063839 | A | 6/2015 |
| KR | 101539633 | B1 | 7/2015 |
| KR | 20150079619 | A | 7/2015 |
| KR | 20150106379 | A | 9/2015 |
| KR | 101610762 | B1 | 4/2016 |
| KR | 101650155 | B1 | 8/2016 |
| KR | 101673182 | B1 | 11/2016 |
| KR | 101687583 | B1 | 12/2016 |
| KR | 101702400 | B1 | 2/2017 |
| KR | 101754395 | B1 | 7/2017 |
| KR | 20170084848 | A | 7/2017 |
| KR | 101770364 | B1 | 8/2017 |
| KR | 20170090654 | A | 8/2017 |
| KR | 20170107603 | A | 9/2017 |
| KR | 101794269 | B1 | 11/2017 |
| KR | 20180059114 | A | 6/2018 |
| KR | 20180092020 | A | 8/2018 |
| KR | 101900491 | B1 | 9/2018 |
| KR | 101901215 | B1 | 9/2018 |
| KR | 101921033 | B1 | 11/2018 |
| KR | 101941863 | B1 | 1/2019 |
| KR | 20190005981 | A | 1/2019 |
| KR | 20190027491 | A | 3/2019 |
| KR | 101955542 | B1 | 5/2019 |
| KR | 20190061187 | A | 6/2019 |
| KR | 20190073169 | A | 6/2019 |
| KR | 102000971 | B1 | 7/2019 |
| KR | 20190001779 | U | 7/2019 |
| KR | 20190103532 | A | 9/2019 |
| KR | 20190112530 | A | 10/2019 |
| KR | 102063730 | B1 | 1/2020 |
| KR | 20200001717 | A | 1/2020 |
| KR | 20200001978 | A | 1/2020 |
| KR | 200491572 | Y1 | 5/2020 |
| KR | 20200000889 | U | 5/2020 |
| KR | 20200050488 | A | 5/2020 |
| KR | 20200052602 | A | 5/2020 |
| KR | 20200056692 | A | 5/2020 |
| KR | 20200056693 | A | 5/2020 |
| KR | 20200056801 | A | 5/2020 |
| KR | 20200056802 | A | 5/2020 |
| KR | 20200057154 | A | 5/2020 |
| KR | 20200061765 | A | 6/2020 |
| KR | 20200133652 | A | 11/2020 |
| KR | 102185926 | B1 | 12/2020 |
| KR | 20210002973 | A | 1/2021 |
| KR | 20210002974 | A | 1/2021 |
| KR | 20210006624 | A | 1/2021 |
| KR | 20210009510 | A | 1/2021 |
| KR | 102234264 | B1 | 3/2021 |
| KR | 20210041171 | A | 4/2021 |
| KR | 20210052126 | A | 5/2021 |
| KR | 20210096894 | A | 8/2021 |
| KR | 20210105758 | A | 8/2021 |
| KR | 20210111197 | A | 9/2021 |
| KR | 20210117049 | A | 9/2021 |
| KR | 102315486 | B1 | 10/2021 |
| KR | 20210149359 | A | 12/2021 |
| KR | 20210153862 | A | 12/2021 |
| KR | 20220004537 | A | 1/2022 |
| KR | 20220007771 | A | 1/2022 |
| KR | 20220009045 | A | 1/2022 |
| KR | 20220009066 | A | 1/2022 |
| KR | 20220011851 | A | 2/2022 |
| KR | 20220012823 | A | 2/2022 |
| KR | 20220012825 | A | 2/2022 |
| KR | 20220029838 | A | 3/2022 |
| KR | 20220052896 | A | 4/2022 |
| KR | 20220055028 | A | 5/2022 |
| KR | 20220055065 | A | 5/2022 |
| KR | 20220072075 | A | 6/2022 |
| KR | 20220108282 | A | 8/2022 |
| KR | 20220122960 | A | 9/2022 |
| KR | 20220123612 | A | 9/2022 |
| KR | 20220140452 | A | 10/2022 |
| KR | 102462186 | B1 | 11/2022 |
| KR | 20220166212 | A | 12/2022 |
| KR | 20230045777 | A | 4/2023 |
| KR | 20230045778 | A | 4/2023 |
| KR | 20230045779 | A | 4/2023 |
| KR | 20230046655 | A | 4/2023 |
| KR | 20230050717 | A | 4/2023 |
| KR | 20230064250 | A | 5/2023 |
| KR | 20230094311 | A | 6/2023 |
| KR | 20230094312 | A | 6/2023 |
| KR | 20230094313 | A | 6/2023 |
| KR | 20230134278 | A | 9/2023 |
| KR | 20230168735 | A | 12/2023 |
| KR | 20230168737 | A | 12/2023 |
| KR | 20230169024 | A | 12/2023 |
| KR | 20240012685 | A | 1/2024 |
| KR | 20240013316 | A | 1/2024 |
| KR | 20240023930 | A | 2/2024 |
| KR | 20240043736 | A | 4/2024 |
| KR | 20240050633 | A | 4/2024 |
| KR | 20240074691 | A | 5/2024 |
| KR | 20240083844 | A | 6/2024 |
| KR | 20240083849 | A | 6/2024 |
| KR | 20240083850 | A | 6/2024 |
| KR | 20240096032 | A | 6/2024 |
| KR | 20240128462 | A | 8/2024 |
| KR | 20240132686 | A | 9/2024 |
| KR | 20240133060 | A | 9/2024 |
| KR | 20240133061 | A | 9/2024 |

(56) References Cited

FOREIGN PATENT DOCUMENTS

| | | | |
|---|---|---|---|
| KR | 20240160880 | A | 11/2024 |
| KR | 20240174636 | A | 12/2024 |
| KR | 102801459 | B1 | 4/2025 |
| KR | 102801469 | B1 | 4/2025 |
| MX | 2012012158 | A | 4/2014 |
| NL | 7510644 | A | 3/1977 |
| NL | 1037451 | C2 | 5/2011 |
| RU | 2212909 | C2 | 9/2003 |
| RU | 2226115 | C2 | 3/2004 |
| RU | 2281128 | C2 | 8/2006 |
| RU | 2373971 | C2 | 11/2009 |
| RU | 2392979 | C2 | 6/2010 |
| RU | 2395267 | C2 | 7/2010 |
| RU | 2496532 | C2 | 10/2013 |
| RU | 2529471 | C2 | 9/2014 |
| RU | 2596053 | C2 | 8/2016 |
| RU | 2637104 | C2 | 11/2017 |
| RU | 2645923 | C2 | 2/2018 |
| SI | 23086 | A | 12/2010 |
| SI | 23195 | A | 4/2011 |
| SI | 24921 | A | 8/2016 |
| SI | 25942 | A | 6/2021 |
| SI | 26251 | A | 3/2023 |
| TW | 510797 | B | 11/2002 |
| TW | 200423986 | A | 11/2004 |
| TW | 201825045 | A | 7/2018 |
| WO | WO-9115263 | A1 | 10/1991 |
| WO | WO-9312835 | A1 | 7/1993 |
| WO | WO-9521655 | A1 | 8/1995 |
| WO | WO-9527533 | A1 | 10/1995 |
| WO | WO-9932191 | A1 | 7/1999 |
| WO | WO-0006251 | A2 | 2/2000 |
| WO | WO-0013749 | A1 | 3/2000 |
| WO | WO-0044346 | A1 | 8/2000 |
| WO | WO-0107111 | A2 | 2/2001 |
| WO | WO-0112089 | A1 | 2/2001 |
| WO | WO 03013334 | A2 | 8/2001 |
| WO | WO-0193797 | A2 | 12/2001 |
| WO | WO-0225675 | A1 | 3/2002 |
| WO | WO 0226147 | A1 | 4/2002 |
| WO | WO-0230511 | A2 | 4/2002 |
| WO | WO-0232504 | A2 | 4/2002 |
| WO | WO 02096514 | A1 | 12/2002 |
| WO | WO-03078596 | A2 | 9/2003 |
| WO | WO 2003075820 | A1 | 9/2003 |
| WO | WO-03079916 | A1 | 10/2003 |
| WO | WO-03090863 | A1 | 11/2003 |
| WO | WO-03103769 | A1 | 12/2003 |
| WO | WO-2004078255 | A1 | 9/2004 |
| WO | WO 2004080526 | A2 | 9/2004 |
| WO | WO 2004080527 | A2 | 9/2004 |
| WO | WO-2004087255 | A1 | 10/2004 |
| WO | WO-2004095385 | A2 | 11/2004 |
| WO | WO-2004095835 | A1 | 11/2004 |
| WO | WO-2004096343 | A2 | 11/2004 |
| WO | WO-2004108211 | A1 | 12/2004 |
| WO | WO-2005032660 | A1 | 4/2005 |
| WO | WO 2005044375 | A1 | 5/2005 |
| WO | WO 2005049132 | A1 | 6/2005 |
| WO | WO 2005061051 | A2 | 7/2005 |
| WO | WO 2005065032 | A2 | 7/2005 |
| WO | WO 2005102188 | A1 | 11/2005 |
| WO | WO 2005105013 | A2 | 11/2005 |
| WO | WO-2005107866 | A1 | 11/2005 |
| WO | WO 2006034306 | A2 | 3/2006 |
| WO | WO 2006050279 | A2 | 5/2006 |
| WO | WO 2006061867 | A1 | 6/2006 |
| WO | WO 2006077567 | A1 | 7/2006 |
| WO | WO 2006077582 | A2 | 7/2006 |
| WO | WO-2006115120 | A1 | 11/2006 |
| WO | WO 2006116728 | A2 | 11/2006 |
| WO | WO 2006133636 | A1 | 12/2006 |
| WO | WO 2007005373 | A1 | 1/2007 |
| WO | WO 2007011583 | A1 | 1/2007 |
| WO | WO 2007051896 | A1 | 5/2007 |
| WO | WO-2007096206 | A1 | 8/2007 |
| WO | WO-2007130308 | A2 | 11/2007 |
| WO | WO-2007131248 | A1 | 11/2007 |
| WO | WO-2007140584 | A1 | 12/2007 |
| WO | WO-2008012827 | A2 | 1/2008 |
| WO | WO-2008049775 | A1 | 5/2008 |
| WO | WO-2008060494 | A2 | 5/2008 |
| WO | WO 2008063478 | A1 | 5/2008 |
| WO | WO 2008085162 | A1 | 7/2008 |
| WO | WO-2008109058 | A1 | 9/2008 |
| WO | WO 2008124112 | A1 | 10/2008 |
| WO | WO-2008127011 | A2 | 10/2008 |
| WO | WO-2008145260 | A2 | 12/2008 |
| WO | WO-2009011708 | A1 | 1/2009 |
| WO | WO-2009013729 | A2 | 1/2009 |
| WO | WO-2009036040 | A1 | 3/2009 |
| WO | WO-2009042863 | A1 | 4/2009 |
| WO | WO-2009044400 | A2 | 4/2009 |
| WO | WO 2009045358 | A1 | 4/2009 |
| WO | WO-2009047628 | A2 | 4/2009 |
| WO | WO-2009083915 | A2 | 7/2009 |
| WO | WO-2009095013 | A2 | 8/2009 |
| WO | WO 2009127840 | A1 | 10/2009 |
| WO | WO-2010007614 | A2 | 1/2010 |
| WO | WO-2010022278 | A1 | 2/2010 |
| WO | WO-2010007614 | A3 | 5/2010 |
| WO | WO 2010095147 | A2 | 8/2010 |
| WO | WO-2010100643 | A2 | 9/2010 |
| WO | WO 2010129997 | A1 | 11/2010 |
| WO | WO-2010135425 | A1 | 11/2010 |
| WO | WO-2010139376 | A1 | 12/2010 |
| WO | WO 2010151619 | A2 | 12/2010 |
| WO | WO-2011011749 | A1 | 1/2011 |
| WO | WO-2011016019 | A1 | 2/2011 |
| WO | WO-2011021184 | A1 | 2/2011 |
| WO | WO-2011044173 | A1 | 4/2011 |
| WO | WO-2011044176 | A1 | 4/2011 |
| WO | WO-2011044178 | A1 | 4/2011 |
| WO | WO-2011044179 | A1 | 4/2011 |
| WO | WO-2011045002 | A1 | 4/2011 |
| WO | WO 2011053607 | A1 | 5/2011 |
| WO | WO 2011058556 | A2 | 5/2011 |
| WO | WO-2011058565 | A2 | 5/2011 |
| WO | WO-2011068727 | A1 | 6/2011 |
| WO | WO 2011085020 | A1 | 7/2011 |
| WO | WO 2011137262 | A1 | 11/2011 |
| WO | WO-2011156495 | A2 | 12/2011 |
| WO | WO-2012003451 | A2 | 1/2012 |
| WO | WO-2012005766 | A1 | 1/2012 |
| WO | WO 2012024169 | A2 | 2/2012 |
| WO | WO-2012029065 | A2 | 3/2012 |
| WO | WO 2012033932 | A3 | 3/2012 |
| WO | WO-2012040243 | A1 | 3/2012 |
| WO | WO-2012072978 | A1 | 6/2012 |
| WO | WO-2012073232 | A1 | 6/2012 |
| WO | WO-2012082960 | A2 | 6/2012 |
| WO | WO 2012102837 | A1 | 8/2012 |
| WO | WO-2012103632 | A1 | 8/2012 |
| WO | WO 2012106735 | A2 | 8/2012 |
| WO | WO-2012119293 | A1 | 9/2012 |
| WO | WO-2012126044 | A1 | 9/2012 |
| WO | WO-2012138169 | A2 | 10/2012 |
| WO | WO-2013019796 | A1 | 2/2013 |
| WO | WO-2013021380 | A1 | 2/2013 |
| WO | WO-2013026393 | A1 | 2/2013 |
| WO | WO-2013035088 | A1 | 3/2013 |
| WO | WO-2013036761 | A1 | 3/2013 |
| WO | WO-2013037618 | A1 | 3/2013 |
| WO | WO-2013074576 | A2 | 5/2013 |
| WO | WO 2012033932 | A2 | 7/2013 |
| WO | WO-2013098815 | A1 | 7/2013 |
| WO | WO 2013121265 | A1 | 8/2013 |
| WO | WO 2013131639 | A1 | 9/2013 |
| WO | WO-2013191699 | A1 | 12/2013 |
| WO | WO 2014004051 | A2 | 1/2014 |
| WO | WO-2014009875 | A2 | 1/2014 |
| WO | WO-2014016820 | A2 | 1/2014 |
| WO | WO 2014031857 | A2 | 2/2014 |
| WO | WO 2014049501 | A1 | 4/2014 |

(56) References Cited

FOREIGN PATENT DOCUMENTS

| | | | |
|---|---|---|---|
| WO | WO-2014105964 | A1 | 7/2014 |
| WO | WO-2014109653 | A1 | 7/2014 |
| WO | WO-2014137344 | A1 | 9/2014 |
| WO | WO-2014141213 | A1 | 9/2014 |
| WO | WO-2014141229 | A1 | 9/2014 |
| WO | WO-2014147624 | A1 | 9/2014 |
| WO | WO-2014149021 | A2 | 9/2014 |
| WO | WO-2014151431 | A2 | 9/2014 |
| WO | WO-2014163020 | A1 | 10/2014 |
| WO | WO-2014164926 | A1 | 10/2014 |
| WO | WO 2014170887 | A2 | 10/2014 |
| WO | WO 2014176420 | A1 | 10/2014 |
| WO | WO-2015004540 | A2 | 1/2015 |
| WO | WO-2015012639 | A1 | 1/2015 |
| WO | WO-2015012672 | A1 | 1/2015 |
| WO | WO 2015040049 | A1 | 3/2015 |
| WO | WO-2015049495 | A1 | 4/2015 |
| WO | WO-2015052705 | A1 | 4/2015 |
| WO | WO-2015066670 | A2 | 5/2015 |
| WO | WO-2015083305 | A1 | 6/2015 |
| WO | WO 2015104454 | A1 | 7/2015 |
| WO | WO 2015114629 | A1 | 8/2015 |
| WO | WO-2015129887 | A1 | 9/2015 |
| WO | WO-2015137733 | A1 | 9/2015 |
| WO | WO-2015150625 | A1 | 10/2015 |
| WO | WO 2015155545 | A1 | 10/2015 |
| WO | WO-2015157725 | A1 | 10/2015 |
| WO | WO 2015170184 | A1 | 11/2015 |
| WO | WO-2015171869 | A1 | 11/2015 |
| WO | WO-2015177670 | A1 | 11/2015 |
| WO | WO-2015177682 | A1 | 11/2015 |
| WO | WO-2015179571 | A1 | 11/2015 |
| WO | WO-2015185352 | A1 | 12/2015 |
| WO | WO-2015185583 | A1 | 12/2015 |
| WO | WO-2015187858 | A1 | 12/2015 |
| WO | WO 2015196164 | A2 | 12/2015 |
| WO | WO 2016005719 | A1 | 1/2016 |
| WO | WO-2016042499 | A1 | 3/2016 |
| WO | WO 2016049284 | A1 | 3/2016 |
| WO | WO 2016059556 | A1 | 4/2016 |
| WO | WO-2016069689 | A1 | 5/2016 |
| WO | WO-2016081767 | A1 | 5/2016 |
| WO | WO-2016104411 | A1 | 6/2016 |
| WO | WO-2016104578 | A1 | 6/2016 |
| WO | WO-2016113661 | A1 | 7/2016 |
| WO | WO-2016116747 | A1 | 7/2016 |
| WO | WO-2016124739 | A1 | 8/2016 |
| WO | WO-2016135996 | A1 | 9/2016 |
| WO | WO 2016137319 | A1 | 9/2016 |
| WO | WO-2016140871 | A1 | 9/2016 |
| WO | WO-2016143145 | A1 | 9/2016 |
| WO | WO-2016149176 | A1 | 9/2016 |
| WO | WO-2016155773 | A1 | 10/2016 |
| WO | WO-2016177780 | A1 | 11/2016 |
| WO | WO 2016183307 | A1 | 11/2016 |
| WO | WO 2016183689 | A1 | 11/2016 |
| WO | WO-2016185464 | A1 | 11/2016 |
| WO | WO-2017002065 | A1 | 1/2017 |
| WO | WO-2017004156 | A1 | 1/2017 |
| WO | WO-2017012895 | A1 | 1/2017 |
| WO | WO-2017040739 | A2 | 3/2017 |
| WO | WO-2017048731 | A1 | 3/2017 |
| WO | WO-2017051412 | A1 | 3/2017 |
| WO | WO-2017055465 | A1 | 4/2017 |
| WO | WO 2017055471 | A1 | 4/2017 |
| WO | WO-2017065239 | A1 | 4/2017 |
| WO | WO 2017066620 | A1 | 4/2017 |
| WO | WO-2017087681 | A1 | 5/2017 |
| WO | WO 2017/106878 | A1 | 6/2017 |
| WO | WO-2017103923 | A1 | 6/2017 |
| WO | WO-2017125909 | A1 | 7/2017 |
| WO | WO-2017130133 | A1 | 8/2017 |
| WO | WO 2017153840 | A1 | 9/2017 |
| WO | WO-2017158498 | A1 | 9/2017 |
| WO | WO-2017159959 | A1 | 9/2017 |
| WO | WO-2017160097 | A2 | 9/2017 |
| WO | WO-2017175907 | A1 | 10/2017 |
| WO | WO-2017176621 | A1 | 10/2017 |
| WO | WO-2017178946 | A1 | 10/2017 |
| WO | WO-2017187184 | A1 | 11/2017 |
| WO | WO-2017189757 | A1 | 11/2017 |
| WO | WO 2017189890 | A1 | 11/2017 |
| WO | WO 2017191624 | A1 | 11/2017 |
| WO | WO-2017196548 | A1 | 11/2017 |
| WO | WO-2017197150 | A1 | 11/2017 |
| WO | WO-2017212253 | A1 | 12/2017 |
| WO | WO 2017212258 | A1 | 12/2017 |
| WO | WO-2017212343 | A1 | 12/2017 |
| WO | WO-2018006086 | A1 | 1/2018 |
| WO | WO-2018008023 | A1 | 1/2018 |
| WO | WO 2018044054 | A1 | 3/2018 |
| WO | WO-2018044825 | A1 | 3/2018 |
| WO | WO-2018045056 | A1 | 3/2018 |
| WO | WO 2018047164 | A1 | 3/2018 |
| WO | WO 2018052958 | A1 | 3/2018 |
| WO | WO-2018057637 | A1 | 3/2018 |
| WO | WO 2018075394 | A1 | 4/2018 |
| WO | WO 2018075514 | A1 | 4/2018 |
| WO | WO-2018078973 | A1 | 5/2018 |
| WO | WO-2018089450 | A1 | 5/2018 |
| WO | WO 2018098417 | A1 | 5/2018 |
| WO | WO-2018116161 | A1 | 6/2018 |
| WO | WO-2018121998 | A2 | 7/2018 |
| WO | WO-2018122535 | A1 | 7/2018 |
| WO | WO-2018125538 | A1 | 7/2018 |
| WO | WO 2018132678 | A1 | 7/2018 |
| WO | WO-2017160097 | A3 | 9/2018 |
| WO | WO-2018160670 | A1 | 9/2018 |
| WO | WO-2018182188 | A1 | 10/2018 |
| WO | WO-2018185369 | A1 | 10/2018 |
| WO | WO-2018189387 | A1 | 10/2018 |
| WO | WO-2018189393 | A1 | 10/2018 |
| WO | WO-2018199661 | A1 | 11/2018 |
| WO | WO-2018206067 | A1 | 11/2018 |
| WO | WO-2018208992 | A1 | 11/2018 |
| WO | WO-2018215879 | A1 | 11/2018 |
| WO | WO 2018221903 | A2 | 12/2018 |
| WO | WO-2018234571 | A1 | 12/2018 |
| WO | WO 2018235629 | A1 | 12/2018 |
| WO | WO 2019021288 | A1 | 1/2019 |
| WO | WO-2019043628 | A2 | 3/2019 |
| WO | WO-2019057511 | A2 | 3/2019 |
| WO | WO 2019083863 | A1 | 5/2019 |
| WO | WO-2019093023 | A1 | 5/2019 |
| WO | WO-2019097488 | A1 | 5/2019 |
| WO | WO 2019099068 | A1 | 5/2019 |
| WO | WO-2019110595 | A1 | 6/2019 |
| WO | WO 2019111053 | A2 | 6/2019 |
| WO | WO-2019112935 | A1 | 6/2019 |
| WO | WO 2019117740 | A2 | 6/2019 |
| WO | WO 2019118709 | A1 | 6/2019 |
| WO | WO-2019120420 | A1 | 6/2019 |
| WO | WO-2019126080 | A1 | 6/2019 |
| WO | WO 2019126792 | A1 | 6/2019 |
| WO | WO-2019138407 | A1 | 7/2019 |
| WO | WO 2019142196 | A1 | 7/2019 |
| WO | WO 2019144316 | A1 | 8/2019 |
| WO | WO 2019145762 | A1 | 8/2019 |
| WO | WO-2019150378 | A1 | 8/2019 |
| WO | WO 2019154834 | A1 | 8/2019 |
| WO | WO 2019154837 | A1 | 8/2019 |
| WO | WO 2019154839 | A1 | 8/2019 |
| WO | WO-2019164173 | A1 | 8/2019 |
| WO | WO 2019164471 | A1 | 8/2019 |
| WO | WO-2019166965 | A1 | 9/2019 |
| WO | WO-2019173866 | A1 | 9/2019 |
| WO | WO-2019183622 | A1 | 9/2019 |
| WO | WO-2019184904 | A1 | 10/2019 |
| WO | WO 2019193000 | A1 | 10/2019 |
| WO | WO 2019212972 | A1 | 11/2019 |
| WO | WO-2019227150 | A1 | 12/2019 |
| WO | WO-2019227203 | A1 | 12/2019 |
| WO | WO-2019239275 | A1 | 12/2019 |
| WO | WO-2020002801 | A1 | 1/2020 |

(56) References Cited

FOREIGN PATENT DOCUMENTS

| | | | |
|---|---|---|---|
| WO | WO-2020011290 | A1 | 1/2020 |
| WO | WO-2020035852 | A2 | 2/2020 |
| WO | WO-2020041502 | A1 | 2/2020 |
| WO | WO 2020041633 | A1 | 2/2020 |
| WO | WO 2020044331 | A1 | 3/2020 |
| WO | WO 2020053848 | A1 | 3/2020 |
| WO | WO 2020065651 | A1 | 4/2020 |
| WO | WO 2020072243 | A1 | 4/2020 |
| WO | WO-2020079218 | A1 | 4/2020 |
| WO | WO-2020086552 | A1 | 4/2020 |
| WO | WO 2020092653 | A1 | 5/2020 |
| WO | WO-2020122374 | A1 | 6/2020 |
| WO | WO-2020142470 | A1 | 7/2020 |
| WO | WO-2020144486 | A1 | 7/2020 |
| WO | WO-2020145185 | A1 | 7/2020 |
| WO | WO-2020163042 | A1 | 8/2020 |
| WO | WO-2020174444 | A1 | 9/2020 |
| WO | WO-2020183508 | A1 | 9/2020 |
| WO | WO-2020185549 | A1 | 9/2020 |
| WO | WO-2020190401 | A1 | 9/2020 |
| WO | WO-2020190514 | A1 | 9/2020 |
| WO | WO 2020194278 | A1 | 10/2020 |
| WO | WO-2020208590 | A1 | 10/2020 |
| WO | WO-2020213819 | A1 | 10/2020 |
| WO | WO-2020213820 | A1 | 10/2020 |
| WO | WO 2020227288 | A1 | 11/2020 |
| WO | WO 2020251177 | A1 | 12/2020 |
| WO | WO-2020252406 | A1 | 12/2020 |
| WO | WO-2020264263 | A1 | 12/2020 |
| WO | WO 2019183306 | A1 | 1/2021 |
| WO | WO 2021003473 | A1 | 1/2021 |
| WO | WO-2021011255 | A1 | 1/2021 |
| WO | WO-2021013654 | A1 | 1/2021 |
| WO | WO-2021023749 | A1 | 2/2021 |
| WO | WO-2021033139 | A1 | 2/2021 |
| WO | WO-2021048854 | A1 | 3/2021 |
| WO | WO-2021050829 | A1 | 3/2021 |
| WO | WO 2012052986 | A2 | 4/2021 |
| WO | WO-2021074453 | A1 | 4/2021 |
| WO | WO-2021074455 | A1 | 4/2021 |
| WO | WO-2021080392 | A1 | 4/2021 |
| WO | WO-2021095889 | A1 | 5/2021 |
| WO | WO-2021102365 | A1 | 5/2021 |
| WO | WO-2021204981 | A1 | 10/2021 |
| WO | WO-2021204982 | A1 | 10/2021 |
| WO | WO 2021232096 | A1 | 11/2021 |
| WO | WO-2021239523 | A1 | 12/2021 |
| WO | WO-2021251571 | A1 | 12/2021 |
| WO | WO-2022016086 | A1 | 1/2022 |
| WO | WO-2022018532 | A1 | 1/2022 |
| WO | WO 2022019695 | A1 | 1/2022 |
| WO | WO 2022019696 | A1 | 1/2022 |
| WO | WO 2022041657 | A1 | 3/2022 |
| WO | WO-2022049360 | A1 | 3/2022 |
| WO | WO-2022063931 | A1 | 3/2022 |
| WO | WO-2022063934 | A1 | 3/2022 |
| WO | WO 2022065800 | A1 | 3/2022 |
| WO | WO-2022076455 | A1 | 4/2022 |
| WO | WO-2022076913 | A1 | 4/2022 |
| WO | WO 2022085989 | A1 | 4/2022 |
| WO | WO 2022099067 | A1 | 5/2022 |
| WO | WO 2022118028 | A1 | 6/2022 |
| WO | WO-2022118347 | A1 | 6/2022 |
| WO | WO 2022119577 | A1 | 6/2022 |
| WO | WO 2022122923 | A1 | 6/2022 |
| WO | WO 2022128991 | A1 | 6/2022 |
| WO | WO-2022133054 | A1 | 6/2022 |
| WO | WO 2022144555 | A1 | 7/2022 |
| WO | WO 2022171218 | A1 | 8/2022 |
| WO | WO 2022182756 | A1 | 9/2022 |
| WO | WO 2022197674 | A2 | 9/2022 |
| WO | WO-2022204725 | A1 | 9/2022 |
| WO | WO-2022204726 | A1 | 9/2022 |
| WO | WO-2022204727 | A1 | 9/2022 |
| WO | WO-2022214197 | A1 | 10/2022 |
| WO | WO-2022221644 | A2 | 10/2022 |
| WO | WO-2022240226 | A1 | 11/2022 |
| WO | WO 2022246320 | A1 | 11/2022 |
| WO | WO 2022256388 | A1 | 12/2022 |
| WO | WO 2023003501 | A1 | 1/2023 |
| WO | WO-2023280332 | A1 | 1/2023 |
| WO | WO 2023281448 | A1 | 1/2023 |
| WO | WO-2023286065 | A1 | 1/2023 |
| WO | WO 2023010656 | A1 | 2/2023 |
| WO | WO 2023011503 | A1 | 2/2023 |
| WO | WO-2023023367 | A1 | 2/2023 |
| WO | WO-2023047662 | A1 | 3/2023 |
| WO | WO 2023066020 | A1 | 4/2023 |
| WO | WO 2023080310 | A1 | 5/2023 |
| WO | WO-2023080329 | A1 | 5/2023 |
| WO | WO-2023094415 | A1 | 6/2023 |
| WO | WO-2023100130 | A1 | 6/2023 |
| WO | WO 2023108881 | A1 | 6/2023 |
| WO | WO 2023118023 | A2 | 6/2023 |
| WO | WO 2023130108 | A1 | 7/2023 |
| WO | WO-2023133573 | A1 | 7/2023 |
| WO | WO-2023135597 | A1 | 7/2023 |
| WO | WO-2023146191 | A1 | 8/2023 |
| WO | WO-2023146875 | A1 | 8/2023 |
| WO | WO-2023169614 | A1 | 9/2023 |
| WO | WO 2023175610 | A1 | 9/2023 |
| WO | WO-2023222910 | A1 | 11/2023 |
| WO | WO 2023238038 | A1 | 12/2023 |
| WO | WO 2023238039 | A1 | 12/2023 |
| WO | WO 2023238040 | A1 | 12/2023 |
| WO | WO 2023238041 | A1 | 12/2023 |
| WO | WO-2024015444 | A1 | 1/2024 |
| WO | WO-2024031086 | A1 | 2/2024 |
| WO | WO-2024234537 | A1 | 11/2024 |
| WO | WO-2025023457 | A1 | 1/2025 |
| WO | WO-2025037714 | A1 | 2/2025 |

OTHER PUBLICATIONS

Mantis, The non-invasive solution that restores natural beauty, improves health, and offers a renewed psychophysical sense of balance, MR991 theramagnetic, 2020, 8 pages.
Mantis Theramagnetic Compact: the compact that guarantees utmost efficiency and maximum performance, theramagnetic, 2020, 8 pages.
Pollegen, K200545, Legend Pro DMA, Indications for use, dated Oct. 20, 2021, 11 pages.
Letter from US Food & Drug Administration to Johari Digital Healthcare Ltd. regarding K212866, attaching 510(K) summary; Dec. 3, 2022; 17 pages.
Lanzamiento de BTL Vanquish ME en Argentina, BTL Aesthetics Int., 2018 at 0:33, 0:34; available at: https://www.youtube.com/watch?v=5yb5IMmN76Q&ab_channel=BTLAestheticsInt, downloaded Jul. 12, 2023; 2 pages.
Magneris—ASTAR—magnetotherapy unit, 2010 at 1:16, 1:35, 1:40 and 1:50 available at: https://www.youtube.com/watch?v=1001LYnaq4g&ab_channel=Astar-aparatydlafizjotera, downloaded Jul. 12, 2023; 2 pages.
Notice of Allowance dated Jul. 21, 2021 for U.S. Appl. No. 17/087,850 (pp. 1-8).
Notice of Allowance dated May 6, 2020 for U.S. Appl. No. 16/194,800 (pp. 1-8).
Notice of Allowance dated Oct. 8, 2019 for U.S. Appl. No. 15/603,162 (pp. 1-8).
Notice of Allowance dated Mar. 24, 2021 for U.S. Appl. No. 17/087,850 (pp. 1-8).
Office Action dated Aug. 15, 2019 for U.S. Appl. No. 16/194,800 (pp. 1-12).
Office Action dated Jul. 10, 2020 for U.S. Appl. No. 15/678,915 (pp. 1-9).
Office Action dated Jun. 14, 2021 for U.S. Appl. No. 15/786,303 (pp. 1-13).
Office Action dated Jun. 28, 2021 for U.S. Appl. No. 16/727,458 (pp. 1-11).
Office Action dated Oct. 7, 2019 for U.S. Appl. No. 15/678,915 (pp. 1-8).

(56) References Cited

OTHER PUBLICATIONS

Venus, Venus legacy marca argentina, Aug. 14, 2014, 20 pages.
File History for U.S. Appl. No. 62/812,123, to Caselino et al., filed Feb. 28, 2019.
File History for U.S. Appl. No. 62/884,099, to Caselino et al., filed Aug. 7, 2019.
File History for U.S. Appl. No. 62/908,741, to Caselino et al., filed Oct. 1, 2019.
Pascual-Leone, Alvaro et al. "Handbook of Transcranial Magnetic Stimulation" 2002 Arnold Publishers, Chapters 1-4, 58 pages.
2018 Cutera University, Clinical Forum, Cutera 20, 26 pages.
501(k) K030708 Slendertone Flex Letter from Department of Health and Humane Serivces, Public Health Service, Jun. 25, 2003, 6 pages.
501(k) K163165 AM-100 Letter from Department of Health and Human Services, Public Health Service, Feb. 16, 2017, 9 pages.
Abulhasan, J.F., et al., "Peripheral Electrical and Magnetic Stimulation to Augment Resistance Training," Journal of Functional Morphology and Kinesiology, 1(3):328-342, (Sep. 2016).
Accent Radiofrequency System, Operator's Manual, Alma Lasers, Wellbeing Through Technology, 2008, 82 Pages.
Agilent Technologies, Inc., "Agilent 33500 Series 30 MHz Function / Arbitrary Waveform Generator User's Guide," Publication No. 33520-90001 (Dec. 2010), 278 pages.
Agilent Technologies, Inc., "Agilent Announces 30 MHz Function/ Arbitrary Waveform Generators," Microwave J., URL: (Aug. 3, 2010), 8 pages.
*Allergan, Inc. et al* v. *BTL Healthcare Technologies A.S.*, PTAB-PGR2021-00015, Paper 16 (Decision Denying Institution of Post-Grant Review), Jun. 17, 2021, 20 pages.
*Allergan, Inc. et al* v. *BTL Healthcare Technologies A.S.*, PTAB-PGR2021-00016, Paper 16 (Decision Denying Institution of Post-Grant Review), Jun. 17, 2021, 20 pages.
*Allergan, Inc. et al* v. *BTL Healthcare Technologies A.S.*, PTAB-PGR2021-00017, Paper 16 (Decision Denying Institution of Post-Grant Review), Jun. 16, 2021, 33 pages.
*Allergan, Inc. et al* v. *BTL Healthcare Technologies A.S.*, PTAB-PGR2021-00018, Paper 16 (Decision Denying Institution of Post-Grant Review), Jun. 16, 2021, 42 pages.
*Allergan, Inc. et al* v. *BTL Healthcare Technologies A.S.*, PTAB-PGR2021-00020, Paper 16 (Decision Denying Institution of Post-Grant Review), Jun. 16, 2021, 35 pages.
*Allergan, Inc. et al* v. *BTL Healthcare Technologies A.S.*, PTAB-PGR2021-00021, Paper 17 (Decision Denying Institution of Post-Grant Review), Jun. 16, 2021, 33 pages.
*Allergan, Inc. et al* v. *BTL Healthcare Technologies A.S.*, PTAB-PGR2021-00022; Ptab- PGR2021-00023; PTAB-PGR2021-00024; PTAB-PGR2021-00025; PTAB-IPR2021-00296; PTAB-IPR2021-00312, Paper 11 (Decision Settlement Prior to Institution of Trial), Jul. 6, 2021, 4 pages.
Alma Lasers., "Accent Radiofrequency System, Operator's Manual," Wellbeing Through Technology, 2008, Chapters 1-8, Appendix A.
Arjunan, P.A., et al., "Computation and Evaluation of Features of Surface Electromyogram to Identify the Force of Muscle Contraction and Muscle Fatigue," BioMed research international 2014:197960, Hindawi Pub. Co, United States (2014).
Avram, M.M. and Harry, R.S., "Cryolipolysis for Subcutaneous Fat Layer Reduction," Lasers in Surgery and Medicine, 41(10):703-708, Wiley-Liss, United States (Dec. 2009).
Bachasson, D., et al., "Quadriceps Function Assessment Using an Incremental Test and Magnetic Neurostimulation: a Reliability Study," Journal of Electromyography and Kinesiology, 23(3):649-658, Elsevier, England, (Jun. 2013).
Baranov, A., Krion, Whole Body Cryotherapy, Russia, 19 Pages.
Barker, A.T, "An Introduction to the Basic Principles of Magnetic Nerve Stimulation," Journal of Clinical Neurophysiology, 8(1):26-37, Lippincott Williams & Wilkins, United States, (Jan. 1991).
Barker, A.T., et al., "Non-Invasive Magnetic Stimulation of Human Motor Cortex," Lancet 1(8437):1106-1107, Elsevier, England (May 1985).
Barker, A.T., "The History and Basic Principles of Magnetic Nerve Stimulation," Electroencephalography and Clinical Neurophysiology 51:3-21, Elsevier, Netherlands (1999).
Barrett, J., et al., "Mechanisms of Action Underlying the Effect of Repetitive Transcranial Magnetic Stimulation on Mood: Behavioral and Brain Imaging Studies," Neuropsychopharmacology 29(6):1172-1189, Nature Publishing Group, England (Jan. 14, 2004).
Behrens, M., et al., "Repetitive Peripheral Magnetic Stimulation (15 Hz RPMS) of the Human Soleus Muscle did not Affect Spinal Excitability," Journal of Sports Science and Medicine, 10(1):39-44, Dept. of Sports Medicine, Medical Faculty of Uludag University, Turkey (Mar. 2011).
Beilin, G., et al., "Electromagnetic Fields Applied to the Reduction of Abdominal Obesity," Journal of Cosmetic & Laser Therapy, 14(1):24-42, Informa Healthcare, England, (Feb. 2012).
Belanger, A-Y., "Chapter 13: Neuromuscular Electrical Stimulation," in Therapeutic Electrophysical Agents: Evidence Behind Practice, 3rd Edition, Lupash, E., ed., pp. 220-255, Lippincott Williams & Wilkins, United States (2015).
Benton, et al., "Functional Electrical Stimulation—A Practical Clinical Guide," Second Edition, The Professional Staff Association of the Rancho Los Amigos Hospital, Inc., 42 pages (1981).
Benton, L.A., et al., "Chapter 2: Physiological Basis of Nerve and Muscle Excitation" and "Chapter 4: General Uses of Electrical Stimulation," in Functional Electrical Stimulation: A Practical Guide, 2nd Edition, pp. 11-30 and 53-71, Rancho Los Amigos Rehabilitation Engineering Center, Downey, CA (1981), 42 pages.
Bergh, U., and Ekblom, B., "Influence of Muscle Temperature on Maximal Muscle Strength and Power Output in Human Skeletal Muscles," Acta Physiologica Scandinavica 107(1):33-37, Blackwell Scientific Publications, England (Aug. 1979).
Binder-Macleod, S.A., et al., "Force Output of Cat Motor Units Stimulated with Trains of Linearly Varying Frequency," Journal of Neurophysiology 61(1):208-217, American Physiological Society, United States (Jan. 1989).
Binder-Macleod, S.A., et al., "Use of a Catchlike Property of Human Skeletal Muscle to Reduce Fatigue," Muscle & Nerve 14(9):850-857, John Wiley & Sons, United States (Sep. 1991).
Bio Medical Research Limited., "Slendertone Flex Abdominal Training System, Instructions for Use," All pages (Aug. 2006).
Bio Medical Research Limited., "Slendertone Flex Max Instruction Manual," All pages (Apr. 2006).
Bio-Medical Research Ltd., K010335, 510(k) Summary, Slendertone Flex, All pages (Sep. 2001).
Bio-Medical Research Ltd., K022855 510(k) Summary, Slendertone, 1-6 (Mar. 2003).
Bischoff, C., et al., "Repetitive Magnetic Nerve Stimulation: Technical Considerations and Clinical Use in the Assessment of Neuromuscular Transmission," Electroencephalography and Clinical Neurophysiology 93(1):15-20, Elsevier, Ireland (Feb. 1994).
Bourland, J.D., et al., "Transchest Magnetic (Eddy-Current) Stimulation of the Dog Heart," Medical & Biological Engineering & Computing 28(2):196-198, Springer, United States (Mar. 1990).
BTL Industries, Inc., K163165 510(k) Summary, AM-100, All pages (Feb. 2017).
BTL Industries, Inc., K180813 510(k) Summary, Emsculpt, All pages (Mar. 2018).
*BTL Industries, Inc.* v. *Allergan Ltd. et al* DDE-1-20-cv-01046, Complaint for Patent Infringement and Exhibits 1-38, 821 pages (Aug. 2020).
*BTL Industries, Inc.* v. *Allergan Ltd. et al.*, DDE-1-20-cv-01046, Order Administratively Closing Case, Jul. 26, 2021, 1 page.
*BTL Industries, Inc.* v. *Allergan Ltd et al* DDE-1-20-cv-01046, Order Granting Motion to Stay Pending Resolution of Proceedings at the International Trade Commission (Unopposed), 2 pages (Oct. 2020).
*BTL Industries, Inc.* v. *Allergan PLC et al* DDE-1-19-cv-02356, Complaint for Patent Infringement and Exhibits 1-34, 375 pages (Dec. 2019).
*BTL Industries, Inc.* v. *Allergan PLC et al* DDE-1-19-cv-02356, Order Granting Stipulation to Stay, Oct. 1, 2020, 1 page.
*BTL Industries, Inc.* v. *Allergan USA, Inc. et al.*, DDE-1-19-cv-02356, Order Administratively Closing Case, Jul. 26, 2021, 1 page.

(56) References Cited

OTHER PUBLICATIONS

Buenos Aires, Oct. 14, 2014, Venus Concept, Provision No. 7246, 56 pages (With Machine Translation).
Burge, S.M and Dawber, R.P., "Hair Follicle Destruction and Regeneration in Guinea Pig Skin After Cutaneous Freeze Injury," Cryobiology, 27(2):153-163, Elsevier, Netherlands (Apr. 1990).
Busso, M. and Denkova, R., "Efficacy of High Intensity Focused Electro-Magnetic (HIFEM) Field Therapy When Used for Non-Invasive Buttocks Augmentation and Lifting: A Clinical Study" American Society for Laser Medicine and Surgery Abstracts, 382 (2018).
Bustamante, V., et al., "Muscle Training With Repetitive Magnetic Stimulation of the Quadriceps in Severe COPD Patients," Respiratory Medicine, 104(2):237-245, Elsevier, England, (Feb. 2010).
Bustamante, V., et al., "Redox Balance Following Magnetic Stimulation Training in the Quadriceps of Patients With Severe COPD," Free Radical Research, 42(11-12):939-948, Informa Healthcare, England, (Nov. 2008).
Callaghan, M.J., et al., "Electric Muscle Stimulation of the Quadriceps in the Treatment of Patellofemoral Pain," Archives of Physical Medicine and Rehabilitation 85(6):956-962, W.B. Saunders, United Staes (Jun. 2004).
Carbonaro, M., et al., "Architectural Changes in Superficial and Deep Compartments of the Tibialis Anterior during Electrical Stimulation over Different Sites," IEEE transactions on Neural Systems and Rehabilitation Engineering 28(11):2557-2565, IEEE, United States (Nov. 2020).
Caress, J.B., et al., "A Novel Method of Inducing Muscle Cramps Using Repetitive Magnetic Stimulation," Muscle Nerve, 23(1):126-128, John Wiley & Sons, United States, (Jan. 2000).
Certain Non-Invasive Aesthetic Body Contouring Devices, Components Thereof, and Methods of Using the Same, Inv. No. 337-TA-1219, BTL's Statement of Suggested Claim Terms to Be Construed Pursuant to Ground Rule 6b, Nov. 4, 2020, 2 pages.
Certain Non-Invasive Aesthetic Body Contouring Devices, Components Thereof, and Methods of Using the Same, Inv. No. 337-TA-1219, Complainant BTL's Proposed Construction of Disputed Claim Terms, Dec. 8, 2020, 19 pages.
Certain Non-Invasive Aesthetic Body Contouring Devices, Components Thereof, and Methods of Using the Same, Inv. No. 337-TA-1219, Complaint, Aug. 5, 2020, 93 pages.
Certain Non-Invasive Aesthetic Body Contouring Devices, Components Thereof, and Methods of Using the Same, Inv. No. 337-TA-1219, Joint Claim Construction Chart, Dec. 14, 2020, 15 pages.
Certain Non-Invasive Aesthetic Body Contouring Devices, Components Thereof, and Methods of Using the Same; Inv. No. 337-TA-1219, Joint Claim Construction Chart, Dec. 18, 2020, 15 pages.
Certain Non-Invasive Aesthetic Body Contouring Devices, Components Thereof, and Methods of Using the Same, Inv. No. 337-TA-1219, Respondents' Allergan Limited, Allergan USA, Inc., Allergan, Inc., Zeltiq Aesthetics, Inc., Zeltiq Ireland Unlimited Company, and Zimmer MedizinSysteme GmbH's Notice of Prior Art, Nov. 20, 2020, 5 pages.
Certain Non-Invasive Aesthetic Body Contouring Devices, Components Thereof, and Methods of Using the Same, Inv. No. 337-TA-1219, Respondents' List of Claim Terms for Construction, Nov. 4, 2020, 8 pages.
Certain Non-Invasive Aesthetic Body Contouring Devices, Components Thereof, and Methods of Using the Same; Inv. No. 337-TA-1219, Respondents' List of Proposed Claim Constructions and Their Intrinsic and Extrinsic Support, filed Dec. 15, 2020, 23 pages.
Certain Non-Invasive Aesthetic Body Contouring Devices, Components Thereof, and Methods of Using the Same, Inv. No. 337-TA-1219, Response of Respondent Zimmer MedizinSysteme GmbH to the Complaint and Notice of Investigation, Oct. 22, 2020, 68 pages.
Certain Non-Invasive Aesthetic Body Contouring Devices, Components Thereof, and Methods of Using the Same, Inv. No. 337-TA-1219, Response of Respondents Allergan Limited, Allergan USA, Inc., Allergan, Inc., Zeltiq Aesthetics, Inc., and Zeltiq IrelandUnlimited Company to the Complaint and Notice of Investigation, Oct. 22, 2020, 69 pages.
Certain Non-Invasive Aesthetic Body-Contouring Devices, Components Thereof, and Methods of Using Same, Notice of Institution of Investigation, Inv. No. 337-TA-1219, Notice of Institution of Investigation, Sep. 2, 2020, 21 pages.
Certain Non-Invasive Aesthetic Body-Contouring Devices, Components Thereof, and Methods of Using the Same, Inv. No. 337-TA-1219, Order No. 21 (Initial Determination), Apr. 28, 2021, 5 pages.
Certain Non-Invasive Aesthetic Body-Contouring Devices, Components Thereof, and Methods of Using the Same, Inv. No. 337-TA-1219, Order No. 30 (Order Concerning the Procedural Schedule), Aug. 4, 2021, 3 pages.
Certain Non-Invasive Aesthetic Body-Contouring Devices, Componesnts Thereof, and Methods of Using the Same, Inv. No. 337-TA-1219, Order No. 17: Amending Procedural Schedule, Apr. 9, 2021, 4 pages.
Certified English Translation of Belyaev, A.G., "Effect of Magnetic Stimulation on the Strength Capacity of Skeletal Muscles," Ph.D. Thesis Abstract, Smolensk State Academy of Physical Culture, Sport, and Tourism, Dec. 11, 2020, 23 pages.
Certified English Translation of Belyaev, A.G., "Effect of Magnetic Stimulation on the Strength Capacity of Skeletal Muscles," Ph.D. Thesis, Smolensk State Academy of Physical Culture, Sport, and Tourism, Dec. 11, 2020, 117 pages.
Chattanooga Group of Encore Medical, L.P., "Intelect SWD 100 User Manual, Operation & Installation Instructions for Intelect SWD 00—Model 1600," All pages (2009).
Chesterton, L.S., et al., "Skin Temperature Response to Cryotherapy," Archives of Physical Medicine and Rehabilitation, 83(4):543-549, W.B. Saunders, United States (Apr. 2002).
Clinical Application of Electro Magnetic Stimulation, Salus-Talent, Korea Society of interventional Muscle and Soft Tissue Stimulation Therapy, CR Technology, 141 pages.
Collins, D.F., et al., "Large Involuntary Forces Consistent With Plateau-Like Behavior of Human Motoneurons," Journal of Neuroscience 21(11):4059-4065, Society for Neuroscience, United States (Jun. 2001).
Colson, S., et al., "Re-Examination of Training Effects by Electrostimulation in the Human Elbow Musculoskeletal System," International Journal of Sports Medicine 21(4):281-288, Stuttgart, Thieme (May 2000).
Course in Physical Therapy, Presentation, Jan. 4, 2013, 156 pages.
CR Technologies, "Salus Talent Pop Manual KFDA First Approval Document" (English Translation), Nov. 25, 2011, 47 pages.
CR Technologies, "Notification of medical device manufacturing item permission, Salus Talent Pop KFDA Approval Document" (English Translation), 3 pages (Sep. 2011).
CR Technology Co, Ltd., "Salus-Talent Double Sales Brochure" 2 pages, (Oct. 2020).
CR Technology Co. Ltd., "Medical Laser Irradiator Salus-Talent-Pop User Manual Version 1.00" (Nov. 2020).
CR Technology Co. Ltd., Salus Talent Pop User Manual, Ver. 1.00, All pages, Approx. 2012.
CR Technology, Salus-Talent, Technical File of Electro-magnetic Stimulator, Document No. TF-C05, 2008, 241 pages.
CR Technology, Technology for Health and Business for Human Being, investor relations, 2008, 21 pages.
CryoGenTech GmbH, Company Profile, Creating CRYO, Medica, 9 pages.
Currier, D. P., "Effects of Electrical and Electromagnetic Stimulation after Anterior Cruciate Ligament Reconstruction," The Journal of Orthopaedic and Sports Physical Therapy 17(4):177-84, Williams and Wilkins, United States (1993).
Cutera, truSculptflex, Brochure, dated 2019, 2 pages.
Cynosure, SculpSure TM, The New Shape of Energy-Based bodyContouring, 2015, Cynosure Inc, 2 pages.
Cynosure, Smooth Shapes XV, Now with Smoothshape petite, Transforming non-invasive Body Shaping, Retrieved from the Internet: (www.cynosure.com), 2011, Cynosure Inc, 8 pages.
Davies, C.T., et al., "Contractile Properties of the Human Triceps Surae With Some Observations on the Effects of Temperature and

(56) References Cited

OTHER PUBLICATIONS

Exercise," European Journal of Applied Physiology and Occupational Physiology 49(2):255-269, Springer Verlag, Germany (Aug. 1982).
Deng, Z.D., et al., "Electric Field Depth-Focality Tradeoff in Transcranial Magnetic Stimulation: Simulation Comparison of 50 Coil Designs," Brain stimulation 6(1):1-13, Elsevier, New York (Jan. 2013).
Depatment of Health and Human Services, 501(k) Letter and Summary for K092476 Body Control System 4M Powered Muscle Stimulator, dated May 7, 2010, 5 pages.
Depatment of Health and Human Services, 501(k) Letter and Summary for K160992 HPM-6000 Powered Muscle Stimulator, dated Oct. 21, 2016, 9 pages.
Depatment of Health and Human Services, 501(k) Letter and Summary for K163415 SlimShape System Powered Muscle Stimulator, dated Apr. 20, 2017, 8 pages.
Depatment of Health and Human Services, 501 (k) Letter and Summary for K182106 Btl 799-2T Powered Muscle Stimulator, dated Oct. 23, 2018, 9 pages.
Depatment of Health and Human Services, 501 (k) Letter and Summary for K190456 Btl 799-2L Powered Muscle Stimulator, dated Jul. 5, 2019, 9 pages.
Depatment of Health and Human Services, 501 (k) Letter and Summary for K192224 Btl 899 Powered Muscle Stimulator, dated Dec. 5, 2019, 11 pages.
Doucet, B., et al., "Neuromuscular Electrical Stimulation for Skeletal Muscle Function, " Yale Journal of Biology & Medicine 85:201-215, Yale Journal of Biology and Medicine, United States (Jun. 2012).
Dudley, G. and Stevenson, S., "Use of Electrical Stimulation in Strength and Power Training," Special Problems in Strength and Power Training :426-435 (2003).
Duncan, D., et al., "Noninvasive Induction of Muscle Fiber Hypertrophy and Hyperplasia: Effects of High-Intensity Focused Electromagnetic Field Evaluated in an In-Vivo Porcine Model: A Pilot Study," Aesthetic Surgery Journal 40(5):568-574, Oxford University Press, United States (Apr. 2020).
DuoMAG Magnetic Stimulator, Alien Technik User Manuel, Jun. 26, 2012,48 pages, Version 2.1.
Dybek, T., et al., "Impact of 10 Sessions of Whole Body Cryostimulation on Aerobic and Anaerobic Capacity and on Selected Blood Count Parameters," Biology of Sport, 29(1):39-43 (Jan. 2012).
Dynatronics., "Better Rehab Solutions for Better Outcomes," Rehabilitation Products Guide 2.3, 2017, 52 pages.
Effective PEMF Magnetic Fat Reduction Slimming Body Beauty Salon Machine (PEMF Star), Wolfbeauty 1980, PEMF Star, China, Retrieved from the Internet: (URL: https://www.ec21.com/product-details/Effective-PEMF-Magnetic-Fat-Reduction--8928746.html), 2019, 5 pages.
Elamed, Magnetic Therapeutic Apparatus for Running Pulse Magfield small-sized ALMAG-01 Manual, allegedly accessed on Nov. 18, 2020, All pages.
Eliminate Stubborn Fat without Surgery or Downtime and Feel Great From Every Angle, Fear No Mirror®, Consultation Guide, Coolsculpting, 2014, 20 pages.
EndyMed PRO, 3 Deep, 3 Dimensional Control of the Target Zone, A Brilliant RadioFrequency Innovation, Eclipse Aesthetics, 7 Pages.
Energist Ltd—Acquired Chromogenez—Old Account, iLipo—Laser Liposuction (i-Lipo), Video Screenshots, Aug. 10, 2009, 5 pages.
Enoka, R.M., "Muscle Strength and Its Development," Sports Medicine 6:146-168, Springer (Oct. 1988).
Epstein, C., et al., "The Oxford Handbook of Transcranial Stimulation," 773 pages (2008).
European Commission, "Neurogenerative Disorders," 10 pages printed Dec. 27, 2016.
European Patent Office, International Search Report and Written Opinion for International Application No. PCT/IB2016/053930, dated Dec. 12, 2016, 19 pages.
Exilis, Operator's Manual, BTL, 2012, 44 Pages.
Faghri, P.D., et al., "The Effects of Functional Electrical Stimulation on Shoulder Subluxation, Arm Function Recovery, and Shoulder Pain in Hemiplegic Stroke Patients," Archives of Physical Medicine and Rehabilitation 75(1):73-79, W.B. Saunders, United States (Jan. 1994).
Fischer, J., et al., "Precise Subpixel Position Measurement with Linear Interpolation of CMOS Sensor Image Data," The 6th IEEE International Conference on Intelligent Data Acquisition and Advanced Computing Systems, 500-504 (Sep. 2011).
Fisher, R., et al., "ILAE Official Report: a Practical Clinical Definition of Epilepsy, " Epilepsia, 55(4):475-482, Blackwell Science, United States (Apr. 2014).
Fujimura, K., et al., "Effects of Repetitive Peripheral Magnetic Stimulation on Shoulder Subluxations Caused by Stroke: A Preliminary Study," Neuromodulation : Journal of the International Neuromodulation Society 23(6):847-851, Wiley-Blackwell, United States (Nov. 2020).
Gaines, M., "Slendertone Abdominal Training System, the First FDA-Cleared Abdominal Belt, Introduced in United States by Compex Technologies on Time for Holiday Gift-Giving," Business Wire 44199 (Oct. 2003).
Geddes, L.A., "History of Magnetic Stimulation of the Nervous System," Journal of Clinical Neurophysiology 8(1):3-9, Lippincott Williams & Wilkins, United States (Jan. 1991).
Goetz, S.M., et al., "Coil Design for Neuromuscular Magnetic Stimulation Based on a Detailed 3-D Thigh Model," IEEE Transactions on Magnetics, 50(6):10, IEEE, (Jun. 2014).
Goodman, B.E., "Channels Active in the Excitability of Nerves and Skeletal Muscles Across the Neuromuscular Junction: Basic Function and Pathophysiology," Advances in Physiology Education 32(2):127-135, American Physiological Society, United States (Jun. 2008).
Gorgey, A., et al., "Effects of Electrical Stimulation Parameters on Fatigue in Skeletal Muscle," The Journal of Orthopaedic and Sports Physical Therapy 39(9):684-692, Williams and Wilkins, United States (Sep. 2009).
Gorodnichev, R.M., et al., "The Effect of Electromagnetic Stimulation on the Parameters of Muscular Strength," Human Physiology 40:65-69 (2014).
Gorodnichev, R.M., "Magnetic Stimulation of Muscles as New Method to Enhance Their Strength," Velikie Luki State Academy of Physical Culture and Sport, Velikie Luki, 2016, 5 pages.
Halaas, Y. and Bernardy, J., "Biochemical Perspective of Fat Physiology after Application of HIFEM Field Technology: Additional Investigation of Fat Disruption Effects in a Porcine Study," American Society for Laser Medicine and Surgery Abstracts, S4 (2019).
Hamnegard, C.H., et al., "Quadriceps Strength Assessed by Magnetic Stimulation of the Femoral Nerve in Normal Subjects," Clinical Physiology and Functional Imaging, 24(5):276-280, Blackwell, England, (Sep. 2004).
Han, B.H., et al., "Development of four-channel magnetic nerve stimulator," 2001 Proceedings of the 23rd Annual EMBS International Conference, pp. 1325-1327, Turkey (2001).
Han, T.R., et al., "Magnetic Stimulation of the Quadriceps Femoris Muscle: Comparison of Pain With Electrical Stimulation," American Journal of Physical Medicine & Rehabilitation, 85(7):593-599, Lippincott Williams & Wilkins, United States, (Jul. 2006).
Harkey, M.S., "Disinhibitory Interventions and Voluntary Quadriceps Activation: A Systematic Review," Journal of Athletic Training 49(3):411-421, National Athletic Trainers' Association, United States (2014).
Hasala, O., et al., Case Study of Treating Acute Ankle Distortion Using TMS, Charles University, Faculty of Physical Education and Sports, Prague, Czech Republic, 4 Pages.
Heidland, A., et al., "Neuromuscular Electrostimulation Techniques: Historical Aspects and Current Possibilities in Treatment of Pain and Muscle Waisting," Clinical Nephrology 79 Suppl 1:S12-S23, Dustri-Verlag Dr. Karl Feistle, Germany (Jan. 2012).
Heisel, Jurgen, Physikalische Medizin, Stuttgart: Georg Thieme Verlag KG, 2005. ISBN 3-13-139881-7. p. 159.

(56) References Cited

OTHER PUBLICATIONS

Hera Estetik Medikal, "Lipostar" dated Jul. 7, 2014, accessed at https://www.youtube.com/watch?v=-R7OnFIK9go, accessed on Dec. 15, 2021.
Hera Estetik Medikal, "Lipostar Manyetik Incelme", accessed at https://www.heraestetik.com/en/urundetay/liposter-manyetik-incelme, accessed on Dec. 15, 2021.
Hill, A., "The Influence of Temperature on the Tension Developed in an Isometric Twitch," Proceeding of the Royal Society B 138:349-354, (Sep. 1951).
Hirvonen, H.E., et al., "Effectiveness of Different Cryotherapies on Pain and Disease Activity in Active Rheumatoid Arthritis. A Randomised Single Blinded Controlled Trial, "Clinical and Experimental Rheumatology, 24(3):295-301, Clinical and Experimental Rheumatology S.A. S, Italy (May-Jun. 2006).
Hovey, C. and Jalinous, R., "The Guide to Magnetic Stimulation" Magstim, Pioneers in Nerve Stimulation and Monitoring, pp. 1-44 (2016).
Hovey, C., et al., "The Guide to Magnetic Stimulation," The Magstim Company Limited, 48 pages (Jul. 2006).
Huang, Y.Z., et al., "Theta Burst Stimulation of the Human Motor Cortex," Neuron 45(2):201-206, Cell Press, United States (Jan. 2005).
I-Lipo by Chromo genex, i-Lipo Ultra is the Intelligent, Non-Surgical Alternative to Liposuction, 2011, 2 pages.
Increasing Physiotherapy Presence in Cosmetology, Spa Inspirations, Jan. 2012, pp. 34-35.
Irazoqui P., Post Grant Review of U.S. Pat. No. 10,695,576, PTAB-PGR2021-00024, filed as EX1085, Dec. 14, 2020, 25 pages.
Iskra Medical, Magneto System, 2012, 2 pages.
Iskra Medical, "Tesla Stym—Functional Magnetic Stimulation FMS," Nov. 2013, http://ww.iskramedical.eu/magneto-therapy-medical/tesla-stym, 5 pages.
Iskra Medical, "Tesla Stym Website," URL: https://web.archive.org/web/20131106123126/http:/www.iskramedical.eu:80/magneto-therapy-medical/tesla-stym (Nov. 6, 2013).
Izumiya, Y., et al., "Fast/Glycolytic Muscle Fiber Growth Reduces Fat Mass and Improves Metabolic Parameters in Obese Mice", Cell Metabolism 7(2):159-172, Cell Press, United States (Feb. 2008).
Jacob, C., et al., "High Intensity Focused Electro-Magnetic Technology (HIFEM) for Non-Invasive Buttock Lifting and Toning of Gluteal Muscles: A Multi-Center Efficacy and Safety Study," Journal of Drugs in Dermatology 17(11):1229-1232, Physicians Continuing Education Corporation, United States (Nov. 2018).
Jacob, C.I., et al., "Safety and Efficacy of a Novel High-Intensity Focused Electromagnetic Technology Device for Noninvasive Abdominal Body Shaping," Journal of Cosmetic Dermatology, 17(5):783-787, Blackwell Science, United States (Oct. 2018).
Jacobm C., and Paskova, "A Novel Non-Invasive Technology Based on Simultaneous Induction of Changes in Adipose and Muscle Tissues: Safety and Efficacy of a High Intensity Focused Electro-Magnetic (HIFEM) Field Device Used for Abdominal Body Shaping," American Society for Laser Medicine and Surgery, 2018 Electronic Posters (ePosters) Town Hall and ePosters, 369, p. 1, Wiley Periodicals, Inc. (2018).
Jeanrenaud, B., "Lipid components of adipose tissue," Handbook of Physiology, Adipose Tissue, Chapter 15, 8 Pages.
Johari Digital Healthcare Ltd., 510(k)—K062439 Powertone Letter from Department of Health and Humane Services Summary, Public Health Service, Jan. 8, 2007, 6 pages.
Johari Digital Healthcare Ltd., "510(k)—K131291 Torc Body Letter from Department of Health and Humane Services", Public Health Service, Jun. 14, 2013, 10 pages.
Johari Digital Healthcare Ltd., K131291 510(k) Summary, TorcBody, All pages (Jun. 2013).
Jutte, L.S., et al., "The Relationship Between Intramuscular Temperature, Skin Temperature, and Adipose Thickness During Cryotherapy and Rewarming," Archives of Physical Medicine and Rehabilitation, 82(6):845-850, W.B. Saunders, United States (Jun. 2001).
Katuscakova, Z.L., et al., High Induction Magnet Therapy in Rehabilitation, Department of Physiactric Rehabilitation, 2012, 72 pages.
Katz, B., et al., "Changes in Subcutaneous Abdominal Fat Thickness Following High-Intensity Focused Electro-Magnetic (HIFEM) Field Treatments: A Multi Center Ultrasound Study," American Society for Laser Medicine and Surgery Abstracts, 360-361 (2018).
Katz, B., et al., "Ultrasound Assessment of Subcutaneous Abdominal Fat Thickness after Treatments with a High-Intensity Focused Electromagnetic Field Device: A Multicenter Study," Dermatologic Surgery 45(12):1542-1548, Williams & Wilkins, United States (Dec. 2019).
Kavanagh, S., et al., "Use of a Neuromuscular Electrical Stimulation Device for Facial Muscle Toning: A Randomized, Controlled Trial," Journal of Cosmetic Dermatology 11(4):261-266, Blackwell Science, United States (Dec. 2012).
Kent, D., and Jacob C., "Computed Tomography (CT) Based Evidence of Simultaneous Changes in Human Adipose and Muscle Tissues Following a High Intensity Focused Electro-Magnetic Field (HIFEM) Application: A New Method for Non-Invasive Body Sculpting," American Society for Laser Medicine and Surgery Abstracts, p. 370 (2018).
Kent, D,E. and Jacob, C.I., Simultaneous Changes in Abdominal Adipose and Muscle Tissues Following Treatments by High-Intensity Focused Electromagnetic HIFEM Technology-Based Device: Computed Tomography Evaluation, Journal of Drugs in Dermatology 18(11):1098-1102, Physicians Continuing Education Corporation, United States (Nov. 2019).
Kim, Y.H., et al.,"The Effect of Cold Air Application on Intra-Articular and Skin Temperatures in the Knee," Yonsei Medical Journal, 43(5):621-626, Yonsei University, Korea (South) (Oct. 2002).
Kinney, B.M. and Lozanova P., "High Intensity Focused Electromagnetic Therapy Evaluated by Magnetic Resonance Imaging: Safety and Efficacy Study of a Dual Tissue Effect Based Non-Invasive Abdominal Body Shaping," Lasers in Surgery and Medicine 51(1):40-46, Wiley-Liss, United States (Jan. 2019).
Kocbach et al., "A Simulation Approach to Optimizing Perfermance of Equipment for Thermostimulation of Muscle Tissue using COMSOL Multiphysics" Article in Biophysics & Bioeng. dated 2011, 26 pages.
Kolin, A., et al., "Stimulation of Irritable Tissues by means of an Alternating Magnetic Field," Proceedings of the Society for Experimental Biology and Medicine 102:251-253, Blackwell Science, United States (Oct. 1959).
Korman, P., et al., "Temperature Changes In Rheumatoid Hand Treated With Nitrogen Vapors and Cold Air," Rheumatology International, 32(10):2987-2992, Springer International, Germany (Oct. 2012).
Kotz, Y., "Theory and Practice of Physical Culture," Training of Skeletal Muscle With Method of Electrostimulation, 64-67 (Mar. 1971).
Kotz, Y., "Theory and Practice of Physical Culture," Training of Skeletal Muscle With Method of Electrostimulation, 66-72 (Apr. 1971).
Krueger, N. et al., "Safety and Efficacy of a New Device Combining Radiofrequency and Low-Frequency Pulsed Electromagnetic Fields for the Treatment of Facial Rhytides," Journal of Drugs in Dermatology 11(11):1306-1309, Physicians Continuing Education Corporation, United States (Nov. 2012).
Kumar, N. and Agnihotri, R.C., "Effect of Frequency and Amplitude of Fes Pulses on Muscle Fatigue During Toning of Muscles," Journal of Scientific and Industrial Research 67(4):288-290, (Apr. 2008).
Lampropoulou, S.I., et al., "Magnetic Versus Electrical Stimulation in the Interpolation Twitch Technique of Elbow Flexors," Journal of Sports Science and Medicine, 11(4):709-718, Dept. of Sports Medicine, Medical Faculty of Uludag University, Turkey (Dec. 2012).
Langford, J. and McCarthy, P.W., "Randomised controlled clinical trial of magnet use in chronic low back pain; a pilot study," Clinical Chiropractic 8(1):13-19, Elsevier (Mar. 2005).
Lee, P.B., et al., "Efficacy of Pulsed Electromagnetic Therapy for Chronic Lower Back Pain: a Randomized, Double-blind, Placeb-

(56) References Cited

OTHER PUBLICATIONS controlled Study," The Journal of International Medical Research 34(2):160-167, Cambridge Medical Publications, England (Mar.-Apr. 2006).
Leitch, M., et al., "Intramuscular Stimulation of Tibialis Anterior in Human Subjects: The Effects of Discharge Variability on Force Production and Fatigue," Physiological Reports 5(15):e13326, Wiley Periodicals, Inc., United States (Aug. 2017).
Leon-Salas, W.D., et al., "A Dual Mode Pulsed Electro-Magnetic Cell Stimulator Produces Acceleration of Myogenic Differentiation," Recent Patents on Biotechnology 7(1):71-81, Bentham Science Publishers, United Arab Emirates (Apr. 2013).
Letter from Department of Health and Human Services, Public Health Service, Dec. 19, 2014, 7 pages.
Lin, V.W., et al., "Functional Magnetic Stimulation: A New Modality for Enhancing Systemic Fibrinolysis," Archives of Physical Medicine and Rehabilitation 80(5):545-550, W.B. Saunders, United States (May 1999).
Lin, V.W., et al., "Functional Magnetic Stimulation for Conditioning of Expiratory Muscles in Patients with Spinal Cord Injury.," Archives of Physical medicine and Rehabilitation 82(2):162-166, W.B. Saunders, United States (Feb. 2001).
Lin, V.W., et al., "Functional Magnetic Stimulation for Restoring Cough in Patients With Tetraplegia," Archives of Physical Medicine and Rehabilitation, 79(5):517-522, W.B. Saunders, United States, (May 1998).
Lin, V.W., et al., "Functional Magnetic Stimulation of Expiratory Muscles: a Noninvasive and New Method for Restoring Cough," Journal of Applied Physiology (1985), 84(4):1144-1150, American Physiological Society, United States, (Apr. 1998).
Lin, V.W., et al., "Functional Magnetic Stimulation of the Respiratory Muscles in Dogs," Muscle & Nerve 21(8):1048-1057, John Wiley & Sons, United States (Aug. 1998).
Linehan, C., et al., Brainwave the Irish EpilepsyAssoication, "The Prevalence of Epilepsy in Ireland" Summary Report,pp. 1-8 (May 2009).
Lotz, B.P., et al., "Preferential Activation of Muscle Fibers with Peripheral Magnetic Stimulation of the Limb," Muscle & Nerve, 12(8):636-639, John Wiley & Sons, United States (Aug. 1989).
*Lumenis Be Ltd.* v. *BTL Healthcare Technologies A.S.*, PTAB-IPR2021-01402, Declaration of Dr. Marom Bikson (EX1002), Sep. 13, 2021, 244 pages.
*Lumenis Be Ltd.* v. *BTL Healthcare Technologies A.S.*, PTAB-IPR2021-01402, U.S. Pat. No. 10,821,295 Petition for Inter Partes Review, Sep. 13, 2021, 81 pages.
*Lumenis Be Ltd.* v. *BTL Healthcare Technologies A.S.*, PTAB-IPR2021-01403, Declaration of Dr. Marom Bikson (EX1002), Sep. 13, 2021, 243 pages.
*Lumenis Be Ltd.* v. *BTL Healthcare Technologies A.S.*, PTAB-IPR2021-01403, U.S. Pat. No. 10,821,295 Petition for Inter Partes Review, Sep. 13, 2021, 84 pages.
*Lumenis Be Ltd.* v. *BTL Healthcare Technologies A.S.*, PTAB-IPR2021-01404, Declaration of Dr. Marom Bikson (EX1002), Sep. 13, 2021, 245 pages.
*Lumenis Be Ltd.* v. *BTL Healthcare Technologies A.S.*, PTAB-IPR2021-01404, U.S. Pat. No. 10,124,187 Petition for Inter Partes Review, Sep. 13, 2021, 82 pages.
*Lumenis Be Ltd.* v. *BTL Healthcare Technologies A.S.*, PTAB-IPR2021-01405, Declaration of Dr. Marom Bikson (EX1002), Sep. 13, 2021, 247 pages.
*Lumenis Be Ltd.* v. *BTL Healthcare Technologies A.S.*, PTAB-IPR2021-01405, U.S. Pat. No. 10,124,187 Petition for Inter Partes Review, Sep. 13, 2021, 86 pages.
*Lumenis Be Ltd.* v. *BTL Healthcare Technologies A.S.*, PTAB-IPR2022-00126, Declaration of Dr. Marom Bikson (EX1002), Nov. 10, 2021, 263 pages.
*Lumenis Be Ltd.* v. *BTL Healthcare Technologies A.S.*, PTAB-IPR2022-00126, U.S. Pat. No. 10,695,576 Petition for Inter Partes Review, Nov. 10, 2021, 83 pages.
*Lumenis Be Ltd.* v. *BTL Healthcare Technologies A.S.*, PTAB-IPR2022-00127, Declaration of Dr. Marom Bikson (EX1002), Nov. 10, 2021, 269 pages.
*Lumenis Be Ltd.* v. *BTL Healthcare Technologies A.S.*, PTAB-IPR2022-00127, U.S. Pat. No. 10,695,576 Petition for Inter Partes Review, Nov. 10, 2021, 84 pages.
*Lumenis Be Ltd.* v. *BTL Healthcare Technologies A.S.*, PTAB-IPR2021-01273, Declaration of Dr. Marom Bikson (EX1002), Aug. 13, 2021, 225 pages.
*Lumenis Be Ltd.* v. *BTL Healthcare Technologies A.S.*, PTAB-IPR2021-01273, U.S. Pat. No. 10,478,634, Petition for Inter Partes Review, Aug. 13, 2021, 70 pages.
*Lumenis Be Ltd.* v. *BTL Healthcare Technologies A.S.*, PTAB-IPR2021-01275, Declaration of Dr. Marom Bikson (EX1002), Aug. 5, 2021, 282 pages.
*Lumenis Be Ltd.* v. *BTL Healthcare Technologies A.S.*, PTAB-IPR2021-01275, U.S. Pat. No. 10,632,321, Petition for Inter Partes Review, Aug. 5, 2021, 92 pages.
*Lumenis Be Ltd.* v. *BTL Healthcare Technologies A.S.*, PTAB-IPR2021-01276, Declaration of Dr. Marom Bikson (EX1002), Aug. 5, 2021, 241 pages.
*Lumenis Be Ltd.* v. *BTL Healthcare Technologies A.S.*, PTAB-IPR2021-01276, U.S. Pat. No. 10,965,575, Petition for Inter Partes Review, Aug. 5, 2021, 79 pages.
*Lumenis Be Ltd.* v. *BTL Healthcare Technologies A.S.*, PTAB-IPR2021-01278, Declaration of Dr. Marom Bikson (EX1002), Aug. 13, 2021, 255 pages.
*Lumenis Be Ltd.* v. *BTL Healthcare Technologies A.S.*, PTAB-IPR2021-01278, U.S. Pat. No. 10,709,894, Petition for Inter Partes Review, Aug. 13, 2021, 85 pages.
*Lumenis Be Ltd.* v. *BTL Healthcare Technologies A.S.*, PTAB-IPR2021-01279, Declaration of Dr. Marom Bikson (EX1002), Aug. 5, 2021, 258 pages.
*Lumenis Be Ltd.* v. *BTL Healthcare Technologies A.S.*, PTAB-IPR2021-01279, U.S. Pat. No. 10,709,895, Petition for Inter Partes Review, Aug. 5, 2021, 88 pages.
*Lumenis Be Ltd.* v. *BTL Healthcare Technologies A.S.*, PTAB-IPR2021-01280, Declaration of Dr. Marom Bikson (EX1002), Aug. 13, 2021, 235 pages.
*Lumenis Be Ltd.* v. *BTL Healthcare Technologies A.S.*, PTAB-IPR2021-01280, U.S. Pat. No. 10,478,634, Petition for Inter Partes Review, Aug. 13, 2021, 69 pages.
*Lumenis Be Ltd.* v. *BTL Healthcare Technologies A.S.*, PTAB-IPR2021-01282, Declaration of Dr. Marom Bikson (EX1002), Aug. 5, 2021, 267 pages.
*Lumenis Be Ltd.* v. *BTL Healthcare Technologies A.S.*, PTAB-IPR2021-01282, U.S. Pat. No. 10,632,321, Petition for Inter Partes Review, Aug. 5, 2021, 89 pages.
*Lumenis Be Ltd.* v. *BTL Healthcare Technologies A.S.*, PTAB-IPR2021-01283, Declaration of Dr. Marom Bikson (EX1002), Aug. 5, 2021, 241 pages.
*Lumenis Be Ltd.* v. *BTL Healthcare Technologies A.S.*, PTAB-IPR2021-01283, U.S. Pat. No. 10,695,575, Petition for Inter Partes Review, Aug. 5, 2021, 84 pages.
*Lumenis Be Ltd.* v. *BTL Healthcare Technologies A.S.*, PTAB-IPR2021-01284, Declaration of Dr. Marom Bikson (EX1002), Aug. 5, 2021, 279 pages.
*Lumenis Be Ltd.* v. *BTL Healthcare Technologies A.S.*, PTAB-IPR2021-01284, U.S. Pat. No. 10,709,895, Petition for Inter Partes Review, Aug. 5, 2021, 93 pages.
*Lumenis Be Ltd.* v. *BTL Healthcare Technologies A.S.*, PTAB-IPR2021-01285, Declaration of Dr. Marom Bikson (EX1002), Aug. 13, 2021, 249 pages.
*Lumenis Be Ltd.* v. *BTL Healthcare Technologies A.S.*, PTAB-IPR2021-01285, U.S. Pat. No. 10,709,894, Petition for Inter Partes Review, Aug. 13, 2021, 79 pages.
Madariaga, V.B., et al., "[Magnetic Stimulation of the Quadriceps: Analysis of 2 Stimulators Used for Diagnostic and Therapeutic Applications]," Archivos De Bronconeumología, 43(7):411-417, Elsevier Espana, Spain, (Jul. 2007).
Maffiuletti, N.A., et al., "Activation of Human Plantar Flexor Muscles Increases After Electromyostimulation Training," Journal

(56) References Cited

OTHER PUBLICATIONS of Applied Physiology 92(4):1383-1392, American Physiological Society, United States (Nov. 2001).

Maffiuletti, N.A., et al., "The Effects of Electromyostimulation Training and Basketball Practice on Muscle Strength and Jumping Ability," International journal of sports medicine 21(6):437-443, Thieme, Germany (Aug. 2000).

MAG and More Gmbh, Magnetic and Life Science System, Power Mag, 12 Pages.

Mag Venture, Magnetic Stimulation, Accessories Catalogue, Accessories Catalogue, 2011, 54 pages.

Magstim Company Limited, K051864 510(k) Summary, Magstim Rapid and Magstim Super Rapid, All pages (Dec. 2005).

Magstim Company US, LLC, K060847 510(k) Summary, Magstim Model 200-2 with Double 70mm Remote Coil, All pages (Sep. 2006).

Magstim Corporation US, K992911 510(k) Summary, Magstim Rapid, All pages (Jan. 2000).

Magventure, MagPro® by MagVenture®, Versatility in Magnetic Stimulation, World Leading Transcranial Magnetic Stimulation Systems, 2011, 6 Pages.

Man, W.D-C., et al., "Magnetic Stimulation for the Measurement of Respiratory and Skeletal Muscle Function," The European Respiratory Journal 24(5):846-60, European Respiratory Society, England (2004).

Manstein, D., et al., "Selective Cryolysis: A Novel Method of Non-Invasive Fat Removal," Lasers in Surgery and Medicine, 40(9):595-604, Wiley-Liss, United States (Nov. 2008).

Mantovani, A., et al., "Applications of Transcranial Magnetic Stimulation to Therapy in Pyschiatry," Psychiatric Times 21(9), Intellisphere, 29 pages (Aug. 2004).

Marek Heinfarth, "Lipostar" dated Jan. 10, 2013, accessed at https://www.youtube.com/watch?v=hZurkn8iU_U, accessed on Dec. 15, 2021.

Markov, M.S., "Pulsed Electromagnetic Field Therapy History, State of the Art and Future," Environment Systems and Decisions 27(4):465-475, Springer (Dec. 2007).

MecoTec Freezing Technology, Presentation Cryoair Whole Body Cryotherapy Chambers, Germany, Jul. 2017, 52 Pages.

Medline, Body Temperature Norms, 2 pages (Year: 2019).

Mekawy et al., "Influence of Electro-lipolysis on Lipid Profile and Central Obesity in Obese Premenopausal Women" Bull. Fac. Ph. Th. Cairo Univ., vol. 17, No. (1), dated Jan. 2012, pp. 59-68.

Mettler J.A., et al., "Low-Frequency Electrical Stimulation With Variable Intensity Preserves Torque," Journal of Electromyography and Kinesiology : Official Journal of the International Society of Electrophysiological Kinesiology 42:49-56, Oxford:Elsevier, England (Oct. 2018).

Mogyoros, I., et al., "Strength-Duration Properties of Human Peripheral Nerve," Brain 119(Pt 2):439-447, Oxford University Press, England (Apr. 1996).

Moon, Chi-Woong"Study on the Pulsed Electromagnetic Fields Effect of Adipocyte Decomposition" Final Report of a Middle-grade Researcher Support Project, Inje University, 2017.

Morrissey. M., "Electromyostimulation from a Clinical Perspective," Sports Medicine 6(1):29- 41, Springer International, New Zealand (Aug. 1988).

Mustafa, B., "Design and Construction of a Low Cost dsPIC Controller Based Repetitive Transcranial Magnetic Stimulator TMS," Journal of medical systems 34(1):15-24, Kluwer Academic/Plenum Publishers, United States (2010).

Nadler, S.F., et al., "The Physiologic Basis and Clinical Applications of Cryotherapy and Thermotherapy for the Pain Practitioner," Pain Physician, 7(3):395-399, American Society of Interventional Pain Physicians, United States (Jul. 2004).

Nassab, R., "The Evidence Behind Noninvasive Body Contouring Devices," Aesthetic Surgery Journal, 35(3):279-293, Oxford University Press, England (Mar. 2015).

National Institute of Neurological Disorders and Stroke, Epilepsy Information Page, www.ninds.nih.gov/disorders/epilepsy/epilepsy.htm, pp. 1-6 (Feb. 1, 2016).

Neotonus, Inc., K973096 510(k) Summary, Neotonus Model 1000 Muscle Stimulator System, All pages (Jun. 1998).

Neotonus, Inc., K973929 510(k) Summary and FDA Correspondence, Neotonus, All pages (May 1998).

Neuro Star , TMS Therapy, Bringing Hope to Patients with Depression, 2013, 6 Pages.

Neurosoft, Ivanovo, Since 1992, Magnetic Stimulator, NEURO-MS, Technical Manual, Neurosoft Ltd, Ivanovo, Russia, 2006, 67 Pages.

Nexstim NBS System, Navigated Brain Stimulation, Noninvasive, direct cortical mapping, 2012, 5 Pages.

Neyroud, D., et al., "Comparison of Electrical Nerve Stimulation, Electrical Muscle Stimulation and Magnetic Nerve Stimulation to Assess the Neuromuscular Function of the Plantar Flexor Muscles," European journal of applied physiology 115(7):1429-1439, Springer-Verlag, Germany (2015).

Nielsen, J.F., et al., "A New High-frequency Magnetic Stimulator With an Oil-cooled Coil," Journal of Clinical Neurophysiology 12(5):460-467, Lippincott Williams & Wilkins, United States (Sep. 1995).

Non Final Office Action mailed Jun. 23, 2017, in U.S. Appl. No. 15/473,390, Schwarz, T., et al., filed Mar. 29, 2017.

Novickij, V., et al., "Compact Microsecond Pulsed Magnetic Field Generator for Application in Bioelectronics," Elektronika ir Elektrotechnika 19(8):25-28 (Oct. 2013).

Novickij, V., et al., "Design and Optimization of Pulsed Magnetic Field Generator for Cell Magneto-Permeabilization," Elektronika ir Elektrotechnika(Electronics and Electrical Engineering) 23(2):21-25 (Apr. 2017).

Novickij, V., et al., "Magneto-Permeabilization of Viable Cell Membrane Using High Pulsed Magnetic Field," IEEE Transactions on Magnetics 51(9), All pages (Sep. 2015).

Novickij, V., et al., "Programmable Pulsed Magnetic Field System for Biological Applications," IEEE Transactions on Magnetics 50(11):5 (Nov. 2014).

NPF Electroapparat, Amplipulse-5Br Manual, allegedly accessed on Nov. 18, 2020, All pages.

Nuerosoft Ltd., "Neurosoft—Neuro-MS Transcranial Magnetic Simulator Technical Manual," All pages (Nov. 2014).

Obsluze, N.K., Usage Instructions, User's Manual, Device for high-induction magnetic stimulation of type designation: Saluter Moti, 2016,88 Pages.

Oliveira, P.De., et al., "Neuromuscular Fatigue After Low-and Medium-frequency Electrical Stimulation in Healthy Adults," Muscle & Nerve 58(2):293-299, John Wiley & Sons, United States (Aug. 2018).

Operating Manual: Magstim D70² Coil, MOP06-EN, Revision 01, The Magstim Company Limited, Feb. 2012, 14 Pages.

Operating Manual: Magstim Magstim 2002, MOP01-EN, Revision 01, The Magstim Company Limited, Sep. 2011, 25 Pages.

Operating Manual: Magstim, Magstim Alpha Coil Range, MOP11-EN, Revision 01, Oct. 2012, 18 Pages.

Operating Manual: Magstim, Magstim Bistim², MOP02-EN, Revision, The Magstim Company Limited, 01, Sep. 2011, 27 Pages.

Operating Manual, Magstim, Model 200, P/N 3001-01, Double 70mm, Remote Coil, P/N 3190-00, The Magstim Company Limited, 2006, 32 pages.

Operating Manual: Magstim R, 2nd, Generation Coil Family, 3100-23-02, Magstim Coils, The Magstim Company Limited, Nov. 2002, 14 Pages.

Operating Manual, Magstim R Air-Cooled Double 70mm Coil System, 1600-23-04, The Magstim Company Limited, 1999, 18 Pages.

Operating Manual: Magstim R, Bistim System, P/N 3234-23-01, The Magstim Company Limited, Nov. 2004, 30 Pages.

Operating Manual: Magstim R, Coils & Accessories, 1623-23-07, Magstim Coils & Accessories, May 2010, 24 Pages.

Operating Manual: Magstim, RAPID2, P/N 3576-23-09, The Magstim Company Ltd, Nov. 2009, 61 Pages.

(56) References Cited

OTHER PUBLICATIONS

Operator's Manual: BTL Emsculpt, BTL Industries Ltd, United Kingdom, 2018, 35 pages.
Operator's Manual: BTL, HPM-6000U, BTL Industries Ltd, United Kingdom, Dec. 2016, 36 pages.
Otte, J.S., et al., "Subcutaneous Adipose Tissue Thickness Alters Cooling Time During Cryotherapy,"Archives of Physical Medicine and Rehabilitation, 83(11):1501-1505, W.B. Saunders, United States (Nov. 2002).
Pain Management Technologies, "Pain Management Technologies Product Catalog," (2012).
Papimi, For Scientific Research, Pap Ion Magnetic Inductor, Presentation, Magnetotherapeutic Device, Nov. 2009, 61 Pages.
Periso SA, CTU mega Diamagnetic Pump 20: Device for Diamagnetic Therapy, CTU Mega 20 Manual, dated Aug. 28, 2019, 44 pages, Pazzallo Switzerland.
Photograph, Alleged Photograph of Components of a Salus Talent Pop Double Device with an Alleged Manufacture date of Nov. 14, 2012, 1 page.
Physiomed, MAG-Expert, Physiomed Manual, Dec. 19, 2012.
Platil, A., "Magnetopneumography Using Optical Position Reference," Sensor Letters 11(1):69-73, ResearchGate (2013).
Podebradsky.K., et al., Clinical study of high-inductive electromagnetic stimulator Salus talent, 2010, 8 pages.
Pohanka, J., et al., "An Embedded Stereovision System: Aspects of Measurement Precision," 12th Biennial Baltic Electronics Conference, pp. 157-160 (Oct. 2010).
Polk, C., "Therapeutic Applications of Low-Frequency Sinusoidal and Pulsed Electric and Magnetic Fields," The Biomedical Engineering Handbook, vol. 1, 2000, Second edition, CRC Press LLC, pp. 1625-1636.
Polkey M.I., et al., "Functional Magnetic Stimulation of the Abdominal Muscles in Humans, " American Journal of Respiratory and Critical Care Medicine 160(2):513-522, American Thoracic Society, United States (Aug. 1999).
Polkey, M.I., et al., "Quadriceps Strength and Fatigue Assessed by Magnetic Stimulation of the Femoral Nerve in Man," Muscle Nerve 19(5):549-555, John Wiley & Sons, United States, (May 1996).
Pollogen, Maximus Non-invasive body shaping System, User Manual, dated May 1, 2012, 44 pages.
Pollogen, TriFractional FAQs, User Manual, dated Aug. 2011, 4 pages.
Pollogen, TriLipo MED Procedure, Brochure, dated Apr. 7, 2021, 76 pages.
Porcari, J.P., et al., "Effects of Electrical Muscle Stimulation on Body Composition, Muscle Strength, and Physical Appearance," Journal of Strength and Conditioning Reasearch 16(2):165-172, Human Kinetics Pub., United States (May 2002).
Porcari, J.P., et al., "The Effects of Neuromuscular Electrical Stimulation Training on Abdominal Strength, Endurance, and Selected Anthropometric Measures," Journal of Sports Science and Medicine 4(1):66-75, Dept. of Sports Medicine, Turkey (Mar. 2005).
Pribula, O. and Fischer, J., "Real Time Precise Position Measurement Based on Low-Cost CMOS Image Sensor," IEEE, 5 pages (2011).
Pribula, O., et al., "Cost-effective Image Acquisition System for Precise Pc-based Measurements," Przeglad Elektrotechniczny (Electrical Review), 259-263, 2011,.
Pribula, O., et al., "Optical Position Sensor Based on Digital Image Processing: Magnetic Field Mapping Improvement," Radioengineering 20 (1):55-60, (Apr. 2011).
Pribula, O., et al., "Real-Time Video Sequences Matching Spatio-Temporal Fingerprint," IEEE, 911-916 (Jun. 2010).
Prouza, O., et al., "High-Intensity Electromagnetic Stimulation Can Reduce Spasticity in Post-Stroke Patients," International Journal of Physiotherapy 5(3):87-91 (2018).
Prouza, O., "Ex-Post Analyza Spot Rebnich Dani," All pages, (2008).
Prouza, O., "Targeted Radiofrequency Therapy for Training Induced Muscle Fatigue—Effective or Not?," International Journal of Physiotherapy 3(6):707-710 (Dec. 2016).
PTAB-IPR2021-00296, U.S. Pat. No. 10,493,293, Petition for Inter Partes Review, Dec. 14, 2020, 117 pages.
PTAB-IPR2021-00312, U.S. Pat. No. 10,478,634, Petition for Inter Partes Review, Dec. 14, 2020, 108 pages.
PTAB-PGR2021-00015, U.S. Pat. No. 10,709,895, Petition for Post-Grant Review, Dec. 14, 2020, 140 pages.
PTAB-PGR2021-00016, U.S. Pat. No. 10,709,895, Petition for Post-Grant Review, Dec. 14, 2020, 144 pages.
PTAB-PGR2021-00017, U.S. Pat. No. 10,632,321, Petition for Post-Grant Review, Dec. 14, 2020, 121 pages.
PTAB-PGR2021-00018, U.S. Pat. No. 10,632,321, Petition for Post-Grant Review, Dec. 14, 2020, 140 pages.
PTAB-PGR2021-00020, U.S. Pat. No. 10,695,575, Petition for Post-Grant Review, Dec. 14, 2020, 112 pages.
PTAB-PGR2021-00021, U.S. Pat. No. 10,695,575, Petition for Post-Grant Review, Dec. 14, 2020, 117 pages.
PTAB-PGR2021-00022, U.S. Pat. No. 10,709,894, Petition for Post-Grant Review, Dec. 14, 2020, 119 pages.
PTAB-PGR2021-00023, U.S. Pat. No. 10,709,894, Petition for Post-Grant Review, Dec. 14, 2020, 136 pages.
PTAB-PGR2021-00024, U.S. Pat. No. 10,695,576, Petition for Post-Grant Review, Dec. 14, 2020, 136 pages.
PTAB-PGR2021-00025, U.S. Pat. No. 10,695,576, Petition for Post-Grant Review, Dec. 14, 2020, 135 pages.
Publication of Medical Device Manufacturing Approval of Salus-Talent-Pro, approval date Mar. 11, 2014, 39 pages.
Quick Start Manuals, Magstim Super Rapid Plus Quick Start, Aalto TMS Laboratory, Aalto School of Science, 2013, 7 Pages.
Radakovic T. and Radakovic N., "The Effectiveness of the Functional Magnetic Stimulation Therapy in Treating Sciatica Syndrome," Open Journal of Therapy and Rehabilitation 3(3):63-69 (2015).
Reaction User Manual, Viora, Doc No. MK-004 A, 2008, 53 Pages.
Reshaping the Future of Your Practice, Cool sculpting, A Revolution in Aesthetic Fat Reduction, 2011, 10 Pages.
Riehl., M., "Chapter 3: TMS Stimulator Design" The Oxford Handbook of Transcranial Stimulation, Wasserman, E.M., ed., pp. 13-23, Oxford University Press, 26 pages. United Kingdom (2008).
Roots, H., and Ranatunga, K.W., "An Analysis of the Temperature Dependence of Force, During Steady Shortening at Different Velocities, in (Mammalian) Fast Muscle Fibres," Journal of Muscle Research and Cell Motility 29(1):9-24, Springer, Netherlands (Jun. 2008).
Ruiz-Esparza, J. and J. Barba Gomez., "The Medical Face Lift: A Noninvasive, Nonsurgical Approach to Tissue Tightening in Facial Skin Using Nonablative Radiofrequency," Dermatologic Surgery 29(4):325-332, Williams & Wilkins, United States (Apr. 2003).
Russian excerpt of Werner, R., Magnetotherapy, Pulsating energy resonance therapy, 41-67 (Jun. 2007).
Rutkove, S., "Effects of Temperature on Neuromuscular Electrophysiology," Muscle & Nerve 24(7):867-882, John Wiley & Sons, United States (Jul. 2001).
Salus Talent Pop, The first sales bill, Authorization No. 20120221-41000096-66667961, 2 pages, (Feb. 2012).
Salus Talent-A, Remed, User Guide, High Intensity Electro Magnetic Field Therapy, 2017, 37 pages.
Sargeant, A.J., "Effect of Muscle Temperature on Leg Extension Force and Short-term Power Output in Humans," European Journal of Applied Physiology and Occupational Physiology 56(6):693-698, Springer Verlag, Germany (Sep. 1987).
Schaefer, D.J., et al., "Review of Patient Safety in Time-Varying Gradient Fields," Journal of Magnetic Resonance Imaging 12:20-29, Wiley-Liss, United States (Jul. 2000).
Shimada, Y., et al., "Effects of therapeutic magnetic stimulation on acute muscle atrophy in rats after hindlimb suspension," Biomedical Research 27(1):23-27, Biomedical Research Foundation, Japan (Feb. 2006).

(56) References Cited

OTHER PUBLICATIONS

Silinskas, V., et al., "Effect of Electrical Myostimulation on the Function of Lower Leg Muscles," Journal of strength and Conditioning Research 31(6):1577-1584, Human Kinetics Pub, United States (2017).
Sport-Elec S.A., K061914 510(k) Summary, Sport-Elec, All pages (Jul. 2007).
Sport-Elec S.A., K081026 510(k) Summary, Sport-Elec, All pages (Nov. 2008).
Starbelle, PEMF Shape, Webpage, dated Feb. 10, 2020, 3 pages, available at http://www.starbelle.cn/info/PEMFShape.html.
Stedman, T.L., "Aponeurosis—Apparatus," in Stedman's Medical Dictionary, 27th Edition, Pugh, M.B., ed., pp. 113-114, Lippincott Williams & Wilkins, Baltimore, MD (2000).
Stevens, J.E., et al., "Neuromuscular Electrical Stimulation for Quadriceps Muscle Strengthening After Bilateral Total Knee Arthroplasty: A Case Series," Journal of Orthopaedic and Sports Physical Therapy 34(1):21-29, Williams and Wilkins, United States (Jan. 2004).
Struppler, A., et al., "Facilitation of Skilled Finger Movements by Repetitive Peripheral Magnetic Stimulation (RPMS)—A New Approach In Central Paresis.," NeuroRehabilitation 18(1):69-82, IOS Press, Amsterdam (2003).
Struppler, A., et al., "Modulatory Effect of Repetitive Peripheral Magnetic Stimulation on Skeletal Muscle Tone in Healthy Subjects: Stabilization of the Elbow Joint," Experimental Brain Research 157(1):59-66, Springer Verlag, Germany (Feb. 2004).
Suarez-Bagnasco, D., et al., "The Excitation Functional for Magnetic Stimulation of Fibers.," Annual International Conference of the IEEE Engineering in Medicine and Biology Society, IEEE Engineering in Medicine and Biology Society, Annual International Conference, 2010:4829-4833, IEEE, United States (2010).
Swallow, E.B., et al., "A Novel Technique for Nonvolitional Assessment of Quadriceps Muscle Endurance in Humans," Journal of Applied Physiology 103(3):739-746, American Physiological Society, United States (Sep. 2007).
Szecsi, J., et al., "A Comparison of Functional Electrical and Magnetic Stimulation for Propelled Cycling of Paretic Patients," Archives of Physical Medicine and Rehabilitation 90(4):564-570, W.B. Saunders, United States, (Apr. 2009).
Szecsi, J., et al., "Force-pain Relationship in Functional Magnetic and Electrical Stimulation of Subjects With Paresis and Preserved Sensation," Clinical Neurophysiology 121(9):1589-1597, Elsevier, Netherlands, (Sep. 2010).
Taylor, J.L, "Magnetic Muscle Stimulation Produces Fatigue Without Effort," Journal of Applied Physiology (1985) 103(3):733-734, American Physiological Society, United States, (Sep. 2007).
Tesla Stym, Iskra Medical, Tone the inner muscle with FMS Functional Magnetic Stimulation, 2013, 4 pages.
The Burn Centre Care, Education, 3 pages, printed from internet Nov. 13, 2017.
The Magstim Company Ltd, K080499 510(k) Summary, Magstim Double 70mm Air Film Coil, All pages (Dec. 2008).
The Magstim Company Ltd., K130403 510(k) Summary, Magstim D702 coil, All pages (Aug. 2013).
Thermi Launches Arvati, powered by Thermi, with newest advances in True Temperature Controlled Radiofrequency Technology, 5 pages (2018).
Thompson, M.T., "Inductance Calculation Techniques—Part II: Approxmiations and Handbook Methods," Power Control and Intelligent Motion, 11 pages (Dec. 1999) http://www.pcim.com/.
Thompson, M.T., "Inductance Calculation Techniques—Part II: Classical Methods," Power Control and Intelligent Motion, 25(12):40-45, (Dec. 1999) http://www.pcim.com/.
Tomek, J., et al., "Magnetopneumography—Incorporation of optical position reference," Journal of Electrical Engineering, All pages (2012).
Torbergsen, T., "Abstracts of the International Course and Symposium in Single Fibre EMG and Quantitative EMG Analysis. Tromsø, Norway, Jun. 4-8, 1984," Muscle & Nerve 9(6):562-574, John Wiley & Sons, United States (Jul.-Aug. 1986).
TSEM Med Swiss SA, Diamagnetic Therapy: A Revolutionary Therapy, CTU Mega 20 Catalogue, dated 2016, 24 pages, Lugano Switzerland.
Turley, J., "Agilent Technologies Announces 30 MHz Function/Arbitrary Waveform Generators with Unparalleled Signal Accuracy," Elec. Eng'g J., URL: (Aug. 4, 2010), 8 pages.
Ultra Slim Professional, The very best body Contouring, Wardphotonics LLC, 2018, 16 pages.
Uro Diagnostic Clinic, Now in UDC, Automated pelvic floor muscle training, QRS International AG, 16 Pages.
U.S. Appl. No. 60/848,720, inventor Burnett, D., filed Sep. 30, 2006 (Not Published).
U.S. Appl. No. 62/331,060, inventor Schwarz, T., filed May 3, 2016 (Not Published).
U.S. Appl. No. 62/331,072, inventor Schwarz, T., filed May 3, 2016 (Not Published).
U.S. Appl. No. 62/331,088, inventor Schwarz, T., filed May 3, 2016 (Not Published).
U.S. Appl. No. 62/333,666, inventor Schwarz, T., filed May 9, 2016 (Not Published).
U.S. Appl. No. 62/351,156, inventor Schwarz, T., filed Jun. 16, 2016 (Not Published).
U.S. Appl. No. 62/357,679, inventor Schwarz, T., filed Jul. 1, 2016 (Not Published).
U.S. Appl. No. 62/440,905, inventors Schwarz, T. et al., filed Dec. 30, 2016 (Not Published).
U.S. Appl. No. 62/440,912, inventors Schwarz, T. et al., filed Dec. 30, 2016 (Not Published).
U.S. Appl. No. 62/440,922, inventor Schwarz, T., filed Dec. 30, 2016 (Not Published).
U.S. Appl. No. 62/440,936, inventor Schwarz, T., filed Dec. 30, 2016 (Not Published).
U.S. Appl. No. 62/440,940, inventor Schwarz, T., filed Dec. 30, 2016 (Not Published).
U.S. Appl. No. 62/441,805, inventor Prouza, O., filed Jan. 3, 2017 (Not Published).
U.S. Appl. No. 62/786,731, inventor Schwarz, T., filed Dec. 31, 2018 (Not Published).
User Guide: Mag Venture, Magpro family, MagPro R30, MagPro R30 with MagOption, MagPro X100, MagPro X100 with MagOption, MagPro software v.5.0, US-edition, MagPro family User Guide, 2010, 52 Pages.
User Guide, Salus Talent Pro, Remed, High Intensity Electro magnetic Field Therapy-2 Channel, 2017, Version M-1.0.0, 45 pages.
User Guide, Salus Talent, Remed, High Intensity Electro magnetic Field Therapy, Version. M-1.0.0, 2017, 40 pages.
User's Manual: BTL-6000, Super Inductive System Elite, BBTL Industries Ltd, United Kingdom, Sep. 2016, 36 pages.
User Manual: Electro-magnetic Stimulator, Salus-Talent, Version 1.00, Rehabilitation Medical Company,2013, 34 Pages.
User Manual: Regenetron Pro, System Information, Regenetron Pro User Manual, Nov. 2014, 7 Pages.
Vance, C., et al., "Effects of Transcutaneous Electrical Nerve Stimulation on Pain, Pain Sensitivity, and Function in People with Knee Osteoarthritis," Physical Therapy 92:898-910 (2012).
Venus Concept Ltd., VenusFreeze MP2, User Manual, dated Jun. 2012, 46 pages.
Venus Concept Ltd., VenusViva, User Manual, dated Aug. 2013, 51 pages.
Venus Legacy, User Manual International, 2009, Venus Concept, 49 pages.
Verges S., et al., "Comparison of Electrical and Magnetic Stimulations to Assess Quadriceps Muscle Function," Journal of Applied Physiology (1985) 106(2):701-710, American Physiological Society, United States, (Feb. 2009).
Wada, K., et al., "Design and Implementation of Multi-Frequency Magnetic Field Generator Producing Sinusoidal Current Waveform for Biological Researches," IEEE, 9 pages (2016).
Wanitphakdeedecha, R., et al., "Treatment of Abdominal Cellulite and Circumference Reduction With Radiofrequency and Dynamic

(56) References Cited

OTHER PUBLICATIONS

Muscle Activation" Article in Journal of Cosmetic and Laser Therapy, dated Apr. 6, 2015, 7 pages.
Ward, A.R. and Shkuratova, N., "Russian Electrical Stimulation: The Early Experiments," Physical therapy 82(10):1019-1030, Oxford University Press, United States (2002).
Wasilewski, M.L., Academy of Aesthetic and Anti-Aging Medicine, Application of magnetic fields with deep stimulation in the fight against local obesity of lower limbs, BTL, 2012, 4 pages.
Web MD, what is normal body temperature? 3 pages, printed Mar. 4, 2019.
Weight to volume aluminum, 2 pages. printed from internet Sep. 25, 2018.
Weight to volume copper, 2 pages printed from internet Sep. 25, 2018.
Weiss, R.A., et al., "Induction of Fat Apoptosis by a Non-Thermal Device: Mechanism of Action of Non-Invasive High-Intensity Electromagnetic Technology in a Porcine Model," Lasers in surgery and medicine 51(1):47-53, Wiley-Liss, United States (Jan. 2019).
Weng, O., "Electromagnetic Activation of the Calf Muscle Pump," UMI Dissertation Publishing (2014).
Woehrle, J., et al., "Dry Needling and its Use in Health Care—A Treatment Modality and Adjunct for Pain Management," Journal of Pain & Relief 4(5):1-3, (Aug. 2015).
Yacyshy, A.F., et al., "The Inclusion of Interstimulus Interval Variability Does Not Mitigate Electrically-evoked Fatigue of the Knee Extensors," European Journal of Applied Physiology 120(12):2649-2656, Springer-Verlag, Germany (Sep. 2020).
ZAO OKB RITM, Electroneurostimulants, Transdermal Scenar-NT Instructions, All Pages (Nov. 2013).
ZAO OKB RITM, Percutaneous Electrical Stimulators With Individual Biofeedback Dosing Impact on Reflex Zones, All pages (2017).
Zeltiq System User Manual—Print and Binding Specifications, Zeltiq Aesthetics, Inc, Mar. 2011, 88 pages.
Zerona, Revear your True Shape, Product Fact Sheet, 3 pages.
Zerona R-Z6 by Erchonia, Specifications, Retrieved from the Internet: (www.myzerona.com), 2015, 1 page.
Zhang, G., et al., "A Method of Nerve Electrical Stimulation by Magnetic Induction," Annual International Conference of the IEEE Engineering in Medicine and Biology Society 2009:622-625, IEEE, United States (2009).
Zhi-De, D., "Electromagnetic Field Modeling of Transcranial Electric and Magnetic Stimulation: Targeting, Individualization, and Safety of Convulsive and Subconvulsive Applications," Academic Commons (2013).
Zhu, Y., et al., "Magnetic Stimulation of Muscle Evokes Cerebral Potentials by Direct Activation of Nerve Afferents: A Study During Muscle Paralysis," Muscle & Nerve 19(12):1570-1575, John Wiley & Sons, United Sates (Dec. 1996).
Jalinous, R., "Technical and Practical Aspects of Magnetic Nerve Stimulation," Journal of Clinical Neurophysiology 8(1):10-25, Raven Press, Ltd., New York (1991).
*Lumenis Be Ltd.* v. *BTL Healthcare Technologies A.S.*, PTAB-IPR2022-00451, U.S. Pat. No. 10,806,943 Petition for Inter Partes Review, Jan. 24, 2022, 87 pages.
*Lumenis Be Ltd.* v. *BTL Healthcare Technologies A.S.*, PTAB-IPR2022-00451, Declaration of Dr. Marom Bikson (EX1002), Jan. 24, 2022, 236 pages.
*Lumenis Be Ltd.* v. *BTL Healthcare Technologies A.S.*, PTAB-IPR2022-00452, U.S. Pat. No. 10,806,943 Petition for Inter Partes Review, Jan. 24, 2022, 81 pages.
*Lumenis Be Ltd.* v. *BTL Healthcare Technologies A.S.*, PTAB-IPR2022-00452, Declaration of Dr. Marom Bikson (EX1002), Jan. 24, 2022, 229 pages.
Operating Manual: Magstim® $200^2$, P/N 3001-23-04, The Magstim Company Limited, Mar. 18, 2005, 34 pages.
Stallknecht, B., et al., "Are blood flow and lipolysis in subcutaneous adipose tissue influenced by contractions in adject muscles in humans?," Am J Physiol Endocrinol Metab 292:E394-E399 (Feb. 2007).
Weyh, T., et al., "Marked differences in the thermal characteristics of figure-of-eight shaped coils used for repetitive transcranial magnetic stimulation," Clinical Neurophysiology 116:1477-1486, Elsevier Ireland Ltd. (Mar. 2005).
Zimmer MedizinSysteme GmbH, K192940 510(k) Summary, Cooltone, 14 pages (Nov. 2019).
Bios s.r.l., K201239 510(k) Summary, NuEra Tight Family, EMS Model, 9 pages (Dec. 2020).
Remed Co., Ltd., K202031 510(k) Summary, Talent-Pro Electromagnetic Stimulator, 11 pages (May 2021).
Zimmer MedizinSysteme GmbH, K203488 510(k) Summary, emField, 9 pages (Feb. 2021).
Lutronic Corporation, K213748 510(k) Summary, CoreLevee, 8 pages (Oct. 2022).
Zimmer MedizinSysteme GmbH, K220601 510(k) Summary, CoolTone, 11 pages (Apr. 2022).
Nanjing Vishee Medical Technology Co., Ltd., K222875 510(k) Summary, MagGraver F200, 12 pages (Mar. 2023).
Storz Medical AG, K203710 510(k) Summary, Storz Medical Magnetolith Muscle Stimulator, 7 pages (May 2021).
Beijing ADSS Development Co., Ltd., K231318 510(k) Summary, Electromagnetic Stimulator Device (Models: EM Contouring and Tesla Duet), 11 pages (Jul. 2023).
Shenzhen KeLiTongDa Industrial Co., Ltd., K231136 510(k) Summary, Fitness Belt (Model: KLT-07), 3 pages, (Jun. 2023).
Nanjing Vishee Medical Technology Co., Ltd., K230767 510(k) Summary, Pelvic Floor Muscle Stimulator, 7 pages (Sep. 2023).
Venus Concept Ltd., K111670 510(k) Summary, Venus Freeze (MP)2, 6 pages (Mar. 2012).
Venus Concept Ltd., K140629 510(k) Summary, Venus Swan (MP)2 System, 7 pages (Jun. 2014).
Venus Concept Ltd., K111784 510(k) Summary, Venus Swan System, 5 pages (Oct. 2011).
Venus Concept Ltd., K143554 510(k) Summary, Venus Legacy CX, 6 pages (Aug. 2015).
Venus Concept Ltd., K182094 510(k) Summary, Family of Venus RF Systems - Heal, 7 pages (May 2018).
Venus Concept Ltd., K191528 510(k) Summary, Venus Legacy Pro Device, 9 pages (Sep. 2019).
Venus Concept Ltd., K191065 510(k) Summary, Venus Viva Device, 12 pages (Apr. 2020).
Venus Concept Ltd., K201164 510(k) Summary, Venus Viva MD Device, 9 pages (Jun. 2020).
Venus Concept Ltd., K201461 510(k) Summary, Family of Venus RF Systems—Venus Freedom, 8 pages (Oct. 2021).
Venus Concept Ltd., K232192 510(k) Summary, Venus Versa Pro System, 11 pages (Sep. 2023).
InMode Ltd., K210877 K10(k) Summary, Evolve System with the T3 Applicator, 18 pages (Oct. 2023).
InMode Ltd., K231495 K10(k) Summary, The Evolve System with the Transform Applicator, 9 pages (Oct. 2023).
InMode Ltd., K191855 K10(k) Summary, EmFace Device, 10 pages (Oct. 2019).
Super Inductive System Seat, leaflet, 2 pages (2021).
Super Inductive System Seat, User's Manual, 20 pages (2019).
Allais, G., et al., "Non-pharmacological Approaches to Chronic Headaches: Transcutaneous Electrical Nerve Stimulation, Lasertherapy and Acupuncture in Transformed Migraine Treatment," Neurological Sciences 24 Suppl 2:S138-S142, Springer-Verlag Italia, Italy (May 2003).
Beijing Sano Laser S&T Development Co., Ltd, K230024 510(k) Summary, Hi-Emt Magshape, (Sep. 2023), 15 pages.
Cefaly Enhanced User Manual, (2023), 116 pages.
Cefaly Technology, K201895 510(k) Summary, Cefaly Dual, (Sep. 2020), 8 pages.
Comorbid Anxiety, Clinical benefits of TMS for patients with Major Depressive disorders, Rev. 1.0; 2 pages.
Electrocore, Inc., K211856 510(k) Summary, GammaCore Sapphire, (Sep. 2021), 12 pages.

(56)                  References Cited

OTHER PUBLICATIONS

ENeura Inc, K162797 510(k) Summary, Spring TMS, (Jun. 2017), 9 pages.
European Commission, Neuodegenerative Disorders, 10 pages printed Dec. 27, 2016.
Fotona d.o.o., K221274 510(k) Summary, StarFormer, (Sep. 2023), 10 pages.
Fotona d.o.o., K234061 510(k) Summary, StarFormer, (Jul. 2024), 7 pages.
Guidance for Insdustry and Food and Drug Administration Staff, (Jul. 2011), 26 pages.
Hebei JT Medical Co., Ltd., K232181 510(k) Summary, Body Contouring Machine, (Apr. 2024), 10 pages.
Magnetic neural stimulation system, (2014), 2 pages.
Magnetic stimulatio equipment, YY/T 0994-2015; 2016, with attached English-language translation, 11 pages.
Magventure—Magpro Family, (Aug. 2021), 30 pages.
Magventure Product Catalog, (2022), 37 pages.
Neurolief Ltd., K212106 510(k) Summary, Relivion, (Aug. 2021), 11 pages.
Neurostar system—instructions for use, (Dec. 2020), 258 pages.
Nu Eyne Co. Ltd., K192773 510(k) Summary, Allive, (Dec. 2019), 14 pages.
Nu Eyne Co., Ltd, K211380 510(k) Summary, Elexir, (Jul. 2021), 15 pages.
Obsluze, "Apparatus for High Induction Magnetic Stimulation," 2016, 42 pages.
Pelvipower—Power from the core, (Oct. 2020), 32 pages.
Shanghai Apolo Medical Technology Co., Ltd., K232409 510(k) Summary, Electromagnetic Stimulation Systems, (Apr. 2024), 8 pages.
Shenzhen Dongdixin Technology Co. Ltd., K210364 510(k) Summary, Migraine TENS Digital Pain Reliever, (Jun. 2021), 11 pages.
Shenzhen Hengbosi Industrial Co., Ltd., K233035 510(k) Summary, Electronic Muscle Stimulator, (Aug. 2024), 4 pages.
Swims America Corp, K230167 510(k) Summary, Back 4, (Sep. 2023), 21 pages.
Theranica Bioelectronics Ltd., K223169 510(k) Summary, Nerivio, (Feb. 2023), 10 pages.
TriLipo MED Procedure, http://download.lifvation.com/Maximus_TriLipoMED_Intro.pdf , Apr. 2013, 76 pages.
Venus Concept Ltd., K211461 510(k) Summary, Family of Venus RF Systems—Venus Freedom, 8 pages (Oct. 2021).
Wat Medical Technology Inc, K172450 510(k) Summary, Tens device-HeadaTern, espresso, (Sep. 2018), 10 pages.
Wonder Face User Manual, (2024), 18 pages with attached English-language summary and partial machine translation.
Zimmer MedizinSysteme GmbH, K230780 510(k) Summary, MFG-05, (Oct. 2023), 9 pages.
FDA letter to Venus Legacy, Dec. 19, 2014, 7 pages.
Final Office Action mailed Sep. 12, 2016, in U.S. Appl. No. 14/873,110, Ladman, J., et al., filed Oct. 1, 2015.
Final Office Action mailed Apr. 18, 2016, in U.S. Appl. No. 14/700,349, Schwarz T., et al., filed Apr. 30, 2015.
Final Office Action mailed Dec. 1, 2016, in U.S. Appl. No. 14/789,658, Ladman, J., et al., filed Jul. 1, 2015.
Final Office Action mailed Jan. 27, 2017 in U.S. Appl. No. 15/060,375, Schwarz, T., et al., filed Mar. 3, 2016.
Final Office Action mailed Jan. 4, 2017, in U.S. Appl. No. 15/073,318, Schwarz, T., et al., filed Mar. 17, 2016.
Final Office Action mailed Jul. 1, 2016, in U.S. Appl. No. 14/870,713, Schwarz, T., et al., filed Sep. 30, 2015.
Final Office Action mailed Jul. 14, 2017, in U.S. Appl. No. 15/344,811, Schwarz, T., et al., filed Nov. 7, 2016.
Final Office Action mailed Jun. 22, 2017, in U.S. Appl. No. 15/151,012, Schwarz, T., et al., filed May 10, 2016.
Final Office Action mailed Jun. 26, 2017, in U.S. Appl. No. 15/099,274, Pribula, O., et al., filed Apr. 14, 2016.
Final Office Action mailed May 20, 2016, in U.S. Appl. No. 14/697,934, Zarsky, J., et al., filed Apr. 28, 2015.

Final Office Action mailed Nov. 4, 2016, in U.S. Appl. No. 14/951,093, Schwarz, T., et al., filed Nov. 24, 2015.
Final Office Action mailed Aug. 12, 2016, in U.S. Appl. No. 14/926,365, Prouza, O., et al., filed Oct. 29, 2015.
Guangzhou HEMS Tech, PEMF Star, May 31, 2019, 5 pages.
Non Final Office Action mailed Dec. 1, 2016, in U.S. Appl. No. 15/151,012, Schwarz, T., et al., filed May 10, 2016.
Non Final Office Action mailed Dec. 12, 2016, in U.S. Appl. No. 15/099,274, Pribula, O., et al., filed Apr. 14, 2016.
Non Final Office Action mailed Dec. 17, 2015, in U.S. Appl. No. 14/697,934, Zarsky, J., et al., filed Apr. 28, 2015.
Non Final Office Action mailed Feb. 10, 2016, in U.S. Appl. No. 14/873,110, Ladman, J., et al., filed Oct. 1, 2015.
Non Final Office Action mailed Feb. 11, 2016, in U.S. Appl. No. 14/926,365, Prouza, P., et al., filed Oct. 29, 2015.
Non Final Office Action mailed Feb. 25, 2016, in U.S. Appl. No. 14/870,713, Schwarz, T., et al., filed Sep. 30, 2015.
Non Final Office Action mailed Jun. 16, 2016, in U.S. Appl. No. 15/073,318, Schwarz, T., et al., filed Mar. 17, 2016.
Non Final Office Action mailed Jun. 27, 2017 in U.S. Appl. No. 15/601,719, Schwarz, T., et al., filed May 22, 2017.
Non Final Office Action mailed Jun. 28, 2017, in U.S. Appl. No. 15/073,318, Schwarz, T., et al., filed Mar. 17, 2016.
Non Final Office Action mailed Jun. 29, 2017, in U.S. Appl. No. 14/789,156 , Ladman, J., et al., filed Jul. 1, 2015.
Non Final Office Action mailed Jun. 30, 2017, in U.S. Appl. No. 15/471,946, Schwarz, T., et al., filed Mar. 28, 2017.
Non Final Office Action mailed Mar. 24, 2017, in U.S. Appl. No. 15/396,073, Schwarz, T., et al., filed Dec. 30, 2016.
Non final Office Action mailed Mar. 28, 2017, in U.S. Appl. No. 15/344,811, Schwarz, T., et al., filed Nov. 7, 2016.
Non Final Office Action mailed May 9, 2016, in U.S. Appl. No. 14/789,658, Ladman, J., et al., filed Jul. 1, 2015.
Non Final Office Action mailed May 9, 2016, in U.S. Appl. No. 14/951,093, Schwarz, T., et al., filed Nov. 24, 2015. .
Non Final Office Action mailed Nov. 4, 2015, in U.S. Appl. No. 14/700,349, Schwarz T., et al., filed Apr. 30, 2015.
Non Final Office Action mailed May 4, 2016, in U.S. Appl. No. 14/873,110, Ladman, J., et al., filed Oct. 1, 2015.
World Health Organization, "Neurological Disorders—Public Health Challenges", pp. 1-115 (2006).
World Health Organization, "The Atlas: Epilepsy Care in the World", pp. 1-96 (2005).
Deleo, V. BTL Healthcare Technologies A.S., Notice of Opposition, Pat. No. EP3316962, Sep. 21, 2022, (with attached English-language translation), 36 pages.
"Deymed DuoMag XT-100 rTMS Stimulator System," uploaded Jan. 26, 2023, retrieved from: https://www.youtube. com/watch?v=19n6S4g1sKQ, 2 pages.
Double 6" Rudy Arm—Universal ¼-20 & ⅜-16. Upgrade Innovations. https://upgradeinnovations.com/product/double-6-rudy-arm/, 7 pages (2024).
Iskra Medical Report, Tesla Stym, (2013), 4 pages.
Manual of Tesla Stym device, dated Mar. 2013 (with attached English-language translation), 36 pages.
Notice of Opposition, European Patent No. EP3316962, *Fotona D.O.O.* v. *BTL Healthcare Technologies A.S.*, dated Sep. 22, 2022, 128 pages.
Pascual-Leone, A., et al., Editors, "Handbook of Magnetic Stimulation," Oxford University Press, (2002), 58 pages.
Photo of Facebook page, dated Apr. 16, 2025, Retrieved from : https://www.facebook.com/lskraMedical/photos/pb.100063238417700.-2207520000/1113882421970896/?type3, 1 page.
Photo of Facebook page, dated Apr. 16, 2025, Retrieved from : https://www.facebook.com/lskramedical/photos/pb.100063238417700.-2207520000/726831297342679/?type=3, 1 page.
Photo of Facebook page, dated Apr. 16, 2025, Retrieved from : https://www.facebook.com/lskraMedical/photos/pb.100063238417700.-2207520000/776626345696507/?type=3, 1 page.
Photo of Facebook page, dated Apr. 16, 2025, Retrieved from : https://wwwyoutubercorn/watch?v=v1s2Czgy6Os, 1 page.

(56) References Cited

OTHER PUBLICATIONS

Photo of Facebook page, dated Apr. 16, 2025, Retrieved from the internet : https://www.facebook.com iskraMedical/pllotos/pb.100063238417700.-2207520000/1113882341970904/ftype=3, 1 page.
"Presentation rTMS Deymed DuoMag XT," uploaded on Oct. 12, 2021, retrieved from: https://vwav.youtube.com/%20watch?v=sPNYsTwHtSo; 3 pages.
SIQ Test Report, Tesla Stym, dated (May 2022), 62 pages.
Stokes, M.G., et al., "Simple Metric for Scaling Motor Threshold Based on Scalp-cortex Distance: Application to Studies Using Transcranial Magnetic Stimulation," Journal of neurophysiology 94(6):4520-4527, American Physiological Society, United States (Dec. 2005).
User's Manual Magneto Stym, Magneto Stym Prestige, dated Apr. 14, 2015, 21 pages.
Video of Tesla Stym, dated Sep. 26, 2014, available at: https://www.youtube.com/watch?v=vLr2Czqv60s, 2 pages.
Wasserman, E.M., et al., Editors, "The Oxford Handbook of Transcranial Stimulation," Oxford University Press, Excerpts, Chapters 1-3, (2008), 36 pages.

* cited by examiner

METHODS AND DEVICES FOR AESTHETIC TREATMENT OF BIOLOGICAL STRUCTURES BY RADIOFREQUENCY AND MAGNETIC ENERGY

CROSS-REFERENCE TO RELATED APPLICATIONS

This application is a Continuation-in-Part of U.S. patent application Ser. No. 17/067,208, filed Oct. 9, 2020; which is a Continuation-in-Part of U.S. patent application Ser. No. 16/844,822, filed Apr. 9, 2020; which claims the benefit of U.S. Provisional Patent Application No. 62/832,738, filed Apr. 11, 2019; U.S. Provisional Patent Application No. 62/832,688, filed Apr. 11, 2019; and U.S. Provisional Patent Application No. 62/932,259, filed Nov. 7, 2019, all of which are incorporated herein by reference in their entireties.

BACKGROUND OF THE INVENTION

Aesthetic medicine includes all treatments resulting in enhancing a visual appearance according to a patient's criteria. Patients want to minimize all imperfections including, for example, unwanted body fat in specific body areas, improve body shape, and remove effects of natural aging. Patients require quick, non-invasive procedures that provide satisfactory results with minimal health risks.

The most common methods used for non-invasive aesthetic applications are based on application of mechanical waves, such as ultrasound or shock wave therapy, or electromagnetic waves, such as radiofrequency treatment or light treatment including laser treatment. The effect of mechanical waves on tissue is based on cavitation, vibration, and/or heat-inducing effects. The effect of applications using electromagnetic waves is based on heat production in the biological structure.

A mechanical treatment using mechanical waves and/or pressure can be used for treatment of cellulite or adipose cells. However, such mechanical treatments have several drawbacks, such as a risk of panniculitis, destruction of untargeted tissues, and/or non-homogenous results.

A thermal treatment including heating is applied to a patient for enhancing a visual appearance of the skin and body by, for example, increasing production of collagen and/or elastin, smoothing the skin, reducing cellulite, and/or removing adipose cells. However, thermal treatment has several drawbacks, such as risk of overheating a patient or even causing thermal damage of unwanted biological structures. A risk of a panniculitis and/or non-homogenous results may be a very common side effect of existing thermal treatments. Further, insufficient blood and/or lymph flow during and/or after the treatment may lead to panniculitis and other health complications after the treatment. Further, the treatment may be uncomfortable, and may be painful.

Muscle stimulation by time-varying magnetic field provides several benefits over known methods for treating biological structures, and allows for non-invasive stimulation of muscles located beneath other muscles. Further, time-varying magnetic fields may be used to provide muscle stimulation to cause muscle contraction through thick layer of adipose tissue. Electrostimulation in order to provide a muscle contraction needs to deliver an electric current from an electrode, through an adipose tissue, to a nerve and/or neuromuscular plate linked with the muscle. The adipose tissue has resistivity higher than the muscle tissue and delivery of electric current from the electrode through insulating adipose tissue to muscle tissue may be less efficient. Targeting of the electric current to an exact muscle may not be precise and stimulating muscle may be very difficult nearly impossible. Additionally, with thicker adipose tissue, electric current delivered by electrotherapy has to be higher and such high amount of electric current propagating and dissipating during long distance may be very uncomfortable for a patient. On the other hand, time-varying magnetic fields induce electric current in the muscle, neuromuscular plate and/or in the nerve, so targeting and muscle stimulation by time-varying magnetic field is easier, more precise, comfortable and more effective. Time-varying magnetic field also enable comfortable stimulation or large number of muscles and/or muscle groups and applicator may not be in direct contact with the patient's body that may also improve hygiene and other parameters of a treatment.

Combination of a radiofrequency (RF) treatment that provides heating up of patient's soft tissue and a magnetic treatment that provides stimulation of patient's muscle tissue may have outstanding synergic effect. Combined treatment may provide improved treatment, may result in shorter treatment periods, increase of patient's comfort during the treatment, enable to combine different treatment effects with a synergic result, improve patient safety and others deeply described later in this document.

To reach the best synergic effect it is preferred to target magnetic treatment providing muscle stimulation and RF treatment to one body area (e.g. same body area) wherein at least one RF electrode providing the RF treatment should be flat and/or correspond with patient's skin to ensure homogenous heating of the patient's soft tissue. To target the RF treatment and the magnetic treatment to the same body area requires to position a magnetic field generating device and an RF electrode nearby each other, e.g. with at least partial overlay of the magnetic field generating device and RF electrode. However, arranging an RF electrode and the magnetic field generating device in close proximity may be problematic, because the time-varying magnetic field generated by the magnetic field generating device may induce unwanted physical effects, such as eddy currents, skin effect and/or other physical effects in the RF electrode. Unwanted physical effects may cause significant energy loss, inefficiency of such device arrangement and also heating of the RF electrode, influencing of the device function, such as incorrect tuning of the device, inaccurate targeting of produced energies, degeneration of produced magnetic, electromagnetic fields and/or other. The RF electrode may be influenced by the magnetic field generating device and vice versa.

A device and method described in this document presents a solution for providing the RF and magnetic treatment with maximized synergic effect and also preserve safety and efficiency of the delivered magnetic and RF (electromagnetic) fields.

SUMMARY OF THE INVENTION

The disclosure provides a treatment devices and methods for providing one or more treatment effects to at least one biological structure in at least one body area. The treatment device provides a unique opportunity how to shape human or animal bodies, improve visual appearance, restore muscle functionality, increase muscle strength, change (e.g. increase) muscle volume, change (e.g. increase) muscle tonus, cause muscle fibre hypertrophy, cause muscle fibre hyperplasia, decrease number and volume of adipose cells and adipose tissue, remove cellulite and/or other. The treatment device and the method may use the application of a radiofrequency (RF) treatment and a magnetic treatment to cause heating of at least one target biological structure within the body area and cause muscle stimulation including muscle contraction, within the proximate or same body area. The treatment device may use an RF electrode as a treatment energy source to produce RF energy (which may be referred as RF field) to provide RF treatment, and a magnetic field generating device as a treatment energy source for generating a time-varying magnetic field to provide magnetic treatment.

The treatment effect provided by the treatment device and method may include muscle stimulation, wherein muscle stimulation may include muscle contraction, e.g., a supramaximal muscle contraction. The treatment effect may include heating of the body area. The treatment device and method may provide a combination of treatment effects, such as muscle stimulation and heating of a body area. The treatment device and method may provide muscle contraction and heating at same time or at different times during the treatment. The treatment device and method may provide muscle contraction and heating of the adipose tissue of the body at the same time or at different times during the treatment. Also, the treatment device and method may provide muscle contraction and heating of the adipose tissue of the same body area at same time or at different times during the treatment. Further, the treatment device and method may provide muscle contraction and heating of the same muscle of the body at the same time or at different times during the treatment. Furthermore, the treatment device and method may provide muscle contraction and heating of the same muscle of the same body area at the same time or at different times during the treatment.

Further, the treatment device and method may provide muscle contraction and heating of skin of the body at the same time or at different times during the treatment. Furthermore, the treatment device and method may provide muscle contraction and heating of the skin of the same body area at the same time or at different times during the treatment.

In order to enhance efficiency and safety of the treatment, to minimize energy loss and unwanted physical effect induced in at least one RF electrode and/or magnetic field generating device, the device may use the one or more segmented RF electrodes, wherein the segmented RF electrode means RF electrode with e.g. one or more apertures, cutouts and/or protrusions to minimize the effects of a nearby time-varying magnetic field produced by the magnetic field generating device. Aperture may be an opening in the body of the RF electrode. The cutout may be an opening in the body of the RF electrode along the border of the RF electrode. Openings in the body of the RF electrode may be defined by view from floor projection, which shows a view of the RF electrode from above. The apertures, cutouts and/or areas outside of protrusions may be filed by air, dielectric and/or other electrically insulating material. The apertures, cutouts and/or protrusions of the RF electrode may minimize induction of eddy currents in the RF electrode, minimize energy loss, and inhibit overheating of the treatment device. Further, the apertures, cutouts and/or protrusions may minimize the influence of the magnetic treatment on the produced RF treatment. The proposed design of the RF electrode enables the same applicator to include a magnetic field generating device and the RF electrode with at least partial overlay, according to the applicator's floor projection, while enabling targeting of RF treatment and magnetic treatment to the same area of the patient's body with the parameters described herein. Incorporation of an RF electrode and a magnetic field generating device in one applicator enables enhanced treatment targeting and positive treatment results with minimal negative effects mentioned above.

Also mutual insulation of at least one RF circuit and at least one magnet circuit prevent interaction between electric and/or electromagnetic signals.

The magnetic field generating device in combination with an energy storage device enables production of a magnetic field with an intensity (which may be magnetic flux density) which evokes a muscle contraction. Energy storage device may be used to store electrical energy enabling accumulation of an electric field having a voltage in a range from 500 V to 15 kV. The energy storage device may supply the magnetic field generating device with the stored electrical energy in an impulse of several microseconds to several milliseconds.

The method of treatment enables heating of at least one body area where is also evoked a muscle contraction that minimizes muscle and/or ligament injury, such as tearing or inflammation. Heating of a skin, a contracted muscle, a contracting muscle, a relaxed muscle, adipose tissue, adipose tissue, and/or adjacent biological structure of the treated body area may shift the threshold when a patient may consider treatment to be uncomfortable.

Therefore, heating may allow a higher amount of electromagnetic energy, (e.g. RF and/or magnetic field) to be delivered to the patient's body in order to provide more muscle work through muscle contractions and subsequent relaxation. Another benefit of application of the RF treatment and the magnetic treatment in the same body area is that the muscle work (provided e.g. by repetitive muscle contractions and relaxations) accelerates blood and lymph flow in the targeted area and so improves dissipation of thermal energy created by the RF treatment. Application of the RF treatment and the magnetic treatment also improves homogeneity of biological structure heating that prevents creation of hot spots, edge effects and/or other undesirable effects. The method of treatment causing muscle stimulation and heating to the same body area may result in hyperacidity of extracellular matrix that leads to apoptosis or necrosis of the adipose tissue. The RF treatment may provide selective heating of adipose tissue that leads to at least one of apoptosis, necrosis, decrease of volume of adipose cells, and cellulite removal.

A treatment device is able to provide muscle contraction and/or heating to a body area of a patient. The muscle contraction may be provided by a magnetic treatment, while heating may be provided by a radiofrequency treatment.

A treatment device providing muscle contraction and/or heating may include at least one magnetic field generating device and/or at least one radiofrequency electrode.

A treatment device providing a magnetic treatment and a radiofrequency treatment to a body area of a patient may include an energy storage device, a magnetic field generating device, a switching device, and optionally a radiofrequency electrode having a plurality of openings.

A treatment device providing a magnetic treatment and a radiofrequency treatment to a body area of a patient may include an energy storage device, a magnetic field generating device, a switching device, and optionally a radiofrequency electrode having a plurality of cutouts.

A treatment device providing a magnetic treatment and a radiofrequency treatment to a body area of a patient may include an energy storage device, a magnetic field generating device, a switching device, and optionally a radiofrequency electrode having a plurality of protrusions.

A treatment device for providing a magnetic treatment and a radiofrequency treatment to a body area of a patient may include an energy storage device, a magnetic field generating device, a switching device, and optionally a radiofrequency electrode, wherein the radiofrequency electrode may be positioned between the magnetic field generating device and a body area of a patient. The radiofrequency electrode may be arranged in overlay with the magnetic field generating device according to a floor projection of an applicator that includes the magnetic field generating device and the radiofrequency electrode.

A treatment device providing a magnetic treatment and a radiofrequency treatment to a body area of a patient may include an energy storage device, a magnetic field generating device, a switching device, and optionally a radiofrequency electrode, wherein the radiofrequency electrode includes at least one layer of a substrate covered by at least one conductive layer.

A treatment device providing a magnetic treatment and a radiofrequency treatment to a body area of a patient may include an energy storage device, a magnetic field generating device, a switching device, a plurality of radiofrequency electrodes, and optionally an impedance element.

A treatment device providing a magnetic treatment and a radiofrequency treatment to a body area of a patient may include an energy storage device, a magnetic field generating device, a switching device, and/or a radiofrequency electrode that includes a metal foam.

A treatment device providing a muscle contraction and/or heating to a body area of a patient may include an applicator including a temperature sensor. A positioning of the temperature sensor and/or wire connection between the temperature sensor and the rest of the treatment device may be designed to minimize the influence of the operation of the applicator. The position of the temperature sensor may include the presence of the temperature sensor in a protrusion of the applicator. The design of the wire connection may include a material and/or its thickness as further disclosed herein.

A treatment device providing a magnetic treatment and a radiofrequency treatment to a body area of a patient may include a main unit and an applicator including at least one magnetic field generating device and at least one radiofrequency electrode. The applicator may be connected to the main unit by a connecting attachment including male contacts and/or female contacts. One or more contacts of the connecting attachment may be used for transfer of signals to and from at least one magnetic field generating device, at least one radiofrequency electrode, or a temperature sensor. Further, the one or more contacts of the connecting attachment may be used for identification of the type of the applicator, transfer of cooling fluid, providing a safety loop, or control of durability of the applicator, as described within this application.

According to one aspect of the disclosure, there is provided a device providing a magnetic treatment and a radiofrequency treatment to a patient, the device including a magnetic field generating device and an RF electrode, wherein the magnetic field generating device provides a muscle contraction, and wherein the RF electrode provides heating of the patient's tissue.

According to another aspect of the disclosure, there is provided a device providing a magnetic treatment, a radiofrequency treatment and a pressure treatment to a patient, the device including a magnetic field generating device, one or more RF electrodes and a pressure outlet, wherein the magnetic field generating device provides a muscle contraction, wherein the one or more RF electrodes provide heating of the patient's tissue, and wherein the pressure treatment provides mechanical impulses. According to one aspect of the disclosure, there is provided a device providing a magnetic treatment, a radiofrequency treatment and a pressure treatment to a patient, the device including an applicator, a magnetic field generating device, one or more RF electrodes, and a pressure outlet, wherein the magnetic field generating device provides a muscle contraction, wherein the one or more RF electrodes provide heating of the patient's tissue, wherein the pressure treatment provides mechanical impulses, and wherein the applicator includes the magnetic field generating device, one or more RF electrodes and the pressure outlet.

BRIEF DESCRIPTION OF THE DRAWINGS

The accompanying drawings, which are incorporated herein and form a part of the specification, illustrate the present disclosure and, together with the description, further serve to explain the principles thereof and to enable a person skilled in the pertinent art to make and use the same.

FIGS. 54*k*-54*n* illustrate exemplary positions of a plurality of RF electrodes within and/or on the applicator.

DETAILED DESCRIPTION

Figure 1A:
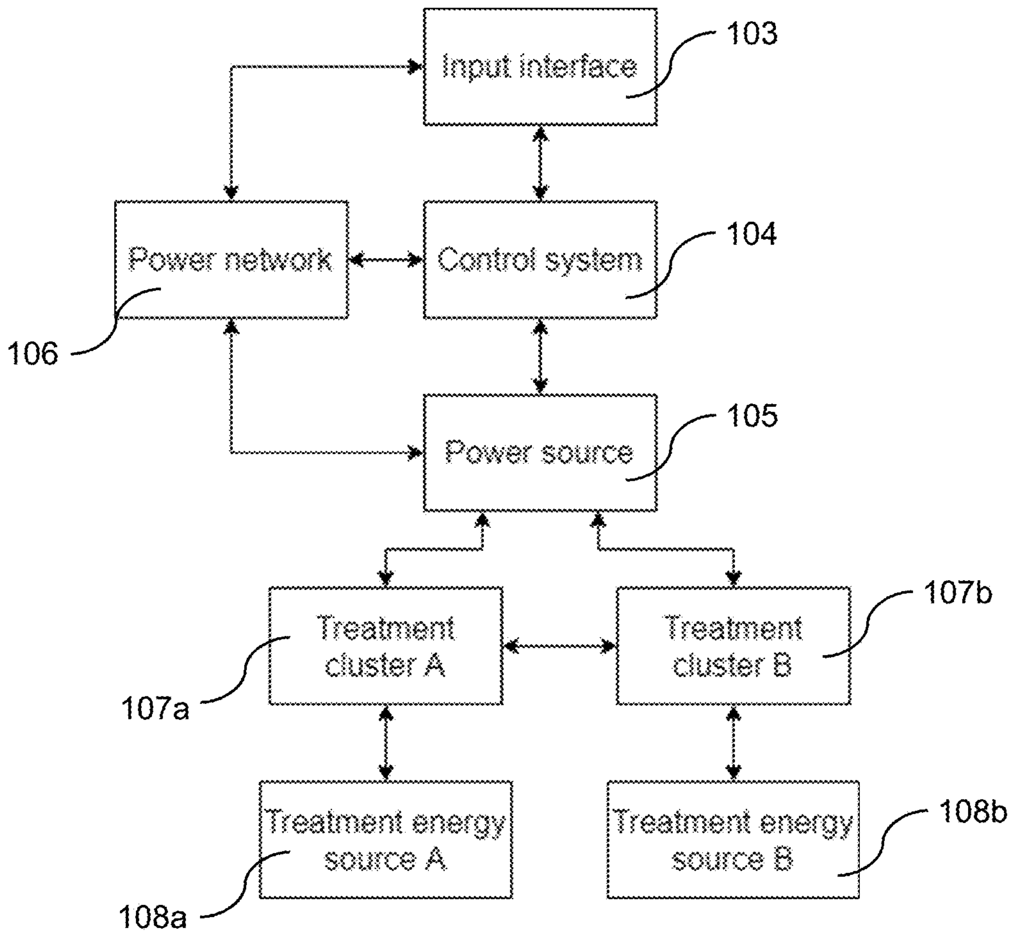
FIGS. 1*a*-1*e* illustrate exemplary diagrams of a treatment device.

The present treatment device and method of use provide new physiotherapy and/or aesthetic treatment by combination of RF treatment and treatment providing muscle stimulation targeted to various treatment effects, such as rejuvenate, heal and/or provide remodeling at least part of at least one biological structure of patient's tissue in at least one body area.

The biological structure may be any tissue in a human and/or animal body which may have of identical function, structure and/or composition. The biological structure may include or be at least part of any type of tissue like: connective tissue (e.g. tendons, ligaments, collagen, elastin fibres), adipose tissue (e.g. adipose cells of subcutaneous adipose tissue and/or visceral adipose tissue), bones, dermis and/or other tissue, such as at least one neuron, neuromuscular plate (neuromuscular junction), muscle cell, one or more individual muscles, muscle group, at least part of a muscle fibre, volume of extracellular matrix, endocrine gland, neural tissue (e.g. peripheral neural tissue, neuron, neuroglia, neuromuscular plate) and/or joint or part of joint. For the purpose of this application, the biological structure may be called target biological structure.

A treatment effect provided to at least part of at least one target biological structure may include muscle contraction (including supramaximal contractions and/or tetanic contractions), muscle twitch, muscle relaxation and heating of biological structure. The muscle contraction and heating may be provided at the same time. Also, the treatment effect may include e.g. remodelling of the biological structure, reducing a number and/or a volume of adipose cells by apoptosis and/or necrosis, muscle strengthening, muscle volume increase, causing of a muscle fibre hypertrophy, muscle fibre hyperplasia, restoration of muscle functionality, myosatellite cells proliferation and/or differentiation into muscle cells, improvement of muscle shape, improving of muscle endurance, muscle definition, muscle relaxation, muscle volume decrease, restructuring of collagen fibre, neocollagenesis, elastogenesis, collagen treatment, improving of blood and lymph flow, accelerate of at least part of at least one target biological structure and/or other functions or benefits. During treatment of body area by the treatment device, more than one treatment effect may be provided and variable treatment effects may be combined.

The treatment effect provided to target biological structure may results in body shaping, improving contour of the body, body toning, muscle toning, muscle shaping, body shaping, breast lifting, buttock lifting, buttock rounding and/or buttock firming. Further, providing a treatment effect may result in body rejuvenation, such as wrinkle reduction, skin rejuvenation, skin tightening, unification of skin colour, reduction of sagging flesh, lip enhancement, cellulite removing, reduction of stretch marks and/or removing of scars. The treatment effect may also lead to accelerating of healing process, anti-edematic effect and/or other physiotherapeutic and treatment result.

The treatment device and method may be used at hospitals, beauty clinics, fitness centers, and/or at a home of the patient.

The treatment device and method may be used for physiotherapeutic treatments including treatment of pain, atrophy, and/or rehabilitation after stroke. The other physiotherapeutic treatments may include treatment of Achilles tendonitis, ankle distortion, anterior tibial syndrome, arthritis of the hand, arthrosis, bursitits, carpal tunnel syndrome, cervical pain, dorsalgia, epicondylitis, facial nerve paralysis, herpes labialis, hip joint arthrosis, impingement syndrome/frozen shoulder, knee arthrosis, knee distortion, lumbosacral pain, nerve repair, onychomycosis, Osgood-Schlatter syndrome, pain relief, painful shoulders, patellar tendinopathy, plantar fasciitis/heel spur, tarsal tunnel syndrome, tendinopathy, and/or tendovaginitis.

The treatment device and method may be used for treatments of pelvic floor tissues including urinary incontinence, fecal incontinence, bladder dysfunction, sexual dysfunction, erectile dysfunction, fertility issues, pelvic pain, vulvodynia, dysmenorrhea, menopausal disorders and/or postmenopausal disorders.

The treatment device and method may provide prevention and/or treatment of lifestyle diseases including atheroscelosis, hypertension, risk of heart attack, risk of stroke, impaired glucose tolerance, gestational impaired glucose tolerance and/or diabetes. The term "diabetes" may encompass diabetes type 1, diabetes type 2, protein-deficient pancreatic diabetes, malnutrition-related diabetes mellitus, fibrocalculous pancreatic diabetes and/or gestational diabetes mellitus. The use of the treatment device and providing muscle stimulation (e.g. muscle contraction) and/or heating to the patient's body may lead to prevention of glucose tolerance or insulin decrease. The use of the treatment device and providing muscle stimulation (e.g. muscle contraction) and/or heating to the patient's body may lead to increase of release of insulin and/or glycogen. The use of the treatment device may lead to balance of glucose blood level by changing the concentration of the glucose in blood. The use of treatment device may lead to balance of triglyceride blood level by changing the concentration of the triglyceride in blood. The use of the treatment device may lead to balance of cholesterol blood level by changing the concentration of the cholesterol in blood. The change of concentration may be achieved by exercise provided by muscle contraction and/or by heating of the patient's body. The use of the device may improve glucose metabolism and/or improve transport of the glucose into the cells. Improvement of glucose transport into cells may lower the concentration of glucose in blood. Such effect may provide improvement of insulin secretion.

The treatment device and method may be used for improvement of sport performance by selective treatment of correct muscle groups. Further, the treatment device and method may be used for recovering of the athletes after exercise and/or injury. Further, the treatment device and method may be used for regeneration of at least one muscle after exercise and/or injury. Further, the treatment device and method may be used for providing the exercise of the muscles and other parts of the patient's body. For such treatment, the device may be used not only in hospitals or beauty clinics, but also in fitness studios and or at home.

The treatment device may provide one or more types of treatment energy wherein treatment energy may include magnetic field (also referred as magnetic energy) and RF field (also referred as RF energy) and/or magnetic field (also referred as magnetic energy). The magnetic field is provided during magnetic treatment. The RF field provided during RF treatment may include electrical component of RF field and magnetic component of RF field. The electrical component of RF field may be referred as RF wave or RF waves. The RF electrode may generate RF field, RF waves and/or other components of RF field. The RF electrode may be an element generating an RF field, RF waves and/or other components of RF field causing heating of biological structure and/or body area.

The magnetic field and/or RF field may be characterized by intensity. In case of magnetic field, the intensity may include magnetic flux density or amplitude of magnetic flux density. In case of RF field, the intensity may include energy flux density of the RF field or RF waves.

A body area may include at least part of patient's body including at least a muscle or a muscle group covered by other soft tissue structure like adipose tissue, skin and/or other. The body area may be treated by the treatment device. The body area may be body part, such as a buttock, saddlebag, love handle, abdominal area, hip, leg, calf, thigh, arm, torso, shoulder, knee, neck, limb, bra fat, face or chin, forehead, back, lower back, chest, flank, pelvic floor and/or any other tissue. For the purpose of the description the term "body area" may be interchangeable with the term "body region".

Skin tissue is composed of three basic elements: epidermis, dermis and hypodermis so called subcutis. The outer and also the thinnest layer of skin is the epidermis. The dermis consists of collagen, elastic tissue and reticular fibres. The hypodermis is the lowest layer of the skin and contains hair follicle roots, lymphatic vessels, collagen tissue, nerves and also fat forming a subcutaneous white adipose tissue (SWAT). Adipose tissue may refer to at least one lipid rich cell, e.g. adipose cell like adipocyte. The adipose cells create lobules which are bounded by connective tissue or fibrous septa (retinaculum cutis).

Another part of adipose tissue, so called visceral adipose tissue, is located in the peritoneal cavity and forms visceral white adipose tissue (VWAT) located between parietal peritoneum and visceral peritoneum, closely below muscle fibres adjoining the hypodermis layer.

A muscle may include at least part of a muscle fibre, whole muscle, muscle group, neuromuscular plate, peripheral nerve and/or nerve innervating of at least one muscle.

Deep muscle may refer to a muscle that is at least partially covered by superficial muscles and/or to a muscle covered by a thick layer of other tissue, such as adipose tissue wherein the thickness of the covering layer may be at least 4, 5, 7, 10 or more centimetres up to 15 cm thick.

Individual muscles may be abdominal muscles including rectus abdominalis, obliquus abdominalis, transversus abdominis, and/or quadratus lumborum. Individual muscles may be muscle of the buttocks including gluteus maximus, gluteus medius and/or gluteus minimus. Individual muscles may be muscles of lower limb including quadriceps femoris, Sartorius, gracilis, biceps femori, adductor magnus longus/brevis, tibialis anterior, extensor digitorum longus, extensor hallucis longus, triceps surae, gastroenemiis lateralis/medialis, soleus, flexor hallucis longus, flexor digitorum longus, extensor digitorum brevis, extensor hallucis brevis, adductor hallucis, abductor halluces, ab/adductor digiti minimi, abductor digiti minimi and/or interossei plantares). Ligament may be Cooper's ligament of breast.

One example may be application of the treatment device and method to patient's abdomen that may provide (or where the treatment may eventually result in) treatment effect such as reducing a number and volume of adipose cells, muscle strengthening, fat removal, restructuring of collagen fibres, accelerate of neocollagenesis and elastogenesis, muscle strengthening, improving of muscle functionality, muscle endurance and muscle shape. These treatment effects may cause circumferential reduction of the abdominal area, removing of saggy belly and/or firming of abdominal area, cellulite reduction, scar reduction and also improving of the body posture by strengthening of the abdominal muscles that may also improve contour of the body, body look and patient's health.

One other example may be application of the treatment device and method to body area comprising buttock that may provide (or where the treatment may eventually result in) treatment effect such as reducing a number and volume of adipose cells, restructuring of collagen fibres, accelerate of neocollagenesis and elastogenesis, muscle strengthening, muscle toning and muscle shaping. These treatment effects may cause waist or buttock circumferential reduction, buttock lifting, buttock rounding, buttock firming and/or cellulite reduction.

Another example may be application of the treatment device and method to body area comprising thighs that may provide (or where the treatment may eventually result in) reduction of a number and volume of adipose cells, muscle strengthening, muscle shaping and muscle toning. The application of the treatment device and method to body area comprising thigh may cause circumferential reduction of the thigh, removing of saggy belly and cellulite reduction.

Still another example may be application of the treatment device and method to body area comprising arm that may provide (or where the treatment may eventually result in) reduction of a number and volume of adipose cells, muscle strengthening, muscle shaping and muscle toning. The application of the treatment device and method to body area comprising arm may cause circumferential reduction of the abdomen, removing of saggy belly and cellulite reduction.

The one or more treatment effects provided to one or more target biological structures may be based on selective targeting of a RF field into one or more biological structures and providing heating together with application of magnetic field causing muscle stimulation (including muscle contraction). The RF treatment may cause selective heating of one or more biological structures, polarizing of extracellular matrix and/or change of cell membrane potential in a patient's body. The magnetic field may be time-varying magnetic field or static magnetic field. When the time-varying magnetic field is used, the magnetic treatment may be referred as time-varying magnetic treatment. The magnetic treatment may cause muscle contraction, muscle relaxation, cell membrane polarization, eddy currents induction and/or other treatment effects caused by generating time-varying magnetic field in at least part of one or more target biological structures. The time-varying magnetic field may induce electric current in biological structure, The induced electric current may lead to muscle contraction. The muscle contractions may be repetitive. Muscle contraction provided by magnetic field may include supramaximal contraction, tetanic contraction and/or incomplete tetanic contraction. In addition, magnetic field may provide muscle twitches.

The treatment effect provided by using of the treatment device and by application of magnetic treatment and RF treatment may be combined. For example, reduction of a number and volume of adipose cells may be achieved together with muscle strengthening, muscle shaping and/or muscle toning during actual treatment or during a time (e.g. three or six months) after treatment. Furthermore, the effect provided by using of the treatment device by application of magnetic treatment and RF treatment may be cumulative. For example, the muscle toning may be achieved by combined reduction of a number and volume of adipose cells which may be achieved together with muscle strengthening.

The method of treatment may provide the treatment effect to at least one of target biological structure by thermal treatment provided by RF field in combination with applied magnetic treatment. The treatment effect to a target biological structure may be provided by heating at least one biological structure and evoking at least a partial muscle contraction or muscle contraction of a muscle by magnetic treatment.

The method of treatment may enable heating of the body area where the muscle contraction by the magnetic field is evoked. The heating may minimize muscle injury and/or ligament injury including tearing or inflammation. Heating of a contracting muscle and/or adjacent biological structure may also shift the threshold of uncomfortable treatment. Therefore, heating caused by the RF field may allow a higher amount of magnetic energy to be delivered into patient's biological structure to do more muscle work. Heating of the muscle and/or adjacent biological structure may also improve the quality of and/or level of muscle contraction. Because of heating provided by RF field, more muscle fibres and/or longer part of the muscle fibre may be able to contract during the magnetic treatment. Heating may also improves penetration of muscle stimuli generated by the magnetic treatment. Additionally, when at least partial muscle contraction or muscle contraction is repeatedly evoked, the patient's threshold of uncomfortable heating may also be shifted higher. Such shifting of the threshold may allow more RF energy to be delivered to the patient's body.

Repeated muscle contraction followed by muscle relaxation in combination with heating may suppress the uncomfortable feeling caused by muscle stimulation (e.g. muscle contraction). Muscle stimulation in combination with heating may provide better regeneration after treatment and/or better prevention of panniculitis and other tissue injury.

Repeated muscle contraction followed by muscle relaxation in combination with RF heating (according to preliminary testing) may have positive results in treatment and/or suppressing symptoms of diabetes. The repetitive muscle contraction induced by provided magnetic field together with heating of the biological structure by RF field may also improve the outcome of diabetes symptoms or positively influence results of diabetes symptoms drug treatment. Success of treatment of diabetes symptoms may be caused by penetration of high amount of radiofrequency energy deep to patient's abdomen area. Such penetration may be caused by simultaneous application of magnet treatment that may cause suppressing of patient's uncomfortable feelings related to high amount of RF energy flux density and increased temperature in the tissue. Also, magnet treatment may cause polarization and depolarization of patient's tissue that may also increase RF energy penetration to patient's body. The RF treatment and/or magnetic treatment may influence glucose metabolism or help with weight loss that may suppress diabetes symptoms. It is a believe that weight loss and exercise of patients with diabetes symptoms may help suppress diabetes symptoms.

Application of RF treatment by RF field combined with magnetic treatment by magnetic field may also positively influence proliferation and differentiation of myosatellite cells into muscle cells. Tests suggest that magnet treatment including time periods with different duration, repetition rate and magnetic flux density (e.g. pulses or trains as defined below) may provide a stimulation needed to start proliferation and differentiation of myosatellite cells.

Testing also suggest that method of treatment providing magnetic field including at least two or at least three successive time periods with different duration, repetition rate and magnetic flux density (e.g. pulses, bursts or trains as defined below) may provide a shock to the muscle. As a consequence, the regeneration process resulting in proliferation and differentiation of myosatellite cells may be started and further accelerated by delivered RF field. Proliferation and differentiation of myosatellite cells may result in muscle strengthening, restoration of muscle functionality, increasing muscle volume and improvement of muscle shape, body tone or muscle tone.

The method of application of at least partial muscle stimulation or muscle contraction together with heating to the same body area may result in hyperacidity of the extracellular matrix. Hyperacidity may lead to apoptosis of adipose tissue and acceleration of weight loss and body volume loss. Hyperacidity may be caused by release of fatty acids into the extracellular matrix, wherein the release of fatty acids may be caused by concentrated high intensity muscle work. Concentrated high intensity muscle work may be provided by high number of repetitive muscle contractions causes by application of time-varying magnetic field generated by described magnetic field generating device and treatment device.

The treatment effect of the RF treatment may be enhanced by magnetic treatment, such as by reducing or eliminating the risk of panniculitis or local skin inflammation since any clustering of the treated adipocytes may be prevented by the improved metabolism. The improved blood and/or lymph flow may contribute to removing adipocytes. The removal of adipocytes may be promoted by a higher number of cells phagocytosing the adipocytes as well. Synergic effects of magnetic treatment and radiofrequency (RF) treatment significantly improves metabolism. Therefore, the possibility of adverse event occurrence is limited, and treatment results induced by the present device and method are reached in shorter time period.

The treatment device and the method of a treatment may provide treatment of the same patient's body area, wherein the magnetic treatment and the RF treatment may be targeted into at least part of one or more biological structures. One or more volumes of patient's body tissue affected by targeted RF and/or magnetic treatment may be in proximity. The volume of at least part of at least one or more affected biological structures of patient's body tissue may be defined as an affected tissue volume wherein the treatment effect provided by treatment device and/or method of treatment described above takes place. The treatment effect may be caused by repeated muscle contraction (provided e.g. magnetic treatment) changing of a tissue temperature (provided e.g. RF treatment), and/or by at least partial polarization and acceleration of molecules in the patient's tissue (preferably provided by RF treatment and magnetic treatment). Changing of a tissue temperature may include e.g. an increasing tissue temperature of at least 3° C. or 4° C. or 5° C. or 6° C. or 7° C. or 10° C. with reference to normal tissue temperature. Further, changing of a tissue temperature may include an increase or decrease of tissue temperature in the range of 1° C. to 50° C. or 2° C. to 30° C. or 2° C. to 25° C. as compared to the untreated tissue located in the same or different body area. Changed tissue temperature may be interpreted as change of temperature in any volume or any area of the biological tissue.

Proximity of affected tissue volumes by at least one RF treatment and/or by at least one magnetic treatment has meaning of a distance between two affected tissue volumes. At least two proximate affected tissue volumes may have at least partial overlay wherein 2% to 15% or 5% to 30% or 2% to 100% or 30% to 60% or 80% to 100% or 40% to 85% of smaller affected tissue volume may be overlaid by larger affected tissue volume. Also the distance between volumes of affected tissue may be in a range of 0.01 cm to 10 cm or in the range of 0.01 cm to 5 cm, 0.01 cm to 3 cm, or 0.01 cm to 1 cm. Alternatively, the overlay in the ranges mentioned above may apply for two or more affected tissue volumes having an identical volume without any differentiation between smaller or larger tissue volumes.

FIGS. 1*a*-1*e* show exemplary schematic diagrams of the treatment device. The diagrams may apply only to main unit and applicator. The treatment device may include input interface 103, control system 104, power source 105, power network 106, one or more treatment clusters 107 and one or more treatment energy sources 108.

Plurality of treatment energy sources 108 may be coupled to or communicate with at least one treatment cluster 107. Control system 104 may be coupled to and communicate with each treatment cluster.

Shown parts of treatment device in FIGS. 1*a*-1*e* may be electrical elements of circuitry. Also, one or more shown parts of diagrams in FIGS. 1*a*-1*e* may include plurality of individual electrical elements. Electrical elements may generate, transfer, modify, receive or transmit electromagnetic signal (e.g. electrical) signal between individual electrical elements. The electromagnetic signal may be characterized by current, voltage, phase, frequency, envelope, value of the current, amplitude of the signal and/or their combination. When the electromagnetic signal reaches the treatment energy source, the respective treatment energy source may generate treatment energy and/or field.

Input interface 103 may receive input from a user. Input interface may include human machine interface (HMI). The HMI may include one or more displays, such as a liquid crystal display (LCD), a light emitting diode (LED) display, an organic LED (OLED) display, which may also include a touch-screen display. HMI may include one or more controlling elements for adjustment or controlling treatment device. Controlling element may be at least one button, lever, dial, switch, knob, slide control, pointer, touchpad and/or keyboard. The input interface may communicate or be coupled to control system or power network.

The user may be an operator (e.g. medical doctor, technician, nurse) or patient himself, however the treatment device may be operated by patient only. In most cases, the treatment device may be operated by the user having an appropriate training. The user may be any person influencing treatment parameters before or during the treatment in most cases with exception of the patient.

Control system 104 may include a master unit or one or more control units. Control system may be an integral part of the input interface 103. Control system 104 may be controlled through the input interface 103. Control system may include one or more controlling elements for adjustment or controlling any part or electrical elements of treatment device. Master unit is a part of treatment device (e.g. applicator and/or main unit) or electrical element of circuitry that may be selected by the user and/or treatment device in order to provide master-slave communication including high priority instructions to other parts of the treatment device. For example, master unit may be a control unit or part of input interface providing high priority instructions to other parts of the treatment device. The treatment device may include a chain of master-slave communications. For example, treatment cluster 107 may include one control unit providing instructions for electrical elements of the treatment cluster 107, while the control unit of treatment cluster 107 is slave to master unit. Control system 104 may be coupled or communicate with input interface 103, one or all power source 105, power network 106, and/or with one or all treatment clusters present in the treatment device. The control system 104 may include one or more processors (e.g. a microprocessors) or process control blocks (PCBs).

The power source 105 may provide electrical energy including electrical signal to one or more treatment clusters. The power source may include module converting AC voltage to DC voltage.

The power network 106 may represent a plug. The power network may represent a connection to power grid. However, the power network may represent a battery for operation of the treatment device without need of a power grid. The power network may provide electrical energy needed to operation to whole treatment device and/or its parts. As shown on exemplary diagrams in FIGS. 1*a*-1*e*, the power network provides electrical energy to input interface 103, control system 104 and power source 105.

The treatment cluster 107 may include one or more electrical elements related to generation of respective treatment energy. For example, the treatment cluster for magnetic treatment (referred as HIFEM) may include e.g. an energy storage element and switching device. For another example, the treatment cluster for RF treatment (referred as RF cluster) may include e.g. power amplifier and/or filter.

The treatment energy source 108 may include a specific source of treatment energy. In case of magnetic treatment, the treatment energy source of magnetic field may be a magnetic field generating device e.g. a magnetic coil. In case of RF treatment, the treatment energy source of RF energy (including RF waves) may be RF electrode.

The treatment device may include one or more treatment circuits. One treatment circuit may include a power source, electrical elements of one treatment cluster and one respective treatment energy source. In case of magnetic treatment, the magnetic circuit may include a power source, HIFEM cluster and magnetic field generating device. In case of RF treatment, the RF circuit may include a power source, RF cluster and magnetic field generating device. The RF circuit may include a power source, RF cluster and at least one RF electrode. The electromagnetic signal generated and/or transmitted within a treatment circuit for RF treatment (also referred as RF circuit) may be referred as RF signal. The wiring connecting respective electrical elements of the one treatment cluster may also be included in the respective cluster. Each of the treatment clusters in FIGS. 1*a*-1*e* described in the detail below may be any of HIFEM, RF or combination.

The one or more treatment circuits and/or their parts may be independently controlled or regulated by any part of control system 104. For example, the speed of operation of HIFEM cluster of one treatment circuit may be regulated independently on the operation of HIFEM cluster of another treatment circuit. In another example, the amount of energy flux density of delivered by operation of RF electrode of one treatment circuit may be set independently from the operation of RF electrode of another treatment circuit.

FIG. 1*a* shows an exemplary diagram of the treatment device including input interface 103, control system 104, power source 105, power network 106, two treatment clusters including treatment cluster A 107*a*, treatment cluster B 107*b*, treatment energy source A 108*a* and treatment energy source B 108*b*. In such case, treatment device may include two treatment circuits. One treatment circuit may include a power source 105, treatment cluster A 107*a* and/or treatment energy source A 108*a*. Another treatment circuit may include a power source 105, treatment cluster B 107*b* and/or treatment energy source B 108*b*. Treatment clusters 107*a* and 107*b* may communicate with each other.

Figure 1B:
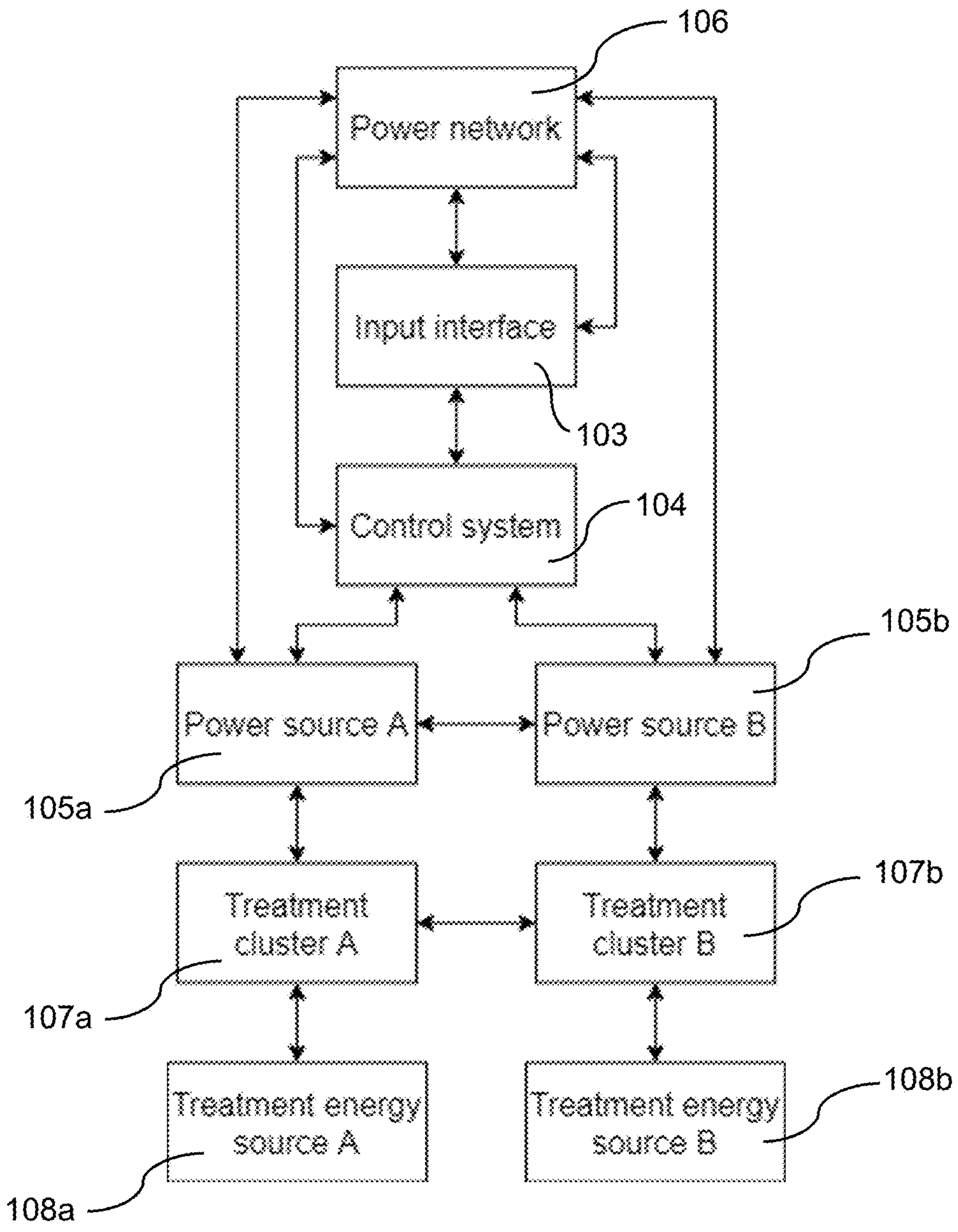

FIG. 1*b* shows an exemplary diagram of the treatment device including input interface 103, control system 104, two power sources including a power source A 105*a* and a power source B 105*b*, power network 106, two treatment clusters including treatment cluster A 107*a* and treatment cluster B 107*b*, treatment energy source A 108*a* and treatment energy source B 108*b*. In such case, treatment device may include two treatment circuits. One treatment circuit may include a power source 105*a*, treatment cluster A 107*a* and/or treatment energy source A 108*a*. Another treatment circuit may include a power source B 105*b*, treatment cluster B 107*b* and/or treatment energy source B 108*b*. Treatment clusters 107*a* and 107*b* may communicate with each other.

Figure 1C:
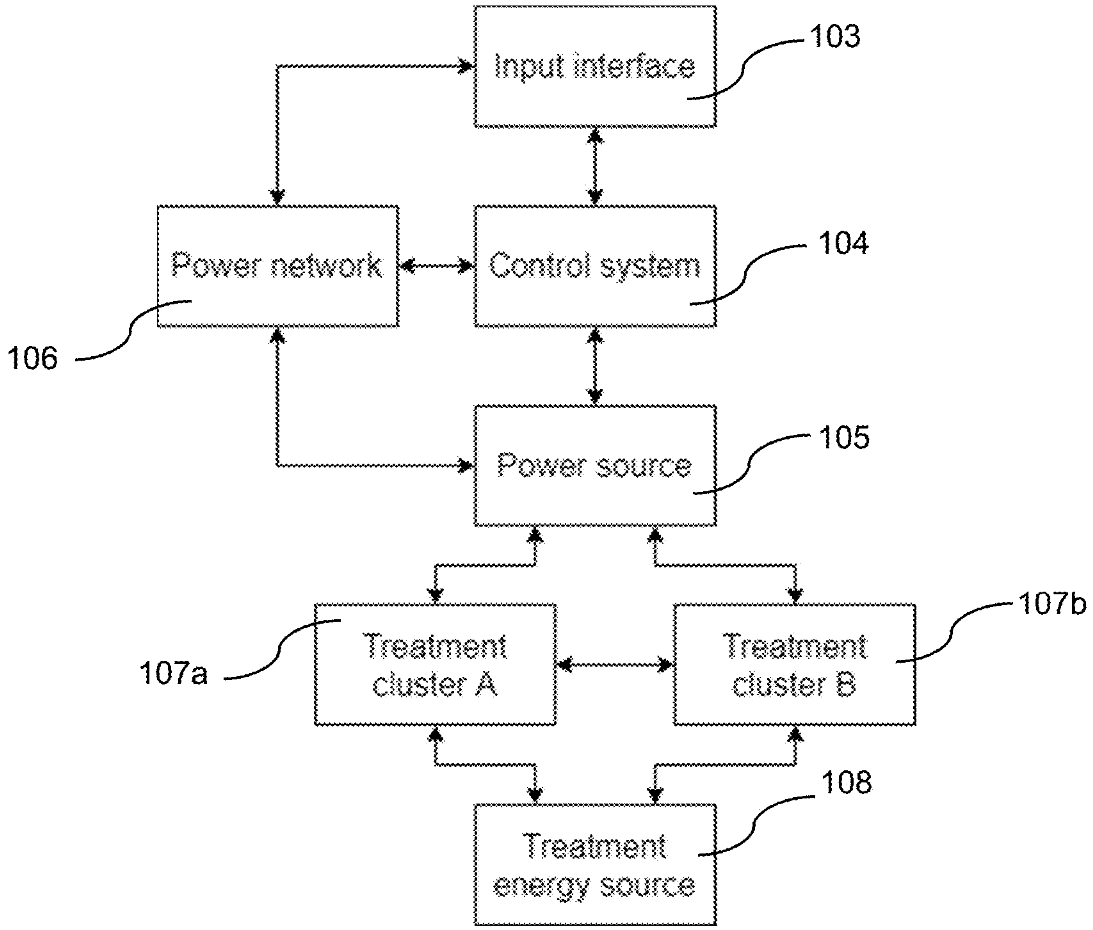

FIG. 1*c* shows an exemplary diagram of the treatment device including input interface 103, control system 104, power source 105, power network 106, two treatment clusters including treatment cluster A 107*a* and treatment cluster B 107*b* and one treatment energy source 108. In such case, treatment device may include two treatment circuits. One treatment circuit may include a power source 105, treatment cluster A 107*a* and/or treatment energy source 108. Another treatment circuit may include the power source 105, treatment cluster B 107*b* and/or treatment energy source 108. Treatment clusters 107*a* and 107*b* may communicate with each other. The shown diagram may include a magnetic field generating device providing both RF treatment and magnetic treatment.

Figure 1D:
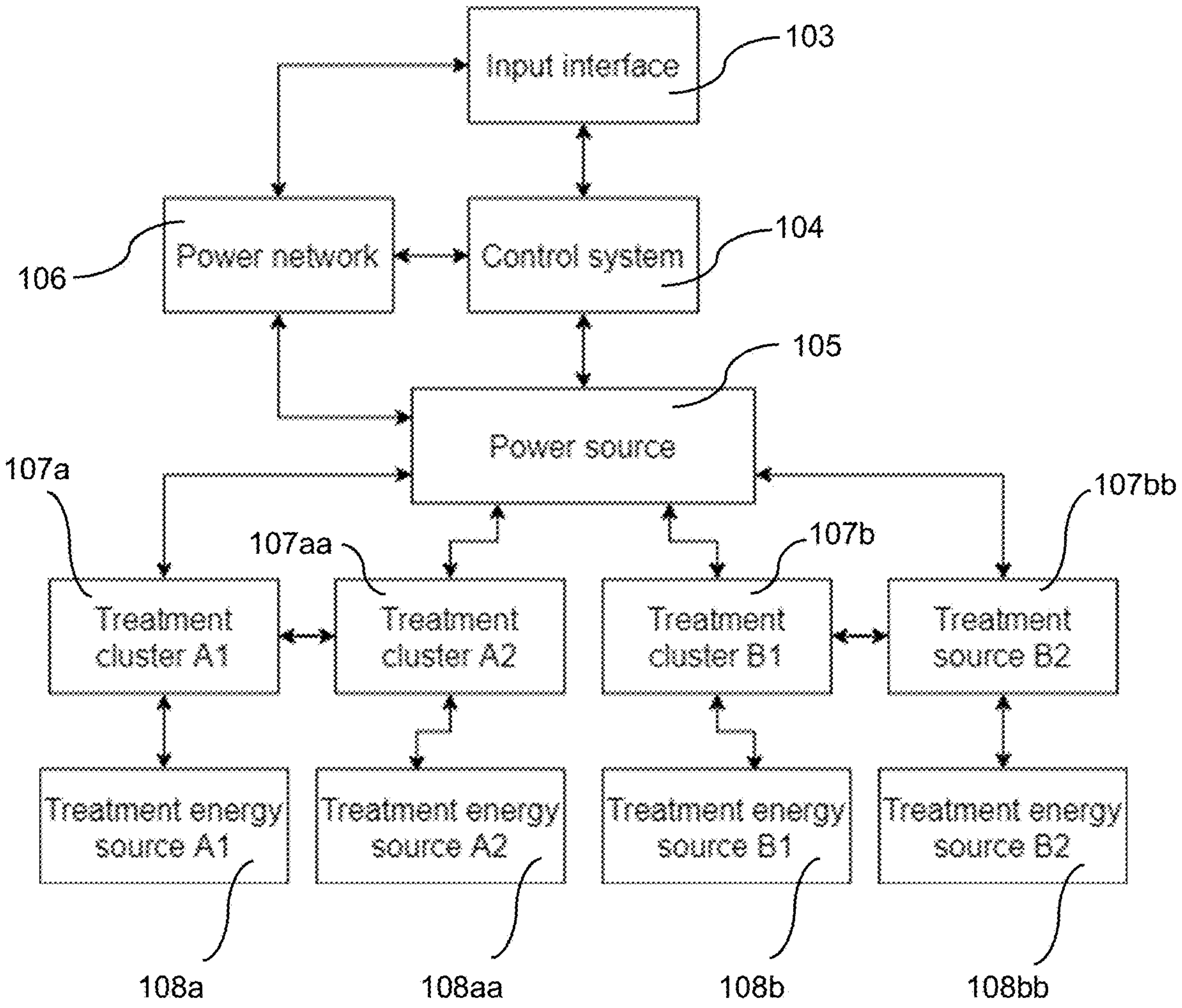

FIG. 1*d* shows an exemplary diagram of the treatment device including input interface 103, control system 104, power source 105, power network 106, four treatment clusters including treatment cluster A1 107*a*, treatment cluster A2 107*aa*, treatment cluster B1 107*b*, treatment cluster B2 107*bb* and four treatment energy sources including treatment energy source A1 108*a*, treatment energy source A2 108*aa*, treatment energy source B1 108*b* and treatment energy source B2 108*bb*. In such case, treatment device may include four treatment circuits. First treatment circuit may include a power source 105, treatment cluster A1 107*a* and/or treatment energy source 108*a*. Second treatment circuit may include the power source 105, treatment cluster A2 107*aa* and/or treatment energy source A2 108*aa*. Third treatment circuit may include a power source 105, treatment cluster B1 107*b* and/or treatment energy source B1 108*b*. Fourth treatment circuit may include a power source 105, treatment cluster B2 107*bb* and/or treatment energy source B2 108*bb*. The treatment energy sources of the first treatment circuit and second treatment circuit may be positioned in one applicator, while the treatment energy sources of the third treatment circuit and fourth treatment circuit may be positioned in another applicator.

Figure 1E:
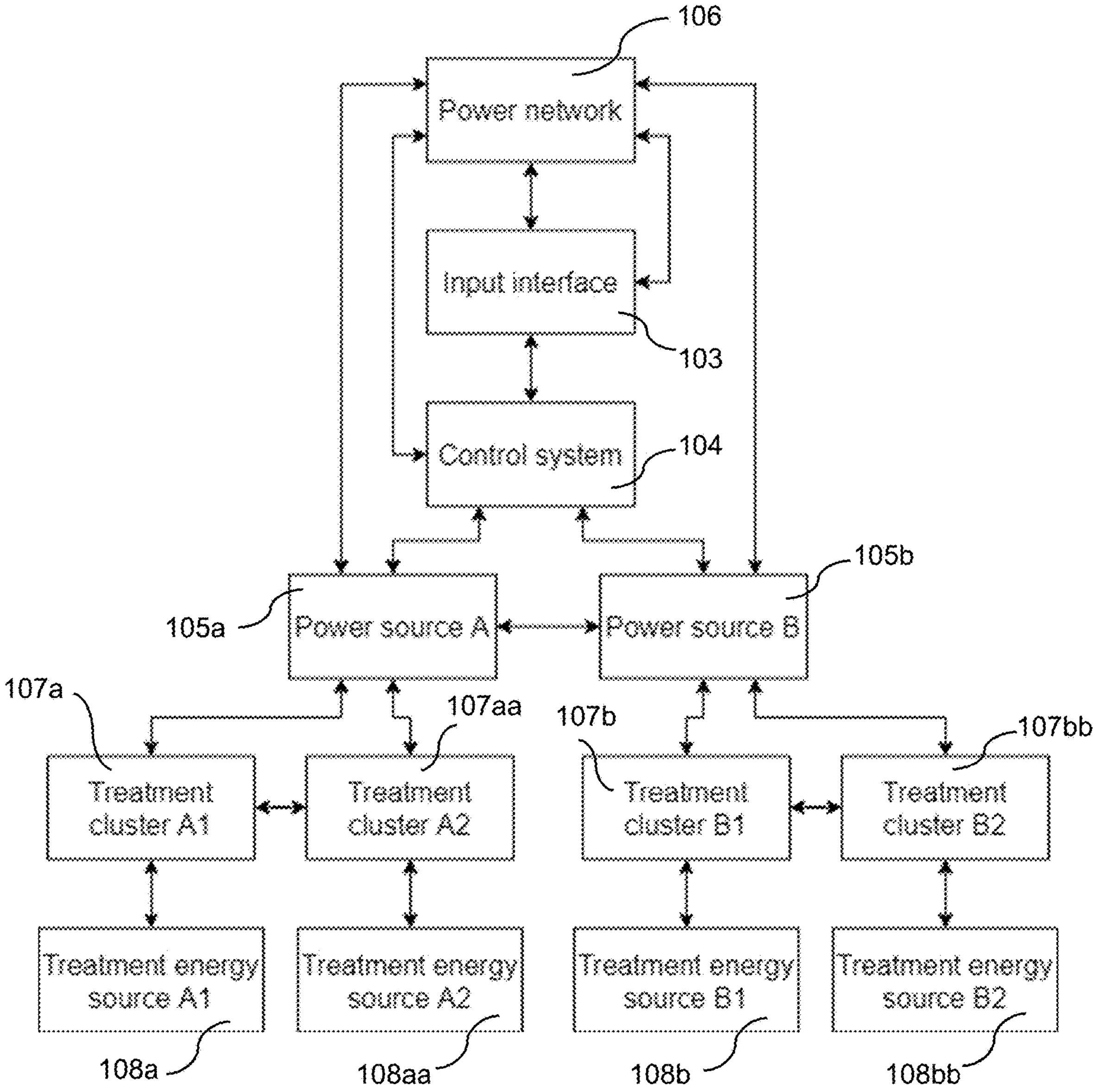

FIG. 1*e* shows an exemplary diagram of the treatment device including input interface 103, control system 104, two power sources including power source A 105*a* and power source B 105*b*, power network 106, four treatment clusters including treatment cluster A1 107*a*, treatment cluster A2 107*aa*, treatment cluster B1 107*b*, treatment cluster B2 107*bb* and four treatment energy sources including treatment energy source A1 108*a*, treatment energy source A2 108*aa*, treatment energy source B1 108*b* and treatment energy source B2 108*bb*. In such case, treatment device may include four treatment circuits. First treatment circuit may include a power source A 105*a*, treatment cluster A1 107*a* and/or treatment energy source 108*a*. Second treatment circuit may include a power source A 105*a*, treatment cluster A2 107*aa* and/or treatment energy source A2 108*aa*. Third treatment circuit may include a power source B 105*b*, treatment cluster B1 107*b* and/or treatment energy source B1 108*b*. Fourth treatment circuit may include a power source B 105*b*, treatment cluster B2 107*bb* and/or treatment energy source B2 108*bb*. The treatment energy sources of the first treatment circuit and second treatment circuit may be positioned in one applicator, while the treatment energy sources of the third treatment circuit and fourth treatment circuit may be positioned in another applicator.

Figure 1F:
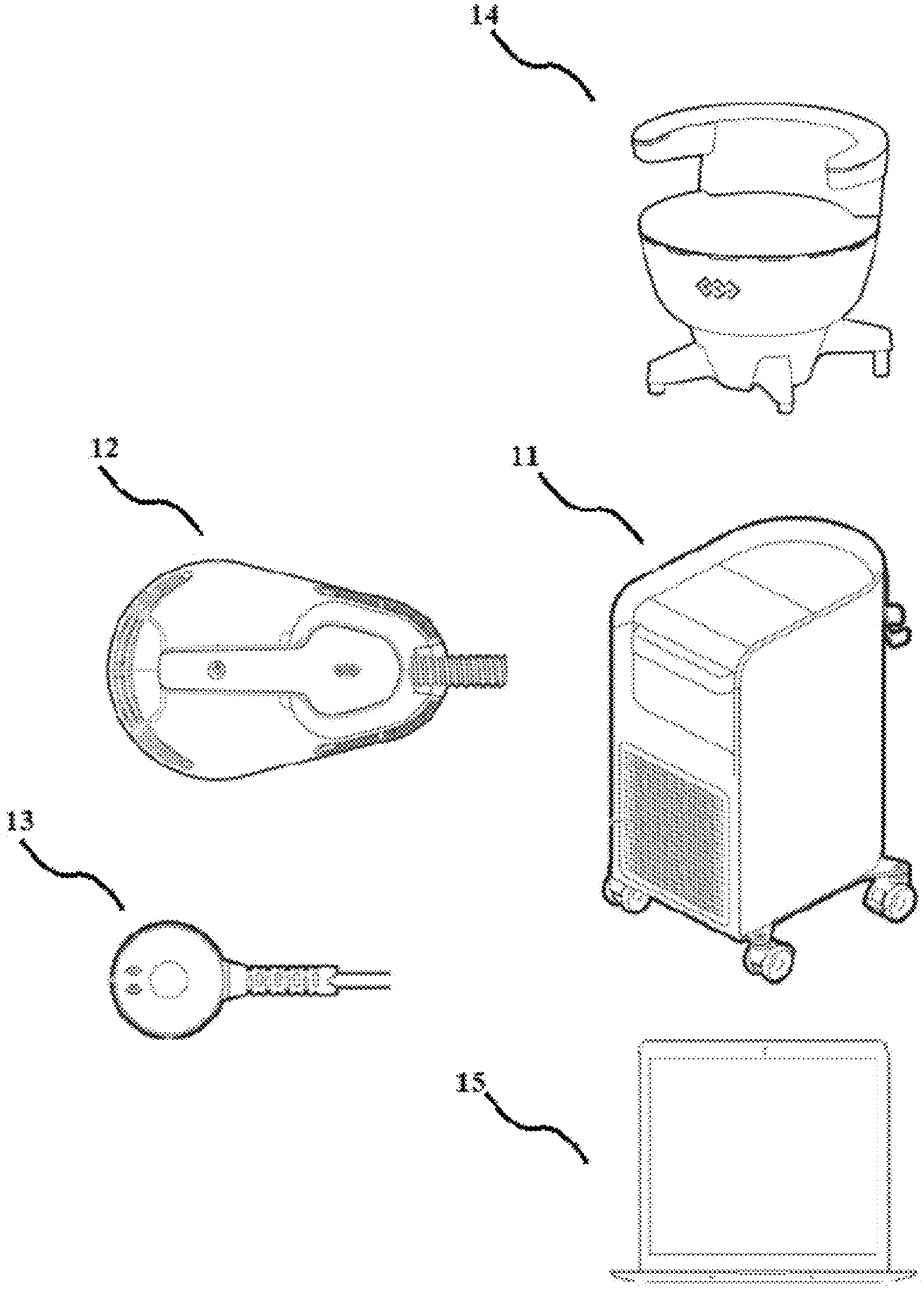
FIG. 1*f* illustrates exemplary individual parts of a treatment device.

FIG. 1*f* illustrates individual parts of the treatment device, including a main unit 11 connected or coupled to at least one applicator 12, a remote control 13, an additional or additional treatment device 14, and/or a communication device 15. The additional treatment device may be on the same level of independency as the whole treatment device.

The treatment device may include a remote control 13. Remote control 13 may include a discomfort button for safety purposes so that when a patient feels any discomfort during the treatment, the user may press the discomfort button. When the discomfort button is pressed, remote control 13 may send a signal to a main unit and stop treatment. Also, the remote control 13 may inform the user through a human machine interface (HMI). In order to stop treatment during discomfort, the operation of the discomfort button may override the instructions from master unit. Alternatively, the discomfort button may be coupled to or be part of the main unit 11.

The main unit 11 may be coupled or connected to one or more additional treatment devices 14 that may be powered by the main unit 11. However, the treatment device including main unit 11 may be paired by software with the one or more additional treatment devices 14. Also, one or more additional treatment devices 14 may be also powered by their own source or sources of energy. The communication device 15, additional treatment device 14, remote control 13 and at least one applicator 12 may each communicate with the main unit 11. Communication may include sending and/or receiving information. Communication may be provided by wire and/or wirelessly, such as by internet network, local network, RF waves, acoustic waves, optical waves, 3G, 4G, 5G, GSM, HUB switch, LTE network, GSM network, Bluetooth and/or other communication methods or protocols.

The additional treatment device 14 may be any device that is able to provide at least one type of treatment energy (e.g.: RF field, magnetic field, ultrasound, light, time-varied mechanical pressure, shock wave, or electric current) to a patient's body to cause treatment effect to at least one target biological structure. The additional treatment device 14 may include at least one electrical element generating treatment energy for at least one treatment, e.g. magnetic, radiofrequency, light, ultrasound, heating, cooling, massage, plasma and/or electrotherapy. The additional treatment device 14 may be able to provide at least one treatment without instructions from the main unit 11. The additional treatment device 14 may communicate with the main unit 11, communication device 15 and/or other additional treatment devices 14. The additional treatment devices 14 may be any other device of the same or other company wherein the device may be able to provide specific one or more type of treatment energy. The additional treatment device 14 may be an extension of the treatment device, wherein the additional treatment device 14 may provide treatment energy with parameters defined by the HMI of the main unit 11.

The communication device 15 may be connected by wire and/or wirelessly to the main unit 11. The communication device 15 may be a computer, such as a laptop or desktop computer, or a mobile electronic device, such as a smartphone, or an electronic tablet. The communication device may send and/or receive information linked with a treatment, functionality of the treatment device, and/or other information. The additional treatment device 14 and/or the communication device 15 may communicate directly with the main unit 11 or indirectly with the main unit 11 through one or more additional or communication devices. In order to provide communication the communication device may include receiver, transmitter and a control unit to process sent and/or received information.

Sent and/or received information from or to an individual part of the treatment device may include data from communication between communication device 15 and the main unit 11, data from communication between applicator 12 and the main unit 11, data from communication between additional treatment device 14 and the main unit 11 and/or data from communication between the remote control 13 and the main unit 11. Sent and/or received information may be stored in a black box, cloud storage space and/or other storage devices. The black box may be part of the main unit 11 or any other part of the treatment device. Other storage device may be USB, other memory device and/or also communication device with internal memory. At least part of sent and/or received information may be also displayed by HMI. Sent and/or received information may be displayed, evaluated and/or changed by the user through the HMI and/or automatically by control system. One type of the sent and/or received information may be predetermined or current value or selection of one or more treatment parameters or patient information. Patient information may include e.g. gender of a patient, age and/or body type of the patient.

Sent and/or received information may also inform external authorities, like a support centre, e.g. a service and/or a sale department, that are also subset of communication devices. Sent and/or received information to external authorities may include information about the condition of the treatment device, history of one or more provided treatments, operational history of the treatment device, software update information, wear out information, durability of the RF electrode, durability of the magnetic field generating device, treatment warnings, treatment credit/billing information, such as information of number of paid treatments or credits, and/or other operation and usage information.

One possible type of sent and/or received information may be recognition of connection of one or more applicators 12, the remote control 13, additional treatment devices 14, and/or communication devices 15, According to information the treatment device may manually or automatically recognize type of connected additional treatment device 14 and/or applicator 12. Automatic recognition may be provided by control system. Based on information about connection of one or more applicators 12, connection of additional treatment devices 14 and/or communication devices 15, the treatment device may provide actualization of HMI, show notification about the connection to applicators and/or possible optimization of new treatment options. Possible optimization of new treatment options may include e.g. adjusting of at least one treatment parameter, implementing additional treatment energy source, change of parameters of new treatment energy source and/or other. The treatment device (e.g. control system) may automatically adjust or offer adjustment of treatment parameters based on newly connected applicator 12 and/or additional treatment devices 14. Recognition of connected applicator 12, additional treatment device 14 and/or communication device 15 may be based on by specific connectors (e.g., a specific pin connector). Also, the recognition of connection may be provided by a specific physical characteristic like an impedance of connected part or by a specific signal provided by the applicator or its connected part to the main unit 11. Connection between individual parts of the treatment device such as the main unit 11, the applicator 12, the remote control 13, the additional treatment device 14 and/or the communication device 15 may be provided by wire and/or wirelessly (e.g. by RFID tag, RF, Bluetooth, and/or light electromagnetic pulses). The applicator 12 may by connected to the main unit 11 by a wire to be powered sufficiently. Alternatively, the application may be connected through a wireless connection in order to communicate with the main unit 11 and/or with communication device 15. Connected applicator 12, additional treatment device 14 and/or communication device 15 may be recognized by software recognition, specific binary ID, manual recognition of the parts selected from the list implemented in the treatment device, and/or by a pairing application.

The connector side in the main unit 11 may include a unit able to read and/or recognize information included in the connector side of the applicator and/or connector side of the additional treatment device. Based on read and/or recognized information, the applicator and/or the additional treatment device may be recognized by main unit 11. The connector side of the main unit 11 may serve as a first side connector of the connection, wherein the connection of the applicator or additional treatment device may serve as a second side connector of the connection. Sending of the information, receiving of the information and/or recognition of the second side connector by the first side connector may be based on binary information received by conductive contact between these two connector sides, by optical reading and/or by recognition provided by the first side connector. Optical recognition may be based on, for example, reading of specific QR codes, barcodes and the like for the specific applicators 12.

The first side connector located in the main unit 11 may include a unit able to read/recognize binary information implemented in the second side connector of a cable from the applicator 12 and/or additional treatment device 14. Implemented information in the second side connector may be stored in an SD card. Based on such implemented information any part of the treatment device may be recognized by the main unit 11.

Communication between individual parts of the treatment device (including e.g. the main unit 11, the remote control, one or more applicators, one or more additional treatment devices and/or communication devices) may be based on peer-to-peer (referred as P2P) and/or master-slave communication. During P2P communication, the individual parts of the treatment device have the same priority of its commands and/or may communicate directly between each other. P2P communication may be used during initial recognition of connected individual parts of the treatment device. P2P communication may be used between some parts of the treatment device during a treatment, such as between communication devices.

Master-slave communication may be used between individual parts of the treatment device for at least a short time during, before and/or after each treatment of individual patient. During master-slave communication, one part of the treatment device may provide commands with the highest priority. The individual part of the treatment device, e.g. as the main unit 11 may provide commands with the highest priority and is referred as master unit. The treatment device may include at least one master-slave communication between an individual electrical element, such as a power source and or one or more control units, where the one or more control units act as master.

The master unit may be selected by a user before, after and/or during the treatment. The user may select master unit from available individual parts or electrical elements of the treatment device. Therefore, the user may select the main unit 11, the applicator 12, the remote control 13, the additional treatment device 14 or the communication device 15 as the master unit. The master unit may be a control unit in selected present in individual part of the treatment device e.g. a control unit in the main unit 11. The user may select the master unit in order to facilitate adjusting of treatment parameters. The user may also select the communication device 15 as a master unit, wherein the communication device selected as master device may provide control of more than one treatment device. The main unit 11 may include a control unit as a master unit that monitor and evaluate at least one parameter of the treatment, such as patient's temperature, voltage on individual elements of the treatment device and/or other, that enable to provide safe treatment even if the connection between. Also, the master unit may be independent electrical element outside of human machine interface. The master unit may be controlled by user through human machine interface.

Alternatively, the master unit may be selected automatically based on a predetermined priority value of the connected parts of the treatment device. Selected master unit may remain unchanged and already selected part of the treatment device may act as the master unit during the whole treatment. However, the selection of master unit may be changed during the treatment based on command priority and/or choice of the user. The master unit may be also determined according to manufacturing configuration or being dependent on factory reset. For example, the remote control 13 may provide command with the highest priority to stop the treatment when patient feels discomfort and the treatment will be stopped without relevance of which individual part of the treatment device was set as the master unit and set parameters of the treatment.

FIGS. 2-5 illustrate several possible master-slave communication schemes that may be used in communication between the main unit 11 and one or more applicators 12, remote controls 13, additional treatment devices 14, and/or communication devices 15. According to FIG. 2, one or more therapy generators 201 generate a modified electrical signal in order to provide a signal to a treatment energy source, such as the RF electrode and/or the magnetic field generating device. The therapy generators 201 may include a group of electrical elements or at least two members of the group of electrical elements present in the circuitry of the treatment device and/or main unit. The group of electrical elements may include a control unit, power source, system of coaxial cables, one or more switches, one or more energy storage devices, one or more pin diodes, one or more LC circuits, one or more LRC circuits, one or more power amplifiers and/or other part of the treatment device actively modifying electrical signal in controlled manner. The therapy generator may provide modifying of electrical signal in controlled manner.

Modifying electrical signal in controlled manner may include e.g. providing and/or controlling impedance adjustment of provided RF treatment based on impedance matching measured across patient's tissue and/or RF electrodes. Actively modified electrical signal may be interpreted such that electrical signal may have different parameters, such as frequency, symmetrisation, amplitude, voltage, phase, intensity, etc. The parameters of electrical signal may be based on requirements of treatment including the type of the patient, treatment parameters. In addition, the parameters of electrical signal may be modified on feedback information, such as measured standing wave ratio of RF energy, temperature of tissue, temperature of RF electrode, temperature of the inside of the applicator, temperature of the surface of the applicator, electric current and voltage of individual elements of the treatment device and/or other.

Figure 2:
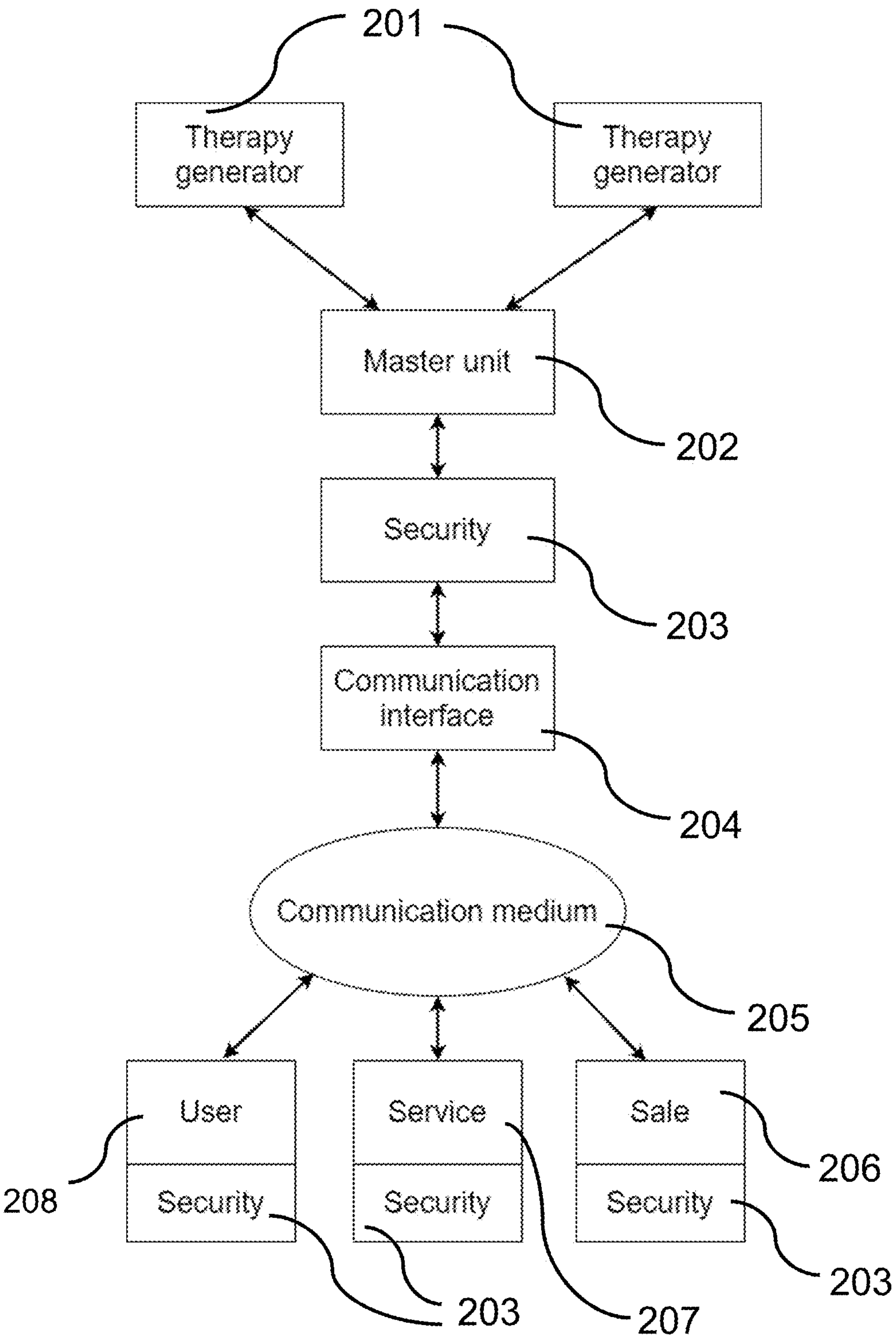
FIG. 2 illustrates an exemplary communication diagram between parts of the treatment device such as an applicator, a remote control, an additional treatment device and a communication device.

The diagram of FIG. 2 shows a security 203 that prevent any unauthorized intrusion to the treatment device communication and protects personal user data and/or account. The security 203 may protect the treatment device from computer viruses, unauthorized access and/or protect the communication between individual parts of the treatment device from reading or change by unauthorized medium or person. The security 203 may provide coding of the information used in communication and/or antivirus services preventing intrusion of unwanted binary code into the treatment device and/or communication. The security 203 may correct mistakes created during the communication. The security 203 may block connection of unauthorized/unwanted external device to the treatment device.

The security 203 in FIG. 2 may be located in the communication diagram between the master unit 202 and a communication interface 204. The security 203 may also be part of an element user 208, a service 207, and/or a sale 206. The security 203 may be located also between the communication interface 204 and a communication medium 205, the therapy generator 201, and/or may be part of them.

The communication interface 204 may include hardware and/or software components that enables to translate electric, electromagnetic, infrared and/or other signal into readable form to enable communication between at least two parts of the treatment device and/or other communicating sides or medium. The communication interface 204 may provide communication and/or coding of the information and/or data. The communication interface 204 may be, for example, a modem or GSM module providing communication between the treatment device and online network or server. The communication interface 204 may be part of the master unit 202, the therapy generator 201, and/or other part of the treatment device.

The communication medium 205 may be medium transferring communication data. The communication medium 205 may be used in communication between the treatment device and the user 208, the service 207 and/or the sale 206. The communication medium 205 may be a wire, SD card, flash memory, coaxial wire, any conductive connection, server, some kind of network on principle, such as RF waves, acoustic waves, optic waves, GSM, 3G, 4G, 5G, HUB switch, Bluetooth, Wi-Fi and/or other medium which may include one or more servers.

Communication data/information may be redirected to the individual parts of the treatment device and/or to individual users or services, such as the user 208, the service 207 and/or the sale 206. Communication data/information may be redirected by the master unit 202, the communication medium 205 and/or the therapy generator 201. For example, server may filter data for the user 208 and filter other communication information that will be redirecting to the service 207, control unit and/or other part of the treatment device.

The element called "user 208" of FIG. 2 may be a representation of the HMI controlled by a user. Alternatively, the element called "user 208" of FIG. 2 may a representation of the other communication device (personal computer, laptop, mobile, tablet, etc.) controlled by user, wherein the communication device may send information to at least one part of the treatment device and/or receive information from at least one part of the treatment device. Information provided by this communication channel may be a type of a treatment protocol, information about treatment effect, actual value and/or predetermined value of one or more treatment parameters, feedback information, selection of treated body area, recommendations of behaviour before and after the treatment and/or other information. At least part of the information may be sent to the user controlling the treatment device and also to the patient, such as by an software application for mobile phone, tablet or laptop.

The service 207 in FIG. 2 may represent a service department that has authorized access to information about the treatment device. The service 207 may be the service department of the company providing or manufacturing the treatment device wherein the communication between the service department of the company and the user may be provided through the HMI, a communication device and/or automatically through pre-programmed software interface.

Information provided by this communication channel may include wear of individual electrical element of the treatment device, durability of any RF electrode and/or magnetic field generating device, malfunction of an individual electrical element, possible software optimization and/or actualization of the device, providing applications for connection of another additional treatment device and/or other. Optimization and/or actualization of the treatment device may include e.g. a remote access to the treatment device software and/or fixing errors.

The sale 206 in FIG. 2 may be a sales department with authorized access to information about the treatment device. The sale 206 may inform the user about a type of accessories which may be added to the treatment device. Further the sale 206 may mediate sales of the plug-in modules and/or mediate sales of accessories of the treatment device. Furthermore, the sale 206 may provide an offer linked with billing and renting system. Information exchanged by communication to or from sale 206 may be, for example, the number of treatments, time of treatments, and/or type of applied treatment, information about applicators and/or others.

The treatment device may include a black box for storing a data regarding the treatment history, operational history, communication between individual parts of the treatment device, data from or for a billing and renting system, operational errors, and/or other information. The data may be accessible to the sale 206, to the service 207 and/or to the user 208 via the communication medium (e.g., a storage cloud and/or server). The treatment device may include a billing and renting system to manage charges for using of the treatment device and/or respective additional treatment devices. The billing and renting system may send such information to a provider in order to prepare the billing invoice. Data from the black box may be downloaded by verified authorized personnel, such as a service technician, accountant and/or other person with administrator access. Verification of the authorized person may be provided by specific key, password, software code of several bits and/or by specific interconnecting cable.

The billing and renting system may be based on credits subtracted from a user account. Credits may be predefined by the provider of the treatment device, e.g. a producer of the treatment device. Credits may be recharged during the time when the treatment device is in operation and/or may be recharged to online account linked with one or more treatment devices of the user and/or provider. Credits may be subtracted according to the selected treatment protocol or body area. Credit value for individual one or more treatments and/or part of the treatment may be displayed to the user before treatment starts, during the treatment and/or after the treatment. If the credit in the user's account runs out, the treatment device may not enable any further treatment until credits are recharged. Credits may be used as a currency changed for individual treatment wherein different treatment may cost a different amount of credits based on the type of the treatment, the duration of the treatment, the number of used applicators, and/or other factors. Credits may be also used for renting or buying individual part of the treatment device, whole treatment device, hardware or software extensions of the treatment device and/or other consumables and spare parts belonging to the treatment device. Interface where the credit system may be recharged may be part of the treatment device, HMI and/or online accessible through website interface.

One or more software extension (e.g. software applications) may be linked with the treatment device and method of treatment. One or more software extensions may be downloaded to any communication device, such as a smartphone, tablet, computer and/or other electronic device. The software extension may communicate with the main unit and/or other part of the treatment device. The communication device with installed software extension may be used for displaying or adjusting of one or more treatment parameters or information associated to the treatment. Such displayable treatment parameters and information associated to the treatment may include e.g. time progress of the treatment, measured size of treated body area before and/or after individual treatments, schematic illustrations of applied bursts or trains, remaining time of the treatment, heart rate of the patient, temperature of patient's body e.g. temperature of the body surface, provided types of treatment, type of the treatment protocol, comparison of patient's body parameters against previous treatment (e.g., body fat percentage) and/or actual treatment effect of the treatment (e.g. muscle contraction or muscle relaxation). The software extension may be also provided to the patient in order to inform them about the schedule of treatments, mapping progress between individual treatments, percentile of treatment results compared to other people and/or recommendations of behaviour before and/or after the treatment. Recommendations of behaviour may include e.g. recommendation what volume of water should patient drink during the day, how should patient's diet look like, what type and volume of exercise should patient provide before and/or after treatment and/or other information that may improve results of treatment.

Communication between individual elements of the communication diagram, such as the therapy generator 201, the master unit 202, the security 203, the communication interface 204, the communication medium 205, the user 208, the service 207 and/or the sale 206 may be bidirectional or multidirectional.

Connection between the user 208, the service 207, the sale 206, communication medium 205 and/or connection between the therapy generator 201 and the master unit 202 may be secured by the security 203 to provide safe communication and eliminate errors. The security 203 may be located between the master unit 202 and the communication interface 204 and/or between the communication medium 205 and the communication interface 204.

Figure 3:
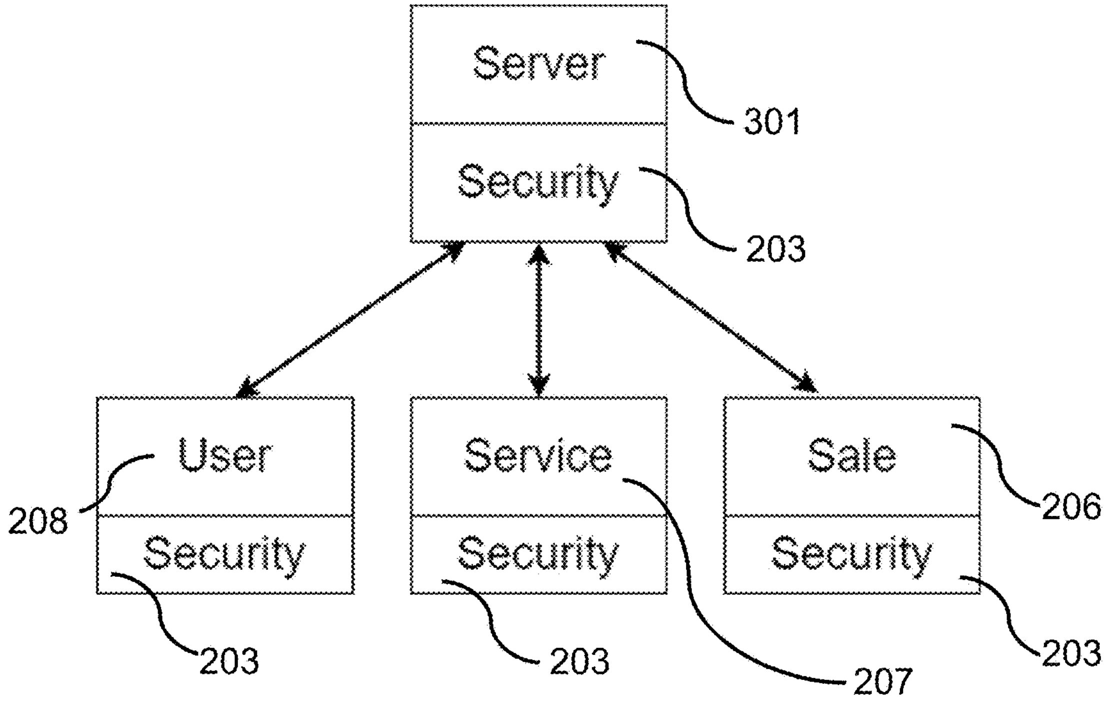
FIG. 3 illustrates an exemplary communication diagram between a server and part of the treatment device such as applicators, remote control and additional treatment devices.

As shown on FIG. 3, another option of remote access communication between the user 208, the service 207, and/or the sale 206 and the treatment device may be provided by a server 301. The server 301 may include the security 203. The security 203 may be implemented in individual access of the user 208, the service 207, and/or the sale 206.

Figure 4:
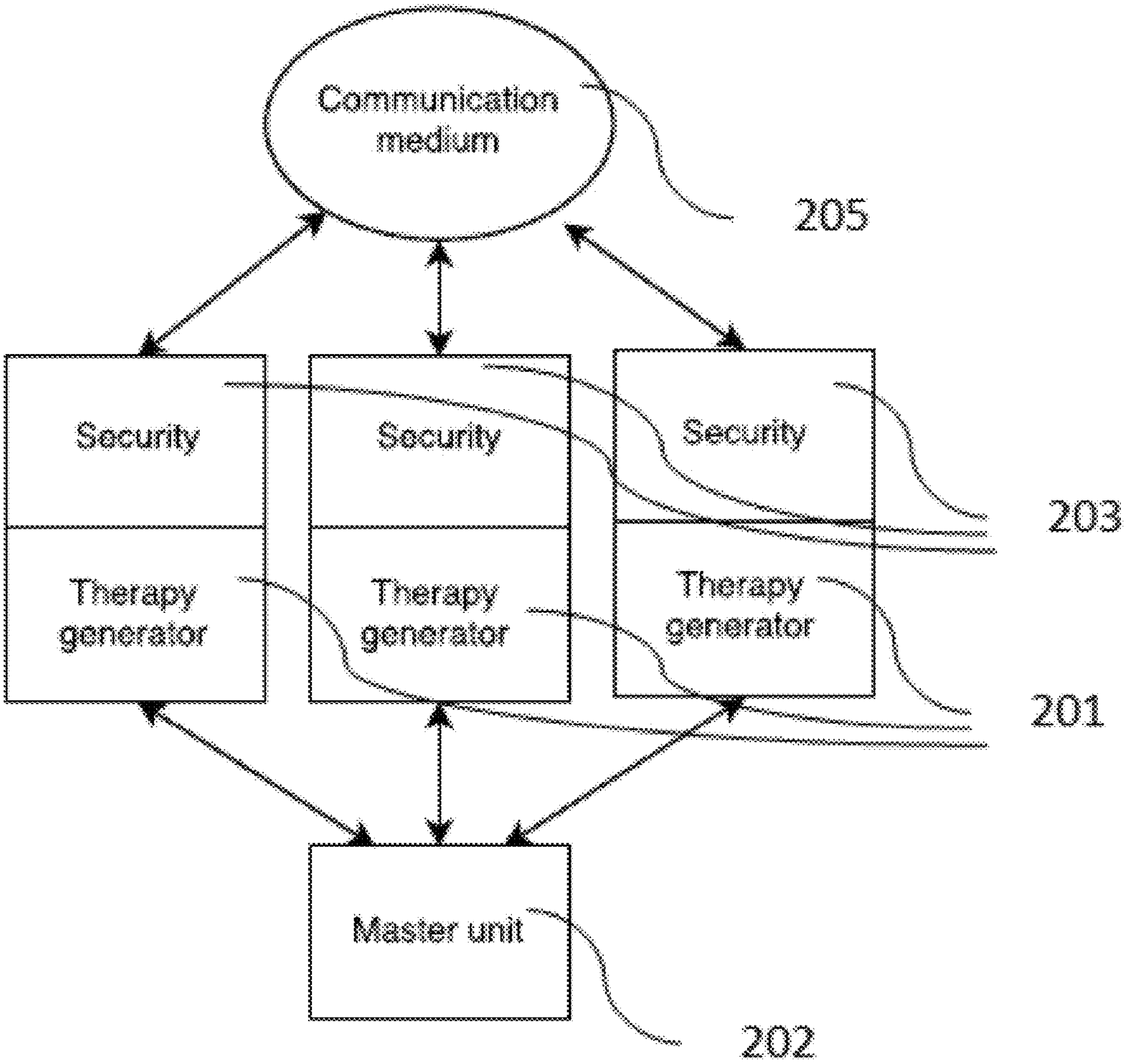
FIG. 4 illustrates an exemplary communication diagram between a communication medium, a therapy generator and a master unit of the treatment device.

As shown in FIG. 4, the communication medium 205 may communicate with one or more therapy generators 201. One or more therapy generator 201 may communicate with the master unit 202. The information from the communication medium 205 may be verified by the security 203 before the therapy generator 201 sends information to the master unit 202.

Figure 5:
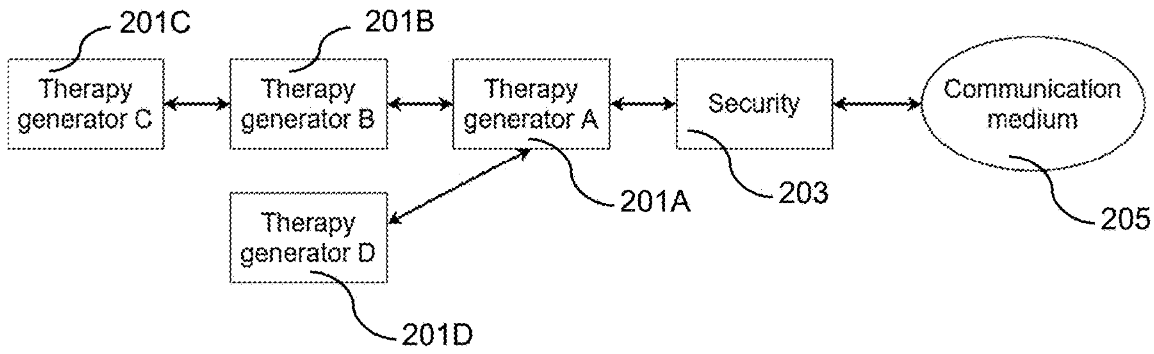
FIG. 5 illustrates a communication between a communication medium and a therapy generator of the treatment device.

FIG. 5 shows a schematic diagram of communication between the communication medium 205 and one or more therapy generators 201A-201D. The therapy generator A 201A may communicate with at least one or more therapy generator 201B-201D. Another therapy generator B 201B may also communicate with one or more therapy generators 201A, 201C, 201D. Therapy generator C 201C may not directly communicate with the therapy generator A 201A and may communicate through therapy generator B 201B. The security 203 may be in the communication pathway between each therapy generator 201A-201D and/or between the therapy generator 201A and the communication medium 205.

Figure 6:
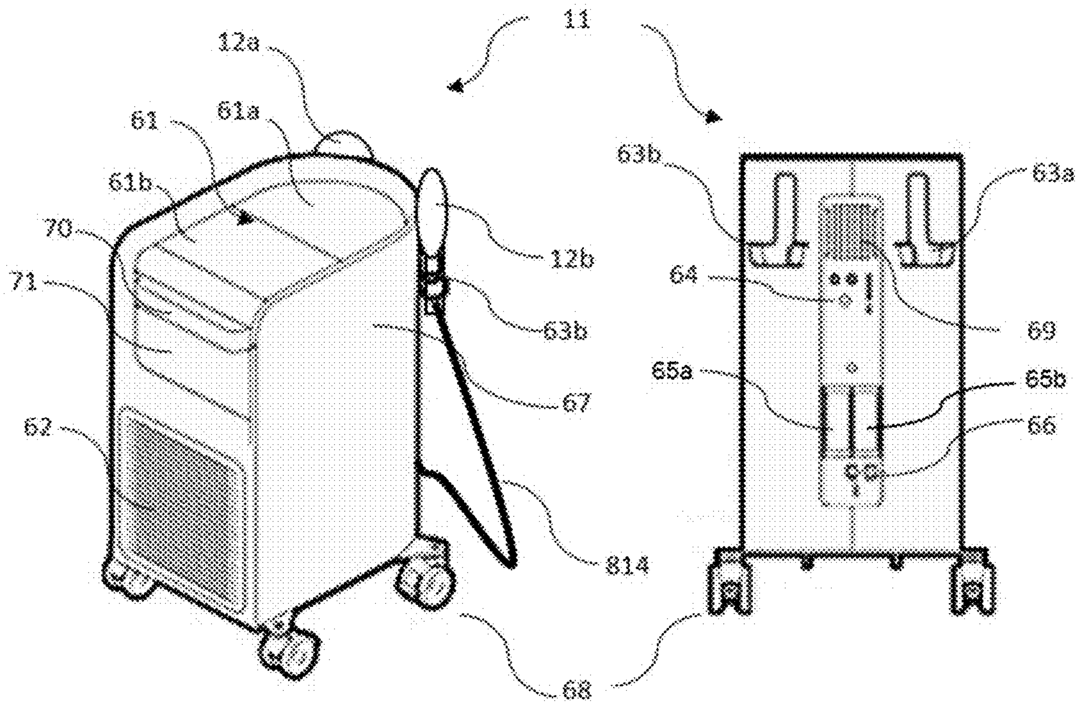
FIG. 6 illustrates different views of an exemplary main unit of the treatment device.

FIG. 6 show the main unit 11 of the treatment device. The main unit 11 may include a HMI 61, a ventilator grid 62, at least one applicator holders 63*a* and 63*b*, at least one device control 64, applicator connectors 65*a* and 65*b*, at least one main power supply input 66, a curved cover 67 of the main unit 11, wheels 68, a main unit cover opening 69, a main unit handle 70, and/or a logo area 71. The main power supply input 66 may provide coupling or connection to the power grid or power network.

The ventilator grid 62 of the treatment device may be designed as one piece and/or may be divided into multiple ventilator grids 62 to provide heat dissipation. The ventilator grid 62 may be facing toward a person operating the main unit 11, facing the floor and not being visible and/or ventilator grid 62 may be on the sides of the main unit 11. The floor-facing location of the ventilator grid may be used to minimize disturbing noise for the patient, because processes like cooling of the main unit 11 and/or electrical elements powered by electric energy may produce noise. Surface area of all ventilator grids 62 on the surface of the main unit 11 may be in a range from 100 $cm^2$ to 15000 $cm^2$, or from 200 $cm^2$ to 1000 $cm^2$, or from 300 $cm^2$ to 800 $cm^2$.

Manipulation with the main unit 11 may be provided by rotating wheels 68 on the bottom of the main unit 11 and/or by the main unit handle 70. The logo area 71 of the company providing the treatment device may be located below the main unit handle 70 and/or anywhere on the curved cover 67 and HMI 61.

As shown in FIG. 6, the front side of the main unit 11 facing the patient may be designed as a curved cover 67 of the main unit. The front side of the main unit 11 facing the patient may have no right angles according to floor projection of the main unit 11. The front side of the main unit 11 facing the patient may be designed as one, two or more pieces covering the inside of the main unit 11. The main unit 11 with curved facing side may improve manipulation of the main unit 11 itself nearby patient's support wherein the risk of collision main unit 11 and various sensitive body parts of the patient (e.g. fingers) is minimized. Facing side of the main unit 11 may also include the main unit cover opening 69. The main unit cover opening 69 may include a thermal camera for monitoring the temperature of the patient or treated body area, a camera for monitoring the location of one or more applicators, movement of the patient and/or other. The main unit cover opening 69 may be represented by opening in the curved cover 67 of the main unit. The main unit cover opening 69 may include one or more connectors for connecting additional treatment devices. Further, the main unit cover opening 69 may include one or more sensors, such as camera, infrared sensor to scan patient's movement, heating of treated body area and/or biological structure. Based on information from such sensors, actual value and/or predetermined value of one or more treatment parameters may be optimized when patient moves, skin surface reach temperature threshold limit, determine treated body area and/or other. The front side of the main unit 11 may also include one or more applicator connectors 65*a* and/or 65*b*.

Figure 52A:
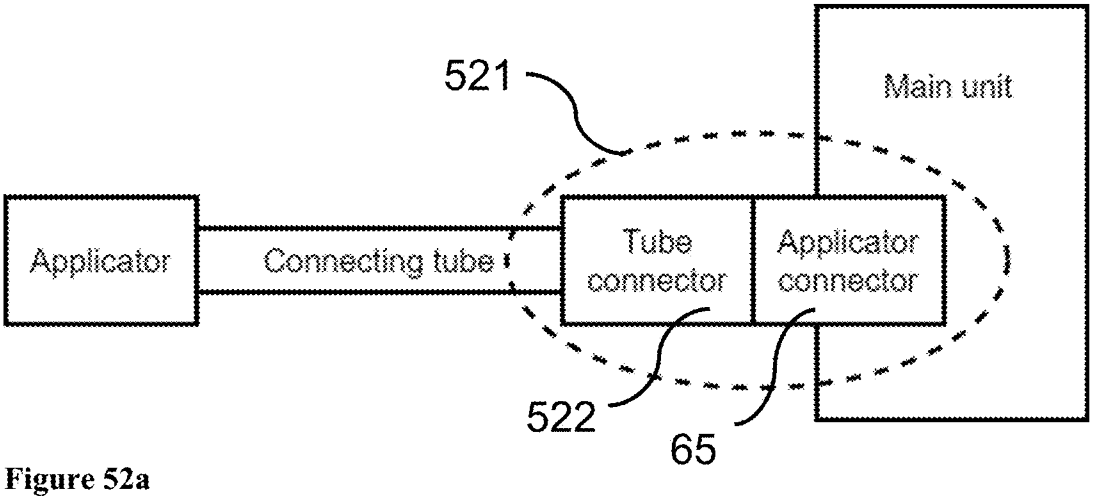
FIG. 52*a* illustrates a connecting attachment between the applicator and the main unit.

FIG. 52*a* illustrates a connecting attachment 521 between a main unit and an applicator. One applicator may be connected to the main unit by a connecting attachment 521, wherein the connecting attachment 521 may include at least one applicator connector 65 and at least one tube connector 522. One applicator may be disconnected from the main unit and replaced by another applicator. The applicator may be connected to the main unit by connecting tube including a tube connector 522 which may be connected to the applicator connector (e.g. applicator connector 65) located on the main unit. The tube connector 522 may be a plug, while the applicator connector 65 may be a socket, or vice versa. The tube connector 522 may be an integral part of the connecting tube. Tube connector 522 and/or applicator connector 65 may include male contacts (e.g. pins) and/or female contacts. In one example, tube connector 522 may include female contacts and/or male contacts.

Figure 52B:
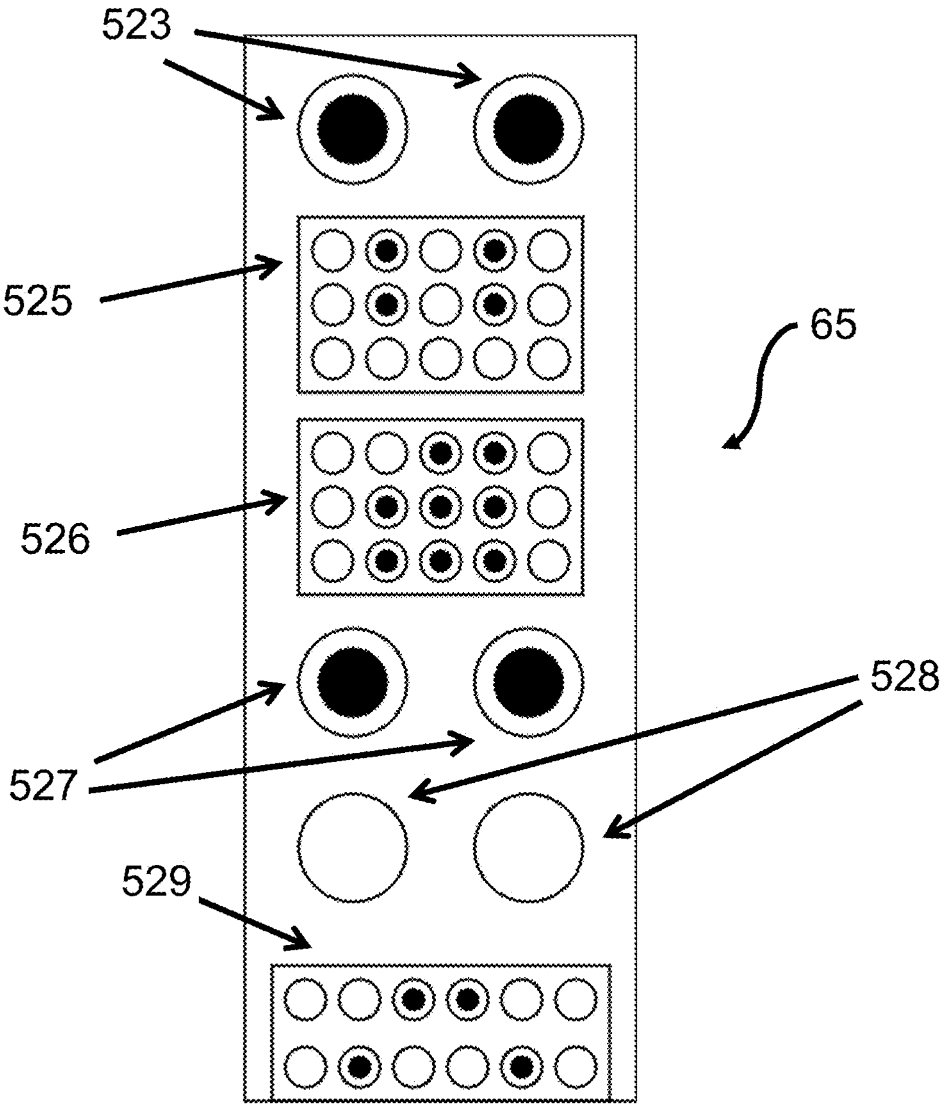
FIG. 52*b* illustrates an applicator connector.

FIG. 52*b* shows an applicator connector 65 having a variety of contacts. In FIG. 52*b*, a colored circle inside another circle represents a contact comprising a pin. The one or more contacts in tube connector 522 and/or applicator connector 65 may be used for transfer of electrical signals used for RF treatment and/or magnetic treatment. For example, two or four pairs of male contacts and female contacts may be used for transfer of electrical signals used for RF treatment. A plurality of pins of contacts 525 (e.g. two or four pins) of applicator connector 65 may be used for transfer of electrical signals for RF treatment. In another example, two pairs of male contacts and female contacts may be used for transfer of electrical signals used for magnetic treatment. The pair of contacts 523 and pair of contacts 527 of applicator connector 65 may be used for transfer of electrical signal for magnetic treatment. The pair of contacts 523 may be used for transfer of electrical signals in the form of high power impulses from the main unit (e.g. from the energy storage device) to the magnetic field generating device of the applicator. The pair of contacts 527 may be used for transfer of electrical signals from the magnetic field generating device back to the main unit (e.g. to the energy storage device).

Further, the one or more contacts in tube connector 522 and/or applicator connector 65 may be used for transfer of electrical signals to or from other electronic elements being part of the applicator, wherein such electronic elements may include a fan (in case of cooling by air), computer memory, a feedback sensor (e.g. temperature sensor) or human machine interface present on the applicator or the connecting tube. The signals from electronic elements may be multiplexed, i.e. transferred by one wire or by a group of wires arranged in one protective shielding. A plurality of pins of contacts 526 of applicator connector 65 may be used for transfer of electrical signals to or from other electronic elements present in the applicator.

Further, the one or more contacts in tube connector and/or applicator connector may be used as a safety loop. For example, the connection between the contacts of applicator connector 65 and tube connector 522 may provide information about safe connection of the connecting tube and/or the applicator with the main unit. When the wires in the tube connector 522 meet the selected pins of the applicator connector 65, the control unit may be informed about closing the safety loop by change of resistance of the selected pins.

Figure 52C:
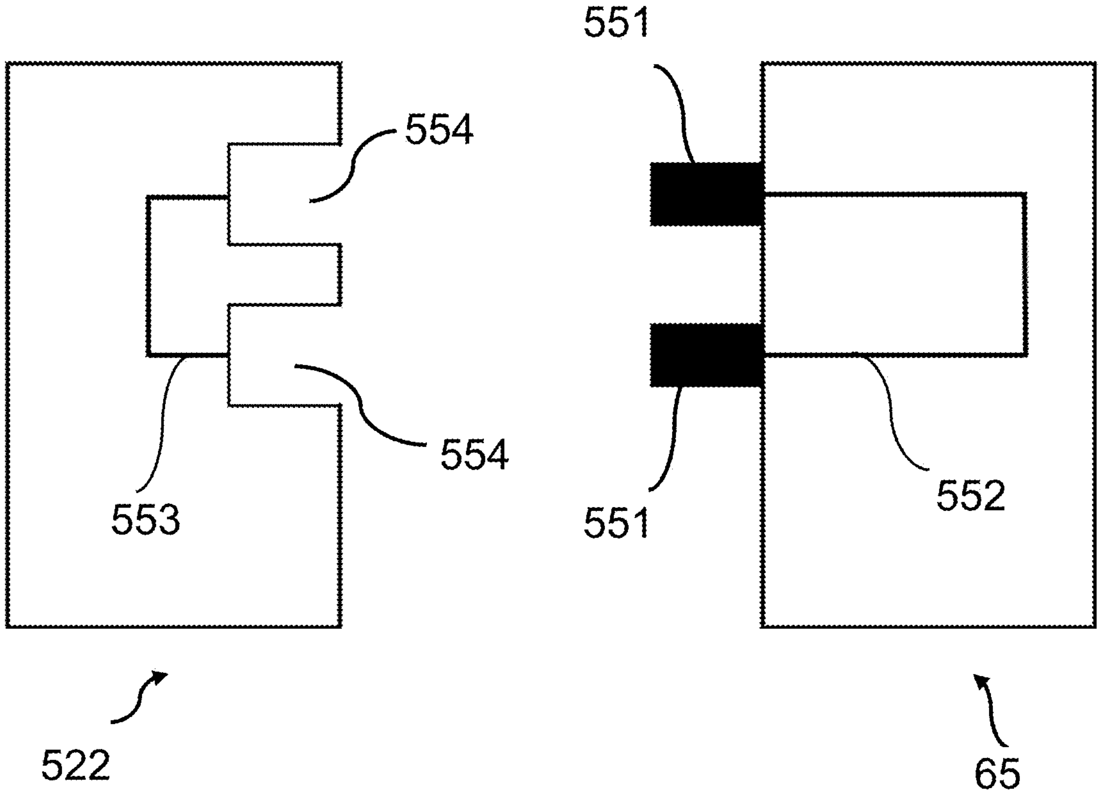
FIGS. 52*c*-52*d* illustrate a connecting attachment between the applicator connector and tube connector in connected and disconnected positions.
Figure 52D:
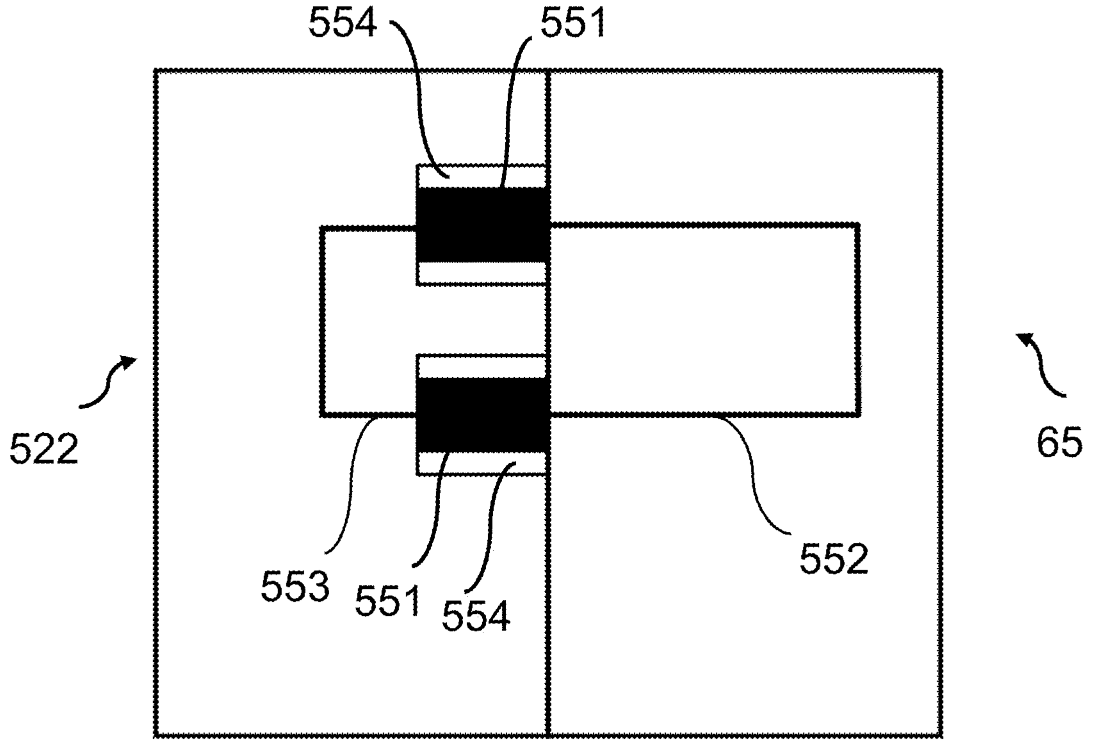

Alternatively, the safety loop may be represented by a safety circuit, whose operation is illustrated at FIGS. 52*c-d*. FIG. 52*c* illustrates an applicator connector 65 having pins 551 and safety wiring 552 of the main unit. The tube connector 522 includes safety wiring 553 of the tube connector 522 and sockets 554 for receiving the pins 551. The conductive pins 551 represent the open ends of safety wiring 552, while the sockets 554 represent the open ends of safety wiring 553. FIG. 52*d* illustrates connecting attachment of applicator connector 65 and tube connector 522 where the pins 551 are connected to sockets 554. By this connection, the safety wiring 552 and 553 are interconnected. The created safety circuit may include safety wiring 552, safety wiring 553, pins 551 and sockets 554. By closing and/or electrical activation of the safety circuit, the control unit may be informed about the connection of the applicator to the main unit. Alternatively, the pins for closing the safety circuit may be located on the tube connector, and the safety wiring 553 may be located in the main unit. When the connectors are not connected and the safety loop is not closed, the control unit may not allow start of the treatment and/or use of treatment energy source. Regarding the FIG. 52*b*, plurality of pins of contacts 526 of applicator connector 65 may be used for closing the safety loop.

Further, the connecting attachment including tube connector and/or applicator connector (e.g. hose) may be used for transfer of cooling fluid between the applicator and the main unit. In such case, the connection attachment may include fluid couplings. Regarding FIG. 52*b*, plurality of fluid couplings 528 of applicator connector 65 may be used for transfer of cooling fluid.

Further, the one or more contacts in tube connector 522 may be used for identification of the applicator by the control unit and/or main unit. For example, the one or more contacts in tube connector 522 may be connected to an electrical element (e.g. an identifying resistor or RFID element), which may be of a type and/or provide a value of resistance assigned to the specific type of the applicator. By this identification, the main unit and/or control unit may identify the type of connected applicator to the applicator connector 65 and then allow the treatment. Different applicators may include applicators for different body areas, such as applicators for a patient's arms, buttocks or abdomen, among other body areas, and/or applicators having different components, such as an applicator having one or more magnetic field generating devices, one or more radiofrequency electrodes, or a combination thereof. If the connected applicator is not identified, the main unit or control unit may not allow treatment. Further, depending on the type of applicator identified, the main unit or control unit may allow only certain treatment protocols based on the type of the applicator identified.

Further, the one or more contacts in tube connector 522 may be used for tracking the total use of the applicator. The applicator may include a computer memory (e.g. a RAM, ROM PROM, EPROM or memory) storing a preset maximum number of working minutes or a preset maximum number of magnetic impulses that the applicator may be used to administer. The control unit and/or main unit may set or recognize the maximum number of working minutes or magnetic impulses according to the type of the applicator. The information transferred to the main unit from the applicator via the connectors may include a number of used working minutes or magnetic impulses. When the number of used working minutes or impulses reaches or equals the preset maximum number stored in the applicator, the human machine interface may display a message and/or the control unit may prevent further treatment by the applicator. Alternatively, the control unit may subtract the number of working minutes or magnetic impulses from the preset number stored in the memory of the applicator. When the number of working minutes or impulses counted by the main unit (e.g. control unit) reaches or equals zero, the human machine interface may display a message and/or the control unit may prevent further treatment by the applicator. Regarding the FIG. 52*b*, the plurality of contacts 529 of applicator connector 65 may be used for tracking the total use of the applicator.

The connection of the tube connector 522 to the applicator connector 65, providing connection of the applicator to the main unit, may be secured or locked by a locking mechanism, such as a bayonet closure, among other removable or temporary connections. The connection of the tube connector to the applicator connector may be secured by at least one locking mechanism, e.g., a locking element connected to a spring. The locking element may include plastic connected to the spring element, wherein the applicator connector and tube connector may each include one locking mechanism.

As shown in FIG. 6, applicator connectors 65*a* and 65*b* facing the patient may be closer to the patient's body than applicators connected to the side facing the operator (e.g. doctor or technician). Accordingly, the length of the connecting tube 814 connecting the applicator with the main unit 11 may be minimized. Manipulation with the applicator and/or plurality of applicators connected by a shorter connecting tube 814 may be easier than with the applicator connected with a longer connecting tube 814.

The front side of the main unit 11 may have no corners and/or angles and may include at least partially elliptical and/or circular curvature. The curvature may have a radius of curvature in a range of 20 cm to 150 cm, 30 cm to 100 cm, 30 cm to 70 cm, or 40 to 60 cm. An angle of the main unit 11 front side curvature may be in a range of 30° to 200°, or of 50° to 180°, or of 90° to 180°. The angle of the curvature may be defined with the same principle as it is defined an angle 30 of a section 26 in FIG. 23 as discussed in further detail below.

The device may further include a remote control for use by the patient and/or operator to signal discomfort during treatment. The remote control may include at least one button in communication with the main unit 11, e.g., by wired or wireless connection. The remote control may be located adjacent to the patient during the treatment. The patient may keep the button in his or her hand and press the button when any discomfort occurs. By pressing the button on the remote control for discomfort, the patient may stop the treatment, and may stop the application of magnetic field and/or radiofrequency energy.

The main unit may include a slot for receiving a card, e.g. SD card. The card may include a counter of working minutes. After inserting the SD card into the slot, the device may recognize the number of working minutes. The device may allow the treatment only for a recognized number of working minutes.

The card may also be used for calibration of the device and/or the applicator. The device may provide a calibration of the applicator, wherein the calibration may include calibration data of the temperature of the applicator, cooling of the RF electrode, cooling of the magnetic field generating device, or calibration of the temperature sensor. After the calibration, the device may save the calibration data to the card. The calibration may be executed by the service, during manufacture and/or by the user.

The main unit 11 may include one or more an applicator holder e.g. 63*a* and 63*b*. Alternatively, one or more applicator holders may be coupled to the main unit 11. Each applicator holder 63*a* and 63*b* may have specific design for different types of the applicator. The applicator holder 63*a* and 63*b* may each hold a single applicator 12*a* or 12*b*. Each applicator holder 63*a*, 63*b* may have several functions. For example, the applicator holders 63*a* and 63*b* may be used for pre-heating or pre-cooling of at least part of the applicator.

Further, the applicator holders 63*a* and 63*b* may include another HMI and be used for displaying information about selected treatment, actual value and/or predetermined value of one or more treatment parameters. Also, the applicator holder 63*a* and/or 63*b* may provide indication whether an applicator is ready to use. Furthermore, the applicator holder 63*a* and/or 63*b* may indicate a current value temperature of at least part of the applicator. The indication may be provided by color flashing or vibration. The applicator holder 63*a* and/or 63*b* may be used to set actual value and/or predetermined value of one or more treatment parameters and/or applicator parameters, such as a temperature of applicator's part contacting the patient.

The main unit 11 may include device control 64 for switching on and off the main unit 11, manual setting of power input parameters and/or other functions. The applicator connectors 65*a* and 65*b* may be used for transfer of electrical and/or electromagnetic signal from the main unit 11 and applicators. The applicator connectors 65*a* and 65*b* may be used for connecting of one or more applicators (via the connecting tube 814), the communication device, the additional treatment device and/or memory storage devices such as USB, SSD disc, diagnostic devices, and/or other memory storage devices known in the state of art. The applicator connectors 65 (e.g. 65*a* and/or 65*b*) for connecting of one, two or more applicators may be located in the main unit 11 or on the side of the main unit 11. The length of coaxial cables may be linked with a frequency of transmitted electrical signal. In order to provide easier manipulation with one or more applicators 12*a* and/or 12*b*, the length of connection from the main unit 11 to e.g. applicator 12*a* (and therefore connecting tube 814) should be as long as possible. However, length of at least one coaxial cable between electrical elements in the main unit 11 may be linked with a frequency of transmitted electrical signal (e.g. RF signal) sent to at least treatment energy source (e.g. RF electrode to provide RF energy). Therefore the length of at least one coaxial cable inside the main unit (e.g. between a power source and the applicator connector 65*a* and/or 65*b*) may be as short as possible. The length of coaxial cable located in the main unit 11 may be in a range of 3 cm to 40 cm, or 7 cm to 30 cm, or 10 cm to 20 cm. In order to optimize manipulation with one or more applicators 12*a* or 12*b* connected to the main unit 11, the applicator connectors 65*a* and 65*b* may be located on the curved front side of the main unit 11.

The HMI 61 may include a touch screen display showing actual value and/or predetermined value of one or more treatment parameters. The touch screen may provide option to choose the displayed treatment parameters and/or adjust them. The HMI 61 may be divided into two display sections 61*a* and selection section 61*b*. The display section 61*a* may display actual value and/or predetermined value of one or more treatment parameters and other information for the user. The selection section 61*b* of the HMI 61 may be used for selection of treatment parameters and/or other adjustment of the treatment. HMI may be included in, coupled to or be part of one or more applicators 12, main unit 11, an additional treatment device 14 and/or in other one or more communication devices 15.

The HMI may be included in the main unit 11. The HMI may be fixed in a horizontal orientation on the main unit 11 or the HMI 61 may be oriented or tilted between 0° to 90° degrees with respect to a floor or other horizontal support surface. The angle between the HMI 61 plane and a floor may be adjusted by at least one joint or may be rotated around at least one Cartesian coordinates. The HMI 61 may be in form of detachable HMI, e.g. a tablet. The HMI 61 may be telescopically and/or rotationally adjusted according to one two or three Cartesian coordinates by a holder that may adjust distance of HMI 61 from the main unit 11 and/or orientation of the HMI 61 with regard to the main unit 11 and the user. The holder may include at least one, two or three implemented joint members.

One HMI 61 may be used for more than one type of the treatment device provided by the provider. The HMI software interface may be part of the main unit software or part of the software included in one or more additional treatment devices and/or communication devices. The software interface may be downloaded and/or actualized by connection with the communication device, the additional treatment device, flash memory device, the remote connection with sales, the service and/or the internet.

Figure 26:
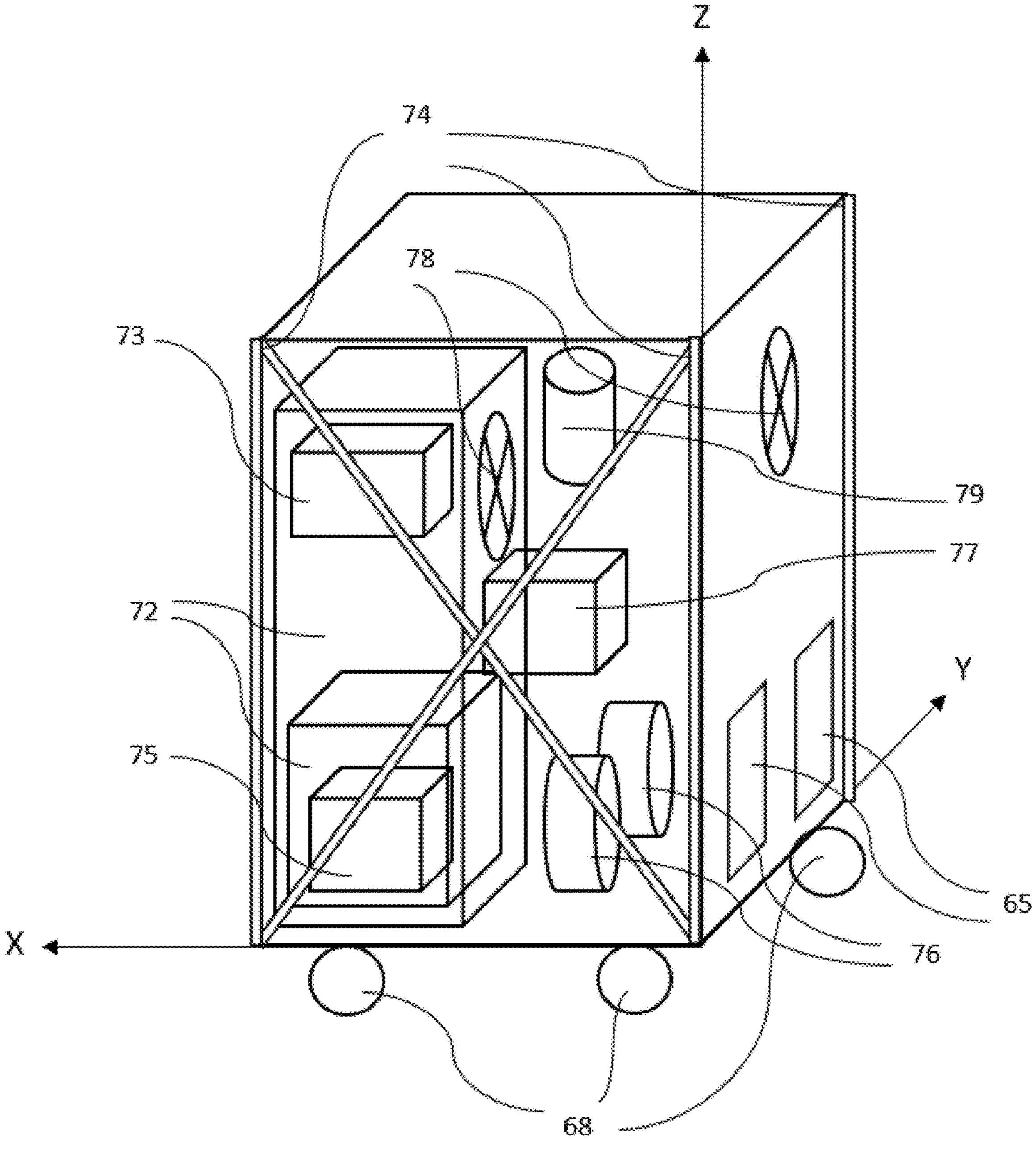
FIG. 26 illustrates an exemplary spatial arrangement of components within a main unit of a treatment device.

FIG. 26 shows exemplary layout of the interior of the main unit 11. The interior of the main unit 11 may include multiple electrical elements, control system, one or more control units of RF circuits, magnet circuits and/or other elements needed for correct function of the treatment device. Location of individual elements in the main unit 11 may be described by Cartesian coordinates with the zero values at the bottom edge of the front side facing the patient. The main unit 11 may include one or more struts 74. At least two struts 74 may create an X-shape that may be fixed at its ends to other vertical struts 74 to create construction for the main unit 11. The main unit 11 may include at least one cooling system 78 configured to cool electrical element such as one or more control units, PCBs, power sources, switches, energy storage devices and/or other electrical element of the treatment device. The cooling system 78 may be used for providing and/or cooling the cooling fluid provided to the applicator. The SYM element 79 may be located in the upper third of Z coordinate and at the first third of the X coordinate nonmatter of Y coordinate. Function of the SYM is explained below. The main unit 11 may also include one or more cases 72 formed from aluminium or other metal materials. The one or more cases 72 may provide electrical, electromagnetic and/or radiation insulation (later only as insulation) of one or more internal parts of the main unit 11 from other part of the main unit 11. For example, at least part of a RF circuit 73 may be located in the last third of X and Z coordinates in one of the cases. The power source 75, powering at least part of RF circuit and/or magnet circuit, may be located in the last third of X coordinate and in the first third of Z coordinate. An energy storage device 76 may be at least partially insulated from one or more RF circuit. When plurality of magnetic circuits is used, the plurality of magnet circuits may be at least partially insulated from each. In order to ensure short length of coaxial cable leading from the energy storage device 76 to applicator connector 65 as mentioned earlier, both elements (energy storage device 76 and applicator connector 65, e.g. 65*a*) may be located in the same half of the X and Z coordinate, such as at the first half of X and Z coordinate. Other electrical elements represented by box 77 of magnet circuit may be located in the first half of X coordinate and second third of Z coordinate.

Figure 7:
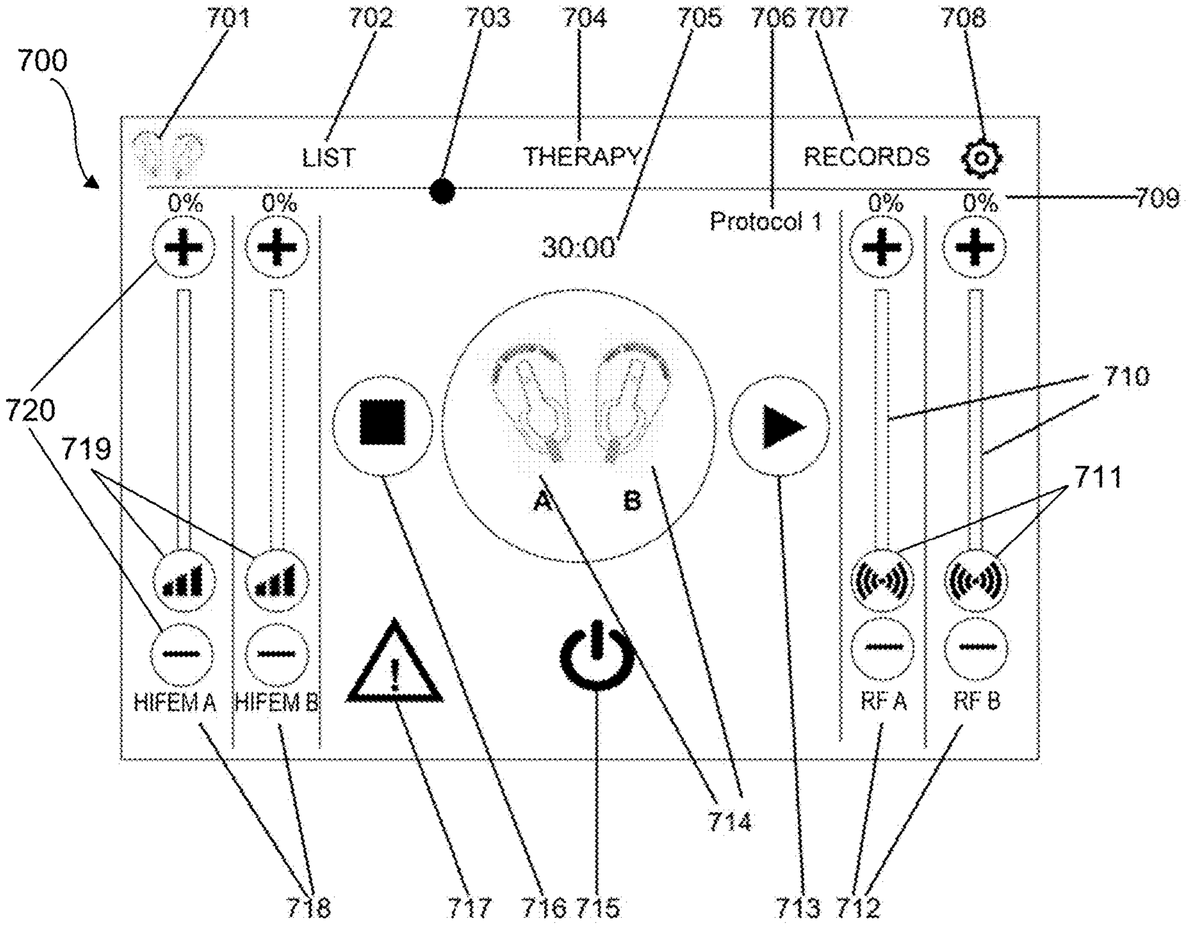
FIG. 7 illustrates an exemplary human machine interface (HMI).

FIG. 7 shows exemplary display interface 700 of the HMI 61. The HMI 61 may display one or more applicator symbols 701. One or more applicator symbols 701 and their colors may represent connection quality, number and/or type of available or connected applicators, additional treatment devices connected to the main unit 11 and/or involved in the treatment. The list 702 may redirect to a page or different display layout where a list of treatment protocols may be recorded or adjusted. The list 702 of treatment protocols may include one or more predetermined values of at one or more treatment parameter (e.g., intensity of magnetic field, intensity of RF field, intensity of magnetic impulses, intensity of magnetic pulses, pulse duration, burst duration, composition of individual burst, duty cycles, shape of envelope, time of treatment, composition of treatment parts, threshold temperature of the biological structure during the treatment, and/or other parameters). The list of treatment parameters may include one or more saved treatment protocols optimized for individual patients or body area. After choosing the treatment protocol, treatment parameters may be additionally optimized by user. Also, the treatment parameters may be adjusted by choosing additional patient's parameters, such as patient body type (e.g. skinny, slim, average weight, overweight, or obese), or a patient's BMI, gender, age group (e.g., younger than 30, 30-39, 40-49, 50-59, 60 and older). Also, the treatment parameters may be additionally optimized by selecting only of a part of treatment protocol.

The HMI 61 may include one or more sliders which may have several functions. For example, the slider 703 may be used as a navigator for selecting which page of the interface is being used, such as the list 702, a therapy icon 704, or a records 707. Also, the slider 703 may be used to indicate how much time is remaining to the end of the treatment.

The therapy icon 704 may represent the interface illustrated in FIG. 7. A timer 705 may represent treatment duration, remaining time of the treatment, and/or lapsed time of the treatment. The "Protocol 1" icon 706 may illustrate the type of number of a protocol selected and/or currently applied or prepared to be applied. The "records" 707 may redirect to another page of the interface with recorded history of treatments, information regarding treated patients, information regarding billing and renting system, information regarding billing information and/or credit cost of the treatment. The "records" 707 may display how many credits are left on the credit account, how many credits were spent, how long the treatment device was used, and/or other billing information. An icon illustrated by a symbol "setting" 708 may redirect user to a setting of the treatment device including the setting of e.g. a melody and/or intensity of the sound produced by the device and/or brightness of the display. The sound produced by the treatment device and/or brightness of the display may be different before and/or during the treatment. The "setting 708" interface may also enable to change date, time, language, type and/or parameters of connection between the main unit and the applicator, the additional treatment device, and/or the communication device. The "setting" 708 interface may include icons for starting a calibration and functionality scan of the treatment device and its connected parts. The "setting" 708 interface may provide software information, software history and/or software actualization, a button for contacting service and/or sending error protocol, type of operation mode (e.g. "basic" or "expert" with allowed additional setting of the treatment device), possibility to recharge credits for treatments, restoring to factory setting, and/or other settings.

Intensity signs 709 may be as illustrated in the form of percentile, number, power and/or in another format. The intensity signs 709 may be located adjacent to an icon that may adjust intensity of the treatment energy source. The intensity signs 709 may be located under, over and/or in an icon (e.g. as a number in an intensity bar 710) and/or as another visualization that may adjust the intensity of the treatment energy source. Each intensity bar 710 representing one treatment energy source of provided energy (e.g. RF field or magnetic field) may have its own intensity signs 709.

The treatment device may include multiple applicators 714, for example, a first applicator A and a second applicator B may be connected to the main unit of the treatment device. In this way, applicators A and B may be applied to different muscles in the same muscle group or to pair muscles, such as a left and right buttock, left and right sides of an abdomen, a left and right thigh, among other paired muscles or cooperating muscles. Number of connected applicators and/or additional treatment devices providing the treatment energy may be lower or higher than two.

As shown in FIG. 7, each applicator may provide magnetic treatment 718 (left HMI part marked as HIFEM A and HIFEM B for the purpose of FIG. 7 and showed in exemplary interface human machine interface) and/or an RF treatment 712 (right HMI part marked as RF A and RF B for the purpose of FIG. 7 and showed in exemplary HMI).

The intensity of each RF field and/or magnetic field may be independently regulated e.g. by scrolling of individual magnetic intensity scroller 719 and/or RF intensity scroller 711 through intensity bars 710. One or more scrollers or intensity bars may be moved independently or may be moved together with another scroller or intensity bar in order to regulate plurality of magnetic fields, plurality of RF fields together and/or plurality of RF and magnetic fields provided by the one applicator together. Also, one or more scrollers or intensity bars may be controlled independently or may be moved together with another scroller or intensity bar in order to regulated plurality of magnetic fields, plurality of RF fields together and/or plurality of RF and magnetic fields provided by two applicators together. One or more intensity bars 710 may be distinguished by a color and may be adjusted by intensity scroller 719 or 711 and/or by an intensity buttons 720. The intensity buttons 720 may change (e.g. increase or decrease) RF field and/or magnetic field intensity by a fixed increment, such as 1% or 2% or 5% or 10% or in a range from 1% to 10% or in a range from 1% to 5% of maximal possible field intensity. Intensity of the magnetic field and/or the RF field may be adjusted independently for each treatment energy source. Also, intensity of the magnetic field and/or RF field may be adjusted by selection and/or connection of one or more applicators, additional treatment devices and/or treatment energy sources.

The operation of one or more RF electrodes and/or magnetic field generating devices may be synchronized and may be controlled by one, two or more intensity scrollers 719 and/or intensity buttons 720. The treatment may be started by a button start 713 that may be automatically (e.g. after starting the treatment) changed into a button pause. The treatment may be restarted and/or stopped by button stop 716 during the treatment. The interface may also show an indicator of a discomfort button 717 that may be activated by patient through a remote control when the treatment is uncomfortable. When the discomfort button 717 is activated treatment may be automatically and immediately interrupted (e.g. paused or stopped). When the discomfort button 717 is activated the treatment device may provide an human perceptible signal including an audible alert, including a sound signal. Further, the human perceptible signal may include a visual alert, including e.g. a flashing color. Based on the discomfort of the patient, the user may adjust e.g. the treatment parameters or treatment protocol, attachment or coupling of the applicator. The interface may also include a software power switch 715 to switch the treatment device on or off.

As shown in FIG. 7, the HMI may include two intensity bars (e.g. 710) for RF treatment and two intensity bars for magnetic treatment. Further, the HMI may include two intensity scrollers (e.g. 711) for RF treatment and two intensity bars (e.g. 719) for magnetic treatment. Furthermore, the HMI may include four intensity buttons for RF treatment and four intensity buttons (e.g. 720 for magnetic treatment. One intensity scroller, one intensity bar and/or two intensity buttons may be provided for one treatment circuit. Therefore, the FIG. 7 may show the HMI of treatment device including two treatment circuits for RF treatment and two treatment circuits for magnetic treatment.

The treatment device may include one or more applicators. The treatment device may include two, three, four, five or more applicators. Each applicator may include at least one, two or more different treatment energy sources, such as one or more RF electrodes providing the RF treatment and one or more magnetic field generating devices providing the magnetic treatment. For example, first applicator may include one RF electrode and one magnetic field generating device, while the second applicator may include another RF electrode and another magnetic field generating device. The RF electrode may not contact the skin of the patient. The RF electrode may be positioned inside the applicator together with the magnetic field generating device. One applicator may be coupled to the main unit by one connecting tube. The connecting tubes of different applicator may be interconnected or separated for each applicator. Alternatively a plurality of applicators may be coupled to the main unit by one common connecting tube. At least one treatment parameter of at least one applicator may be changed independently from the other one or more applicators and/or additional treatment device.

One or more applicators, additional treatment devices and/or communication devices may be mechanically connected with the main unit by one or more wires and/or by the fluid conduits. One or more wires and/or fluid conduits may be located and lead through the connecting tube. The one or more wires coupled between main unit and the applicator may be used for transfer of electric signal (representing e.g. RF signal) to RF electrode positioned in an applicator in order to generate RF energy. The one or more wires may be used for providing electric current to magnetic field generating device positioned in the applicator in order to generate impulses of the magnetic field. Same wire and/or different wires coupling the applicator and the main unit 11 may be used for communication between the main unit 11 and the applicator 12 and/or for collecting feedback information. Feedback application may include e.g. measured signal parameters and/or impedimetric characteristics of the wire before and/or during the treatment. The fluid conduit between the main unit 11 and the applicator 12 may guide liquid, oil, water, vapors, gas and/or other temperature regulating cooling fluid.

One or more applicators may be coupled to patient's body and/or body area by one or more straps, one or more belts, or by creating vacuum under the applicator. Also, applicator may be coupled to the body area by a supporting matrix or by an adhesive layer located on at least part of the applicator's surface and contacting the patient's body or clothing. The applicator may be coupled to the body area by pushing the applicator to the patient's body area or clothing by an adjustable mechanical positioning arm wherein the applicator may be detachably coupled to the positioning arm including at least one, two or more joints. The belt may be at least partially elastic and may create a closed loop, such as by hook and loop fasteners (by Velcro), buckles, studs, and/or other fastening mechanisms may be used for adjusting a length. The belt may be coupled to body area and may include a fastening mechanism for coupling the applicator to the belt and/or patient's skin or clothing. Such fastening mechanism may be for example, a belt with pockets for the applicator. Coupling the applicator to the body area may include attaching or positioning of the applicator to the proximity of or in contact with the body area. Alternatively, the applicator may not contact the body area. One or more applicators may be coupled to the body area before or during the application of one or more types of treatment, (e.g. RF treatment or magnetic treatment). Also, the applicator may be coupled to the body area, skin or clothing by a cover from soft material, which may be folded around the applicator and/or the part of the body area. Furthermore, the applicator may be covered in soft material cover providing other coupling points for attachment of belt, folding soft material or any other coupling option mentioned herein.

The belt may be a length adjustable belt which may be at least partially flexible. One or more belts may couple or fix and/or attach one, two or more applicators to the patient's body or body area. The belt may be coupled to one applicator 800 or one belt may couple two or more applicators to the patient's body. When the plurality of applicators (e.g. two, three or more) are used, one applicator may be coupled to the body area of the patient by one belt while another applicator may be coupled to the body area by different belt. Alternatively, a plurality of applicators (e.g. two, three or more) may be coupled to the body area of the patient by one same belt. At least one applicator coupled by the belt may be fixed statically with regard to patient's body for at least part of the treatment. The at least one applicator that is coupled by the belt to patient's body may be repositioned once or more times during the treatment either manually by the operator or automatically to ensure optimal treatment effect and treatment comfort for the patient.

Coupling the applicator and/or additional treatment device to a patient's body may include placing the applicator in proximity of the patient's body and/or body area. In case of proximate coupling, the shortest distance between the applicator and the patient's skin may be in a range of 0.01 cm to 10 cm, or 0.01 cm to 5 cm, or 0.01 to 2 cm, or 0.01 to 1 cm, or 0.01 to 5 mm, or 0.01 to 2 mm. However, the applicator may be also placed in direct contact with the patient's skin. In case of direct contact, there may be no meaningful distance between the application and the patient's skin. In case of proximate or direct contact, the intervening material may be positioned between the applicator and patient's skin or clothing or body area. The intervening material may be an air gap, bolus, supporting matrix, part of the belt, textile, other clothing, gel, liquid absorbing material or metal.

Figure 22:
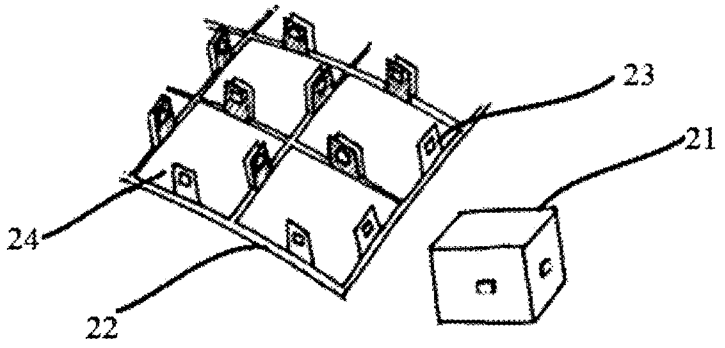
FIG. 22 illustrates a supporting matrix for attaching of an applicator and/or an additional treatment device to a patient's body.

FIG. 22 depicts an exemplary attachment of the applicator and/or additionally treatment device 21 to a patient's body with use of a supporting matrix 22. The supporting matrix 22, as illustrated in FIG. 22, may be shaped as a grid and/or scaffold. The grid and/or scaffold is at least partially flexible and attached to patient's body. The supporting matrix may be used for coupling the applicator and/or additional treatment device 21 in proximity to the patient's body in defined location referred as an applicator's spot 24 by a fastening member 23. The supporting matrix may be polymeric scaffold-like in FIG. 22, substrate like a textile/polymeric sheet and or other. The fastening member may be one or more elements such a locking mechanism, hinge, bayonet like system, Velcro for fastening the applicator and/or additional treatment device 21.

Figure 24:
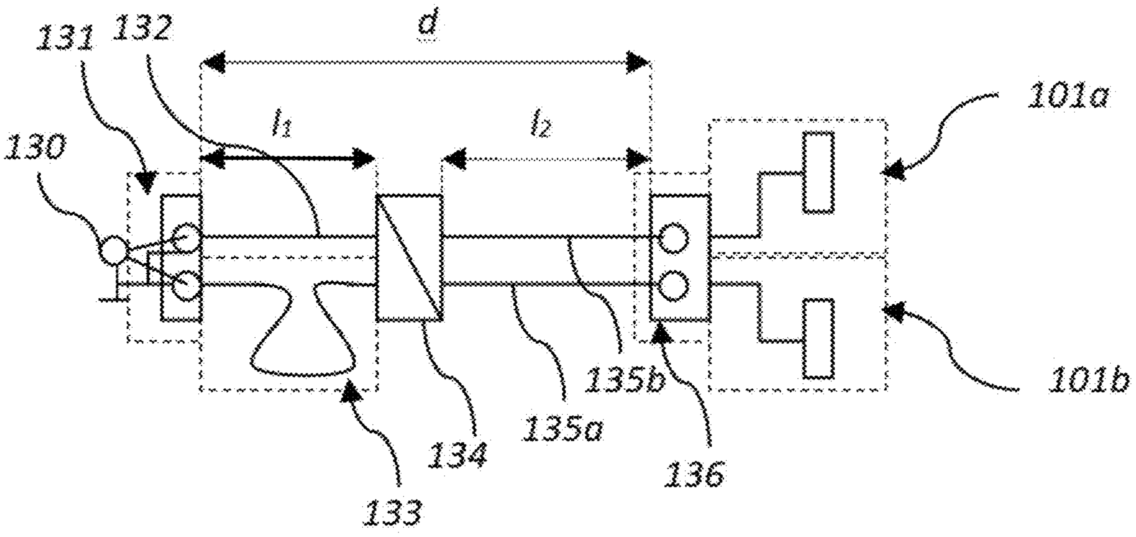
FIG. 24 illustrates an exemplary symmetrisation element SYM.
Figure 25:
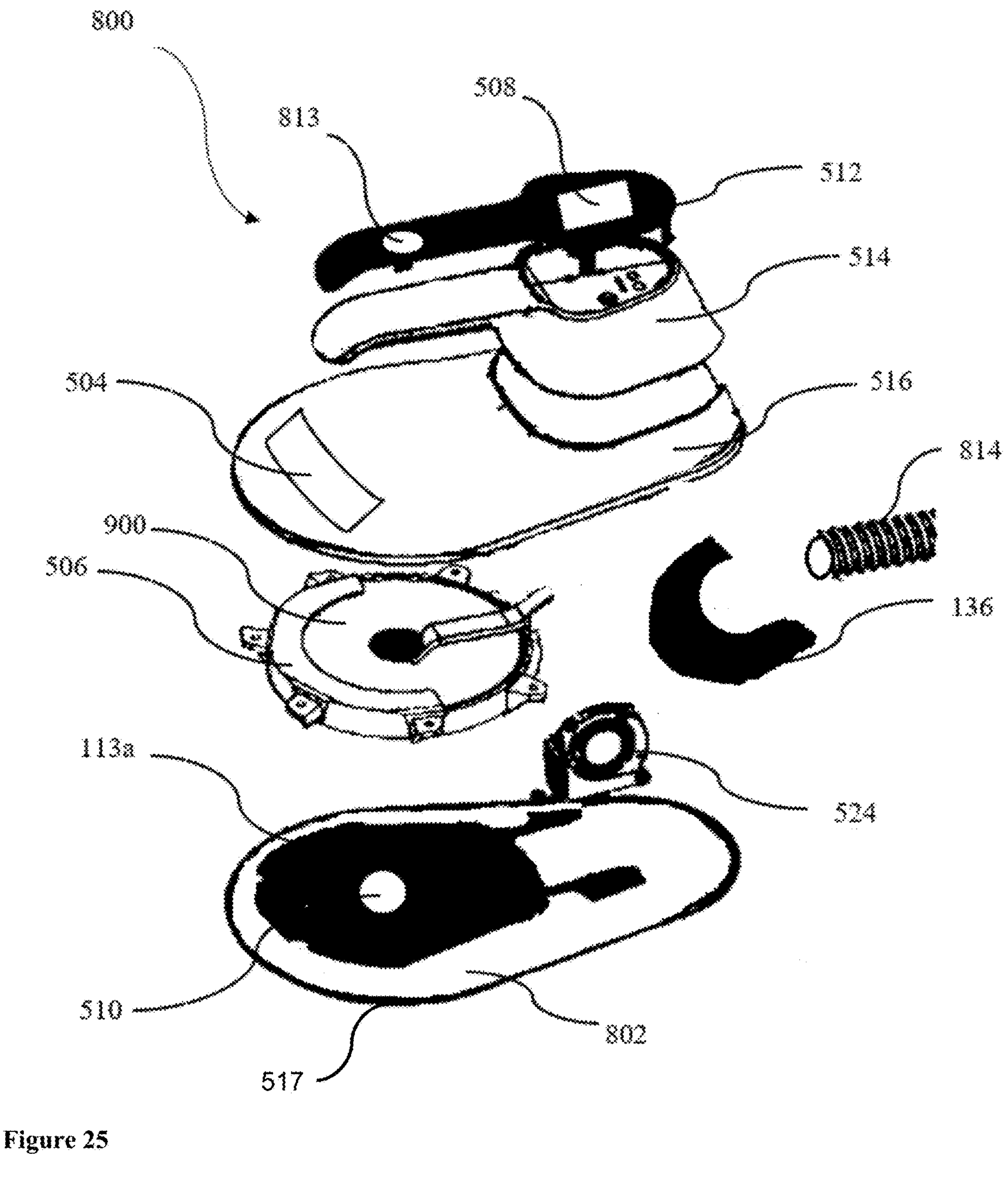
FIG. 25 illustrates an exploded view of applicator elements.

As shown in FIG. 25, the applicator 800 may include one or more parts defining casing of the applicator, which can be connected to the main unit by connecting tube 814. Also, the applicator may include one or more parts hidden in the applicator further defining function and functionality of the applicator. Casing of the applicator may include different parts e.g. a handle cover 512, a handle 514, a top cover 516, a second side portion 802 creating bottom cover 517 of the applicator. Handle cover 512 may include a marker 813 and/or HMI 508 for e.g. displaying and/or adjusting actual value and/or predetermined value of one or more treatment parameters. The handle 514 may be used for manipulation with the applicator 800 and/or for coupling the applicator 800 to patient's body area. The top cover 516 may define interior of the applicator. The top cover 516 may include an air opening 504 enabling air flowing to or from the interior of the applicator to cool electrical elements located in the interior of the applicator. The electrical elements located inside the interior of the applicator may include e.g. RF electrode, magnetic field generating device and/or temperature sensor 510. The RF electrode may be positioned on the substrate 113*a*. The RF electrode may be positioned on a side of the substrate 113*a* closer to the patient. The second side portion 802 creates a bottom cover 517 of the applicator. The bottom cover 517 may be positioned closer to the patient than the top cover 516 of the applicator 800. Therefore, the RF electrode may be positioned between the substrate 113*a* and the bottom cover 517. The second side portion 802 may include one or more protruding shapes, grooves and/or other. Power, energy, one or more electromagnetic signal and/or cooling fluid may be delivered to applicator via connecting tube 814. In addition, cooling of one or more electrically powered element in the applicator (e.g. a magnetic field generating device 900 and/or substrate 113*a* with at least one RF electrode) may be provided by a fan 524 fixed to the top cover 516 and/or to the second side portion 802. The RF electrode substrate 113*a* may include a temperature sensor 510 configured to determine a temperature in the applicator, of at least part of bottom cover 517, of a body area and/or of a biological structure of a patient. The RF electrode located on the substrate may be connected to pairing element 136 reconnecting coaxial cables. The pairing element 136 is further described with regard to the FIG. 24. FIG. 25 also illustrates a frame 506 that may be used to fix the magnetic field generating device to the top cover 516 and/or to the second side portion 802. The frame 506 may be configured to eliminate noises and vibrations during magnetic treatment. The magnetic field generating device 900 may be housed within the casing of the applicator 800. Also, the radiofrequency electrode may be housed within the casing of the applicator 800. Further, a plurality of radiofrequency electrodes may be housed within the casing of the applicator 800. By housing the magnetic field generating device 900 within the casing of the applicator 800, the magnetic field generating device 900 may not be in contact with the body of the patient. Also, by housing the radiofrequency electrode within the casing of the applicator 800, the radiofrequency electrode may not be in contact with the body of the patient. Further, by housing the magnetic field generating device 900 and radiofrequency electrode within the casing of the applicator 800, the magnetic field generating device 900 and radiofrequency electrode may not be in contact with the body of the patient.

The applicator may be designed as shown in exemplary FIGS. 8*a*-8*d*. The applicator 800 as illustrated in FIGS. 8*a*-8*d* may be used for treatment of body area.

One or more RF electrodes may be located in the applicator 800 between the magnetic field generating device and patient's body area. The RF electrode may be shaped to at least partially match a curvature of the first side portion 801, a second side portion 802, and/or a curvature of the patient's body area. The magnetic field generating device may at least partially match a curvature of the first side portion 801, the second side portion 802 and/or a curvature of the patient's body area. The RF electrode and/or the magnetic field generating device may be curved in order to focus and/or provide better targeting of the RF treatment and/or magnetic treatment. The first side portion 801 may be configured to maintain the position of the limb within the first side portion 801 during the treatment. The first side portion 801 may provide a stable position and/or equilibrium for the treated body area. The position of the limb of the patient may be maintained in the first side portion 801 even though the limb may move by the muscle contractions. The lateral movement and/or rotation of a limb may be limited due to the first side portion 801 and/or belt 817 in such way that the limb may be in stable position. The rotational movement with respect to the applicator 800 may be limited by coupling the applicator 800 to the body area, at least part the treated body limb by a belt. In addition, when part of the arm is treated by magnetic and/or RF treatment, at least part of the limb may be also attached to patient's trunk to minimize movement of the limb.

The second side portion 802 may be located on the opposite side of the applicator 800 with respect to the first side portion 801. The second side portion 802 may be substantially planar, or the second side portion 802 may be at least partially concave and/or convex. The applicator 800 may be coupled to the patient by a positioning mechanism, such as a belt 817, as illustrated in FIGS. 8*a* and 8*b*.

Figure 8A:
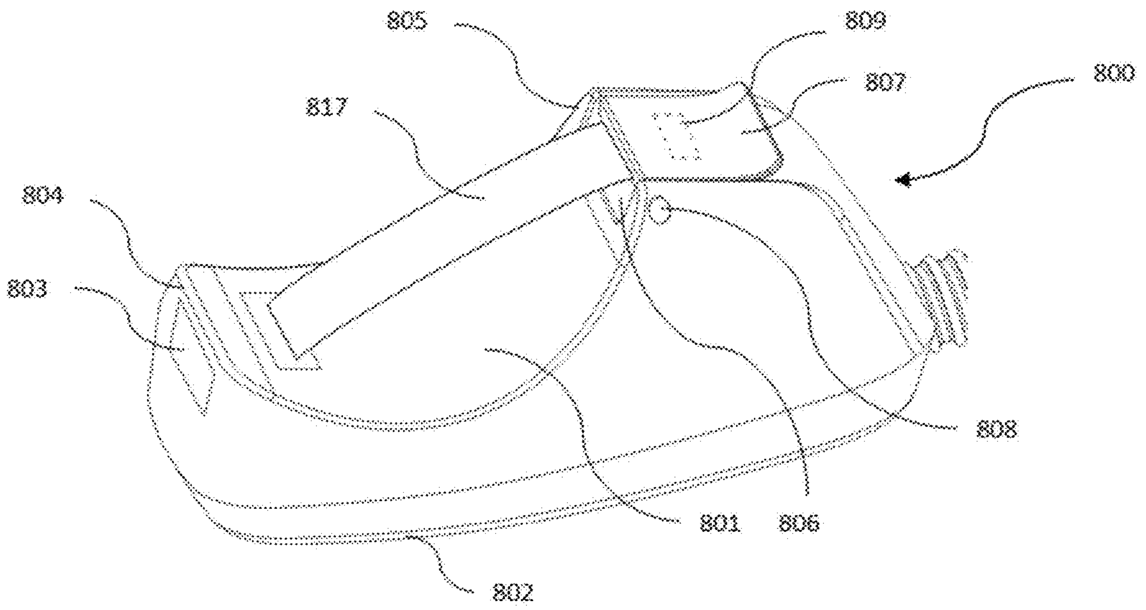
FIGS. 8*a*-8*e* illustrate parts of an exemplary applicator from the outer view.

FIG. 8*a* describes an applicator including the positioning mechanism which may be fixed in a recess 803 at a first end 804 of the first side portion 801 and a recess 806 at a second end 805 of the first side portion 801. The positioning mechanism, such as a belt or strap, may be fastened or its length may be adjusted by a clip 807. The clip 807 may move around the pin 808 in a clockwise or counter-clockwise direction. The clip 807 may be biased by a spring. Alternatively, the clip 807 may be locked by a suitable locking mechanism, or by any other movement restraining manner. The clip 807 may include a fastener 809 on lower side of the clip 807 for fixing a correct length of the positioning mechanism. The fastener 809 may be a hook-and-loop fastener, Velcro fastener, pin type fastener, among other mechanical fasteners. Coupling the applicator 800 to the patient's body as described above may be mostly used when the patient's body area is attached to the first side portion 801 of the applicator 800. The RF electrode and/or magnetic field generating device may be shaped to at least partially match a curvature of the first side portion 801. The RF electrode and/or the magnetic field generating device may be curved in order to focus and/or provide better targeting of the RF treatment and/or magnetic treatment.

Figure 8B:
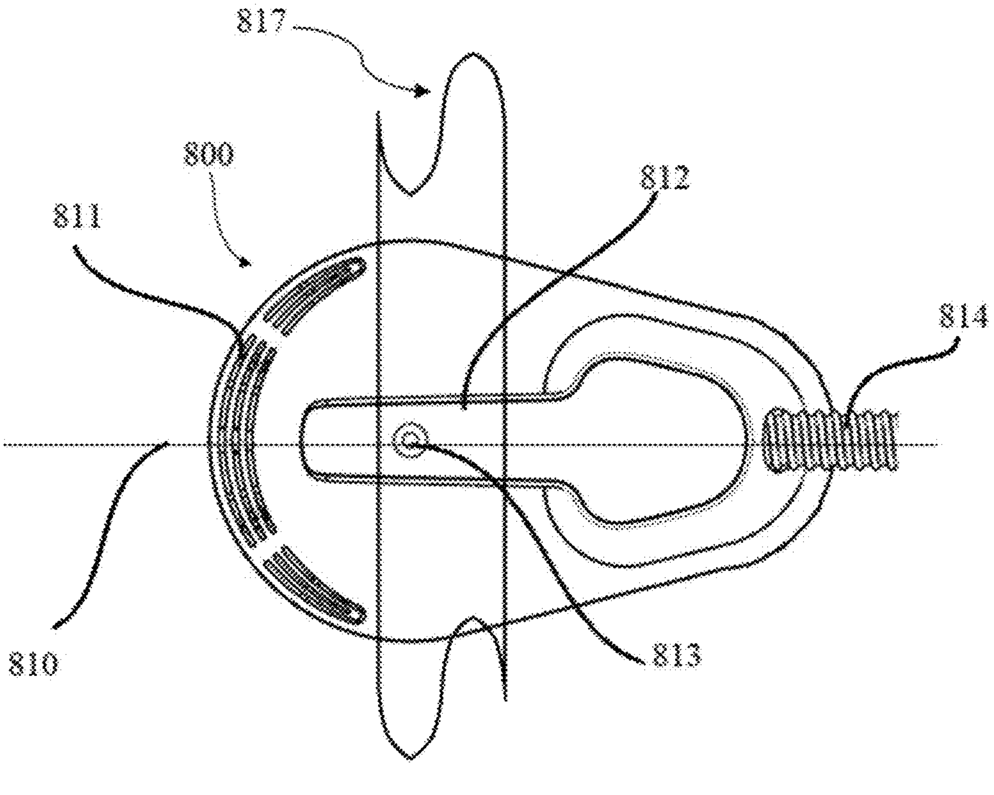
Figure 8C:
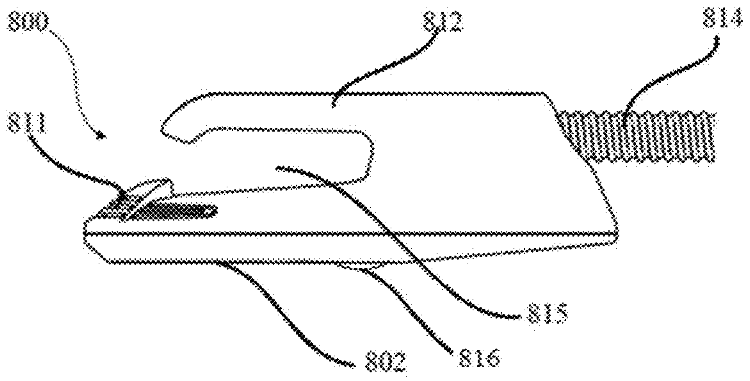

FIGS. 8*b* and 8*c* show an applicator including the positioning mechanism which may be guided perpendicularly to a curvature of the first side portion 801 and/or perpendicularly to an axis 810 of the applicator. The positioning mechanism may be positioned or guided through a concavity 815 of the handle 812. Also, the positioning mechanism (e.g. belt) may be positioned or guided below the handle 812 and above the magnetic field generating device. Further, the positioning mechanism (e.g. belt) may be positioned on the handle 812 by e.g. a clip. Belt 817 may also be guided in any direction through and/or on the applicator 800 to hold the applicator 800 to the patient's skin. Coupling the applicator 800 to the patient's body as described above may be mostly used when the patient's body area is attached to the second side portion 802 of the applicator 800. The RF electrode and/or magnetic field generating device may be shaped to at least partially match the first side portion 801. The RF electrode and/or the magnetic field generating device may be flat or curved in order to focus and/or provide better targeting of the RF treatment and/or magnetic treatment.

FIG. 8*b* illustrates a top view of an applicator 800. Applicator 800 may include a marker 813 corresponding with the location of magnetic field generating device within the applicator 800. The marker 813 may be located above the centre of the magnetic field generating device. The marker 813 may enable easy and comfortable positioning of the applicator 800 by the user. A recess in a surface of the applicator 800 may be used as the marker 813. Alternatively, the marker 813 may be a different surface modification of a part of the applicator's cover, such as a different color, different roughness, presence of one or one light source (e.g. light emitting diode LED), a specific curvature of the casing of the applicator, logo of the manufacturing or distributing company and/or other. The casing of the applicator may include at least two colors. A first color may be on applicator's casing over the magnetic field generating device to enable correct positioning of the applicator, and the rest of the applicator may have a second color that differs from the first color. The color may be interpreted as a paint reflecting and/or absorbing specific wavelengths of light. Similar to marker 813, applicator may include a second marker to show a location of the at least one RF electrode.

As shown in in FIGS. 8*b* and 8*c*, applicator may include an outlet 811. The outlet 811 may enable circulation of the air in the applicator 800 and heat dissipation of heat generated by at one or more magnetic field generating devices and/or RF electrodes positioned in applicator and supplied by energy through one or more wire inside of a connecting tube 814. The connecting tube 814 may also include the fluid conduit that may provide or guide cooling fluid from the main unit 11 to the applicator 800.

The applicator 800 may further include one or more temperature sensors 816 as shown for example in FIG. 8*c*. The temperature sensor 816 may protrude from the casing of the applicator 800 e.g. such as from the surface of the second side portion 802 and/or from the first side portion 801. The temperature sensor 816 may protrude from the casing of the applicator 800 in order to create higher pressure to part of the treated body area by the applicator 800 and to provide better measurement of the temperature in the biological structure, of the body area and/or on the patient's body.

Figure 8D:
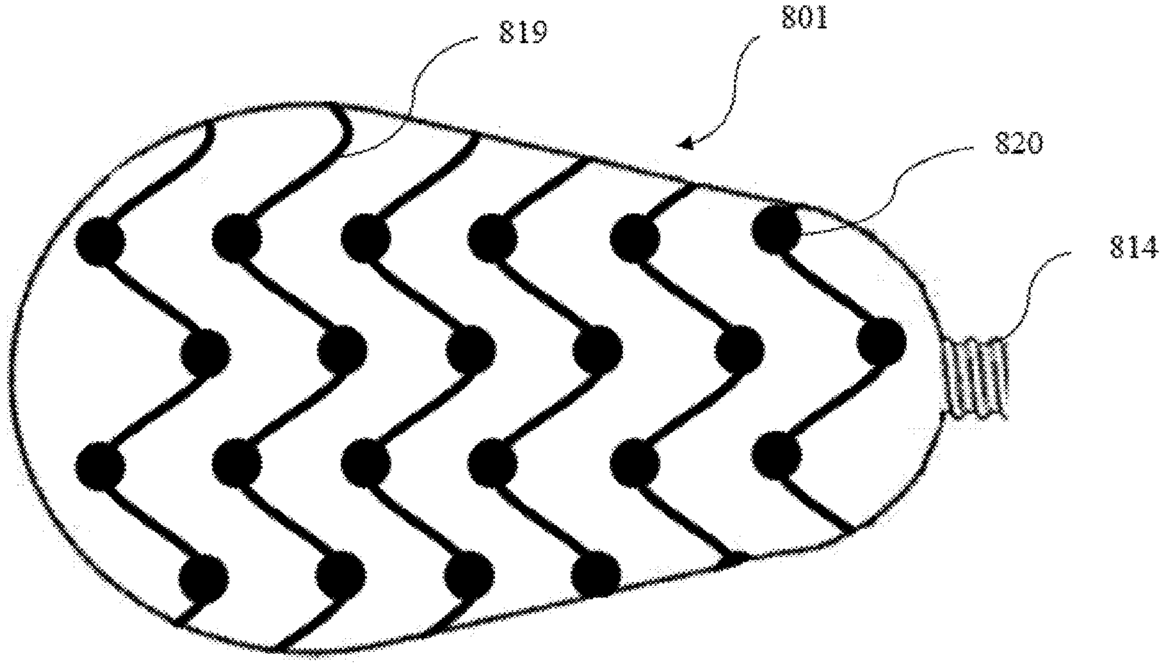
Figure 8E:
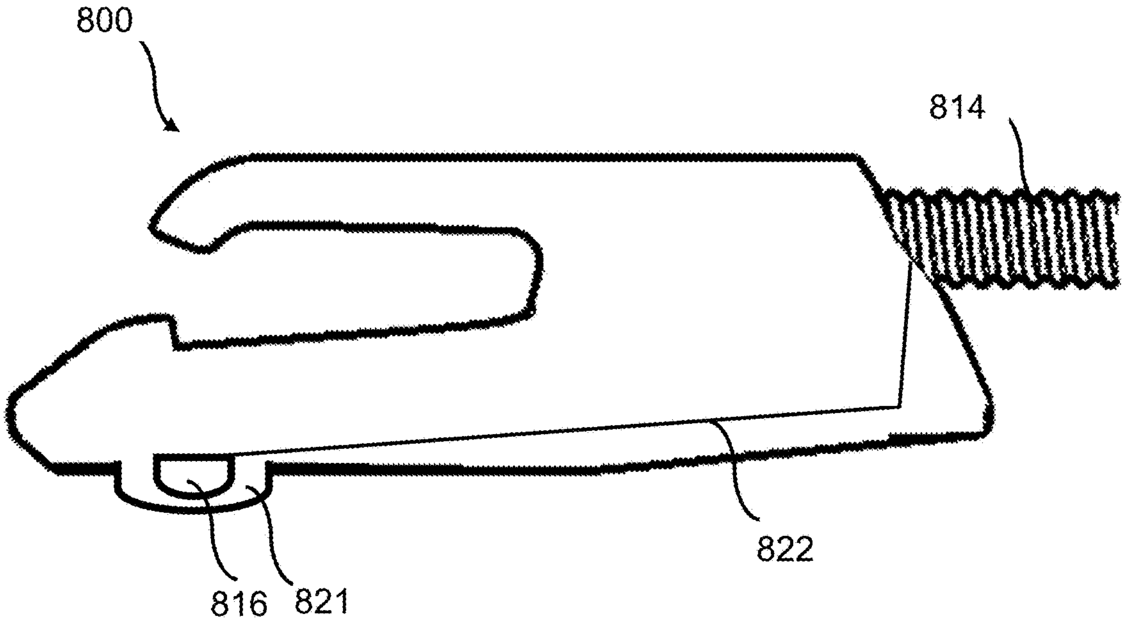

FIG. 8*e* shows exemplary placement of the temperature sensor 816 within the applicator 800. The temperature sensor 816 may be located in a protruding part 821 of the applicator. Protruding part 821 of the applicator 800 may protrude from the surface of the applicator being in contact with the patient, such that the protruding part 821 with the temperature sensor is pressed into the patient's skin and is kept closer to the surface of the patient than the other electrical elements of the applicator.

The second side portion 802 and/or the first side portion 801 may be heated and/or cooled. Heating of the second side portion 802 and/or the first side portion 801 may be used e.g. at the beginning of the treatment to reach treatment temperature sooner. Treatment temperature may include temperature of body area and/or biological structure increased by application of RF waves which may be appropriate for application of magnetic field. Cooling or heating by portions of the applicator may be used for maintaining constant temperature on the patient's skin. Also, cooling or heating by portions of the applicator may be used to achieve higher treatment temperatures in the patient's biological structure deeper than 0.5 cm under the patient's skin. Cooling a part of an applicator that is in contact with the patient (e.g., the second side portion 802 and/or the first side portion 801 of the applicator) may be used for minimizing a patient's sweating. The patient's skin may be cooled by cooling fluid (e.g. air) flowing and/or blowing from the applicator and/or other part of the treatment device. Cooling of the patient's skin may be provided by thermal diffusion between a cooled part of the applicator contacting patient's skin and the patient's skin. The cooled part of the applicator may be cooled by cooling fluid flowing in the applicator and/or by Peltier element using Peltier's effect.

Patient's sweating may be uncomfortable for the patient and may adversely affect feedback information collection, contact with the applicator and patient's skin, and/or lead to lower adhesion of the applicator to the patient's skin. To prevent sweating of the patient's skin, cooling of contact applicator's area (e.g. first side portion 801 and/or second side portion 802) may be used. The second side portion 802 and/or the first side portion 801 may include grooves 819 that may be supplied by cooling fluid through applicator's apertures 820 where liquid and/or gas, (e.g. air, oil or water) may flow as illustrated in FIG. 8*d*. The first side portion or second side portion of the applicator may include applicator's holes or applicator's apertures 820 where air from the applicator 800 may be guided to remove heat, moisture and/or sweat from the patient's skin. The holes or apertures may be presented in the grooves 819. The holes may be used for providing an active substance on the patient. The contacting part of the applicator being in contact with the body area may include a fluid absorbing material, such as sponge, hydrophilic material, non-woven organic and/or polymeric textile, which may at least partially remove sweat from the patient's skin and/or improve conductivity between the patient and applicator 800. Reduction of patient's sweating in at least part of treated body area may be provided by reduction of sweat gland activity. Reduction of activity of sweat gland may be provided by application of a pulsed magnetic field, intensive light, heat shock provided by periodic hypothermia of patient's skin by applied active substance on and/or to the patient, such as glycopyrronium tosylate, and/or by other mechanisms.

Figure 23:
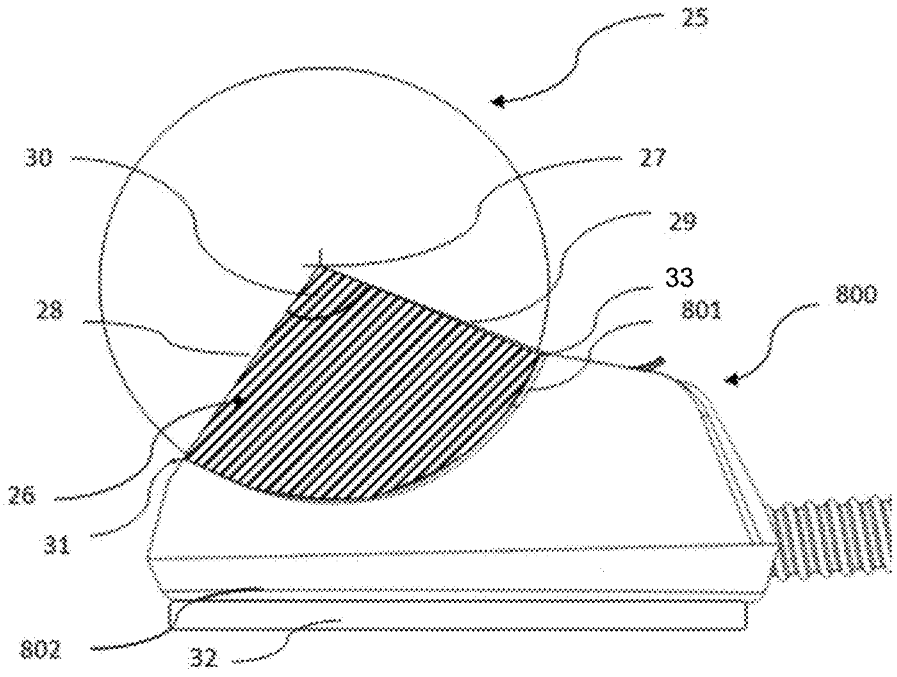
FIG. 23 illustrates a section of exemplary curved applicator's first side portion.

FIG. 23 illustrates an exemplary applicator including a concavity. The applicator may be designed with the first side portion 801 being at least partially convex. The first side portion 801 may alternatively be V-shaped or U-shaped. The curvature radius may correspond with a size of the patient's limb. The second side portion 802 may alternatively or additionally be at least partially convex.

The patient may lay in a supine position or sit on a patient support such as a bed, a couch or a chair. An arm of the patient may be set on the first side portion 801 of the applicator 800. The first side portion 801 may be in direct contact with the patient and RF treatment in combination with magnetic treatment may be applied. Also, a strap or belt may be guided through the concavity 815 to attach the applicator to the patient's body.

The first side portion 801 may have at least partial elliptical or circular shape according to a vertical cross section, wherein the total curvature 25 according to FIG. 23 may be defined as part of an ellipse or circle fitted to a curvature of at least part of the first side portion 801. A section where curvature of the first side portion 801 matches the fitted ellipse or circle may be called the section 26. The section 26 is defined as an angle 30 between two the line 28 and line 29. The line 28 and the line 29 cross a centre of symmetry 27 and points 31 and 33 located in the section 26 with the longest distance according to fitted part of an ellipse or circle copying curvature of the applicator 800. The centre of symmetry 27 is a centre of fitted ellipse and/or fitted circle. The angle 30 defining section 26 of the first side portion 801 may be at least 5° or in a range from 10° to 270°, 30° to 235°, 45° to 180°, or 60° to 135°. A curvature radius of at least part of fitted circle to the first side portion 801 may be in a range of 50 mm to 1250 mm, or in the range of 10 mm to 750 mm, or in the range of 50 mm to 500 mm, or in the range of 60 mm to 250 mm. The second side portion 802 may be curved on at least part of its surface wherein the section 26 of the second side portion 802 may be at least 5° or in a range from 10° to 270°, 30° to 235°, 45° to 180°, or 60° to 135°. Further a curvature radius of at least part of fitted circle to the second side portion 802 may be in a range of 50 mm to 1250 mm, 10 mm to 750 mm, 50 mm to 500 mm, or 60 mm to 250 mm.

One or more applicators and/or additional treatment devices may include a bolus 32, as shown for example in FIG. 23. The bolus 32 may refer to a layer of material located between the applicator or RF electrode positioned on the surface of the applicator and the patient's body area or skin (including epidermis of patient's skin or clothing). The bolus 32 may refer to a layer of material located between the RF electrode positioned on the surface of the applicator and the patient's body area or skin. Also, the bolus 32 may be an independent part from the applicator 800. The bolus 32 may be attached to the first side portion 801 and/or to the second side portion 802 of the applicator 800. The bolus 32 may be removable and detachable from the applicator 800. The bolus 32 may be mechanically coupled to the first side portion 801 and/or to the second side portion 802 of the applicator 800. The bolus 32 may be made of a solid, flexible material and/or a composition of solid and flexible materials may be used as a bolus. The bolus 32 may include a fluid material, such as water, gel, or fluid solution including ceramic, metal, polymeric and/or other particles enclosed in a flexible sac made of biocompatible material. The bolus 32 may be profiled, wherein a thickness of the bolus 32 as a layer between RF electrode and patient's skin may have a different thickness. Thickness of the bolus 32 may be higher in a location where an energy flux density of the RF treatment (including RF field) would be high enough to create uncomfortable hot spots and/or non-homogeneous temperature distribution. The bolus 32 allows for more homogenous biological structure heating and minimizes edge effects. Edge effects may also be minimized by different dielectric properties of the bolus across the bolus volume and/or bolus area. The bolus 32 may have higher thickness under the at least part of the edge of the RF electrode. The thickness of the bolus under the at least part of the edge of the RF electrode may be at least 5%, 10%, 15%, or 20% greater than a thickness of the bolus 32 under the at least part of a centre of the RF electrode wherein no apertures, cutout and/or protrusions are taken into account. The bolus 32 may have a higher thickness under at least part of the bipolar RF electrode and/or under at least part of a distance between at least two bipolar RF electrodes. The bolus 32 may be in such locations thicker by about at least 5%, 10%, 15%, or 20% than a thickness of the bolus 32 where the distance between two nearest points of two different bipolar RF electrodes is at least 5%, 10%, 15%, or 20% more. The bolus 32 may also improve transfer of treatment energy (e.g. magnetic field and/or RF field) to at least one biological structure and minimize energy reflection by providing gradual transition of dielectric properties between two different interfaces of the applicator and the biological structure. The bolus 32 may profile or focus the RF field and/or magnetic field to enhance the effect of the treatment, and/or provide deeper tissue penetration of the treatment.

The bolus 32 may also be a fluid absorbing material, such as a foam material, textile material, or gel material to provide better conductivity of the environment between the applicator and a patient's body. Better conductivity of the contact part of the applicator may be useful for better adjusting of the RF signal of the applied RF treatment to the patient's body and/or for better collecting of feedback information. The bolus 32 may mediate conductive contact between the RF electrode and the patient's skin or body area. Also, the bolus 32 may serve as a non-conductive or dielectric material modifying energy transfer to the patient's body, providing cooling of the patient's skin, removing sweat from the patient's skin and/or providing heating, such as capacitive heating of the patient's body. Fluid absorbing material serving as a bolus 32 may also provide better heat conductivity therefore temperature of the biological structure and/or the applicator may be faster, easier and more precisely regulated. The bolus 32 may also include additional RF electrode to provide the RF treatment.

As mentioned previously, the treatment device may include one, two, three, four, six or more applicators and/or additional treatment devices providing the magnetic treatment and/or the RF treatment. Each applicator, additional treatment device and/or treatment energy source (e.g. magnetic field generating device and/or the RF electrode) may have its own treatment circuit for energy transfer, wherein each treatment circuit may be independently regulated in each parameter of provided treatment energy by control system. Each applicator, treatment device, or treatment energy source may be adjusted and provide treatment independently and/or two or more applicators, treatment energy sources, and/or additional treatment devices may be adjusted as a group, and may be adjusted simultaneously, synchronously and/or may cooperate between each other.

When the treatment device includes two or more applicators, they may be coupled to contact or to be proximate to different parts of the body. In one example the first applicator may be coupled to contact or to be proximate to left buttock while the second applicator may be coupled to contact or to be proximate to right buttock. In another example, the first applicator may be coupled to contact or to be proximate to left side of abdominal area while the second applicator may be coupled to contact or to be proximate to right side of abdominal area. In still another example the first applicator may be coupled to contact or to be proximate to left thigh while the second applicator may be coupled to contact or to be proximate to right thigh. In still another example the first applicator may be coupled to contact or to be proximate to left calf while the second applicator may be coupled to contact or to be proximate to right calf. The plurality of applicators may be beneficial for treatment of cooperating muscles and/or pair muscles.

One or more applicators and/or the additional treatment devices may include the magnetic field generating device (e.g. a magnetic coil) generating magnetic field for a magnetic treatment. The magnetic field generating device may generate the RF field for the RF treatment. The essence is that the produced frequencies of the electromagnetic field has far different values. The magnetic field generating device may produce a dominant magnetic field vector for the magnetic treatment during lower frequencies of produced electromagnetic field. However, the magnetic field generating device may produce a dominant electromagnetic field vector for the magnetic treatment during higher frequencies of electromagnetic field which may be used for the RF treatment. The magnetic field generating device in the high frequency electromagnetic field domain may provide RF field similar to the RF field provided by the RF electrode. When one magnetic field generating device may be used for providing both the RF treatment and the magnetic treatment, the difference between frequencies for the RF treatment and the magnetic treatment production may be in a range from 500 kHz to 5 GHz, or from 500 kHz to 2.5 GHz, or from 400 kHz to 800 kHz, or from 2 GHz to 2.5 GHz. Also, when one magnetic field generating device is used for providing both the RF treatment and the magnetic treatment, the frequencies for the RF treatment may correspond with frequencies in the range of 100 kHz to 3 GHz, 400 kHz to 900 MHz, or 500 kHz to 3 GHz.

One or more applicators and/or additional treatment devices may include one or more RF electrodes and one or more magnetic field generating devices, wherein the RF electrodes have different characteristics, structure and/or design than the magnetic field generating device. The one or more RF electrodes may not contact the surface of the patient. The one or more RF electrodes may be located inside of the applicator together with the magnetic field generating device. The RF electrode may operate as a unipolar electrode, monopolar electrode, bipolar electrode, and/or as a multipolar electrode. One or more RF electrodes may be used for capacitive, inductive, or resistive heating of biological structure or body area. Also, the inductive RF electrode may be coiled.

The applicator may include two bipolar RF electrodes. The bipolar electrodes may transfer the RF field between two bipolar RF electrodes located in at least one applicator. Bipolar electrodes may increase safety and targeting of provided RF treatment, as compared to electrodes of monopolar type. Bipolar electrodes may provide electromagnetic field passing through a patient's tissue located around and between RF electrodes, wherein due to impedance matching, it is possible to prevent creation of standing electromagnetic waves in the patient's tissue and prevent unwanted thermal injury of non-targeted tissue. Also, the distance between bipolar electrodes influences the depth of RF wave penetration allowing for enhanced targeting of the RF treatment. The bipolar RF electrodes include a positive RF electrode and a negative RF electrode, wherein the mutual polarity of the bipolar RF electrodes is changing because the polarity of the RF signal is changing from positive to negative phase of the RF signal, as given by frequency of the RF signal and resulting RF waves. The bipolar RF electrodes are powered, e.g., by wiring 100*a* and 100*b* as shown in FIGS. 14*a*-14*e*, which are connected to the rest of elements of the RF circuit (e.g. power amplifier and/or symmetrisation element).

The applicator may include one or more multipolar RF electrodes, wherein the respective electrodes are charged on a different charge (value and/or polarity e.g. in a phase shift of RF signal or RF signals).

The applicator may include a monopolar RF electrode or more monopolar electrodes. Monopolar electrodes may transfer radiofrequency energy between an active electrode and a passive electrode, wherein the active electrode may be part of the applicator and the passive electrode having larger surface area may be located at least 5 cm, 10 cm, or 20 cm from the applicator. A grounded electrode may be used as the passive electrode. The grounded electrode may be on the opposite side of the patient's body than the applicator is attached.

The magnetic treatment may be provided by the magnetic field generating device may be made from a conductive material, such as a metal, including for example copper. The magnetic field generating device may be formed as a coil of different size and shape. The magnetic field generating device may be a coil of multiple windings wherein one loop of the coil may include one or multiple wires. An individual loop of one or more wires may be insulated from the other turns or loops of one or more wires. Regarding the magnetic coil, each loop of wiring may be called a turn. Further, individual wires in one turn or loop may be insulated from each other. The shape of the magnetic field generating device may be optimized with regard to the applicator size and design. The coil may be wound in order to match at least part of the applicator's shape according to the applicator's floor projection. The coil winding may be at least partially circular, oval and/or may have any other shapes that match to a shape of the applicator or a portion thereof. The loops of winding may be stacked on top of each other, may be arranged side by side, or stacking of the winding may be combined side by side and on top of other windings. The coil may be flat. The magnetic field generating device may include a magnetic coil and an impregnation material which may prevent the wire motion during operation of the magnetic coil. The impregnation material may be an electrically insulating material preventing the current passing between the turns or loops. The impregnation material may be positioned on the surface of and/or within the magnetic coil. The impregnation material may include a resin (e.g. epoxy resin).

FIG. 9 illustrates a floor projection of an exemplary magnetic field generating device 900. The magnetic field generating device may be circular, ellipsoidal, rectangular or it may have other shapes. The magnetic field generating device may be planar. The magnetic field generating device may be curved e.g. in order to fit the applicator and/or curve of body. The magnetic field generating device 900 may be characterized by dimensions including an outer diameter D, an inner diameter d, an inner radius r and an outer radius R. The magnetic field generating device 900 may be further characterized by areas A1 and A2. Area A2 may represent a winding area of the coil while A1 may represent a magnetic core or area without any magnetic core or windings.

The area A1 is associated with dimensions r and d. The area A1 may include no windings of the coil, and may be filled by air, oil, polymeric material. The area A1 may represent a magnetic core wherein the magnetic core may be an air core. Alternatively, the magnetic core may be a permeable material having high field saturation, such as a solid core from soft iron, iron alloys, laminated silicon steel, silicon alloys, vitreous metal, permendur, permalloy, powdered metals or ceramics and/or other materials.

The area A2 is associated with dimensions of outer radius R and outer diameter D.

The dimension of inner radius r may be in the range from 1% to 90% of the dimension of outer radius R, or in the range from 2% to 80% or from 3% to 60% or from 4% to 50%, from 8% to 30%, or from 20% to 40% or from 30% to 50% of the dimension of outer radius R. The dimensions of inner radius r and outer radius R may be used for achieving a convenient shape of the generated magnetic field.

The outer diameter D of the magnetic device may be in a range of 30 mm to 250 mm, or of 40 mm to 150 mm, or of 50 mm to 135 mm or of 90 mm to 125 mm, and the dimension of inner radius r may be in a range of 1% to 70% or 1% to 50% or 30% to 50%, 5% to 25%, or 8% to 16% of the dimension of outer radius R. For example, the dimension of outer radius R may be 50 mm and the dimension r may be 5 mm. The area A1 may be omitted and the magnetic field generating device may include only area A2 with the coil winding.

As discussed, the area A2 may include a plurality of windings. One winding may include one or more wires. The windings may be tightly arranged, and one winding may be touching the adjacent winding to provide magnetic field with high magnetic flux density. The winding area A2 may be in the range from 4 $cm^2$ to 790 $cm^2$, from 15 $cm^2$ to 600 $cm^2$, from 45 $cm^2$ to 450 $cm^2$ or from 80 $cm^2$ to 300 $cm^2$ or from 80 $cm^2$ to 150 $cm^2$ or from 80 $cm^2$ to 130 $cm^2$.

Alternatively, the windings may include a gap between each winding. The gap may be between 0.01% to 50%, or 0.1% to 25%, or 0.1% to 10%, or 0.1% to 5%, or 0.001% to 1% of the dimension R-r. Such construction may facilitate cooling and insulation of individual winding of the magnetic field generating device. Further, the shape of the generated magnetic field may be modified by such construction of the magnetic field generating device.

The wire of the coil winding may have a different cross-section area. The cross-sectional area of the winding wire may be larger at the centre of the winding where the coil winding radius is smaller. Such cross-section area of the wire may be from 2% to 50%, from 5% to 30%, or from 10% to 20% larger than the cross-sectional area of the same wire measured on the outer winding turn of the magnetic field generating device, wherein the coil winding radius is larger. The cross-sectional area of the winding wire of the magnetic field generating device may be larger on the outer coil winding turn of the magnetic field generating device where the coil winding radius is larger. Such cross-sectional area of the wire may be from 2% to 50%, from 5% to 30%, or from 10% to 20% larger than the cross-section area of the same wire measured on the inner turn of the magnetic field generating device wherein the coil winding radius is smaller.

The principles and parameters described above may be used in order to modify the shape of the provided magnetic field to the patient's body, provide a more homogenous and/or targeted muscle stimulation (e.g. muscle contraction), reduce expansion of the magnetic field generating device during the treatment and/or increase durability of the magnetic field generating device. The magnetic field generating device may expand and shrink during generation of time-varying magnetic field and this could cause damage of the magnetic field generating device. Different cross-sectional areas of used conductive material (e.g. wire, metallic stripe or creating winding of the magnetic field generating device) may minimize the destructive effect of expanding and shrinking the magnetic field generating device.

As discussed above, the cross-sectional area of the used conductive material, (e.g. wire, metallic stripe and/or creating winding of the magnetic field generating device) may vary between individual loops of wiring in a range of 2% to 50%, or of 5% to 30%, or of 10% to 20% in order to improve focusation of the provided magnetic treatment, to increase durability of the magnetic field generating device, to minimize heating of the magnetic field generating device, and/or for other reasons.

Further, stacking of the wiring and/or isolating and/or dilatation layer between individual conductive windings of the magnetic field generating device may not be constant and may be different based on the wire cross-sectional area, radius of the winding, required shape of provided magnetic field and/or other parameters.

Figure 9A:
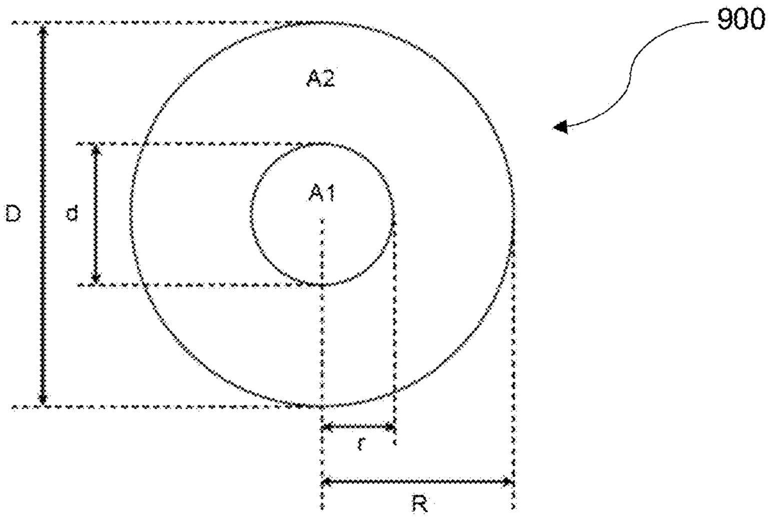
FIG. 9*a* illustrates an exemplary magnetic field generating device from the applicator's floor projection.
Figure 9B:
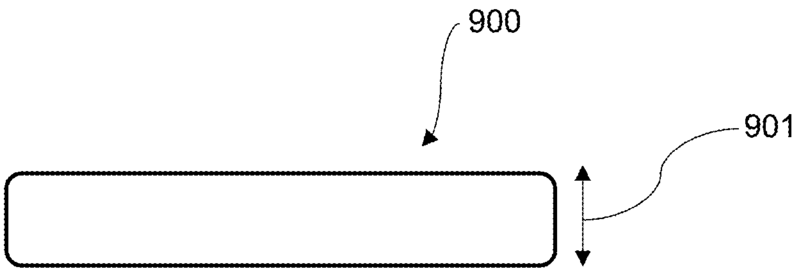
FIG. 9*b* illustrates a thickness of exemplary magnetic field generating device.

A thickness 901 of the magnetic field generating device 900 shown on FIG. 9*b* may be in a range of 0.3 cm to 6 cm, or of 0.5 cm to 5 cm, or of 1 cm to 3 cm from the applicator's side view.

A total surface of the magnetic field generating device surface according to the applicator's floor projection, i.e. area A1+A2, may be in a range from 5 $cm^2$ to 800 $cm^2$, 10 $cm^2$ to 400 $cm^2$, 20 $cm^2$ to 300 $cm^2$ or 50 $cm^2$ to 150 $cm^2$.

The ratio of the area A1 and winding area A2 may be in a range of 0.01 to 0.8, or 0.02 to 0.5 or 0.1 to 0.3 according to the applicator's floor projection. The ratio between the winding area A2 of the magnetic field generating device and the area of RF electrodes located in same applicator according to the applicator's floor projection may be in a range of 0.01 to 4, or 0.5 to 3, or 0.5 to 2, 0.3 to 1, or 0.2 to 0.5, or 0.6 to 1.7, or 0.8 to 1.5, or 0.9 to 1.2.

FIGS. 10*a*-10*g* show the location of one or more RF electrodes 101 with regard to at least one magnetic field generating device 900 in an applicator 800. The location of the RF electrodes 101, 102 and/or the magnetic field generating device 900 may crucially influence the effectiveness and targeting of the treatment energy sources. The RF electrodes and magnetic field generating device may be located within the applicator.

Figure 10A:
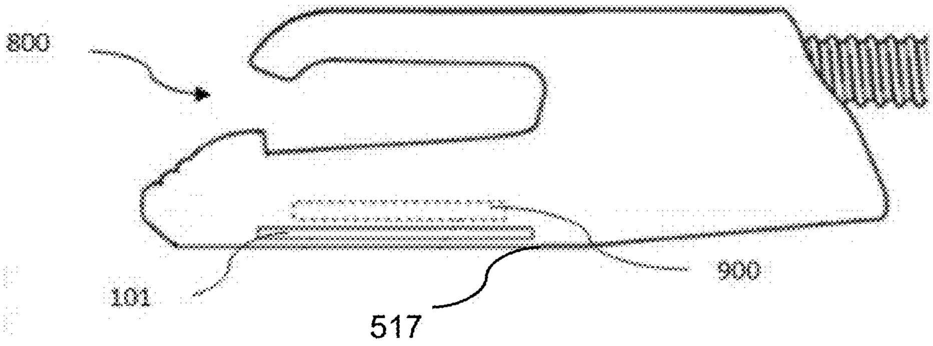
FIGS. 10*a*-10*u* illustrate possible locations of an exemplary RF electrode with regard to an exemplary magnetic field generating device.
Figure 10B:
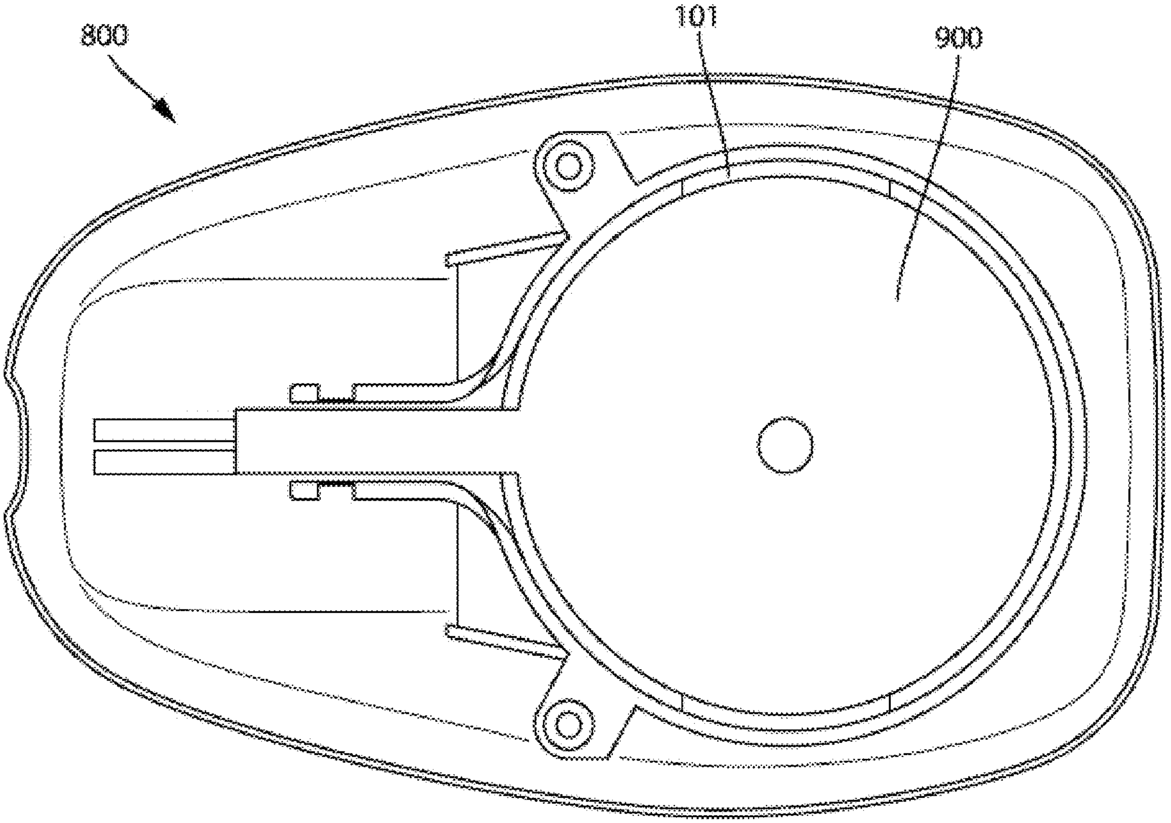
Figure 10C:
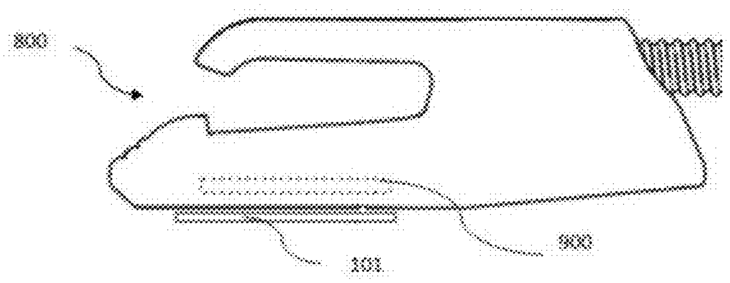

One or more RF electrodes 101, 102 may be located inside of the applicator 800, as illustrated in the FIGS. 10*a*, 10*b*, 10*d*, 10*e*, 10*f*, 10*g* and/or outside of the applicator 800, as illustrated in the FIG. 10*c*.

As shown in FIGS. 10*a*-10*e* and 10*g*, at least one RF electrode may be in at least partial overlay with the area A2 or A1 of at least one magnetic field generating device according to applicator's floor projection. Such arrangement may enable the best synergic effect of the magnetic and RF treatments, improve homogeneity of tissue heating by the RF treatment, improve targeting of the magnetic and RF treatment, and also minimize the health risk.

FIG. 10*a* illustrates a side view of the applicator including at least one RF electrode and magnetic field generating device. Shown applicator may include the at least one RF electrode 101 which may be located under the magnetic field generating device 900 in the applicator 800. The RF electrode 101 may be positioned between bottom cover 517 of the applicator 800 and magnetic field generating device 900. FIG. 10*b* illustrates an upper view of the same type of applicator including RF electrode and magnetic field generating device. As shown in FIGS. 10*a* and 10*b*, the at least one RF electrode 101 may be very thin in order to reduce unwanted physical effects caused by the time-varying magnetic field. FIG. 10*b* illustrates that the at least one RF electrode 101 may be almost completely in overlay with the magnetic field generating device 900.

FIG. 10*c* illustrates another exemplary applicator including at least one RF electrode and magnetic field generating device. According to FIG. 10*c*, the at least one RF electrode 101 may be located outside of the applicator 800, such as on or adjacent to an exterior surface of the applicator 800. RF electrode outside of the applicator may have better insulation from the magnetic field generating device and/or from other conductive elements radiating electromagnetic field from the applicator. Better insulation may decrease the influence of unwanted physical effects induced in the at least one RF electrode 101 by radiating electromagnetic field and/or time-varying magnetic field. One or more RF electrodes 101 located outside of the applicator as illustrated in FIG. 10*c* may also have better contact with the patient's body and so operation of tuning electrical element of an RF circuit may be improved. Further, transferring of the RF treatment to at least one patient's target biological structure may be enhanced.

Figure 10D:
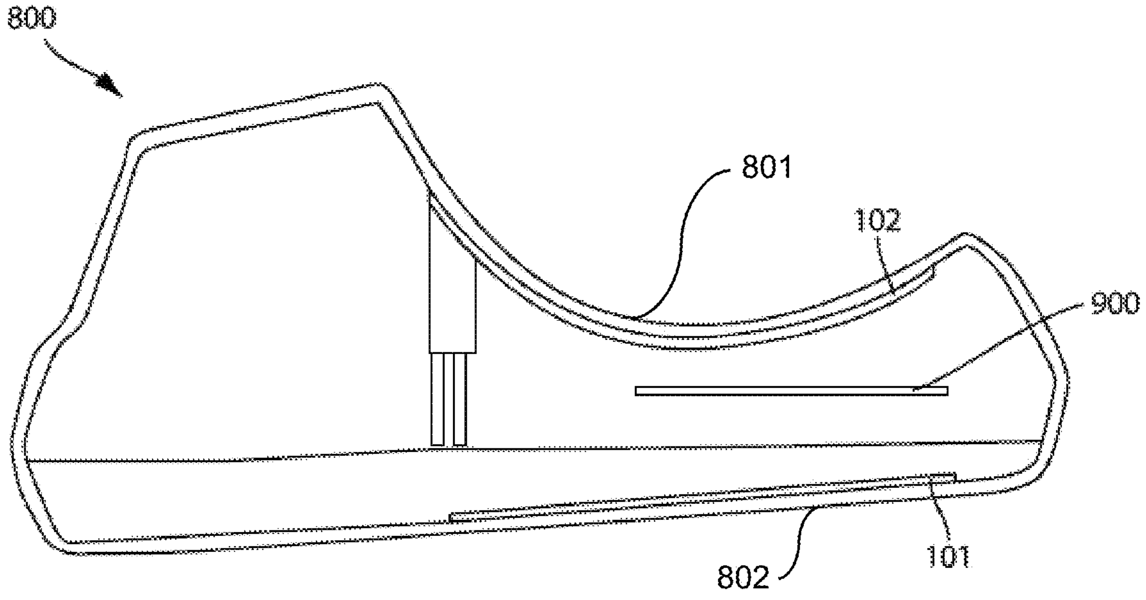

FIG. 10*d* illustrates another exemplary applicator including at least one RF electrode and magnetic field generating device. The at least one RF electrode 101 may be positioned below the magnetic field generating device 900. Applicator 800 may also include another at least one RF electrode 102 located above the magnetic field generating device 900, wherein both RF electrode and magnetic field generating device may be positioned in one applicator 800. The first side portion 801 having curved at least one RF electrode 102 in proximity or on its surface may be used for treating a curved body area (e.g. at least part of thighs, hips, neck and/or arms). The second side portion 802 with a flat at least one RF electrode 101 in proximity or on its surface may be used for treating body area where flat or nearly flat side of the applicator will be more suitable, such as an abdomen area or buttock.

Figure 10E:
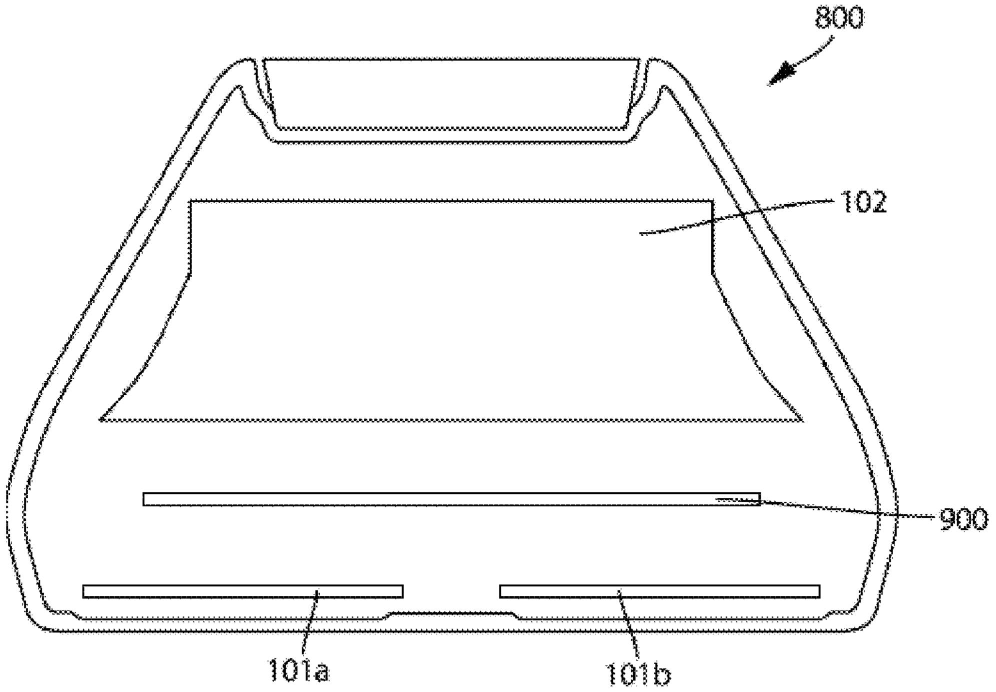

FIG. 10*e* shows a front side view of a similar applicator 800 as in FIG. 10*d*. FIG. 10*e* illustrates that the RF electrode 101 may be in fact two electrodes 101*a* and 101*b*. The electrodes 101*a* and 101*b* may be bipolar electrodes. Therefore, the applicator may include two bipolar electrodes 101*a* and 101*b* below the magnetic field generating device 900. When the applicator 800 includes two bipolar RF electrodes, the bipolar RF electrodes may be positioned between the bottom cover and magnetic field generating device 900. Further, FIG. 10*e* shows another RF electrode 102 positioned above the magnetic field generating device 900.

Figure 10F:
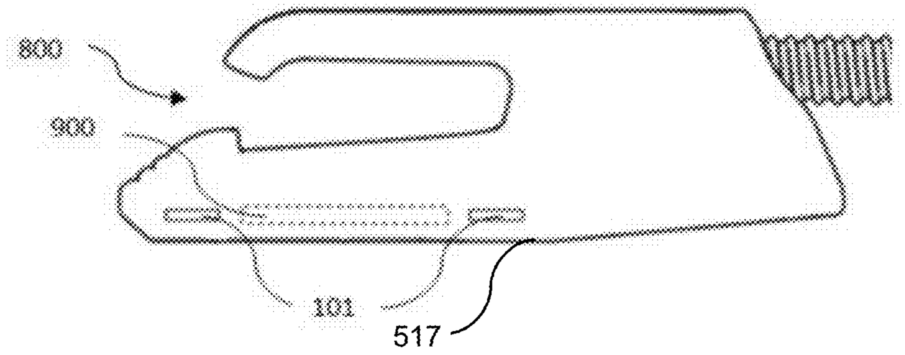

FIG. 10*f* illustrates another exemplary applicator 800 including RF electrode and magnetic field generating device. The applicator may include one or more RF electrodes 101 which may have minimal or no overlay with at least one magnetic field generating device 900 according to applicator's floor projection. The applicator may include two RF electrodes 101 having no or minimal overlay with magnetic field generating device.

At least one radiofrequency electrode 101 may be located in the applicator 800 under the magnetic field generating device 900 as illustrated for example in FIG. 10*a*, under the applicator 800 as illustrated in FIG. 10*c*, and/or at least one RF electrode 101 may be at least partially located next to the magnetic field generating device 900 as illustrated in FIG. 10*f*. In addition, at least one RF electrode may be located above the applicator and/or above the magnetic field generating device. The RF electrode and/or the applicator may be in contact with the patient.

Figure 10G:
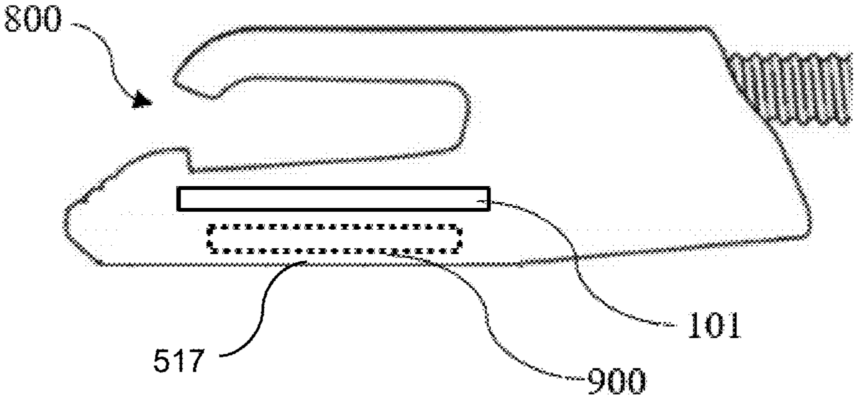

FIG. 10*g* illustrates another exemplary applicator 800 including RF electrode and magnetic field generating device. The applicator may at least one RF electrode 101 which may be located above the magnetic field generating device 900. The magnetic field generating device 900 may be positioned between a bottom cover 517 of the applicator 800 and the RF electrode 101. The heating provided by the RF electrode positioned above the magnetic field generating device may be provided also to the magnetic field generating device itself.

Figure 10H:
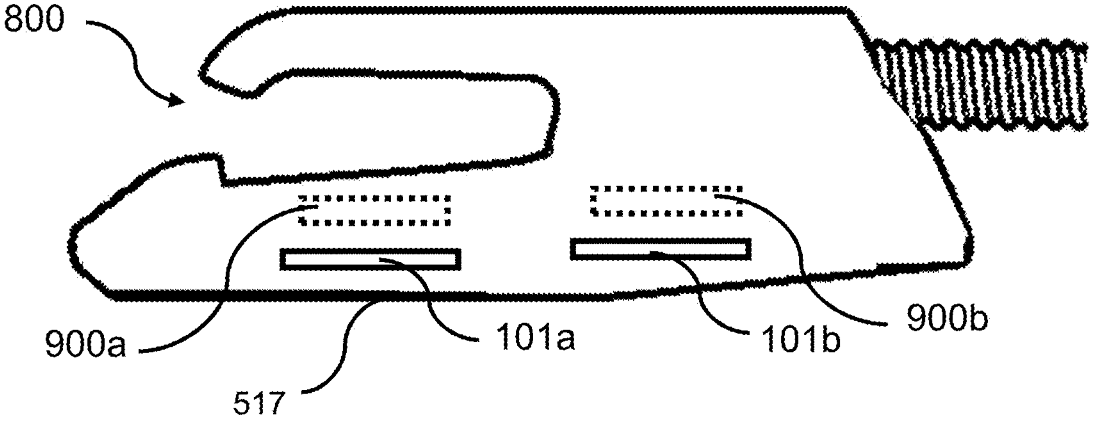

FIG. 10*h* illustrates another exemplary applicator 800 having two magnetic field generating devices 900*a* and 900*b* in one applicator, and specifically having a first RF electrode 101*a*, a first magnetic field generating device 900*a*, a second RF electrode 101*b*, and a second magnetic field generating device 900*b*. The first RF electrode 101*a* may be positioned between the patient's body and first magnetic field generating device 900*a*, while the second RF electrode 101*b* may be positioned between the patient's body and the second magnetic field generating device 900*b*. Also, the first RF electrode 101*a* may be positioned between the bottom cover 517 and the first magnetic field generating device 900*a*, and the second RF electrode 101*b* may be positioned between the bottom cover 517 and the second magnetic field generating device 900*b*.

The magnetic field generating device and the one or more RF electrodes may be positioned differently in relation to the tissue of the patient's body and/or body area. Also, the magnetic field generating device and the one or more RF electrodes may be positioned differently in relation to the bottom cover of the applicator. As mentioned, the RF electrode may be a monopolar RF electrode, a bipolar RF electrode, or a multipolar RF electrode.

The RF electrode may be coated by a coating material that is configured to prevent spark discharge or plasma discharge in order to avoid pain sensation to the patient. The coating material may include an electrically insulating material. The coating material may include a metal oxide (e.g. aluminium oxide) and/or a plastic material (e.g., epoxy material). The coating may be positioned on the side of the RF electrode that is arranged closer to the patient when the device is in use.

Figure 10I:
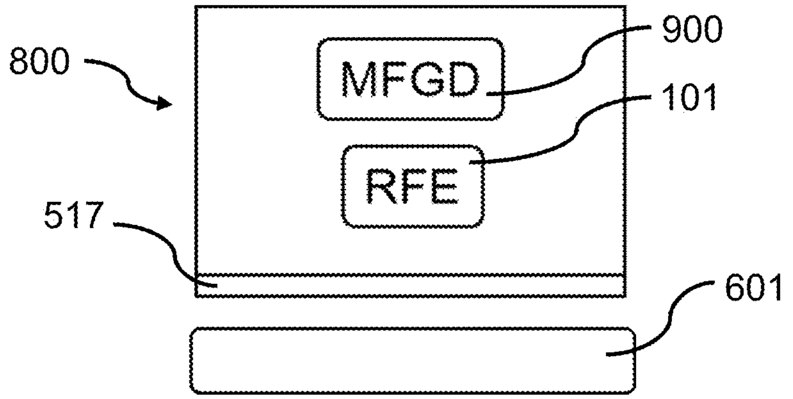

FIG. 10*i* illustrates a cross sectional view of an exemplary applicator 800 that includes a magnetic field generating device (MFGD) 900 and an RF electrode (RFE) 101, wherein the RF electrode 101 is positioned in overlay and/or between the magnetic field generating device 900 and the tissue 601 of the patient. The RF electrode 101 is positioned between the magnetic field generating device 900 and the bottom cover 517 of the applicator 800.

Figure 10J:
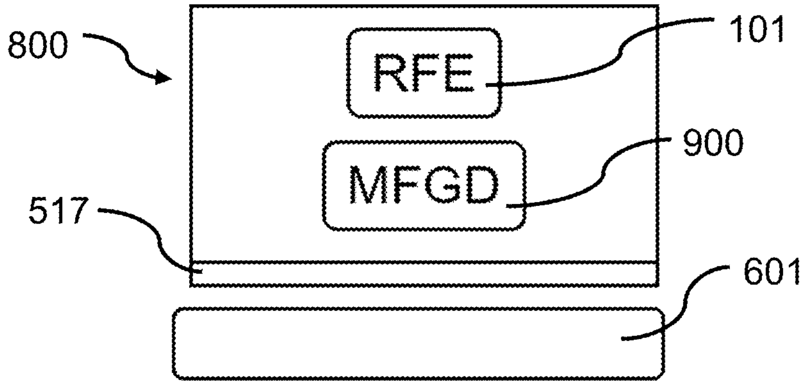

FIG. 10*j* illustrates a cross sectional view of another exemplary applicator 800 that includes a magnetic field generating device 900 and an RF electrode 101, wherein the magnetic field generating device 900 is positioned in overlay and/or between the RF electrode 101 and the tissue 601 of the patient. The magnetic field generating device 900 is positioned between the RF electrode 101 and the bottom cover 517 of the applicator 800.

Figure 10K:
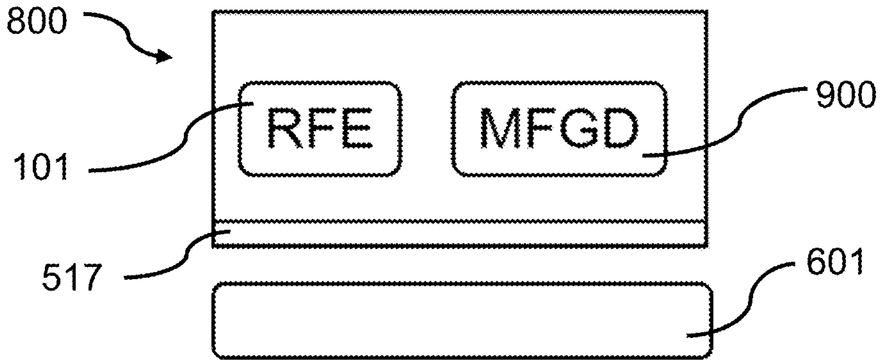

FIG. 10*k* illustrates a cross sectional view of another exemplary applicator 800 that includes a magnetic field generating device 900 and an RF electrode 101, wherein the RF electrode 101 is positioned next to the magnetic field generating device 900. The magnetic field generating device 900 may be beside the RF electrode 101. The RF electrode 101 may be arranged in the same plane as the magnetic field generating device 900. An upper edge of the RF electrode 101 may be positioned in the same horizontal plane as an upper edge of the magnetic field generating device 900. The RF electrode 101 may be separated from the magnetic field generating device 900 by air, oil and/or plastic material.

Figure 10L:
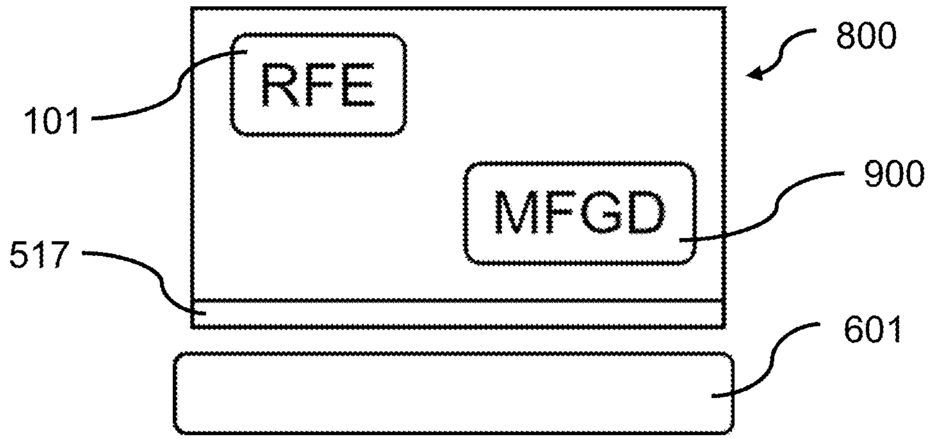

FIG. 10*l* illustrates a cross sectional view of another exemplary applicator 800 that includes a magnetic field generating device 900 and an RF electrode 101, wherein the RF electrode 101 is not positioned in overlay with the magnetic field generating device 900. An upper edge of the RF electrode 101 may be positioned in a different horizontal plane than an upper edge of the magnetic field generating device 900. The upper edge of the RF electrode 101 may be positioned in a horizontal plane that is a greater distance from the bottom cover 517 than a horizontal plane along which the upper edge of the magnetic field generating device 900 is positioned.

Figure 10M:
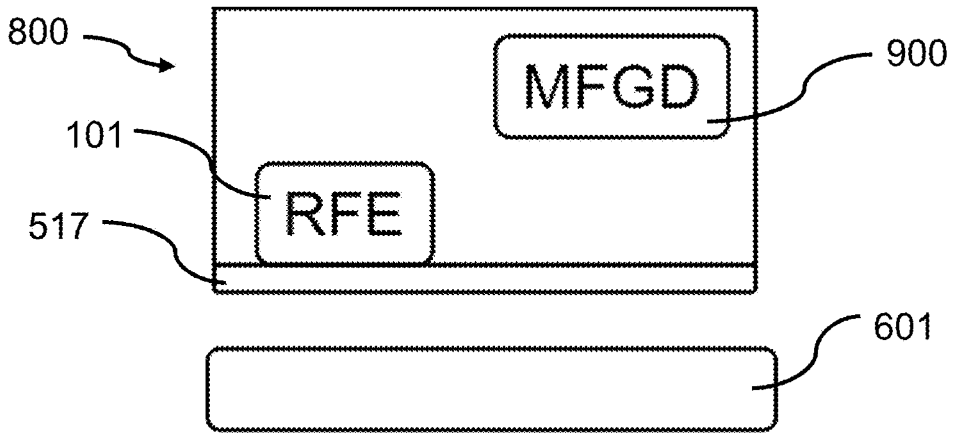
Figure 10N:
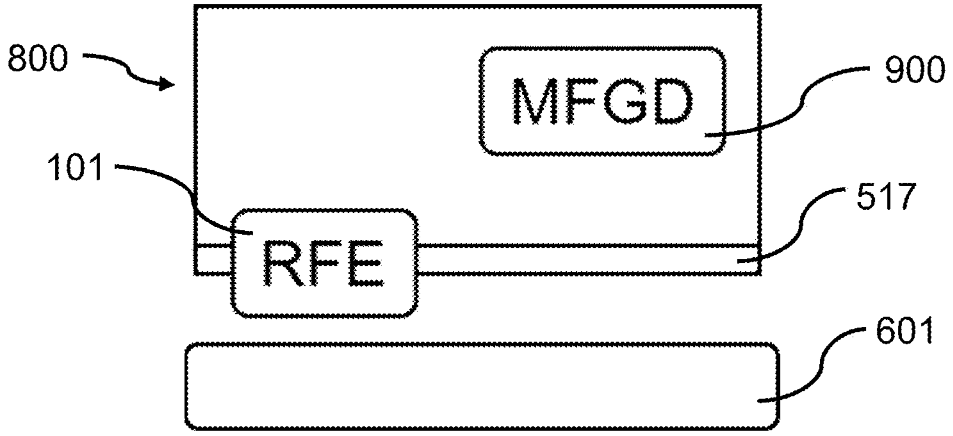
Figure 10O:
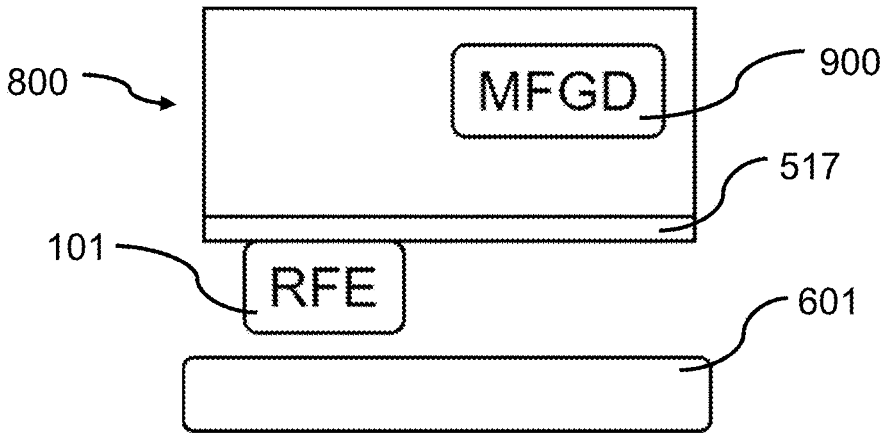
Figure 10P:
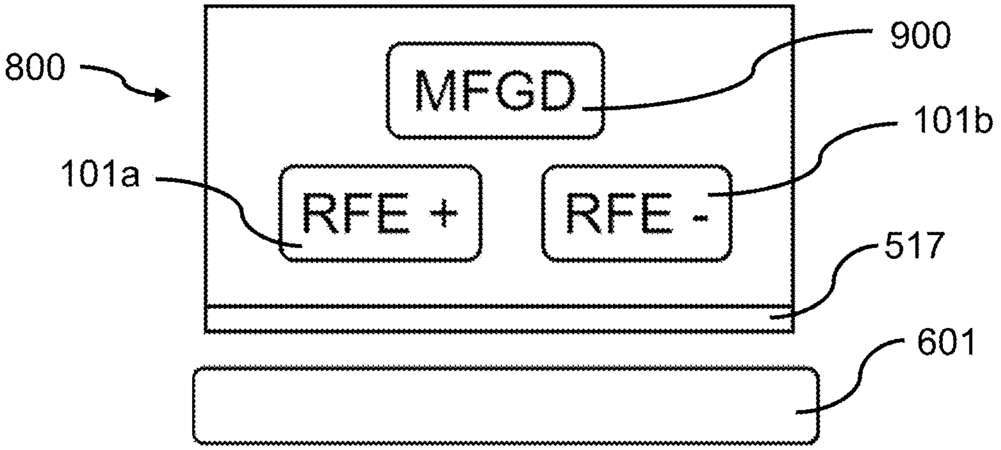
Figure 10Q:
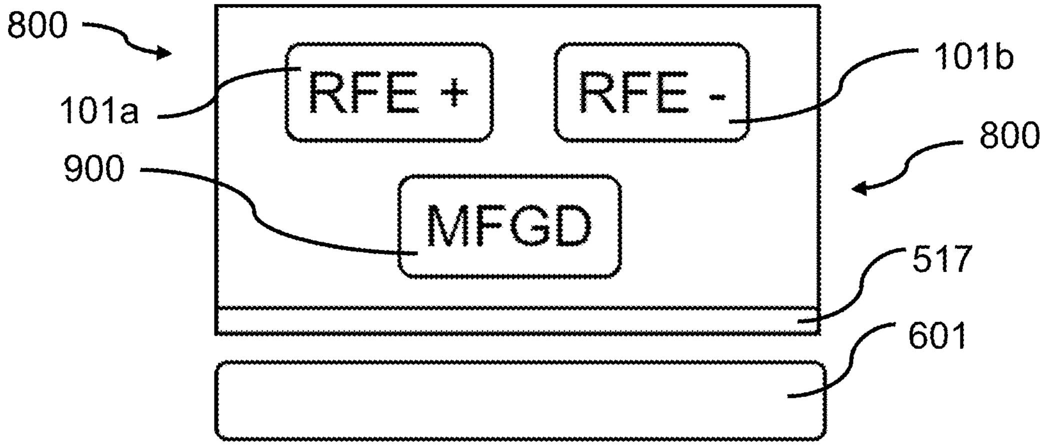
Figure 10R:
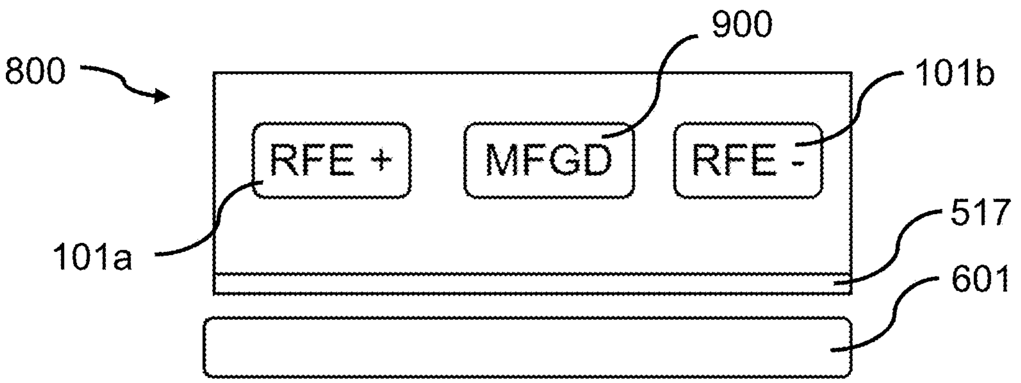
Figure 10S:
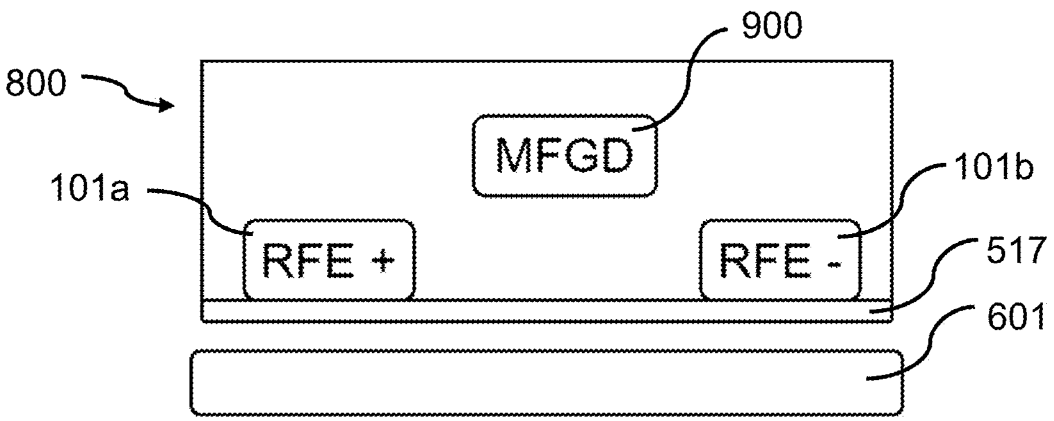
Figure 10T:
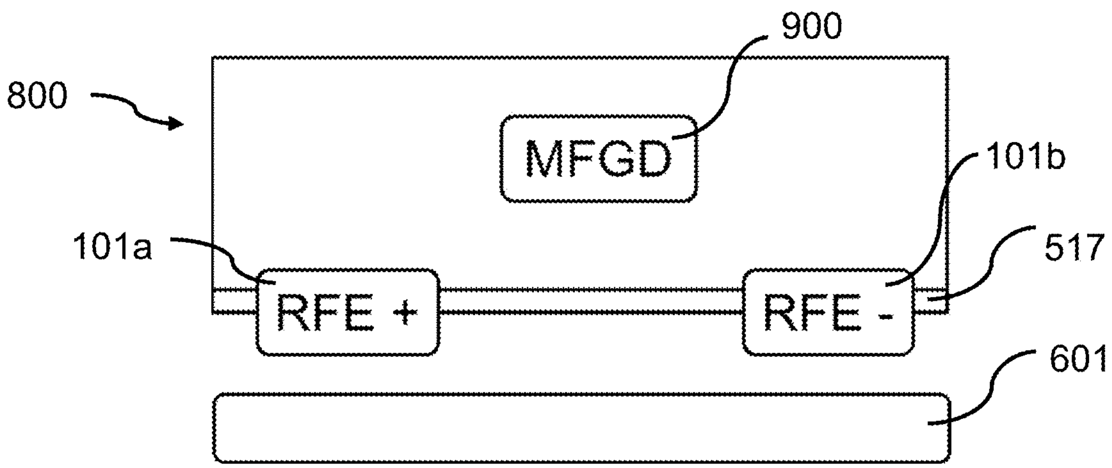
Figure 10U:
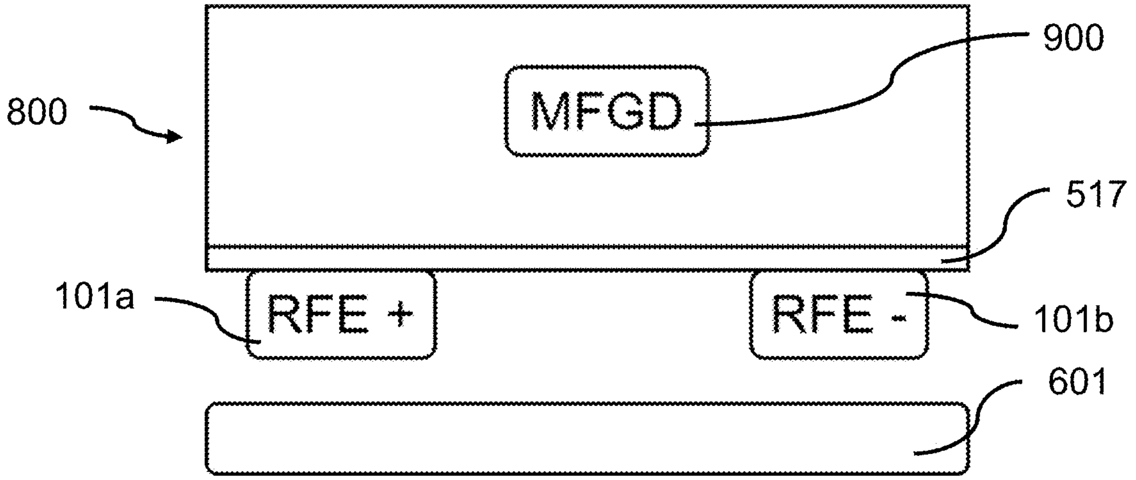

FIG. 10*m* illustrates a cross sectional view of another exemplary applicator 800 that includes a magnetic field generating device 900 and an RF electrode 101, wherein the RF electrode 101 is not positioned in overlay with the magnetic field generating device 900. An upper edge of the RF electrode 101 may be positioned in a different horizontal plane than an upper edge of the magnetic field generating device 900. The upper edge of the RF electrode 101 may be positioned in a horizontal plane that is a shorter distance from the bottom cover 517 than a horizontal plane along which the upper edge of the magnetic field generating device 900 is positioned. The RF electrode 101 and/or its coating may be in contact with the bottom cover 517 of the applicator 800. Further, the magnetic field generating device 900 may be in contact with the bottom cover 517. For example, the RF electrode 101 and/or magnetic field generating device 900 may be glued or fastened to the bottom cover 517.

FIG. **10*n* illustrates a cross sectional view of another exemplary applicator 800 that includes a magnetic field generating device 900 and an RF electrode 101, wherein the RF electrode 101 protrudes through the bottom cover 517. In this way, the RF electrode 101 and/or its coating may be in contact with the patient, while the one or more wirings powering the RF electrode 101 may be positioned in the applicator 800. The RF electrode may be thin enough, so that the bottom cover 517 and the RF electrode may be in contact with the tissue 601. The RF electrode 101 may be detachable from the applicator 800 and may be replaceable. Further, the magnetic field generating device 900 may be in contact with the bottom cover 517. For example, the RF electrode 101 and/or magnetic field generating device 900 may be glued or fastened to the bottom cover 517**.

FIG. **10*o* illustrates a cross sectional view of another exemplary applicator 800 that includes a magnetic field generating device 900 and an RF electrode 101, wherein the RF electrode 101 is positioned below and/or attached to the bottom cover 517 of the applicator 800. The RF electrode 101 may be in contact with the patient. The one or more wirings powering the RF electrode 101 may lead through e.g. a hole in the bottom cover 517. The RF electrode may be thin enough, so that the bottom cover 517 and the RF electrode may be in contact with the tissue 601. The RF electrode 101 may be detachable from the applicator 800 and/or may be replaceable. Further, the magnetic field generating device 900 may be in contact with the bottom cover 517. For example, the RF electrode 101 and/or magnetic field generating device 900 may be glued or fastened to the bottom cover 517**.

FIG. **10*p* illustrates a cross sectional view of another exemplary applicator 800 that includes the magnetic field generating device 900 and a pair of bipolar RF electrodes 101*a*, 101*b*. The pair of bipolar RF electrodes 101*a*, 101*b* may include first RF electrode 101*a* and second RF electrode 101*b*, wherein the pair of bipolar RF electrodes 101*a*, 101*b* is positioned in overlay and/or between the magnetic field generating device 900 and the tissue 601 of the patient. Further, the pair of bipolar RF electrodes 101*a*, 101*b* is positioned between the magnetic field generating device 900 and the bottom cover 517 of the applicator 800**.

FIG. **10*q* illustrates a cross sectional view of another exemplary applicator 800 that includes a magnetic field generating device 900 and a pair of bipolar RF electrodes 101*a*, 101*b* including a first RF electrode 101*a* and a second RF electrode 101*b*. The magnetic field generating device 900 is positioned in overlay and/or between the pair of bipolar RF electrodes 101*a*, 101*b* and the tissue 601 of the patient. Further, the magnetic field generating device 900 is positioned between the pair of bipolar RF electrodes 101*a*, 101*b* and the bottom cover 517**.

FIG. **10*r* illustrates a cross sectional view of another exemplary applicator 800 that includes the magnetic field generating device 900 and a pair of bipolar RF electrodes 101*a*, 101*b* including first RF electrode 101*a* and second RF electrode 101*b*. The pair of bipolar RF electrodes 101*a*, 101*b* is positioned next to the magnetic field generating device 900. An upper edge of one or both of the RF electrodes 101*a*, 101*b* may be positioned in the same horizontal plane as an upper edge of the magnetic field generating device 900**.

FIG. **10*s* illustrates a cross sectional view of another exemplary applicator 800 that includes the magnetic field generating device 900 and a pair of bipolar RF electrodes 101*a*, 101*b* including first RF electrode 101*a* and a second RF electrode 101*b*. The pair of bipolar RF electrodes 101*a*, 101*b* is not positioned in overlay with the magnetic field generating device 900. An upper edge of the pair of bipolar RF electrodes 101*a*, 101*b* may be positioned in a different horizontal plane than an upper edge of the magnetic field generating device 900. The upper edge of the pair of bipolar RF electrodes 101*a*, 101*b* may be positioned in a horizontal plane that is a shorter distance from the bottom cover 517 than a horizontal plane in which the upper edge of the magnetic field generating device 900 is positioned. The pair of bipolar RF electrodes 101*a*, 101*b* and/or the electrode coatings may be in contact with the bottom cover 517 of the applicator 800. Further, the magnetic field generating device 900 may be in contact with the bottom cover 517. For example, the RF electrodes and/or magnetic field generating device 900 may be glued or fastened to the bottom cover 517**.

FIG. **10*t* illustrates a cross sectional view of another exemplary applicator 800 that includes a magnetic field generating device 900 and a pair of bipolar RF electrodes 101*a*, 101*b* including first RF electrode 101*a* and second RF electrode 101*b*. The pair of bipolar RF electrodes 101*a*, 101*b* protrudes through the bottom cover 517 of the applicator 800. The pair of bipolar RF electrodes 101*a*, 101*b* and/or their coatings may be in contact with the tissue 601 of the patient. The RF electrodes may be thin enough, so that the bottom cover 517 and the RF electrodes may be in contact with the tissue 601. The RF electrode 101 may be detachable from the applicator 800 and may be replaceable. Further, the magnetic field generating device 900 may be in contact with the bottom cover 517. For example, the RF electrodes and/or magnetic field generating device 900 may be glued or fastened to the bottom cover 517**.

FIG. **10*u* illustrates a cross sectional view of another exemplary applicator 800 that includes a magnetic field generating device 900 and a pair of bipolar RF electrodes 101*a*, 101*b* including first RF electrode 101*a* and second RF electrode 101*b*. The pair of bipolar RF electrodes 101*a*, 101*b* is positioned below and/or attached to the bottom cover 517 of the applicator 800. The pair of bipolar RF electrodes 101*a*, 101*b* may be in contact with the tissue 601 of the patient. The RF electrodes may be thin enough, so that the bottom cover 517 and the RF electrodes may be in contact with the tissue 601. The pair of bipolar RF electrodes 101*a*, 101*b* may be detachable from the applicator 800 and may be replaceable. Further, the magnetic field generating device 900 may be in contact with the bottom cover 517. For example, the RF electrodes and/or magnetic field generating device 900 may be glued or fastened to the bottom cover 517**.

As described herein, the one or more RF electrodes may be positioned between the magnetic field generating device and the patient. Also, the one or more RF electrodes may be positioned between the magnetic field generating device and the bottom cover of the applicator. Such an arrangement of the RF electrode relative to the magnetic field generating device and/or bottom cover may be beneficial for transfer of radiofrequency field to the patient. When one or more RF electrodes are positioned between the magnetic field generating device and the bottom cover of the applicator such that the one or more RF electrodes are arranged closer to the patient, the provided radiofrequency waves are not absorbed by the magnetic field generating device to as great of an extent as it would be if the RF electrodes were positioned above the magnetic field generating device. Also, by positioning the one or more RF electrodes between the magnetic field generating device and the patient and separated from the magnetic field generating device, the radiofrequency field is not absorbed by the magnetic field generating device and may be provided to the patient. The one or more RF electrodes and the magnetic field generating device may be separated by air, plastic, or dielectric material.

However, the one or more RF electrodes may be in contact with the magnetic field generating device.

One or more RF electrodes positioned on the one applicator and/or more the applicators 800 may be placed in contact with the patient. Also, one or more RF electrodes and/or applicators may be separated from the patient by an air gap, bolus, dielectric material, insulating material, gel, and/or other material.

One or more RF electrodes 101, 102 and/or magnetic field generating devices 900 within one applicator may be spaced from each other by an air gap, by material of a printed circuit board, insulator, cooling fluid, and/or other material. The distance between a conductive part of the magnetic field generating device and the nearest RF electrode may be in a range of 0.1 mm to 100 mm or 0.5 mm to 50 mm or 1 mm to 50 mm or 2 mm to 30 mm or 0.5 mm to 15 mm or 0.5 mm to 5 mm. Spacing between the magnetic field generating device and the RF electrode may be also provided in the form of an insulating barrier that separate a RF circuit from a magnetic circuit and prevents affecting one treatment circuit or treatment energy source by other treatment circuit or other treatment energy source. The magnetic field generating device positioned closer to patient's body may be able to stimulate and provide the treatment effect to at least part of at least one target biological structure more effectively and deeply than the magnetic field generating device that is in a larger distance from the patient's body.

The magnetic field generating device and/or one or more RF electrodes included in or on the applicator may be cooled during the treatment. Cooling of the magnetic field generating device and/or one or more RF electrodes may be provided by an element based on the Peltier effect and/or by flowing of a cooling fluid, such as air, water, oil and/or a fluid within the applicator or in proximity of the applicator. The cooling fluid may be flowed or guided around one or more magnetic field generating devices, one or more RF electrodes, between the magnetic field generating device and at least part of at least one RF electrode. Cooling fluid may flow only on the top and/or bottom of the magnetic field generating device. Cooling fluid may be a fluid, such as gas, oil, water and/or liquid. The cooling fluid may be delivered to the applicator from the main unit where the cooling fluid may be tempered. The cooling fluid may be delivered to applicator and to the proximity of magnetic field generating device and/or RF electrode. The cooling fluid may be delivered to the applicator by connecting tube coupled to the main unit. The connecting tube may include the fluid conduit, which may serve as path for the cooling fluid between applicator and the main unit.

The main unit may include one or more cooling tanks where the cooling fluid may be stored and/or cooled. Each cooling tank may include one or more pumps, wherein one pump may provide flow of the cooling fluid to one applicator. Alternatively, one pump may provide flow of the cooling fluid to plurality of applicators (e.g. two applicators). Further, the main unit may include one cooling tank storing and/or cooling the cooling fluid for one respective applicator or plurality of applicators. For example, when the treatment device includes two applicators, the main unit may include one cooling tank providing the cooling fluid for both applicators. In another example, when the treatment device includes two applicators, the main unit may include two cooling tanks providing cooling of the cooling fluid. Each cooling tank may provide cooling of the cooling fluid to one particular applicator either synchronously or independently. Cooling tank or fluid conduit may include a temperature sensor for measuring temperature of cooling fluid.

The fluid conduit may be a plastic tube. The plastic tube may lead from cooling tank to the applicator and then back to cooling tank. When the treatment device includes e.g. two applicators, the fluid conduit may lead from the cooling tank to one applicator and then back to cooling tank while the second fluid conduit may lead from the same or different cooling tank to second applicator and then back to the cooling tank. However, fluid conduit may lead from cooling tank to first applicator, then lead to second applicator and finally to cooling tank.

When the RF electrode is positioned in the proximity of magnetic field generating device, the time-varying magnetic field generated by the magnetic field generating device may induce unwanted physical effects in the RF electrode. Unwanted physical effects induced by time-varying magnetic field may include e.g. induction of eddy currents, overheating of RF electrode, skin effect, and/or causing other electric and/or electromagnetic effects like a phase shift in the RF electrode. Such unwanted physical effects may lead to treatment device malfunction, energy loss, decreased treatment effect, increased energy consumption, overheating of at least applicator's part, e.g., RF electrode, collecting false feedback information, malfunctioning of signal adjustment provided to the RF electrode and/or other unwanted effects. Also, the unwanted physical effects may be related to the treatment itself, e.g. to effectiveness of the treatment. The RF electrode may block or limit transmissivity of the magnetic field through the RF electrode. When the magnetic field generated by the magnetic field generating device is prevented from transmitting through the RF electrode, the effect of magnetic field (e.g. muscle contraction) may not be achieved.

The disclosure provides methods or designs how to prevent and/or minimize one or more unwanted physical effects induced in the RF electrode by the magnetic field. The methods or designs described in the application may prevent the unwanted effects related to the transmissivity of the magnetic field through the RF electrode. The same methods or designs may help to minimize shielding of the magnetic field by the RF electrode. The RF electrode may be arranged in minimal or no overlay with the magnetic field generating device according to the floor projection of the applicator. Also, the RF electrode may be specially designed as described below. Further, the RF electrode may have a reduced thickness. The RF electrode may be manufactured from a conductive material that reduces induction of unwanted physical effects and heating of the RF electrode. Other possibilities are described below. One or more RF electrodes providing RF energy during the treatment by a treatment device as described herein may use at least one of these possibilities, at least two possibilities, and/or a combination of all possibilities.

The RF electrode may be arranged in minimal or no overlay with the magnetic field generating device according to the floor projection of the applicator.

FIG. 11 illustrates an example in which the RF electrode 101*a* may be located under, next to, and/or above the magnetic field generating device 900 and have no or minimal overlay with the magnetic field generating device 900 according to the applicator's floor projection. As shown on FIG. 11 the electrode 101*a* may be located outside of area A2.

Figure 11A:
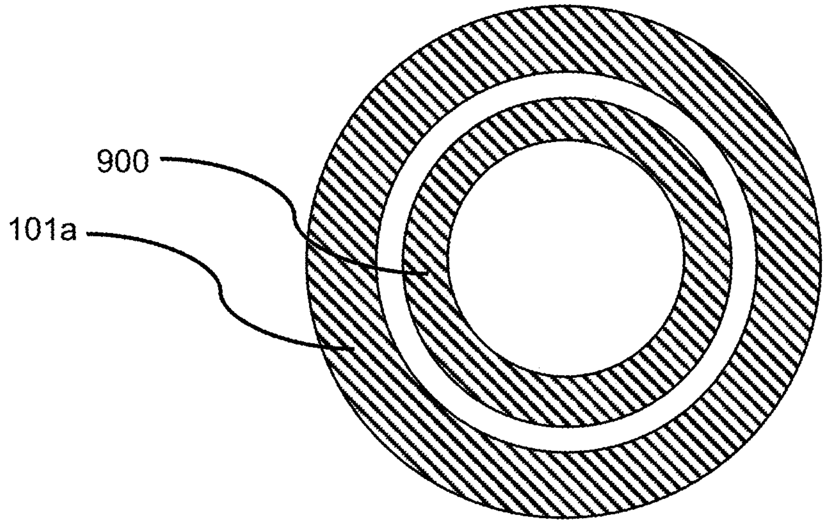
FIGS. 11*a*-11*i* illustrate cross sectional views of a location of an exemplary RF electrode located with regard to an exemplary magnetic field generating device.
Figure 11B:
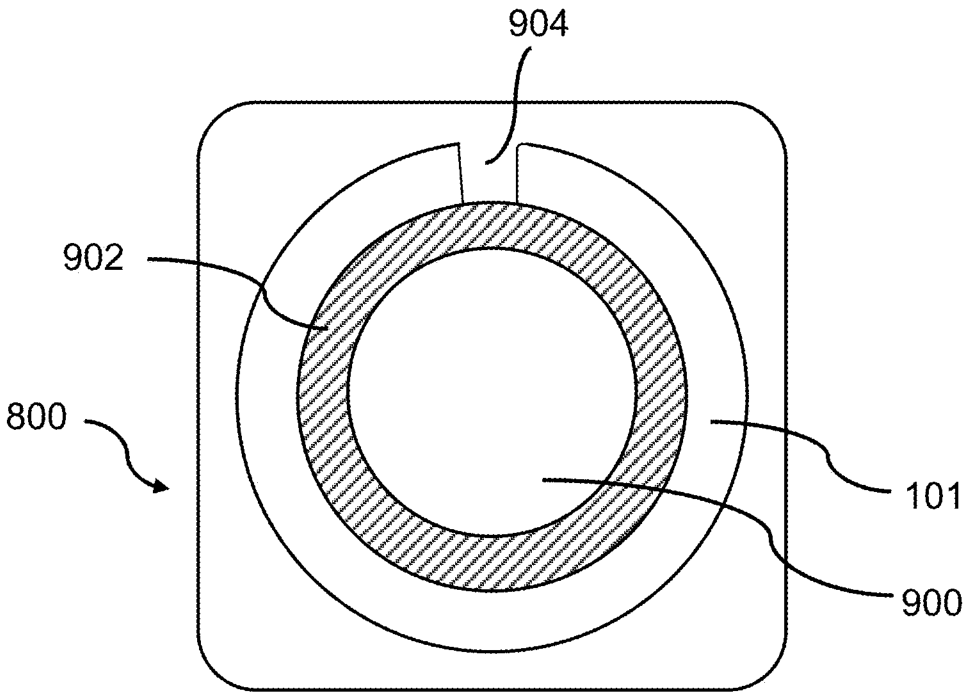

FIG. 11*b* illustrates an example of a transverse cross sectional view of the applicator 800, wherein the RF electrode 101 is located next to the magnetic field generating device 900. The RF electrode 101 may be in the same horizontal plane as the magnetic field generating device and without any overlay. The RF electrode 101 may surround the magnetic field generating device 900. The RF electrode 101 and the magnetic field generating device 900 may be separated from each other by a space 902 that may be filled by air and/or insulating material (e.g. plastic material). The distance between the RF electrode 101 and the magnetic field generating device 900 may be in a range of 0.1 mm to 10 cm, to ensure the transfer of the radiofrequency waves. In the example shown in FIG. 11*b*, the RF electrode 101 may have a form of an open ring. Thus, the RF electrode 101 may have the form of a ring having a gap 904. In this example, the RF electrode 101 may be a monopolar or unipolar RF electrode.

Figure 11C:
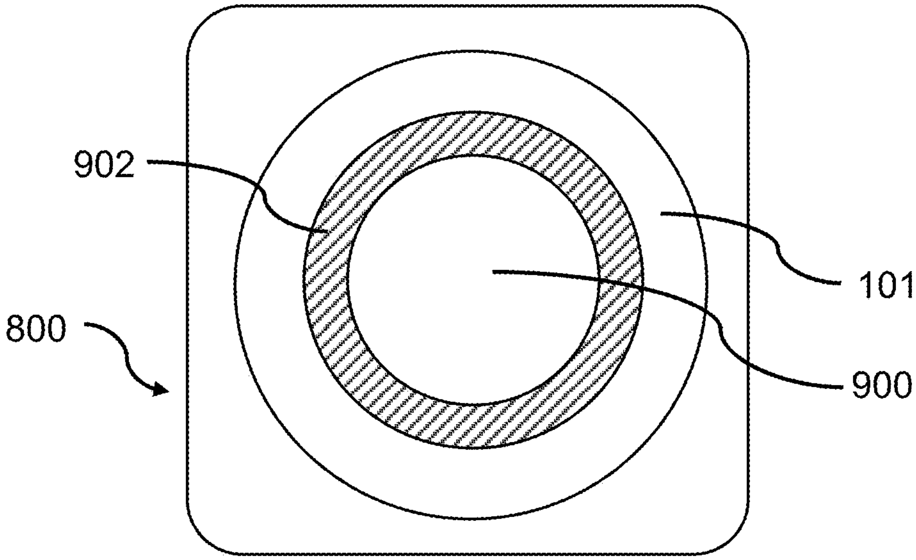

FIG. 11*c* illustrates another example of a transverse cross sectional view of an applicator 800, wherein the RF electrode 101 is located next to the magnetic field generating device 900. The RF electrode 101 may surround the magnetic field generating device 900. The RF electrode 101 may be in the same horizontal plane as the magnetic field generating device 900 and without any overlay. The RF electrode 101 and the magnetic field generating device 900 may be separated from one another by a space 902 that may be filled by air and/or an insulating material (e.g. plastic material). In the example shown in FIG. 11*c*, the RF electrode 101 may have the form of a closed ring around the magnetic field generating device 900. In this example, the RF electrode 101 may be a monopolar or unipolar RF electrode.

Figure 11D:
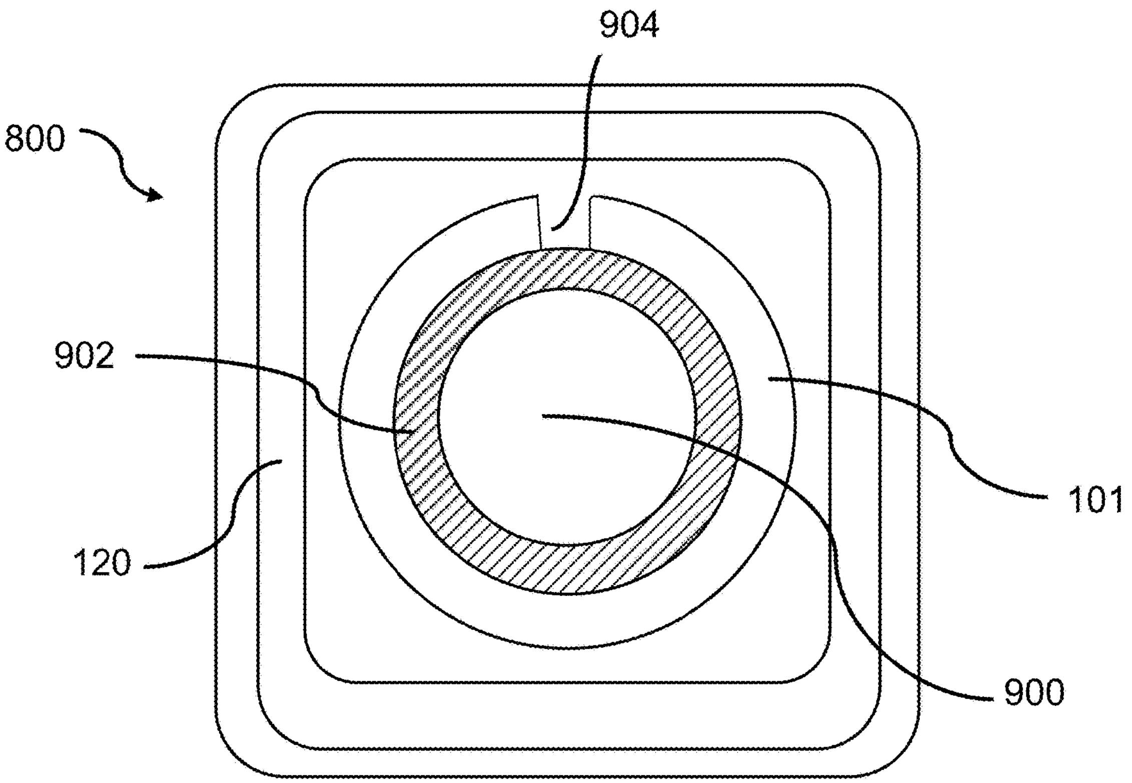

FIG. 11*d* illustrates another example of a transverse cross sectional view of the applicator 800, wherein the applicator 800 includes the active RF electrode 101, a grounding plate 120, and the magnetic field generating device 900. The grounding plate 120 is separated by air and/or an insulating material (e.g. plastic material) from the active RF electrode 101. The active RF electrode 101 may be a monopolar RF electrode.

Figure 11E:
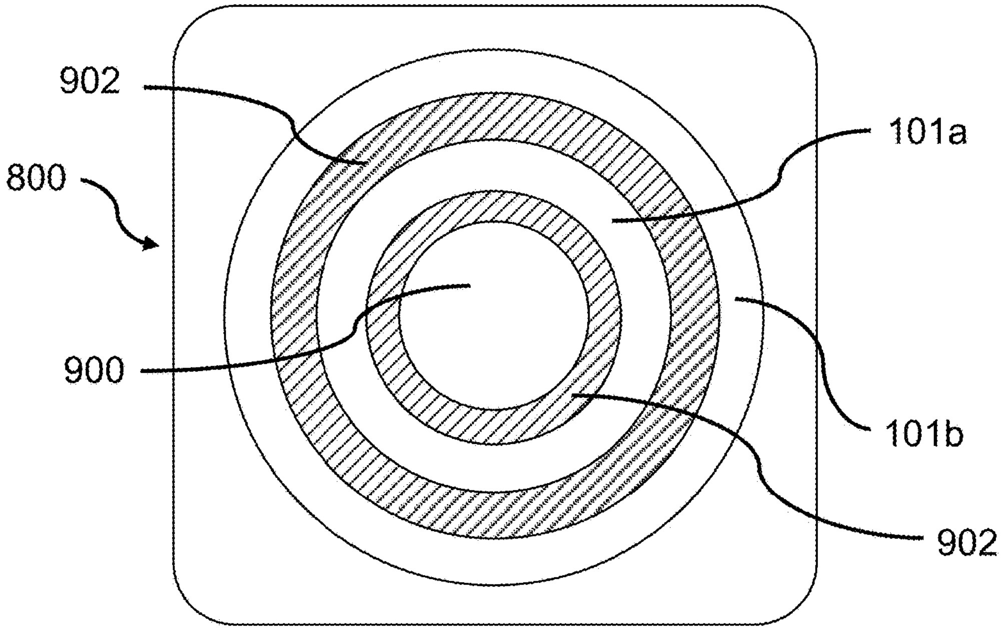

FIG. 11*e* illustrates another example of a transverse cross sectional view of the applicator 800, wherein the applicator 800 includes a plurality of RF electrodes 101*a*, 101*b* and a magnetic field generating device 900. The RF electrodes 101*a*, 101*b* may be bipolar RF electrodes surrounding the magnetic field generating device 900. The RF electrodes 101*a*, 101*b* may be in the form of two closed rings, two open rings, or one ring may be open and the other may be closed. The RF electrodes 101*a*, 101*b* may be spaced from one another and from the magnetic field generating device 900 by spaces 902 that may be filled by air and/or an insulating material (e.g. plastic material).

Figure 11F:
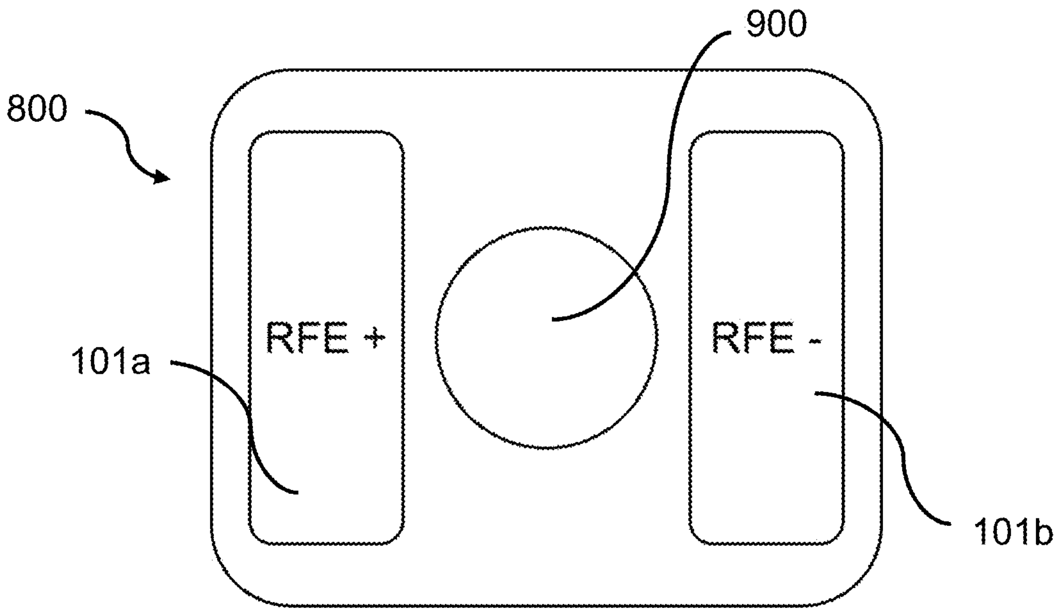

FIG. 11*f* illustrates another example of a transverse cross sectional view of the applicator 800, wherein the applicator 800 includes a plurality of RF electrodes 101*a*, 101*b* and a magnetic field generating device 900. A first RF electrode 101*a* may be a positive RF electrode, while a second RF electrode 101*b* may be a negative RF electrode. The mutual polarity of RF electrodes changes with the frequency of the RF signal. The RF electrodes 101*a*, 101*b* may not be in overlay with the magnetic field generating device 900. Two RF electrodes 101*a*, 101*b* are located next to the magnetic field generating device 900. Two RF electrodes 101*a*, 101*b* and the magnetic field generating device 900 may be separated from each other by air and/or an insulating material (e.g. plastic material). The plurality of RF electrodes 101*a*, 101*b* may be controlled by the control system to deliver the radiofrequency waves.

Figure 11G:
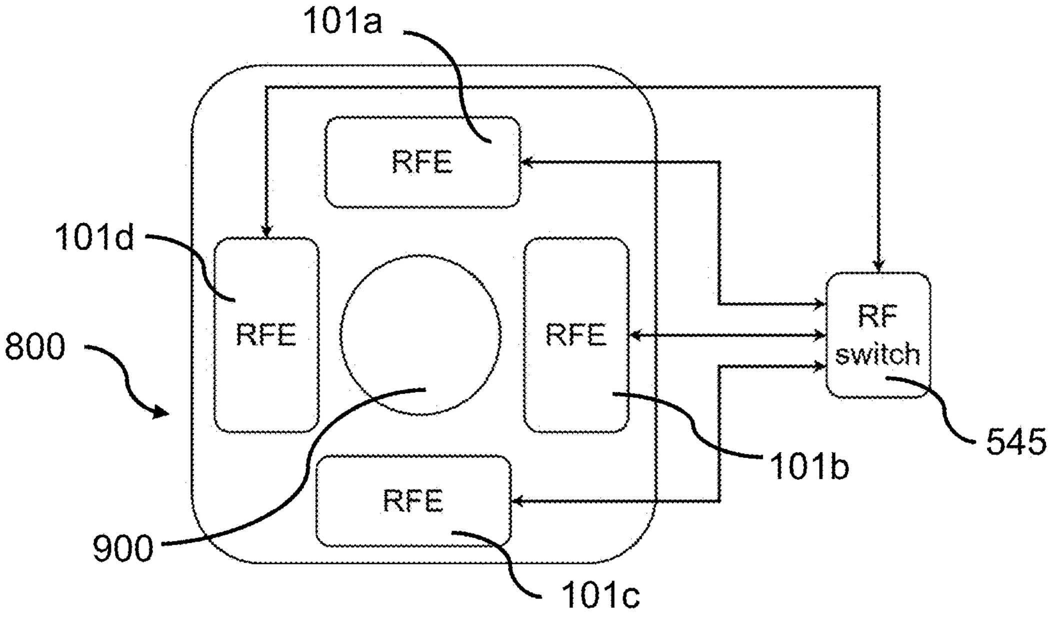

FIG. 11*g* illustrates another example of a transverse cross sectional view of the applicator 800, wherein the applicator 800 includes a plurality of RF electrodes 101*a*, 101*b*, 101*c*, 101*d* and a magnetic field generating device 900. The RF electrodes 101*a*-101*d* may be arranged in the same horizontal plane as the magnetic field generating device 900 and without any overlay. As shown in exemplary FIG. 11*g*, one or more of the plurality of RF electrodes 101*a*-101*d* are located next to the magnetic field generating device 900. The plurality of RF electrodes 101*a*-101*d* and the magnetic field generating device 900 may be separated from each other by air and/or an insulating material (e.g. plastic material). Each of the plurality of RF electrodes 101*a*-101*d* may be a monopolar RF electrode or a unipolar RF electrode. However, RF electrodes 101*a*-101*d* may operate in a multipolar manner. Further, the activation of the RF electrodes may be provided by one or more RF switches 545 providing power to one or more RF electrodes. The RF switch or switches may be positioned in the applicator 800 and/or in the main unit.

Figure 11H:
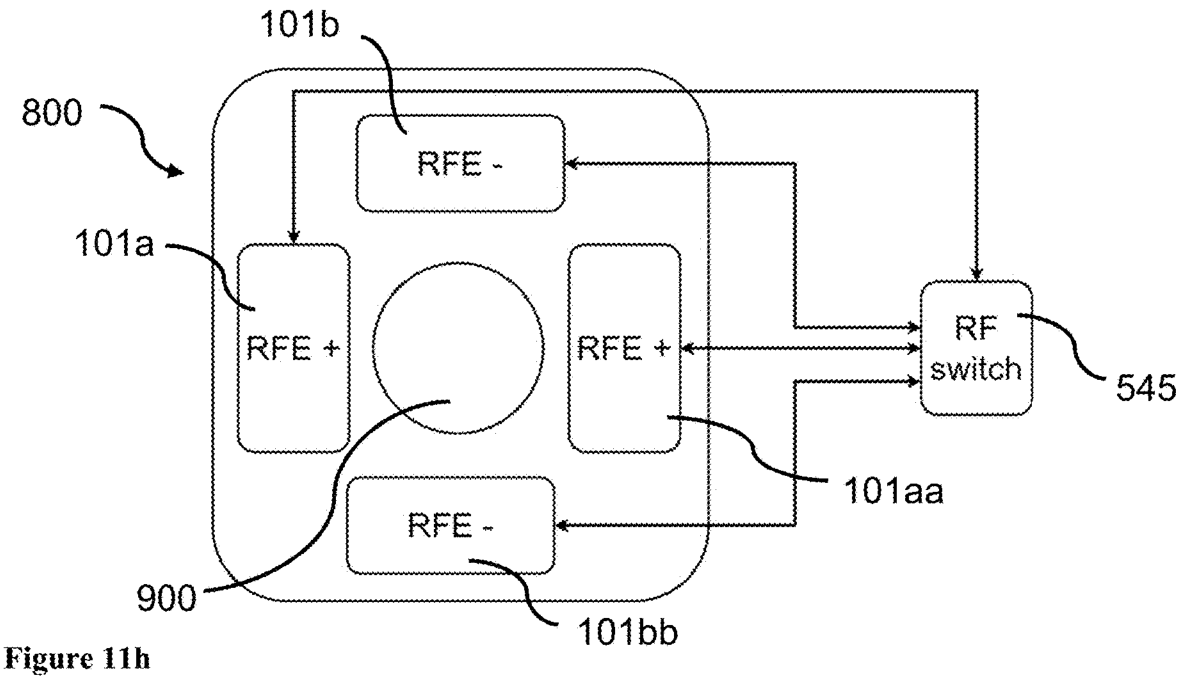

FIG. 11*h* illustrates another example of a transverse cross sectional view of the applicator 800, wherein the applicator 800 includes a plurality of RF electrodes 101*a*, 101*b*, 101*aa*, 101*bb* and a magnetic field generating device 900. The RF electrodes 101*a* and 101*aa* may be positive RF electrodes, while the RF electrodes 101*b* and 101*bb* may be negative RF electrodes. The mutual polarity of the RF electrodes changes with the frequency of the RF signal. Therefore, two bipolar RF electrode pairs are present in the example of FIG. 11*h*. The activation of the RF electrodes may be controlled by a control system, so the transfer of the RF waves may be influenced by this control. For example, a first pair of RF electrodes 101*a*, 101*b* may be active, while a second pair of RF electrodes 101*aa*, 101*bb* may be inactive. In another example, the two pairs of RF electrodes may be activated in a predetermined order, wherein when the first pair of RF electrodes 101*a*, 101*b* is active, the second pair of RF electrodes 101*aa*, 101*bb* is inactivated, and when the first pair is inactive, the second pair becomes active. Further, the activation of the RF electrodes may be provided by one or more RF switches 545 providing power to the one or more RF electrodes. The RF switch 545 may be positioned in the applicator 800 and/or in the main unit. Also, the signal leading to the RF electrodes may be split or divided by a splitter.

Figure 11I:
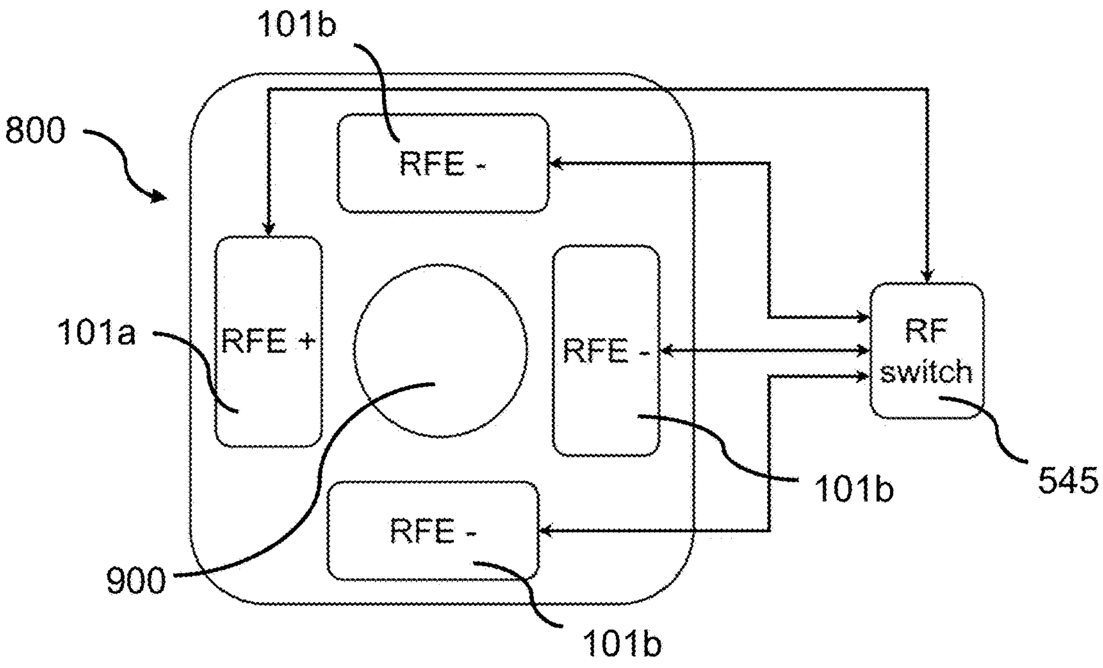

FIG. 11*i* illustrates another example of a transverse cross sectional view of the applicator 800, wherein the applicator 800 includes a plurality of RF electrodes 101*a*, 101*b* and a magnetic field generating device 900. A first RF electrode 101*a* may be a positive RF electrode, while the remaining three RF electrodes 101*b* may be negative RF electrodes.

The mutual polarity of RF electrodes changes with the frequency of the RF signal. The RF waves may be transferred between the positive RF electrode 101*a* and one or more of the negative RF electrodes 101*b*. Also, since the mutual polarity of RF electrodes is changing, the RF waves may be transferred between the RF electrodes 101*b* and the RF electrode 101*a*. Further, the activation of the RF electrodes may be provided by one or more RF switches 545 providing power to one or more RF electrodes. The RF switch 545 may be positioned in the applicator 800 and/or in the main unit.

Regarding FIGS. 11*g*, 11*h* and 11*i*, the plurality of RF electrodes may be controlled by the control system to deliver the radiofrequency waves. The control system may include the control unit, wherein the control unit may include a microprocessor. In one example, in FIG. 11*g*, the pair of RF electrodes 101*a* and 101*c* may be active, while the RF electrodes 101*b* and 101*d* may be inactive. In another example, the RF electrodes may be activated in a predetermined order, where the RF electrode 101*a* is active, then inactivated, and RF electrode 101*b* is activated. In another example related to FIG. 11*h*, the first pair of bipolar RF electrodes 101*a* and 101*b* may be active, while the second pair of bipolar RF electrodes 101*aa* and 101*bb* is not active. In still another example related to FIG. 11*i*, the one, two or three negative RF electrodes 101*b* may be active at the same time, so the RF waves may transfer between the positive RF electrode 101*a* and each of the negative RF electrodes 101*b*. In still another example, the activation of the RF electrodes may follow a clockwise or counter-clockwise direction. The at least two RF electrodes may be active simultaneously with the magnetic field generating device. The activation of the RF electrodes may be provided by one or more RF switches 545 positioned in the applicator and/or main unit. Also, the signal leading to the RF electrodes may be split or divided by a splitter.

The activation of one or more RF electrodes, as shown for example in FIGS. 11*g*, 11*h* and 11*i*, may be provided by one or more RF switches 545. The RF switch 545 may be located in the main unit and/or applicator. Each RF electrode may be connected to one RF switch 545 or more than one RF electrode may be connected to one RF switch 545, wherein the RF switch may be connected to one or more electrical elements of the RF circuit. The RF switch 545 may include an electrical element providing a switchable connection of the output of the RF signal (e.g. any electrical element connected to the power source of RF treatment and/or power amplifier) to the input of the RF signal (e.g. RF electrode). Also, activation or deactivation of one RF electrode may be controlled by more than one RF switch 545. The RF switch 545 may include a relay, electrically controlled switch, voltage controlled switch, current controlled switch, mechanical switch, diode, PIN diode, piezo switch, transistor, thyristor and/or vacuum tube, among others. The RF switch may be positioned in the circuit between the splitter and the one or more RF electrodes. The RF switch may have a drain-source capacitance in a range of 0.1 picofarad to 10 nanofarad, 0.1 picofarad to 1 nanofarad, or 1 picofarad to 990 picofarad.

Figure 12:
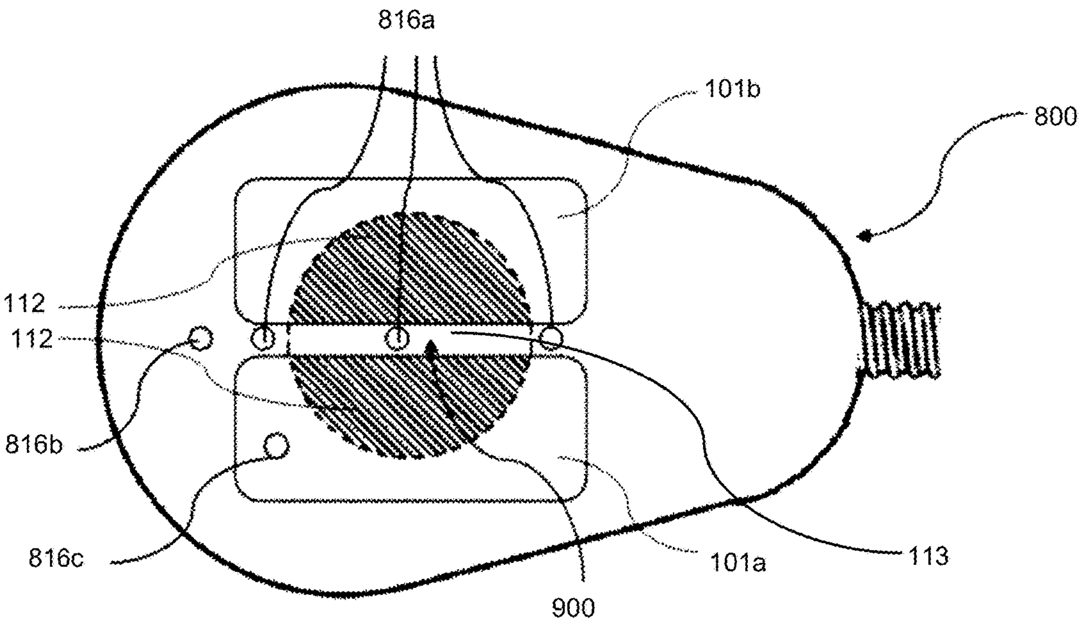
FIG. 12 illustrates a floor projection of an applicator including RF electrodes and a magnetic field generating device with partial overlay according to the applicator's floor projection.

FIG. 12 illustrates an exemplary applicator including a magnetic field generating device and one or more RF electrodes. The applicator may include at least one magnetic field generating device and at least one RF electrode. The applicator 800 may include two RF electrodes 101*a* and 101*b* spaced by a gap 113. Two RF electrodes 101*a* and/or 101*b* may be in at least partial overlay 112 with the winding area A2 and/or area A1 of the magnetic field generating device 900 according to the applicator's floor projection. The partial overlay 112 is represented by a hatched area in FIG. 12. When two elements overlay, the upper element is superimposed on the part of the lower element. When the magnetic field generating device and RF electrode are in overlay, the surface of the magnetic field generating device is superimposed above the surface area of the RF electrode. The floor projection may be represented by a picture of the applicator 800 taken from the bottom of the applicator by X-ray. Such partial overlay 112 may be in a range from 1% to 100%, or from 1% to 99%, or from 1% to 70%, or from 5% to 50%, or from 5% to 40%, or from 10% to 30%, or from 25% to 100%, or from 10% to 100%, or from 30% to 95%, or from 40% to 100%, or from 70% to 100%, or from 80% to 95% or from 30% to 70% of the area of one RF electrode area according to the floor projection of the applicator. Overlay of two areas may refer to a ratio between these two different areas.

One or more temperature sensors 816*a* may be located between bipolar RF electrodes 101*a*, 101*b* as illustrated in FIG. 12. When the applicator 800 includes two bipolar RF electrodes, the bipolar RF electrodes may be positioned between a bottom cover of the applicator 800 and the magnetic field generating device 900. One or more temperature sensors 816*a* may be at least partially encircled by at least one RF electrode 101*a* and 101*b* according to the applicator's floor projection as illustrated by temperature sensors 816*a* in FIG. 12. The highest amount of RF energy may flow between bipolar electrodes 101*a* and 101*b*. Therefore, a volume of the body area or the treated tissue between or directly below bipolar electrodes may have the highest temperature and should be measured as an actual temperature or temperature reference to predetermined temperature. However, the temperature sensor may be placed inside applicator or on the surface of the applicator.

A characteristic shape of the RF electrode may create inhomogeneous temperature distribution of the heat during the treatment. It may be useful to place the temperature sensor 816*b* such that it is not located between RF bipolar electrodes 101*a*, 101*b* in such way that the temperature sensor is not encircled by bipolar electrodes 101*a*, 101*b*. The temperature sensor may be placed inside applicator or on the surface of the applicator. Also, the temperature sensor 816*c* may be located under the RF electrode. However, in some aspects, the temperature sensor may be located in different locations of the applicator rather than under the RF electrode. The material of the first side portion 801 and/or the second side portion 802 covering at least part of the temperature sensor 816 (e.g. 816*a*, 816*b* or 816*c*) and contacting the patient's body may be manufactured from the same material as the first side portion 801 and/or the second side portion 802. However, the material of the first side portion 801 or second side portion 802 covering the temperature sensor 816 may be from a different material than the remainder of the first side portion 801 or second side portion 802, such as a material with a higher thermal conductivity, e.g. ceramic, titanium, aluminum, or other metallic material or alloy. The temperature sensor 816 may be a thermistor. Specifically, the temperature sensor 816 may be a negative temperature coefficient (NTC) thermistor. The temperature sensor 816 (e.g. 816*a*, 816*b* or 816*c*) may be fixed or coupled to the first side portion 801 and/or second side portion 802 by thermally conductive material, such as a thermal epoxy layer, with good thermal conductivity. The wire connection (see, e.g., wire connection 822 in FIG. 8*e*) between the temperature sensor 816 and the rest of the device may be heated by operation of the magnetic field generating device and/or RF electrode, which is undesirable. The design of the wire connection 822 may prevent influence of the operation of the magnetic field generating device and/or RF electrode on the readings provided by the temperature sensor, which is also undesirable. The wire connection 822 between the temperature sensor 816 and rest of the treatment device may be represented by one, two or more conductive wires with diameter in a range of 0.05 mm to 3 mm, or of 0.01 mm to 1 mm, or of 0.1 mm to 0.5 mm. The wire connection 822 including a conductive wire with described diameter may be advantageous because of minimizing of thermal transfer between the wire and the temperature sensor 816. The wire connection 822 to the temperature sensor 816 may have thermal conductivity in a range of 5 $W \cdot m^{-1} \cdot K^{-1}$ to 320 $W \cdot m^{-1} \cdot K^{-1}$, or 6 $W \cdot m^{-1} \cdot K^{-1}$ to 230 $W \cdot m^{-1} \cdot K^{-1}$, or 6 $W \cdot m^{-1} \cdot K^{-1}$ to 160 $W \cdot m^{-1} \cdot K^{-1}$, or 20 $W \cdot m^{-1} \cdot K^{-1}$ to 110 $W \cdot m^{-1} \cdot K^{-1}$, or 45 $W \cdot m^{-1} \cdot K^{-1}$ to 100 $W \cdot m^{-1} \cdot K^{-1}$, or 50 $W \cdot m^{-1} \cdot K^{-1}$ to 95 $W \cdot m^{-1} \cdot K^{-1}$. A material of wire connection 822 may be e.g.: nickel, monel, platinum, osmium, niobium, potassium, steel, germanium, aluminium, cobalt, magnesium copper and/or their alloys. At least part of the wire connection 822 connected to the temperature sensor 816 may be thermally insulated by sheathing or shielding, such as by rubber tubing. The temperature sensor 816 may be an optical temperature sensor, such as an infrared IR thermosensor, which may be part of the applicator and/or in the main unit. During treatment, the optical temperature sensor may be located in contact with the patient's skin or in a range of 0.1 cm to 3 cm, or 0.2 cm to 2 cm from the patient's skin. The optical temperature sensor may collect information from the patient's skin through the optical cable.

One or more RF electrodes located with at least partial overlay under the magnetic field generating device may provide synergic effect of the magnetic treatment and the RF treatment. Stronger or more intensive treatment result may be provided with RF electrodes located with at least partial overlay under the magnetic field generating device. The generated RF field and the magnetic field from treatment energy sources in such configuration may be targeted to the same body area and/or target biological structures. This may result in better heating of stimulated muscles and adjacent tissues, better suppressing of uncomfortable feeling caused by muscle stimulation (e.g. muscle contraction), better regeneration after treatment and/or better prevention of panniculitis and other tissue injury.

The RF electrode may comprise a special design as described below for minimizing or eliminating unwanted physical effects.

In one aspect of the disclosure, unwanted physical effects induced by a magnetic field in the RF electrode positioned in proximity or at least partial overlay with the magnetic field generating device may be further minimized or eliminated by using a segmented RF electrode. The segmented RF electrode may comprise apertures, cutouts and/or protrusions. The areas of apertures and/or cutouts may be created by air, dielectric and/or other electrically insulating material. The electrode may comprise various protrusions. The plurality of apertures and/or cutouts may be visible from the floor projection of such electrode. Another parameter minimizing or eliminating the presence of the unwanted physical effects may be the thickness of the RF electrode. If a conductive material of the RF electrode is thin and an area of the RF electrode is at least partially separated by an insulator, loops of eddy currents induced by magnetic field may be very small and so induction in such areas is minimized.

The RF electrode may include one or more apertures or cutouts which may segment the conductive area of the RF electrode and/or perimeter of the RF electrode. The RF electrode is therefore segmented in comparison to a regular electrode by disruption of the surface area (i.e., an electrode with no apertures or cutouts). The two or more apertures or cutouts of the one RF electrode may be asymmetrical. The one or more aperture and cutout may have e.g. rectangular or circular shape. An aperture may be any hole and/or opening in the electrode area of the RF electrode according to applicator's floor projection. The apertures and/or cutouts may have regular, irregular, symmetrical and/or asymmetrical shape. The apertures and/or cutouts may be filled by e.g. air, dielectric and/or other electrically insulating material (e.g. dielectric material of printed circuit board). When the RF electrode includes two or more apertures or cutouts, the apertures or cutouts may have the same point of symmetry and/or line of symmetry. The distance between two closest points located on the borders of two different apertures and cutouts of RF electrode may be in a range from 0.1 mm to 50 mm or 0.1 mm to 15 mm or from 0.1 mm to 10 mm or from 0.1 mm to 8 mm. When the RF electrode is in at least partial overlay with magnetic field generating device, the RF electrode may include larger apertures and cutouts in part of the conductive surface, which is closer to the center of the magnetic field generating device. The RF electrode including a plurality of openings (e.g. apertures or cutouts) and/or protrusions may be positioned below the magnetic field generating device. The RF electrode including a plurality of openings (e.g. apertures or cutouts) and/or protrusions may be positioned between the magnetic field generating device and the patient.

Figure 13A:
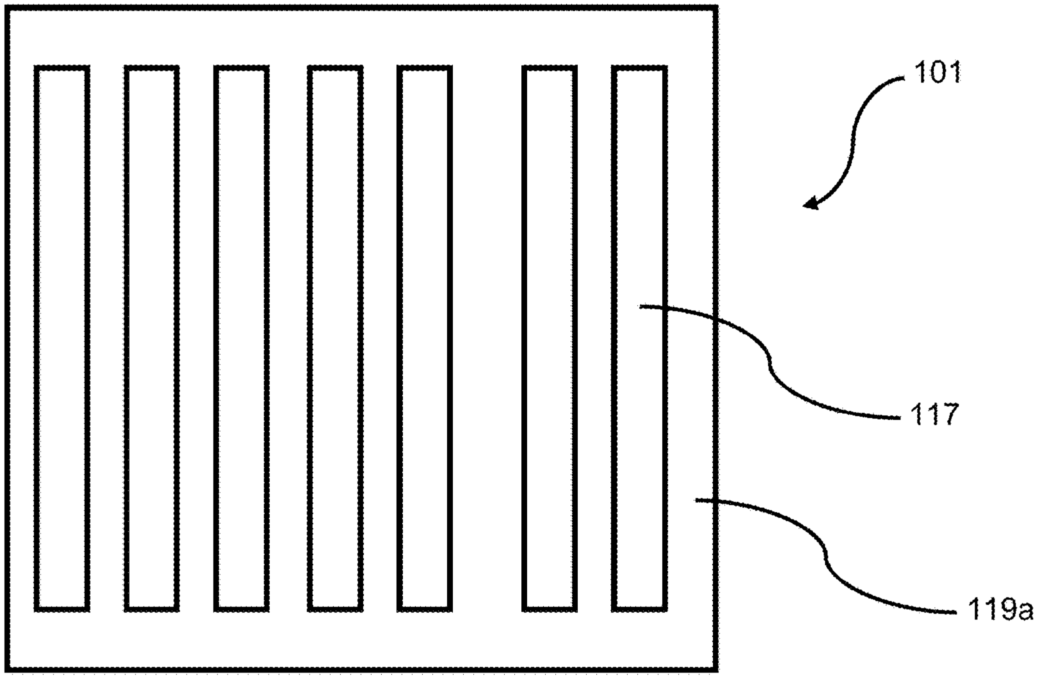
FIGS. 13*a*-13*b* illustrate exemplary RF electrodes with apertures.

FIG. 13*a* illustrates an exemplary RF electrode wherein the RF electrode 101 includes an electrode area 119*a* and defines one or more apertures 117 in the conductive area of the RF electrode. The apertures 117 may be elongated slots having a rectangular shape. One aperture 117 may be parallel to another apertures.

Figure 13B:
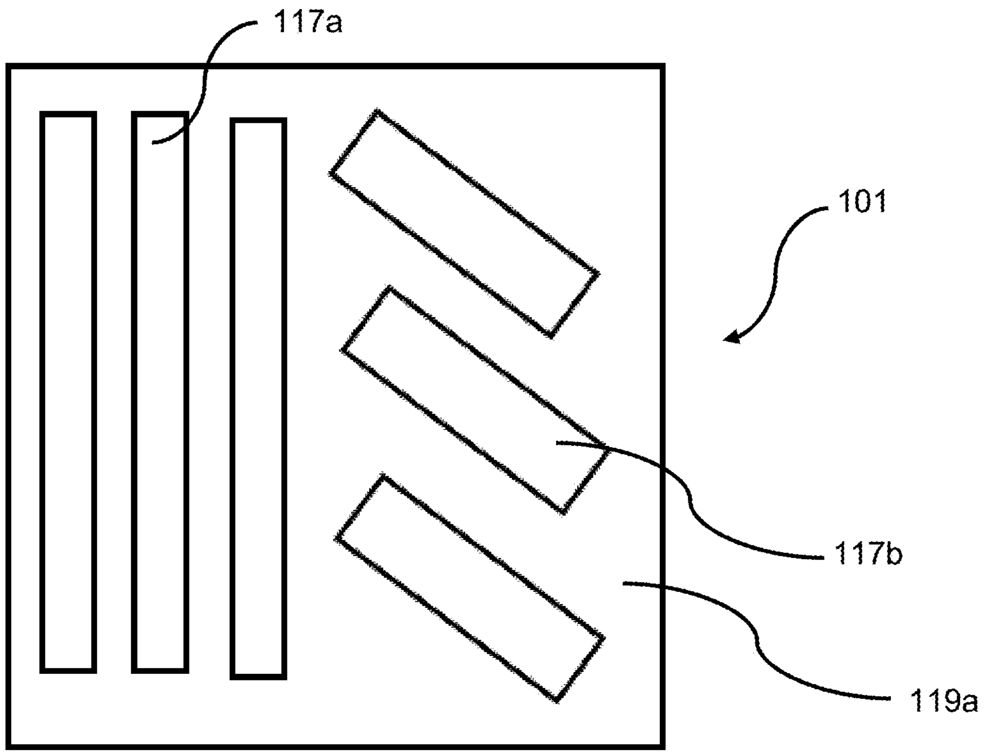

FIG. 13*b* illustrates another exemplary of RF electrode wherein he RF electrode 101 includes an electrode area 119*a* and one or more apertures 117*a* and 117*b* in the conductive area of the RF electrode. Apertures 117*a* are not parallel to apertures 117*b*.

Figure 13C:
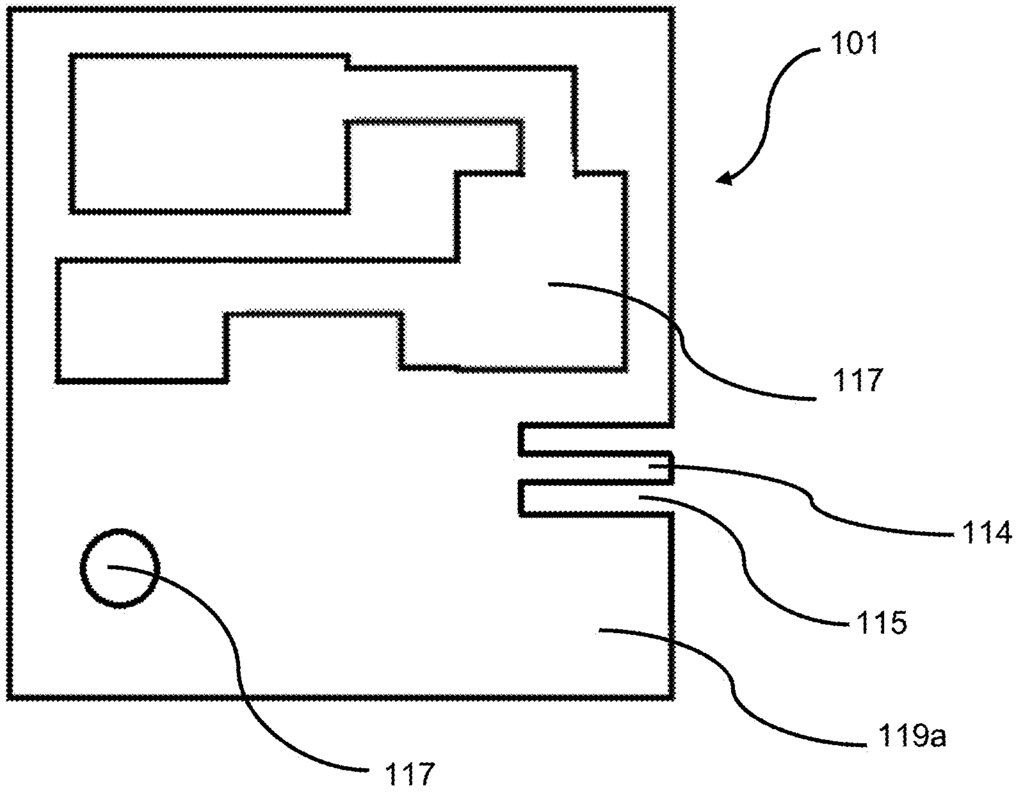
FIG. 13*c* illustrates an exemplary RF electrode with apertures, protrusions and cutouts.

FIG. 13*c* illustrates another exemplary RF electrode wherein the RF electrode 101 includes an electrode area 119*a* and combination of one or more apertures 117 in the conductive area, cutout 115 in the conductive area and protrusion 114 of the RF electrode.

Figure 13D:
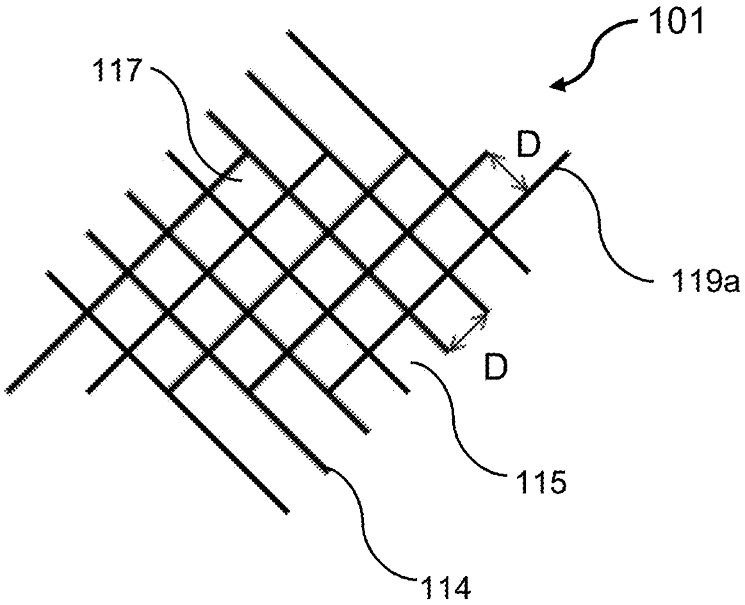
FIG. 13*d* illustrates another exemplary RF electrode with apertures and cutouts.

FIG. 13*d* illustrates another exemplary RF electrode wherein the RF electrode 101 includes a combination of one or more apertures 117 at the conductive area and the cutouts 115 in the electrode area. The lines represent thin line (e.g. single wire) of electrode area 119*a* of RF electrode. The RF electrode may be a grid of conductive wires or a mesh of conductive wires. The protrusion 114 may define one or more cutouts 115 at a perimeter of the electrode. The distance D between the borders of individual lines (e.g. wires or grouped wires) may be in a range of 0.01 mm to 100 mm, or 0.1 mm to 50 mm, or 0.1 mm to 10 mm.

Figure 13E:
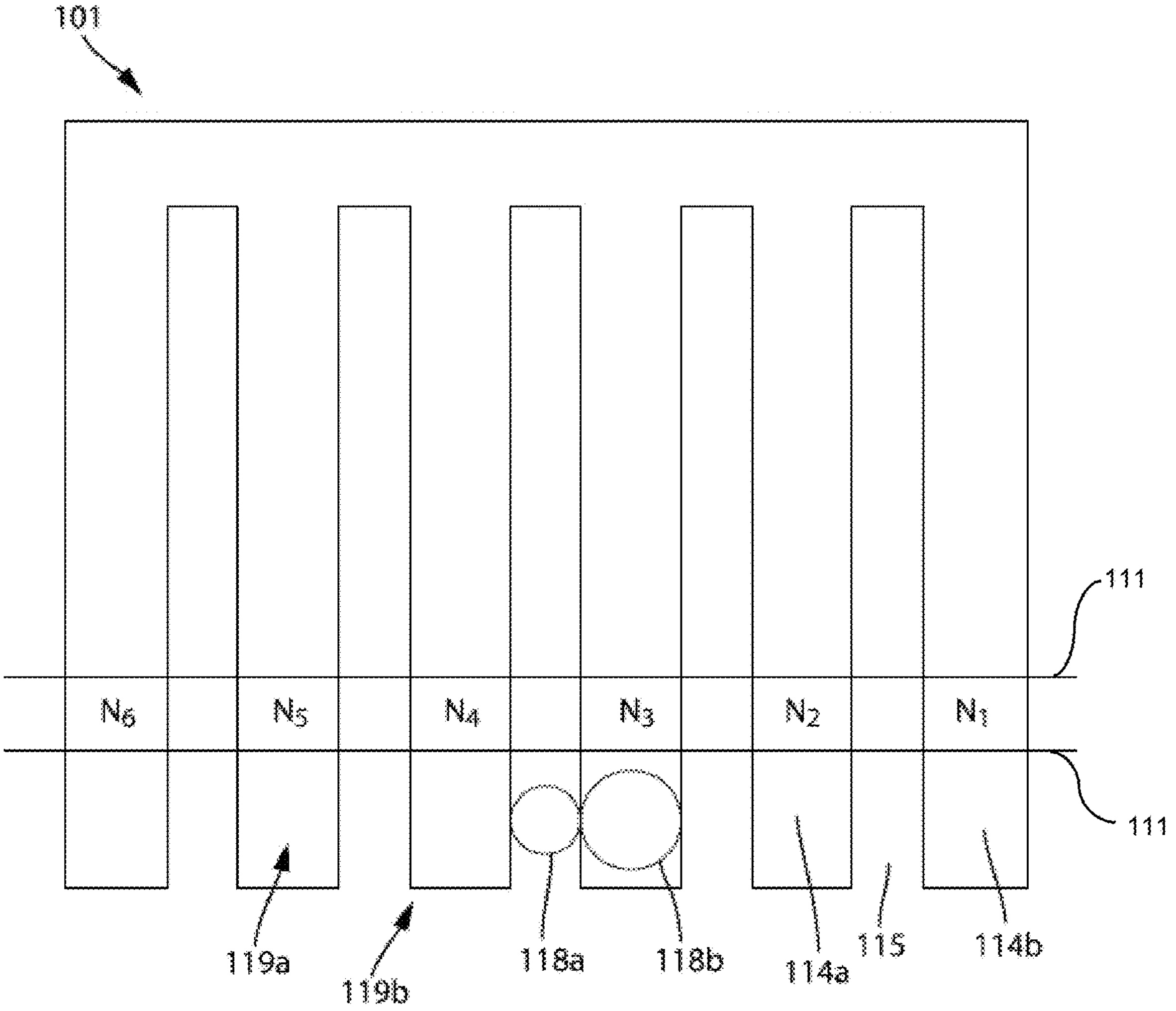
FIG. 13*e* illustrates an exemplary RF electrode with protrusions.

FIG. 13*e* illustrates another exemplary RF electrode including protrusions and cutouts. The RF electrode 101 has an electrode area 119*a*, a border length 119*b*, and a plurality of protrusions illustrated as $N_{\#}$. The protrusions may define protrusion cutouts (e.g. cutout 115 wherein the cutout may be an opening or gap). The protrusions may define cutouts (e.g. cutout 115 wherein the cutout may be an opening or gap). The RF electrode 101 may include at least two, three or five protrusions 114 (e.g. 114*a*, 114*b*) or more. The protrusions 114 may be separated from one another by cutout 115. Similarly, the RF electrode 101 may include one, two, three or more protrusion cutouts. A first protrusion 114*a* and a second protrusion 114*b* of the plurality of protrusions may be arranged generally parallel to one another. The protrusions 114 may be spaced at a fixed interval and may be regularly arranged. Protrusions 114*a*, 114*b* may be shaped as rods or pins having a generally linear shape. Protrusions 114*a* and 114*b* may be made of a conductive material. Cutout 115 may be filled by air, dielectric, or other electrically insulating material. The distance between protrusions is such distance, that at least one circle 118*a* which may be hypothetically inscribed into cutout 115 and between two protrusions 114*a* and 114*b*. The at least one circle 118*a* may have a diameter in a range from 0.001 to 30 mmm or 0.005 mm to 15 mm, or from 0.01 mm to 10 mm or 0.01 mm to 8 mm or from 0.01 mm to 7 mm, or from 0.01 mm to 5 mm or from 0.01 mm to 3 mm or from 0.01 mm to 2 mm, wherein each circle may have at least one tangential point located on the first protrusion 114*a* and at least one tangential point located on the second protrusion 114*b*. Each circle 118*a* may have different tangential points. The cutout 115 may be symmetrical and/or asymmetrical along its length. The cutout 115 may create a constant distance between protrusions 114*a* and 114*b*. The distance between protrusions 114*a* and 114*b* may not be constant along the length of the protrusions. The smallest distance between two nearest protrusions 114*a*, 114*b* may be with increasing length of the protrusions increasing and/or decreasing.

The protrusions 114 or cutouts 115 may have symmetrical, asymmetrical, irregular and/or regular shape. The size, shape and/or symmetry of individual protrusions 114 may be the same and/or different across the RF electrode 101. For example, each protrusion 114 may have the same shape, the same dimensions, and/or symmetry.

The protrusions 114 may be characterized by the hypothetically inscribed circle 118*b* directly into protrusion. The hypothetically inscribed circle 118*b* to the protrusion 114 may have diameter in a range of 0.001 mm to 30 mm, or of 0.01 mm to 15 mm, or of 0.2 mm to 10 mm, or of 0.2 mm to 7 mm or of 0.1 to 3 mm. The hypothetically inscribed circle may not cross the border of the protrusion in which it is inscribed. The magnetic flux density B measured on at least part of the RF electrode surface area may be in a range of 0.1 T to 5 T, or in range of 0.2 T to 4 T, or in range of 0.3 T to 3 T, or of 0.5 T to 5 T, or in range of 0.7 T to 4 T, or in range of 1 T to 3 T. The magnetic flux density B measured on at least part of the RF electrode surface area may be measured during the treatment. The RF electrode surface area may include surface area of conductive surface of the RF electrode.

The magnetic flux density B measured on the at least one protrusion of the RF electrode may be in a range of 0.1 T to 5 T, or in range of 0.2 T to 4 T, or in range of 0.3 T to 3 T, or of 0.5 T to 5 T, or in range of 0.7 T to 4 T, or in range of 1 T to 3 T. The magnetic flux density B measured in the at least one aperture of the RF electrode surface area may be in a range of 0.1 T to 5 T, or in range of 0.2 T to 4 T, or in range of 0.3 T to 3 T, or of 0.5 T to 5 T, or in range of 0.7 T to 4 T, or in range of 1 T to 3 T. The magnetic flux density B measured in the at least one cutout of the RF electrode surface area may be in a range of 0.1 T to 5 T, or in range of 0.2 T to 4 T, or in range of 0.3 T to 3 T, or of 0.5 T to 5 T, or in range of 0.7 T to 4 T, or in range of 1 T to 3 T. The magnetic flux density measured in the cutout and/or the aperture may be measured by fluxmeter and/or its probe positioned in a center of the cutout and/or opening.

The number of protrusions $N_{\#}$ included in one RF electrode means the highest possible number of conductive areas electrically insulated from each other that may be created between and/or by two parallel cuts 111 across the surface of the RF electrode. The distance between two parallel cuts 111 may be in a range of 1 mm to 50 mm or 2 mm to 35 or 5 mm to 20 mm. The number of protrusions $N_{\#}$ may be in range of 5 to 1000, or of 10 to 600, or of 20 to 400, or of 50 to 400, or of 100 to 400 or of 15 to 200, or of 30 to 100, or of 40 to 150, or of 25 to 75.

The total number of protrusions in one RF electrode regardless of the parallel cuts 111 may be in the range of 5 to 1000, or of 10 to 600, or of 20 to 400, or of 50 to 400, or of 100 to 400 or of 15 to 200, or of 30 to 100, or of 40 to 150, or of 25 to 140.

The total number of apertures or cutouts in one RF electrode regardless of the parallel cuts 111 may be in the range of 5 to 1000, or of 10 to 600, or of 20 to 400, or of 50 to 400, or of 100 to 400 or of 15 to 200, or of 30 to 100, or of 40 to 150, or of 25 to 140.

The number of apertures, cutouts and/or protrusions in one RF electrode located below the coil including its core may be in a range 5 to 1000, or of 10 to 600, or of 20 to 400, or of 50 to 400, or of 100 to 400 or of 15 to 200, or of 30 to 100, or of 40 to 150, or of 25 to 140.

Number of an individual protrusions included in one RF electrode may be in range of 1 to 8000 or of 2 to 8000 or of 5 to 8000 or of 3 to 5000 or of 5 to 1000 or of 5 to 500 or of 10 to 500 or of 5 to 220 or of 10 to 100 in the area of size 2 cm multiplied 1 cm.

In order to provide a radiofrequency field with a consistent output, the plurality of apertures of the RF electrode may be divided into a first plurality of apertures and a second plurality of apertures. First plurality of apertures may be located below and in overlay with the magnetic field generating device, while the second plurality of apertures may be located outside of overlay with the magnetic field generating device, i.e., not below the magnetic field generating device. The presence of a second plurality of apertures and surrounding electrode area of the RF electrode located outside of the overlay with the magnetic field generating device may prevent mechanical and/or electrical stress of the first plurality of apertures and surrounding electrode area of the RF electrode, which may result in variation of the radiofrequency field output. Also, the presence of a second plurality of apertures and surrounding electrode area of the RF electrode located outside of the overlay with the magnetic field generating may improve cooling of the RF electrode. A number of apertures of the first plurality of apertures may be in a range of 5 to 1000, or of 10 to 600, or of 20 to 400, or of 50 to 400, or of 100 to 400 or of 15 to 200, or of 30 to 100, or of 40 to 150, or of 25 to 140. A number of apertures of the second plurality of apertures may be in a range of 5 to 1000, or of 10 to 600, or of 20 to 400, or of 50 to 400, or of 100 to 400 or of 15 to 200, or of 30 to 100, or of 40 to 150, or of 25 to 140.

Figure 53A:
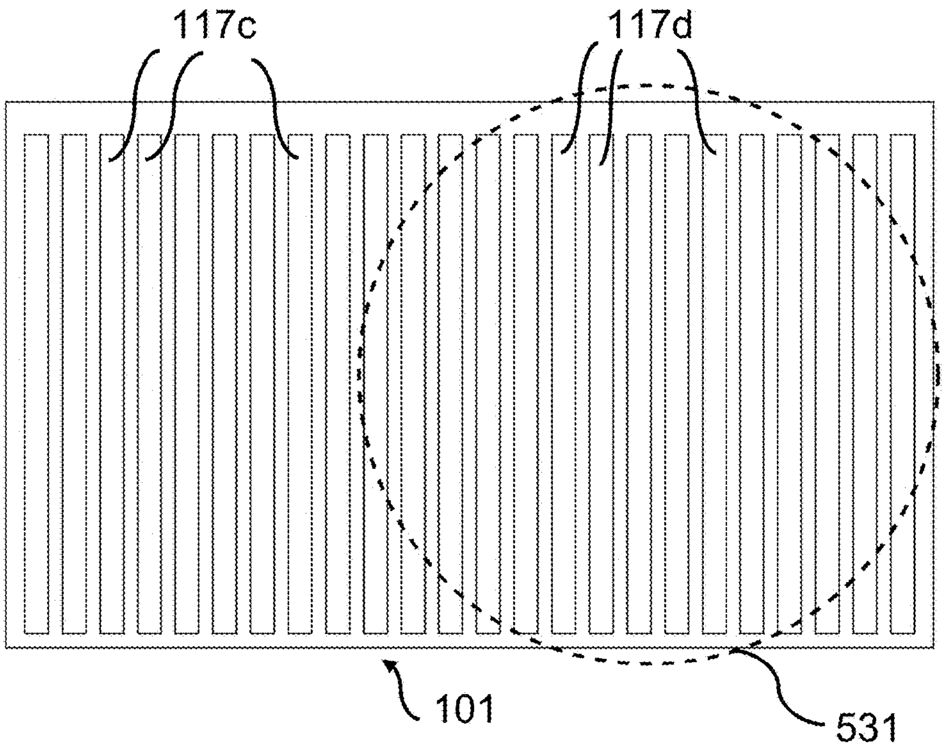
FIGS. 53*a*-53*c* illustrate exemplary RF electrodes according to one aspect of the disclosure.

FIG. 53*a* illustrates an RF electrode 101 having a plurality of apertures 117*c*, 117*d*. A magnetic field generating device 531 overlaying RF electrode 101 is symbolized by a dashed line. A first plurality of apertures 117*d* may be located below the magnetic field generating device 531, and apertures 117*c* may be located outside the overlay with the magnetic field generating device 531.

Figure 53B:
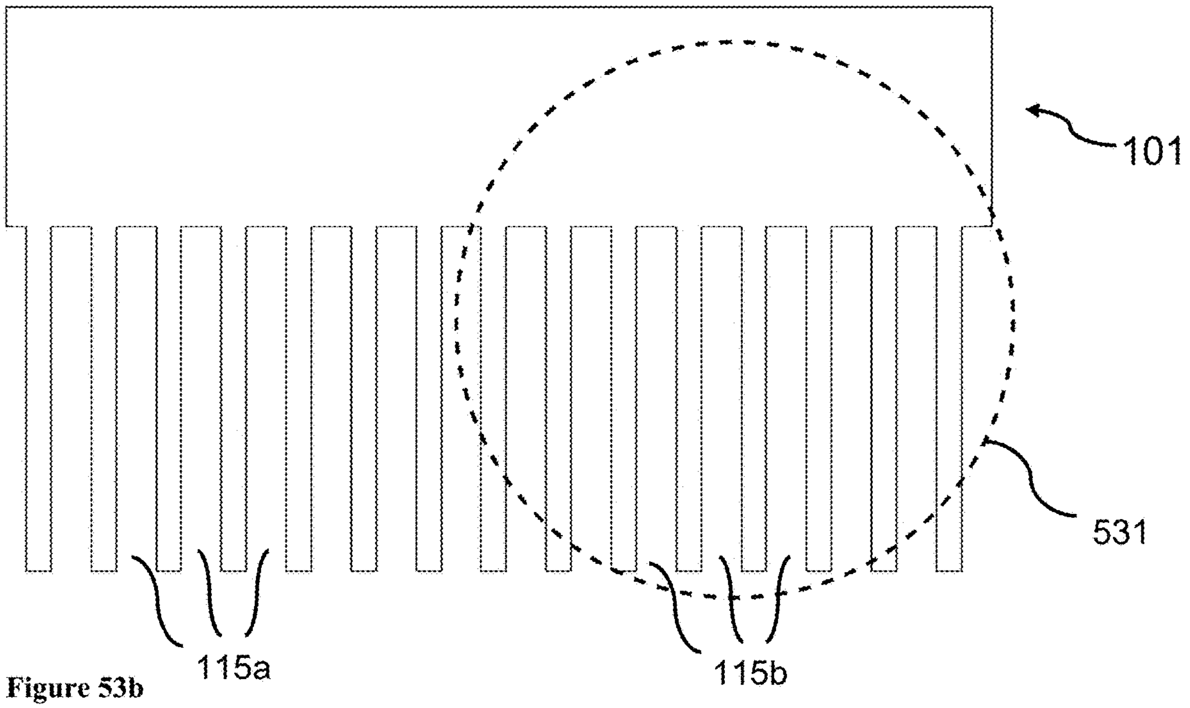

In order to provide radiofrequency field with a consistent output, the plurality of cutouts of the RF electrode may be divided to a first plurality of cutouts and a second plurality of cutouts. The first plurality of cutouts may be located below and in overlay with the magnetic field generating device, while the second plurality of cutouts may be located outside of the overlay with the magnetic field generating device, therefore not below the magnetic field generating device. The presence of a second plurality of cutouts and surrounding electrode area of the RF electrode located outside of the overlay with the magnetic field generating device may prevent mechanical and/or electrical stress of the first plurality of cutouts and surrounding electrode area of the RF electrode. Also, the presence of a second plurality of cutouts and surrounding electrode area of the RF electrode located outside of the overlay with the magnetic field generating may improve cooling of the RF electrode. A number of the first plurality of cutouts may be in a range of 5 to 1000, or of 10 to 600, or of 20 to 400, or of 50 to 400, or of 100 to 400 or of 15 to 200, or of 30 to 100, or of 40 to 150, or of 25 to 140. A number of the second plurality of cutouts may be in a range of 5 to 1000, or of 10 to 600, or of 20 to 400, or of 50 to 400, or of 100 to 400 or of 15 to 200, or of 30 to 100, or of 40 to 150, or of 25 to 140. FIG. 53*b* illustrates the RF electrode 101 having cutouts 115*a*, 115*b*. The magnetic field generating device 531 is symbolized by a dashed line. A first plurality of cutouts 115*b* is located below the magnetic field generating device. A second plurality of cutouts 115*a* is located outside of the overlay with the magnetic field generating device.

Figure 53C:
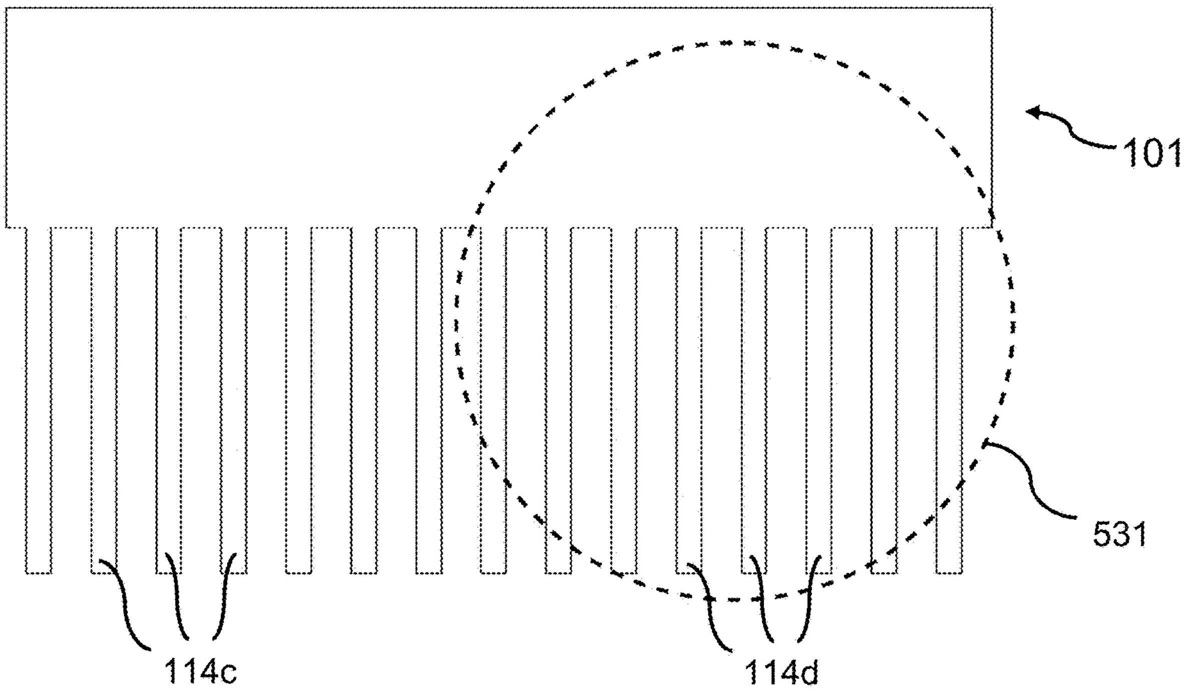

In order to provide radiofrequency field with a consistent output, the plurality of protrusions of the RF electrode may be divided into a first plurality of protrusions and a second plurality of protrusions. The first plurality of protrusions may be located below and in overlay with the magnetic field generating device, while the second plurality of protrusions may be located outside of the overlay with the magnetic field generating device, i.e., not below the magnetic field generating device. The presence of a second plurality of protrusions of the RF electrode located outside of the overlay with the magnetic field generating device may prevent mechanical and/or electrical stress of the first plurality of protrusions of the RF electrode. Also, the presence of a second plurality of protrusions of the RF electrode located outside of the overlay with the magnetic field generating may improve cooling of the RF electrode. A number of the first plurality of protrusions may be in a range of 5 to 1000, or of 10 to 600, or of 20 to 400, or of 50 to 400, or of 100 to 400 or of 15 to 200, or of 30 to 100, or of 40 to 150, or of 25 to 140. A number of the second plurality of protrusions may be in a range of 5 to 1000, or of 10 to 600, or of 20 to 400, or of 50 to 400, or of 100 to 400 or of 15 to 200, or of 30 to 100, or of 40 to 150, or of 25 to 140. FIG. 53*c* illustrates the RF electrode 101 having protrusions 114*c*, 114*d*. The magnetic field generating device 531 is symbolized by a dashed line. A first plurality of protrusions 114*d* are located below the magnetic field generating device 531. A second plurality of protrusions 114*c* are located outside of the overlay with the magnetic field generating device 531.

The magnetic flux density B and/or amplitude of magnetic flux density as measured on at least part of the RF electrode 101 may be in a range of 0.1 T to 5 T, 0.2 T to 4 T, 0.3 T to 3 T, 0.7 T to 5 T, 1 T to 4 T, or 1.5 T to 3 T during the treatment. The electrode may be defined by a protrusion density $\rho_p$ according to Equation 1, $$\rho_p = \frac{n}{lB} \quad \text{Equation 1}$$

wherein n symbolize a number of a protrusions intersecting a magnetic field line of force of magnetic flux density B [T] and l [cm] symbolizes a length of intersected the magnetic field line of force by these protrusions. The length l may be at least 1 cm long and magnetic field line of force may have a magnetic flux density B [T] of at least 0.3 T or 0.7 T. The protrusion density according to the treatment device may be in at least part of the RF electrode in a range of 0.3 $cm^{-1}\cdot T^{-1}$ to 72 $cm^{-1}\cdot T^{-1}$, or of 0.4 $cm^{-1}\cdot T^{-1}$ to 10 $cm^{-1}\cdot T^{-1}$, or of 0.4 $cm^{-1}\cdot T^{-1}$ to 7 $cm^{-1}\cdot T^{-1}$, or of 0.5 $cm^{-1}\cdot T^{-1}$ to 6 $cm^{-1}\cdot T^{-1}$, or of 0.8 $cm^{-1}\cdot T^{-1}$ to 5.2 $cm^{-1}\cdot T^{-1}$.

Protrusions may be wider (i.e. they may have a greater thickness) where the magnetic flux density is lower and thinner where magnetic flux density is higher. Further, protrusion density $\rho_p$ may be higher where the magnetic flux density is higher.

An electrode area of one or more RF electrodes in one applicator or one additional treatment device may be in a range from 1 $cm^2$ to 2500 $cm^2$, or 25 $cm^2$ to 800 $cm^2$, or 30 $cm^2$ to 600 $cm^2$, or 30 $cm^2$ to 400 $cm^2$, or from 50 $cm^2$ to 300 $cm^2$, or from 40 $cm^2$ to 200 $cm^2$ according to the applicator's floor projection.

The RF electrode may have a border ratio. Border ratio may be defined as the ratio between circumference and area of the electrode. An example of border ratio is shown in FIG. 13*e*, where the circumference may be depicted as the border length 119*b* and area of the RF electrode is depicted by the electrode area 119*a* of the RF electrode according to the applicator's floor projection. The electrode area 119*a* is the area of the RF electrode without wires supplying the RF electrodes and without sum of the circumference of all apertures and/or cutouts. The border length 119*b* is the sum of electrode's circumference and all circumferences of apertures inscribed inside the electrode, if there exist any. The border ratio of the RF electrode may be in a range of 10 $m^{-1}$ to 50 000 $m^{-1}$ or of 50 $m^{-1}$ to 40 000 $m^{-1}$ or of 150 $m^{-1}$ to 20 000 $m^{-1}$ or of 200 $m^{-1}$ to 10 000 $m^{-1}$ or of 200 $m^{-1}$ to 4000 $m^{-1}$ or of 300 $m^{-1}$ to 10 000 $m^{-1}$ or of 300 $m^{-1}$ to 4000 $m^{-1}$ or of 500 $m^{-1}$ to 4000 $m^{-1}$ or 10 $m^{-1}$ to 20 000 $m^{-1}$ or 20 $m^{-1}$ to 10 000 $m^{-1}$ or 30 $m^{-1}$ to 5 000 $m^{-1}$.

According to the applicator's floor projection, at least one RF electrode may have a border ratio in a range of 10 $m^{-1}$ to 50 000 $m^{-1}$ or of 50 $m^{-1}$ to 40 000 $m^{-1}$ or of 150 $m^{-1}$ to 20000 $m^{-1}$ or of 250 $m^{-1}$ to 10000 $m^{-1}$ or of 200 $m^{-1}$ to 4000 $m^{-1}$ or of 300 $m^{-1}$ to 1000 $m^{-1}$ or of 400 $m^{-1}$ to 4000 $m^{-1}$ or of 400 $m^{-1}$ to 1200 $m^{-1}$ or of 500 $m^{-1}$ to 2000 $m^{-1}$ or 10 $m^{-1}$ to 20 000 $m^{-1}$ or 20 $m^{-1}$ to 10 000 $m^{-1}$ or 30 $m^{-1}$ to 5 000 $m^{-1}$ in a locations where a magnetic flux density B on at least part of the RF electrode's surface may be in a range of 0.1 T to 7 T, or of 0.3 T to 5 T, or of 0.5 to 3 T, or of 0.5 T to 7 T, or in a range of 0.7 T to 5 T, or in range of 1 T to 4 T. With increasing magnetic flux density B across the RF electrode area may be an increased border ratio.

The ratio between the border ratio and the magnetic flux density B on RF electrode surface area may be called a charging ratio. The charging ratio may be related to square surface area of RF electrode of at least 1.5 $cm^2$ and magnetic flux density in a range of 0.1 T to 7 T, or of 0.3 T to 5 T, or of 0.5 to 3 T, or of 1 T to 5 T, or of 1.2 T to 5 T. The charging ratio of at least part of the RF electrode may be in a range from 70 $m^{-1}\cdot T^{-1}$ to 30000 $m^{-1}\cdot T^{-1}$, or from 100 $m^{-1}\cdot T^{-1}$ to 5000 $m^{-1}\cdot T^{-1}$, or from 100 $m^{-1}\cdot T^{-1}$ to 2000 $m^{-1}\cdot T^{-1}$, or from 120 $m^{-1}\cdot T^{-1}$ to 1200 $m^{-1}\cdot T^{-1}$, or from 120 $m^{-1}\cdot T^{-1}$ to 600 $m^{-1}\cdot T^{-1}$ or from 230 $m^{-1}\cdot T^{-1}$ to 600 $m^{-1}\cdot T^{-1}$. Square surface area of RF electrode may include a surface area having square shape.

With higher border ratio and/or charging ratio, induced unwanted physical effects in the RF electrode may be lower because the RF electrode may include partially insulated protrusions from each other. With higher border ratio and/or charging ratio, possible hypothetically inscribed circles into protrusions has to be also smaller and so loops of induced eddy current has to be smaller. Therefore, induced eddy currents are smaller and induced unwanted physical effect induced in the RF electrode is lower or minimized.

The ratio between an area of one side of all RF electrodes (floor projection) and one side of all winding areas of all magnetic field generating devices (area A2 as shown in FIG. 9*a*) in one applicator and according to its floor projection may be in a range of 0.1 to 15, or of 0.5 to 8, or of 0.5 to 4, or of 0.5 to 2.

Figure 16:
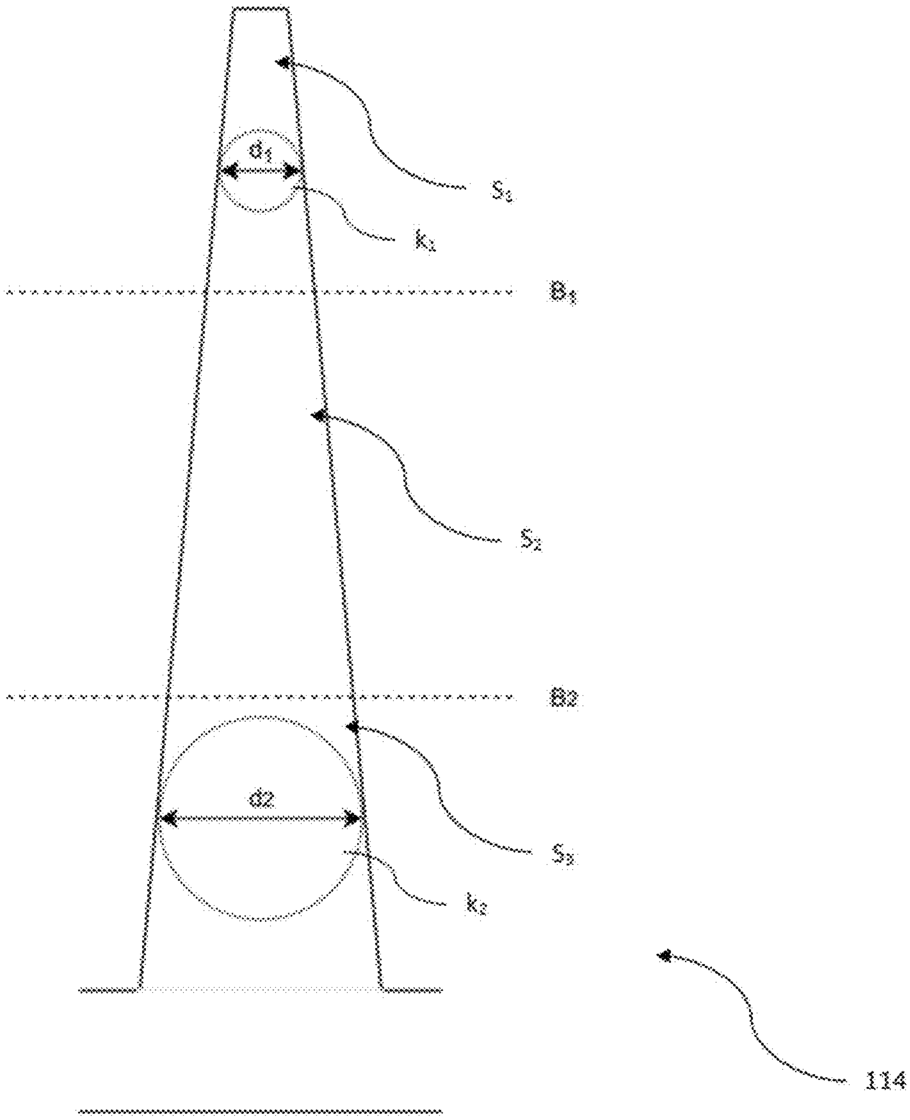
FIG. 16 illustrates one exemplary protrusion intersecting magnetic field lines with a difference higher than 0.1 T.

As illustrated in FIG. 16, if one protrusion 114 is intersected by magnetic field lines $B_1$ and Ba where absolute value of $|B_1|$ is higher than absolute value of $|B_2|$ and $|B_1|-|B_2 0.05<|T$, then the protrusion may be divided into three areas by lines of forces $B_1$ and $B_2$. In other words, the protrusion 114, as is illustrated in FIG. 16, may be divided into thirds $S_1$, $S_2$, $S_3$ that have the same length according to direction of magnetic field gradient and $S_1$ is exposed to higher magnetic flux density than $S_3$. Area $S_1$ may be placed in the highest magnetic flux density, $S_2$ may be placed in middle magnetic flux density and $S_3$ may be placed in the lowest magnetic flux density. The maximal hypothetically inscribed circle $k_1$ with diameter $d_1$ inscribed in the area $S_1$ may have smaller diameter than the maximal inscribed circle $k_2$ with diameter $d_2$ inscribed in the area $S_3$. The diameter $d_2$ may be greater than diameter $d_1$ of 2% to 1500%, or of 5% to 500%, or of 10% to 300%, or of 10% to 200%, or of 10% to 100%, or of 5% to 90%, or of 20% to 70%, or 5% to 20% of the diameter $d_1$. In such case, protrusions may be thinner where the magnetic flux density is higher, such as at least partially pyramidal shape of the protrusion may be created. In addition, protrusions may be thinner where magnetic flux density is higher.

The RF electrode may have different sizes and shapes. The plurality of RF electrodes may include bipolar electrodes. The bipolar electrodes may be parallel electrodes, such as shown in FIGS. 14*a*-14*e*, or concentric electrodes it is shown in FIGS. 15*a*-15*c*. The same type of RF electrodes 101 illustrated in FIGS. 14*a*-14*e* and FIGS. 15*a*-15*c* that may be located close to the second side portion of the applicator may be used as RF electrodes 102 located close to the first side portion and/or for any other one or more RF electrodes.

Shape and arrangement of RF electrodes of at least one applicator may be based on size shape and symmetry of body location (anatomy) where at least one applicator will be attached. Positioning and different shapes of the RF electrode may be beneficial in order to avoid creating of hot spots, provide homogeneous heating of as large treated body area, as possibility to avoid needs of moving with one or more applicators.

Figure 14A:
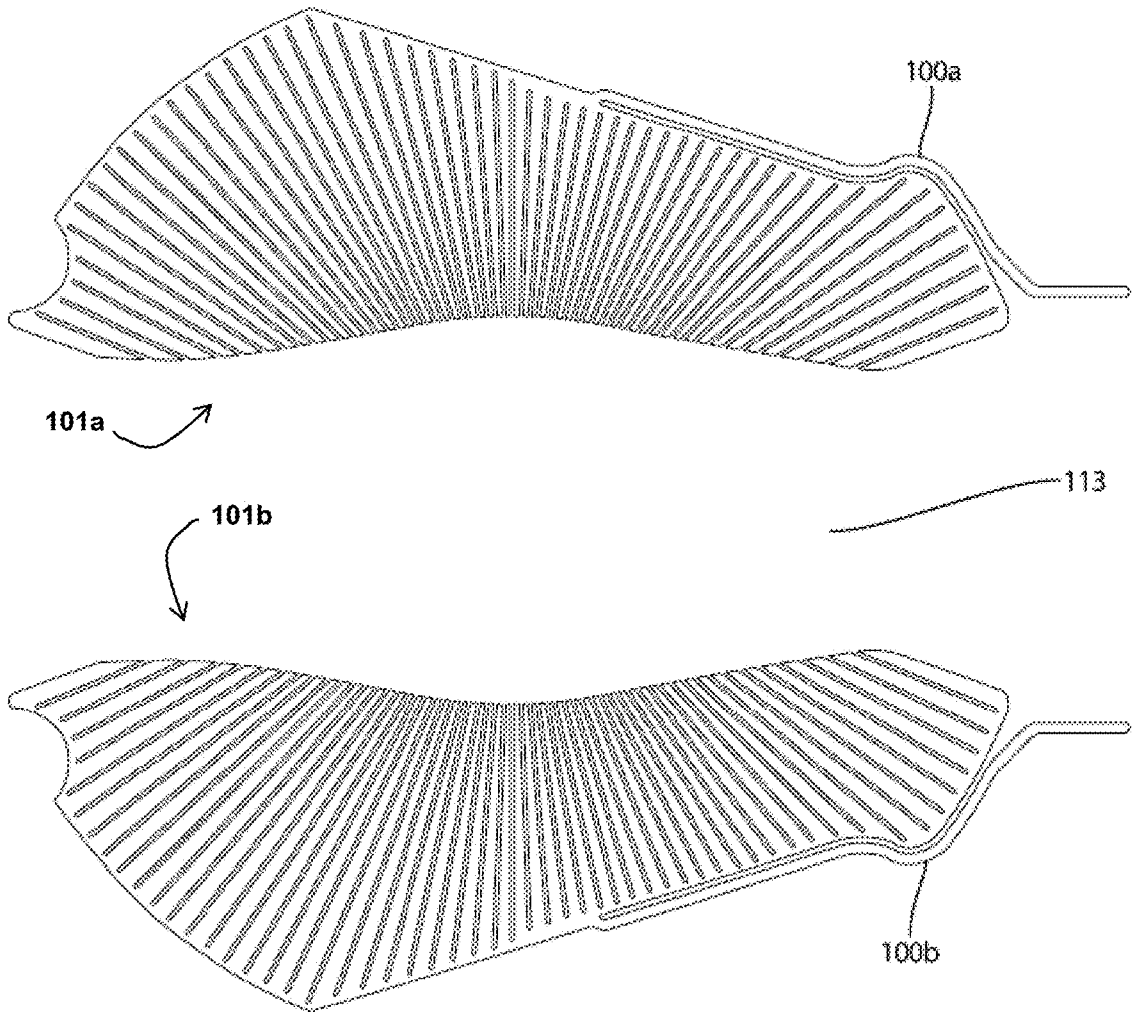
FIGS. 14*a*-14*e* illustrate parallel pairs of bipolar RF electrodes with protrusions.
Figure 14B:
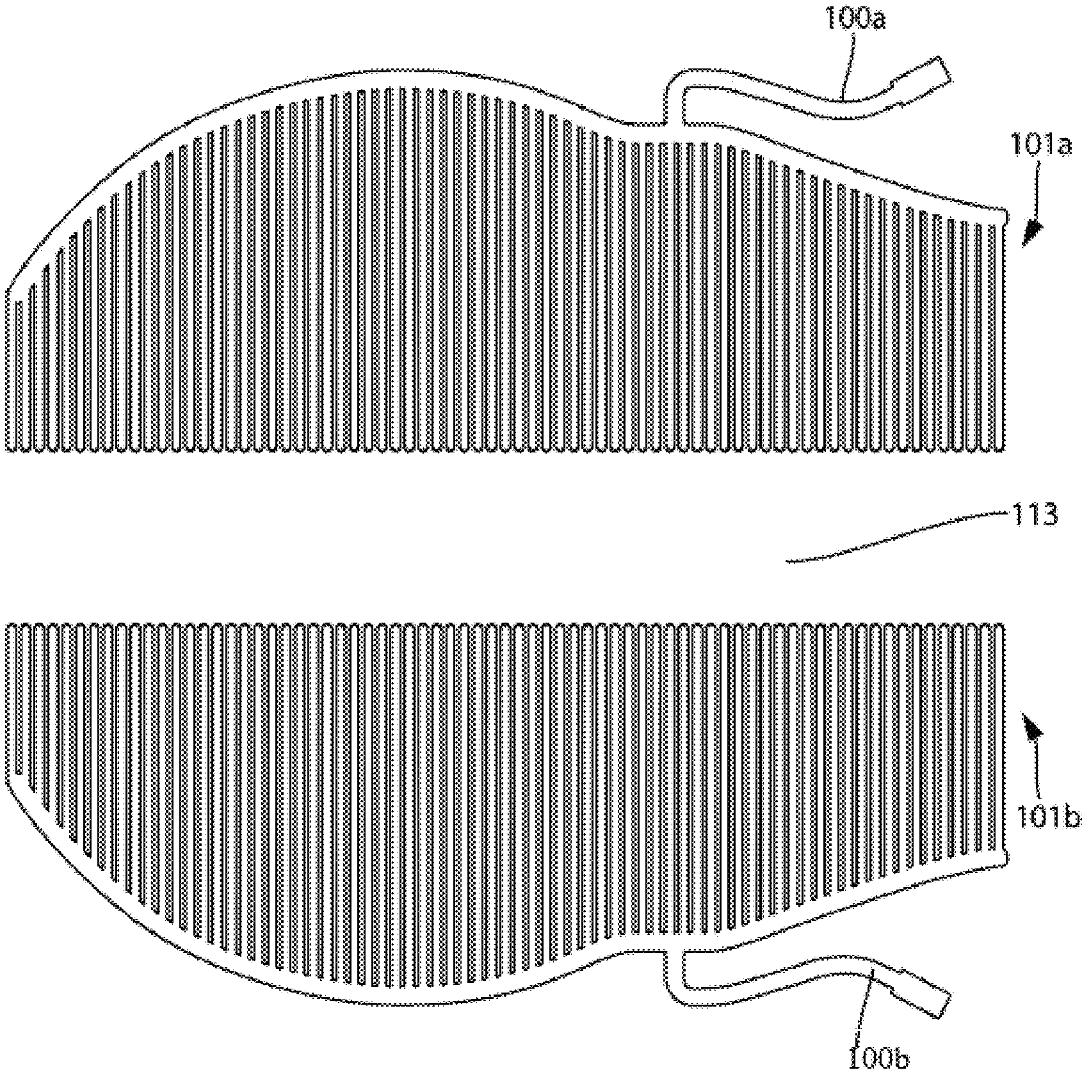
Figure 14C:
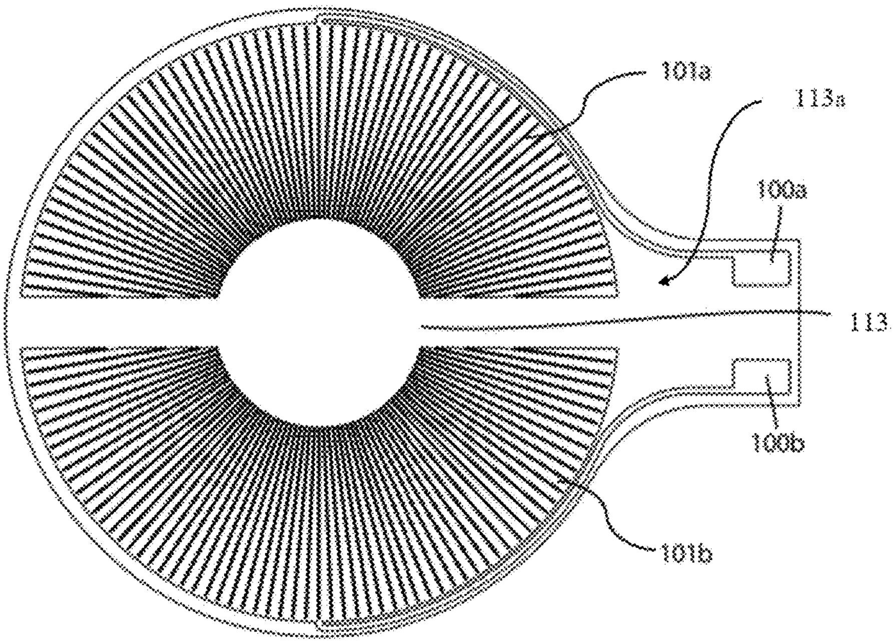
Figure 14D:
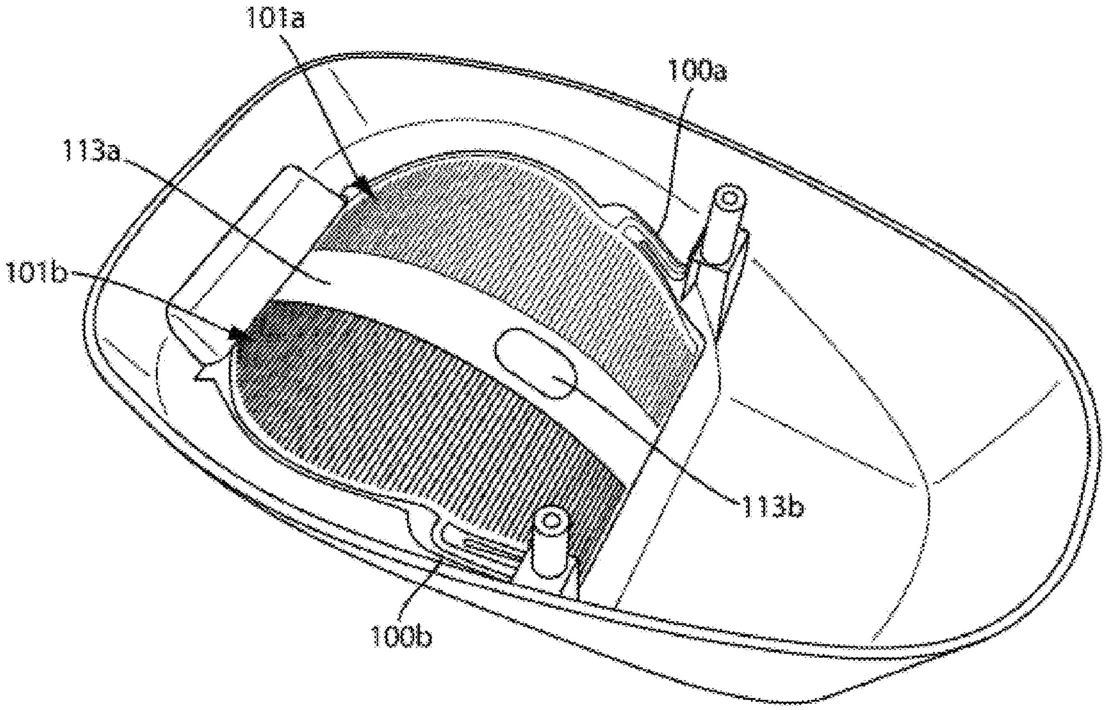
Figure 14E:
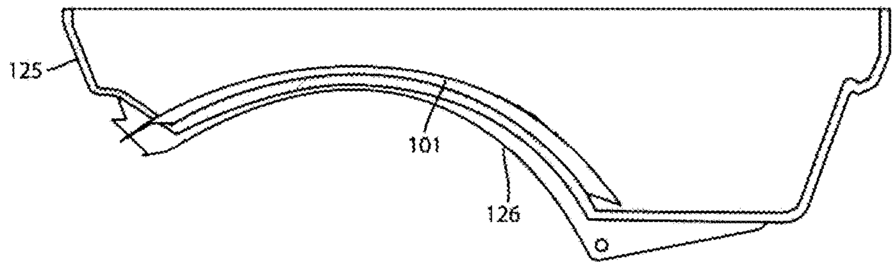
Figure 15A:
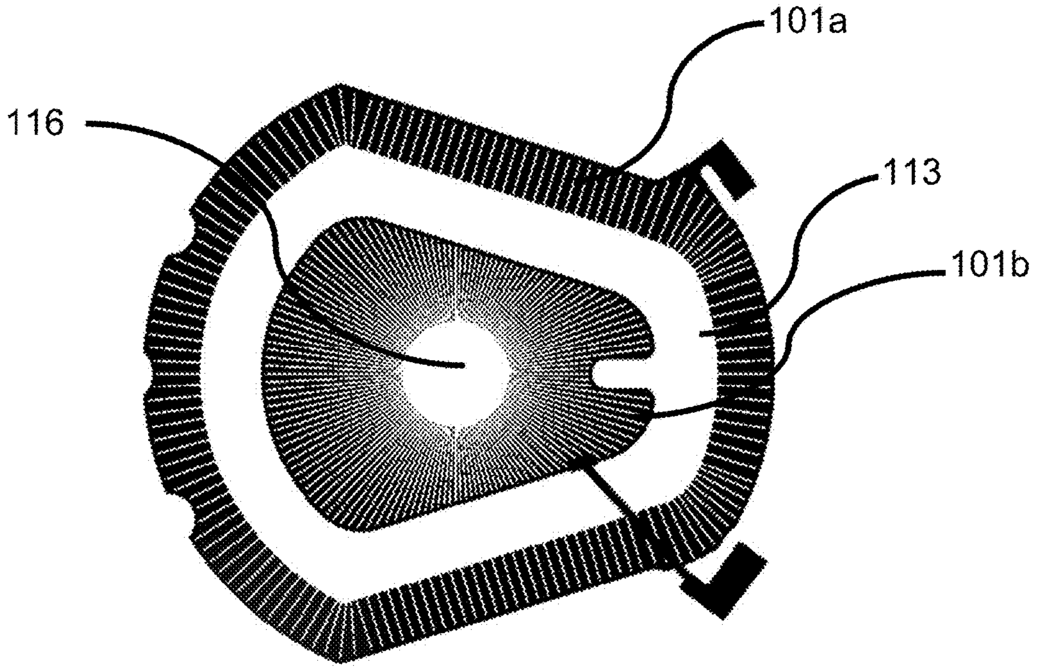
FIGS. 15*a*-15*c* illustrate bipolar RF electrode pairs with protrusions, wherein a first RF electrode at least partially encircles a second RF electrode of RF electrodes pair.
Figure 15B:
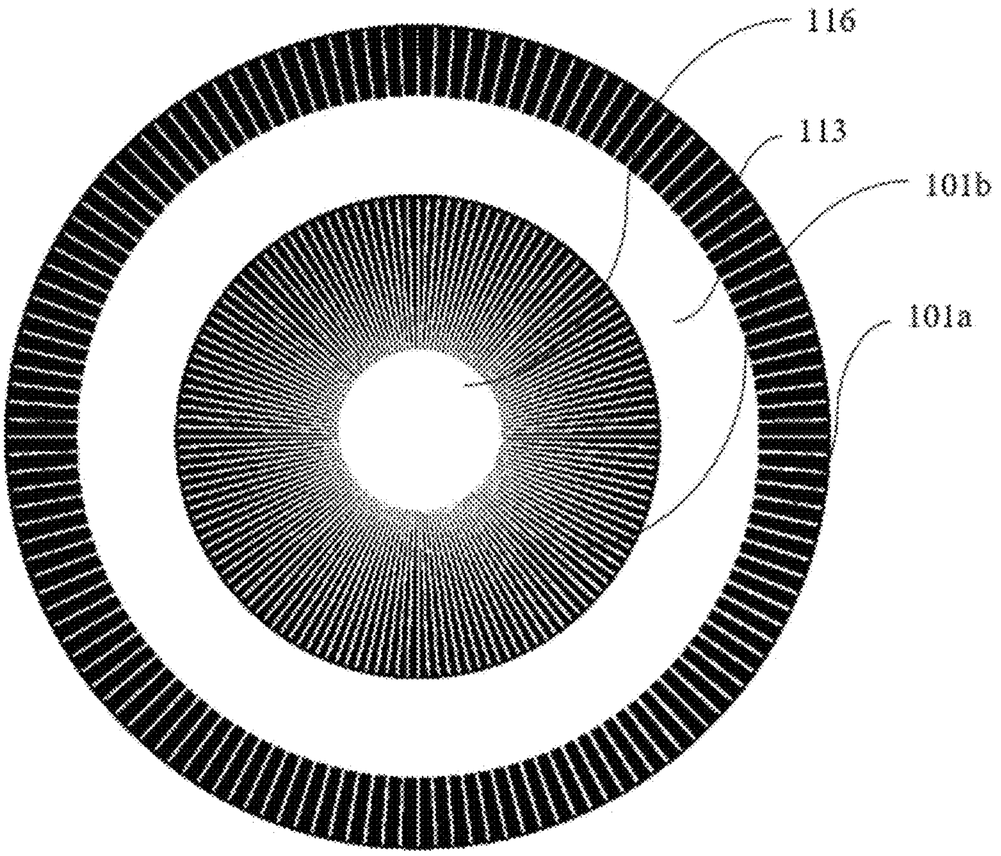
Figure 15C:
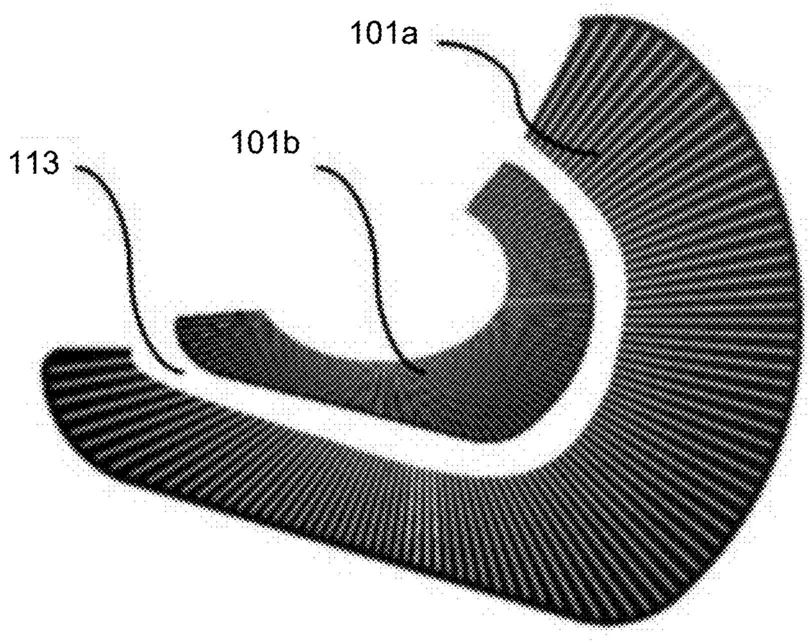

FIG. 14*a* illustrates an example of symmetrical positioning of RF electrodes. FIG. 14*b* illustrates another example of symmetrical positioning of RF electrodes. FIG. 14*c* illustrates still another example of symmetrical positioning of RF electrodes. FIG. 14*d* illustrates view of an applicator including symmetrical positioning of RF electrodes. FIG. 14*e* illustrates a side view of an applicator including example of symmetrical positioning of RF electrodes.

According to examples of RF electrodes shown in FIGS. 14*a*-14*e*, the applicator may include at least one pair of parallel bipolar RF electrodes 101*a* and 101*b* spaced by a gap 113. The RF electrodes are powered by wiring 100*a* and 100*b*. As illustrated in FIGS. 14*a*, 14*b* and 14*d*, RF electrodes 101*a*, 101*b* may be symmetrical, and may be mirror images. The shape of individual RF electrodes 101*a* and 101*b* may be irregular or asymmetrical wherein the length and/or area of at least 40%, 50%, 70%, 90%, or 99% of all protrusions in one RF electrode may be different. Body anatomy and testing may prove that such kind of RF electrodes could provide the most comfortable and efficient treatment of body areas, such as abdomen area, buttock, arms and/or thighs.

As illustrated in FIG. 14*c*, RF electrodes 101*a*, 101*b* may be at least partially symmetrical according to at least one axis or point of symmetry, such as according to linear symmetry, point symmetry, and rotational symmetry. For example, each electrode may be semi-circular or C-shaped. Further, the gap 113 between RF electrodes 101*a* and 101*b* may be irregular and/or may be designed according to at least one axis of symmetry, such as linear axis of symmetry with mirror symmetry. Thus, in case when electrodes 101*a* and 101*b* may be semi-circular, gap 113 may be circular. Use of such symmetrical electrode may be beneficial for treating body area where such symmetry may be required to highlight symmetry of body area (e.g. buttocks or hips).

The gap 113 between RF electrodes 101*a* and 101*b* may include air, cooling fluid, oil, water, dielectric material, fluid, and/or any other electric insulator, such as a substrate from composite material used in printed board circuits. The RF electrode 101*a* and 101*b* may be formed from copper foil and/or layer deposited on such substrate. The gap 113 may influence a shape of the electromagnetic field (e.g. RF field) produced by RF electrodes and the depth of electromagnetic field penetration into a patient's body tissue. Also, the distance between the at least two RF electrodes 101*a* and 101*b* may create the gap 113 which may have at least partially circular, elliptic and/or parabolic shape, as illustrated in FIG. 14*a*. The gap 113 may have regular shape for spacing RF electrodes with constant distance as illustrated in FIG. 14*b*.

The gap 113 between the RF electrodes 101*a* and 101*b* may be designed to provide a passage of amount in the range of 2% to 70% or 5% to 50% or 15% to 40% of the magnetic field generated by the magnetic field generating device. The distance between the nearest parts of at least two different RF electrodes in one applicator may be in a range of 0.1 cm to 25 cm, or of 0.2 cm to 15 cm, or of 2 cm to 10 cm, or of 2 cm to 5 cm.

The gap 113 between two RF electrodes may be designed in a plane of the RF bipolar electrodes wherein the gap 113 may at least partially overlay a location where the magnetic flux density generated by the magnetic field generating device has the highest absolute value. The gap 113 may be located in such location in order to optimize treatment efficiency and minimize energy loss.

It should be noted that strong magnetic field having high derivative of the magnetic flux density dB/dt may induce unwanted physical effects even in the RF electrode with protrusions, apertures and/or cutouts. The gap 113 may be positioned or located in the location where the absolute value of magnetic flux density is highest. As a result, the plurality of RF electrodes positioned around the gap 113 may be then affected by lower amount of magnetic flux density.

Plurality of RF electrodes (e.g. two RF electrodes 101*a* and 101*b*) may be located on a substrate 113*a* as shown in the FIG. 14*d*. Substrate 113*a* may be used as filler of the gap 113 between RF electrodes and of one or more cutouts 115.

As shown in FIGS. 14*d* and 25, the substrate 113*a* and one or more RF electrodes may be curved into required shape and/or radius to fit to patient's body area. RF electrodes 101*a* or 101*b* may be curved along a lower cover 125 of applicator 800, particularly along a curved portion 126 of lower cover 125. As shown in FIG. 14*d*, the substrate 113*a* may define a substrate gap 113*b* for at least one sensor, such as temperature sensor. Substrate gap 113*b* may further enable passage of one or more wires, cooling fluid, and/or for implementing another treatment energy source, such as a light treatment energy source (e.g. LED, laser diode) providing illumination or additional heating of the biological structure and/or body area.

FIGS. 15*a*, 15*b* and 15*c* illustrate two RF electrodes 101*a* and 101*b*, wherein at least one RF electrode 101*a* may at least partially surround another RF electrode 101*b*. The RF electrodes 101*a* and 101*b* may be spaced by gap 113 including e.g. substrate 113*a* with the same insulating properties as described above with respect to FIGS. 14*a*-14*e*. RF electrode 101*b* may include a hole 116 in order to minimize shielding of magnetic field and inducing of unwanted physical effects induced in the RF electrode 101*b*. The hole 116 may be located in the RF electrode plane where the magnetic flux density of the magnetic field generated by magnetic field generating device reaches highest values during the treatment. The hole 116 may be circular, or may have other shapes, such as oval, square, triangle, or rectangle, among others. The hole 116 may have an area of 0.05 $cm^2$ to 1000 $cm^2$, or 0.05 $cm^2$ to 100 $cm^2$, or of 3 $cm^2$ to 71 $cm^2$, or of 3 $cm^2$ to 40 $cm^2$, or of 3 $cm^2$ to 20 $cm^2$, or of 3 $cm^2$ to 15 $cm^2$, or of 0.5 $cm^2$ to 2.5 $cm^2$. The RF electrodes may be fully or partially concentric.

FIG. 15*a* illustrates two RF electrodes 101*a* and 101*b* may which be noncircular with at least one linear and/or point symmetry. Shown electrodes 101*a* and 101*b* may have no centre of symmetry. Shown RF electrode 101*a* may include a hole 116 in its centre where the magnetic flux density is the highest in order to minimize induction of unwanted physical effect in the RF electrode by magnetic field.

FIG. 15*b* illustrates two RF electrodes 101*a* and 101*b* may have a circular shape with rotational symmetry. The RF electrodes 101*a* and 101*b* may have the same centre of symmetry. Shown RF electrode 101*a* may include a hole 116 in its centre where the magnetic flux density is the highest in order to minimize induction of unwanted physical effects in the RF electrode by magnetic field.

FIG. 15*c* illustrates two RF electrodes 101*a* and 101*b* may have no symmetry and no centre of symmetry.

In order to minimize or eliminate unwanted physical effects, the RF electrode may include a reduced thickness. Thickness of the RF electrode may be in a range of 0.01 mm to 50 mm, or 0.01 mm to 10 mm, or 0.01 mm to 5 mm, or 0.01 mm to 3 mm, or 0.01 mm to 1 mm, or 0.1 mm to 1 mm, or 0.005 mm to 0.1 mm, or 0.01 mm to 0.2 mm.

The RF electrode may include one or more layers of substrate covered by a conductive layer, such as by a thin conductive layer. The thin conductive layer may be plated onto the substrate, e.g. by electroplating. Thickness of the conductive layer of RF electrode may be in a range of 0.01 mm to 50 mm, or 0.01 mm to 10 mm, or 0.01 mm to 5 mm, or 0.01 mm to 3 mm, or 0.01 mm to 1 mm, or 0.1 mm to 1 mm, or 0.005 mm to 0.1 mm, or 0.01 mm to 0.2 mm. One type of the RF electrode may be designed by a similar method as printed circuit boards (PCB) are prepared, wherein a thin, conductive layer may be deposited into and/or onto a substrate with insulating properties. However, the substrate may have dielectric properties or conductive properties. In other words, the RF electrode may include a conductive layer deposited on the layer of substrate. The substrate material forming the substrate layer of the electrode may be rigid or flexible. The substrate may include one, two or more conductive layers from a material such as copper, silver, nickel, aluminum, alloys of nickel and zinc, Mu-metal, austenitic stainless steel and/or other materials, creating the RF electrode. Also, a combination of materials may be used for conductive layer, e.g. nickel-copper combination.

The conductive layer may fully or partially cover the layer of substrate. The substrate may be covered or plated by a conductive layer of the RF electrode on the side of the substrate facing toward the patient and/or on the side of the substrate facing away from the patient. The thickness of the substrate material may be in a range of 0.01 mm to 45 mm, or 0.01 mm to 10 mm, or 0.01 mm to 5 mm, or 0.01 mm to 3 mm, or 0.01 mm to 2 mm, or 0.1 mm to 2 mm, or 0.5 mm to 1.5 mm, or 0.05 mm to 1 mm. The substrate material may be polymeric, ceramic, copolymeric sheet, phenol resin layer, epoxy resin layer, fiberglass fabric other textile fabric, polymeric fabric and/or other. The substrate may be at least partially flexible and/or rigid. Also, the substrate material may be a foam material, including plastic foam, polyolefin foam, polyurethane foam, or carbon foam. The foam may provide increased flexibility and protection to the conductive layer during vibrations, which may occur during treatment. The substrate material may be a textile. The substrate material may be a nanomaterial, e.g., nanotubes or nanoparticles.

The conductive layer deposited on the substrate layer may include any design of cutouts, protrusions and/or apertures as shown in any of FIGS. 13*a*, 13*b*, 13*c*, 13*d*, 13*e*. Also, it is possible that the conductive layer may not include any opening or protrusions. The conductive layer may include a sheet of conductive material. Conductive layer may be plated on the substrate layer. Further, the conductive layers plated on both sides of the substrate layer may be connected through suturing the one or more conducting wires (e.g. by metal loading through the substrate layer), such that the conductive layers and the substrate layer can be seen as one RF electrode. Conductive layer may be made of aluminum, copper, nickel, cobalt, manganese, zinc, iron, titanium, silver, brass, platinum, palladium and/or others from which may create alloys, such as Mu-metal, permalloy, electrical steel, ferritic steel, ferrite, stainless steel. The surface resistance $R_S$ of the RF electrode may be in a range of 0.00005 $\Omega/cm^2$ to 15 $\Omega/cm^2$ or 0.0001 $\Omega/cm^2$ to 10 $\Omega/cm^2$ 0.0002 $\Omega/cm^2$ to 5 $\Omega/cm^2$. The volume resistance $R_V$ of the RF electrode may be in a range of 0.0001 $\Omega/mm^2$ to 20 $\Omega/mm^2$ or 0.0001 $\Omega/mm^2$ to 10 $\Omega/mm^2$ or 0.001 $\Omega/mm^2$ to 8 $\Omega/mm^2$.

Figure 54A:
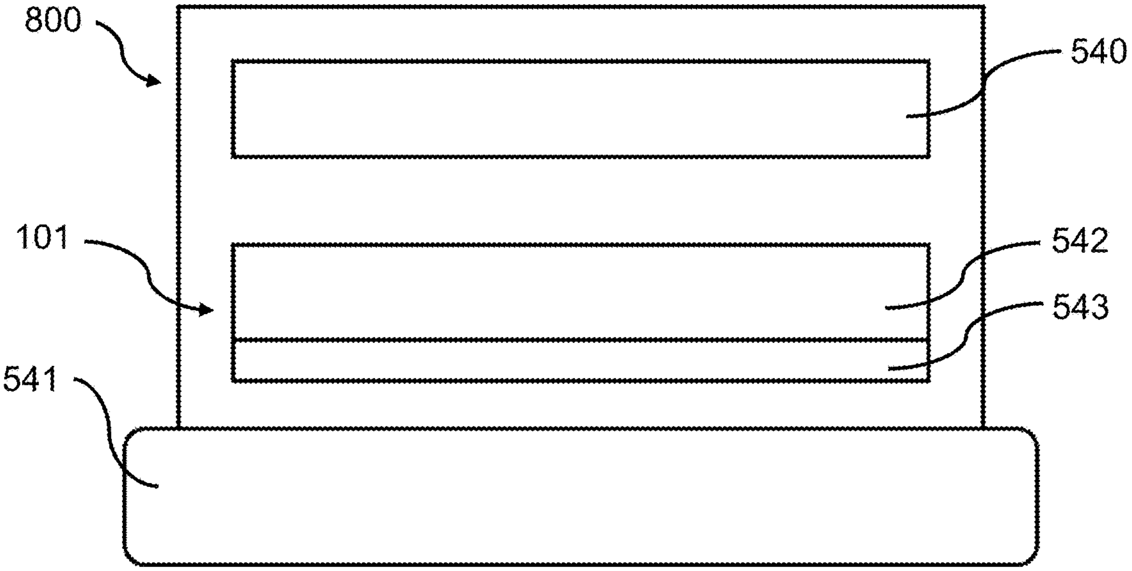
FIGS. 54*a*-54*f* illustrate exemplary applicators comprising an RF electrode including a substrate.

FIG. 54*a* illustrates an applicator 800 including a magnetic field generating device 540, and a RF electrode 101 positioned adjacent to a body area 541 of a patient. The RF electrode 101 may include a substrate 542 covered by a conductive layer 543. As shown in FIG. 54*a*, the conductive layer 543 may be positioned between the substrate 542 and the body area 541 of the patient. The conductive layer 543 may cover the side of the substrate 542 which is closer to the body area 541 of the patient. Positioning of the conductive layer 543 closer to the patient may prevent unwanted physical effects by distancing the conductive layer 543 from the magnetic field generating device 540.

Figure 54B:
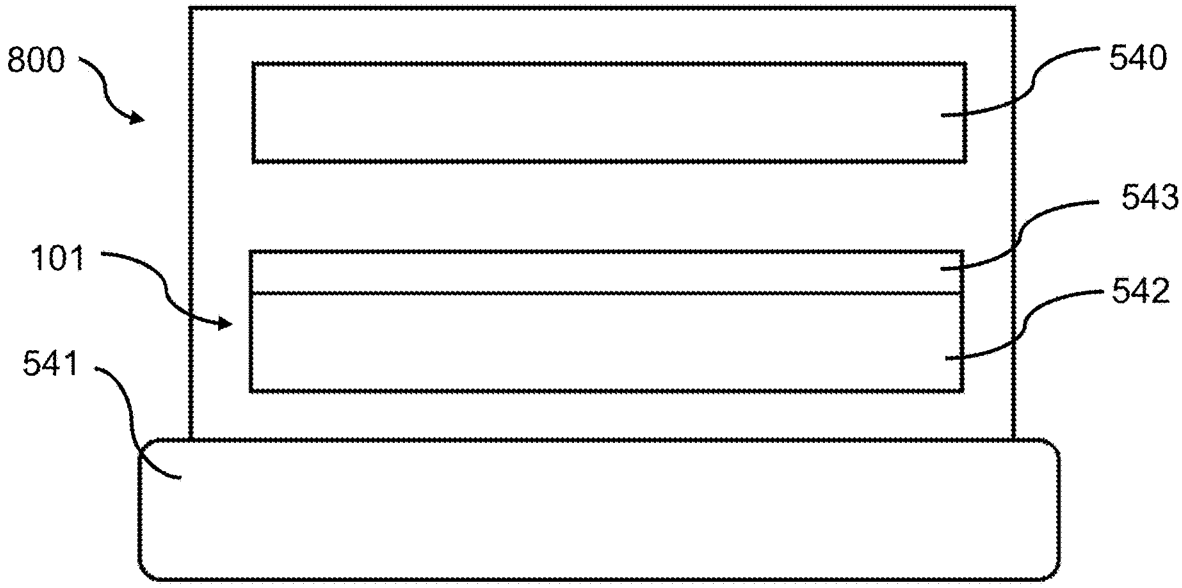

FIG. 54*b* illustrates an applicator 800, where the RF electrode 101 includes a substrate 542 covered by a conductive layer 543 on a side closer to the magnetic field generating device 540. Positioning of the conductive layer

543 closer to the magnetic field generating device 540 may prevent stress provided to the substrate 542.

Figure 54C:
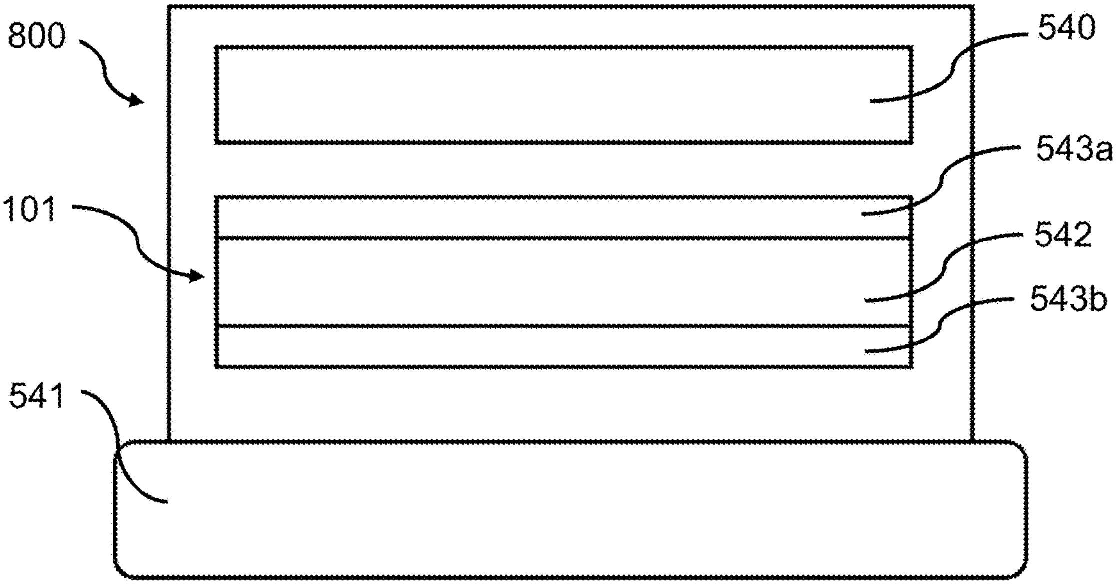

FIG. 54*c* illustrates an applicator 800, where the RF electrode 101 includes a substrate 542 covered by conductive layers 543*a* and 543*b* on both sides of the substrate 542. Positioning the conductive layers on both sides of the substrate 542 may prevent stress provided to the substrate 542 and lead to the uniform manufacture of the RF electrode.

Figure 54D:
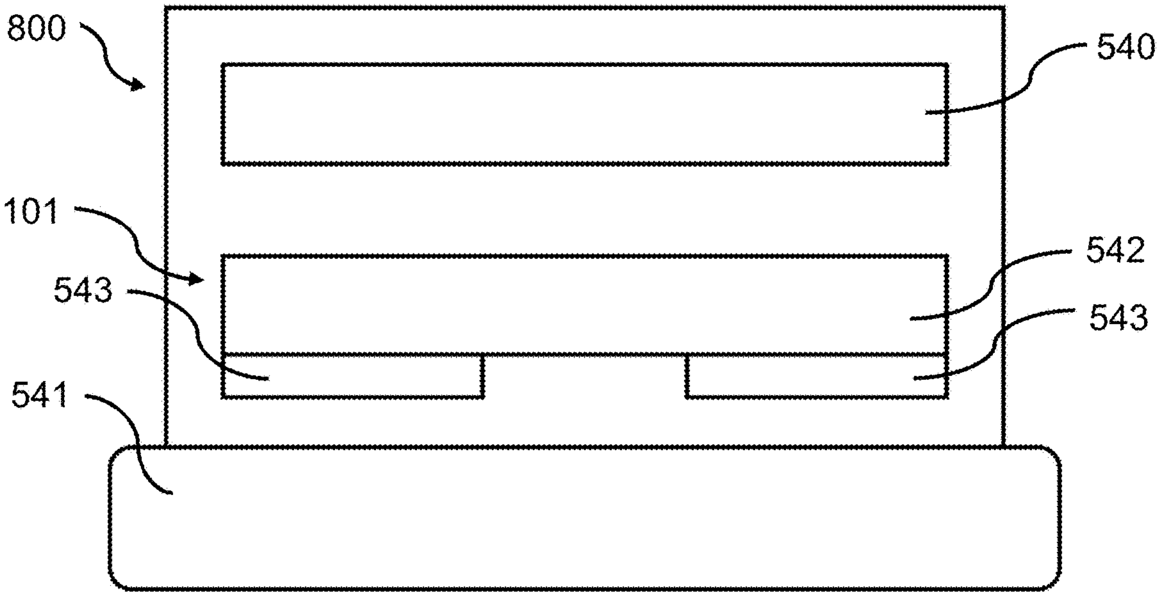

FIG. 54*d* illustrates an applicator 800, wherein the RF electrode 101 includes a substrate 542 covered by a conductive layer 543 on a side closer to the body area 541, and wherein the conductive layer 543 may be applied as a discontinuous layer. The discontinuity of the conductive layer 543 may include any example including protrusions, cutouts or apertures. Similarly, the discontinuity of the conductive layer 543 may provide lower generation of the eddy currents in the conductive layer 543 of the RF electrode 101.

Figure 54E:
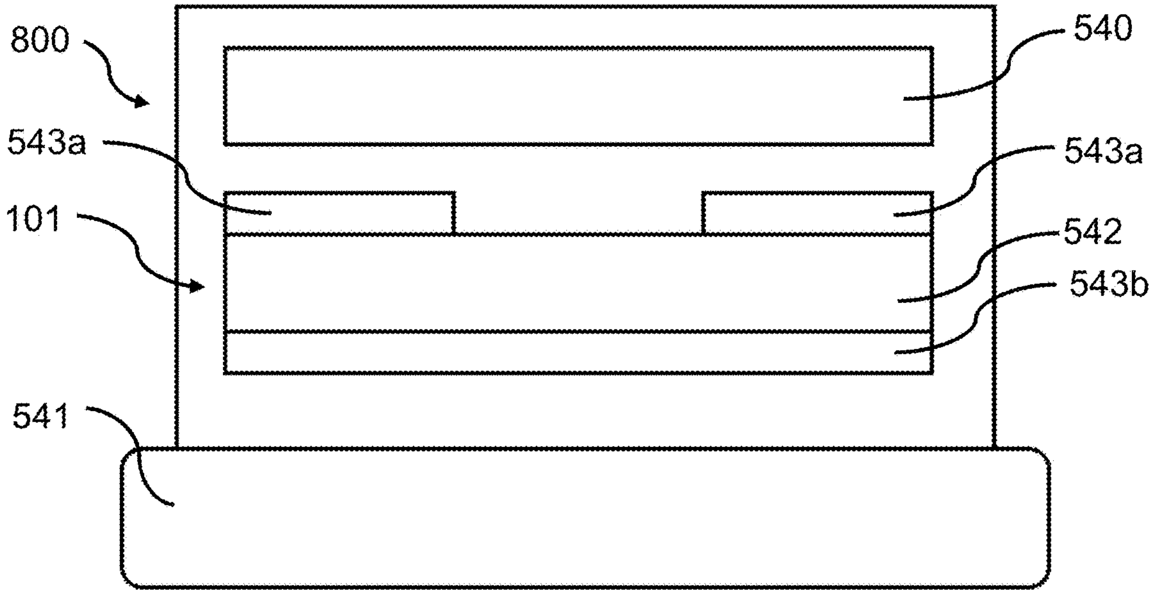

FIG. 54*e* illustrates an applicator 800, where the RF electrode 101 includes a substrate 542 covered by conductive layers 543*a* and 543*b* on both sides of the substrate 542, wherein the conductive layer 543*a* may not be applied as a continuous layer. The conductive layer 543*a* may be applied discontinuously on the side of the substrate 542 closer to the magnetic field generating device 540. The discontinuity of the conductive layer 543*a* may include any example including protrusions, cutouts or apertures. Similarly, the discontinuity of the conductive layer 543*a* may provide lower generation of the eddy currents in the conductive layer 543*a* of the RF electrode 101.

Figure 54F:
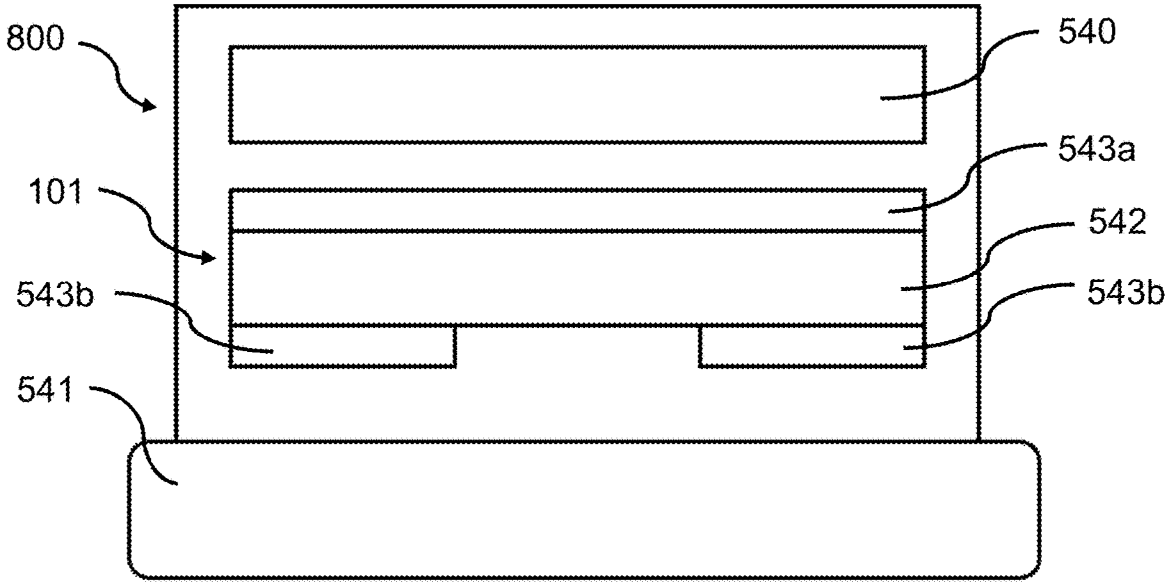

FIG. 54*f* illustrates an applicator 800, where the RF electrode 101 includes a substrate 542 covered by conductive layers 543*a* and 543*b* on both sides of the substrate 542, wherein the conductive layer 543*b* may not be applied as a continuous layer. The layer 543*b* may be applied discontinuously on the side of the substrate 542 closer to the body area 541. The discontinuity of the conductive layer 543*b* may include any example including protrusions, cutouts or apertures. Similarly, the discontinuity of the conductive layer 543*b* may provide lower generation of eddy currents in the conductive layer 543*b* of the RF electrode 101.

Figure 54G:
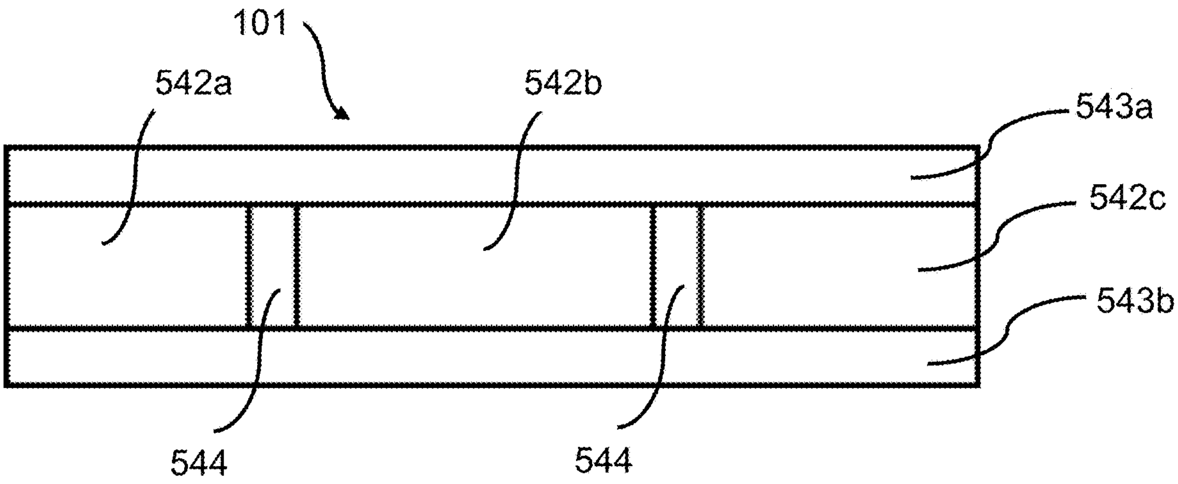
FIG. 54*g* illustrates an RF electrode including sutures.

FIG. 54*g* illustrates the RF electrode 101 including a substrate 542 with parts 542*a-c*, wherein the substrate 542 is covered by conductive layers 543*a* and 543*b*. The conductive layers 543*a*, 543*b* may be connected through substrate 542 by sutures 544, wherein the sutures 544 may be made from conductive or semiconductive material.

The illustrated positions of the RF electrode in FIGS. 54*a*-54*g* are only exemplary. One or more RF electrodes may be positioned above the magnetic field generating device or next to the magnetic field generating device.

The RF electrode may be a system of thin conductive wires, flat stripes, strips, sheets or the like.

The RF electrode may be manufactured from a conductive material that reduces induction of unwanted physical effects and heating of the RF electrode.

The RF electrodes may be made of specific conductive materials, reducing induction of unwanted physical effects in the RF electrode. Such materials may have relative permeability in a range of 4 to 1,000,000, or 20 to 300,000, or 200 to 250,000, or 300 to 100,000, or 300 to 18,000, or 1,000 to 8,000. Material of the RF electrode may include carbon, aluminum, copper, nickel, cobalt, manganese, zinc, iron, titanium, silver, brass, platinum, palladium and/or others from which may create alloys, such as Mu-metal, permalloy, electrical steel, ferritic steel, ferrite, stainless steel of the same. In addition, the RF electrode may be made from mixed metal oxides and/or fixed powder from metal oxides, metal from m-metal elements to minimize induction of eddy currents and heating of the RF electrode and also in order to minimize energy loss of time-varying magnetic field.

As mentioned, the RF electrode may include a conductive layer. The conductive layer may be deposited on a substrate, but the substrate is optional. The RF electrode may comprise only the conductive layer. One or more RF electrodes may be positioned in the same plane or in different planes. For example, two RF electrodes may be arranged in one horizontal plane, while a third RF electrode may be arranged in a different horizontal plane, e.g. a parallel horizontal plane. The RF electrodes arranged in different planes may be in overlay with one another. The RF electrodes may be separated by air or an insulating material (e.g. plastic). For example, the RF electrodes may be separated by a plastic used in a printed circuit board (PCB). The configuration, distance, and overlay of the RF electrodes may provide different depths of penetration of the RF waves and therefore different depths of heating to the body of the patient, e.g., dermis and epidermis, or only the epidermis.

Figure 54H:
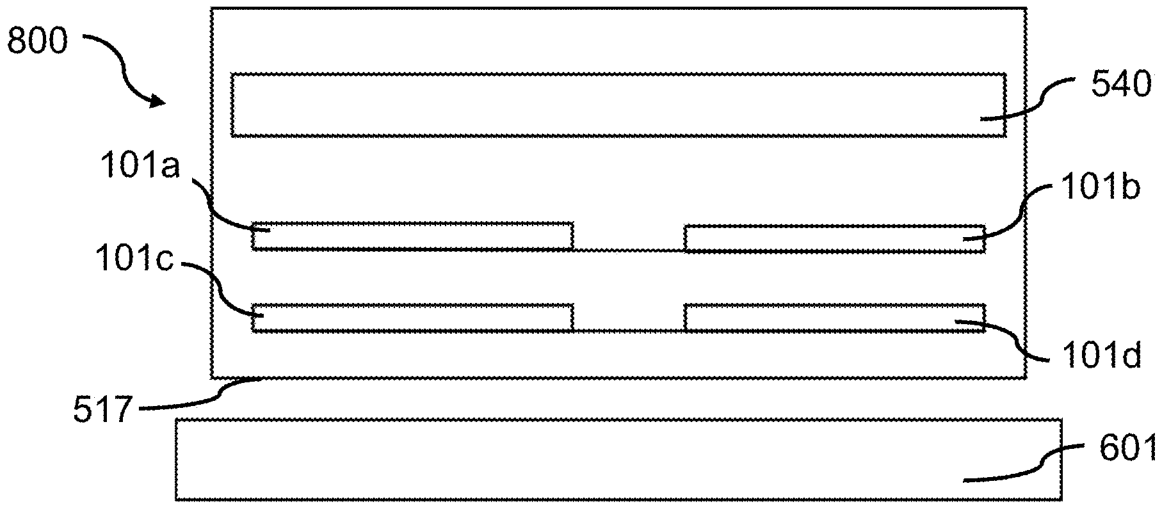
FIGS. 54*h*-54*j* illustrate an exemplary applicator including a plurality of RF electrodes.

FIG. 54*h* illustrates a longitudinal cross sectional view of an applicator 800, with a magnetic field generating device 540 and RF electrodes 101*a*-101*d*. The RF electrodes 101*a*, 101*b* are positioned in a first plane, while the RF electrodes 101*c*, 101*d* are positioned in a second plane that is different from the first plane. Both pairs of RF electrodes may be positioned between the magnetic field generating device 540 and the tissue 601 of the patient. Also, both pairs of RF electrodes may be positioned between the magnetic field generating device 540 and the bottom cover 517 of the applicator 800.

Figure 54I:
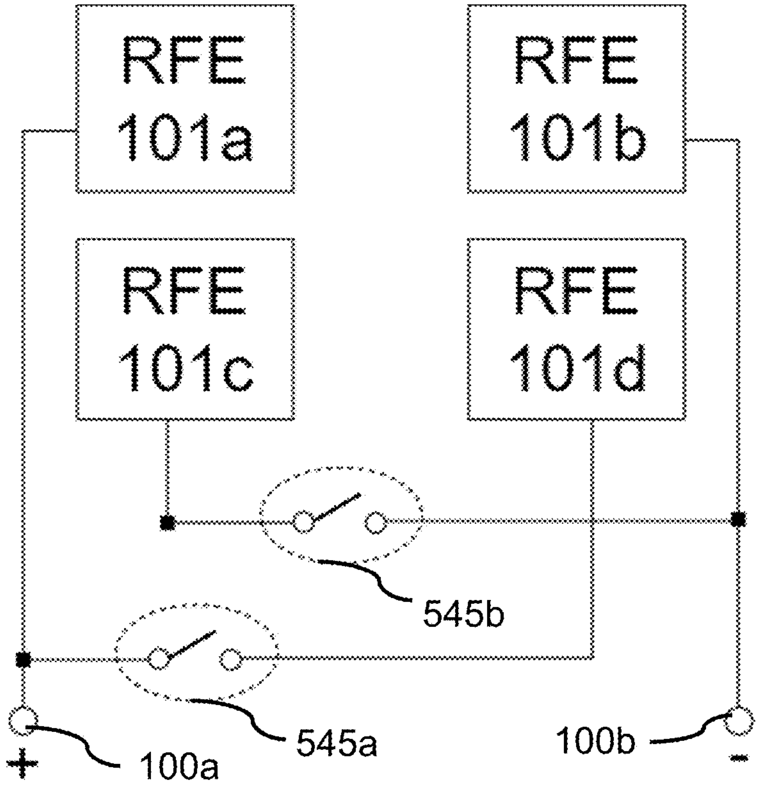

FIG. 54*i* illustrates a schematic arrangement of four RF electrodes and a related circuit including two wirings 100*a* and 100*b*, providing the RF signal. Although the wirings 100*a* and 100*b* are shown with positive or negative polarity, their mutual polarity is changing with the frequency of the RF signal. With the changing polarity of the wirings, the mutual polarity of the RF electrodes connected to the wirings is also changing. The RF electrode 101*a* is directly connected to the wiring 100*a*, while the RF electrode 101*b* is directly connected to the wiring 100*b*. Two RF electrodes 101*a* and 101*b* may establish a first bipolar electrode pair, when the wirings 100*a* and 100*b* are active, meaning they are providing the RF signal. The RF electrode 101*d* is connected to the wiring 100*a* through RF switch 545*a*, while the RF electrode 101*c* is connected to the wiring 100*b* through RF switch 545*b*. The RF switches 545*a*, 545*b* may be closed or open (as shown in FIG. 54*i*). When the wirings 100*a* and 100*b* are active and the RF switches 545*a*, 545*b* are open, the RF electrodes 101*c* and 101*d* are not active. When the wirings 100*a* and 100*b* are active and the RF switches 545*a* and 545*b* are closed, the RF electrodes 101*c* and 101*d* establish a second bipolar electrode pair. When both bipolar electrode pairs are active, the position of the RF switches 545*a*, 545*b* and related connection of circuit results in the presence of one RF electrode (e.g. 101*a*) above an RF electrode of opposite polarity (e.g. 101*c*). When both bipolar electrode pairs are active at same time, the second bipolar electrode pair may absorb at least part of the RF waves generated by the first bipolar electrode pair. However, the second bipolar electrode pair may also generate RF waves. Since the RF waves generated by the first bipolar electrode pair are partly absorbed by the second bipolar electrode pair, the RF waves generated by the first bipolar electrode pair may not be able to penetrate the treated tissue to deeper layers. However, the RF waves generated by the second bipolar electrode pair are closer to the patient and may be able to reach the deeper layers of tissue. Therefore, the illustrated schematic arrangement of four RF electrodes and the related circuit may be able to provide heating of deep tissue layers and shallow tissue layers at the same time during a treatment session. The deep tissue layer(s) may include the hypodermis and/or muscular layer, while the shallow tissue layer(s) may include the dermis and/or epidermis. Further, similar results may be achieved by closing only one of the RF switches 545*a* or 545*b*.

Figure 54J:
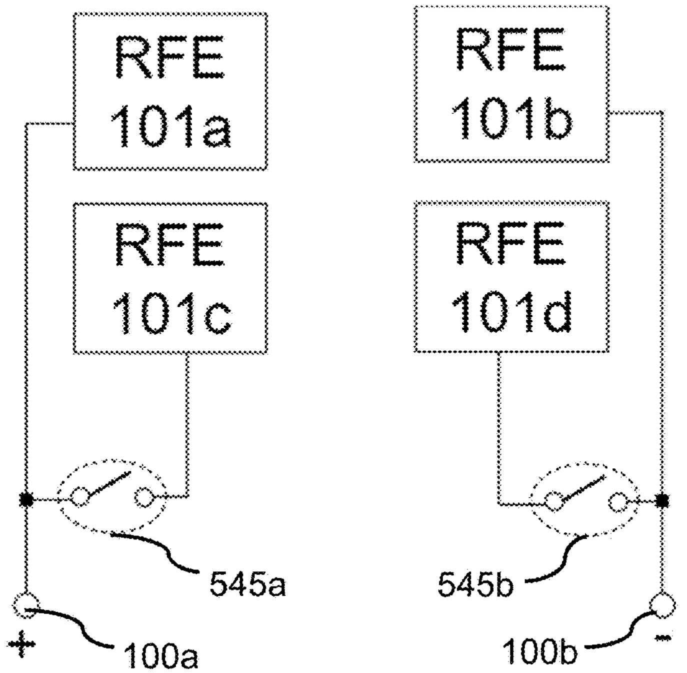

FIG. 54*j* illustrates another schematic arrangement of four RF electrodes and a related circuit including two wirings 100*a* and 100*b* providing RF signal. Although the wirings 100*a* and 100*b* are shown with positive or negative polarity, their mutual polarity is changing with the frequency of the RF signal. With the changing polarity of the wirings 100*a*, 100*b*, the mutual polarity of the RF electrodes connected to the wirings is also changing. The RF electrode 101*a* is directly connected to the wiring 100*a*, while the RF electrode 101*b* is directly connected to the wiring 100*b*. Two RF electrodes 101*a* and 101*b* may establish a first bipolar electrode pair, when the wirings 100*a* and 100*b* are active, meaning they are providing the RF signal. The RF electrode 101*c* is connected to the wiring 100*a* through RF switch 545*a*, while the RF electrode 101*d* is connected to the wiring 100*b* through RF switch 545*b*. The RF switches 545*a*, 545*b* may be closed or open (as shown in FIG. 54*j*). When the wirings 100*a*, 100*b* are active and the RF switches 545*a*, 545*b* are open, the RF electrodes 101*c*, 101*d* are not active. When the wirings 100*a*, 100*b* are active and the RF switches 545*a*, 545*b* are closed, the RF electrodes 101*c*, 101*d* establish a second bipolar electrode pair. When both bipolar electrode pairs are active at the same time, the second bipolar electrode pair may absorb at least part of the RF waves generated by the first bipolar electrode pair. However, since one RF electrode is positioned below another RF electrode with the same polarity, the amount of absorbed RF waves may be lower than in the example of FIG. 54*i*. Further, as shown in FIG. 54*i*, when two RF electrodes 101*c*, 101*d* are positioned closer to each other than the RF electrodes 101*a* and 101*b*, the bipolar electrode pair comprising the RF electrodes 101*c*, 101*d* may provide RF waves providing heating of one or more shallow tissue layers. Therefore, when both bipolar electrode pairs are active at the same time, the RF waves provided by RF electrodes 101*c*, 101*d* may provide heating of one or more shallow tissue layers, while the RF waves provided by RF electrodes 101*a*, 101*b* may provide heating of one or more deeper tissue layers of the same body area. It should be noted that the position of the pairs of RF electrodes providing heating of different tissue layers may be switched, i.e. when the RF electrodes 101*a*, 101*b* are positioned closer to each other than RF electrodes 101*c*, 101*d*, the RF waves provided by RF electrodes 101*a*, 101*b* may provide heating of one or more shallow tissue layers, while the RF waves provided by RF electrodes 101*c*, 101*d* may provide heating of one or more deeper tissue layer of the same body area.

Figure 54K:
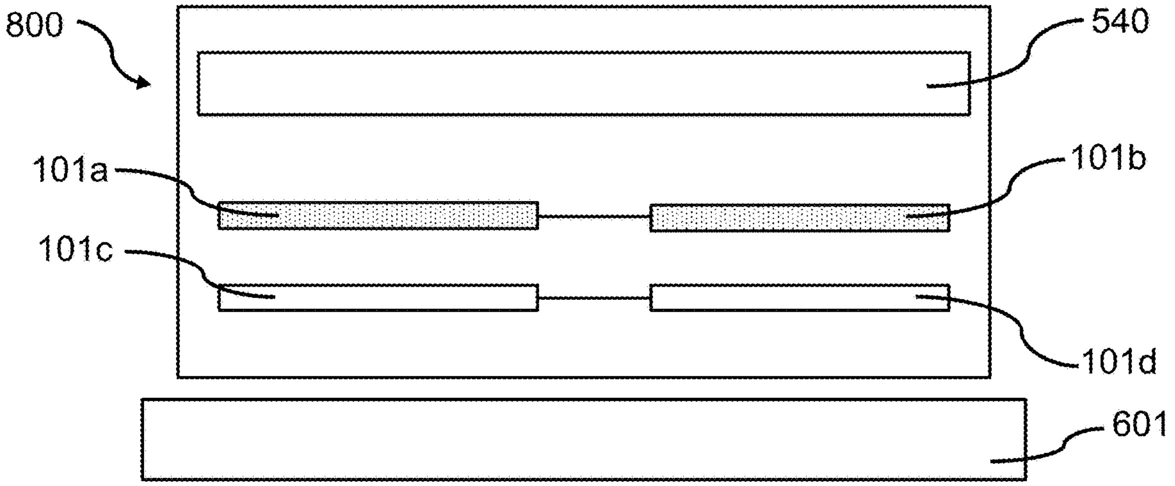
Figure 54I:
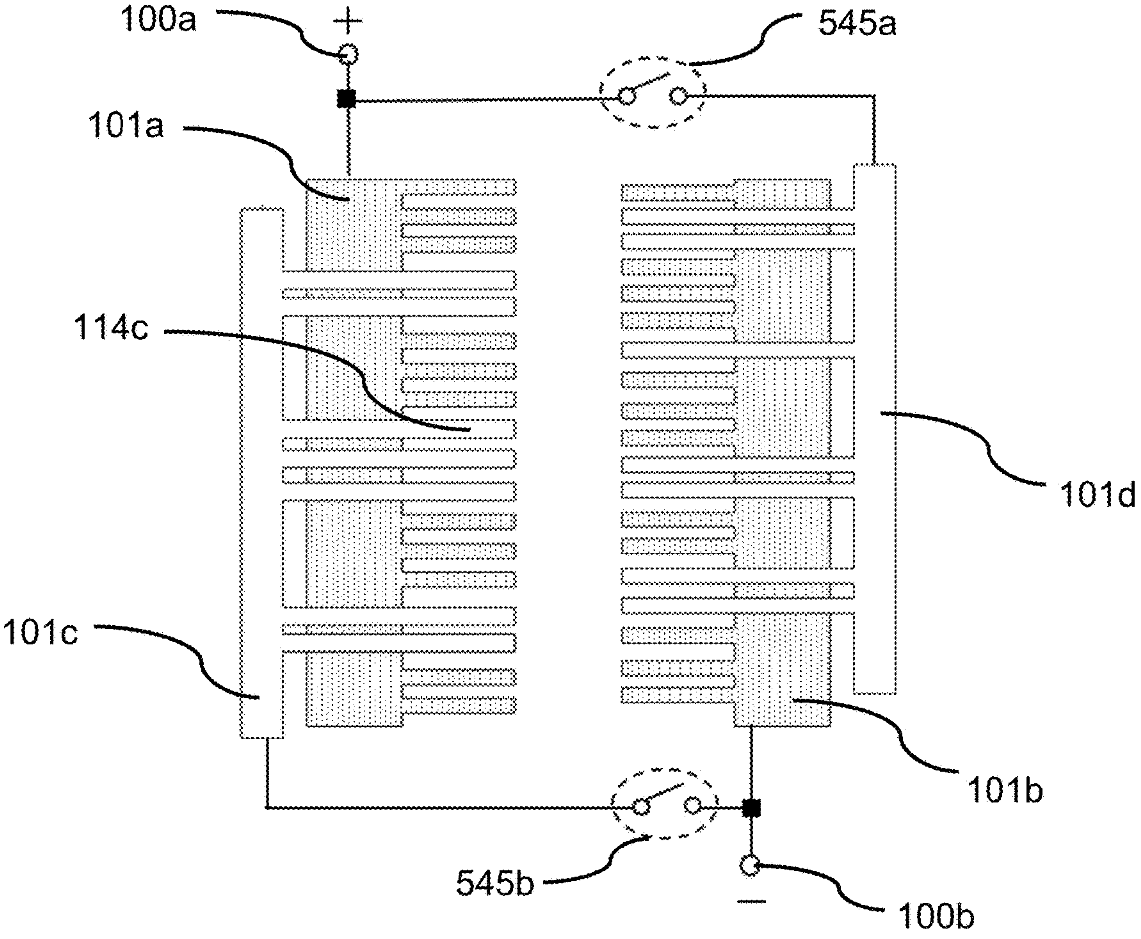

FIG. 54*k* illustrates another longitudinal cross sectional view of an applicator 800, with a magnetic field generating device 540 and RF electrodes 101*a*-101*d*. The RF electrodes 101*a*, 101*b* are positioned in a first plane, while the RF electrodes 101*c*, 101*d* are positioned in a second plane that is different from the first plane. Both pairs of RF electrodes may be positioned between the magnetic field generating device 540 and the tissue 601 of the patient. However, only one pair of RF electrodes may be present. The following FIGS. 54*i*-54*k* are views from below the applicator. Therefore, FIGS. 54*i*-54*k* may be viewed as further examples of the positioning of the RF electrodes.

FIG. 54*l* illustrates an example of FIG. 54*i*, where four RF electrodes 101*a*-101*d* are RF electrodes with openings, e.g. cutouts and protrusions. As shown, the RF electrode 101*c* being below the RF electrode 101*a* has at least one protrusion 114*c* below the RF electrode 101*a*. The RF electrodes 101*a* and 101*d* may be connected by an electrical circuit comprising the RF switch 545*a*. When the RF switches 545*a* and 545*b* are open, the RF electrodes 101*c* and 101*d* are not powered and only bipolar RF electrodes 101*a* and 101*b* establishing first bipolar electrode pair are active. When the RF switches 545*a* and 545*b* are closed, the RF electrodes 101*c* and 101*d* are powered and the second bipolar electrode pair is active together with the first bipolar electrode pair. The advantages of this connection of the RF electrodes and RF switches is described in relation to FIG. 54*i*.

Figure 54M:
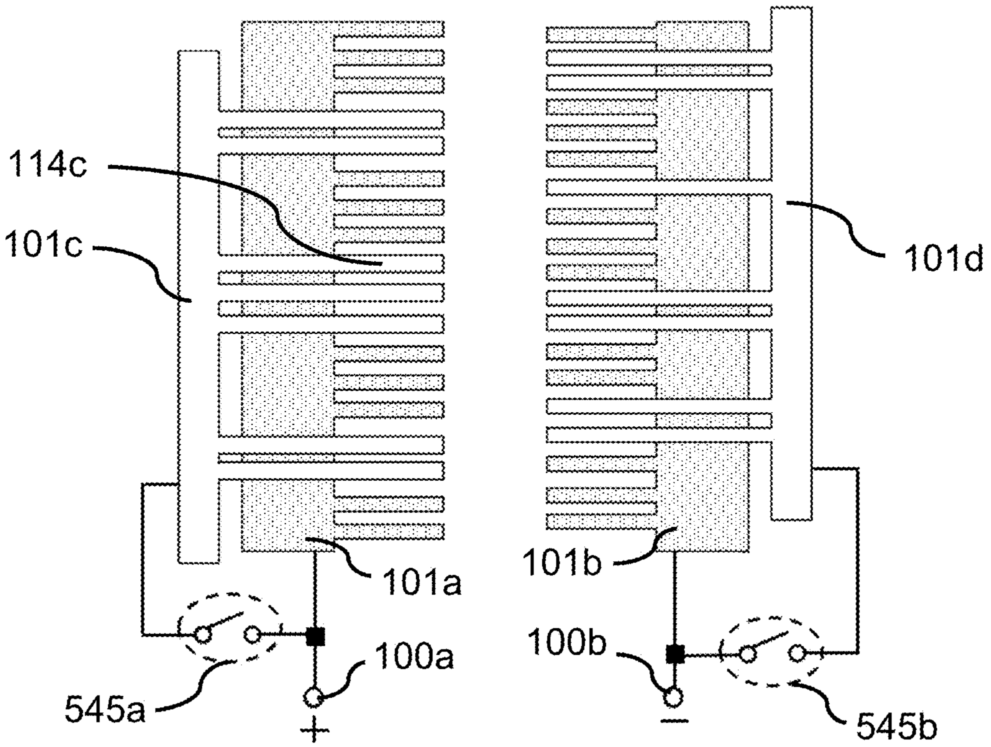

FIG. 54*m* illustrates an example of FIG. 54*j*, where four electrodes 101*a*-101*d* are RF electrodes with openings, e.g. cutouts and protrusions. As shown, the RF electrode 101*c* being below the RF electrode 101*a* has at least one protrusion 114*c* below the RF electrode 101*a*. The RF electrodes 101*a* and 101*c* may be connected by an electrical circuit comprising an RF switch 545*a*, while the RF electrodes 101*b* and 101*d* are connected by an electrical circuit comprising an RF switch 545*b*. The advantages of this connection of the RF electrodes is described in relation to FIG. 54*j*. When two RF electrodes 101*c* and 101*d* are positioned closer to each other than the RF electrodes 101*a* and 101*b*, the bipolar electrode pair comprising the RF electrodes 101*c* and 101*d* may provide RF waves providing the heating of one or more shallow tissue layers. In such case, the one or more protrusions of the RF electrode 101*c* may be positioned between the protrusions of the RF electrode 101*d*.

Figure 54N:
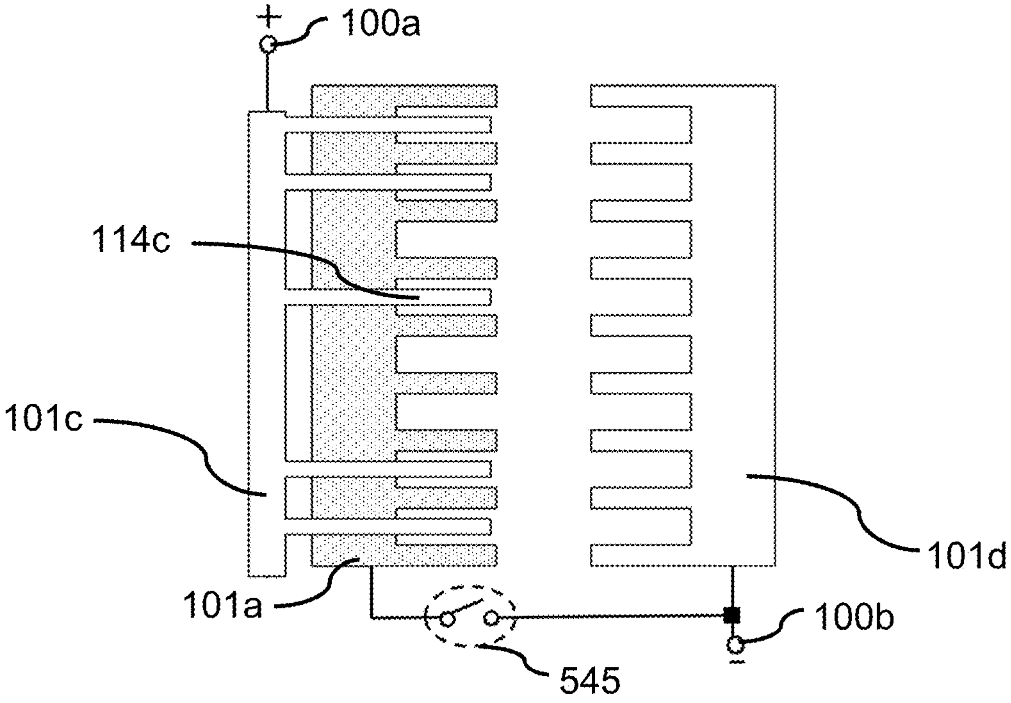

FIGS. 54*l* and 54*m* are exemplary illustrations of the possible connection of the RF switch to the RF electrodes. Also, FIGS. 54*l* and 54*m* are exemplary illustrations of possible connections of the wiring to the RF electrodes above the other two bipolar electrodes. It is possible to connect the wiring 100*a* and/or wiring 100*b* to the RF electrodes 101*c* and/or 101*d* positioned below the RF electrodes 101*a* and 101*b*. It is also possible to have only one pair of RF electrodes in one plane and another RF electrode in different plane. FIG. 54*n* illustrates an example of such different configuration of one bipolar pair and one RF electrode. The three RF electrodes 101*a*, 101*c*, and 101*d* are RF electrodes having openings, e.g. cutouts and protrusions. As shown, the RF electrode 101*c* is arranged below the RF electrode 101*a* and has one or more protrusions 114*c* below the RF electrode 101*a*. The RF electrode 101*c* is directly connected to wiring 100*a*, while the RF electrode 101*d* is directly connected to wiring 100*b*. The RF electrodes 101*c* and 101*d* establish a bipolar electrode pair. RF electrode 101*a* is positioned above the RF electrode 101*c* and is connected to the wiring 100*b* through RF switch 545. When the RF switch 545 is closed, the RF electrode 101*a* positioned above the RF electrode 101*c* becomes active and has an opposite polarity relative to RF electrode 101*c*. The direction of radiofrequency waves traveling between the bipolar electrode pair (i.e. the RF electrodes 101*c* and 101*d*) is altered by the presence of active RF electrode 101*a*. As a result, the RF waves may reach only a shallow depth of the tissue. In this way, the radiofrequency waves may provide a different depth of heating to the body of the patient.

When one pair of bipolar RF electrodes is housed within the applicator, the applicator may include a motion mechanism configured to allow the distance between the RF electrodes to be selectively adjusted in order to change the depth of heating by the RF waves generated by the RF electrodes. For example, the motion mechanism may include a rotor or shaft configured to move a first RF electrode closer to (or farther from) a second RF electrode or to move both RF electrodes toward (or away from) a center of the applicator.

Figure 55A:
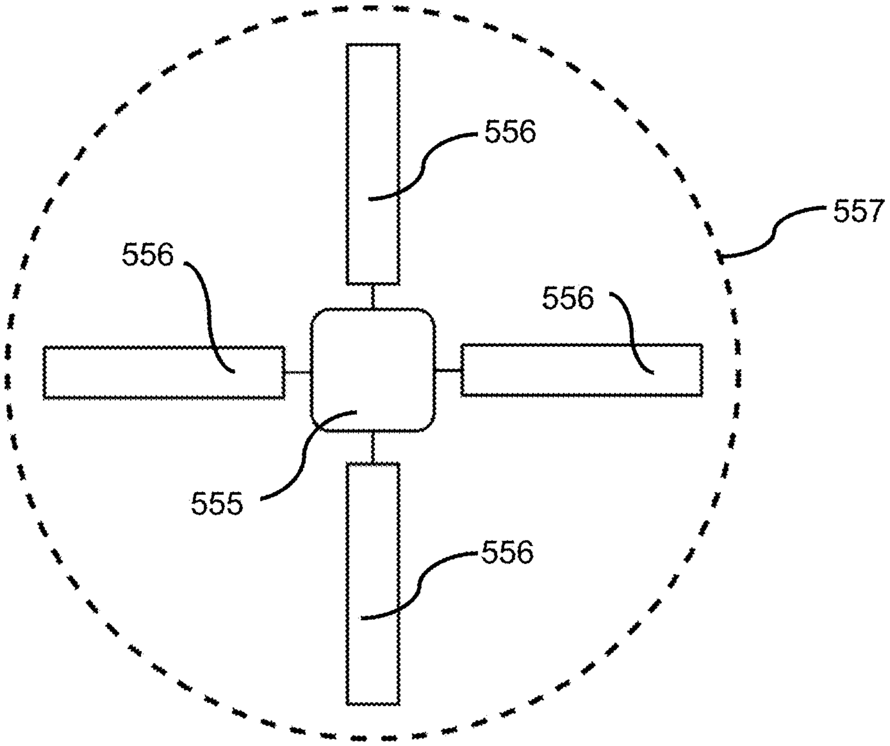
FIGS. 55*a*-55*b* illustrate an impedance element.
Figure 55B:
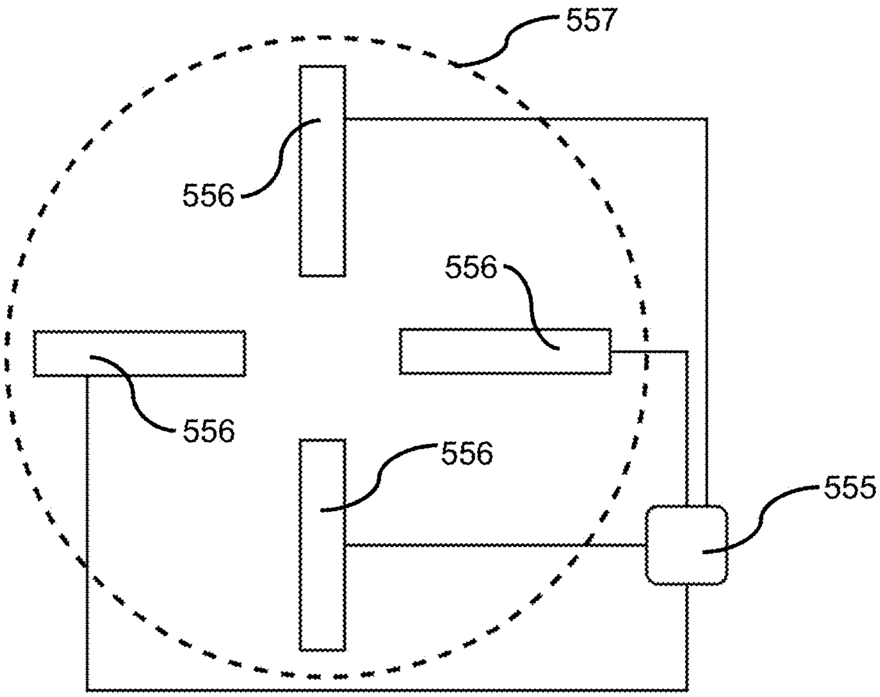

Unwanted physical effects may be minimized or eliminated by using a combination of a magnetic field generating device with a plurality of RF electrodes together with an impedance element. A plurality of RF electrodes may be connected to at least one impedance element. As illustrated in FIG. 55*a*, the at least one RF electrode of the plurality of RF electrodes 556 and the impedance element 555 may be positioned below and in at least in partial overlay with the magnetic field generating device 557. The at least one RF electrode of the plurality of RF electrodes 556 and the impedance element 555 may be positioned between the magnetic field generating device 557 and the body of the patient. Alternatively, as shown in FIG. 55*b*, the impedance element 555 may be positioned in a position other than below the magnetic field generating device 557. The impedance element 555 may be part of the RF circuit. During the operation of the magnetic field generating device 557 and/or RF electrodes 556, the impedance element 555 may provide and/or spread RF signal in the surface, such that the RF signal may be delivered to the plurality of RF electrodes 556. During the simultaneous or sequential operation of the magnetic circuit, the impedance element 555 may be perceived by the line of forces of the magnetic field as a part of the disconnected electric circuit. In such configuration, the impedance element may not significantly influence the transmissivity of the magnetic field. By using the impedance element, the RF electrodes positioned below and/or in at least partial overlay with the magnetic field generating device 557 may include RF electrodes without openings and/or protrusions.

The impedance element 555 may include one or more electrical elements. The impedance element 555 may be an impedance filter element. The impedance element 555 may be a low-pass filter, high-pass filter, band-pass filter, or band-stop filter. The impedance element 555 may include a capacitor, e.g. a film capacitor, electrolytic capacitor, ceramic capacitor, polymer capacitor, Mica capacitor, glass capacitor, super capacitor, and/or tantalum capacitor. The impedance element 555 may include a magnetic coil which may have a smaller diameter than the magnetic field generating device used to generate the magnetic field. The impedance element 555 may include a resistor. The impedance element 555 may be positioned on the applicator by surface-mount technology. The impedance element 555 may be connected by wires to one or more RF electrodes 556 of the plurality of RF electrodes positioned in at least partial overlay with magnetic field generating device 557. The impedance element 555 may be positioned in direct contact with the one or more RF electrodes 556 of the plurality of RF electrodes positioned in at least partial overlay with magnetic field generating device 557, e.g. by surface-mount technology. The impedance element 555 may be a leadless element, so the absence of leads may prevent influence of the magnetic field generated by magnetic field generating device.

Unwanted physical effects related to use of a combination of magnetic field with radiofrequency waves may be minimized or eliminated by using an RF electrode made from a metal foam. The metal foam may be a structure that includes a solid metal body with pores. Pores may be filed by fluid, e.g., a gas. The presence of the plurality of pores within the metal foam may provide discontinuity of the solid material for presence of eddy currents generated by magnetic field generating device. The metal may be aluminum, steel, zinc, tin, nickel, copper, silver, Mu-metal, and/or others. Also, the alloys based on mentioned metals may be used. The pore sizes of the pores in the metal foam may be in a range of 50 μm to 5,000 μm, or 200 μm to 4,000 μm, or 300 μm to 3,000 μm. The porosity, defined as percentage of pores in the metal foam, may be in a range of 10% to 99%, or 25% to 99%, or 50% to 99%.

Unwanted physical effects related to the use of a combination of magnetic field with radiofrequency waves may be minimized or eliminated by using an RF electrode including a textile made from one or more conductive fibers. Such conductive fibers may be manufactured from fibers comprising metal, metallic alloys, metal coated with insulating material, dielectric material coated with metal, and/or insulating material coated with metal. The dielectric material or insulating material may provide higher mechanical stability. The metal may include silver, steel, nickel, gold, copper, aluminum, chromium, tungsten, and/or their alloys. The diameter of the fiber may be in a range of 0.1 μm to 2,000 μm, or 0.5 μm to 1000 μm, or 1 μm to 250 μm. The warp density of the textile, defined as the number of warp threads per inch of the textile, may be in a range of 30 ends per inch to 250 ends per inch, or 35 ends per inch to 230 ends per inch, or or 40 ends per inch to 220 ends per inch. The weft density, defined as the number of weft threads per inch of the textile, may be in a range of 20 picks per inch to 300 picks per inch, or 30 picks per inch to 275 picks per inch, or 40 picks per inch to 200 picks per inch. The use of RF electrode designed as a textile may provide prevention of unwanted physical effects, because the textile may include openings and/or advantageous positioning of the at least one fibers.

The RF electrode may include a conductive polymer, e.g., in the form of a polymer salt. Such conductive polymer may include an aromatic ring and/or at least one double bond. The conductive polymer may include a nitrogen and/or sulphur atom. For example, the conductive polymer may include poly(pyrrole)s (PPY), poly(thiophene)s (PT), poly(3,4-ethylendioxythiophene) (PEDOT), poly(p-phenylene sulfide) (PPS), polyanilines (PANT), poly(acetylene)s (PAC), and/or poly(p-phenylene vinylene) (PPV).

One or more RF electrodes providing RF energy during the treatment by described treatment device may use at least one of the possibilities, at least two possibilities and or combination of possibilities how to minimize or eliminate unwanted physical effects induced by magnetic field as described above. Also, one or more characterizations of any possibility may be used for manufacture, design and operation of the treatment device.

In one example, a combination of designs mentioned above may include the use of an RF electrode having a substrate plated on at least one side with a conductive layer made of a conductive material, e.g., copper and/or nickel, and the RF electrode may include a plurality of openings in the conductive area of the RF electrode.

In another example, an RF electrode may have a substrate plated on at least one side with a conductive layer, wherein the electrode areas may not include any openings. The treatment device combining RF treatment with magnetic treatment may include one or more treatment circuits. The treatment circuit for RF treatment may include power source, RF electrode and/or all electrical elements described herein for RF cluster. The treatment circuit for magnetic treatment may include power source, magnetic field generating device, all electrical elements described herein for magnetic cluster HIFEM. Plurality of treatment circuits providing same or different treatment may include common power source. Alternatively, each treatment circuit may include its own power source. Operation of all treatment circuits may be regulated by one master unit or one or more control units. The HMI, master unit and/or one or more control unit may be used for selection, control and/or adjustment of one or more treatment parameters for each applicator and/or each treatment energy source (e.g. RF electrode or magnetic field generating device). Treatment parameters may be selected, controlled and/or adjusted by HMI, master unit, and/or one or more control unit independently for each applicator.

Further, the RF electrode may include different RF electrode portions, wherein the delivery of the RF signal into the RF electrode portions may be controlled by the control system. For example, the RF electrode may include two or more RF electrode portions. The temperature of each RF electrode portion may be detected by one or more temperature sensors, wherein the temperature sensors are positioned in close proximity of the RF electrode portion or in contact with RF electrode portion. The one or more temperature sensors may communicate with any part of the control system. Based on this feedback, the control system may control and manipulate the delivery of the RF signal to each RF electrode portion.

Figure 17:
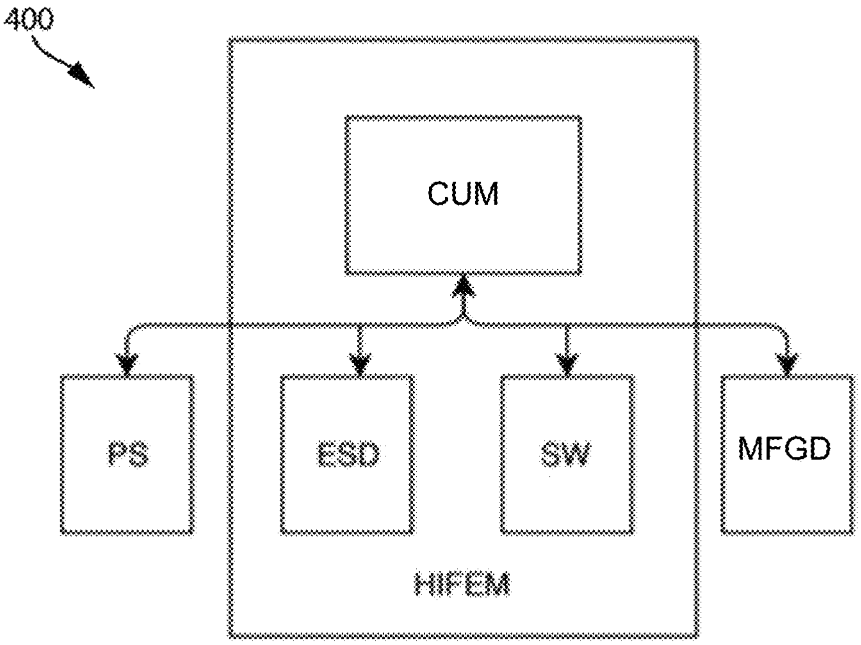
FIG. 17 illustrates an exemplary schema of a magnetic circuit.

FIG. 17 illustrates exemplary electrical elements of a magnetic circuit 400. The electrical signal passing through the magnetic circuit 400 may be transformed into a form of one or more pulses of electrical signal. The electric pulses may be provided to magnetic field generating device in order to generate impulses of time-varying magnetic field. Individual electrical elements of the magnetic circuit may be a power source (PS), an energy storage device (ESD), a switch (SW), magnetic field generating device (MFGD) and control unit of magnetic circuit (CUM). The magnetic circuit may include treatment cluster for magnetic treatment called as HIFEM cluster. The HIFEM cluster may include e.g. ESD, SW and/or CUM. Control unit of magnetic circuit CUM may be part of the control system. Control unit of magnetic cluster CUM and/or other electrical element of magnetic circuit may be slave of the master unit. The HIFEM cluster, control system and/or CUM may provide or control storage of electric energy in ESD by controlling the amount of stored electrical energy. HIFEM cluster, control system and/or CUM may provide modification of electrical signal, adjustment of parameters of electric signal transferred through HIFEM cluster, safe operation of the circuit and/or charging or recharging of the ESD. For example, the HIFEM cluster or control system may provide adjustment of magnetic flux density of magnetic field provided by MFGD by adjustment of voltage and/or current of electrical pulses transferred to MFGD. Modification of the electrical signal may include a distortion of signal transmitted in magnetic circuit, envelope distortion in shape, amplitude and/or frequency domain, adding noise to the transferred electrical signal and/or other degradation of transmitted original signal entering the magnetic circuit. One CUM may control and/or operate one or more magnetic treatment circuits.

Figure 18A:
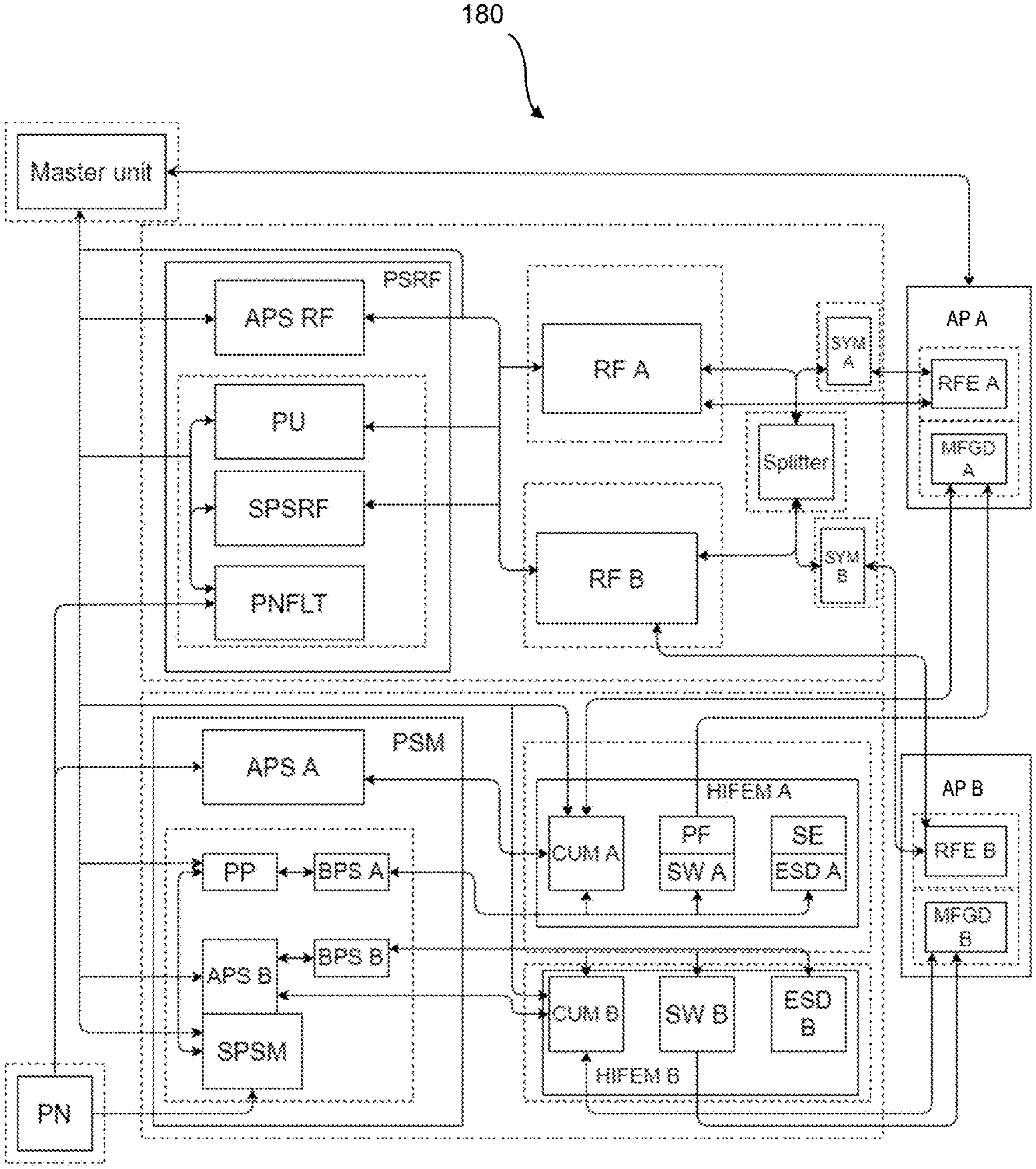
FIG. 18*a* illustrates an exemplary schema of electrical elements of a treatment device.

The energy storage device ESD, may accumulate electrical energy, which may be provided to magnetic field generating device in the form of electric signal (e.g. in form of high power impulses) of energy. The ESD may include one, two, three or more capacitors. The ESD may also include one or more other electrical elements such as a safety element, such as a voltage sensor, a high voltage indicator, and/or discharging resistors, as shown in FIG. 18*a*. The voltage sensor and the high voltage indicator may provide feedback information to the switch SW and or to control unit CUM. The discharging resistor being a part of the magnetic circuit may provide discharging of at least one capacitor in case of hazardous situation. Discharging of one or more ESD may be controlled by the control unit CUM. Released electrical energy from the ESD may be delivered as high power impulse and/or pulse to at least part of the magnetic circuit e.g. to the magnetic field generating device MFGD.

A capacitance of energy storage device may be in the range of 5 nF to 100 mF, or in the range of 25 nF to 50 mF, or in the range of 100 nF to 10 mF, or in the range of 1 μF to 1 mF, or in the range of 5 μF to 500 μF or in the range of 10 μF to 180 μF, or in the range of 20 μF to 80 μF.

The energy storage device may be charged on a voltage in a range from 250 V to 50 kV, 700 V to 5 kV, 700 V to 3 kV, or 1 kV to 1.8 kV.

The energy storage device may provide a current pulse discharge in a range from 100 A to 5 kA, 200 A to 3 kA, 400 A to 3 kA, or 700 A to 2.5 kA. The current may correspond with a value of the peak magnetic flux density generated by the magnetic field generating device.

By discharging of the energy storage device, a high power current pulse may be produced with an energy in a range of 5 J to 300 J, 10 J to 200 J, or 30 J to 150 J.

The switch SW may include any switching device, such as a diode, pin diode, MOSFET, JFET, IGBT, BJT, thyristor and/or a combination thereof. The switch may include a pulse filter providing modification of the electrical signal. The pulse filter may suppress switching voltage ripples created by the switch during discharging of the ESD.

The magnetic circuit may be commanded to repetitively switch on/off the switch SW and discharge the energy storage device ESD to the magnetic field generating device, e.g. the coil in order to generate the time-varying magnetic field.

An inductance of the magnetic field generating device may be up to 1 H, or in the range of 1 nH to 500 mH, 1 nH to 50 mH, 50 nH to 10 mH, 500 nH to 1 mH, or in the range of 1 μH to 500 μH or in the range of 10 μH to 60 μH.

The magnetic field generating device may emit no radiation (e.g. gamma radiation).

The magnet circuit may include a series connection of the switch SW and the magnetic field generating device. The switch SW and the magnetic field generating device together may be connected in parallel with the energy storage device ESD. The energy storage device ESD may be charged by the power source PS. After that, the energy storage device ESD may be discharged through the switch SW to the magnetic field generating device MFGD. During a second half-period of LC resonance, the polarity on the energy storage device ESD may be reversed in comparison with the power source PS. As a result, there may be twice the voltage of the power source. Hence, the power source and all parts connected in the magnetic circuit may be designed for a high voltage load and protective resistors may be placed between the power source and the energy storage device.

The magnetic field generating device MFGD and an energy storage device ESD may be connected in series. The magnetic field generating device MFGD may be disposed in parallel to the switch SW. The energy storage device ESD may be charged through the magnetic field generating device. To provide an energy impulse to generate a magnetic impulse (or pulse to generate a magnetic pulse), controlled shorting of the power source takes place through the switch SW. In this way the high voltage load at the terminals of the power source PS during the second half-period of LC resonance associated with known devices is avoided. The voltage on the terminals of the power source PS during second half-period of LC resonance may have a voltage equal to the voltage drop on the switch SW.

The switch may be any kind of switching device. Depending on the type of the switch, the load of the power source may be reduced to a few Volts, e.g., 1-10 volts. Consequently, it is not necessary to protect the power source from a high voltage load, e.g., thousands of Volts. Accordingly, the use of protective resistors and/or protection circuits may be reduced or eliminated.

Figure 18B:
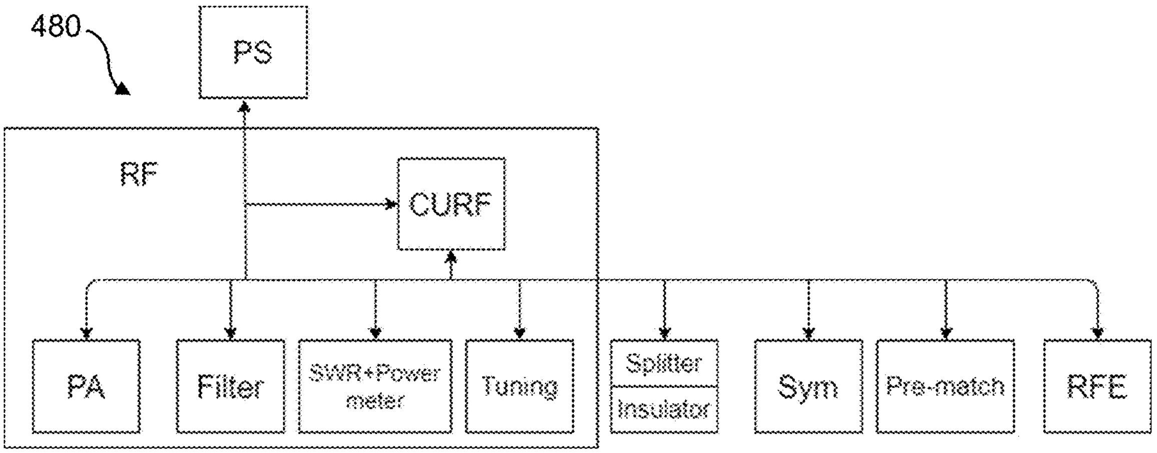
FIG. 18*b* illustrates an exemplary schema of a RF circuit.

FIG. 18*b* illustrates exemplary electrical elements of an RF circuit 480. The RF circuit may provide an adjusted and/or modified electromagnetic signal (electrical signal) to an RF electrode (RFE). The RF circuit may include power source (PS), treatment cluster for RF treatment (area marked as RF), control unit of RF cluster (CURF), power amplifier (PA), filter, standing wave ratio combined with power meter (SWR+Power meter), tuning element (tuning), splitter, insulator, symmetrisation element (SYM), pre-match and RF electrode (RFE). Treatment cluster for RF treatment may include e.g. control unit of RF cluster (CURF), power amplifier (PA), filter, standing wave ratio combined with power meter (SWR+Power meter) and/or tuning element (tuning). Control unit of RF circuit CURF may be part of the control system. Control unit of RF circuit CURF and/or other electrical element of RF circuit may be slave of the master unit. One or more electrical elements described as a part of RF circuit may be dismissed, some of the electrical elements may be merged to one with similar function and/or some of the electrical elements may be added to improve functionality of the circuit.

The power source of the RF circuit may provide an electric signal of a voltage in a range of 1 V to 5 kV, or 5 V to 140 V, or 10 V to 120 V, or 15 V to 50 V, or 20 V to 50 V. The power source of the RF circuit and the power source of the RF treatment may be identical. The power source of the RF treatment may also be called the adapter. The adapter may provide a voltage in a range of 5 to 100 Volts, 10 to 80 Volts or 15 to 45 Volts. For example, the adapted may provide a voltage of 24 Volts. The adapter may include a filter.

The CURF may control operation of any electrical element of RF circuit. The CURF may regulate or modify parameters of the electrical signal transferred through the RF circuit. Parameters of the signal, e.g., voltage, phase, frequency, envelope, value of the current, amplitude of the signal and/or other may be influenced by individual electrical elements of the RF circuit that may be controlled by CURF, control system and/or electrical properties of individual electrical elements of RF circuit. Electrical elements influencing signal in the RF circuit may be, for example, a power source (PS), a power amplifier (PA), a filter, a SWR+Power meter, a tuning, a splitter, an insulator, symmetrisation element changing unbalanced signal to balanced signal (SYM), pre-match and/or RF electrode generating RF waves. Modification of the electrical signal may include a distortion of signal transmitted in RF circuit, envelope distortion in shape, amplitude and/or frequency domain, adding noise to the transferred electrical signal and/or other degradation of transmitted original signal entering the RF circuit. One CURF may control and/or operate one or more treatment circuits of RF treatment.

The power amplifier PA may produce RF signal of respective frequency for generation of RF waves by RF electrode. The power amplifier may be or may include unipolar transistor, bipolar transistor, MOSFET, JFET LDMOS transistor, field effect transistor, transistor, gallium nitride field effect transistor or vacuum tube. The PA may be able to increase an amplitude of provided signal and/or modified signal to electric signal (e.g. RF signal). The power amplifier may generate the RF signal of the desired power and/or frequency. For example, the power amplifier may generate an RF signal having a frequency in a range of 100 kHz to 3 GHz, 400 kHz to 3 GHz or 400 kHz to 10 MHz. For example, the power amplifier may generate an RF signal having a frequency of 475 kHz, 1 MHz, 2 MHz, 4 MHz, 6 MHz, 13.56 MHz, 40.68 MHz, 27.12 MHz, or 2.45 GHz. The power amplifier may generate this frequency with deviation in a range of 1% to 10%.

The filter may include one or more filters which may suppress unwanted frequency of signal transmitted from the power amplifier. One or more filters may filter and provide treatment with defined band of frequencies. One or more filters may be used to filter the electrical signal such as electric signal in the RF circuit, according to signal frequency domain to let pass only band of wanted frequencies. The filter may be able to filter out unsuitable signal frequencies based on internal software and/or hardware setting of the filter. The filter may operate according to communication with other one or more electrical elements e.g. the CURF. The one or more filters may be located between a power source of RF signal PSRF and the RFE. However, the device may include additional filters located between various other electrical elements of the device.

The SWR+Power meter may measure output power of RF energy and evaluate the quality of impedance matching between the power amplifier and applicator. The SWR+Power meter may include a SWR meter that may measure the standing wave ratio in a direction of a wave transmission. The SWR+Power meter may include a power meter that may measure amplitude of such standing waves. The SWR+Power meter may communicate with the CURF and/or with the tuning element. The SWR+Power meter may provide a feedback information in order to prevent creation of the standing wave in the patient's body, provide better signal adjustment by the tuning element and to provide safer treatment and energy transfer to biological structure more effectively in more targeted manner. For example, the SWR+Power meter may include a power divider that provides part of the power to the detector, which informs the control system about the parameters of the transferred electrical signal.

Tuning element may provide improvement of the impedance matching. The tuning element may include, e.g. capacitor, LC and/or RLC circuit. The tuning element may provide controlled tuning of the RF circuit system capacity, wherein the RF circuit system includes individual electrical elements of the RF circuit and also currently treated tissue of the patient under the influence of the provided RF waves. Tuning of the RF circuit may be provided before and/or during the treatment. The tuning element may also be called a transmatch. The tuning element may include a coil and/or relay, e.g. an electromagnetic relay.

The symmetrisation element SYM may convert the signal from unbalanced input to balanced output. The SYM may be a balun and/or a balun transformer including wound coaxial cable to balance signal between RF electrodes. The SYM element may be a balun of any type including coaxial balun, voltage balun and/or current balun. The SYM element may provide signal symmetrisation between the first and the second bipolar RF electrode e.g. by creating λ/2 phase shift of the RF signal guided through the coaxial cables to the first and the second bipolar RF electrode. The symmetrization element may be present in the applicator or in the main unit. The symmetrization element may also include a toroid coil.

The splitter may split the RF signal transferred/delivered in the RF circuit by a coaxial cable. Divided signal may have the same phase of each divided signal part and/or the divided signals may have constant phase shift from each other. For example, the splitter may provide a first part of the RF signal to a first RF electrode and a second part of the RF signal to a second RF electrode of a bipolar electrode system. The splitter may be shared for one, two or more independent RF circuits or each RF circuit may have its own splitter. Also, the splitter may provide a first part of the RF signal to a first RF electrode and a second part of the RF signal to a second RF electrode of a bipolar RF electrode system, wherein the first and second RF electrodes are housed in one applicator. Further, the splitter may provide a first part of the RF signal to a first RF electrode and a second part of the RF signal to a second RF electrode of a bipolar RF electrode system, wherein the first RF electrode is housed within a first applicator and the second RF electrode is housed within a second applicator. In case of a monopolar system, the splitter may provide a first part of the RF signal to a first active monopolar RF electrode and a second part of the RF signal to a second active monopolar RF electrode, wherein the first and second RF electrodes are housed in one applicator. Further, the splitter may provide a first part of the RF signal to a first active monopolar RF electrode and a second part of the RF signal to a second active monopolar RF electrode, wherein the first RF electrode is housed in a first applicator and the second RF electrode is housed within a second applicator.

The treatment device may include one or more splitters. The one or more splitters may be positioned within the main unit and/or the applicator. A splitter may comprise any part providing division and/or a split of the electrical cable (e.g. transmission line and/or coaxial cable) communicating the RF signal into at least two electrical cables (e.g. transmission lines and/or coaxial cables). Also, the splitter may be any part that may split and/or divide the power from one output into two or more outputs. In one example, the splitter may comprise a dividing part made from plastic. The splitter may comprise a control unit which is a part of control system. The splitter may split and/or divide the power and/or RF signal equally between two or more outputs. Also, the splitter may split and/or divide the power and/or RF signal to two or more outputs not equally, but by a ratio determined or controlled by the control system.

An insulator may be combined with the splitter and/or may be located before and/or after splitter with regard of transporting RF signal to the RF electrode. The insulator may be electrical insulation of at least part of the RF circuit from the magnetic circuit. The insulator may be used to minimize influence of the magnetic circuit to the RF circuit.

The pre-match may be used in the devices using coaxial cables. The pre-match may include a small coil, condenser and/or resistor.

The RF electrode (RFE), acting as a treatment energy source, may include one or more unipolar RF electrodes, one or more monopolar RF electrodes and/or one or more pairs of bipolar RF electrodes.

The power source PS of the RF circuit, power amplifier PA, filter, SWR+Power meter, tuning, SYM, splitter, insulator and/or pre-match may be at least partially and/or completely replaced by an HF generator supplying the rest of the circuit, including the RF electrode, with a high frequency electric signal.

FIG. 24 illustrates one of examples of the symmetrisation element SYM. Input coaxial cable 130 provides electrical signal (e.g. RF signal) to the splitter 131 that may split RF signal into two branches. The splitter 131 may also include an insulating element, such as at least one, two, three or more serial connected capacitors creating insulating length in a range of 4 mm to 100 mm, or 20 mm to 50 mm. The SYM may be established or represented by the different length of the coaxial cables guided or leading to pair of bipolar RF electrodes. The difference in length between coaxial cables 132 and 133 in location $l_1$ may be in a range of 0.4 to 0.6, or 0.46 to 0.55 of the λ, where λ may be wavelength of the guided RF signal in the coaxial cable 132 and/or coaxial cable 133. The length of the coaxial cable 132 may be in a range of 1 cm to 5 m, 5 cm to 90 cm or 10 cm to 50 cm. The length of the coaxial cables **132+135*b* may be in a range of λ/4 10%, or ±5%, or their multiples by positive integer. The length of the coaxial cable 133 may be in a range of 2 m to 12 m, or 2.2 m to 8 m. The length of the coaxial cable 133 may be in a range of λ/2±10%, or ±5%, plus the length of cable 132. The length of the coaxial cables 133+135*a* may be in a range of 3λ/4±10%, or ±5%. In a summary the coaxial cables 132+135*b* are shifted in relation to the coaxial cables 133+135*a* of λ/2 10%, or ±5%. This part of the SYM may cause phase shift 180° of the RF signal delivered to one RF electrodes 101*a* and 101*b*. The RF electrodes 101*a* and 101*b* may be part of one applicator or the RF electrode 101*a* may be part of first applicator and RF electrode 101*b* may be part of second applicator. A connector 134 may be used for connecting one or more applicators to the main unit. The connector 134 may be the applicator connector 65. The part 12 may represent a connecting tube of the applicator. The length of the coaxial cables 135*a* and 135*b* in this connecting tube may be in a range of 1 m to 6 m, or of 1.1 m to 4 m or of λ/4±10% or ±5%. A pairing element 136 may be conductive connection of the conductive shielding part of the coaxial cables 135*a* and 135*b*. The pairing element 136 may have a surface area in a range of 0.5 $cm^2$ to 100 $cm^2$, 1 $cm^2$ to 80 $cm^2$ or 1.5 $cm^2$ to 50 $cm^2$. The pairing element 136 may include material of height electric conductivity, such as copper, silver, gold, nickel, or aluminum, wherein the impedance of the pairing element 136 may be near to zero. The pairing element 136** or between pairing element and electrode may be placed a capacitor, resistor and/or inductor.

The RF circuit and/or the magnetic circuit may be at least partially located in one or more applicators. The wire connection between the applicator, an additional treatment device and/or the main unit may be also considered as a part of the RF circuit and/or magnetic circuit element because of the impedance, resistivity and/or length of the wire connection. One or more electrical elements of the magnetic circuit shown in FIG. 17, RF circuit shown in FIGS. **18*b* and 18*a*** may be dismissed, may be sorted in different order and/or two or more electrical elements may create one individual combined electrical element. Adjusting of the signal provided to the RF circuit may be at least partially provided by or inside another different circuit of the treatment device e.g.: magnetic circuit and/or other.

FIG. **18*a* illustrates an exemplary schema 180** of electrical elements of treatment device. The exemplary schema include two independent power sources including power source for RF treatment (PSRF) and power source for magnetic treatment (PSM) connected to one power network (PN). The PSRF may provide electromagnetic signal to two independent treatment clusters for RF treatment RF A and/or RF B. The PSM may provide electromagnetic signal to one or more clusters of magnetic treatment HIFEM A and/or HIFEM B. One or more the power sources may be also powering other parts of the treatment device, such as a human machine interface (HMI), or the master unit, among others. Each magnetic circuit and/or RF circuit may have its own control units (CUM A, CUM B and CURF A and CURF B). CURF A and CURF B may be control units of RF treatment cluster for RF treatment A (RF A) and treatment cluster for RF treatment B (RF B) respectively.

Control units may include one or more PCBs or microprocessors. One or more control units may communicate between each other and/or with the master unit that may be selected as a master unit for other control units in master-slave communication. The master unit may be the first or only control unit that communicates with the HMI. The master unit may control units CUM A and CUM B. The master unit may be a control unit including one or more PCBs and/or microprocessors. Master unit or control unit A (CUM A) or control unit B (CUM B) may be coupled to human machine interface. Also, the master unit may be human machine interface HMI or be coupled to the human machine interface HMI.

FIG. 18*a* illustrates two parts of the treatment device, wherein the first part may provide the RF treatment and the second part may provide the magnetic treatment. Two parts of the treatment device may be insulated from each other. The treatment device may include one or more insulated electrical elements and/or parts of the treatment device and individual circuits from each other in a manner of shielding voltage barrier, distance barrier and/or radiation barrier. Examples of insulated parts may be represented by a dashed line in FIG. 18*a*. It is also possible that individual electrical elements of the treatment device may be insulated from at least one part of the treatment device. Insulation of such parts and/or electrical elements may be provided by material of high dielectric constant, by distance of individual parts and/or electrical elements, by system of capacitors or resistors. Also, any shielding known from electronic, physics, by aluminium boxes and/or by other manner may be used.

The RF treatment and/or magnetic treatment may be provided by at least one, two, three, four or more treatment circuit (which may be located in the main unit) and/or applicators wherein one treatment circuit may include RF cluster or magnetic cluster. Each applicator A and B (AP A and AP B) may include at least one electrical element of one, two or more treatment circuits. Each applicator may include at least one, two or more different treatment energy sources, such as one or more RF electrodes providing the RF treatment and one or more magnetic field generating devices providing the magnetic treatment. As shown in FIG. 18*a*, the treatment device may include first applicator (AP A) and second applicator (AP B). The first applicator (AP A) may include a first RF electrode (RFE A) from first RF circuit and a first magnetic field generating device (MFGD A) from a first magnetic circuit. The second applicator (AP B) may include a second RF electrode (RFE B) from a second RF circuit and a second magnetic field generating device (MFGD B) from a second magnetic circuit. In a different example, a first applicator may include a first magnetic field generating device and a a first pair of bipolar RF electrodes, while a second applicator may include a second magnetic field generating device and a second pair of bipolar RF electrodes. In another example, a first applicator may include a first magnetic field generating device, a second magnetic field generating device, and a first pair of bipolar RF electrodes, while a second applicator may include a third magnetic field generating device, a fourth magnetic field generating device, and a second pair of bipolar RF electrodes. Two applicators may be connected to a main unit separately and may be individually positioned in proximity of the body area before or during the treatment, when they are coupled to the body area and in contact with the body area.

FIG. 18*a* also illustrates other individual parts of the treatment device, such as treatment cluster for RF treatment (RF A), treatment cluster for RF treatment (RF B), treatment cluster for magnetic treatment HIFEM A, treatment cluster for magnetic treatment HIFEM B in the magnetic circuit, power source for RF treatment (PSRF), power source for magnetic treatment (PSM), applicator A (AP A), applicator B (AP B). All parts, except the applicators, may be located in the main unit. Shown splitter, symmetrisation element (SYM A), and symmetrisation element (SYM B) are parts of two RF circuits. The splitter shown on FIG. 18*a* may be common for the RF circuits. The power source for RF treatment (PSRF) may include steady power source of RF circuit (SPSRF), auxiliary power source of RF circuit (APS RF), power network filter PNFLT and/or power unit (PU). Individual electrical elements may not be included with other electrical elements in PSRF. The power source for magnetic treatment (PSM) may include auxiliary power source A (APS A), auxiliary power source B (APS B), steady power source of magnetic circuit (SPSM), power pump (PP), board power source A (BPS A) and/or board power source B (BPS B). Individual electrical elements may not be included with other electrical elements in PSM. Treatment cluster for magnetic treatment HIFEM A of the magnetic circuit may include control unit A (CUM A), energy storage device A (ESD A), switch A (SW A), safety element (SE) and/or pulse filter (PF). Treatment cluster for magnetic treatment HIFEM B of the magnetic circuit may include control unit B (CUM B), energy storage device B (ESD B) and/or switch B (SW B). Although not shown on FIG. 18*a*, the treatment cluster for magnetic treatment HIFEM B may also include pulse filter (PF) and/or safety element (SE). Individual electrical elements may be insulated from each other. However, individual electrical elements and/or circuit parts may be merged and/or shared with other circuit parts. As an example, one control unit may be at least partially shared with two or more RF circuits and/or magnetic circuits, and one control unit may regulate power or power network or power source providing power for the RF circuit and also for the magnetic circuit. Another example may be at least one auxiliary power source and/or steady power source shared with at least two RF and/or magnetic circuits.

Figure 18C:
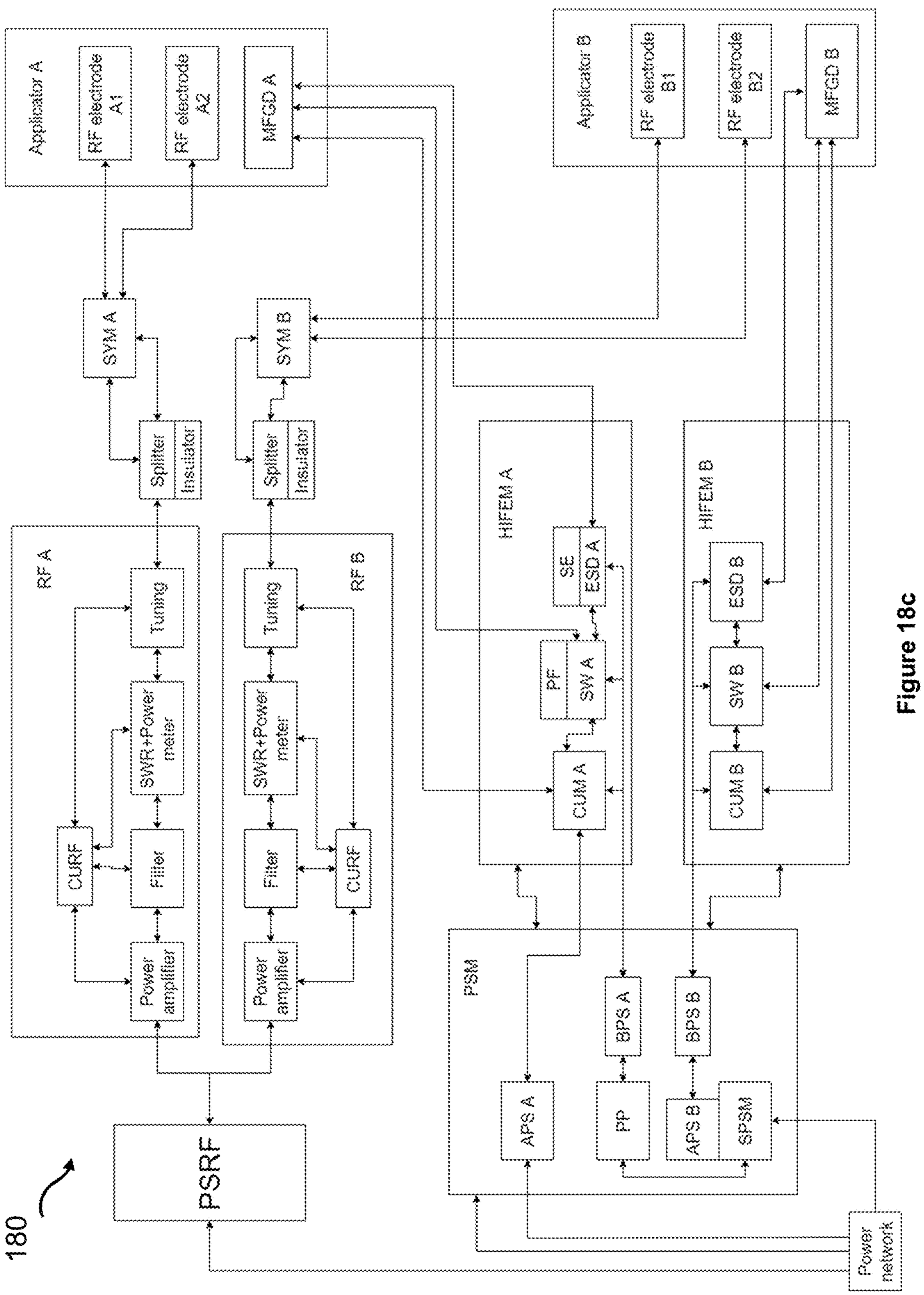
FIGS. 18*c*-18*i* illustrate exemplary schemas of electrical elements of a treatment device.

FIG. 18*c* illustrates another exemplary schema 180 of electrical elements. In FIG. 18*c*, both electrical cables outputting from the splitter are symmetrized by the SYM element.

Figure 18D:
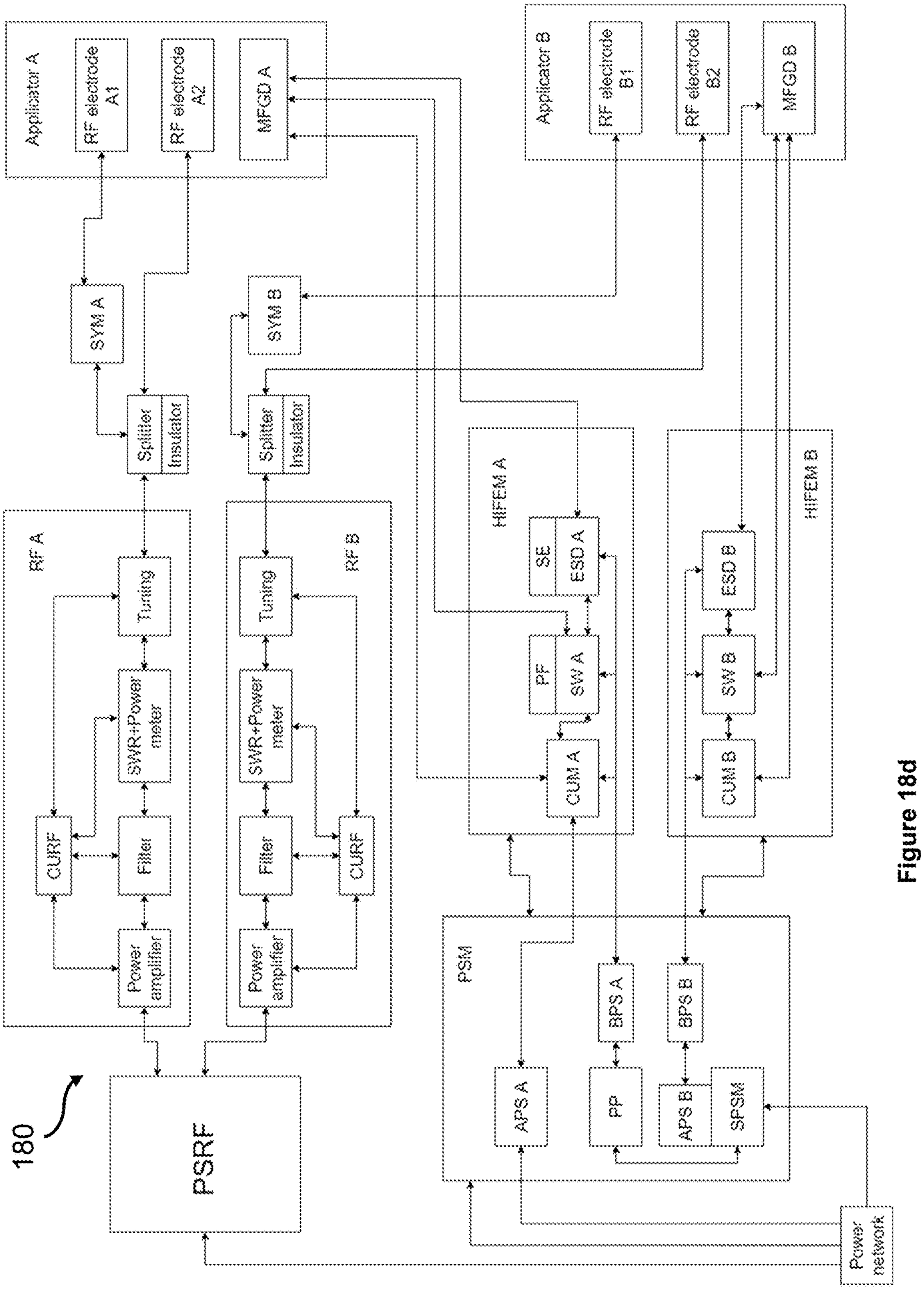

FIG. 18*d* illustrates another exemplary schema 180 of electrical elements. In FIG. 18*d*, a first electrical cable outputting from the splitter is symmetrized by the SYM element, while a second electrical cable leads directly to the corresponding RF electrode. The SYM element may include different lengths of this cable to delay the electrical signal within this cable in order to achieve a phase delay.

Figure 18E:
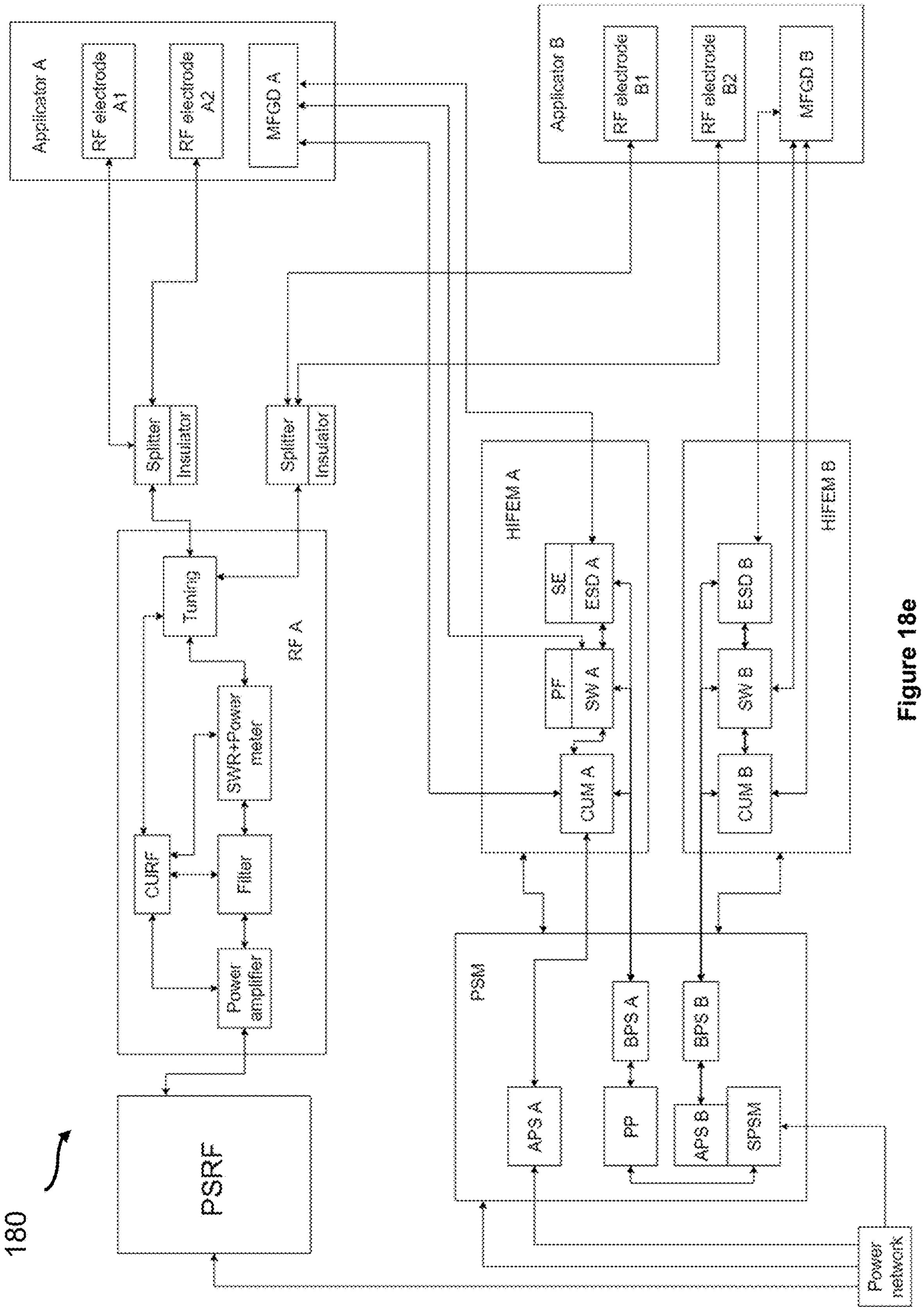

FIG. 18*e* illustrates another exemplary schema 180 of electrical elements. In FIG. 18*e*, two pairs of RF electrodes are powered by one RF cluster. Therefore, two pairs of RF electrodes may be connected to the one power amplifier. Similarly, when there is only one RF electrode in each applicator, two RF electrodes may be connected to the one power amplifier. The FIG. 18*e* shows two splitters, one for each pair of RF electrodes. However, there may only one splitter present, which would split or divide the signal to all four RF electrodes.

Figure 18F:
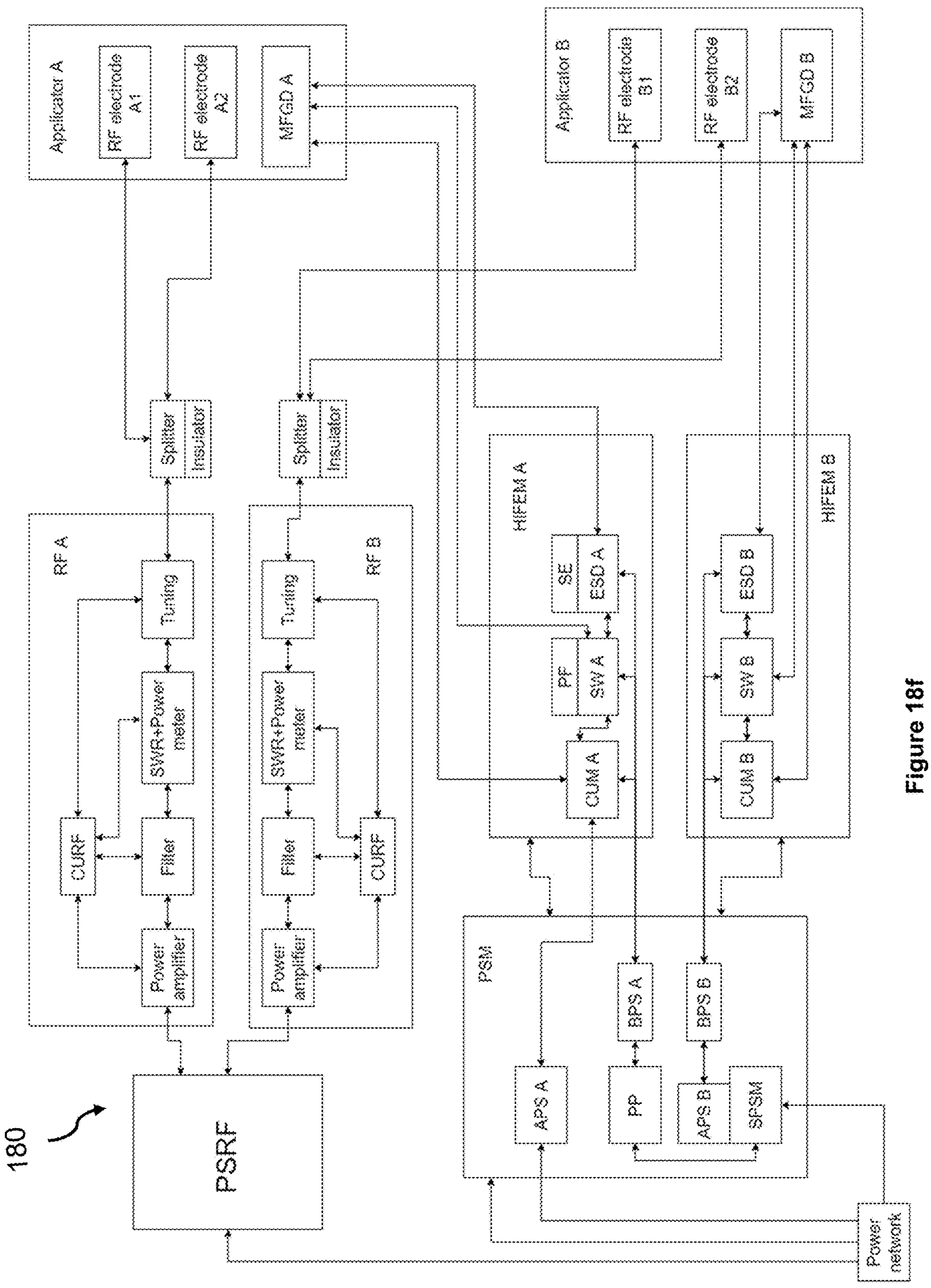

FIG. 18*f* illustrates another exemplary schema 180 of electrical elements. As shown in FIG. 18*f*, none of the electrical cables outputting from the splitter are symmetrized by a SYM element. This configuration may be useful for a monopolar configuration of the RF electrode, when the one or more RF electrodes within the applicator are monopolar and there is another grounding plate placed on the patient. Similarly, this configuration may be useful for a unipolar configuration of the RF electrode, when the one or more RF electrodes within the applicator are unipolar. However, the splitter may be omitted and each RF electrode may be directly connected to its own treatment circuit (e.g. RF A). Each RF electrode may be connected to its own PSRF. The RF circuit may not include all shown elements. For example, the SWR+Power meter may be omitted in case of use of a lower RF frequency.

Figure 18G:
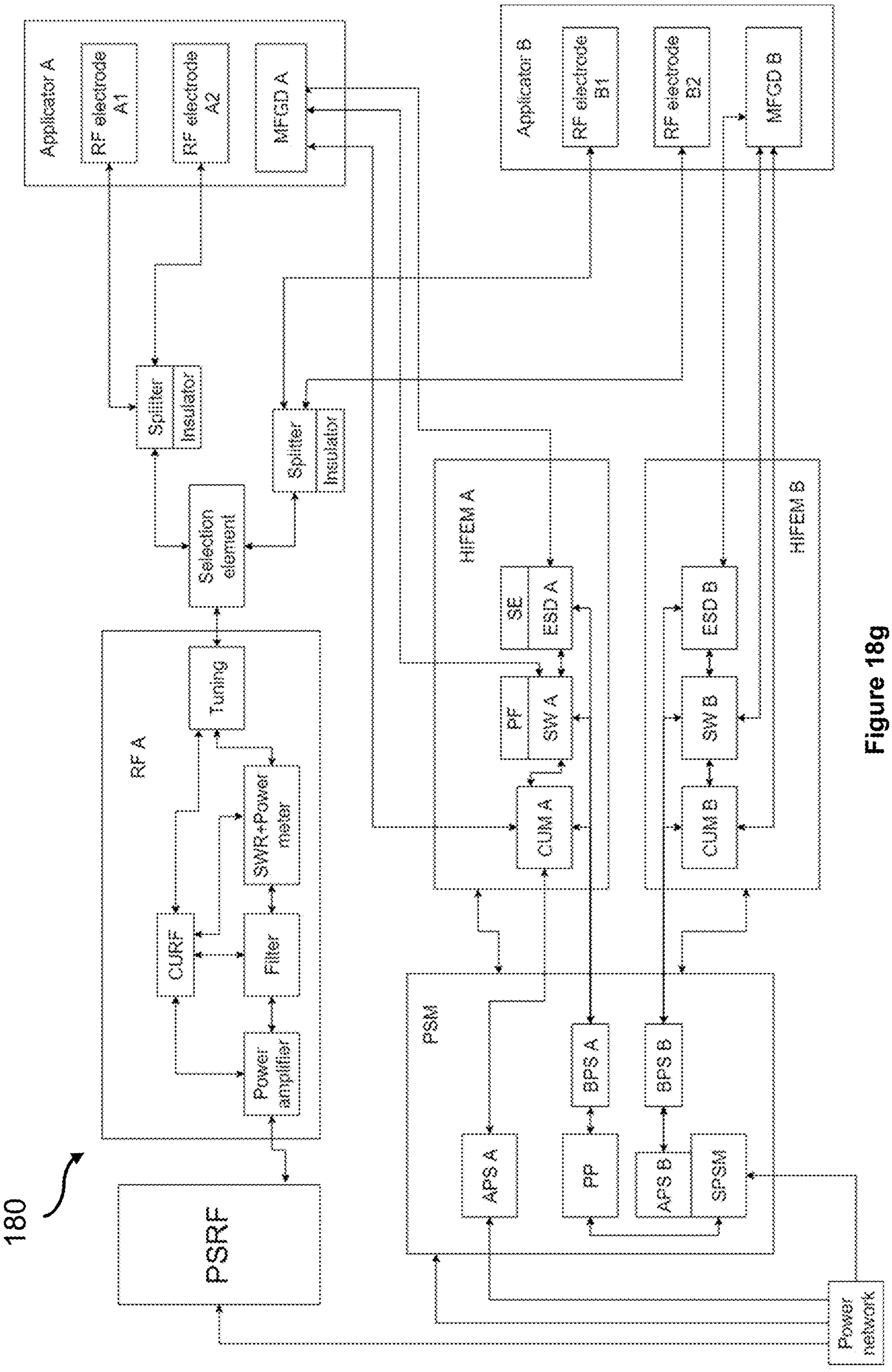

FIG. 18*g* illustrates another exemplary schema 180 of electrical elements. In FIG. 18*g*, two pairs of RF electrodes are powered by one RF cluster. Therefore, two pairs of RF electrodes may be connected to one power amplifier. Similarly, when there is only one RF electrode in each applicator, two RF electrodes may be connected to one power amplifier. FIG. 18*g* also shows two splitters, one for each pair of RF electrodes. However, there may only one splitter present, which would split or divide the signal to all four RF electrodes. FIG. 18*g* further shows a Selection element, which may be present within the RF circuit. The Selection element may be configured to provide the RF signal to the first pair of RF electrodes or to the second pair of RF electrodes in order to activate them at different times. The Selection element may be configured to provide the RF signal to two pairs of RF electrodes through one or more splitters at same time or different time during the treatment session.

Figure 18H:
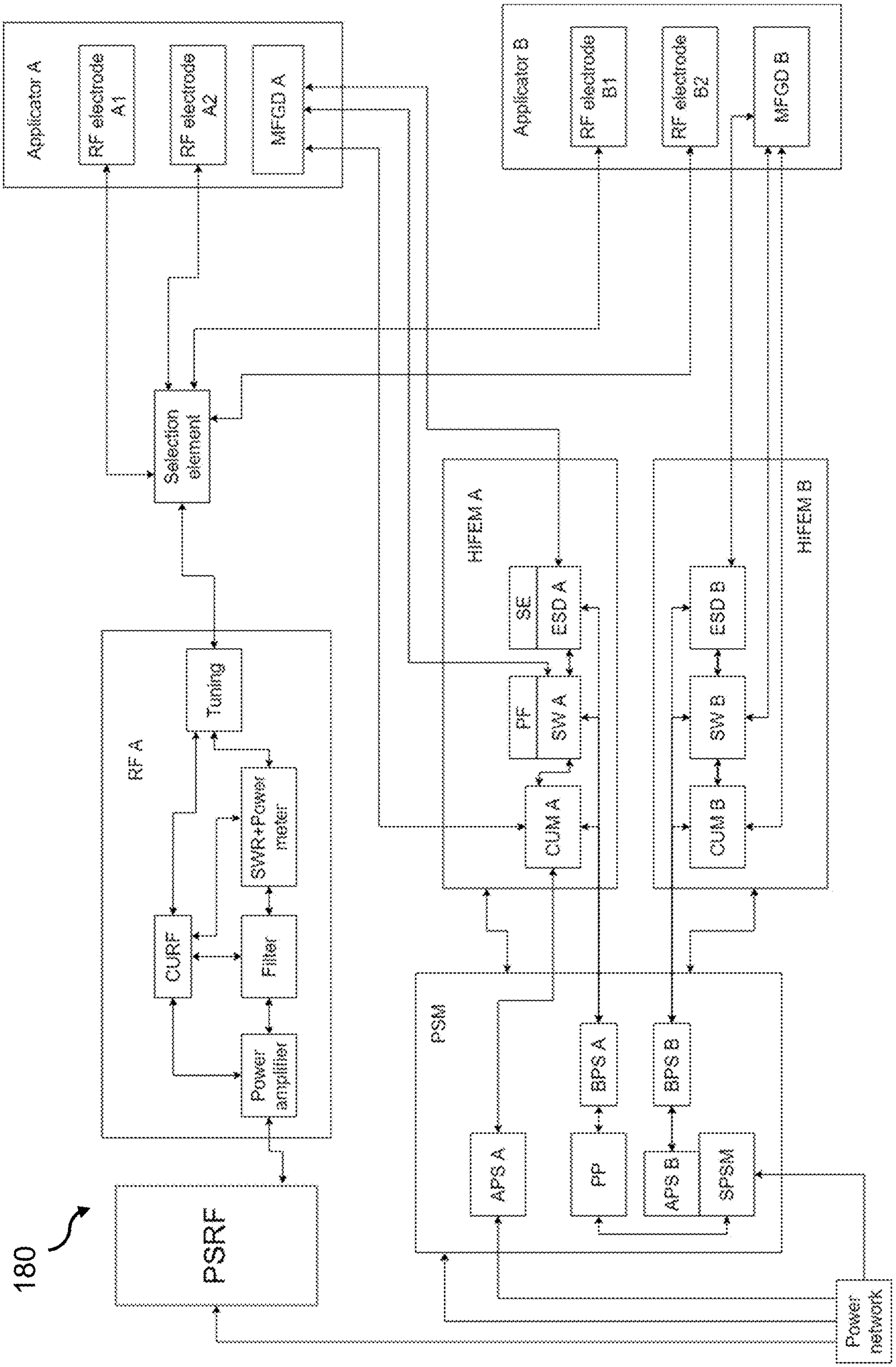

FIG. 18*h* illustrates another exemplary schema 180 of electrical elements. In FIG. 18*h*, two pairs of RF electrodes within one applicator are powered by one RF cluster. Therefore, two pairs of RF electrodes may be connected to one power amplifier. Similarly, when there is only one RF electrode in each applicator, two RF electrodes may be connected to one power amplifier. FIG. 18*h* further shows a Selection element, which may be present within the RF circuit. The Selection element may be configured to provide the RF signal to one or more RF electrodes in order to activate them at different times. FIG. 18*h* depicts a Selection element and no splitters. By incorporating one or more Selection elements according to the schema, the Selection element may provide RF signal only to one RF electrode. However, the Selection element may provide RF signal to a plurality of RF electrodes of the same applicator and/or different applicators.

Figure 18I:
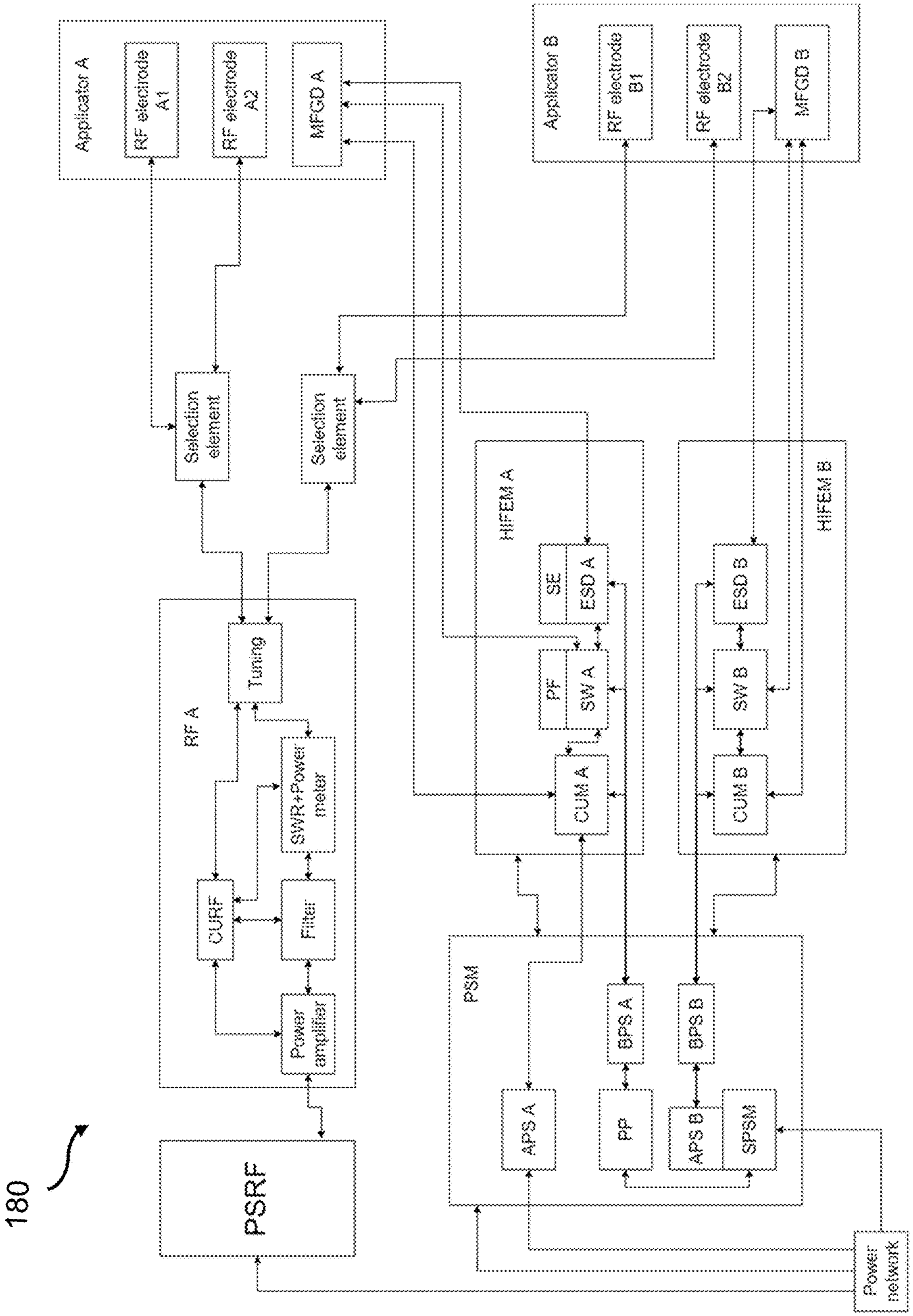

FIG. 18*i* illustrates another exemplary schema 180 of electrical elements. In FIG. 18*h*, two pairs of RF electrodes within one applicator are powered by one RF cluster. Therefore, two pairs of RF electrodes may be connected to one power amplifier. FIG. 18*i* further shows two Selection elements, which may be present within the RF circuit. A first Selection element may be configured to provide the RF signal to one or more RF electrodes within a first applicator in order to activate them at different times. A second Selection element may be configured to provide the RF signal to one or more RF electrodes within a second applicator in order to activate them at different times and/or at the same time. FIG. 18*i* includes two Selection elements and no splitters. By incorporating two Selection elements according to the schema, each Selection element may provide RF signal only to the one or more RF electrodes of one applicator.

The Selection element shown in FIGS. 18*g*, 18*h* and 18*i* may be configured to select to which RF electrode, RF electrodes or RF electrode pair, or plurality of RF electrodes the RF signal is delivered. One or more Selection elements may be positioned in the main unit of the device and/or in the applicator. The Selection element may include a pin diode, relay, multiplexer, demultiplexer and/or pair of multiplexers and demultiplexers. The Selection element may include a multiple-input and multiple-output switch. The multiplexer may include a multiple-input, single output switch. The demultiplexer may include a single-input, multiple output switch. The Selection element may include an RF switch. Further, the Selection element may include two or more of a pin diode, relay, multiplexer, demultiplexer and/or pair of multiplexer and demultiplexer connected in parallel. The parallel configuration may be useful when activation of a plurality of electrodes is required. Regarding the position of the Selection element within the circuits shown in FIGS. 18*g*, 18*h* and 18*i*, this position is exemplary. It may be possible to position the Selection element between any electrical element of the RF cluster or the RF circuit. Therefore, the Selection element may be positioned between the SWR+Power meter and the tuning, between the power amplifier and the filter, or between the filter and the SWR+ power meter.

As shown in FIGS. 18*a*, 18*c*, 18*d* and 18*f*, two treatment clusters for RF treatment (RF A and RF B) are shown to be connected to one power source for RF treatment. However, the device may include two power sources for RF treatment and each power source for RF treatment may be connected to one RF electrode. Further, FIG. 18*c* shows one splitter for an electrical cable coming from one treatment cluster, e.g., RF A, and another splitter for an electrical cable coming from another treatment cluster, e.g., RF B. As described earlier, the splitter splits and/or divides the RF signal to two electrical cables. The two electrical cables from each splitter are connected to two RF electrodes within one applicator. As shown, the two RF electrodes within one applicator are connected to the two electrical cables originating from one splitter. However, it may be possible to connect two electrodes within one applicator to two electrical cables, wherein a first electrical cable originates from one splitter and a second electrical cable originates from another splitter.

Treatment cluster for magnetic treatment HIFEM A may provide magnetic treatment independently on treatment cluster for magnetic treatment HIFEM B. Alternatively, the treatment device may include just one treatment cluster for magnetic treatment HIFEM or the treatment device may include two or more individual treatment clusters for magnetic treatment HIFEM, wherein some of the treatment cluster for magnetic treatment HIFEM may share individual electrical elements such as a control unit, energy storage device, pulse filter and/or other.

As shown in FIG. 18*a*, the treatment cluster for magnetic treatment HIFEM, e.g. HIFEM A, may include the control unit, e.g. CUM A. The control unit, e.g. CUM A, may control a charging and/or discharging of the energy storage device, e.g. ESD A, processing feedback information and/or adjusting parameters of individual electrical elements and/or treatment clusters for magnetic treatment HIFEM. In addition, the control unit (e.g. CUM A) may control adjusting parameters or operation of electrical elements, e.g. BPS A from circuit part PSM, switch, PF, ESD A from the treatment cluster for magnetic treatment HIFEM A and/or processing information from the sensors in the applicator AP A and/or AP B. The control unit (e.g. CUM A) may also communicate with another one or more magnetic and/or RF circuits and/or including master unit. The power source PSM, the energy storage device ESD and/or the switch SW may be at least partially regulated by the control unit of the magnetic circuit, e.g. CUM A. The control unit (e.g. CUM A) or master unit and/or one or more individual electrical elements of the circuit may be regulated by any other electrical element based on mutual communication between them. The master unit may be able to adjust treatment parameters of the magnetic treatment and/or the RF treatment based on feedback information provided from the sensors and/or based on communication with other control units, e.g. the master unit. One control unit CUM or CURF may regulate independently one or more circuits providing magnetic and/or RF treatment. At least one control unit may use peer-to-peer communication and/or master-slave communication with other control units (e.g. CUM A may be slave control unit of the master unit).

The treatment device may include one, two, three or more ESD, wherein each ESD may include one, two, three or more capacitors. One ESD may provide energy to one, two, three or more treatment energy sources, such as magnetic field generating devices providing magnetic treatment. Each coil may be coupled to its own respective ESD or more than one ESD. The ESD may include one or more other electrical elements such as a safety element SE, such as a voltage sensor, a high voltage indicator, and/or discharging resistors, as shown in FIG. 18*a*. The voltage sensor and the high voltage indicator may provide feedback information to the switch SW and/or to control unit, e.g., CUM A. The discharging resistor as part of the SE may provide discharging of at least one capacitor in case of hazardous situation. Discharging of one or more ESD may be controlled by the control unit e.g. CUM A or CUM B. The signal provided from the energy storage device ESD through the switch SW to the magnetic field generating device may be modified by a pulse filter (PF). The PF may be part of the switch SW and/or may be positioned between the switch SW and the magnetic field generating device, e.g., MFGD A. The PF may suppress switching voltage ripples created by the switch during discharging of the ESD. The proposed circuit may repetitively switch on/off the switch SW and discharge the energy storage device ESD to the magnetic field generating device, e.g. the MGFD A in order to generate the time-varying magnetic field. As shown in FIG. 18*a*, one or more electrical elements of the magnetic circuit and/or RF circuit may be omitted and/or combined to another. For example, one or more individual electrical elements of PSRF and/or PSM may be combined to one, but independency of individual circuits may be decreased. Also electrical elements the PF, the SE and/or other may be independent electrical element. Also individual treatment circuits, e.g. RF circuits, may be different from each other as can be seen in FIGS. 18*a* and 18*b*, wherein electrical elements, such as a filter, a SWR+Power meter, a tuning, a splitter, an insulator, a SYM and/or a pre-match may be dismissed and/or combined to one. Dismissing and/or combining of individual electrical elements may results in decreased efficiency of energy transfer to patients body without tuning, higher energy loss because of absence the SYM, pre-match and/or tuning, malfunctioning of signal adjusting in the circuit and incorrect feedback information without the SWR+Power meter, the splitter and the insulator and/or the treatment device may be dangerous to patient without the filter, the SWR+Power meter, the SYM and/or the tuning element.

Control units CUM A and CUM B may serve as slaves of the master unit which may command both control units CUM A and CUM B to discharge the electrical current to respective magnetic field generating devices (e.g. MFGD A and MFGD B). Therefore, the control of each control unit CUM A and CUM B is independent. Alternatively, CUM B may be slave of the CUM A, while CUM A itself may be slave of master unit. Therefore, when master unit commands the CUM A to discharge electrical current into the magnetic field generating device (e.g. MFGD A), the CUM A may command the CUM B to discharge electrical current to another magnetic field generating device (e.g. MFGD B) positioned in different applicator. In another alternative, additional control unit may be positioned between master unit and control units CUM A and CUM B, wherein such additional control unit may provide e.g. timing of discharges. By both these approaches, the pulses of magnetic field may be applied synchronously or simultaneously.

When the treatment device includes more than one magnetic field generating device and method of treatment include using more than one magnetic field generating device (e.g., a coil), each coil may be connected to respective magnetic circuit. However, one coil may be connected to plurality of magnetic circuits. Also, the power source PSM may be used for at least two magnetic field generating devices.

The power source, e.g. PSM and/or PSRF may provide an electric energy to at least one or at least one individual electrical element of RF circuit, magnetic circuit, and/or to other part of the treatment device e.g. to the master unit, HMI, energy storage device (e.g. ESD A and/or ESD B), to control unit (e.g. CUM A and/or CUM B) and/or to the switch (e.g. SW A or SW B). The power source may include one or more elements transforming electric energy from the power network connection PN as illustrated in FIG. 18*a*. Several individual electrical elements of the power source, of the RF circuit and/or magnetic circuit may be constructed as one common electrical element and do not have to be constructed as individual electrical elements as illustrated in FIG. 18*a*. Each RF and/or magnetic circuit may have its own power source and/or at least one electrical element of the power source powering just one of the RF and/or the magnetic circuit. Also, at least part of one power source may be powering at least two different circuits before and/or during at least part of the treatment. The power source may include one or more parts shared with individual electrical circuits that may be at least partially electrically isolated from each other.

One or more electrical elements of the power source for RF treatment (e.g. a steady power source of magnetic circuit (SPSM), an auxiliary power sources APS A and/or APS B, a power pump PP, board power source BPS A and/or BPS B) may provide electric energy to individual electrical elements of the RF circuit and/or magnetic circuit directly and/or indirectly. Directly provided electric energy is provided through conductive connection between two electrical elements wherein no other electrical element of the circuit is in serial connection between directly powered electrical elements. Insulating and/or other electrical elements of the circuits such as resistors, insulating capacitors and the like may be not considered to be an electrical element. Indirectly powered electrical elements may be powered by one or more other elements providing electric energy through any other element that may change parameters of provide electric energy, such as current value, frequency, phase, amplitude and/or other.

The power source PSM illustrated in FIG. 18*a* in more detail may include connection to a power network PN. The PN may provide filtering and/or other adjustment of an input electric signal from the power network, such as the frequency and current value. The PN may also be used as an insulating element creating a barrier between the treatment device and the power network. The PN may include a one or more of capacitors, resistors and/or filters filtering signal returning from the treatment device The PN may include a plug or connection to a plug. The PN may be coupled to a plug or power grid. The PSM may include one or more steady power source (e.g. steady power source of magnetic circuit SPSM), auxiliary power sources (e.g. APS A and/or APS B), one or more power pumps PP; and/or one or more board power sources (e.g. BPS A and/or BPS B). As illustrated in FIG. 18*a*, the treatment device may include at least two electrically insulated magnetic and/or RF circuits that may be controlled at least partially independently, e.g. intensity of generated magnetic field by the magnetic field generating devices MFGD A and the MFGD B connected to treatment clusters for magnetic treatment HIFEM A and HIFEM B may be different. Steady power source (SPSM) may provide steady output voltage under different power network conditions. Steady power source SPSM may be connected to the auxiliary power source (e.g. APS A and/or APS B). Two auxiliary power sources may be combined and create one electrical element. Steady output voltage produced by steady power source and/or by auxiliary power source may be in a range of 1 V to 1000 V, or 20 V to 140 V, or 50 V to 700 V, or 120 V to 500 V, or 240 V to 450 V.

One or more auxiliary power sources may be powering one or more control units of the individual circuits. APS may be also powering one or more board power source BPS, e.g. BPS A and/or BPS B. APS may be also powering master unit HMI and/or other elements of the treatment device. Because of APS, at least one control unit and/or master unit may provide processing/adjusting of the electric signal in RF and/or magnet circuit precisely, independently and/or also individual electrical element of the treatment device may be protected from the overload. The board power source (e.g. element BPS A and/or BPS B) may be used as a source of electric energy for at least one element of magnetic circuit (e.g. energy storage device ESD A and/or B). Alternatively, one or more elements of the power source PSM may be combined and/or dismissed.

The power source may serve as high voltage generator providing voltage to a magnetic circuit and/or RF circuit. The voltage provided by power source may be in a range from 500 V to 50 kV, or from 700 V to 5 kV, or from 700 V to 3 kV, or from 1 kV to 1.8 kV. The power source is able to deliver a sufficient amount of electrical energy to each circuit, such as to any electrical element (e.g. the energy storage device ESD A) and to the magnetic field generating device (e.g. MFGD A). The magnetic field generating device may repeatedly generate a time-varying magnetic field with parameters sufficient to cause muscle contraction.

According to FIG. 18*a*, RF circuits have their own power source PSRF that may be at least partially different from the PSM. The PSRF may include element electrical PNFLT suppressing electromagnetic emission from the internal parts of the PN and/or from the any part of the RF circuit. Electrical element PNFLT may represent power network filter. However, PNFLT may be also part of the PN. The PSRF may include SPSRF providing steady output voltage under different power network conditions to auxiliary power source of a RF circuit APS RF, control unit of the RF circuit, a power unit PU and/or other electrical elements using direct current supply. As further illustrated in FIG. 18*a*, APS RF may include its own mechanism transforming alternating current to direct current independently to SPSRF. The APS RF may be able to power control unit of the treatment cluster for RF treatment RF A and/or master unit while SPSRF may independently power control unit of the treatment cluster for RF treatment RF B. The power unit PU of the RF circuit may be powering one or more RF circuits or at least one electrical element of the RF circuit, such as power amplifiers and/or other electrical elements of the treatment cluster for RF treatment RF A and/or treatment cluster for RF treatment RF B creating and/or adjusting high frequency signal.

At least one electrical element described as PSM, PSRF, APS, SPSM and/or SPSRF may be shared by at least one RF circuit and magnetic circuit.

Control units CURF may work as slave of the master unit, which may command CURF to provide RF signal through RF circuit to RF electrode. In case of two control units CURF both control units work as slaves of the master unit which may command both control units CURF to provide RF signal to respective RF electrodes. Therefore, the control of each control unit from possible plurality of CURF is independent. Alternatively, first CURF may be slave of second CURF, while first CURF itself may be slave of master unit. Therefore, when master unit commands the first CURF to discharge electrical current into the first RF electrode, the first CURF may command the second CURF to discharge electrical current to second RF electrode positioned in different applicator. In another alternative, additional control unit may be positioned between master unit and plurality of control units CURF, wherein such additional control unit may provide e.g. timing of discharges. By both of these principles, the pulses of the RF field may be applied continuously or in a pulsed manner.

Treatment clusters for magnetic HIFEM A and HIFEM B shown in FIGS. 17, 18*a* and 18*b* may be controlled through one or more sliders or scrollers related to HMI parts marked as HIFEM A and HIFEM B 718 shown on FIG. 7. Through related intensity scrollers, intensity bars and/or intensity sliders shown on human machine interface HMI, the user may control or adjust speed of operation of one or more electrical elements of treatment clusters for magnetic energy HIFEM A and/or HIFEM B.

Also, treatment cluster for RF treatment RF A and treatment cluster for RF treatment RF B shown in FIGS. 17, 18*a* and 18*b* may be controlled through sliders, bars or intensity scrollers related to HMI parts marked as RF A and RF B 712 shown on FIG. 7. Through related intensity scrollers, intensity bars and/or intensity sliders shown on human machine interface HMI, the user may control or adjust speed of operation of one or more electrical elements of treatment clusters for RF treatment RF A and/or RF B. Also, by using the related intensity scrollers, intensity bars and/or intensity sliders the user may control or adjust speed of electrical signal transmission through or between one or more electrical elements of treatment clusters for RF treatment RF A or RF B.

The treatment device may include two or more applicator, each applicator may include one magnetic field generating device and one or two RF electrodes. Inductance of first magnetic field generating device positioned in first applicator may be identical as inductance of second magnetic field generating device positioned in the second applicator. Also, number of turns, winding area and/or area without winding of the first magnetic field generating device in the first applicator may be identical as number of turns, winding area and/or area without winding of the second magnetic field generating device in the second applicator. The first magnetic field generating device in the first applicator may provide identical magnetic field as the second magnetic field generating device in the second applicator. The identical magnetic fields provided by plurality of magnetic field generating devices during same or another treatment sessions may have same treatment parameters e.g. number of pulses in train, number of pulses in burst, same amplitude of magnetic flux density of impulses, same shape of envelope or other. However, reasonable deviation e.g. from amplitude of magnetic flux density may be tolerated in the identical magnetic field. The deviation of amplitudes of magnetic flux density or average magnetic flux density as measured by fluxmeter or oscilloscope may be in the range of 0.1% to 10% or 0.1% to 5%.

Alternatively, the inductance of magnetic field generating devices in both applicator may be different. Also, magnetic fields provided by plurality of magnetic field magnetic devices during the same or another treatment sessions may have different treatment parameters.

When the treatment device has two or more applicators, each applicator may include one magnetic field generating device and one or two RF electrodes. The size or area of one RF electrode positioned in first applicator may be identical to another RF electrode positioned in the second applicator. First applicator and second applicator may provide identical RF fields provided during same or another treatment sessions, wherein identical RF fields may have same treatment parameters, e.g. frequency, wavelength, phase, time duration, power and intensity of RF field. However, first applicator and second applicator may provide two RF fields during the same or different treatment sessions, wherein two RF fields may have the different treatment parameters.

Alternatively, the size of area of RF electrodes in both applicators may be different. Also, magnetic fields provided by plurality of magnetic field generating devices during the same or another treatment sessions may have different treatment parameters.

Figure 19A:
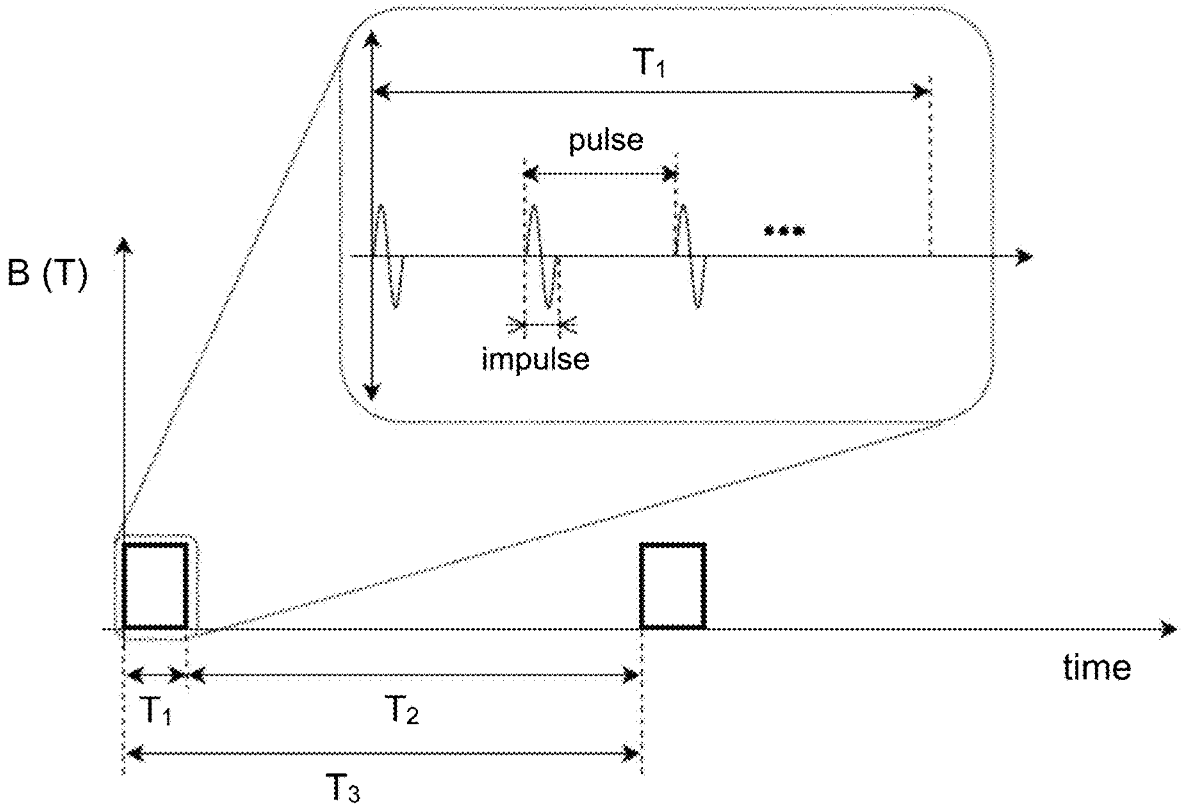
FIG. 19*a* illustrates an exemplary composition of magnetic field including impulses or pulses.
Figure 19B:
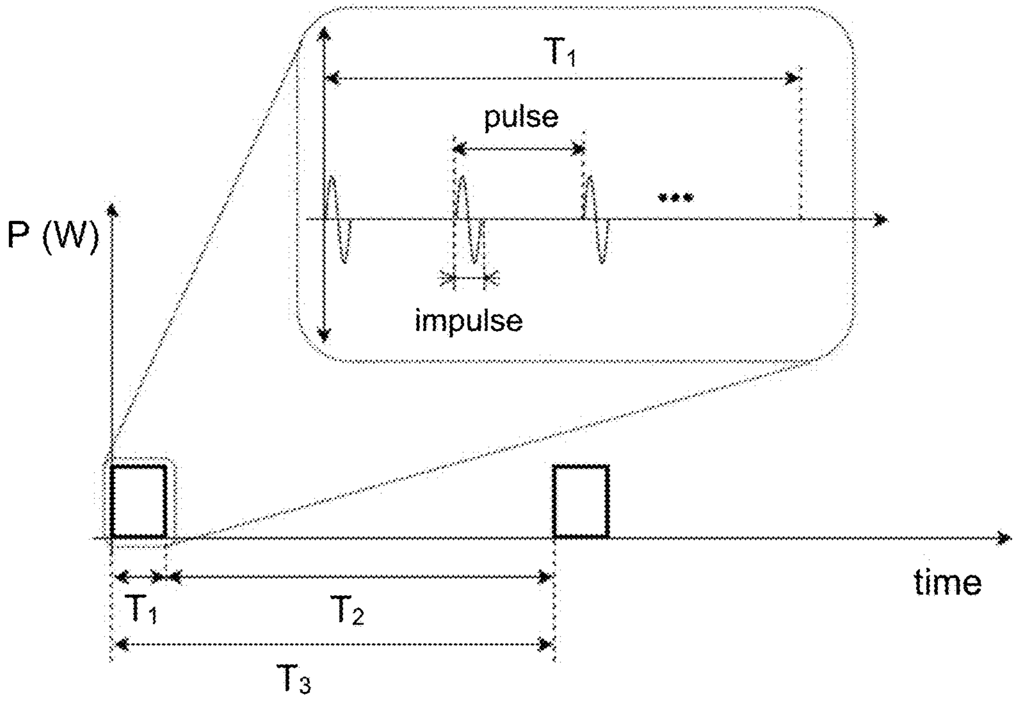
FIG. 19*b* illustrates an exemplary composition of radiofrequency field including impulses or pulses.

FIG. 19*a* shows an exemplary composition of a magnetic field (e.g. time-varying magnetic field) provided by the magnetic field generating device. FIG. 19*a* shows an exemplary composition of an RF field. FIG. 19*b* shows the exemplary composition of the RF field applied in a pulsed manner, comprising pulses and impulses. Therefore, especially in description of FIGS. 19*a* and 19*b*, the term "impulse" may refer to "magnetic impulse" or "RF impulse". Similarly, the term "pulse" may refer to "magnetic pulse" or "RF pulse". Also, term "train" may refer to "magnetic train". Term "magnetic train" may include train of magnetic pulses wherein the train of magnetic pulses may be understood as a plurality of magnetic pulses wherein one pulse follows another. As the magnetic pulse may include one magnetic impulse, the term "magnetic train" may include also a train of magnetic impulses. The term "burst" may refer to a "magnetic burst".

As shown in FIG. 19*a* or 19*b*, an impulse may refer to a time period of applied treatment energy (e.g. magnetic field) with sufficient intensity to cause at least partial treatment effect, such as an at least partial muscle contraction, muscle contraction, change of temperature of the biological structure and/or nerve stimulation. The magnetic impulse may include one biphasic shape as shown on FIG. 19*a*. The magnetic impulse may include amplitude of magnetic flux density.

A magnetic pulse may refer to a time period including an impulse and a passive time period of the pulse. The magnetic pulse may refer to a time period of one magnetic impulse and a passive time period, i.e. time duration between two impulses from rise/fall edge to subsequent of following rise/fall edge. The passive time duration of a pulse may include either applying no treatment energy to the patient's body and/or application of the treatment energy insufficient to cause at least a partial treatment effect due to insufficient treatment energy intensity (e.g. magnetic flux density) and/or frequency of delivered treatment energy. Such time period may be called a pulse duration. As shown on FIG. 19*a*, each pulse may include one biphasic shape lasting for a time period called an impulse duration. Alternatively, the impulses or pulses may be monophasic.

As further shown on FIG. 19*a* or 19*b*, the plurality of pulses may form the train. The train may refer to a plurality of pulses, wherein one train may comprise at least two pulses wherein pulses follow one by another. Train may last time period lasting $T_1$ shown in FIG. 19*a* or 19*b*.

The magnetic train may include plurality of magnetic pulses in the range of 2 magnetic pulses to 200 000 magnetic pulses or 2 magnetic pulses to 150 000 magnetic pulses or 2 magnetic pulses to 100 000 magnetic pulses. Magnetic train may cause multiple at least partial muscle contractions or muscle contractions followed one by one, at least one incomplete tetanus muscle contraction, at least one supramaximal contraction or at least one complete tetanus muscle contraction. During application of one train, magnetic field may provide one muscle contraction followed by muscle relaxation. The muscle relaxation may be followed by another muscle contraction during the application of one train. During one train, the muscle work cycle (which may include muscle contraction followed by muscle relaxation) may be repeated at least twice, three, four or more times.

The burst may refer to one train provided during time period $T_1$ and a time period $T_2$ which may represent a time period when no treatment effect is caused. The time period $T_2$ may be a time period providing passive treatment where no treatment energy is applied to a patient's body and/or applied treatment energy is insufficient to cause the treatment effect. The time period $T_3$ shown in FIG. 19*a* or 19*b* may represent the time duration of the burst.

The magnetic train of a time-varying magnetic field may be followed by a static magnetic field and/or the magnetic train may be followed by a time-varying magnetic field of frequency and/or magnetic flux density insufficient to cause at least a partial muscle contraction or muscle contraction. For example, the burst may provide at least one at least partial muscle contraction followed by no muscle contraction. In another example, the burst may provide at least one muscle contraction followed by no muscle contraction. The treatment may include a number of magnetic bursts in a range of 15 to 25,000, or in a range of 40 to 10,000, or in a range of 75 to 2,500, or in a range of 150 to 1,500, or in a range of 300 to 750 or up 100,000. The repetition rate in the subsequent bursts may incrementally increase/decrease with an increment of 1 to 200 Hz, or of 2 to 20 Hz, or of 5 Hz to 15 Hz, or more than 5 Hz. Alternatively, the amplitude of magnetic flux density may vary in the subsequent bursts, such as incrementally increase/decrease with an increment of at least 1%, 2%, or 5% or more of the previous pulse frequency. During application of one burst, magnetic field may provide one muscle contraction followed by muscle relaxation. The muscle relaxation may be followed by another muscle contraction during the application of same burst. During one burst, the muscle work cycle (which may include muscle contraction followed by muscle relaxation) may be repeated at least twice, three, four or more times.

Also, a treatment duty cycle may be associated with an application of a pulsed treatment energy of the magnetic field as illustrated in FIG. 19*a*. The treatment duty cycle may refer to a ratio between time of active treatment $T_1$ and sum of time of an active and a passive treatment during one cycle $T_3$.

An exemplary treatment duty cycle is illustrated in FIG. 19*a* or FIG. 19*b*. Duty cycle of 10% means that $T_1$ of active treatment last 2 s and passive treatment $T_2$ last 18 s. In this exemplary treatment the period including active and passive treatment period $T_3$ lasts 20 seconds. The treatment duty cycle may be defined as a ratio between $T_1$ and $T_3$. The treatment duty cycle may be in a range from 1:100 (which means 1%) to 24:25 (which means 96%) or 1:50 (which means 2%) to 4:6 (which means 67%) or 1:50 (which means 2%) to 1:2 (which means 50%) or 1:50 to 1:3 (which means 33%) or 1:50 (which means 2%) to 1:4 (which means 25%) or 1:20 (which means 5%) to 1:8 (which means 12.5%) or 1:100 (which means 1%) to 1:8 (which means 12.5%) or at least 1:4 (which means at least 25%).

An exemplary application of a burst repetition rate of 4 Hz may be the time-varying magnetic field applied to the patient with a repetition rate of 200 Hz and with a treatment duty cycle of 50% in trains lasting 125 ms, i.e. each train includes 25 pulses. An alternative exemplary application of a burst repetition rate of 6 bursts per minute may be the time-varying magnetic field applied to the patient with a repetition rate of 1 Hz and with a treatment duty cycle of 30% in trains lasting 3 s; i.e., each train includes 3 pulses.

The FIG. 19*b* may also show exemplary composition of magnetic component provided by the RF electrode.

When the treatment device uses plurality of applicators (e.g. two), each applicator may include one magnetic field generating device. As each magnetic field generating device may provide one respective magnetic field, the plurality of applicators may provide different magnetic fields. In that case the amplitude of magnetic flux density of magnetic impulses or pulses may be same or different, as specified by user through HMI and/or by one or more control units.

The impulses of one magnetic field provided by one magnetic field generating device (e.g. magnetic coil) may be generated and applied synchronously as the impulses of another magnetic field provided by another magnetic field generating device. During treatment session with the treatment device including two magnetic field generating device, the impulses of one magnetic field provided by one magnetic field generating device may be generated synchronously with the impulses of second magnetic field provided by second magnetic field generating device. Synchronous generation may include simultaneous generation.

The synchronous generation of magnetic impulses may be provided by synchronous operation of switches, energy storage devices, magnetic field generating devices and/or other electrical elements of the plurality of magnetic treatment circuit. However, the synchronous operation of electrical elements of magnetic treatment circuit may be commanded, adjusted or controlled by user through HMI, master unit and/or more control unit.

Figure 27A:
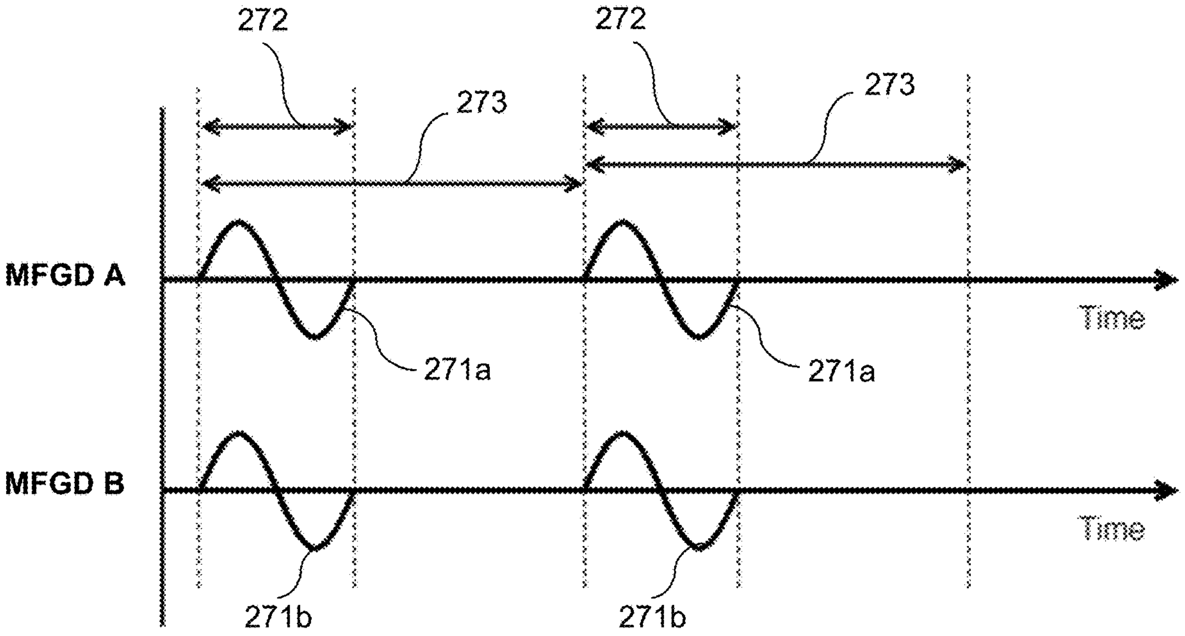
FIGS. 27*a*-27*d* illustrate an example of synchronous application of magnetic fields.

The FIG. 27*a* shows simultaneous type of synchronous generation of magnetic impulses on two exemplary magnetic field generating devices. The magnetic field generating device A (MFGD A) may generate first magnetic field including plurality of biphasic magnetic impulses 271*a*. The magnetic field generating device B (MFGD B) may generate second magnetic field including plurality of magnetic impulses 271*b*. The magnetic impulses of both magnetic fields are generated during the impulse duration 272 of the magnetic impulses 271*a* of the first magnetic field. Also, the impulse of both magnetic fields are generated within the pulse duration 273 of the first magnetic field. Simultaneous generation of magnetic field means that the magnetic impulse 271*a* of the first time-varying magnetic field is generated at the same the time as the magnetic impulse 271*b* of the second time-varying magnetic field.

The synchronous generation of magnetic fields may include generating a first pulse of the first time-varying magnetic field such that the first pulse lasts for a time period, wherein the time period lasts from a beginning of a first impulse of the first time-varying magnetic field to a beginning of a next consecutive impulse of the first time-varying magnetic field and generating a second pulse of the second time-varying magnetic field by the second magnetic field generating device such that the second pulse lasts from a beginning of a first impulse of the second time-varying magnetic field to a beginning of a next consecutive impulse of the second time-varying magnetic field. Synchronous generation of magnetic field means that the first impulse of the second time-varying magnetic field is generated during the time period of the first pulse.

Figure 27B:
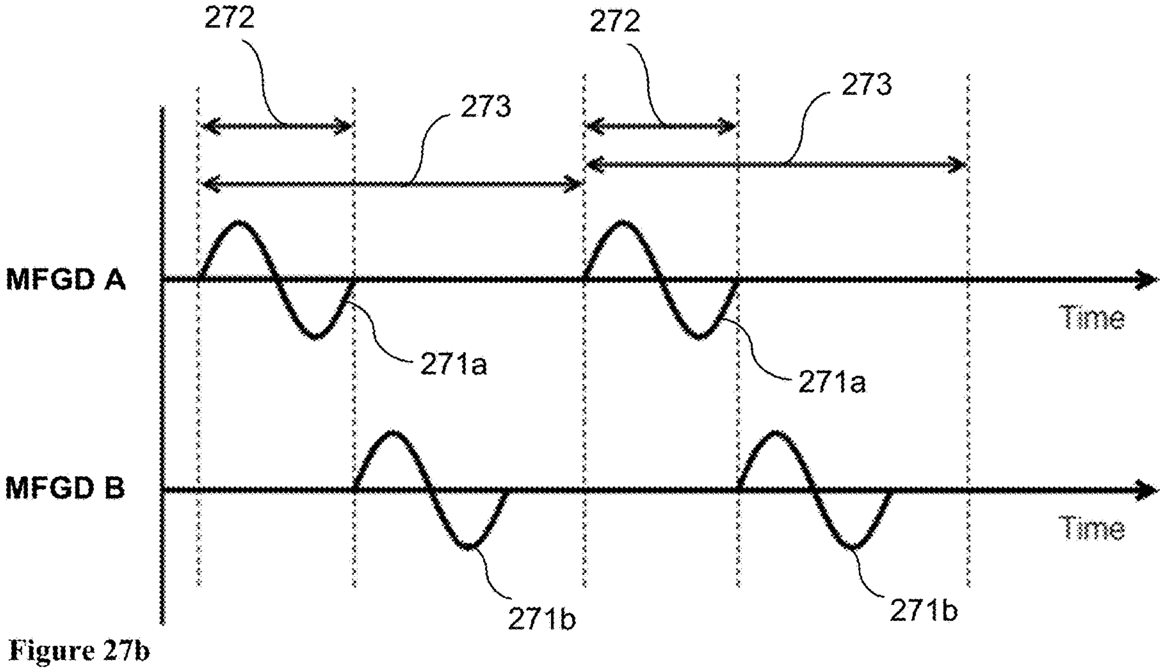

FIG. 27*b* shows an example of synchronous generation of magnetic impulses. The magnetic field generating device A (MFGD A) may generate first magnetic field including plurality of biphasic magnetic impulses 271*a*. The magnetic field generating device B (MFGD B) may generate second magnetic field including plurality of magnetic impulses 271*b*. The magnetic impulses 271*b* of second magnetic field may be generated during the pulse duration 273 of pulse of the first magnetic field, but outside of impulse duration 272 of impulse of first magnetic field.

Figure 27C:
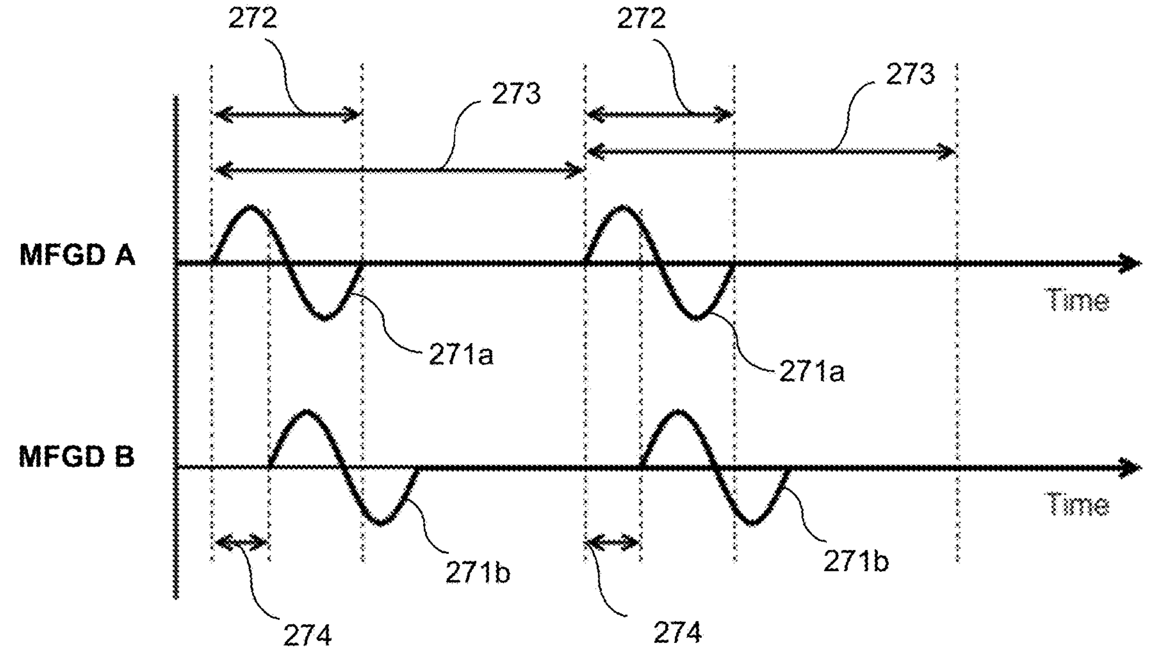

FIG. 27*c* shows another example of synchronous generation of magnetic impulses. The magnetic field generating device A (MFGD A) may generate first magnetic field including plurality of biphasic magnetic impulses 271*a*. The magnetic field generating device B (MFGD B) may generate second magnetic field including plurality of magnetic impulses 271*b*. The magnetic impulse 271*b* of second magnetic field may be generated during the pulse duration 273 of pulse of the first magnetic field. Also, the magnetic impulse 271*b* of second magnetic field may be generated during the impulse duration 272 of pulse of the first magnetic field. The beginning of the magnetic impulse 271*b* of second magnetic field may be distanced from the beginning of the impulse 271*a* of the first magnetic field by a time period called impulse shift 274. The impulse shift may be in a range of 5 μs to 10 ms or 5 μs to 1000 μs or 1 μs to 800 μs.

Figure 27D:
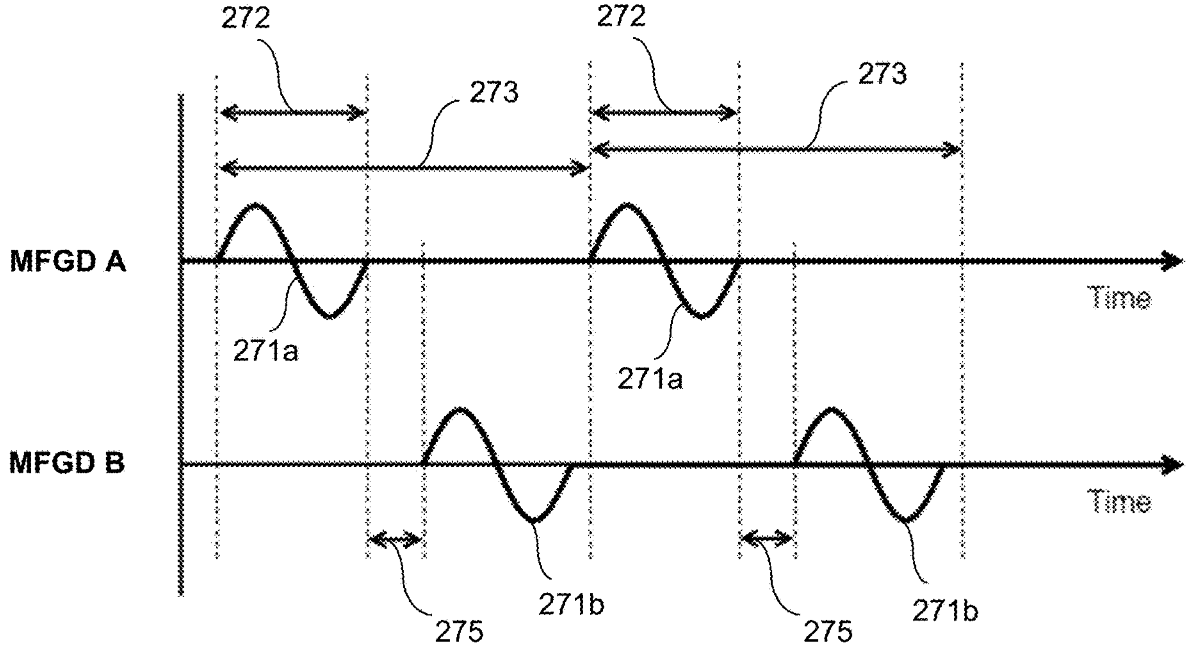

FIG. 27*d* shows still another example of synchronous generation of magnetic impulses. The magnetic field generating device A (MFGD A) may generate first magnetic field including plurality of biphasic magnetic impulses 271*a*. The magnetic field generating device B (MFGD B) may generate second magnetic field including plurality of magnetic impulses 271*b*. The magnetic impulse 271*b* of second magnetic field may be generated within the pulse duration 273 of the pulse of the first magnetic field. The magnetic impulse 271*b* of second magnetic field may be generated outside of impulse duration 272 of the impulse of the first magnetic field. The beginning of the magnetic impulse 271*b* of second magnetic field may be distanced from the end of the magnetic impulse 271*a* of the first magnetic field by a time period called impulse distance period 275. The impulse distance period may last in a range of 5 μs to 10 ms or 5 μs to 1000 μs or 1 μs to 800 μs.

Beside synchronous generation, the magnetic impulses of plurality of magnetic fields may be generated separately. Separated generation of magnetic impulses of magnetic fields may include generation of impulses of one magnetic field are generated outside of pulse duration of another magnetic field.

Figure 27E:
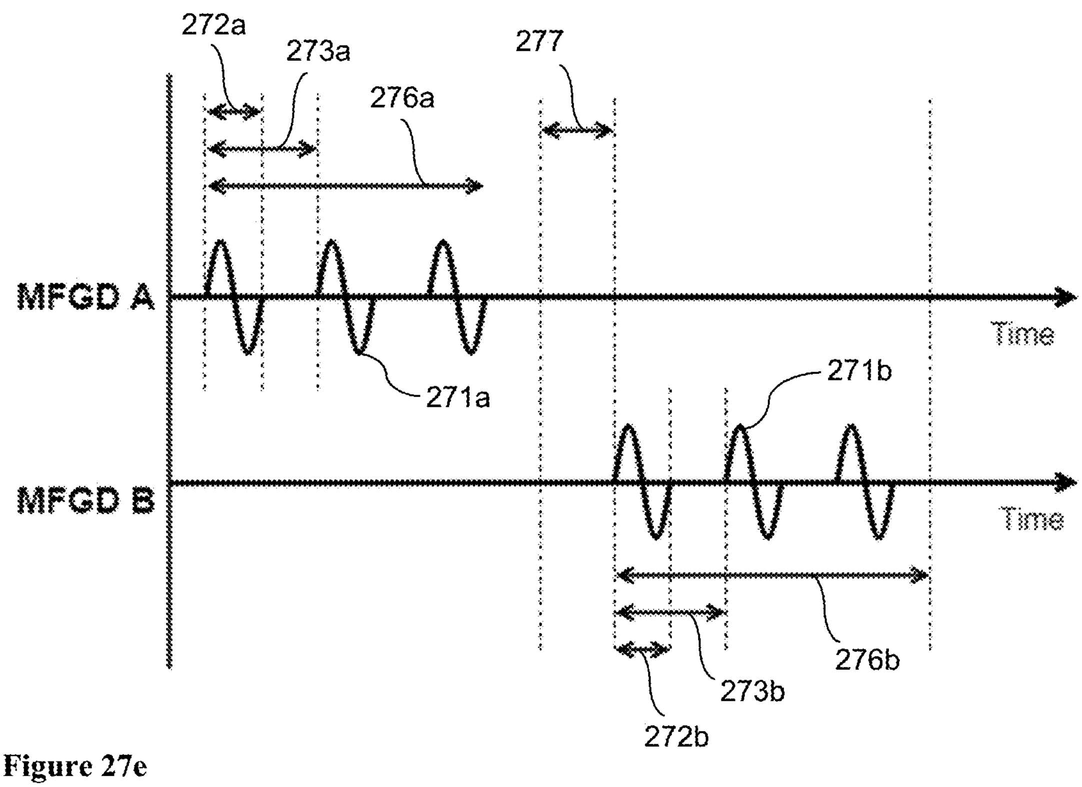
FIG. 27*e* illustrates an example of separate application of magnetic fields.

FIG. 27*e* shows example of separate generation of magnetic impulses. The magnetic field generating device A may generate first magnetic field including train of biphasic magnetic impulses 271*a* having impulse duration 272*a*. Each magnetic impulse 271*a* is part of a pulse having pulse duration 273*a*. The impulse duration 272*a* of first magnetic field may be part of pulse duration 273*a* of first magnetic field. The train of first magnetic field may have train duration 276*a*. The magnetic field generating device B may generate another magnetic field including another train of plurality of magnetic impulses 271*b* having impulse duration 272*b*. Each magnetic impulse 271*b* is part of a pulse having pulse duration 273*b*. The impulse duration 272*b* of second magnetic field may be part of pulse duration 273*b* of second magnetic field. The train of second magnetic field may have train duration 276*b*. The train having train duration 276*a* is generated by magnetic field generating device A in different time than train having train duration 276*b* generated by magnetic field generating device B. Both train may be separated by separation period 277 may be in the range of 1 ms to 30 s. During separation period 277, no magnetic field generating device may be active meaning that the energy storage device providing current pulses may not store any energy.

All examples of synchronous or separated generation of magnetic impulses may be applied during one treatment session. Also, the impulse shift and/or impulse distance period may be calculated for any magnetic impulse 271*b* of second or another magnetic field, which may be positioned according to any example given by FIGS. 27B-27E. The impulse shift and/or impulse distance period may be measured and calculated from oscilloscope measurement. The synchronous generation of magnetic impulses may lead and be extrapolated to synchronous generation of magnetic pulses and/or trains by two or more magnetic field generating devices. Similarly, the separated generation of magnetic impulses may lead and be extrapolated to separated generation of magnetic pulses and/or trains by two or more magnetic field generating devices.

The adjustment or control provided by master unit and/or one or more control units may be used for creation or shaping of magnetic envelope or RF envelope. For example, the magnetic impulses or RF impulses may be modulated in amplitude of each impulse or plurality of impulses to enable assembly of various envelopes. Similarly, the amplitude of RF energy may be modulated in amplitude to assemble various envelopes. The master unit and/or one or more control units may be configured to provide the assembly of one or more envelopes described herein. Differently shaped magnetic envelopes and/or RF envelopes (referred herein also as envelopes) may be differently perceived by the patient. The envelope or all envelopes as shown on Figures of this application may be fitted curve through amplitude of magnetic flux density of impulses, pulses or trains and/or amplitudes of power output of RF impulses of RF waves.

The envelope may be a magnetic envelope formed from magnetic impulses. The magnetic envelope formed from impulses may include plurality of impulses, e.g. at least two, three, four or more subsequent magnetic impulses. The subsequent magnetic impulses of such magnetic envelope may follow each other. In case of such envelope, the envelope duration may begin by first impulse and end with the last impulse of the plurality of impulses. The envelope may include one train of magnetic impulses. The envelope may be a fitted curve through amplitudes of magnetic flux density of impulses. The envelope formed by magnetic impulses may therefore define train shape according to modulation in magnetic flux density, repetition rate and/or impulse duration of magnetic impulses. Accordingly, the envelope may be an RF envelope formed by RF impulses and their modulation of envelope, repetition rate or impulse duration of RF impulse of RF wave.

The envelope may be a magnetic envelope formed by magnetic pulses. The magnetic envelope formed by pulses may include plurality of pulses (e.g. at least two, three, four or more subsequent magnetic pulses), wherein pulses follow each other without any missing pulse. In such case, the envelope duration may begin by impulse of first pulse and end with a passive time duration of last impulse of the plurality of pulses. The envelope formed by magnetic pulses may therefore define train shape in according to modulation in magnetic flux density, repetition rate and/or impulse duration. The envelope may include one train of magnetic pulses. The train consists of magnetic pulses in a pattern that repeats at least two times during the protocol. The magnetic envelope may be a fitted curve through amplitudes of magnetic flux density of pulses.

The envelope may be a magnetic envelope formed from magnetic trains. The magnetic envelope formed from trains may include plurality of trains (e.g. at least two, three, four or more subsequent magnetic trains), wherein trains follow each other with time duration between the train. In such case, the envelope duration may begin by impulse of first pulse of the first train and end with a passive time duration of the plurality of pulses. The plurality of trains in one envelope may be separated by missing pulses including impulses. The number of missing pulses may be in a range of 1 to 20 or 1 to 10.

The envelope may be modulated on various offset values of magnetic flux density. The offset value may be in the range of 0.01 T to 1 T or 0.1 to 1 T or 0.2 to 0.9 T. The offset value may correspond to non-zero value of magnetic flux density.

During one treatment session, treatment device may apply various number of envelopes. Two or more envelopes of magnetic field may be combined to create possible resulting shape.

In examples mentioned above, the envelope may begin by first impulse. Further, the envelope continue through duration of first respective pulse including first impulse. Further, the envelope may end with a passive time duration of last pulse, wherein the last pulse may follow the first pulse. This option is shown on following figures showing exemplary shapes of envelope of magnetic pulses. As shown on following figures, the shape of envelope may be provided by modulation of magnetic flux density. The shape of RF envelope may be provided by modulation of amplitude of power or impulses of RF waves.

Figure 28:
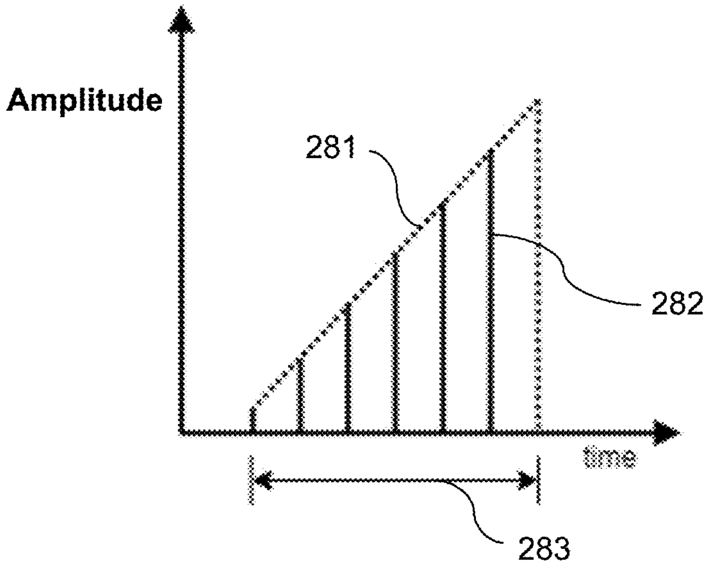
FIG. 28 illustrates an exemplary increasing envelope of magnetic field.

FIG. 28 is an exemplary illustration of an increasing envelope 281 formed from magnetic impulses 282, wherein one magnetic impulse 282 is followed by one passive time period of the magnetic pulse. Amplitude of magnetic flux density of subsequent impulses in the increasing envelope is increasing. The amplitude of magnetic flux density of one impulse is higher than amplitude of magnetic flux density of preceding impulse. Similarly, the amplitude of magnetic flux density of second impulse is higher than amplitude of magnetic flux density of the first impulse. The increasing amplitude may be used for muscle preparation. The envelope duration 283 of the increasing envelope 281 begins from first impulse of the first pulse to end of the passive time duration of last pulse. Similarly, the amplitude of RF waves may be modulated in amplitude to assemble increasing envelope 281.

Figure 29:
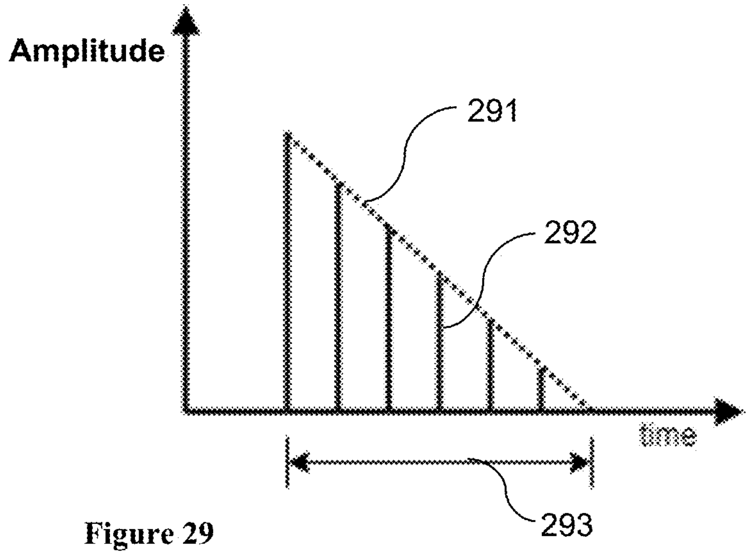
FIG. 29 illustrates an exemplary decreasing envelope of magnetic field.

FIG. 29 is an exemplary illustration of a decreasing envelope 291 formed from magnetic impulses 292. Amplitude of magnetic flux density of subsequent impulses in the decreasing envelope is decreasing. The amplitude of magnetic flux density of one impulse is lower than amplitude of magnetic flux density of preceding impulse. Similarly, the amplitude of magnetic flux density of second impulse is lower than amplitude of magnetic flux density of the first impulse. The envelope duration 293 of the decreasing envelope 291 begins from first impulse of the first pulse to end of the passive time duration of last pulse. Similarly, the amplitude of RF waves may be modulated in amplitude to assemble decreasing envelope 291.

Figure 30:
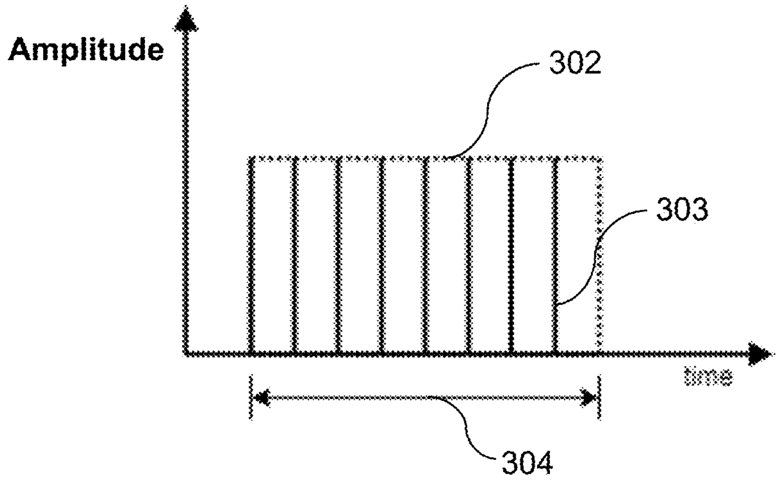
FIG. 30 illustrates an exemplary rectangular envelope of magnetic field.

FIG. 30 is an exemplary illustration of a rectangular envelope 302 formed from magnetic impulses 303. Amplitude of magnetic flux density of impulses in the rectangular envelope may be constant. However, the amplitude of magnetic flux density of subsequent impulses may oscillate around predetermined value of amplitude of magnetic flux density in range of 0.01% to 5%. The amplitude of magnetic flux density of first impulse may be identical as the amplitude of magnetic flux density of the second impulse, wherein the second impulse follows the first impulse. The envelope duration 304 of the rectangular envelope 302 begins from first impulse of the first pulse to end of the passive time duration of last pulse. The rectangular envelope may be used for inducing of muscle contraction or muscle twitches. Similarly, the amplitude of RF waves may be modulated in amplitude to assemble rectangular envelope 302.

Figure 31:
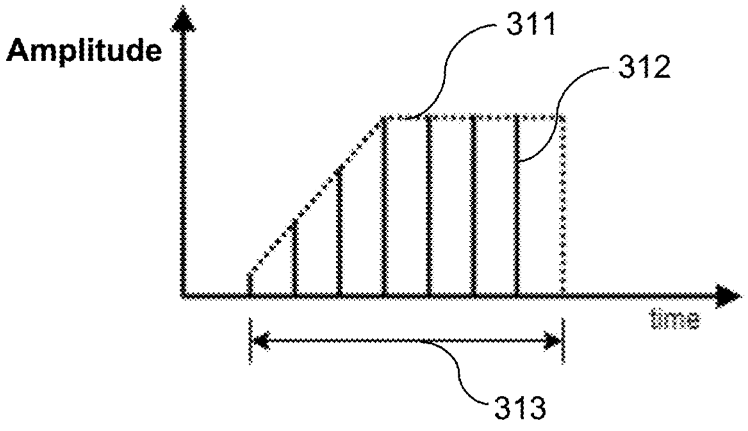
FIG. 31 illustrates an exemplary combined envelope of magnetic field.

FIG. 31 is an exemplary illustration of a combined envelope 311, which may be hypothetically seen as combination of increasing envelope and rectangular envelope. Combined envelope 311 includes magnetic impulses 312. Amplitude of magnetic flux density of impulses in the combined envelope may be increasing for in a range of 1% to 95% or 5% to 90% or 10% to 80% of the time duration of the whole combined envelope. The amplitude of magnetic flux density of subsequent impulses in the rectangular part of the combined envelope may oscillate around predetermined value of amplitude of magnetic flux density in range of 0.01% to 5%. The envelope duration 313 of the combined envelope 311 begins from first impulse of the first pulse to end of the passive time duration of last pulse. The combined envelope as shown on FIG. 31 may be used for preparation of muscle and inducing of muscle contraction or muscle twitches. Similarly, the amplitude of RF waves may be modulated in amplitude to assemble envelope 311.

Figure 32:
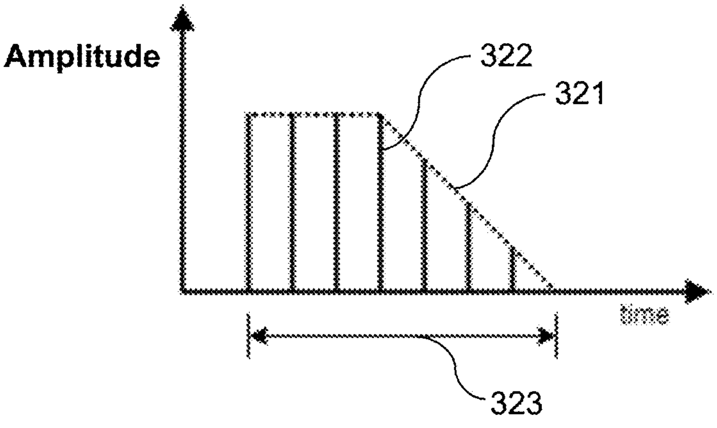
FIG. 32 illustrates another exemplary combined envelope of magnetic field.

FIG. 32 is an exemplary illustration of a combined envelope 321, which may be hypothetically seen as combination of rectangular envelope and decreasing envelope. Combined envelope 321 includes magnetic impulses 322. Amplitude of magnetic flux density of impulses in the combined envelope may be decreasing for in a range of 1% to 95% or 5% to 90% or 10% to 80% of the time duration of the whole combined envelope. The amplitude of magnetic flux density of subsequent impulses in the rectangular part of the combined envelope may oscillate around predetermined value of amplitude of magnetic flux density in range of 0.01% to 5%. The envelope duration 323 of the combined envelope 321 begins from first impulse of the first pulse to end of the passive time duration of last pulse. The combined envelope as shown on FIG. 32 may be used for inducing of muscle contraction or muscle twitches and subsequent end of the muscle stimulation. Similarly, the amplitude of RF waves may be modulated in amplitude to assemble combined envelope 321.

Figure 33:
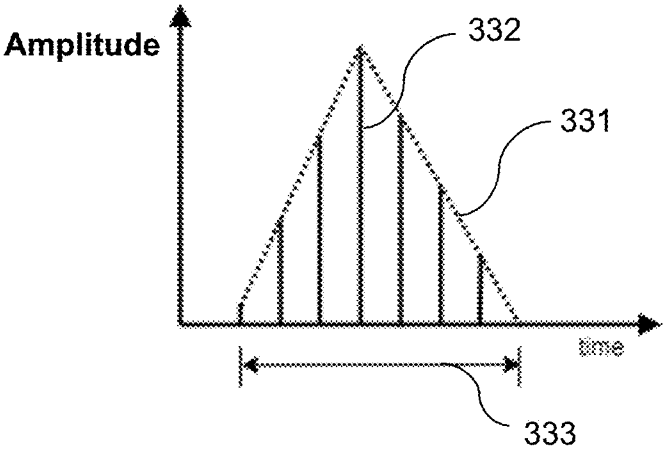
FIG. 33 illustrates an exemplary triangular envelope of magnetic field.

FIG. 33 is an exemplary illustration of triangular envelope 331, which can be understood as a combination of the increasing envelope immediately followed by the decreasing envelope. Triangular envelope 331 may include magnetic impulses 332. The triangular shape of the envelope may not be symmetrical. Also, the straightness of one or more lines of the triangular shape may be interrupted by another type of envelope mentioned herein, e.g. rectangular envelope. One triangular envelope may closely follow another triangular envelope or be joined to another triangular envelope. By joining two triangular envelopes, the resulting envelope may have the saw-tooth shape. The envelope duration 333 of the triangular envelope 331 begins from first impulse of the first pulse to end of the passive time duration of last pulse. Similarly, the amplitude of RF waves may be modulated in amplitude to assemble triangular envelope 331.

Figure 34:
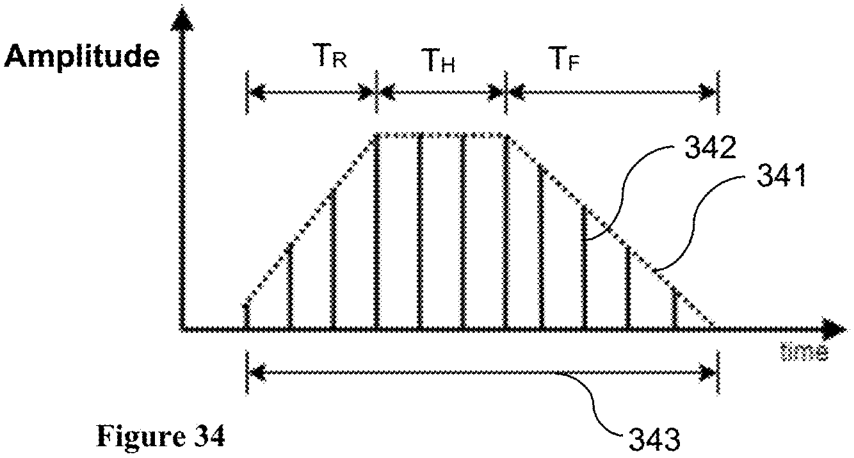
FIG. 34 illustrates an exemplary trapezoidal envelope of magnetic field.

FIG. 34 is an exemplary illustration of a trapezoidal envelope 341. The trapezoidal envelope 341 may include magnetic impulses 342. The trapezoidal envelope may include increasing (rising) time period $T_R$, hold time period $T_H$ and decreasing (fall) time period $T_F$. During increasing time period, the amplitude of magnetic flux density of subsequent impulses is increasing. Further, during increasing time period the amplitude of magnetic flux density of one impulse is higher than amplitude of magnetic flux density of preceding impulse. During hold time period, the amplitude of magnetic flux density of subsequent impulses may oscillate around predetermined value of amplitude of magnetic flux density in range of 0.01% to 5%. During decreasing time period, the amplitude of magnetic flux density of subsequent impulses is decreasing. Further, during decreasing time period the amplitude of magnetic flux density of one impulse is lower than amplitude of magnetic flux density of preceding impulse. Hold period may be interrupted by another hold time period of having different predetermined value of the magnetic flux density. The envelope duration 343 of the trapezoidal envelope 341 begins from first impulse of the first pulse to end of the passive time duration of last pulse. Similarly, the amplitude of RF waves may be modulated in amplitude to assemble trapezoidal envelope 341.

A trapezoidal envelope may be perceived by the patient as the most comfortable for muscle tissue stimulation. Trapezoidal envelope respects natural course of muscle contraction, i.e. the muscle contraction may be time-varying. Strength of natural muscle contraction increases, holds at the highest strength and decreases. The trapezoidal envelope corresponds with natural muscle contraction, i.e. the strength of the muscle contraction may correspond with the magnetic flux density. The magnetic flux density during the duration of the trapezoidal envelope increases, holds and decreases. Same shape of envelope may have RF field formed from RF impulses having appropriate amplitude.

The trapezoidal envelope may be at least once interrupted by one or more impulses, pulses, bursts and/or trains that do not fit to the trapezoidal envelope shape, but after this interruption the trapezoidal envelope may continue.

Also, the trapezoidal envelope may include plurality of trains, e.g. two, three four or more trains. In case of trapezoidal shape, the envelope may include three trains. The first train may include impulses with increasing magnetic flux density. Magnetic flux density of one impulse may be higher than magnetic flux density of the second impulse following the first impulse. The second train may include impulses with constant magnetic flux density. However, the operation of the treatment device may not provide strictly constant magnetic flux density for each impulse, therefore the magnetic flux density may oscillate in range of 0.1 to 5%. The third train may include impulses with decreasing magnetic flux density. Magnetic flux density of one impulse may be lower than magnetic flux density of the second impulse following the first impulse.

Furthermore, trapezoidal envelope may include plurality of bursts, e.g. two, three four or more bursts. In case of trapezoidal shape, the envelope may include three bursts. The first burst may include impulses with increasing magnetic flux density. Magnetic flux density of one impulse may be higher than magnetic flux density of the second impulse following the first impulse. The second bursts may include impulses with constant magnetic flux density. However, the operation of the treatment device may not provide strictly constant magnetic flux density for each impulse, therefore the magnetic flux density may oscillate in range of 0.1 to 5%. The third bursts may include impulses with decreasing magnetic flux density. Magnetic flux density of one impulse may be lower than magnetic flux density of the second impulse following the first impulse.

Figure 20:
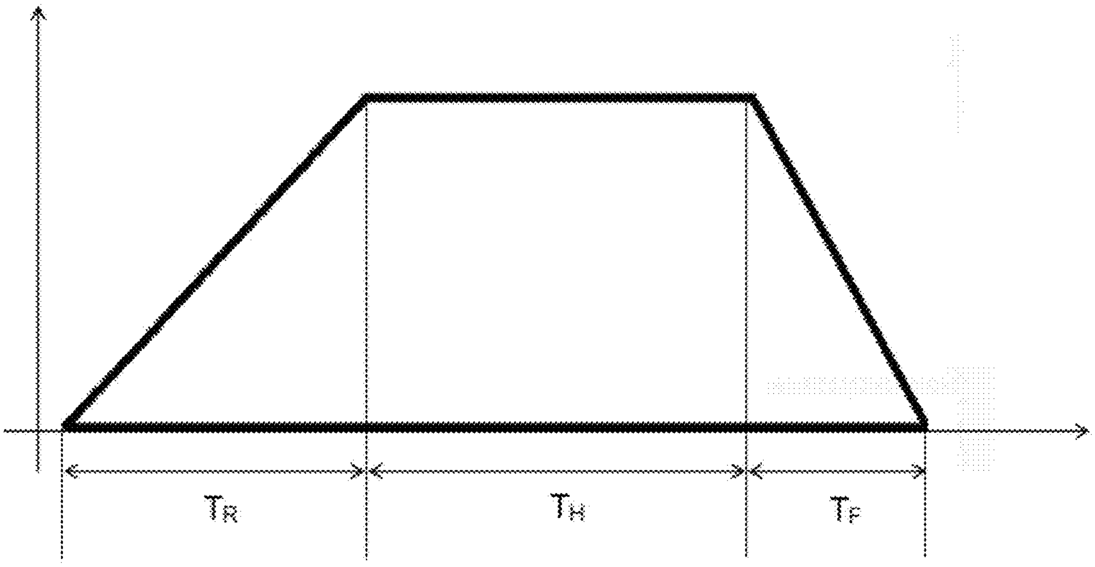
FIG. 20 illustrates a trapezoidal envelope.

FIG. 20 illustrates another exemplary trapezoidal envelope. The vertical axis may represent magnetic flux density, and the horizontal axis may represent time. A trapezoidal envelope may be a fitted curve through amplitudes of magnetic flux density of impulses applied during a train, where $T_R$ is time period with increasing magnetic flux density called increasing transient time, i.e. the amplitude of the magnetic flux density may increase. $T_H$ is time period with maximal magnetic flux density, i.e. the amplitude of the magnetic flux density may be constant. $T_F$ is time period with decreasing magnetic flux density, i.e. the amplitude of the magnetic flux density may decrease. A sum of $T_R$, $T_H$ and $T_F$ may be trapezoidal envelope duration that may corresponds with muscle contraction.

The trapezoidal envelope may decrease energy consumption. Due to lower energy consumption, the trapezoidal shape may enable improved cooling of the magnetic field generating device. Further, the resistive losses may be reduced due to lower temperature of the magnetic field generating device. Different repetition rates may cause different types of muscle contractions. Each type of muscle contraction may consume different amounts of energy.

Figure 35:
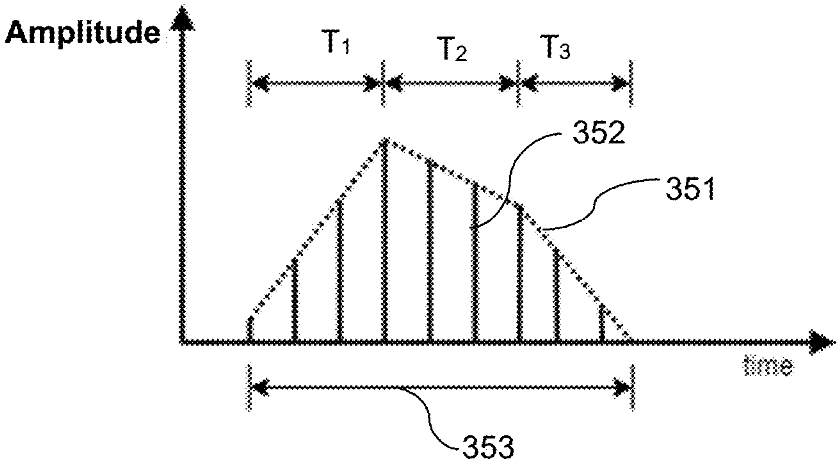
FIG. 35 illustrates another exemplary trapezoidal envelope of magnetic field.

FIG. 35 is an exemplary illustration of a trapezoidal envelope 351 including an increasing time period $T_1$, a first decreasing time period $T_2$ and a second decreasing time period $T_3$. The trapezoidal envelope 351 includes magnetic impulses 352. Increasing time period includes impulses with increasing amplitude of magnetic flux density. First decreasing time period and second decreasing time period includes impulses with decreasing amplitude of the magnetic flux density. On the shown example, first decreasing time period follows the increasing time period and precedes the second decreasing time period. The amplitude of magnetic flux density of subsequent impulses is shown to decrease more steeply during the second decreasing time period. Alternatively, the amplitude of magnetic flux density of subsequent impulses may decrease more steeply during the first decreasing time period. The envelope duration 353 of the trapezoidal envelope 351 begins from first impulse of the first pulse to end of the passive time duration of last pulse. Accordingly, the envelope may be a magnetic envelopes formed from RF impulses. Similarly, the amplitude of RF waves may be modulated in amplitude to assemble trapezoidal envelope 351.

Figure 36:
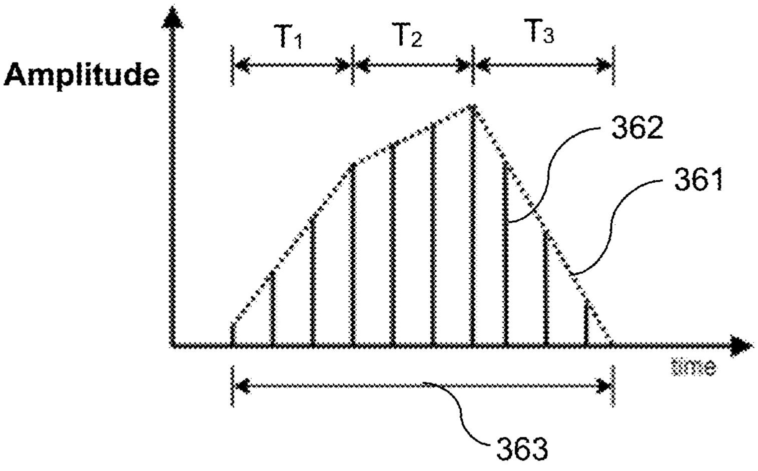
FIG. 36 illustrates another exemplary trapezoidal envelope of magnetic field.

FIG. 36 is an exemplary illustration of a trapezoidal envelope 361 including a first increasing time period, a second increasing time period and a decreasing time period. The trapezoidal envelope 361 includes magnetic impulses 362. First increasing time period and second increasing time period include impulses with increasing amplitude of magnetic flux density. First increasing time period and second increasing time period include impulses with increasing amplitude of the magnetic flux density. On the shown example, second increasing time period follows the first increasing time period and precedes the decreasing time period. The amplitude of magnetic flux density of subsequent impulses is shown to increase more steeply during the first increasing time period. Alternatively, the amplitude of magnetic flux density of subsequent impulses may increase more steeply during the second increasing time period. The envelope duration 363 of the trapezoidal envelope 361 begins from first impulse of the first pulse to end of the passive time duration of last pulse. Similarly, the amplitude of RF waves may be modulated in amplitude to assemble trapezoidal envelope 361.

Figure 37:
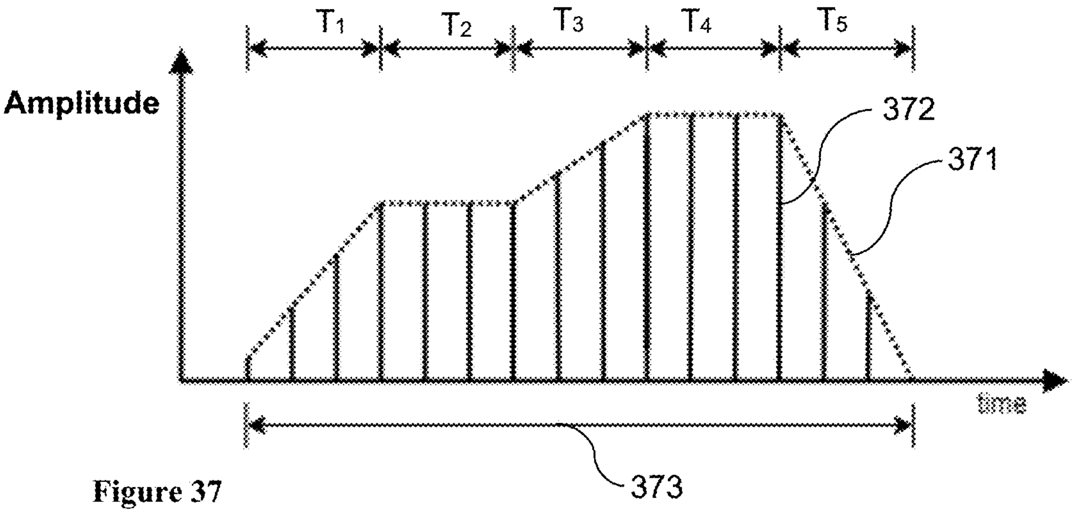
FIG. 37 illustrates an exemplary step envelope of magnetic field.

FIG. 37 is an exemplary illustration of a step envelope 371 including a first increasing time period $T_1$, first hold time period $T_2$, second increasing time period, second hold time period and a decreasing time period. The step envelope 371 includes magnetic impulses 372. During first and second increasing time periods the amplitude of magnetic flux density of subsequent impulses may increase. During decreasing time period the amplitude of magnetic flux density of subsequent impulses may decrease. During hold time period the amplitude of magnetic flux density of subsequent impulses may be constant or may oscillate around predetermined value of amplitude of magnetic flux density in range of 0.01% to 5%. The envelope duration 373 of the step envelope 371 begins from first impulse of the first pulse to end of the passive time duration of last pulse. Similarly, the amplitude of RF waves may be modulated in amplitude to assemble step envelope 371.

Figure 38:
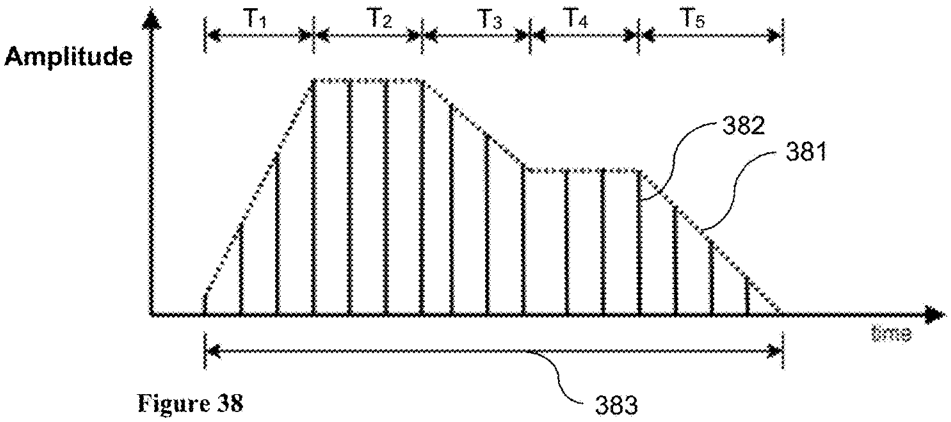
FIG. 38 illustrates another exemplary step envelope of magnetic field.

FIG. 38 is an exemplary illustration of a step envelope 381 including a first increasing time period $T_1$, first hold time period $T_2$, first decreasing time period $T_3$, second hold time period $T_4$ and a second decreasing time period $T_5$. The step envelope 381 includes magnetic impulses 382. During increasing time period the amplitude of magnetic flux density of subsequent impulses may increase. During first and second decreasing time periods the amplitude of magnetic flux density of subsequent impulses may decrease. During hold time period the amplitude of magnetic flux density of subsequent impulses may be constant or may oscillate around predetermined value of amplitude of magnetic flux density in range of 0.01% to 5%. The envelope duration 383 of the step envelope 381 begins from first impulse of the first pulse to end of the passive time duration of last pulse. Similarly, the amplitude of RF waves may be modulated in amplitude to assemble envelope 381.

Figure 39:
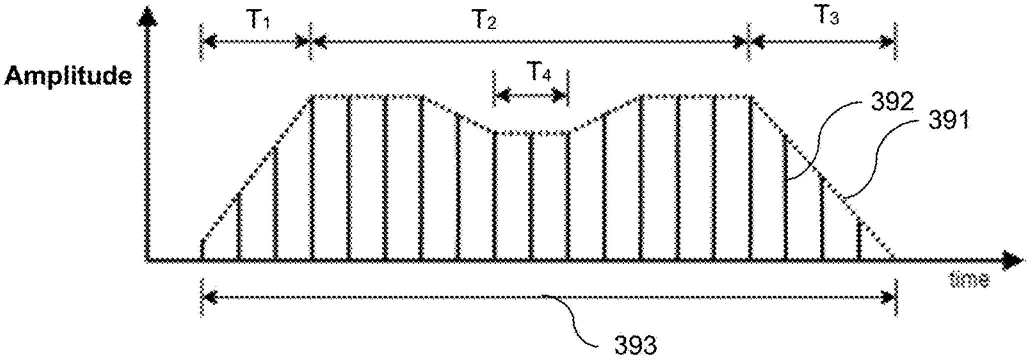
FIG. 39 illustrates another exemplary trapezoidal envelope of magnetic field.

FIG. 39 is an exemplary illustration of another type of trapezoidal envelope 391 including magnetic impulses 392. The trapezoidal envelope may include increasing time period $T_1$, hold time period $T_2$ and decreasing time period $T_3$. During increasing time period, the amplitude of magnetic flux density of subsequent impulses is increasing. Further, during increasing time period the amplitude of magnetic flux density of one impulse is higher than amplitude of magnetic flux density of preceding impulse. During hold time period, the amplitude of magnetic flux density of subsequent impulses may oscillate around predetermined value of amplitude of magnetic flux density in range of 0.01% to 5%. During decreasing time period, the amplitude of magnetic flux density of subsequent impulses is decreasing. Further, during decreasing time period the amplitude of magnetic flux density of one impulse is lower than amplitude of magnetic flux density of preceding impulse. Hold period may include another hold time period $T_4$ of having different predetermined value of the magnetic flux density. The envelope duration 393 of the envelope 391 begins from first impulse of the first pulse to end of the passive time duration of last pulse. Similarly, the amplitude of RF waves and/or RF impulses may be modulated in amplitude to assemble envelope 391.

Figure 40:
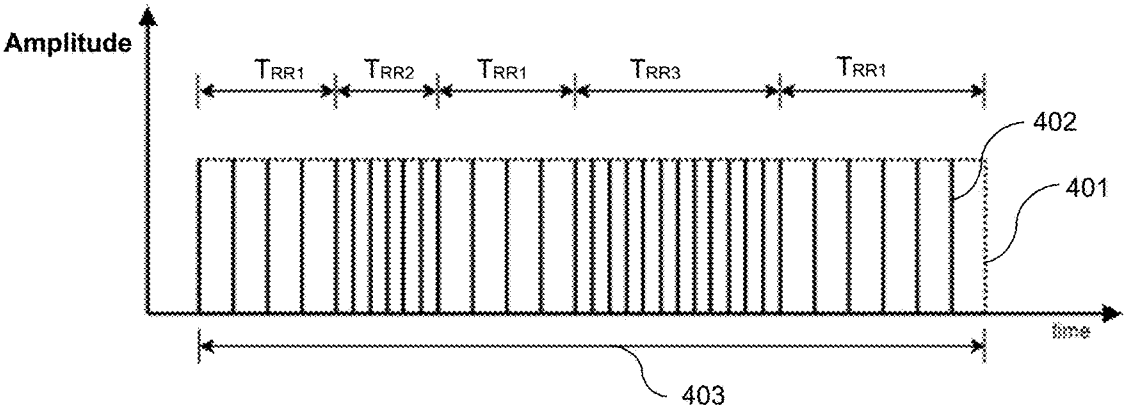
FIG. 40 illustrates an example of envelope of magnetic field including modulation in domain of repetition rate.

The envelope may include combined modulation of magnetic flux density and repetition rate. FIG. 40 shows exemplary illustration of rectangular envelope 401 with constant amplitude of magnetic flux density. The rectangular envelope 401 may include magnetic impulses 402. Time periods $T_{RR2}$ and $T_{RR3}$ shows impulses having higher repetition frequency than rest of the magnetic impulses during $T_{RR1}$ of shown rectangular envelope. Shown time periods $T_{RR2}$ and $T_{RR3}$ may provide stronger muscle contraction than the rest of the shown rectangular envelope. However, all shown envelopes may include modulation in repetition rate domain. The envelope duration 403 of the rectangular envelope 401 begins from first impulse of the first pulse to end of the passive time duration of last pulse. Accordingly, the envelope may be RF envelopes formed from RF impulses. Their amplitude may also form an amplitude, called RF envelope. Similarly, the amplitude and/or repetition rate of RF impulses may be modulated in amplitude to assemble envelopes 401.

Figure 41:
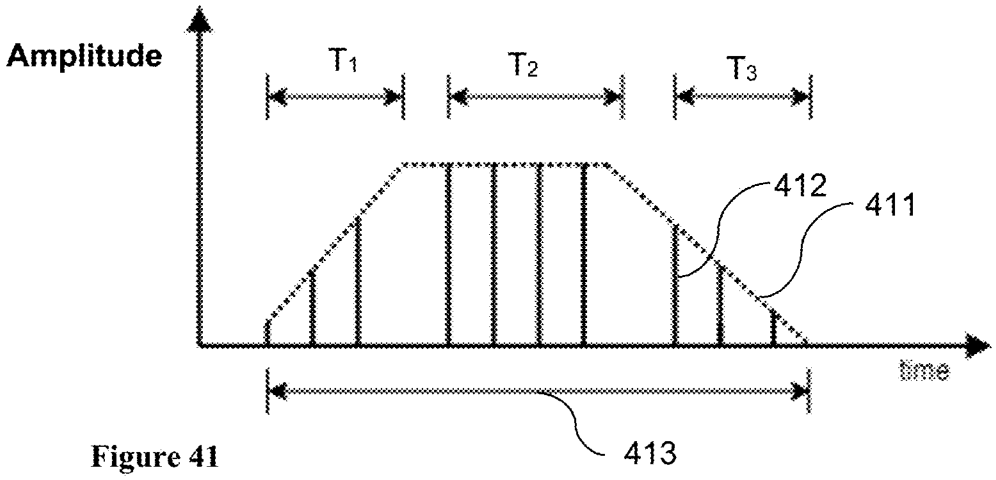
FIG. 41 illustrates an exemplary trapezoidal envelope formed from trains of magnetic field.

As mentioned, the envelope may be formed from magnetic trains separated by one or more missing pulses. FIG. 41 shows the envelope formed from magnetic trains including magnetic impulses 412. As shown, first train including train of impulses with increasing magnetic flux density has duration $T_1$. Second train of including impulses with constant or oscillating magnetic flux density has duration $T_2$. Third train of including impulses with decreasing magnetic flux density has duration $T_3$. The envelope 411 including plurality of trains has trapezoidal shape. The time durations between durations $T_1$ and $T_2$ or durations $T_2$ and $T_3$ may represent time gaps where the missing pulses including missing impulses would be positioned. The envelope duration 413 of the envelope 411 begins from first impulse of the first pulse to end of the passive time duration of last pulse. Similarly, the amplitude of RF waves or RF impulses may be modulated in amplitude to assemble envelopes 411.

Figure 42:
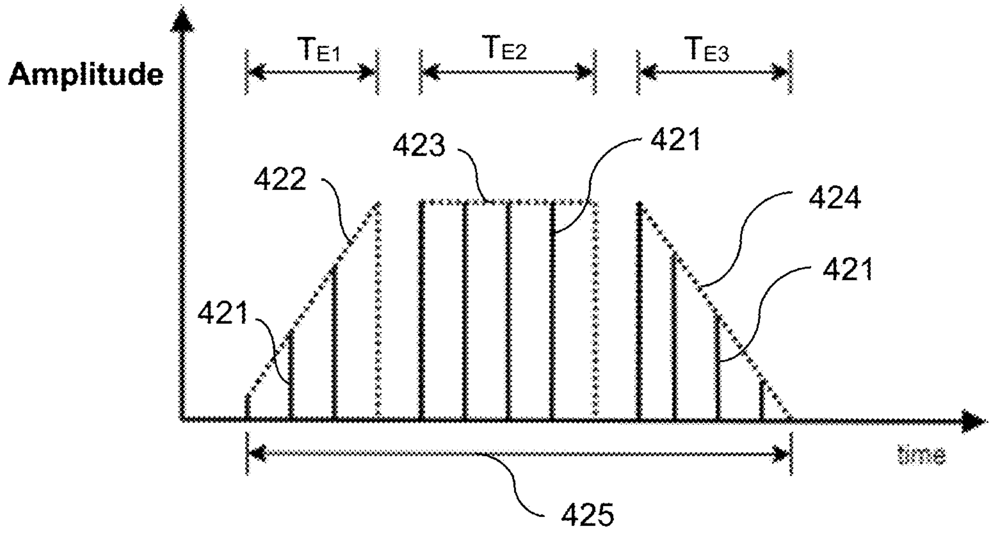
FIG. 42 illustrates another exemplary combined envelope of magnetic field.

During treatment, the magnetic envelopes may be combined. FIG. 42 shows an example of combination of magnetic envelopes. The increasing envelope 422 having increasing shape includes train of magnetic impulses 421. The increasing envelope 422 may have duration $T_{E1}$. The rectangular envelope 423 includes train of magnetic impulses 421. The rectangular envelope may have duration $T_{E2}$. The decreasing envelope 424 includes train of magnetic impulses 421. The decreasing envelope 424 may have duration $T_{E3}$. A resulting subperiod of treatment protocol formed by combination of the first, second and third envelope, may provide same or similar treatment effect as trapezoidal envelope shown e.g. on FIG. 34 and FIG. 20. A resulting subperiod of treatment protocol has duration 425 from from first impulse of the first pulse to end of the passive time duration of last pulse of the treatment subperiod. Similarly, the amplitude of RF waves and/or RF impulses may be modulated in amplitude to assemble combination of envelopes.

Figure 43:
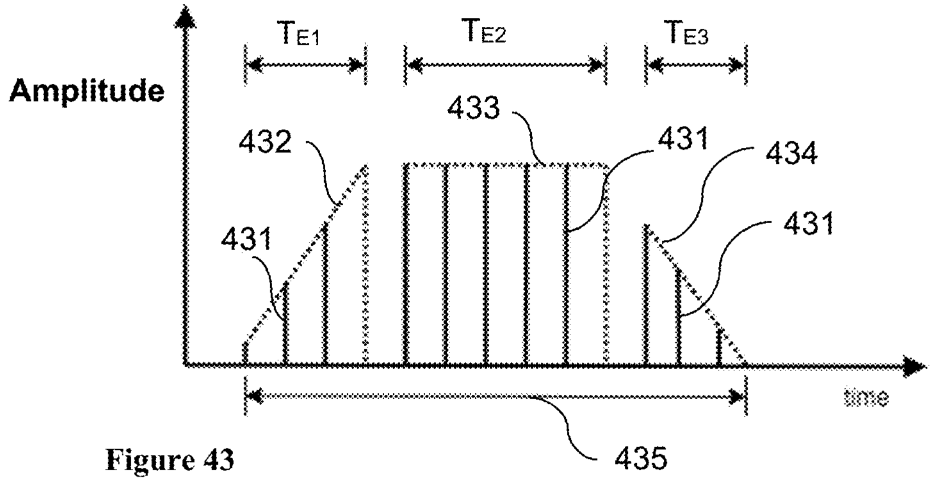
FIG. 43 illustrates another exemplary combined envelope of magnetic field.

FIG. 43 illustrates another example of combination of magnetic envelopes, wherein the decreasing period has different magnetic flux density than rectangular envelope. This example may illustrate, that combination of magnetic envelopes may include envelopes with different magnetic flux density. The increasing envelope 432 having increasing shape includes train of magnetic impulses 431. The increasing envelope may have duration TEL The rectangular envelope 433 includes train of magnetic impulses 431. The rectangular envelope may have duration $T_{E2}$. The decreasing envelope includes train of magnetic impulses 431. The decreasing envelope 434 may have duration $T_{E3}$. A resulting subperiod of treatment protocol formed by combination of the first, second and third envelope, may provide same or similar treatment effect as trapezoidal envelope shown e.g. on FIGS. 34 and 20. A resulting subperiod of treatment protocol has duration 435 from first impulse of the first pulse to end of the passive time duration of last pulse of the treatment subperiod. Similarly, the amplitude of RF waves or RF impulses may be modulated in amplitude to assemble combination of envelopes.

Figure 44:
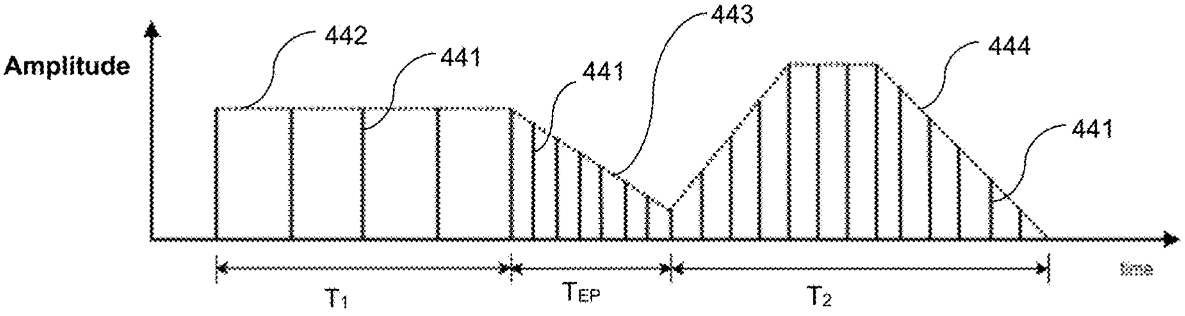
FIG. 44 illustrates two exemplary envelopes of magnetic field with an example of inter-envelope period.
Figure 45A:
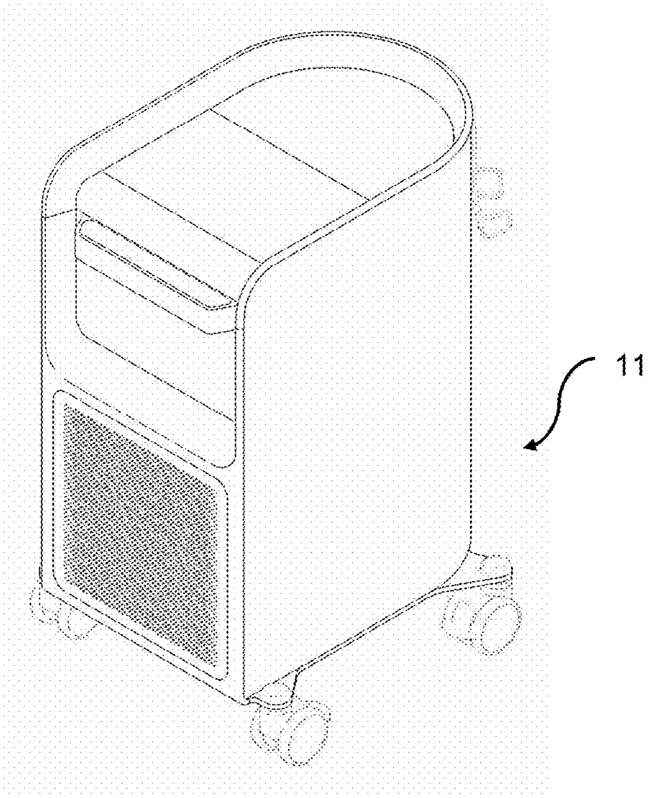
FIG. 45*a* illustrates a front perspective view of a main unit of a treatment device according to an embodiment.
Figure 45B:
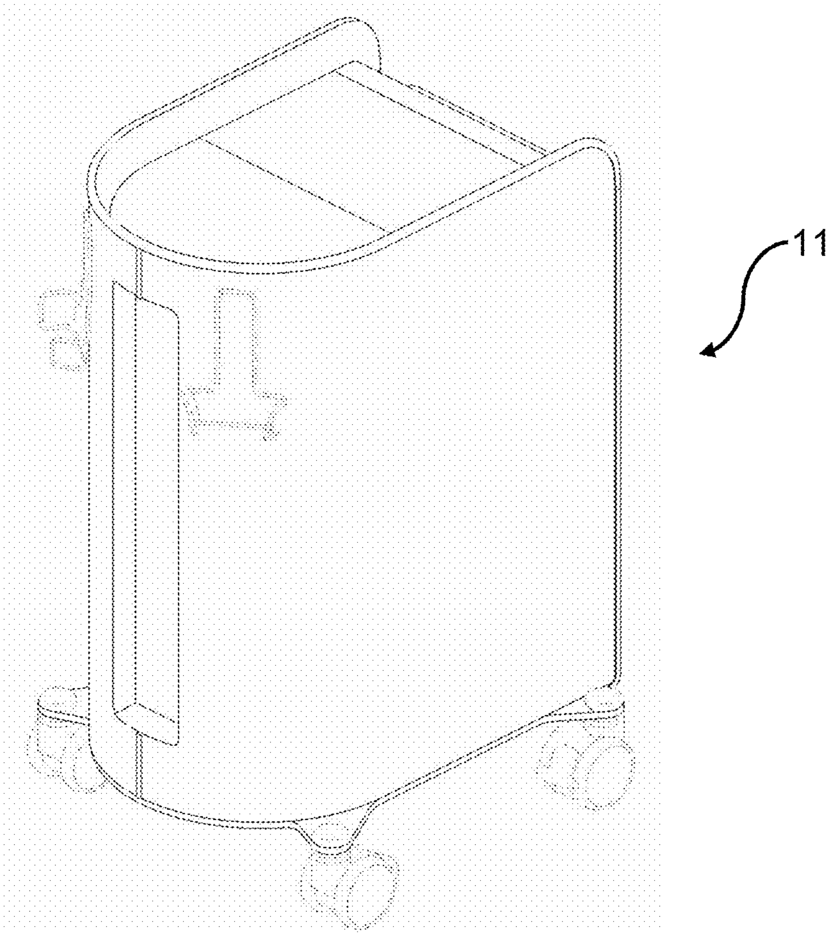
FIG. 45*b* illustrates a rear perspective view of the main unit of the treatment device of FIG. 45*a*.
Figure 46:
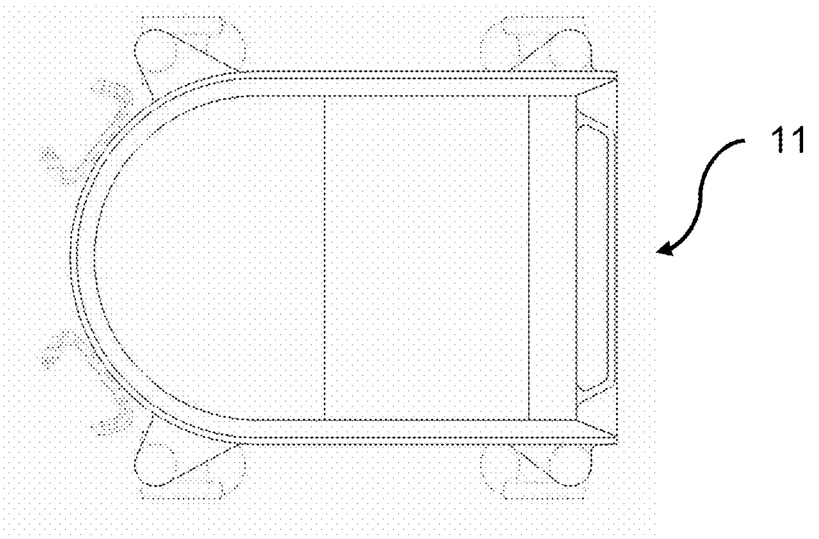
FIG. 46 illustrates a top view of the main unit of the treatment device of FIG. 45*a*.
Figure 47:
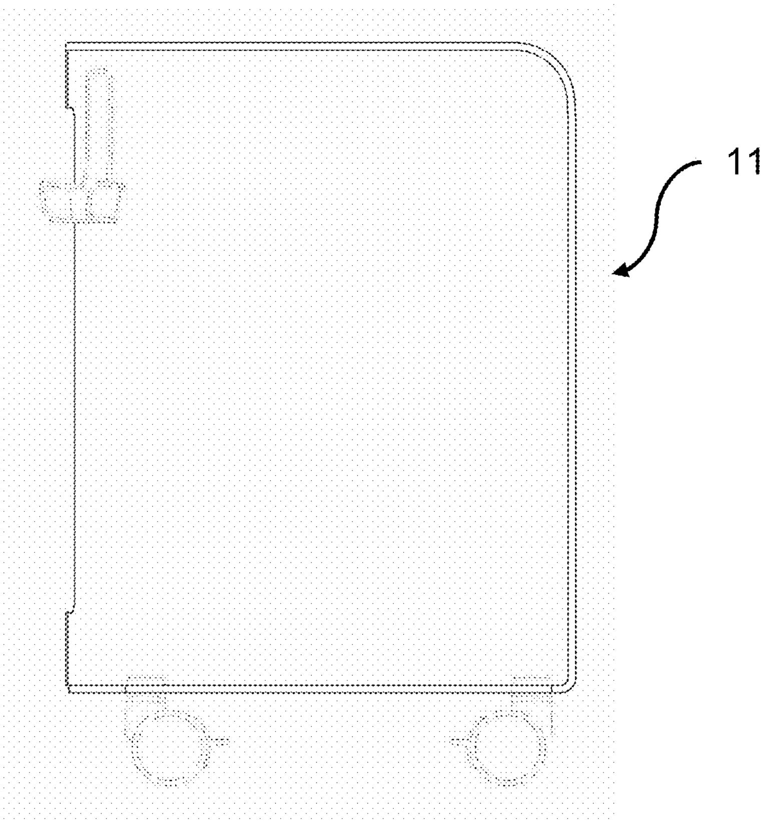
FIG. 47 illustrates a left side view of the main unit of the treatment device of FIG. 45*a*.
Figure 48:
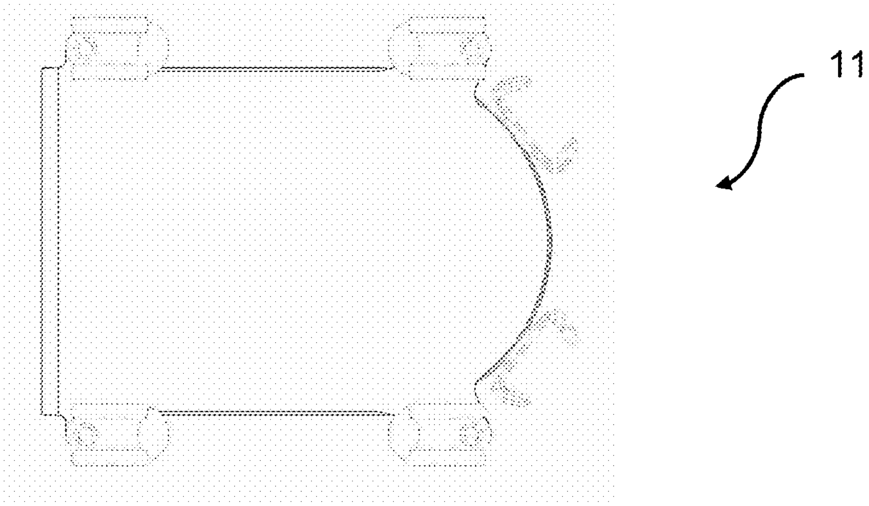
FIG. 48 illustrates a bottom view of the main unit of the treatment device of FIG. 45*a*.
Figure 49:
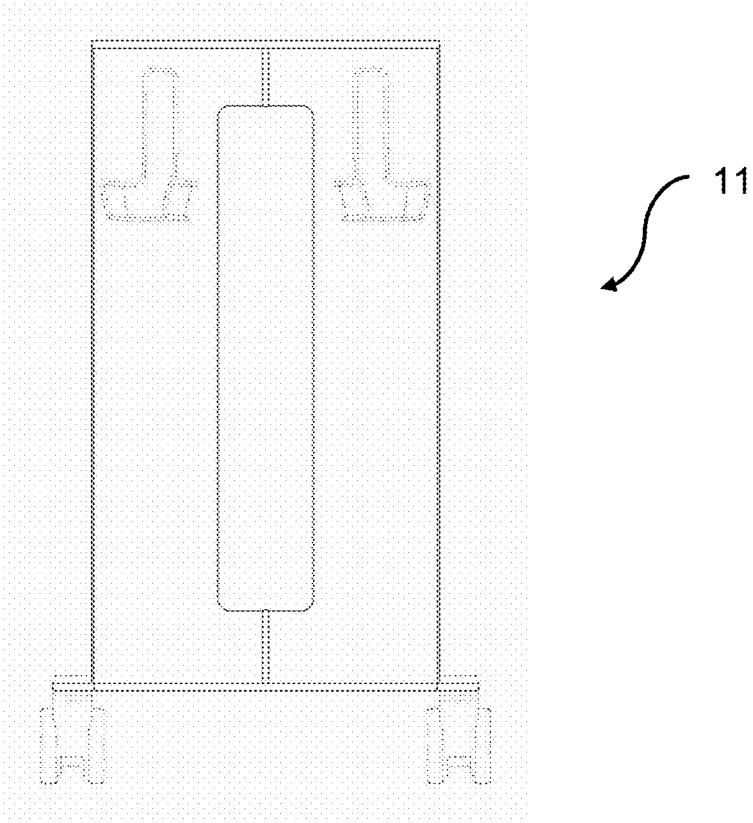
FIG. 49 illustrates a rear view of the main unit of the treatment device of FIG. 45*a*.
Figure 50:
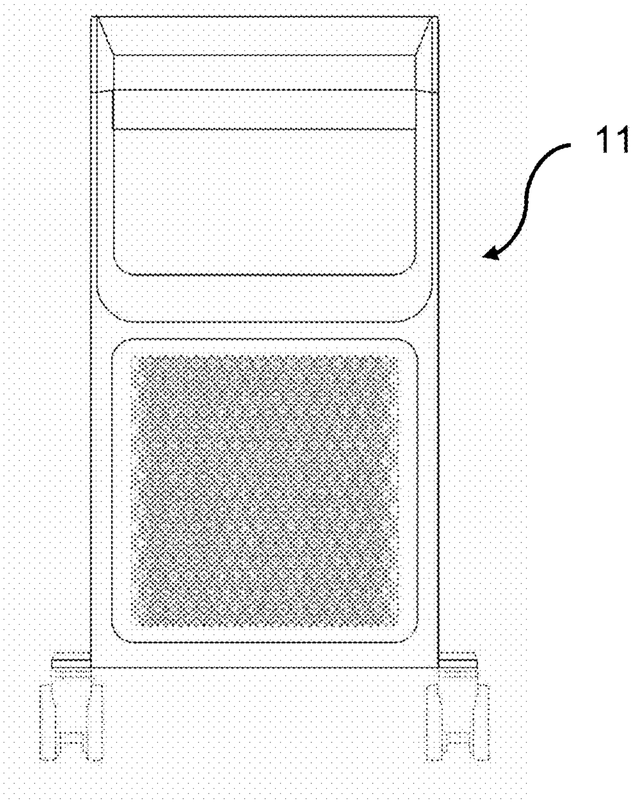
FIG. 50 illustrates a front view of the main unit of the treatment device of FIG. 45*a*.
Figure 51:
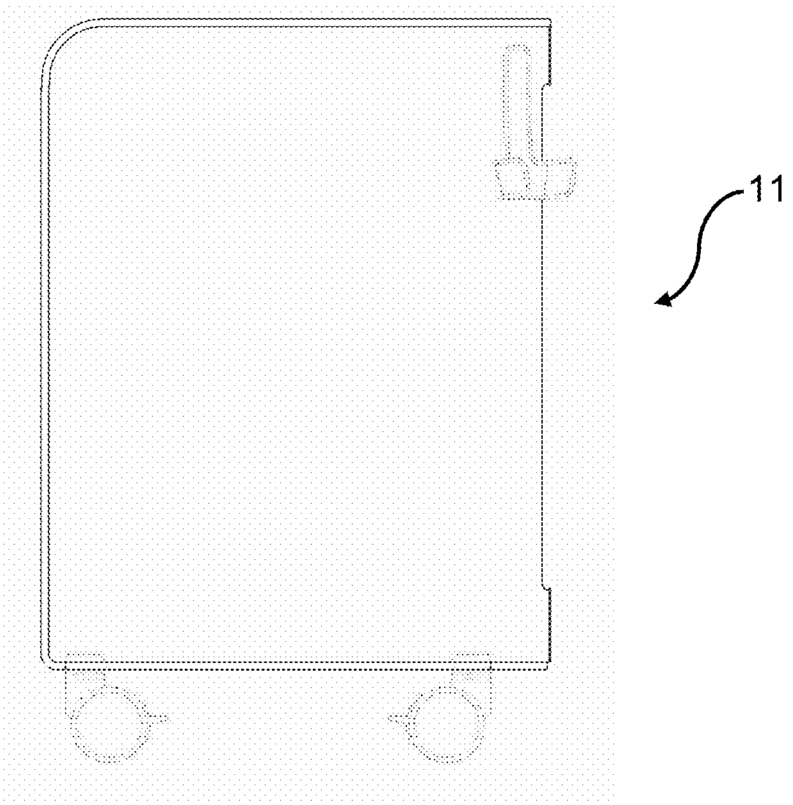
FIG. 51 illustrates a right side view of the main unit of the treatment device of FIG. 45*a*.

FIG. 44 two exemplary envelopes of magnetic field with an example of inter-envelope period i.e. time period between envelopes. Time period between envelopes may include time of no magnetic stimulation. However, the time period between envelopes may include magnetic impulses providing insufficient or unrecognizable muscle stimulation (including e.g. muscle contraction and muscle relaxation). The magnetic impulses generated during time period between envelopes may also form envelope. The magnetic impulses providing insufficient or unrecognizable muscle stimulation may be generated by discharging of energy storage device to magnetic field generating coil in order to discharge the resting capacity. The energy storage device may be then charged by power source to higher amount of electrical current and/or voltage in order to provide high power current impulses to magnetic field generating device. Rectangular envelope 442 having duration $T_1$ may include magnetic impulses 441. Trapezoidal envelope 444 having duration $T_2$ may include magnetic impulses 441. The inter-envelope time period having duration $T_{EP}$ may include envelope 443 (e.g. having decreasing shape) given by magnetic flux density of magnetic impulses 441 within the inter-envelope time period. Alternatively, the inter-envelope time period may include single impulses providing muscle twitches. Accordingly, the envelope may be a magnetic envelopes formed from RF impulses. Their amplitude may also form an amplitude, called RF envelope. The time period between RF envelopes may include time of no heating.

The RF treatment (RF field) may be generated by treatment energy source (e.g. RF electrode) in continual operation, pulsed operation or operation including cycles. The continual operation is provided during continual RF treatment. The pulsed operation is provided during pulsed RF treatment.

During the continual operation, RF electrode may generate RF field for the whole treatment or in one time duration during the treatment, as commanded by master unit one or more control units. The RF electrode may generate RF wave having a sine shape. In other words, the RF electrode may generate radio frequency waveform having sine shape.

Other shapes are possible, e.g. sawtooth, triangle or square according to amplitudes of RF wave.

The continual RF treatment may have one of the highest synergic effects with provided magnetic treatment due to continual heating of the patient's target biological structures, highest effect to polarization of the patient's target biological structures and to ensure deep magnetic field penetration and high effect of generated magnetic field to a patient's tissue, such as to promote muscle contraction.

During the pulsed generation the RF electrode may generate RF field for two or more active time periods of the treatment, wherein the time periods may be separated by passive time periods. Active time period of pulsed RF treatment may represent the time period during which the RF electrode is active and generates RF field. The active time period may be in the range of 1 s to 15 minutes, or 30 s to 10 minutes, or 5 s to 900 s, or 30 s to 300 s, or 60 s to 360 s. The passive time period of RF pulsed treatment may represent the time period during which the RF electrode is inactive and does not generate RF field. The passive time period of RF pulsed treatment may be in the range of 1 s to 15 minutes, or 10 s to 10 minutes, or 5 s to 600 s, or 5 s to 300 s, or from 10 s to 180 s. Pulsed generation and its parameters may vary during the treatment.

The user may select, control or adjust various treatment protocols of the treatment device through the control unit or the master unit of the treatment device. Also, the master unit and/or control unit may select, control or adjust treatment protocols body area or another option selected by the user. In addition, the master unit and/or control unit may select, control or adjust treatment various treatment parameters according to feedback provided by any sensor mentioned above.

The treatment protocol may include a selection of one or more treatment parameters and their predetermined values as assigned to respective protocol. Further, the treatment protocol may include various types of combined treatment by magnetic treatment and RF treatment.

Regarding the treatment parameters, the user may control or adjust various treatment parameters of the treatment device through the control system including master unit or one or more control units of the treatment device. The master unit and/or control unit may control or adjust treatment parameters according to treatment protocol, body area or another option selected by the user. In addition, the master unit and/or control unit may control or adjust treatment various treatment parameters according to feedback provided by any sensor mentioned above. The master unit or one or more control unit may provide adjustment of treatment parameters of magnetic field including magnetic flux density, amplitude of magnetic flux density, impulse duration, pulse duration, repetition rate of impulses, repetition rate of pulses, train duration, number of impulses and/or pulses in train, burst duration, composition of magnetic burst, composition of magnetic train, number of envelopes, duty cycle, shape of envelopes and/or maximal of the magnetic flux density derivative. The master unit or one or more control unit may provide adjustment of treatment parameters of RF field including frequency of RF field, duty cycle of RF field, intensity of RF field, energy flux provided by RF field, power of RF field, amplitude of power of RF field and/or amplitude of power of RF waves, wherein the RF waves may refer to electrical component of RF field. Treatment parameters may be controlled or adjusted in following ranges.

In addition, treatment parameters may include, for example, the treatment time, temperature of magnetic field generating device, temperature of RF electrode, temperature of the applicator, temperature of the cooling tank, selection of targeted body area, number of connected applicator, temperature of cooling fluid (as measured in a fluid conduit, connecting tube, applicator or cooling tank by an appropriate temperature sensor), selected body area and/or others.

Different magnetic flux density, pulse duration, composition of trains and/or bursts may have different influence on muscle tissue. One part of a magnetic treatment may cause, for example, muscle training in order to increase muscle strength, muscle volume, muscle toning, and other parts of the magnetic treatment may cause muscle relaxation. The signal provided to the RF electrode may be modulated with regard to capacity of the circuit created by two bipolar RF electrodes and the patient's body, preventing creation of standing radiofrequency waves in the applicator and/or a patient, or other. The modulation of the radiofrequency field may be provided in the frequency domain, intensity domain, impulse duration, and/or other parameters. The goal of individual radiofrequency treatment, magnetic treatment and/or their combination is to reach the most complex and/or efficient treatment of the target biological structure. The modulation in the time domain may provide active and passive periods of stimulation. Passive period may occur when the RF treatment and/or magnetic treatment includes a period with no muscle stimulation and/or no change of temperature or other treatment effect provided by RF field of target biological structure. During a passive period, there may not be generated a magnetic field and/or RF field. Also, during a passive period, magnetic field and RF field may be generated but the intensity of the magnetic field and/or the RF field may not be sufficient to provide treatment effect of at least one of the target biological structure.

The magnetic flux density of the magnetic field may be in a range from 0.1 T to 7 T, or in a range from 0.5 T to 7 T, or in a range from 0.5 T to 5 T, or in range from 0.5 T to 4 T, or in range from 0.5 T to 2 T. Such definition may include the amplitude of magnetic flux density of the magnetic field. Shown ranges of magnetic flux density may be used for causing muscle contraction. The magnetic flux density and/or amplitude of the magnetic flux density may be measured by fluxmeter or by oscilloscope. The disclosed ranges of magnetic flux density may be measured on the surface of the magnetic field generating device or on the surface of the applicator being in contact with the patient.

A repetition rate may refer to a frequency of firing the magnetic impulses. The repetition rate may be derived from the time duration of the magnetic pulse. The repetition rate of the magnetic impulses may be in the range of 0.1 Hz to 700 Hz, or from 1 Hz to 700 Hz, or from 1 Hz to 500 Hz, or in the range of 1 Hz to 300 Hz, or 1 Hz to 150 Hz. As each magnetic pulse includes one magnetic impulse, the repetition rate of magnetic pulses is equal to repetition rate of magnetic impulses. The duration of magnetic impulses may be in a range from 1 μs to 10 ms, or from 3 μs to 3 ms, or from 3 μs to 3 ms, or from 3 μs to 1 ms, or 10 μs to 2000 μs, or 50 μs to 1000 μs, or from 100 μs to 800 μs. The repetition rate of impulses may be measured from recording of the oscilloscope measurement.

The train duration may be in the range of 1 ms to 300 s or from 1 ms to 80 s or from 2 ms to 60 s or 4 ms to 30 s, or from 8 ms to 10 s, or from 25 ms to 3 s. A time between two subsequent trains may be in a range of 5 ms to 100 s, or of 10 ms to 50 s, or of 200 ms to 25 s, or of 500 ms to 10 s, or of 750 ms to 5 s or from 300 ms to 20 s. The repetition rate may be measured from recording of the oscilloscope measurement.

The burst duration may be in a range of 10 ms to 100 seconds, or from 100 ms to 15 s, or from 500 ms to 7 s, or from 500 ms to 5 s. The repetition rate of magnetic bursts may be in a range of 0.01 Hz to 150 Hz, or of 0.02 Hz to 100 Hz, or in the range of 0.05 Hz to 50 Hz, or 0.05 Hz to 10 Hz, or of 0.05 Hz to 2 Hz. The repetition rate may be measured from recording of the oscilloscope measurement.

Another parameter to provide effective magnetic treatment and causing muscle contraction is a derivative of the magnetic flux density defined by dB/dt, where: dB is magnetic flux density derivative [T] and dt is time derivative [s]. The magnetic flux density derivative is related to magnetic field. The magnetic flux density derivative may be defined as the amount of induced electric current in the tissue and so it may serve as one of the key parameters to in providing muscle contraction. The higher the magnetic flux density derivative, the stronger muscle contraction is. The magnetic flux density derivative may be calculated from the equation mentioned above.

The maximal value of the magnetic flux density derivative may be up to 5 MT/s, or in the ranges of 0.3 to 800 kT/s, 0.5 to 400 kT/s, 1 to 300 kT/s, 1.5 to 250 kT/s, 2 to 200 kT/s, or 2.5 to 150 kT/s.

The frequency of the RF field (e.g. RF waves) may be in the range of hundreds of kHz to tens of GHz, e.g. in the range of 100 kHz to 3 GHz, or 500 kHz to 3 GHz, 400 kHz to 900 MHz or 500 kHz to 900 MHz or around 13.56 MHz, 40.68 MHz, 27.12 MHz, or 2.45 GHz.

An energy flux provided by RF field (e.g. RF waves) may be in the range of 0.001 $W/cm^2$ to 1,500 $W/cm^2$, or 0.001 $W/cm^2$ to 15 $W/cm^2$, or 0.01 $W/cm^2$ to 1,000 $W/cm^2$, or of 0.01 $W/cm^2$ to 5 $W/cm^2$, or of 0.08 $W/cm^2$ to 1 $W/cm^2$ or of 0.1 $W/cm^2$ to 0.7 $W/cm^2$. The term "around" should be interpreted as in the range of 5% of the recited value.

The voltage of electromagnetic signal provided by power source of treatment circuit for RF treatment may be in the range of 1 V to 5 kV, or 5 V to 140 V, or 10 V to 120 V, or 15 V to 50 V, or 20 V to 50 V.

The power provided by power source or adapter may be in a range of 100 W to 1000 W, or 150 W to 600 W. The power provided by power source or adapter may be 220 W or 400 W.

The temperature in the biological structure, temperature on the surface of treated body area, temperature in the body area, temperature of the inside of the applicator, temperature of the RF electrode and/or temperature of the magnetic field generating device may be measured e.g. by the temperature sensor 816 implemented in the applicator shown in FIG. 8*c*. The temperature of the RF electrode and/or magnetic field generating device may be maintained in a range from 38° C. to 150° C., 38° C. to 100° C., or from 40° C. to 80° C., 40° C. to 60° C. or 41° C. to 60° C., or 42° C. to 60° C. The temperature on the surface of treated body area, temperature in the treated body and/or in the biological structure may be increased to the temperature in a range of 38° C. to 60° C., or of 40° C. to 52° C., or of 41° C. to 50° C., or of 41° C. to 48° C., or of 42° C. to 48° C., or of 42° C. to 45° C. The values of temperature described above may be achieved during 5 s to 600 s, 10 s to 300 s, or 30 s to 180 s after RF treatment and/or magnetic treatment starts. After that, the value temperature may be maintained constant during the treatment with maximal temperature deviation in a range of 5° C. 3° C., or 2° C., or 1° C.

At the beginning of the treatment a starting temperature on the patient's skin and/or in the biological structure may be increased to the starting temperature in range from 42° C. to 60° C., or from 45° C. to 54° C., or from 48° C. to 60° C., or from 48° C. to 52° C. and/or to a temperature 3° C., or 5° C., or 8° C. above the temperature when apoptotic process begins but not over 60° C. After 45 s to 360 s, or after 60 s to 300 s, or after 120 s to 400 s, or after 300 s to 500 s when the starting temperature was reached, the intensity of the RF field may be decreased and a temperature on the patient's skin and/or temperature in the biological structure may be maintained at the temperature in a range from 41° C. to 50° C., or from 42° C. to 48° C. According to another method of the treatment, the temperature of the biological structure may be during the treatment at least two times decreased and increased in a range of 2° C. to 10° C., 2° C. to 8° C., or 3° C. to 6° C. while at least one applicator is attached to the same patient's body area, such as an abdominal area, buttock, arm, leg and/or other body area.

Temperature in the biological structure may be calculated according to mathematic model, correlation function, in combination with at least one or more measured characteristic. Such measured characteristic may include temperature on the patient's skin, capacitance between RF electrodes, Volt-Ampere characteristic of RF bipolar electrodes and/or Volt-Ampere characteristic of connected electrical elements to RF electrodes.

The treatment duration may be from 5 minutes to 120 minutes, or from 5 minutes to 60 minutes, or from 15 minutes to 40 minutes. During one week, one, two or three treatments of the same body area may be provided. Also, one pause between two subsequent treatments may be one, two or three weeks.

The sum of energy flux density of the RF treatment and the magnetic treatment applied to the patient during the treatment, may be in a range from 0.03 $mW/mm^2$ to 1.2 $W/mm^2$, or in the range from 0.05 $mW/mm^2$ to 0.9 $W/mm^2$, or in the range from 0.01 $mW/mm^2$ to 0.65 $W/mm^2$. A portion of the energy flux density of magnetic treatment during the simultaneous application of RF treatment and active magnetic treatment may be in a range from 1% to 70%, 3% to 50%, 5% to 30%, or 1% to 20% of treatment time.

The power output of RF energy (i.e. RF field) provided by one RF electrode may be in a range of 0.005 W to 350 W, 0.1 W to 200 W, 0.1 W to 150 W, 1 W to 100 W, or 3 W to 50 W.

Figure 21:
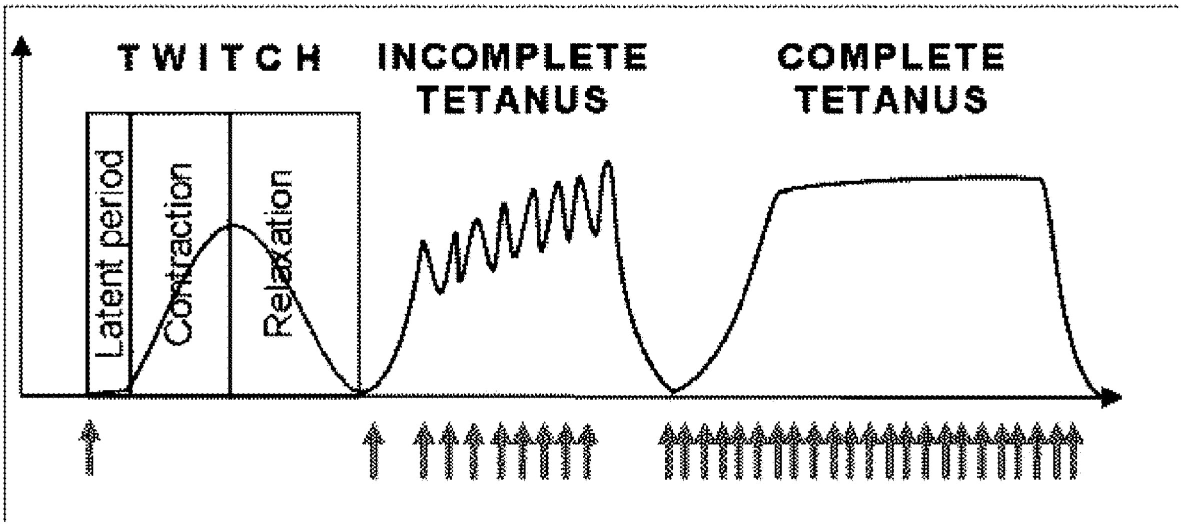
FIG. 21 illustrates different types of muscle stimulation.

FIG. 21 illustrates different types of muscle contraction, which may be provided by treatment device and achieved by application of magnetic field or combination of magnetic field and RF field. The muscle contraction may differ in energy consumption and muscle targeting, e.g., muscle strengthening, muscle volume increase/decrease, muscle endurance, muscle relaxation, warming up of the muscle and/or other effects. The vertical axis may represent a strength of the muscle contraction, and the horizontal axis may represent time. The arrows may represent magnetic impulses and/or pulses applied to the muscle of the patient.

Low repetition rate of the time-varying magnetic field pulses, e.g. in a range of 1 Hz to 15 Hz, may cause a twitch. Low repetition rate may be sufficiently low to enable the treated muscle to fully relax. The energy consumption of the treated muscle may be low due to low repetition rate. However, the low repetition rate may cause for active relaxation of muscle e.g. between two contractions.

Intermediate repetition rate of the time-varying magnetic field pulses may cause incomplete tetanus muscle contraction, intermediate repetition rate may be in a range of 15 Hz to 29 Hz. Incomplete tetanus muscle contraction may be defined by a repetition rate in a range of 10 Hz to 30 Hz. The muscle may not fully relax. The muscle may be partially relaxed. The muscle contraction strength may increase with constant magnetic flux density applied.

Higher repetition rate of the time-varying magnetic field pulses may cause complete tetanus muscle contraction. Higher repetition rates may be for example in a range of 30 Hz to 150 Hz, or 30 Hz to 90 Hz, or 30 Hz to 60 Hz. The complete tetanus muscle contraction may cause the strongest supramaximal muscle contraction. The supramaximal muscle contraction may be stronger than volitional muscle contraction. The energy consumption may be higher. The strengthening effect may be improved. Further, it is believed that at repetition rates of at least 30 Hz, the adipose cells may be reduced in volume and/or in number.

Even higher repetition rate of the time-varying magnetic field pulses over 90 Hz may suppress and/or block pain excitement transmission at different levels or neural system and/or pain receptors. The higher repetition rate may be at least 100 Hz, at least 120 Hz, or at least 140 Hz, or in a range of 100 Hz to 230 Hz, or 120 Hz to 200 Hz, or 140 Hz to 180 Hz. The application of time-varying magnetic field to the muscle of the patient may cause a pain relieving effect.

High repetition rate of the time-varying magnetic field pulses in a range of 120 Hz to 300 Hz, or 150 Hz to 250 Hz, or 180 Hz to 350 Hz, or higher than 200 Hz may cause a myorelaxation effect.

A quality of the muscle contraction caused by the time-varying magnetic field may be characterized by parameters such as a contractile force of the muscle contraction, a muscle-tendon length, a relative shortening of the muscle or a shortening velocity of the muscle.

The contractile force of the muscle contraction may reach a contractile force of at least 0.1 $N/cm^2$ and up to 250 $N/cm^2$. The contractile force may be in a range from 0.5 $N/cm^2$ to 200 $N/cm^2$, or in the range from 1 $N/cm^2$ to 150 $N/cm^2$, or in the range from 2 $N/cm^2$ to 100 $N/cm^2$.

The muscle-tendon length may reach up to 65% of a rest muscle-tendon length. The muscle-tendon length may be in a range of 1 to 65% of the rest muscle-tendon length, or in a range of 3 to 55% of the rest muscle-tendon length, or in a range of 5% to 50% of the rest muscle-tendon length.

The muscle may be shortened during the muscle contraction up to 60% of a resting muscle length. The muscle shortening may be in a range of 0.1% to 50% of the resting muscle length, or in the range of 0.5% to 40% of the resting muscle length, or in the range of 1% to 25% of the resting muscle length.

The muscle may shorten at a velocity of up to 10 cm/s. The muscle shortening velocity may be in a range of 0.1 cm/s to 7.5 cm/s, or in the range of 0.2 cm/s to 5 cm/s, or in the range of 0.5 cm/s to 3 cm/s.

A time-varying magnetic field may be applied to the patient in order to cause a muscle shaping effect by muscle contraction. The muscle may obtain increased tonus and/or volume. Strength of the muscle may increase as well.

Regarding the types of combined treatment by RF treatment and magnetic treatment, the treatment device may be configured to provide different treatment energies (e.g. RF field and magnetic field) in various time periods during one treatment session. The user may control or adjust the treatment through the HMI. HMI may be coupled to master unit and/or one or more control units. Also, the master unit and/or control unit may control or adjust application of different treatment energies according to treatment protocol, body area or another option selected by the user. In addition, the master unit and/or control unit may control or adjust application of different treatment energies according to feedback provided by any sensor mentioned above. Therefore, master unit and/or one or more control units may control or adjust the treatment and providing of treatment energies (e.g. RF treatment and magnetic treatment) in various time periods during one treatment session. All shown types of applications of magnetic treatment and RF treatment may be provided by treatment device.

One type of combined application of magnetic treatment with RF treatment may be simultaneous application. During simultaneous application both magnetic treatment and RF treatment may applied in same time during whole or most of treatment session. In one example, simultaneous application may be achieved by application of one or more sections of magnetic field with application of continuous RF field. In another example, pulsed magnetic treatment may be applied during continual RF treatment. In still another example, simultaneous application may be achieved by continual application of RF treatment together with e.g. one, or two long train of magnetic pulses. In such case, long train of magnetic pulses should include magnetic pulses having repetition rate of values in range of 1 Hz to 15 Hz or 1 Hz to 10 Hz. When only one or two long magnetic trains are used for the whole treatment session, train duration of such trains may be in the range of 5 s to 90 minutes or 10 s to 80 minutes or 15 minutes to 45 minutes.

Muscle contraction caused by the time-varying magnetic field with or during simultaneous RF treatment may include more affected muscle fibres. Also, the targeted biological structure (e.g. muscle) may be more contracted with applied lower magnetic flux density of magnetic field as compared to situation without simultaneous RF treatment.

Simultaneous application of the RF treatment and the magnetic treatment into the same body area may improve dissipation of heat created by the RF treatment. This effect is based on increased blood circulation in treated body area or vicinity of treated area. Also, induced muscle work may improve homogeneity of heating and dissipation of heat induced and provided by RF field.

Further, the simultaneous application of the RF treatment and the magnetic treatment into the same body area may be used for treatment with blood restriction of the muscle and/or body area. In this example, the magnetic field may keep the body area and/or its surrounding area contracted and limit the blood flow into the the body area. By providing heating, the muscle with constricted blood flow may be better prepared for regeneration.

Another type of combined application of magnetic treatment with RF treatment may be separate application. During separate application both magnetic treatment and RF treatment may applied in different time during treatment session. RF treatment may be provided before, after, and/or between magnetic envelopes, bursts, trains, pulses and/or impulses of magnetic treatment.

The ratio between a time when the magnetic treatment is applied and a time when the RF treatment is applied may be in a range of 0.2% to 80%, or 2% to 60%, or 5% to 50%, or 20% to 60%. The time of applied magnetic treatment for this calculation is the sum of all pulse durations during the treatment.

Another type of combined application of magnetic treatment with RF treatment may be dependent application. Application of one treatment energy may be dependent on start or one or more treatment parameter of another treatment energy. Dependent application may be started or regulated according to feedback from one or more sensor. For example, start of application of RF treatment may be dependent on start of magnetic treatment or start of train, burst and/or envelope. When the thermal dissipation provided by a muscle work (including muscle contraction and/or relaxation) is not provided, health risk of unwanted tissue damage caused by overheating may occur. In another example, start of application of magnetic treatment may be dependent on the start, time duration or intensity of RF treatment. The magnetic treatment may preferably start after the biological structure is sufficiently heated. The magnetic treatment providing at least partial muscle contraction or muscle contraction may improve blood and lymph flow, provide massage of the adjacent tissues and provides better redistribution of the heat induced in the patient's body by the RF treatment.

The device and method may include a combination of magnetic field and mechanical treatment. The device and method may include different combinations of radiofrequency treatment and mechanical treatment.

The device and method may provide a combination of magnetic treatment, radiofrequency treatment, and mechanical treatment. The device and method may include applying a combination of magnetic treatment, radiofrequency treatment and mechanical treatment to a body area. The device may include an applicator that is configured to provide magnetic treatment, radiofrequency treatment and mechanical treatment to a body and/or body area. Also, the treatment device may include a main unit housing the electrical elements configured to provide magnetic treatment, radiofrequency treatment and mechanical treatment to a body and/or body area.

Combined application of mechanical treatment with magnetic treatment and/or radiofrequency treatment may prevent possible drawbacks of mechanical treatment alone, such as a risk of panniculitis, destruction of untargeted tissues, and/or non-homogenous results by providing muscle contraction and/or heating.

The treatment device may include one or more applicators, wherein each applicator may include its own casing. One applicator may include one or more magnetic field generating devices, one or more RF electrodes, and/or one or more pressure outlets. One applicator may include one or more magnetic field generating devices, one or more RF electrodes, one or more pressure outlets, and/or one or more ultrasound transducers. In one example, one applicator may include one magnetic field generating device, two RF electrodes, and one pressure outlet.

In one aspect of the disclosure, the mechanical treatment may include pressure treatment. The pressure treatment may include positive pressure treatment and/or negative pressure treatment to the body and/or body area. The positive pressure treatment may include application of mechanical impulses (e.g. positive pressure impulses) with an amplitude of intensity, wherein the mechanical impulses are applied as fluid pulses from the compressor to the tissue. The negative pressure treatment may include providing mechanical impulses (e.g. negative pressure impulses) by drawing out fluid from the adjacent area of the tissue by the action of the compressor. The mechanical treatment may also include constriction. More than one type of mechanical treatment may be applied at the same time during the treatment session. The mechanical treatment may include providing of one or more mechanical impulses (e.g. pressure impulses) to the body and/or body area.

The positive pressure treatment and/or negative pressure treatment may be used for massage of the body area, providing pressure waves, skin improvement, and/or treatment of cellulite. The positive pressure treatment and/or negative pressure treatment may also provide destruction of fat globuli and/or fibrous septa. The positive pressure treatment may provide improvement of treatment by RF waves, since the positive pressure treatment may improve homogenization of heating in the body area and/or on the surface of the body area. The positive pressure treatment may include providing positive pressure impulses to the body of the patient, body area of the patient, skin of the patient, and/or skin of the body area. The positive pressure treatment and/or negative pressure treatment may not heat the body of the patient.

The elements needed for generation of pressure treatment may include a silencer, one or more filters, a compressor, one or more valves, a condensate separator, an air pressure tank, and coupling elements as described in further detail herein. It should be understood that not all elements shown in relation to pressure treatment are electrical elements, since not all of them must be powered by electricity. For example, the silencer may not be powered by electricity.

Figure 56A:
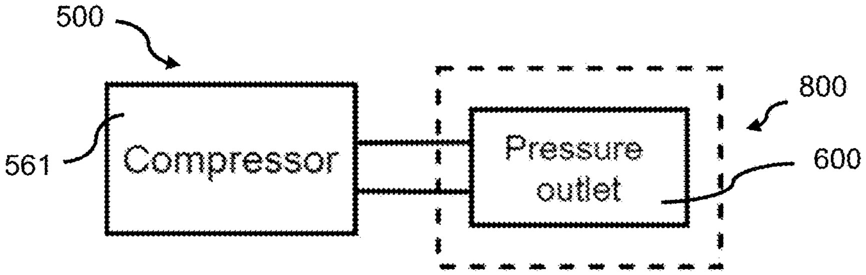
FIGS. 56*a*-56*e* illustrate exemplary schemas of electrical elements for mechanical treatment.

FIG. 56*a* illustrates an exemplary schema 500 of a circuit of electrical elements needed for generation of positive pressure treatment and/or negative pressure treatment. The circuit may include a compressor 561 and a pressure outlet 600. The pressure outlet 600 may be part of the applicator 800.

Figure 56B:
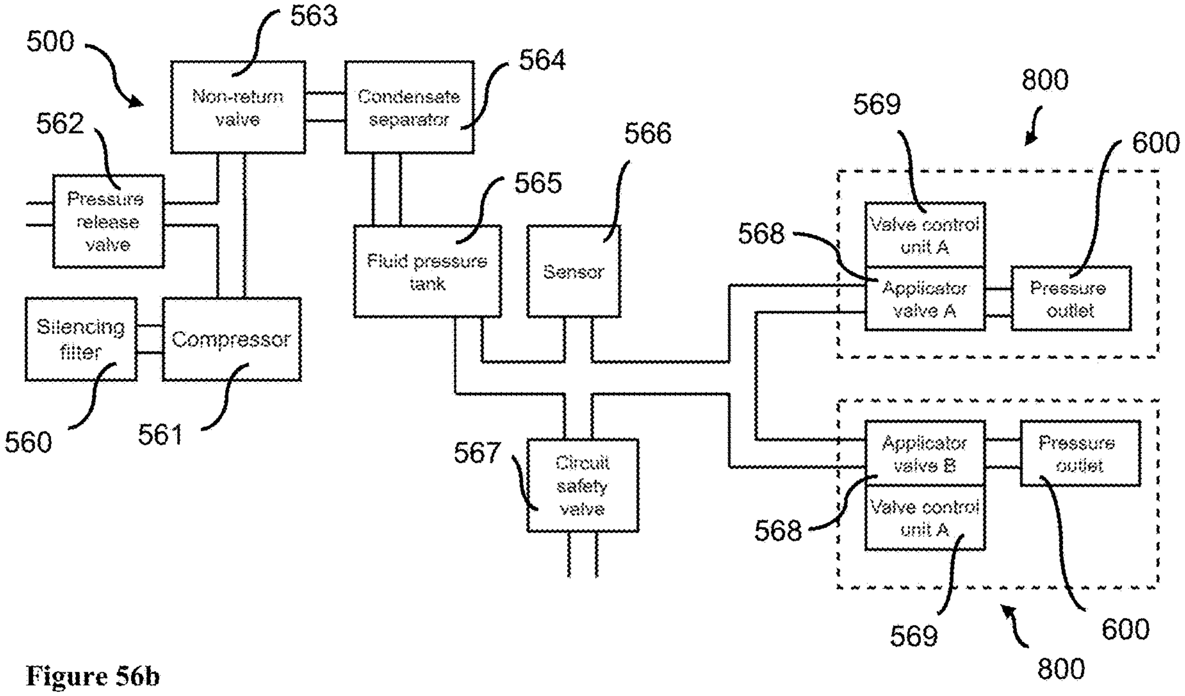

FIG. 56*b* illustrates an exemplary schema 500 of a circuit of elements needed for generation of a positive pressure treatment. In this exemplary schema, the circuit may include one or more of following elements: a silencing filter 560, a compressor 561, a pressure release valve 562, a non-return valve 563, a condensate separator 564, a fluid pressure tank 565, a sensor 566, a circuit safety valve 567, an applicator valve 568, a valve control unit 569, and a pressure outlet 600. The applicator valve 568, valve control unit 569 and pressure outlet 560 may be parts of the applicator 800. The silencing filter 560 and the condensate separator 564 may be parts of the compressor 561.

Figure 56C:
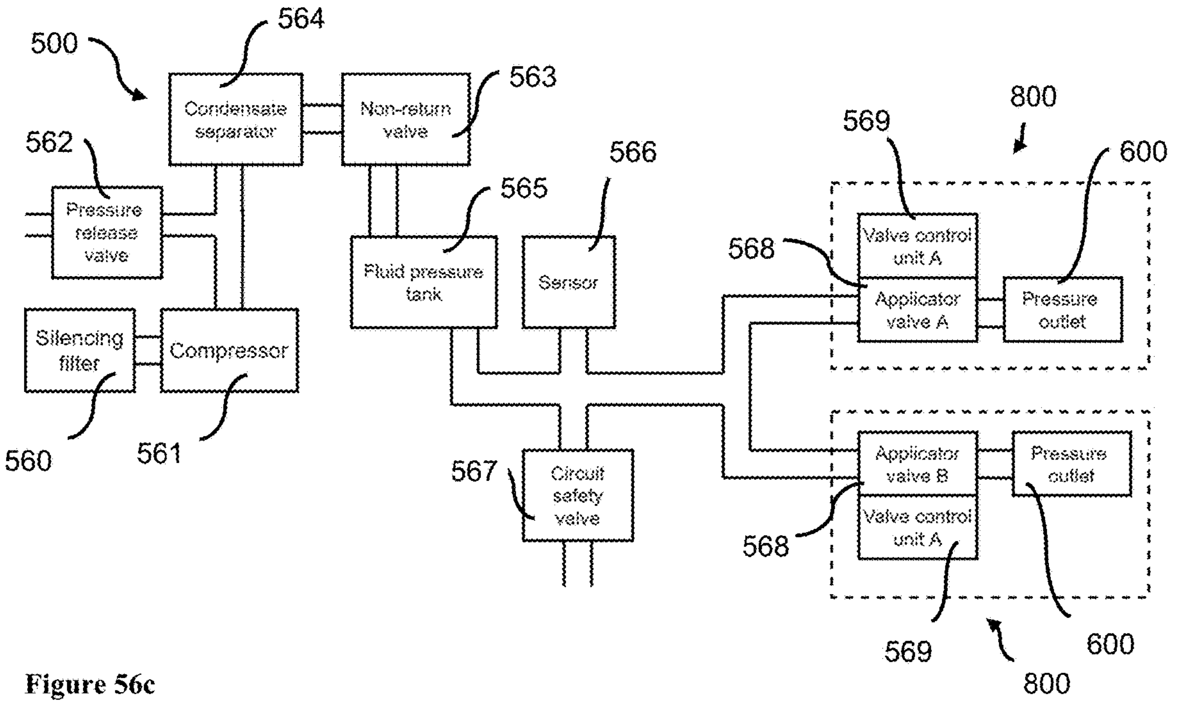

FIG. 56*c* illustrates another exemplary schema 500 of a circuit of elements needed for generation of a positive pressure treatment. FIG. 56*c* is similar to the schema 500 of FIG. 56*b*, but the non-return valve 563 follows, i.e., is downstream of, the condensate separator 564.

Figure 56D:
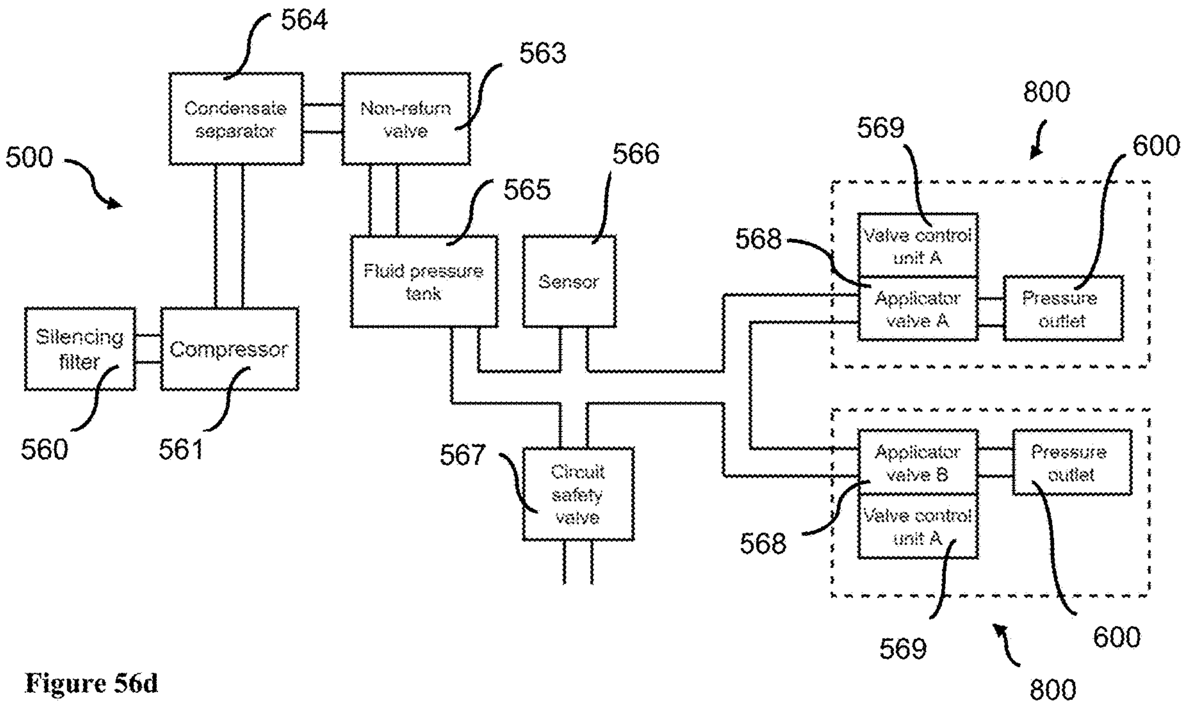

FIG. 56*d* illustrates another exemplary schema 500 of a circuit of elements needed for generation of a positive pressure treatment. FIG. 56*d* is similar to the schema 500 of FIG. 56*c*, but the pressure release valve 562 is omitted. For example, this architecture may be possible, when the compressor 561 includes a brushless DC electrical motor.

Figure 56E:
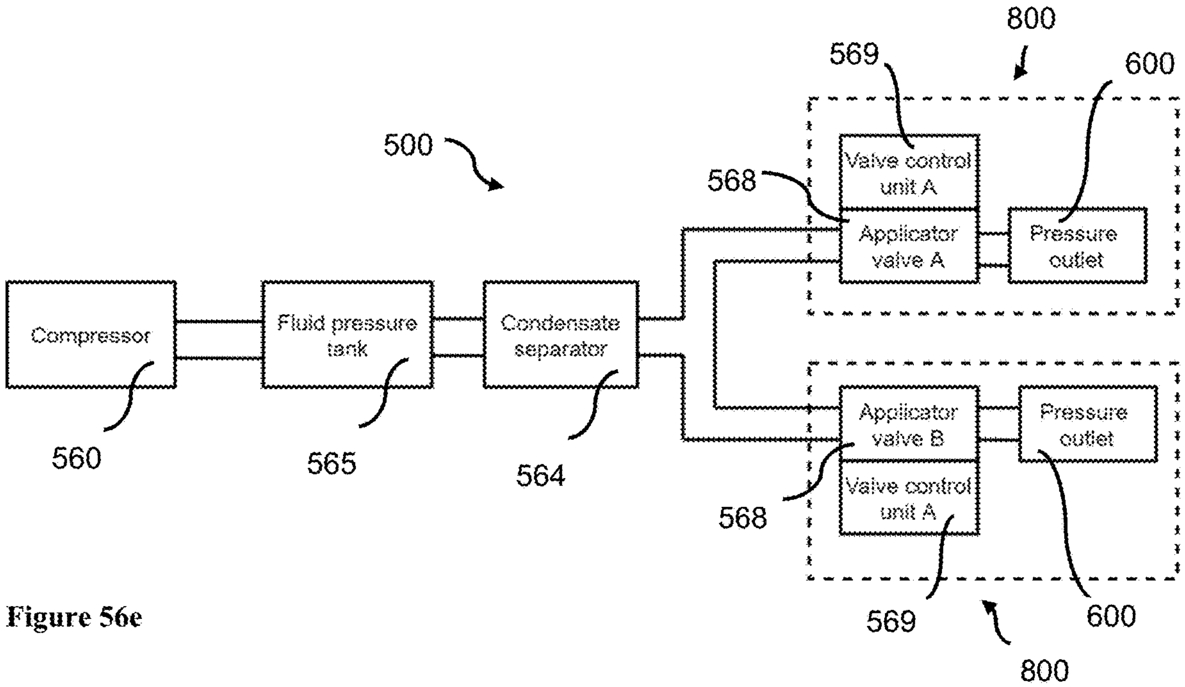

FIG. 56*e* illustrates an exemplary schema 500 of a circuit of elements needed for generation of a negative pressure treatment. This circuit may include one or more applicators 800 including the valve control unit 569, the applicator valve 568 and the pressure outlet 600. In the case of negative pressure treatment, the pressure outlet 600 may provide negative pressure treatment by drawing the fluid (e.g. air) possibly together with the tissue to form a protrusion on the tissue below the applicator 800. The direction of the fluid in the compressor 560 is reversed as compared to FIGS. 56*b*-56*d*. The compressor 561 may include or may act as vacuum pump, evacuating the fluid from the pressure outlet 600. When the pressure outlet 600 evacuates the fluid from the pressure outlet 600, it provides the negative pressure impulses. Since the fluid is evacuated into the device, the frequency of the negative pressure impulses may influence internal parts of the device. The fluid pressure tank 565 may act as a damper of frequency and/or negative pressure impulse within the device, in order to protect the compressor 560. The fluid pressure tank 565 may also damp the amplitude of negative pressure coming into the device. The fluid pressure tank 565 may or may not be present.

The device may include a circuit or combination of circuits that includes a combination of a magnetic and RF circuits with a pressure treatment circuit. For example, a device may include one or more individual exemplary circuits and/or electrical elements as shown respectively any of FIGS. 56*a*, 56*b*, 56*c* and 56*c* providing positive pressure treatment and/or FIG. 56*e* providing negative pressure treatment and a circuit and/or electrical elements shown any of FIGS. 17, 18*a*-18*i*, 54*i*-54*j* and 54*l*-54*n*. The circuit including the RF, magnetic and pressure treatment circuits and/or electrical elements may be controlled by one control system a control unit, wherein the control unit may include a microprocessor. The circuit and/or electrical elements from those Figures may cooperate during providing the treatment, as commanded by the control system and or one or more suitable sensors mentioned.

Figure 56F:
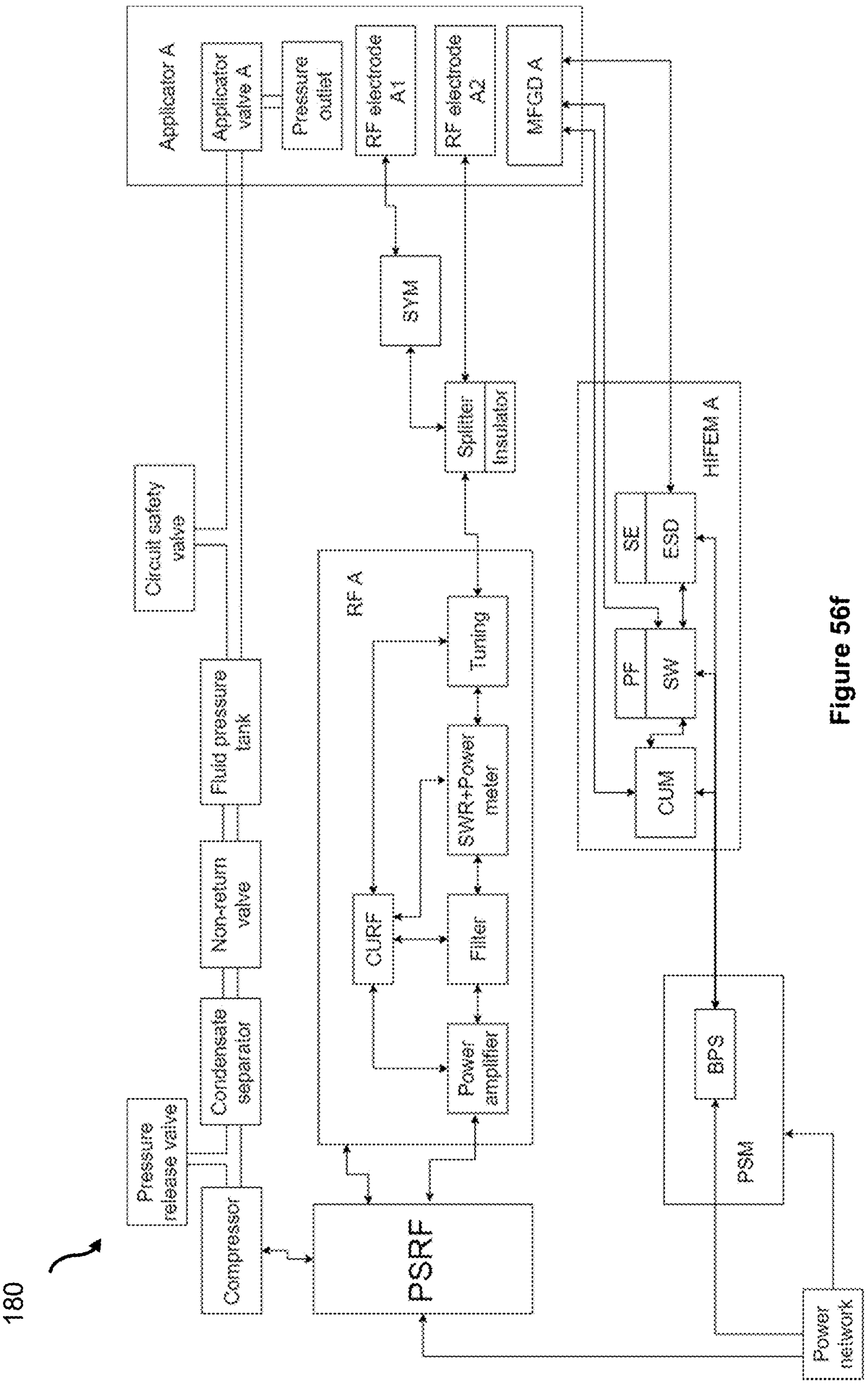
FIG. 56*f* illustrates an exemplary schema of electrical elements of a treatment device.

FIG. 56*f* illustrates an exemplary schema 180 of a combination of circuits of electrical elements for providing magnetic treatment, radiofrequency treatment and positive pressure treatment. Compressor is shown to be connected and powered by the power source for RF treatment. However, the compressor may be directly connected to and powered by the power network. The circuit of elements needed for positive pressure treatment may be replaced by any circuit shown on FIG. 56*a*-56*e*.

With respect to schema 500 of a circuit of elements needed for generation of a pressure treatment, the silencing filter 560 is configured to silence the compressor 561 and/or to remove unwanted and/or solid particles from the fluid to be compressed by the compressor 561. The function of the silencing filter 560 may be divided into two elements (e.g. a silencer and a fluid filter), which may be also present in the circuit of the positive pressure treatment. The silencing filter 560, fluid filter, and/or silencer may be part of the compressor 561.

The compressor 561 may comprise a fluid compressor. The compressor 561 may comprise an element providing compressed fluid (e.g. air) to the applicator 800. Also, the direction of the fluid may be reversed, so the compressor 561 may pull the fluid from the applicator 800 and the tissue may be pulled to the pressure outlet 600 and/or to the vicinity of the applicator 800. The compressor 561 may comprise an air compressor providing compressed air. The compressor 561 may comprise a pump and/or one or more pistons. For example, the compressor 561 may include plurality (e.g. two) pistons. The compressor 561 may be positioned in the main unit of the device. The compressor 561 may be positioned in the bottom part of the main unit due to vibration and water condensation related to compressing fluid (e.g. air). The compressor 561 may compress the fluid continually or at predetermined intervals as controlled by the control system. In order to prevent vibrations, the compressor 561 may be positioned within the main unit and may be isolated by a bushing, e.g., a vibration isolator. For example, the compressor 561 may be isolated from the rest of the main unit by synthetic rubber and/or polyurethane. The compressor may comprise a motor, for example DC electric motor, AC electric motor, or brushless DC electric motor. The compressor may include its own control unit, which may be connected to and/or controlled by the control unit. The control of the compressor may be part of the control system. The compressor may have a flow rate in a range of 2 litres per minutes to 300 litres per minute, or 4 litres per minute to 200 litres per minutes, or 5 litres per minute to 150 liters per minute, wherein the flow rate is at 6 bar. The power of the compressor may be in a range of 100 W to 1500 W, 150 W to 1350 W, or 200 W to 1000 W.

The pressure release valve 562 may be configured to balance the pressure of the fluid within the circuit. The pressure release valve 562 positioned between the compressor 561 and the condensate separator 564 may be controlled by the control system according to the pressure in the fluid pressure tank 565. The presence of pressure release valve 562 in the circuit 500 may also lead to energy savings. When the compressor 561 provides compressed fluid to the fluid pressure tank 565, the pressure of the fluid in the circuit part between the compressor 561 and fluid pressure tank 565 remains high. However, when the fluid pressure tank 565 includes fluid with sufficient pressure, the compressor 561 may be stopped or set on low power operation. During this operation of the compressor 561, the pressure release valve 562 may decrease the pressure of the fluid in the part of the circuit between the compressor 561 and the fluid pressure tank 565. When the compressor 561 then shifts to high power operation, it may need a lower amount of energy to compress fluid in the part of the circuit having lower pressure.

The non-return valve 563 may allow fluid to flow through it in only one direction.

The condensate separator 564 may be configured for further filtration of the fluid. The condensate separator 564 may be configured to separate moisture originating from pressurizing the fluid and/or decreasing the pressure in the circuit.

The fluid pressure tank 565 may be configured to store the fluid and to provide fluid under pressure to the circuit, e.g. in the direction of the pressure outlet 600. The fluid pressure tank 565 may be an air pressure tank configured to store the air and provide air under pressure to the circuit, e.g. in the direction of the pressure outlet 600. The fluid pressure tank 565 is configured to be filled by compressed fluid by the compressor 561. The fluid pressure tank 565 may include a tank pressure sensor and a tank safety valve. When the fluid in the fluid pressure tank 565 has a pressure above a safe value, the tank pressure sensor may detect it, provide information to the control system, and the control system may control the tank safety valve to open and decrease pressure inside the fluid pressure tank 565. The fluid pressure tank 565 may be configured to withstand the pressure of the fluid in a range of 0.5 bar to 150 bar, 1 bar to 100 bar or 1 bar to 80 bar.

The sensor 566 may communicate with and provide feedback to a control unit of pressure treatment, which may be part of the control system and/or may comprise a microprocessor. The control unit of pressure treatment may be controlled by the master unit. The sensor 566 may detect pressure of the fluid, duration of mechanical impulse (e.g. pressure impulse), repetition rate of the pressure impulse, or intensity of pressure impulse.

The circuit safety valve 567 may be configured to balance the pressure of the fluid within the circuit. The circuit safety valve 567 may be opened and lower the pressure of the fluid within the circuit in case of power loss, change of settings and/or change between the treatment protocols. The circuit safety valve 567 may include a regulation valve to prevent complete loss of pressure from the circuit.

As shown in FIGS. 56*b*-56*e*, the circuit may be divided into a plurality of branches. FIG. 56*b*-56*e* show examples in which the circuit 500 is divided into two branches leading to two applicators. In one example, the pressure of the fluid in both branches may be identical or within a deviation in a range of 0.01% to 10%, 0.1% to 5%, or 0.1% to 3%. In another example, the pressure of the fluid in the first applicator 800 in the first branch may be different than the pressure of the fluid in the second applicator 800 in the second branch. Such division may be provided by a dividing pressure element, e.g. a proportional valve controlled by the control system.

The applicator valve 568 may be configured to provide control of the pressurized fluid to the pressure outlet 600. The applicator valve 568 may include or may be adjacent to the applicator pressure sensor measuring pressure of the fluid flowing to the pressure outlet 600, wherein the applicator pressure sensor may be located within the applicator and/or the connecting tube.

The valve control unit 569 may be configured to control the applicator valve 568. The valve control unit 569 may include a microprocessor. The valve control unit 569 may communicate with, be controlled by and/or be a part of the control system. For example, the valve control unit 569 may communicate with the master unit comprising a microprocessor, which may be positioned in the main unit of the device. The presence of an additional control unit (i.e. valve control unit 569) for pressure treatment within the applicator may provide faster control of the pressure treatment with the mechanical impulses without delay between communication from the master unit directly to the applicator valves 568. Furthermore, when the device uses multiple applicators (e.g. arm applicator or abdomen applicator), this additional control unit may store information needed for identification of the applicator. When the applicator is connected to the main unit, the master unit and/or control system may start to communicate with this control unit positioned within the applicator and verify the type of the applicator. Furthermore, the control unit positioned in the applicator may control and/or provide additional control of the operation of one or more RF electrodes and/or magnetic field generating devices.

The applicator valve 568, valve control unit 569 and pressure outlet 600 may be positioned in the applicator 800. As shown in FIG. 56*b*, the device may include two applicators 800, wherein each applicator 800 includes one pressure outlet 600. However, the applicator 800 may include more than one pressure outlet 600, for example, two or more. Also, one applicator 800 may include a number of applicator valves 568 and/or valve control units 569 corresponding to the number of pressure outlets 600. In another example, the applicator 800 may include only one valve control unit 569 and/or applicator valve 568 with a plurality (e.g. two) of pressure outlets 600.

The pressure outlet 600 may comprise an element providing the positive pressure treatment or negative pressure treatment to the body of the patient, body area, skin of body area and/or skin of patient's body. The pressure outlet 600 may comprise a cavity or an orifice through which the pressurized fluid flows to or from the body of the patient and/or body area. The pressure outlet 600 may be made from paramagnetic and/or diamagnetic material. For example, the pressure outlet 600 may be manufactured from a plastic material. The pressure outlet 600 may include a tube through which the fluid is applied to or from the tissue. The tube may include a tapering section that tapers or narrows toward the opening of the pressure outlet, so as to form a relatively small diameter opening relative to a diameter of a remainder of the tube. Alternatively, the tube may include an expansion section that widens toward the opening of the pressure outlet, so as to form a relatively large diameter opening relative to a diameter of a remainder of the tube. The tapering section or expansion section may be positioned on and/or within the bottom cover of the applicator. The expansion section may create a cavity, to which the tube enters. However, the expansion section or tapering section may be part of the tube. The expansion section may have a generally circular shape on the bottom cover, wherein the circular shape of the expansion section may have a diameter in a range of 1 mm to 15 cm, 2 mm to 12 cm, or 5 mm to 10 cm. Further, the expansion section and/or tapering section may be detachable and replaceable. The pressure outlet may include a fluid directing element configured to allow modification of the direction of the fluid flow. Such fluid direction element may include a solid element (e.g. from plastic) having a shape of a spiral curve.

The one or more pressure outlets 600 may be positioned in different positions on the applicator 800. For example, the one or more pressure outlets 600 may be positioned in the center of the applicator 800. In another example, the one or more pressure outlets 600 may be positioned in the center of the magnetic field generating device. In yet another example, the one or more pressure outlets 600 may be positioned on the sides of the applicator 800. In yet another example, the one or more pressure outlets 600 may be positioned on the sides of the magnetic field generating device and/or RF electrode.

Figure 57A:
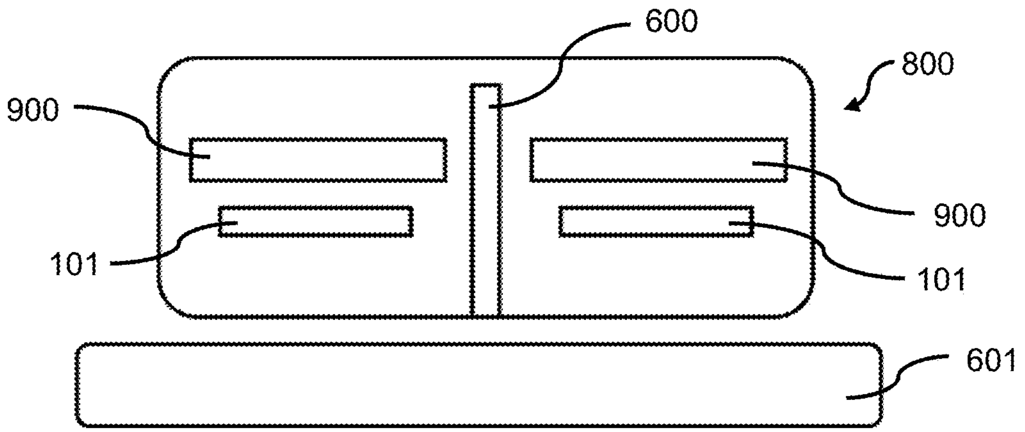
FIGS. 57*a*-57*g* illustrate exemplary applicators including a pressure outlet.

FIG. 57*a* shows a longitudinal cross sectional view of the applicator 800 with the pressure outlet 600 positioned in the center of the applicator 800. The exemplary applicator 800 is shown with two magnetic field generating devices 900 and two RF electrodes 101, wherein both RF electrode 101 are positioned between the magnetic field generating device 900 and the tissue 601 of the patient. When the pressure outlet 600 is positioned in the center of the applicator, the positive or negative pressure may be applied to the center of the same spot on the body area, where the muscle contraction by magnetic treatment and heating by radiofrequency treatment is provided.

Figure 57B:
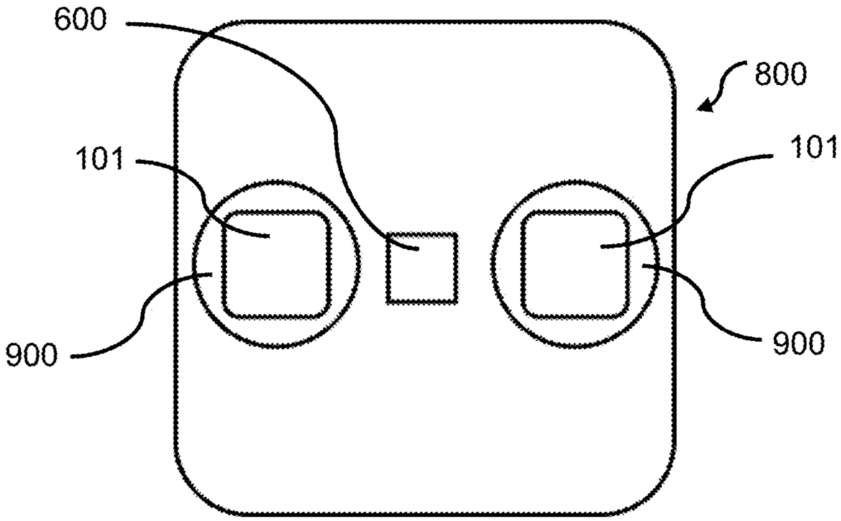

FIG. 57*b* shows a transverse cross sectional view of the applicator 800 with the pressure outlet 600 positioned in the center of the applicator 800. The exemplary applicator 800 is shown with two magnetic field generating devices 900 and two RF electrodes 101. When the pressure outlet 600 is positioned in the center of the applicator and next to the magnetic field generating device 900, the pressure outlet 600 provides pressure treatment to the body region directly below the magnetic field generating device 900.

Figure 57C:
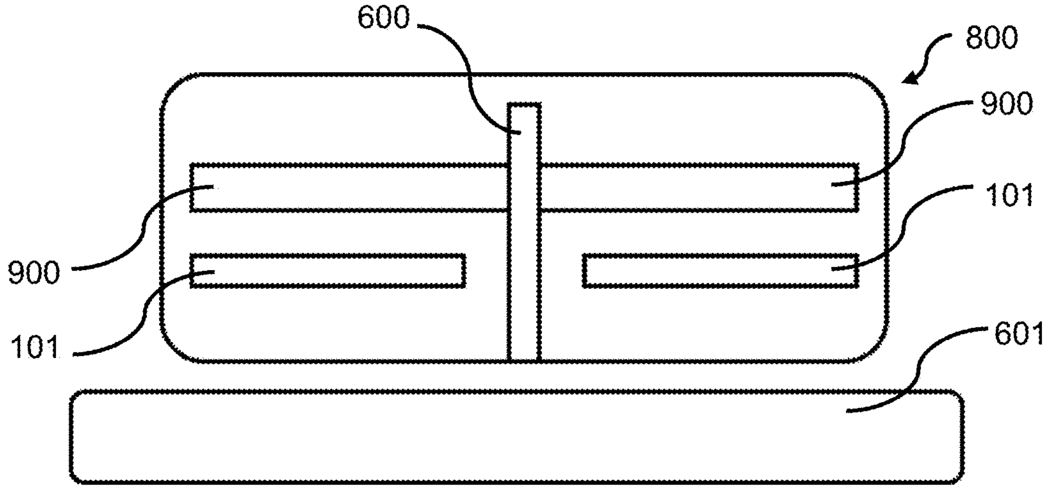

FIG. 57*c* shows a longitudinal cross sectional view of the applicator 800 with the pressure outlet 600 positioned in the center of the magnetic field generating device 900. The exemplary applicator 800 is shown with one magnetic field generating device 900 and two RF electrodes 101, wherein both RF electrodes 101 are positioned between the magnetic field generating device 900 and the tissue 601 of the patient. The pressure outlet 600 may be surrounded by the magnetic field generating device 900 of the applicator 800. When the pressure outlet 600 is positioned in the center of the magnetic field generating device, the positive or negative pressure is as close as possible to the same spot on the body area, where the muscle contraction by magnetic treatment and heating by radiofrequency treatment is provided.

Figure 57D:
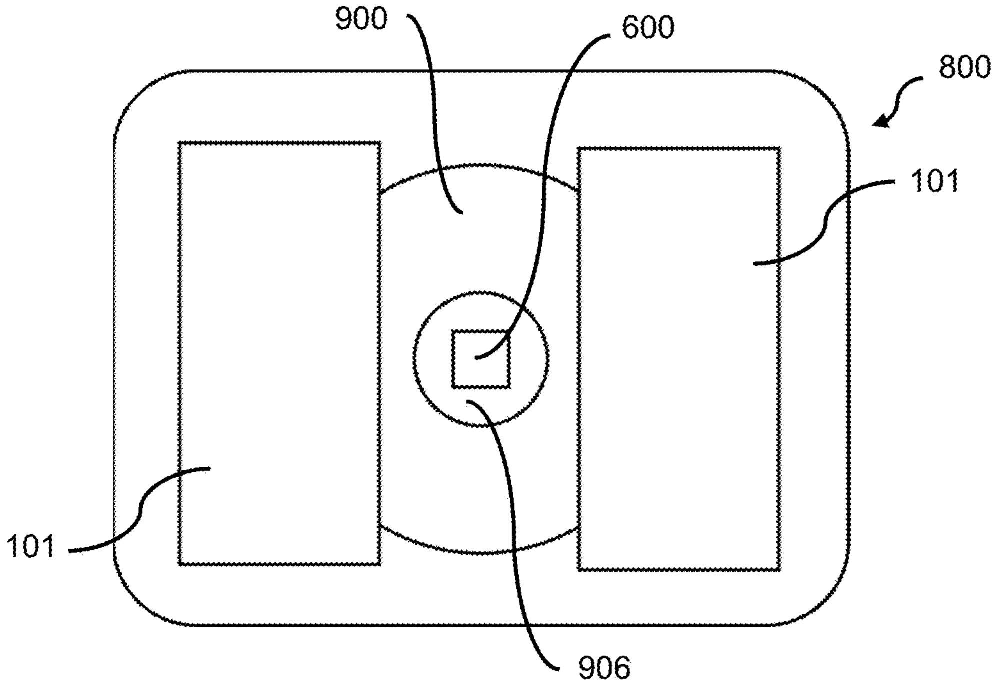

FIG. 57*d* shows a transverse cross sectional view of the applicator 800 with the pressure outlet 600 positioned in the center of the magnetic field generating device 900. The exemplary applicator 800 is shown with one magnetic field generating device 900 and two RF electrodes 101. The pressure outlet 600 may be positioned in a center of the gap 906 of the magnetic field generating device 900, where no winding of the magnetic field generating device 900 may be present. When the pressure outlet 600 is positioned in the center of the applicator, the positive or negative pressure may be applied to the center of the same spot on the body area, where the muscle contraction by magnetic treatment and heating by radiofrequency treatment is provided.

Figure 57E:
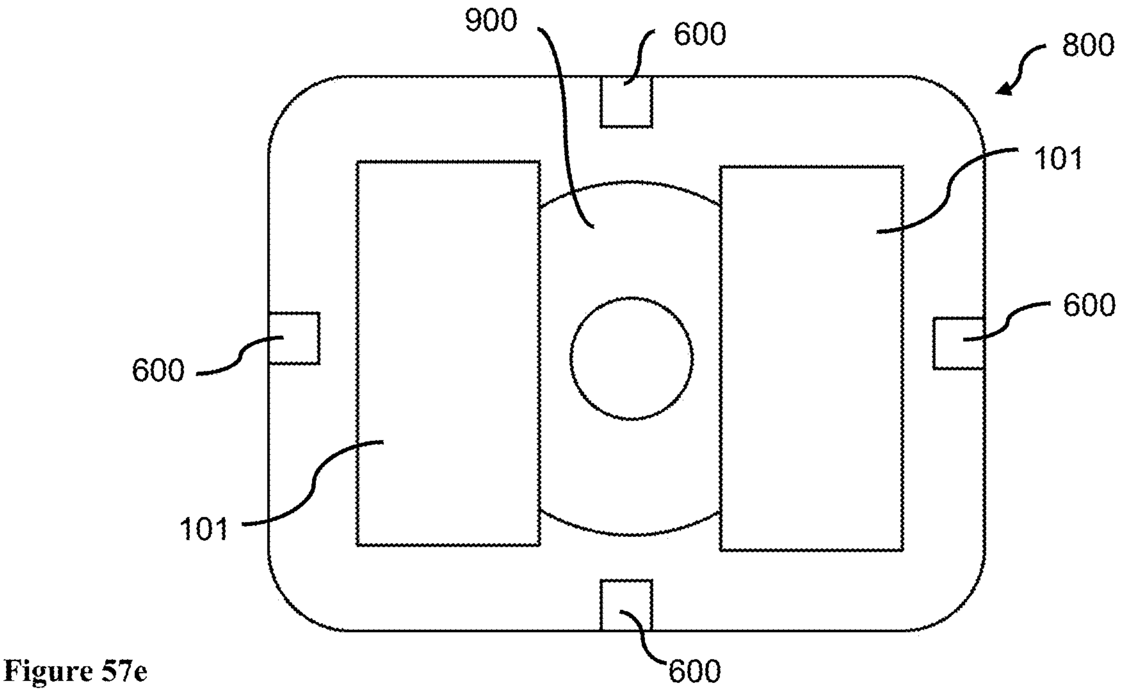

FIG. 57*e* shows a transverse cross sectional view of the applicator 800 with pressure outlets 600 positioned on the sides of the applicator 800. The exemplary applicator 800 is shown with one magnetic field generating device 900 and two RF electrodes 101. When the pressure outlets 600 are positioned on the sides of the applicator, the applied positive or negative pressure may provide additional cooling of the tissue from the sides. Also, when the pressure outlets 600 are positioned on the sides of the applicator 800, the pressure outlets 600 are not influenced by the magnetic field generating device 900, at they may be influenced when positioned closer to the magnetic field generating device 900.

Figure 57F:
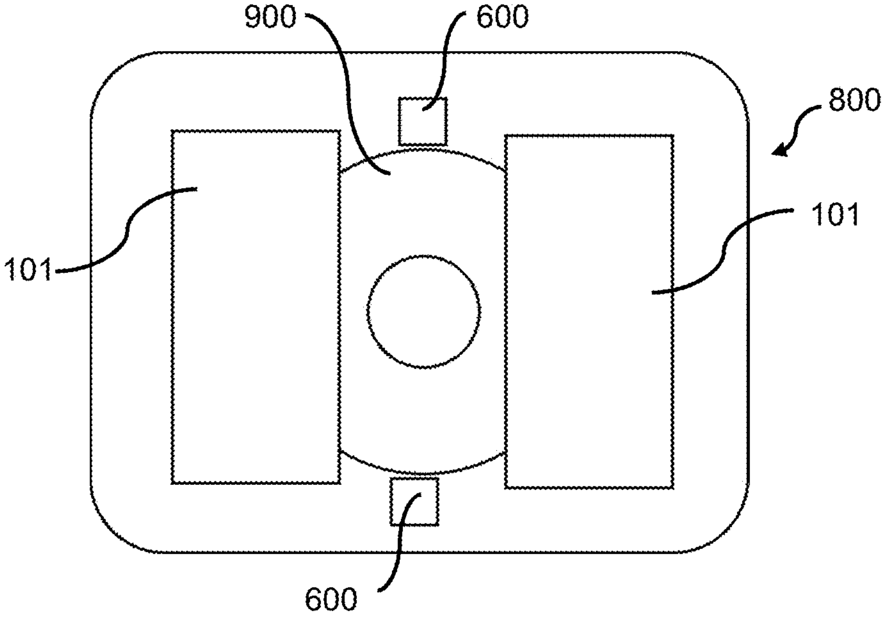

FIG. 57*f* shows a transverse cross sectional view of the applicator 800 with pressure outlets 600 positioned on the sides of the magnetic field generating device 900. The exemplary applicator 800 is shown with one magnetic field generating device 900 and two RF electrodes 101. When the pressure outlets 600 are positioned on the sides of the magnetic field generating device 900, the applied positive or negative pressure may provide different temperature reception. As shown in FIG. 57*f*, the RF electrode provides heating, while the pressure outlets 600 positioned in different positions provide pressure treatment.

Figure 57G:
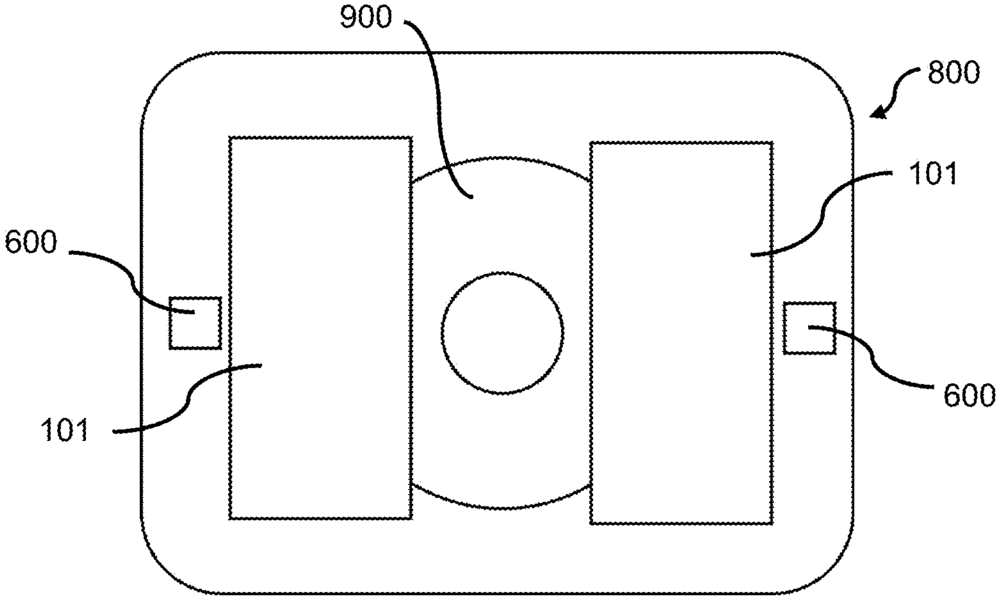

FIG. 57*g* shows a transverse cross sectional view of the applicator 800 with the pressure outlet 600 positioned on the sides of the RF electrodes 101. The exemplary applicator 800 is shown with one magnetic field generating device 900 and two RF electrodes 101. When the pressure outlets 600 are positioned on the sides of the RF electrodes, the applied positive or negative pressure may also provide different temperature reception. As shown in FIG. 57*g*, the RF electrode provides heating, while the pressure outlets 600 positioned in different positions close to the RF electrodes provide pressure treatment.

The presence of one or more pressure outlets and delivery of positive and/or negative pressure to the skin of the body area may influence the operation of the temperature sensor present on the applicator of the treatment device. Accordingly, the applicator may include a rim close to and/or around the opening of the pressure outlet on the applicator surface close to the body of the patient. The rim may at least partially surround the pressure outlet or it may surround the whole pressure outlet. The rim may also provide recess to the tissue patient, providing the space for application of the mechanical impulses. When the rim provides the recess on the surface of the tissue, the mechanical impulses are percepted to be more intensive by the treated patient.

Figure 58A:
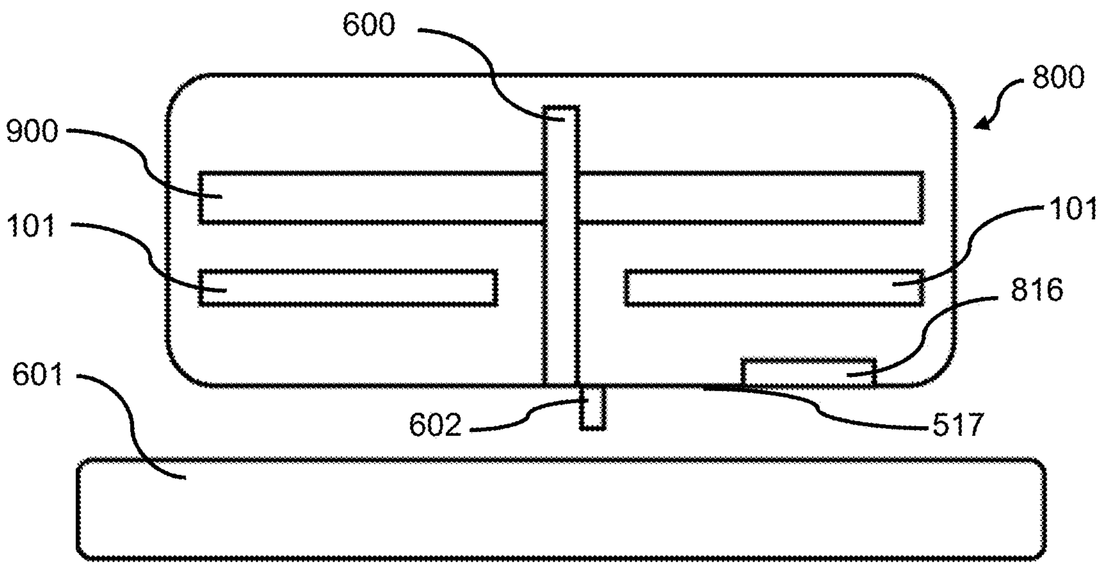
FIGS. 58*a*-58*b* illustrate exemplary applicators comprising a pressure outlet and a rim.

FIG. 58*a* illustrates a longitudinal cross sectional view of an exemplary applicator 800 that includes one magnetic field generating device 900, two RF electrodes 101, a pressure outlet 600, and a temperature sensor 816. The applicator 800 further includes a rim 602, which is positioned adjacent to the pressure outlet 600 on the bottom cover 517 of the applicator 800 in order to block the flow of the pressurized fluid in the direction of the part of the bottom cover 517 of the applicator 800 below the temperature sensor 816.

Figure 58B:
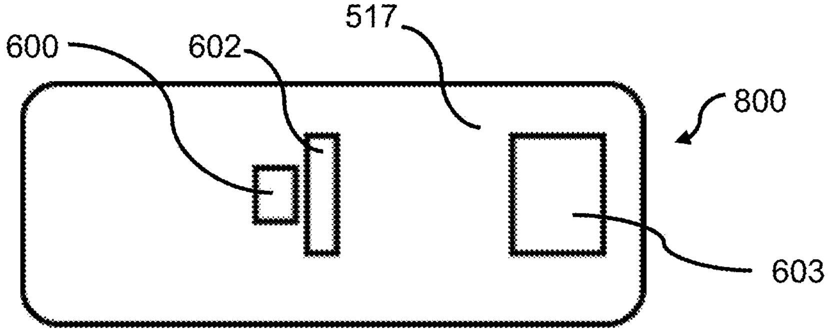

FIG. 58*b* shows a bottom view of the applicator 800 with the pressure outlet 600 and rim 602. The area 603 represents the surface of the applicator 800 below the temperature sensor 816. The rim 602 is positioned to stop the flow of the pressurized fluid from the pressure outlet 600 in the direction of the surface 603.

Figure 59:
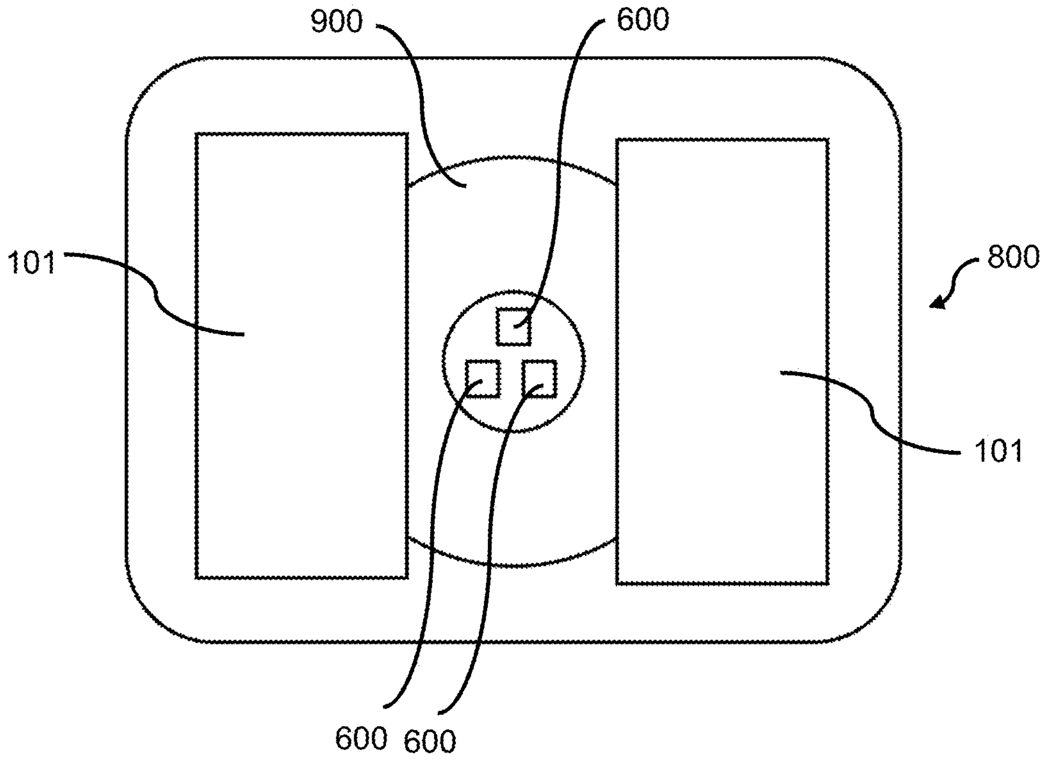
FIG. 59 illustrates an exemplary applicator comprising multiple pressure outlets.

As mentioned and further shown in a transverse cross sectional view of an applicator 800 in FIG. 59, the applicator 800 may have more than one pressure outlet 600 in the center of the magnetic field generating device 900. The delivery of the pressurized fluid by the plurality of pressure outlets 600 may be controlled by the control system. For example, the control may include delivery of the pressurized fluid from only one pressure outlet 600 of the plurality of pressure outlets 600. In another example, the activation of the pressure outlets 600 may follow a clockwise or counter-clockwise pattern.

The repetition rate of pressure impulses may be in a range of 0.1 Hz to 2000 Hz, 0.2 Hz to 1000 Hz, 0.25 Hz to 500 Hz, 0.3 Hz to 250 Hz, or 0.5 Hz to 100 Hz. The positive pressure and/or negative pressure of the fluid in the pressure outlet 600 may be in a range of 0.01 bar to 50 bar, 0.05 bar to 25 bar, 0.05 bar to 10 bar, or 0.05 bar to 6 bar, wherein 1 bar equals 100,000 Pascals. The duration of pressure impulse may be in a range of or 0.1 ms to 1000 ms, 0.2 ms to 250 ms, or 1 ms to 150 ms. The flow rate of the pressure impulse, referred also as amplitude of pressure impulse, may be in a range of 0.1 liters per minute to 200 liters per minute, 0.25 liters per minute to 150 liters per minute, or 0.5 liters per minute to 100 liters per minute, as measured in the pressure outlet in the plane of the bottom cover of the applicator. The pressure impulse may provide a pressure wave having a velocity of about 340 meters per second. All of these parameters may be controlled by the control system of the device, e.g., using feedback from one or more sensors as mentioned herein and/or by the human machine interface (HMI) comprising the display.

The mechanical treatment may include providing acoustic and/or ultrasound energy to the body and/or body area.

The ultrasound energy may be generated by one or more ultrasound sources. The ultrasound source may include an ultrasound transducer. The ultrasound transducer may include a piezoelectric transducer and/or capacitive transducer. The one or more ultrasound transducers may be located in the main unit and/or the applicator. The one or more ultrasound transducers may be connected to the power network through electrical elements present in the main unit and/or applicator of the device.

The ultrasound treatment may be used for massage of the body area, skin improvement, and/or treatment of cellulite. The ultrasound treatment may also provide destruction of fat globuli and/or fibrous septa. The ultrasound may not heat the body of the patient. The ultrasound treatment may also provide improvement of treatment by RF waves, since the ultrasound treatment may improve homogenization of heating in the body area and/or on the surface of the body area. The ultrasound treatment may include applying ultrasound impulses to the body of the patient, body area of the patient, skin of the patient and/or skin of the body area. The one or more ultrasound transducers may be positioned between a bottom cover of the applicator and the magnetic field generating device. Also, the one or more ultrasound transducers may be positioned next to and/or above the magnetic field generating device. The one or more ultrasound transducers may be positioned between the body of the patient and magnetic field generating device.

A plurality of ultrasound transducers may be controlled by the control system to provide ultrasound energy. The plurality of ultrasound transducers may provide the ultrasound energy at the same time or at different times. Also, the two or more ultrasound transducers may be controlled to provide ultrasound energy in such manner, that one or more standing waves and/or resonance of the ultrasound energy may provide variation in the ultrasound energy perception.

Figure 60A:
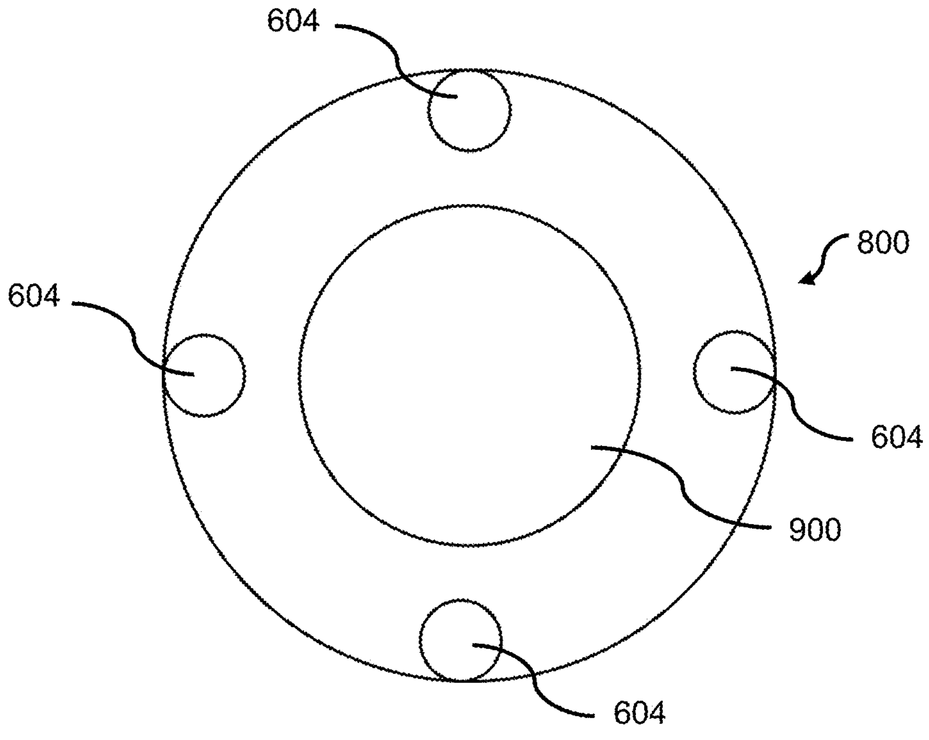
FIGS. 60*a*-60*e* illustrate exemplary applicators comprising an ultrasound transducer.

FIG. 60*a* illustrates a transverse cross sectional view of an exemplary applicator 800 that includes one magnetic field generating device 900 and a plurality of ultrasound transducers 604. The ultrasound transducers 604 may be positioned around the magnetic field generating device 900.

Figure 60B:
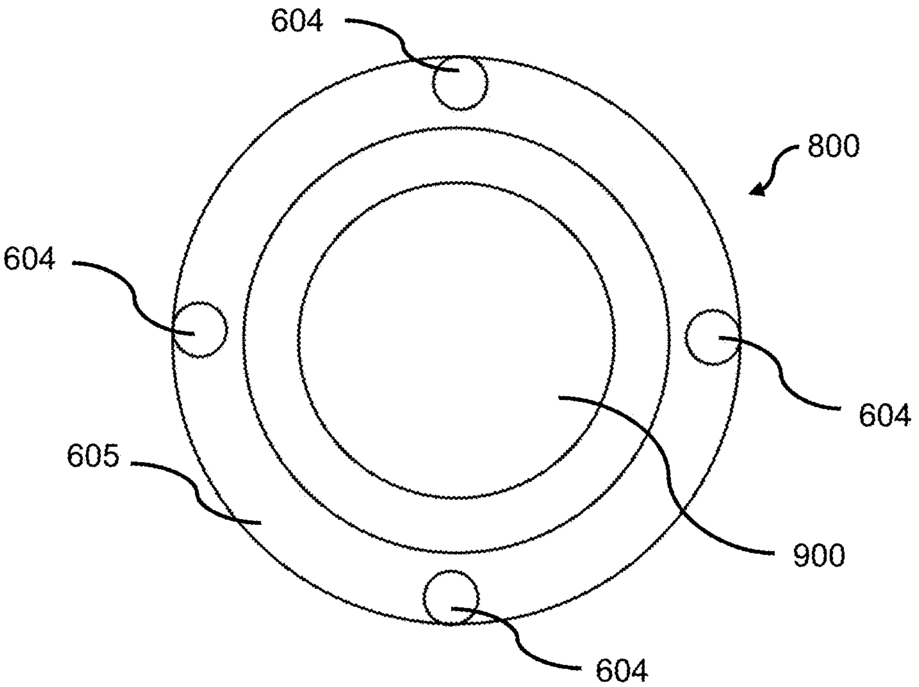

FIG. 60*b* illustrates a transverse cross sectional view of another exemplary applicator 800 that includes one magnetic field generating device 900 and a plurality of ultrasound transducers 604, wherein the plurality of ultrasound transducers 604 is located in and/or on the surface of a vibration element 605, such as a vibration plate. When the plurality of ultrasound transducers 604 are active, the ultrasound energy may also generate vibrations, which are then transferred through the vibration element 605 to the patient's body and/or body area.

Figure 60C:
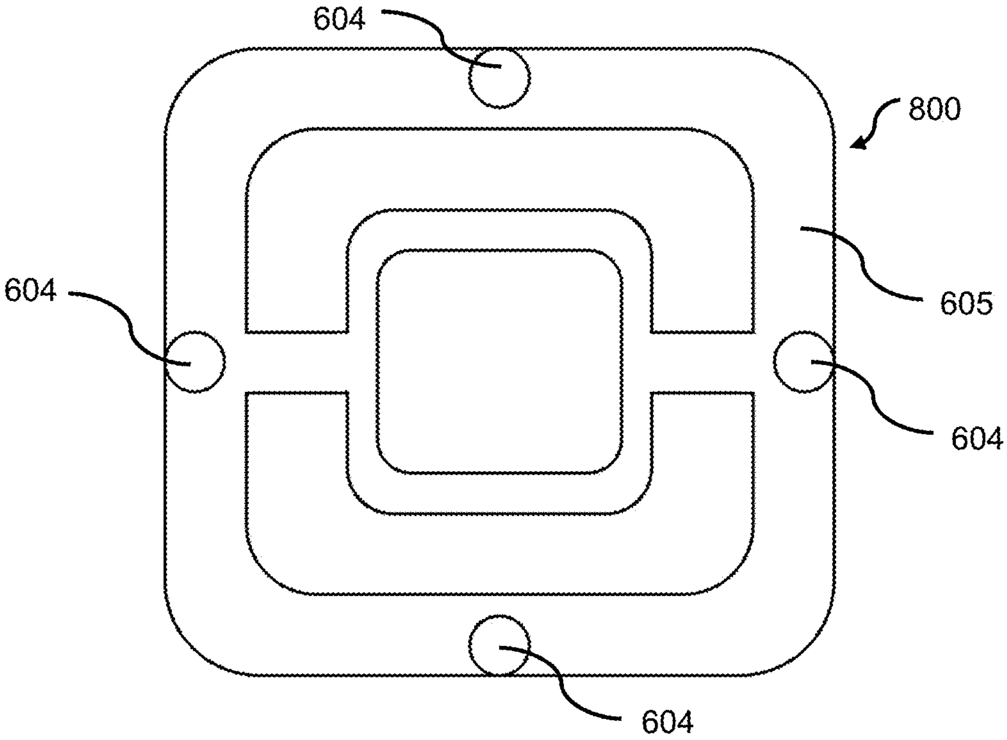

FIG. 60*c* illustrates a transverse cross sectional view of another exemplary applicator 800 that includes a vibration element 605. The one or more ultrasound transducers 604 are located in and/or on the surface of a vibration element 605. The vibration element 605 or a part of the vibration element 605 may be located between a bottom cover of the applicator 800 and the magnetic field generating device. Also, the vibration element 605 may be positioned next to and/or above the magnetic field generating device. The vibration element 605 may be positioned between the body of the patient and the magnetic field generating device.

Regarding the examples shown in FIGS. 60*b* and 60*c*, the one or more ultrasound transducers 604 may be located in the vicinity of the vibration element 605, but not in and/or on the vibration element 605.

The vibration element may include a material having a different acoustic impedance than the rest of the applicator, e.g., the casing of the applicator and/or electrical elements of the applicator. Therefore, the vibration element may be influenced by one or more ultrasound transducers to a greater extent than the rest of the applicator. The vibration material may include a metal or plastic material.

Figure 60D:
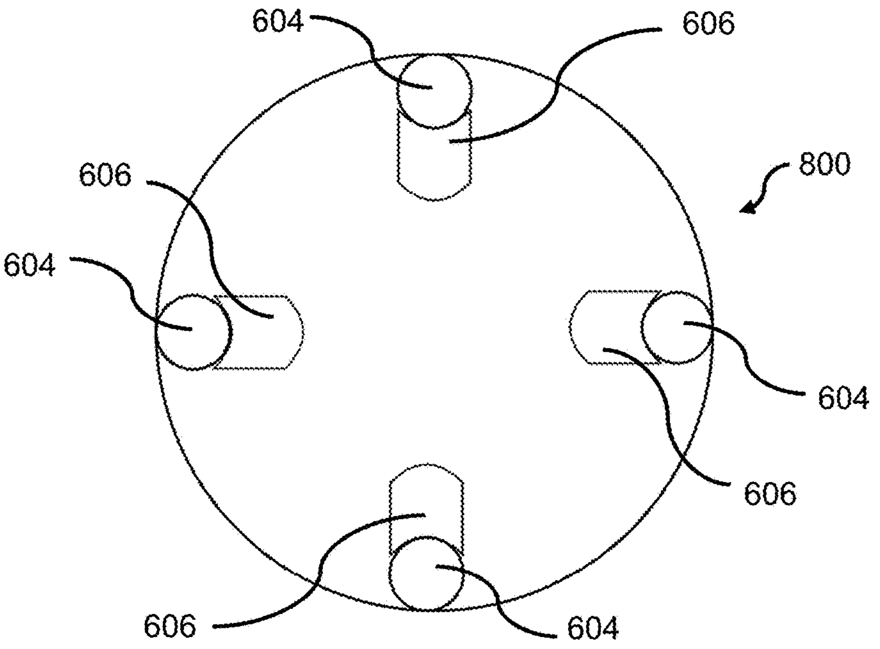

FIG. 60*d* illustrates a transverse cross sectional view of an exemplary applicator 800 including a plurality of ultrasound transducers 604 and reflecting elements 606. The reflecting elements 606 are shown to be connected to the ultrasound transducers 604. One reflecting element 606 may be located within or on the surface of the applicator 800. The ultrasound energy provided by the ultrasound transducers 604 may be reflected by reflecting element 606 in one direction or in more than one direction. The reflected ultrasound energy, together with the non-reflected ultrasound energy may be applied to the patient.

Figure 60E:
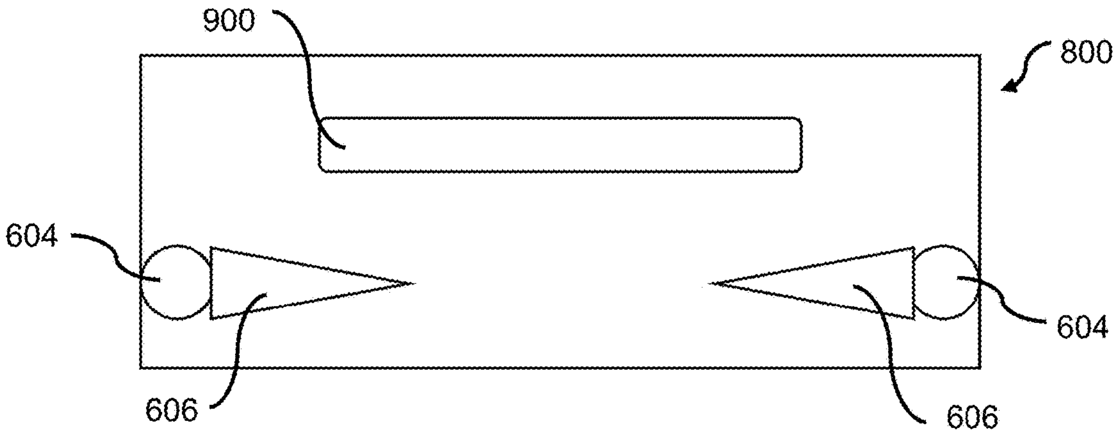

FIG. 60*e* illustrates a cross sectional view of an exemplary applicator 800 that includes a plurality of ultrasound transducers 604 and reflecting elements 606. The reflecting elements 606 are shown to have a pyramidal shape, but may have different shapes. The reflecting element may comprise a plastic material.

The ultrasound energy may be in a range of 100 Hz to 5 GHz, 500 Hz to 500 MHz, or 800 Hz to 100 MHz. Energy flux provided by ultrasound energy may be in a range of 0.001 $W \cdot cm^{-2}$ to 500 $W \cdot cm^{-2}$ or 0.005 $W \cdot cm^{-2}$ to 350 $W \cdot cm^{-2}$ or 0.05 $W \cdot cm^{-2}$ to 250 $W \cdot cm^{-2}$.

The mechanical treatment may include providing mechanical energy to the body and/or body area by a mechanical element. The mechanical element may include a roller. The mechanical element may include a pneumatic massager, e.g. shockwave generator. The mechanical element may be positioned within the applicator and/or on the surface of the applicator. The mechanical element may include a constriction strap and/or constriction cuff. The mechanical element may be part of the treatment device. The mechanical element may be an integral part of the applicator. However, the constriction strap and/or constriction cuff may be a separate part that is added to or secured to the applicator during the treatment. In the case the mechanical element is a constriction strap or a constriction cuff, the applicator of the device still may include the combinations of magnetic treatment, radiofrequency treatment and mechanical treatment (e.g. pressure treatment, negative pressure treatment and/or ultrasound treatment).

The mechanical element may provide constriction by its own weight and/or use. For example, the constriction strap or constriction cuff may provide pressure by securing it around the body. For another example, the constriction strap or constriction cuff may provide pressure by securing the one or more applicators to the body, together with the belt. For another example, the belt used for coupling the applicator to the body may provide the mechanical treatment, when it is properly secured with high intensity.

The mechanical element may provide the mechanical treatment comprising the constriction of the body, part of a treated body area, treated body area and/or one or more parts of the body surrounding the treated body area, wherein the treated area may include a body area under treatment by magnetic, radiofrequency and/or mechanical treatment.

The constriction provided by the mechanical element (e.g. constriction strap or constriction cuff) may provide blood flow restriction, which may lead to enhanced muscle growth as provided by the magnetic treatment during or after the treatment session. Further, the blood flow restriction may lead to enhanced effects of heating provided by the radiofrequency treatment during or after the treatment session.

The mechanical element (e.g. constriction strap or constriction cuff) may be positioned before and/or during the magnetic, radiofrequency and/or mechanical treatment. The mechanical element may be positioned on different parts of the body. Also, the mechanical element may provide blood restriction in different parts of body. For example, in case of treatment of the arm, the mechanical element may provide blood restriction in the upper part of the arm about 5 cm to 15 cm below the shoulder joint. For another example, in case of treatment of the thigh, the mechanical element may provide blood restriction at the level of gluteal fold and/or about 5 cm to 15 cm below the gluteal fold. For another example, in case of treatment of the calf, the mechanical element may provide blood restriction below the knee about 5 cm to 15 cm below the fossa poplitea.

The constriction provided by the mechanical element (e.g. constriction strap or constriction cuff) may restrict blood flow in one or more arteries or veins. Also, the constriction provided the mechanical element may provide enhancement of muscle growth for one or more muscles. For example, in case of treatment of the arm, the mechanical element may restrict blood flow in the brachial artery and/or provide enhancement of muscle growth for biceps brachii and/or triceps brachii. For another example, in case of treatment of the thigh, the mechanical element may restrict blood flow in the femoral artery and/or provide enhancement of muscle growth for musculi femoris, hamstring muscles in the back of the thigh, the quadriceps muscles in the front of the thigh and/or the adductor muscles on the inside of the thigh. For another example, in case of treatment of the calf, the mechanical element may restrict blood flow in the fibular artery and/or provide enhancement of muscle growth for triceps surae muscle, soleus muscle, and/or gastrocnemius muscle.

The control system including the microprocessor may control the device to provide different treatment protocols.

The treatment protocol may be divided into two or more treatment sections. The number of treatment section may be in the range of 2 to 50, or 2 to 30, or 2 to 15 for one protocol.

Each treatment section of the treatment protocol may include different treatment parameters and/or types of combined treatment of magnetic treatment and RF treatment as described above. Also, one or more treatment sections of the treatment protocol may include predetermined treatment parameters of magnetic treatment, RF treatment, and/or mechanical treatment.

One treatment section may last for a section time, wherein section time may be in a range of 10 s to 30 minutes, or 15 s to 25 minutes, or 20 s to 20 minutes. Different sections may have different treatment effects in one or more treated biological structures, e.g., a muscle and adipose tissue. For example, one treatment section may provide high intensity muscle exercise where muscle contractions are intensive and a high number of such contractions is provided, wherein a higher repetition rate of magnetic pulses with high energy flux density may be used during one treatment section. Another treatment section may have a muscle relaxation effect, wherein the low and/or the high repetition rate of magnetic pulses may be used and/or also lower magnetic flux density of magnetic field may be used.

Treatment protocol may include different setting of power output of RF treatment, as commanded or controlled by control system of the treatment device. One setting may be a constant power output, wherein the power output during the treatment protocol may be same. Another setting may be an oscillating power output of RF treatment. The power output of RF treatment may oscillate around predetermined value of power output in a range of 0.1% to 5% of predetermined power output. Still another setting may be a varying power output of RF energy, wherein the power output of RF treatment is varied during treatment protocol. The variation of power output of RF treatment may be provided in one or more power output variation steps, wherein one power output variation step may include one change of value of power output of RF treatment applied by one or more RF electrodes. The change of power output of RF treatment from one value to another value during power output variation step may be in the range of 0.1 W to 50 W, or 0.1 W to 30 W, or 0.1 W to 20 W. The power output variation step may have time duration in the range of 0.1 s to 10 min or 0.1 s to 5 min.

Regarding the variation of power output of RF energy, the power output of RF energy may have different values during different time period of treatment protocol. Therefore, RF treatment may have different value of power output during first time period followed by power output variation step followed by second time period having different value of power output of RF treatment. The first time period having one value of power output of RF treatment may be in a range of 1 s to 15 min or 10 s to 10 min. The second time period having another value of power output of RF treatment may be in a range of 1 s to 45 min or 4 s to 59 min or 5 s to 35 min. For example, RF treatment may have value of power output about 20 W during first time and 10 W during second time period.

First exemplary treatment protocol may include two treatment section. First treatment section may include envelopes of magnetic pulses, wherein the envelopes may include pulses having repetition rate in the range of 1 to 10 Hz. Envelopes of first treatment section may have rectangular or trapezoidal shape. Duration of first treatment section may be from 3 minutes to 15 minutes. Second treatment section may include envelopes of magnetic pulses, wherein the envelopes may include pulses having repetition rate in the range of 15 to 45 Hz. Envelopes of second treatment section may have rectangular or trapezoidal shape. Duration of first treatment section may be from 3 minutes to 15 minutes. The treatment sections may be repeated one after another. The RF treatment may be applied continuously during the whole treatment protocol. The RF treatment may include one or two power output variation steps.

Second exemplary treatment protocol may include three treatment section. First treatment section may include envelopes of magnetic pulses, wherein the envelopes may include pulses having repetition rate in the range of 5 to 50 Hz. Envelopes of first treatment section may have rectangular or trapezoidal shape. Duration of first treatment section may be from 3 minutes to 15 minutes. Second treatment section may include envelopes of magnetic pulses, wherein the envelopes may include pulses having repetition rate in the range of 15 to 45 Hz. Envelopes of second treatment section may have rectangular or trapezoidal shape. Duration of first treatment section may be from 3 minutes to 15 minutes. Third treatment section may include envelopes of magnetic pulses, wherein the envelopes may include pulses having repetition rate in the range of 10 to 40 Hz. Envelopes of third treatment section may have rectangular or trapezoidal shape. Duration of third treatment section may be from 3 minutes to 15 minutes. The treatment sections may be repeated one after another. The RF treatment may be applied continuously during the whole treatment protocol. The RF treatment may include one or two power output variation steps. The one power output variation step may be initiated in a range of 1 or 20 minutes after the start of the treatment protocol. In one example, the one power output variation step may be initiated three minutes after the start of the treatment protocol.

The treatment protocol may include a combination of a magnetic treatment, an RF treatment, and a mechanical treatment. The treatments may be applied simultaneously or sequentially. The specific type of treatment selected may depend on a variety of factors including the age of the patient and/or treated body part.

Treatment sections describing magnetic treatment parameters mentioned below are part of the protocols referred to as the magnetic treatment protocols, since they mostly discuss parameters of the magnetic treatment. Generally, the device may provide and/or control the modulation of duration of magnetic impulse, repetition rate of magnetic impulse and/or amplitude of magnetic field density of magnetic impulse, number of magnetic impulses in the magnetic train, duration of the magnetic train, number of magnetic impulses in the magnetic burst, duration of the magnetic burst and/or duration of a time period when no treatment effect is caused. The control of the modulation may be provided by the control system and/or the human machine interface. The exemplary magnetic treatment protocols may include one or more treatment sections. During any treatment section, the repetition rate of magnetic impulses may be changed from a first value to a second value.

One or more treatment sections may comprise magnetic impulses having a repetition rate in a range of 5 Hz to 150 Hz. One or more treatment sections may comprise one or more trains of magnetic impulses having an amplitude of magnetic flux density to form one or more trapezoidal envelopes. The treatment section may comprise one train having magnetic impulses with one repetition rate, wherein the magnetic impulses have amplitude of magnetic flux density to form one trapezoidal envelope, wherein the treatment section may comprise one or more of such trains. The trapezoidal envelope may comprise an increasing time period in a range of 0.1 s to 20 s, 0.15 s to 10 s, or 0.25 to 8 s. The trapezoidal envelope may further comprise a hold time period in a range of 0.1 s to 25 s, 0.15 s to 15 s, or 0.25 s to 10 s. The trapezoidal envelope may further comprise a decreasing time period in a range of 0.1 s to 20 s, 0.15 s to 10 s, or 0.25 to 8 s. The train of magnetic impulses may be followed by the time period of no magnetic stimulation in a range of 1 to 60 seconds. The treatment section may have a duration in a range of 10 seconds to 5,000 seconds.

First exemplary treatment section of magnetic treatment protocols comprises magnetic impulses having a repetition rate of 21 Hz to 40 Hz. Further, the first exemplary treatment section comprises one or more trains of magnetic impulses having amplitude of magnetic flux density to form one or more trapezoidal envelopes, wherein the trapezoidal envelope comprises increasing time period of 0.25 s to 1.5 s, hold time period of 2 s to 5 s, and decrease time period of 0.5 s to 4 s.

Second exemplary treatment section of magnetic treatment protocols comprises magnetic impulses having repetition rate of 1 Hz to 20 Hz. Further, the second exemplary treatment section comprises one or more trains of magnetic impulses having amplitude of magnetic flux density to form one or more trapezoidal envelopes, wherein the trapezoidal envelope comprises increasing time period of 2 s to 8 s, hold time period of 1 s to 2 s, and decrease time period of 2 s to 8 s.

Third exemplary treatment section of magnetic treatment protocol comprises magnetic impulses having repetition rate of 25 Hz to 50 Hz. Further, the third exemplary treatment section comprises one or more trains of magnetic impulses having an amplitude of magnetic flux density to form one or more rectangular envelopes, One or more magnetic treatment protocols may include one or more described exemplary treatment sections of magnetic treatment protocol.

Following exemplary protocols are referred as the radiofrequency treatment protocols, since they mostly discuss parameters of the radiofrequency treatment. Generally, the device may provide and/or control the modulation of duration of radiofrequency impulse, repetition rate of radiofrequency impulse, and/or amplitude of intensity (e.g. power output) of radiofrequency impulse. The control of the modulation may be provided by the control system and/or human machine interface. The exemplary radiofrequency treatment protocols may comprise one or more treatment sections.

One or more exemplary radiofrequency treatment protocols, including the radiofrequency treatment may be applied in a continual manner during the treatment session without changing the parameters set at the beginning of the treatment session.

One or more exemplary radiofrequency treatment protocols, including the radiofrequency treatment may be applied in a continual manner during the whole treatment session with changing the parameters set at the beginning of the treatment session.

One or more exemplary radiofrequency treatment protocols may be applied at the same time or different time as the magnetic treatment providing the muscle contraction. This configuration may lead to provide all benefits as described within this application for combination of magnetic and radiofrequency treatment.

A first exemplary radiofrequency treatment protocol comprises two treatment sections having different power output of the RF waves. The first treatment section comprises RF waves having a power output in a range of 10 W to 50 W, while the second treatment section comprises RF waves having a power output in a range of 2 W to 25 W, wherein the first power output is different from the second power output. Duration of the first treatment section may be in a range of 0.5 minute to 15 minutes, or 1 minute to 7 minutes. In one configuration applied for example to the abdomen, the first power output is in a range of 20 W to 30 W, while the second power output is in a range of 15 W to 30 W. In another configuration applied for example to the buttock, the first power output is in a range of 15 W to 30 W, while the second power output is in a range of 12 W to 30 W. In still another configuration applied for example to the calf, the first power output is in a range of 10 W to 30 W, while the second power output is in a range of 2 W to 30 W. In still another configuration applied for example to the arm, the first power output is in a range of 10 W to 30 W, while the second power output is in a range of 5 W to 30 W. In still another configuration applied for example to the inner thigh, the first power output is in a range of 15 W to 30 W, while the second power output is in a range of 5 W to 30 W. In still another configuration applied for example to the abdomen, the first power output is in a range of 15 W to 30 W, while the second power output is in a range of 12 W to 30 W. In still another configuration applied for example to a back of the thigh and/or a front of the thigh, the first power output is in a range of 10 W to 30 W, while the second power output is in a range of 5 W to 30 W. In still another configuration applied for example to the outer thigh and/or front part of thigh, the first power output is in a range of 15 W to 30 W, while the second power output is in a range of 10 W to 30 W. The power output variation step may be located between two treatment sections. The first treatment section may be used for heating boost to heat the tissue (e.g. body region and/or biological structure) to the desired temperature, while the second treatment section may be used for maintaining of the desired temperature during the rest of the treatment. The desired temperature may be in a range of 38° C. to 60° C., or of 40° C. to 52° C., or of 41° C. to 50° C., or of 41° C. to 48° C., or of 42° C. to 48° C., or of 42° C. to 45° C.

A second exemplary radiofrequency treatment protocol comprises three treatment sections having different power output of the RF waves. The first treatment section comprises RF waves having a power output in a range of 10 W to 35 W, the second treatment section comprises RF waves having a power output in a range of 2 W to 18 W, while the third treatment section comprises RF waves having a power output in a range of 5 W to 50 W. The first power output is different from the second power output and the third power output is different from either of the first and second power output. Duration of the first treatment section may be in a range of 0.5 minute to 15 minutes or 1 minute to 7 minutes.

The following exemplary protocols are referred to as the mechanical treatment protocols, since they mostly discuss parameters of the mechanical treatment. Generally, the device may provide and/or control the modulation of: the duration of mechanical impulse, repetition rate of mechanical impulse, and/or amplitude of pressure (e.g. positive pressure and/or negative pressure) of fluid in the pressure outlet. The control of the modulation may be provided by the control system and/or human machine interface. The exemplary mechanical treatment protocols may comprise one or more treatment sections.

One or more exemplary mechanical treatment protocols, including the mechanical treatment (e.g. providing pressure impulses) may be applied in a continual manner during the treatment session without changing the parameters set at the beginning of the treatment session.

One or more exemplary mechanical treatment protocols, including the mechanical treatment (e.g. providing pressure impulses) may be applied in a continual manner during the treatment session with changing the parameters set at the beginning of the treatment session.

One or more exemplary mechanical treatment protocols, including the mechanical treatment (e.g. providing pressure impulses) may be applied at the same time as the magnetic treatment providing the muscle contraction. This configuration may lead to relief of pain and/or skin massage during the muscle contraction to better withstand the muscle contraction.

One or more exemplary mechanical treatment protocols, including the mechanical treatment (e.g. providing pressure impulses) may be applied at a different time than the magnetic treatment providing the muscle contraction. This mechanical treatment protocol may provide mechanical treatment (e.g. massage) to the body area and/or muscles during a time when the muscle contraction is not present. This configuration may lead to faster relief of the pain, relief of the muscle fatigue, and/or regeneration of the muscle between the muscle contractions and may help to prepare the muscle for following muscle contractions by decreasing a concentration of lactic acid within the body area.

One or more exemplary mechanical treatment protocols, including the mechanical treatment (e.g. providing pressure impulses) may be applied at the same time as the radiofrequency treatment providing heating of the body area. This configuration may lead to enhancement of homogenization of heating within the body area.

One or more exemplary mechanical treatment protocols, including the mechanical treatment (e.g. providing pressure impulses) may be applied at a different time than the radiofrequency treatment providing heating of the body area. This configuration may lead to regeneration and/or cooling of the muscles and/or body area.

The first exemplary mechanical treatment protocol includes two treatment sections having different repetition rates of the pressure impulses. The first treatment section comprises mechanical impulses having a repetition rate in a range of 1 Hz to 10 Hz, while the second treatment section comprises a repetition rate in a range of 5 Hz to 25 Hz, wherein the first repetition rate is different from the second repetition rate. In one configuration, the first repetition rate is 8 Hz, while the second treatment section is 15 Hz.

A second exemplary mechanical treatment protocol comprises three treatment sections having repetition rates of the pressure impulses. The first treatment section comprises mechanical impulses having a repetition rate in a range of 1 Hz to 10 Hz, the second treatment section comprises pressure impulses having a repetition rate in a range of 10 Hz to 25 Hz, while the third treatment section comprises mechanical impulses having a repetition rate in a range of 5 Hz to 15 Hz, wherein one (e.g. first) repetition rate is different from the other repetition rates (e.g. second and third). In one configuration, the first repetition rate is 8 Hz, the second treatment section is 12 Hz and the third repetition rate is 12 Hz.

A third exemplary mechanical treatment protocol comprises three treatment sections having repetition rates of the pressure impulses. The first treatment section comprises mechanical impulses having a repetition rate in a range of 1 Hz to 10 Hz, the second treatment section comprises mechanical impulses having a repetition rate in a range of 10 Hz to 25 Hz, while the third treatment section comprises mechanical impulses having repetition rate in a range of 5 Hz to 20 Hz, wherein the first, second and third repetition rates are different. In one configuration, the first repetition rate is 5 Hz, the second treatment section is 18 Hz, and the third repetition rate is 14 Hz.

The duration of the mechanical impulses may be varied during the treatment sections of any of the three exemplary mechanical treatment protocols. The duration of the pressure impulses may be shorter when the repetition rate is higher, while the duration of the pressure impulses may be longer when the repetition rate is lower. For example, the duration of the pressure impulses is in a range of 0.5 ms to 15 ms when the repetition rate is in a range of 15 Hz to 100 Hz, while the duration of the pressure impulses is in a range of 15.1 ms to 40 ms when the repetition rate is in a range of 0.1 Hz to 14.9 Hz. Thus, an exemplary treatment protocol may include a combination of any of the magnetic, RF and mechanical treatment protocols discussed above.

The FIGS. 45*a*, 45*b* and 46-51 show different views of a main unit 11 of a treatment device according to an embodiment.

All of the examples, parts of description and methods may be used separately or in any combination.

Novel systems and methods have been described. The invention should be interpreted in the broadest sense, hence various changes and substitutions may be made of course without departing from the spirit and scope of the invention. The invention therefore should not be limited, except by the following claims and their equivalents.

Following patent applications are incorporated herein by reference in their entireties:

U.S. patent application Ser. No. 14/789,156 filed Jul. 1, 2015; U.S. patent application Ser. No. 14/789,658 filed Jul. 1, 2015; U.S. patent application Ser. No. 14/783,110 filed Oct. 1, 2015; U.S. patent application Ser. No. 14/926,365 filed Oct. 29, 2015; U.S. patent application Ser. No. 14/951,093 filed Nov. 24, 2015; U.S. patent application Ser. No. 15/073,318 filed Mar. 17, 2016; U.S. patent application Ser. No. 15/099,274 filed Apr. 14, 2016; U.S. patent application Ser. No. 15/151,012 filed May 10, 2016; U.S. patent application Ser. No. 15/344,811 filed Nov. 7, 2016; U.S. patent application Ser. No. 15/178,455 filed Jun. 9, 2016; U.S. patent application Ser. No. 15/396,073 filed Dec. 30, 2016; U.S. patent application Ser. No. 15/404,384 filed Jan. 12, 2017; U.S. Provisional Patent Application No. 62/357,679 filed Jul. 1, 2016; U.S. Provisional Patent Application No. 62/440,905 filed Dec. 30, 2016; U.S. Provisional Patent Application No. 62/440,912 filed Dec. 30, 2016; U.S. Provisional Patent Application No. 62/440,922 filed Dec. 30, 2016; U.S. Provisional Patent Application No. 62/441,805 filed Jan. 3, 2017; U.S. Provisional Patent Application No. 62/440,936 filed Dec. 30, 2016; U.S. Provisional Patent Application No. 62/440,940 filed Dec. 30, 2016; U.S. patent application Ser. No. 15/446,951 filed Mar. 1, 2017; U.S. patent application Ser. No. 15/473,390 filed Mar. 29, 2017; U.S. patent application Ser. No. 15/601,719 filed May 22, 2017; U.S. patent application Ser. No. 15/677,371 filed Aug. 15, 2017; U.S. patent application Ser. No. 15/860,443 filed Jan. 2, 2018; U.S. patent application Ser. No. 15/862,410 filed Jan. 4, 2018; U.S. patent application Ser. No. 15/954, 783 filed Apr. 17, 2018; U.S. patent application Ser. No. 16/034,752 filed Jul. 13, 2018; U.S. patent application Ser. No. 16/034,793 filed Jul. 13, 2018; U.S. patent application Ser. No. 16/042,093 filed Jul. 23, 2018; U.S. patent application Ser. No. 16/196,798 filed Nov. 20, 2018; U.S. patent application Ser. No. 16/196,837 filed Nov. 20, 2018; U.S. patent application Ser. No. 16/218,735 filed Dec. 13, 2018; U.S. patent application Ser. No. 16/219,724 filed Dec. 13, 2018; U.S. Provisional Patent Application No. 62/786,731 filed Dec. 31, 2018; U.S. patent application Ser. No. 16/266, 570 filed Feb. 4, 2019; U.S. patent application Ser. No. 16/266,494 filed Feb. 4, 2019; U.S. patent application Ser. No. 16/294,034 filed Mar. 6, 2019; U.S. patent application Ser. No. 16/560,790 filed Sep. 4, 2019; U.S. patent application Ser. No. 16/567,866 filed Sep. 11, 2019; U.S. patent application Ser. No. 16/664,524 filed Oct. 25, 2019; U.S. patent application Ser. No. 16/673,784 filed Nov. 4, 2019; U.S. patent application Ser. No. 16/673,683 filed Nov. 4, 2019; U.S. patent application Ser. No. 16/674,144 filed Nov. 5, 2019; U.S. patent application Ser. No. 16/827,330 filed Mar. 23, 2020 and International Patent Application No. PCT/IB/2016/053930 filed Jun. 30, 2016.

List of abbreviations related to FIGS. 17, 18 and 18a and others. The (A/B) means that respective element of the list may be shown with respective letter. For example, ESD (A/B) means that ESD A and/or ESD B are shown in at least one Figure.

PS power source
ESD (A/B) energy storage device
SW (A/B) switch
HIFEM (A/B) treatment cluster for magnetic treatment
MFGD (A/B) magnetic field generating device
CUM (A/B) control unit of magnetic circuit
APS RF auxiliary power source of RF circuit
PU power unit
SPSRF steady power source of RF circuit
PNFLT power network filter
PSRF power source for RF treatment
RF (A/B) treatment cluster for RF treatment
SYM (A/B) symmetrisation element
AP (A/B) applicator
RFE (A/B) RF electrode
APS (A/B) auxiliary power source
PSM power source for magnetic treatment
BPS (A/B) board power source
SPSM steady power source of magnetic circuit
PN power network
PF pulse filter
SE safety element
PA power amplifier
CURF control unit of RF circuit
What is claimed is:

1. An applicator comprising:
a top cover;
a bottom cover configured to be positioned closer to a patient than the top cover;
a magnetic field generating device configured to provide a time-varying magnetic field having a magnetic flux density in a range of 0.1 Tesla to 7 Tesla;
a radiofrequency electrode configured to provide a radiofrequency field, wherein the radiofrequency field is configured to cause heating of tissue of a body area of the patient; and
a pressure outlet comprising an opening positioned on the bottom cover of the applicator,
wherein the pressure outlet is connected to a compressor configured to generate a pressurized fluid;

wherein the compressor is connected to a fluid pressure tank configured to store the pressurized fluid; and
wherein the compressor and the fluid pressure tank are positioned outside of the applicator; and
wherein the pressure outlet is configured to provide a pressurized fluid, wherein the pressurized fluid is configured to provide a positive pressure to the body area of the patient.

2. The applicator of claim 1, further comprising a concavity.

3. The applicator of claim 1, further comprising a handle forming a concavity.

4. The applicator of claim 1, wherein the pressure outlet comprises a tube positioned through a core of the magnetic field generating device.

5. The applicator of claim 1, further comprising:
an applicator valve; and
a control unit configured to control the applicator valve.

6. The applicator of claim 1, further comprising a pressure sensor configured to measure a pressure of the pressurized fluid.

7. An applicator comprising:
a magnetic field generating device configured to provide a time-varying magnetic field having a magnetic flux density in a range of 0.1 Tesla to 7 Tesla;
a radiofrequency electrode configured to provide a radiofrequency field, wherein the radiofrequency field is configured to cause heating of tissue of a body area of a patient;
a pressure outlet comprising a cavity, wherein the pressure outlet is configured to provide a pressurized fluid to the patient; and
a rim positioned on a surface of the applicator and proximate to the cavity,
wherein the pressurized fluid is configured to provide a positive pressure to the body area of the patient.

8. The applicator of claim 7, further comprising a top cover and a bottom cover, wherein the bottom cover is closer to the patient than the top cover and wherein the rim is positioned on the bottom cover.

9. The applicator of claim 7, wherein the rim is further positioned around the cavity of the pressure outlet.

10. The applicator of claim 7, wherein the applicator is configured to be coupled to a main unit of a treatment device by a connecting tube.

11. The applicator of claim 7, further comprising a fan configured to cool the magnetic field generating device.

12. The applicator of claim 7, wherein the applicator is configured to be coupled to a main unit of a treatment device by a connecting tube, and wherein the connecting tube comprises a fluid conduit.

13. The applicator of claim 7, wherein the pressure outlet comprises an expansion section that widens towards the body area of the patient.

14. The applicator of claim 7, wherein the pressure outlet comprises an expansion section that widens toward a bottom cover of the applicator.

15. An applicator comprising:
a magnetic field generating device configured to provide a time-varying magnetic field having a magnetic flux density in a range of 0.1 Tesla to 7 Tesla;
a first radiofrequency electrode and a second radiofrequency electrode;

wherein the applicator is configured to provide a radiofrequency field, wherein the radiofrequency field is configured to cause heating of tissue of a body area of a patient; and a pressure outlet configured to provide a pressurized fluid, wherein the pressurized fluid is configured to provide a positive pressure to the body area of the patient;

wherein a portion of the pressure outlet is positioned between the first radiofrequency electrode and the second radiofrequency electrode; and wherein the pressure outlet comprises:

a tube positioned between the first radiofrequency electrode and the second radiofrequency electrode; and a cavity having a diameter larger than a diameter of the tube.

16. The applicator of claim 15, further comprising a rim positioned on a bottom cover.

17. The applicator of claim 15, further comprising a top cover and a bottom cover, wherein the bottom cover is closer to the patient than the top cover and wherein the cavity is part of the bottom cover.

18. The applicator of claim 15, wherein the applicator is configured to be coupled to a main unit of a treatment device by a connecting tube.

19. The applicator of claim 15, wherein the pressure outlet comprises a plastic material.

20. The applicator of claim 19, wherein the diameter of the cavity is in a range of 2 mm to 12 cm.

* * * * *